US011608346B2

United States Patent
Koltun et al.

(10) Patent No.: US 11,608,346 B2
(45) Date of Patent: Mar. 21, 2023

(54) RAS INHIBITORS

(71) Applicant: Revolution Medicines, Inc., Redwood City, CA (US)

(72) Inventors: Elena S. Koltun, Foster City, CA (US); James Cregg, Belmont, CA (US); Adrian L. Gill, Atherton, CA (US)

(73) Assignee: Revolution Medicines, Inc., Redwood City, CA (US)

( * ) Notice: Subject to any disclaimer, the term of this patent is extended or adjusted under 35 U.S.C. 154(b) by 0 days.

(21) Appl. No.: 17/088,986

(22) Filed: Nov. 4, 2020

(65) Prior Publication Data

US 2021/0130369 A1 May 6, 2021

Related U.S. Application Data

(60) Provisional application No. 63/043,601, filed on Jun. 24, 2020, provisional application No. 63/000,375, filed on Mar. 26, 2020, provisional application No. 62/951,763, filed on Dec. 20, 2019, provisional application No. 62/930,394, filed on Nov. 4, 2019.

(51) Int. Cl.
| | | |
|---|---|---|
| *C07D 498/18* | (2006.01) | |
| *C07D 401/14* | (2006.01) | |
| *C07D 498/22* | (2006.01) | |
| *C07D 513/22* | (2006.01) | |
| *C07D 519/00* | (2006.01) | |
| *A61P 35/00* | (2006.01) | |

(52) U.S. Cl.
CPC ............ *C07D 498/18* (2013.01); *A61P 35/00* (2018.01); *C07D 401/14* (2013.01); *C07D 498/22* (2013.01); *C07D 513/22* (2013.01); *C07D 519/00* (2013.01)

(58) Field of Classification Search
CPC .. C07D 498/18; C07D 401/14; C07D 498/22; C07D 513/22; C07D 519/00; A61P 35/00; C07K 5/06034; C07K 5/0606; C07K 5/06191; A61K 31/504; A61K 31/541; A61K 31/55
See application file for complete search history.

(56) References Cited

U.S. PATENT DOCUMENTS

| | | | |
|---|---|---|---|
| 6,183,965 B1 | 2/2001 | Verdine et al. | |
| 6,372,712 B1 | 4/2002 | Briesewitz et al. | |
| 6,686,454 B1 | 2/2004 | Yatscoff et al. | |
| 6,713,607 B2 | 3/2004 | Caggiano et al. | |
| 7,220,552 B1 | 5/2007 | Crabtree et al. | |
| 7,396,660 B2 | 7/2008 | Huang et al. | |
| 7,851,183 B2 | 12/2010 | Zotchev et al. | |
| 8,664,186 B2 | 3/2014 | Aigle et al. | |
| 9,250,237 B2 | 2/2016 | Liu et al. | |
| 9,260,484 B2 | 2/2016 | Briesewitz et al. | |
| 9,428,845 B1 | 8/2016 | Verdine et al. | |
| 9,989,535 B2 | 6/2018 | Verdine et al. | |
| 10,039,839 B2 | 8/2018 | Verdine et al. | |
| 10,203,323 B2 | 2/2019 | Verdine et al. | |
| 10,466,249 B2 | 11/2019 | Verdine et al. | |
| 10,533,016 B2 | 1/2020 | Verdine et al. | |
| 10,948,495 B2 | 3/2021 | Verdine et al. | |
| 10,989,710 B2 | 4/2021 | Verdine et al. | |
| 11,059,830 B2 | 7/2021 | Verdine et al. | |
| 2002/0110874 A1 | 8/2002 | Khosla et al. | |
| 2002/0147133 A1 | 10/2002 | Briesewitz et al. | |
| 2003/0153053 A1 | 8/2003 | Reid | |
| 2003/0175901 A1 | 9/2003 | Reeves et al. | |
| 2004/0087496 A1 | 5/2004 | Kim et al. | |
| 2004/0157768 A1 | 8/2004 | Or et al. | |
| 2005/0233431 A1 | 10/2005 | Ashley et al. | |
| 2007/0203168 A1 | 8/2007 | Zhao | |
| 2007/0218502 A1 | 9/2007 | Hahn et al. | |
| 2007/0265333 A1 | 11/2007 | Fu et al. | |
| 2011/0117606 A1 | 5/2011 | Jorgensen et al. | |
| 2012/0208720 A1 | 8/2012 | Kashiwagi et al. | |
| 2012/0270800 A1 | 10/2012 | Verdine et al. | |
| 2013/0072439 A1 | 3/2013 | Nash et al. | |
| 2014/0073581 A1 | 3/2014 | Liu et al. | |
| 2014/0316104 A1 | 10/2014 | Fischer et al. | |
| 2015/0250896 A1 | 9/2015 | Zhao | |
| 2015/0307855 A1 | 10/2015 | Yuzawa et al. | |
| 2016/0199506 A1 | 7/2016 | Verdine et al. | |
| 2016/0296528 A1 | 10/2016 | Pastor Fernandez et al. | |
| 2016/0341719 A1 | 11/2016 | Verdine et al. | |
| 2017/0190734 A1 | 7/2017 | Aciro et al. | |
| 2018/0318434 A1 | 11/2018 | Verdine et al. | |
| 2020/0197391 A1 | 6/2020 | Jin et al. | |
| 2020/0199102 A1 | 6/2020 | Mulvihill et al. | |
| 2021/0130303 A1 | 5/2021 | Koltun et al. | |
| 2021/0130326 A1 | 5/2021 | Aggen et al. | |
| 2021/0130369 A1 | 5/2021 | Koltun et al. | |
| 2021/0285955 A1 | 9/2021 | Mulvihill et al. | |
| 2021/0405060 A1 | 12/2021 | Verdine et al. | |
| 2022/0082556 A1 | 3/2022 | Verdine et al. | |
| 2022/0105185 A1 | 4/2022 | Aay et al. | |
| 2022/0143202 A1 | 5/2022 | Verdine et al. | |
| 2022/0144849 A1 | 5/2022 | Verdine et al. | |

FOREIGN PATENT DOCUMENTS

| | | |
|---|---|---|
| EP | 0194972 A2 | 9/1986 |
| EP | 0393934 A1 | 10/1990 |
| EP | 0562853 A1 | 9/1993 |
| EP | 1079859-61 | 7/2010 |
| JP | H10-508315 A | 8/1998 |
| KR | 10-2009-0041971 A | 4/2009 |
| WO | WO-86/02080 A1 | 4/1986 |
| WO | WO-95/32294 A1 | 11/1995 |
| WO | WO-96/20216 A1 | 7/1996 |
| WO | WO-98/01546 A2 | 1/1998 |

(Continued)

OTHER PUBLICATIONS

Guo, Z., "Rapamycin-inspired macrocycles with new target specificity." Nature chemistry 11.3 (2019): 254-263.*

(Continued)

*Primary Examiner* — John M Mauro
(74) *Attorney, Agent, or Firm* — Clark & Elbing LLP

(57) ABSTRACT

The disclosure features macrocyclic compounds, and pharmaceutical compositions and protein complexes thereof, capable of inhibiting Ras proteins, and their uses in the treatment of cancers.

7 Claims, 1 Drawing Sheet

(56) References Cited

FOREIGN PATENT DOCUMENTS

| | | |
|---|---|---|
| WO | WO-98/07743 A1 | 2/1998 |
| WO | WO-98/12217 A1 | 3/1998 |
| WO | WO-99/61055 A1 | 12/1999 |
| WO | WO-00/47724 A2 | 8/2000 |
| WO | WO-01/36460 A2 | 5/2001 |
| WO | WO-01/36612 A1 | 5/2001 |
| WO | WO-01/90070 A2 | 11/2001 |
| WO | WO-03/033010 A1 | 4/2003 |
| WO | WO-2008/069824 A2 | 6/2008 |
| WO | WO-2010/031185 A1 | 3/2010 |
| WO | WO-2010/034243 A1 | 4/2010 |
| WO | WO-2010/088573 A1 | 8/2010 |
| WO | WO-2012/075048 A2 | 6/2012 |
| WO | WO-2012/078915 A1 | 6/2012 |
| WO | WO-2012/174489 A2 | 12/2012 |
| WO | WO-2013/185090 A1 | 12/2013 |
| WO | WO-2013/185093 A1 | 12/2013 |
| WO | WO-2013/185103 A1 | 12/2013 |
| WO | WO-2014/009774 A1 | 1/2014 |
| WO | WO-2014/187959 A1 | 11/2014 |
| WO | WO-2015/132784 A1 | 9/2015 |
| WO | WO-2016/112279 A1 | 7/2016 |
| WO | WO-2016/112295 A1 | 7/2016 |
| WO | WO-2016/160362 A1 | 10/2016 |
| WO | WO-2017/059267 A1 | 4/2017 |
| WO | WO-2018/081592 A2 | 5/2018 |
| WO | WO-2018/091634 A1 | 5/2018 |
| WO | WO-2018/187401 A1 | 10/2018 |
| WO | WO-2018/187423 A1 | 10/2018 |
| WO | WO-2018/217651 A1 | 11/2018 |
| WO | WO-2020/101736 A1 | 5/2020 |
| WO | WO-2020/132597 A1 | 6/2020 |
| WO | WO-2021/091956 A1 | 5/2021 |
| WO | WO-2021/091967 A1 | 5/2021 |
| WO | WO-2021/091982 A1 | 5/2021 |
| WO | WO-2022/060836 A1 | 3/2022 |

OTHER PUBLICATIONS

U.S. Appl. No. 61/418,038, Johns Hopkins University.

"Registration No. 333-235968: Amendment No. 2 to Forms S-1 Registration Statement Under the Securities Act of 1933 for Revolution Medicines, Inc.," United States Securities and Exchange Commission, Washington, D.C., 20549, dated Feb. 11, 2020 (354 pages).

"SMART™ Drugs: Engineering Nature's Solution to the Undruggable Target Challenge," WarpDrive Bio, 2016, available <http://www.warpdrivebio.com/docs/Warp%20Drive%20Bio_SMART%20Drugs%20Platform_2016.pdf> (31 pages).

"Streptomyces iranensis regulatory protein LuxR," EBI Database Accession No. CDR13506 (2014) (2 pages).

"Streptomyces rapamycinicus NRRL 5491 hypothetical protein," EBI Database Accession No. AGP59507 (2014) (2 pages).

"Substructure Search Report on Specifically Substituted Macrocycles—Substances Only," prepared by Science IP, dated Dec. 17, 2014 (6177 pages).

"Translating Frontier Oncology Targets to Outsmart Cancer™," Corporate Overview Q3-2020, Revolution Medicines, Aug. 20, 2020 (35 pages).

Aebi et al., "Synthesis, Conformation, and Immunosuppressive Activities of Three Analogues of Cyclosporin A Modified in the 1-Position," J Med Chem. 33(3):999-1009 (1990).

Allain et al., "Cyclophilin B mediates cyclosporin A incorporation in human blood T-lymphocytes through the specific binding of complexed drug to the cell surface," Biochem J. 317 (Pt 2):565-70 (1996).

Andrei et al., "Stabilization of protein-protein interactions in drug discovery," Expert Opin Drug Discov. 12(9):925-40 (2017) (17 pages).

Antunes et al., "A mutational analysis defines Vibrio fischeri LuxR binding sites," J Bacteriol. 190(13):4392-7 (2008).

Archibald et al., "Discovery and Evaluation of Potent, Cysteine-based alpha4beta1 Integrin Antagonists," Bioorg Med Chem Lett. 10(9):993-995 (2000).

Baillie, "Targeted Covalent Inhibitors for Drug Design," Covalent Inhibitor Drug Discovery & Development Symposium PBSS, Feb. 7, Foster City, California. (2019) (16 pages).

Banaszynski et al., "Characterization of the FKBP.rapamycin.FRB ternary complex," J Am Chem Soc. 127(13):4715-21 (2005).

Baranasic et al., "Draft Genome Sequence of Streptomyces rapamycinicus Strain NRRL 5491, the Producer of the Immunosuppressant Rapamycin," Genome Announc. 1(4):e00581-13 (2013) (2 pages).

Bayle et al., "Rapamycin analogs with differential binding specificity permit orthogonal control of protein activity," Chem Biol. 13(1):99-107 (2006).

Bender et al., "Periodate Oxidation of alpha-Keto gamma-Lactams. Enol Oxidation and beta-Lactam Formation. Mechanism of Periodate Hydroxylation Reactions," J Org Chem. 43(17):3354-3362(1978).

Benjamin et al., "Rapamycin passes the torch: a new generation of mTOR inhibitors," Nat Rev Drug Discov. 10(11):868-80 (2011).

Bhuyan et al., "Antioxidant activity of peptide-based angiotensin converting enzyme inhibitors," Org Biomol Chem. 10(11):2237-47 (2012).

Blodgett et al., "Unusual transformations in the biosynthesis of the antibiotic phosphinothricin tripeptide," Nat Chem Biol. 3(8):480-5 (2007).

Briesewitz et al., "Affinity modulation of small-molecule ligands by borrowing endogenous protein surfaces," Proc Natl Acad Sci U.S.A. 96(5):1953-8 (1999).

Bruce, "In vivo protein complex topologies: sights through a cross-linking lens," Proteomics. 12(10):1565-75 (2012).

Burgess et al., "Controlled translocation of palladium(II) within a 22 ring atom macrocyclic ligand," Dalton Trans. 43(45):17006-16 (2014) (12 pages).

Chaurasia et al., "Molecular insights into the stabilization of protein-protein interactions with small molecule: The FKBP12-rapamycin-FRB case study," Chem Phys Lett. 587:68-74 (2013).

Che et al., "Inducing protein-protein interactions with molecular glues," Bioorganic & Medicinal Chemistry Letters (2018).

Chevalier et al., "Straightforward synthesis of bioconjugatable azo dyes. Part 1: Black Hole Quencher-1 (BHQ-1) scaffold," Tetrahedron Lett. 55(50):6759-63 (2014).

Ding et al., "Insights into Bacterial 6-Methylsalicylic Acid Synthase and Its Engineering to Orsellinic Acid Synthase for Spirotetronate Generation," Chem Biol. 17(5):495-503 (2010).

Eberle et al., "Preparation of Functionalized Ethers of Cyclosporin A," Tetrahedron Lett. 35(35):6477-6480(1994).

Findlay et al., "The structure of demethoxyrapamycin," Can J Chem. 60:2046-7 (1982).

Garg et al., "Elucidation of the Cryptic Epimerase Activity of Redox-Inactive Ketoreductase Domains from Modular Polyketide Synthases by Tandem Equilibrium Isotope Exchange," J Am Chem Soc. 136(29):10190-10193 (2014).

Gill et al., "Discovery of Small Molecule Inhibitors of the Oncogenic, GTP-Bound (ON) Form of KRAS$^{G12C}$ and KRAS$^{G13C}$," Revolution Medicines (1 page).

Gill, "Discovery of Small Molecule Inhibitors of Oncogenic Mutants of RAS," Revolution Medicines, ACS, Apr. 2, Orlando (2019) (23 pages).

Gordon et al., "A SARS-CoV-2 Protein Interaction Map Reveals Targets for Drug Repurposing," Nature. 583(7816):459-68 (2020).

Guerra et al., "LAL regulators SCO0877 and SCO7173 as pleiotropic modulators of phosphate starvation response and actinorhodin biosynthesis in Streptomyces coelicolor," PLoS One. 7(2):e31475 (2012) (11 pages).

Hansson et al., "Bioengineering and Semisynthesis of an Optimized Cyclophilin Inhibitor for Treatment of Chronic Viral Infection," Chem Biol. 22(2):285-92 (2015) (24 pages).

He et al., "The LuxR family members GdmRI and GdmRII are positive regulators of geldanamycin biosynthesis in Streptomyces hygroscopicus 17997," Arch Microbiol. 189(5):501-10 (2008).

(56) References Cited

OTHER PUBLICATIONS

Hong et al., "Evidence for an iterative module in chain elongation on the azalomycin polyketide synthase," Beilstein J Org Chem. 12:2164-2172 (2016).

Horn et al., "Draft Genome Sequence of Streptomyces iranensis," Genome Announc. 2(4):e00616-14 (2014) (2 Pages).

Horton et al., "Engineering hybrid genes without the use of restriction enzymes: gene splicing by overlap extension," Gene. 77(1):61-8 (1989).

Hosted et al., "Use of rpsL for dominance selection and gene replacement in *Streptomyces roseosporus*" J Bacteriol. 179(1): 180-6 (1997).

Huang et al., "Conjugation to Albumin-Binding Molecule Tags as a Strategy to Improve Both Efficacy and Pharmacokinetic Properties of the Complement Inhibitor Compstatin," ChemMedChem. 9(10):2223-6 (2014).

Huang et al., "Enhanced rapamycin production in *Streptomyces hygroscopicus* by integrative expression of aveR, a LAL family transcriptional regulator," World J Microbiol Biotechnol. 27:2103-9 (2011).

Hubler et al., "Synthetic routes to NEtXaa4-cyclosporin A derivatives as potential anti-HIV I drugs," Tetrahedron Lett. 41:7193-6 (2000).

International Search Report and Written Opinion for International Application No. PCT/US2020/058801, dated Dec. 23, 2020 (15 pages).

Ishizawa et al., "TRAP display: a high-speed selection method for the generation of functional polypeptides," J Am Chem. 135(14):5433-40 (2013).

Jarvis, "Have drug hunters finally cracked KRas?—After decades of failures, researchers see promise in fresh approaches to developing drugs that block cancer's toughest target," Chemical & Engineering News. 94(23):28-33. <https://cen.acs.org/articles/94/i23/drug-hunters-finally-cracked-KRas.html>, retrieved on Oct. 14, 2018 (2016) (9 pages).

Kawakami et al., "In vitro selection of multiple libraries created by genetic code reprogramming to discover macrocyclic peptides that antagonize VEGFR2 activity in living cells," ACS Chem Biol. 8(6):1205-14 (2013).

Kelsey, "Approaches to Inhibiting RAS-Driven Tumors Beyond KRAS$^{G12C}$," RAS Targeted Drug Development, Revolution Medicines, Sep. 16, 2020 (24 pages).

Kendrew et al., "Recombinant strains for the enhanced production of bioengineered rapalogs," Metab Eng. 15:167-73 (2013).

Kuhn et al., "Synthesis of Functional Ras Lipoproteins and Fluorescent Derivatives," J Am Chem Soc. 123(6):1023-35 (2001).

Kuramochi et al., "Identification of Small Molecule Binding Molecules by Affinity Purification Using a Specific Ligand Immobilized on PEGA Resin," Bioconjug Chem. 19(12):2417-26 (2008).

Laureti et al., "Identification of a bioactive 51-membered macrolide complex by activation of a silent polyketide synthase in Streptomyces ambofaciens," Proc Natl Acad Sci USA. 108(15):6258-63 (2011).

Laureti et al., Supporting Material for "Identification of a bioactive 51-membered macrolide complex by activation of a silent polyketide synthase in Streptomyces ambofaciens," Proc Natl Acad Sci U.S.A. 108(15):6258-63 (2011), accessed via <https://www.pnas.org/content/suppl/2011/03/24/1019077108.DCSupplemental> (41 pages).

Lee et al., "Current implications of cyclophilins in human cancers," J Exp Clin Cancer Res. 29(1):97 (2010) (6 pages).

Leskiw et al., "TTA codons in some genes prevent their expression in a class of developmental, antibiotic-negative, *Streptomyces* mutants," Proc Natl Acad Sci USA. 88(6):2461-5 (1991).

Li et al., "A simple and efficient route to the FKBP-binding domain from rapamycin," available in PMC Sep. 28, 2012, published in final edited form as: Tetrahedron Lett. 52(39):5070-2 (2011) (7 pages).

Luengo et al., "Structure-activity studies of rapamycin analogs: evidence that the C-7 methoxy group is part of the effector domain and positioned at the FKBP12-FRAP interface," Chem Biol. 2(7):471-81 (1995).

Mackman et al., "Discovery of a Potent and Orally Bioavailable Cyclophilin Inhibitor Derived from the Sanglifehrin Macrocycle," J Med Chem. 61(21):9473-9499 (2018).

Majumder et al. "Interaction of aryl hydrocarbon receptor-interacting protein-like 1 with the farnesyl moiety," J Biol Chem. 288(29):21320-21328 (2013).

McGregor et al., "Expanding the Scope of Electrophiles Capable of Targeting K-Ras Oncogenes," Biochemistry. 56(25):3178-3183 (2017).

Meyer et al., "Selective palladation of a large (32 ring atom) macrocyclic ligand at a bis(N-heterocyclic carbene) coordination pocket through transmetallation of the corresponding mercury(II) derivative," Dalton Trans. 41(46):14059-67 (2012) (10 pages).

Mo et al., "Interspecies Complementation of the LuxR Family Pathway-Specific Regulator Involved in Macrolide Biosynthesis," J Microbiol Biotechnol. 26(1):66-71 (2016).

Moore et al., "RAS-targeted therapies: is the undruggable drugged?" Nat Rev Drug Discov. 19(8):533-52 (2020).

Mullard, "Cracking KRAS," Nature Publishing Group (2019) (14 pages).

Murphy et al., "Isolation and characterisation of amphotericin B analogues and truncated polyketide intermediates produced by genetic engineering of *Streptomyces nodosus*" Org Biomol Chem. 8(16):3758-70 (2010).

Ochi et al., "New strategies for drug discovery: activation of silent or weakly expressed microbial gene clusters," Appl Microbiol Biotechnol. 97(1):87-98 (2013).

Ostrem et al., "Direct small-molecule inhibitors of KRAS: from structural insights to mechanism-based design," Nat Rev Drug Discov. 15(11):771-785 (2016).

Ostrem et al., "K-Ras(G12C) inhibitors allosterically control GTP affinity and effector interactions," Nature. 503(7477):548-51 (2013) (14 pages).

Papageorgiou et al., "Improved binding affinity for cyclophilin A by a cyclosporin derivative singly modified at its effector domain," J Med Chem. 37(22):3674-6 (1994).

Pfeifer et al., "Biosynthesis of complex polyketides in a metabolically engineered strain of *E. coli*," Science. 291 (5509):1790-2 (2001) (4 pages).

Power et al., "Engineered Synthesis of 7-Oxo- and 15-Deoxy-15-Oxo-Amphotericins: Insights into Structure-Activity Relationships in Polyene Antibiotics," Chem Biol. 15(1):78-86 (2008).

PubChem CID 130196149, <https://pubchem.ncbi.nlm.nih.gov/compound/130196149>, retrieved on Apr. 1, 2020 (10 pages).

Quesniaux et al., "Cyclophilin binds to the region of cyclosporine involved in its immunosuppressive activity," Eur J Immunol. 17(9):1359-65 (1987).

Quesniaux et al., "Study of the conformation of cyclosporine in aqueous medium by means of monoclonal antibodies," Int J Pept Protein Res. 31(2):173-85 (1988).

Ranganathan et al., "Knowledge-based design of bimodular and trimodular polyketide synthases based on domain and module swaps: a route to simple statin analogues," Chem Biol. 6(10):731-41 (1999).

Ray et al., "New Electrophiles and Strategies for Mechanism-Based and Targeted Covalent Inhibitor Design," Biochemistry. 58(52):5234-5244 (2019).

Reid et al. "A model of structure and catalysis for ketoreductase domains in modular polyketide synthases," Biochemistry. 42(1):72-79 (2003).

Revill et al., "Genetically engineered analogs of ascomycin for nerve regeneration," J Pharmacol Exp Ther. 302(3):1278-85 (2002).

Revolution Medicines, "Translating Frontier Oncology Targets to Outsmart Cancer™: Corporate Overview Q4-2020," dated Nov. 12, 2020 (30 pages).

Ruan et al., "Binding of rapamycin analogs to calcium channels and FKBP52 contributes to their neuroprotective activities," Proc Natl Acad Sci U S A. 105(1):33-8 (2008).

Rudolph, "Covalent Modification In Drug Discovery—A Chemist's Perspective," Pharmaceutical & BioScience Society. Dated Feb. 7, 2019 (39 pages).

Sànchez-Tilló, et al., "Cyclophilin A is required for M-CSF-dependent macrophage proliferation," Eur J Immunol. 36(9):2515-2524 (2006).

(56) References Cited

OTHER PUBLICATIONS

Schulze et al., "Tri-Complex Inhibitors of the Oncogenic, GTP-Bound Form of KRAS$^{G12C}$ Overcome RTK-Mediated Escape Mechanisms and Drive Tumor Regressions in Vivo," Revolution Medicines (1 page).
Schutt, "Safety Considerations for Covalent Inhibitors," Pharmaceutical & BioScience Society. Dated Feb. 7, 2019 (36 pages).
Schwecke et al., "The biosynthetic gene cluster for the polyketide immunosuppressant rapamycin," Proc Natl Acad Sci U S A. 92(17):7839-43 (1995).
Sebastiano et al., "Impact of Dynamically Exposed Polarity on Permeability and Solubility of Chameleonic Drugs Beyond the Rule of 5," J Med Chem. 61:4189-4202 (2018).
Shigdel et al., "Genomic discovery of an evolutionarily programmed modality for small-molecule targeting of an intractable protein surface," Proc Natl Acad Sci U S A. 117(29):17195-203 (2020).
Sieber et al., "Novel inhibitors of the calcineurin/NFATc hub—alternatives to CsA and FK506?" Cell Commun Signal. 7:25 (2009) (19 pages).
Smith, "Translating Frontier Oncology Targets to Outsmart Cancer," RAS-Targeted Drug Discovery Summit, Revolution Medicines, Sep. 19, 2019 (29 pages).
Smulik et al., "Synthesis of cyclosporin A-derived affinity reagents by olefin metathesis," Org Lett. 4(12):2051-4 (2002).
Steadman et al., "Discovery of Potent Cyclophilin Inhibitors Based on the Structural Simplification of Sanglifehrin A," J Med Chem. 60:1000-1017 (2017).
Stewart et al., "Development of Inhibitors of the Activated Form of KRAS$^{G12C}$," AACR Targeting RAS-Driven Cancers, Dec. 9-12, San Diego, California. Poster B37 (2018).
STN record of WO 2014/009774, available online Jan. 16, 2014 (4 pages).
STN record of WO 98/12217, available online Mar. 26, 1998 (6 pages).
Sun et al. "Design and structure-based study of new potential FKBP12 inhibitors," Biophys J. 85(5):3194-3201 (2003).
Sweeney et al., "From chemical tools to clinical medicines: non-immunosuppressive cyclophilin inhibitors derived from the cyclosporin and sanglifehrin scaffolds," J Med Chem. 57(17):7145-59 (2014) (63 pages).
Sànchez-Tilló et al., "Cyclophilin A is required for M-CSF-dependent macrophage proliferation," Eur J Immunol. 36(9):2515-24 (2006).
Takakusagi et al., "Efficient one-cycle affinity selection of binding proteins or peptides specific for a small-molecule using a T7 phage display pool," Bioorg Med Chem. 16(22):9837-46 (2008).
Tanaka et al., "Clinical Acquired Resistance to KRAS$^{G12C}$ Inhibition through a Novel KRAS Switch-II Pocket Mutation and Polyclonal Alterations Converging on RAS-MAPK Reactivation," Cancer Discov. 11(8):1913-1922 (2021).
Tang et al., "Generation of New Epothilones by Genetic Engineering of a Polyketide Synthase in Myxococcus xanthus," J Antibiot (Tokyo). 58(3):178-184 (2005).
UniProtKB Accession No. A0A061A6I8, Sep. 3, 2014, available <http://www.uniprot.org/uniprot/A0A061A6I8>, (12 pages).
UniProtKB Accession No. Q54296, "Polyketide synthase," <https://www.uniprot.org/uniprot/A0A61A6I8.txt?version=14>, retrieved May 29, 2020 (12 pages).
UniProtKB Accession No. Q54296, Nov. 1, 1996, available <http://www.uniprot.org/uniprot/Q54296>, (12 pages).
UniProtKB Accession No. Q54297, Nov. 1, 1996, available <https://www.uniprot.org/uniprot/Q54297.txt>, (3 pages).
Upadhyaya et al., "Direct Ras Inhibitors Identified From a Structurally Rigidified Bicyclic Peptide Library," available in PMC Oct. 21, 2015, published in final edited form as: Tetrahedron. 70(42):7714-7720 (2014) (15 pages).
Vakiti et al., "Stereoselective synthesis of C17-C34 fragment of antascomicin A," Tetrahedron Lett. 55(47):6438-40 (2014).
Vignot et al., "mTOR-targeted therapy of cancer with rapamycin derivatives," Ann Oncol. 16(4):525-37 (2005).
Wagner et al., "New naturally occurring amino acids," Angew Chem Int Ed Engl. 22(11):816-28 (1983).
Wang et al., "Thermodynamic analysis of cyclosporin a binding to cyclophilin a in a lung tumor tissue lysate," Anal Chem. 76(15):4343-8 (2004).
Weissman et al., "Combinatorial biosynthesis of reduced polyketides," Nat Rev Microbiol. 3(12):925-36 (2005).
Weissman, "Genetic engineering of modular PKSs: from combinatorial biosynthesis to synthetic biology," Nat Prod Rep. 33(2):203-230 (2016).
Wilson et al., "Comparative X-ray structures of the major binding protein for the immunosuppressant FK506 (tacrolimus) in unliganded form and in complex with FK506 and rapamycin," Acta Cryst. D51:511-21 (1995).
Wright et al., "Multivalent binding in the design of bioactive compounds," Curr Org Chem. 5(11):1107-31 (2001).
Wu et al., "Creating diverse target-binding surfaces on FKBP12: synthesis and evaluation of a rapamycin analogue library," available in PMC Sep. 12, 2012, published in final edited form as: ACS Comb Sci. 13(5):486-95 (2011) (22 pages).
Wu et al., "Inhibition of ras-effector interactions by cyclic peptides," Med Chem Commun. 4(2):378-82 (2013).
Wu et al., "Synthesis of Ketone Analogues of Prolyl and Pipecolyl Ester FKBP12 Ligands," J Med Chem. 45(16):3558-3568 (2002).
Zhang et al. "Bifunctional Small-Molecule Ligands of K-Ras Induce Its Association with Immunophilin Proteins," Angew Chem Int Ed Engl. 131:16460-16465 (2019).
Zhou et al., "Biophysical and biochemical characterization of KRAS$^{G12C}$ inhibition through a novel modality," AACR Targeting RAS-Driven Cancers, Dec. 9-12, San Diego, California. Poster A06 (2018).

\* cited by examiner

RAS INHIBITORS

CROSS-REFERENCE TO RELATED APPLICATIONS

The present application claims the benefit of priority to U.S. Application No. 62/930,394, filed on Nov. 4, 2019; U.S. Application No. 62/951,763, filed on Dec. 20, 2019; U.S. Application No. 63/000,375, filed on Mar. 26, 2020; and U.S. Application No. 63/043,601, filed on Jun. 24, 2020, all of which are hereby incorporated by reference in their entirety.

BACKGROUND

The vast majority of small molecule drugs act by binding a functionally important pocket on a target protein, thereby modulating the activity of that protein. For example, cholesterol-lowering drugs known as statins bind the enzyme active site of HMG-CoA reductase, thus preventing the enzyme from engaging with its substrates. The fact that many such drug/target interacting pairs are known may have misled some into believing that a small molecule modulator could be discovered for most, if not all, proteins provided a reasonable amount of time, effort, and resources. This is far from the case. Current estimates are that only about 10% of all human proteins are targetable by small molecules. Bojadzic and Buchwald, Curr Top Med Chem 18: 674-699 (2019). The other 90% are currently considered refractory or intractable toward above-mentioned small molecule drug discovery. Such targets are commonly referred to as "undruggable." These undruggable targets include a vast and largely untapped reservoir of medically important human proteins. Thus, there exists a great deal of interest in discovering new molecular modalities capable of modulating the function of such undruggable targets.

It has been well established in literature that Ras proteins (K-Ras, H-Ras and N-Ras) play an essential role in various human cancers and are therefore appropriate targets for anticancer therapy. Indeed, mutations in Ras proteins account for approximately 30% of all human cancers in the United States, many of which are fatal. Dysregulation of Ras proteins by activating mutations, overexpression or upstream activation is common in human tumors, and activating mutations in Ras are frequently found in human cancer. For example, activating mutations at codon 12 in Ras proteins function by inhibiting both GTPase-activating protein (GAP)-dependent and intrinsic hydrolysis rates of GTP, significantly skewing the population of Ras mutant proteins to the "on" (GTP-bound) state (Ras(ON)), leading to oncogenic MAPK signaling. Notably, Ras exhibits a picomolar affinity for GTP, enabling Ras to be activated even in the presence of low concentrations of this nucleotide. Mutations at codons 13 (e.g., G13D) and 61 (e.g., Q61K) of Ras are also responsible for oncogenic activity in some cancers.

Despite extensive drug discovery efforts against Ras during the last several decades, a drug directly targeting Ras is still not approved. Additional efforts are needed to uncover additional medicines for cancers driven by the various Ras mutations.

SUMMARY

Provided herein are Ras inhibitors. The approach described herein entails formation of a high affinity three-component complex between a synthetic ligand and two intracellular proteins which do not interact under normal physiological conditions: the target protein of interest (e.g., Ras), and a widely expressed cytosolic chaperone (presenter protein) in the cell (e.g., cyclophilin A). More specifically, in some embodiments, the inhibitors of Ras described herein induce a new binding pocket in Ras by driving formation of a high affinity tri-complex between the Ras protein and the widely expressed cytosolic chaperone, cyclophilin A (CYPA). Without being bound by theory, the inventors believe that one way the inhibitory effect on Ras is effected by compounds of the invention and the complexes they form is by steric occlusion of the interaction site between Ras and downstream effector molecules, such as RAF and PI3K, which are required for propagating the oncogenic signal.

As such, in some embodiments, the disclosure features a compound, or pharmaceutically acceptable salt thereof, of structural Formula I:

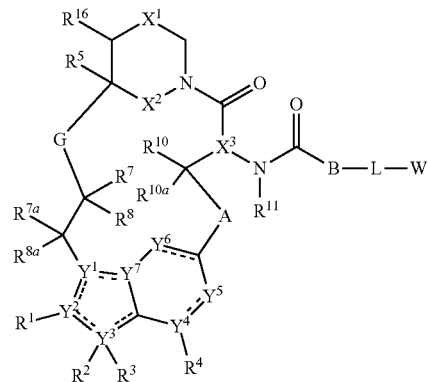

Formula I wherein the dotted lines represent zero, one, two, three, or four non-adjacent double bonds; A is —N(H or CH$_3$)C(O)—(CH$_2$)— where the amino nitrogen is bound to the carbon atom of —CH(R$^{10}$)—, optionally substituted 3 to 6-membered cycloalkylene, optionally substituted 3 to 6-membered heterocycloalkylene, optionally substituted 6-membered arylene, or optionally substituted 5 to 10-membered heteroarylene;

B is absent, —CH(R$^9$)—, or >C=CR$^9$R$^{9'}$ where the carbon is bound to the carbonyl carbon of —N(R$^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

G is optionally substituted C$_1$-C$_4$ alkylene, optionally substituted C$_1$-C$_4$ alkenylene, optionally substituted C$_1$-C$_4$ heteroalkylene, —C(O)O—CH(R$^6$)— where C is bound to —C(R$^7$R$^8$)—, —C(O)NH—CH(R$^6$)—where C is bound to —C(R$^7$R$^8$)—, optionally substituted C$_1$-C$_4$ heteroalkylene, or 3 to 8-membered heteroarylene;

L is absent or a linker;

W is hydrogen, cyano, S(O)$_2$R', optionally substituted amino, optionally substituted amido, optionally substituted C$_1$-C$_4$ alkoxy, optionally substituted C$_1$-C$_4$ hydroxyalkyl, optionally substituted C$_1$-C$_4$ aminoalkyl, optionally substituted C$_1$-C$_4$ haloalkyl, optionally substituted C$_1$-C$_4$ alkyl, optionally substituted C$_1$-C$_4$ guanidinoalkyl, C$_0$-C$_4$ alkyl optionally substituted 3 to 11-membered heterocycloalkyl, optionally substituted 3 to 8-membered cycloalkyl, or optionally substituted 3 to 8-membered heteroaryl;

X$^1$ is optionally substituted C$_1$-C$_2$ alkylene, NR, O, or S(O)$_n$;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ is CH, CH$_2$, or N;

$Y^6$ is C(O), CH, CH$_2$, or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl, or $R^1$ and $R^2$ combine with the atoms to which they are attached to form an optionally substituted 3 to 14-membered heterocycloalkyl;

$R^2$ is absent, hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl;

$R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=CR$^7$R$^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7a}$ and $R^{8a}$ are, independently, hydrogen, halo, optionally substituted $C_1$-$C_3$ alkyl, or combine with the carbon to which they are attached to form a carbonyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is hydrogen, F, optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl, or $R^9$ and L combine with the atoms to which they are attached to form an optionally substituted 3 to 14-membered heterocycloalkyl;

$R^{9'}$ is hydrogen or optionally substituted $C_1$-$C_6$ alkyl;

$R^{10}$ is hydrogen, halo, hydroxy, $C_1$-$C_3$ alkoxy, or $C_1$-$C_3$ alkyl;

$R^{10a}$ is hydrogen or halo;

$R^{11}$ is hydrogen or $C_1$-$C_3$ alkyl. Also provided are pharmaceutical compositions comprising a compound of Formula I, or a pharmaceutically acceptable salt thereof, and a pharmaceutically acceptable excipient; and $R^{16}$ is hydrogen or $C_1$-$C_3$ alkyl (e.g., methyl).

Also provided is a method of treating cancer in a subject in need thereof, the method comprising administering to the subject a therapeutically effective amount of a compound of the present invention, or a pharmaceutically acceptable salt thereof.

In some embodiments, a method is provided of treating a Ras protein-related disorder in a subject in need thereof, the method comprising administering to the subject a therapeutically effective amount of a compound of the present invention, or a pharmaceutically acceptable salt thereof.

Further provided is a method of inhibiting a Ras protein in a cell, the method comprising contacting the cell with an effective amount of a compound of the present invention, or a pharmaceutically acceptable salt thereof.

It is specifically contemplated that any limitation discussed with respect to one embodiment of the invention may apply to any other embodiment of the invention. Furthermore, any compound or composition of the invention may be used in any method of the invention, and any method of the invention may be used to produce or to utilize any compound or composition of the invention.

DEFINITIONS AND CHEMICAL TERMS

Figure 1A:
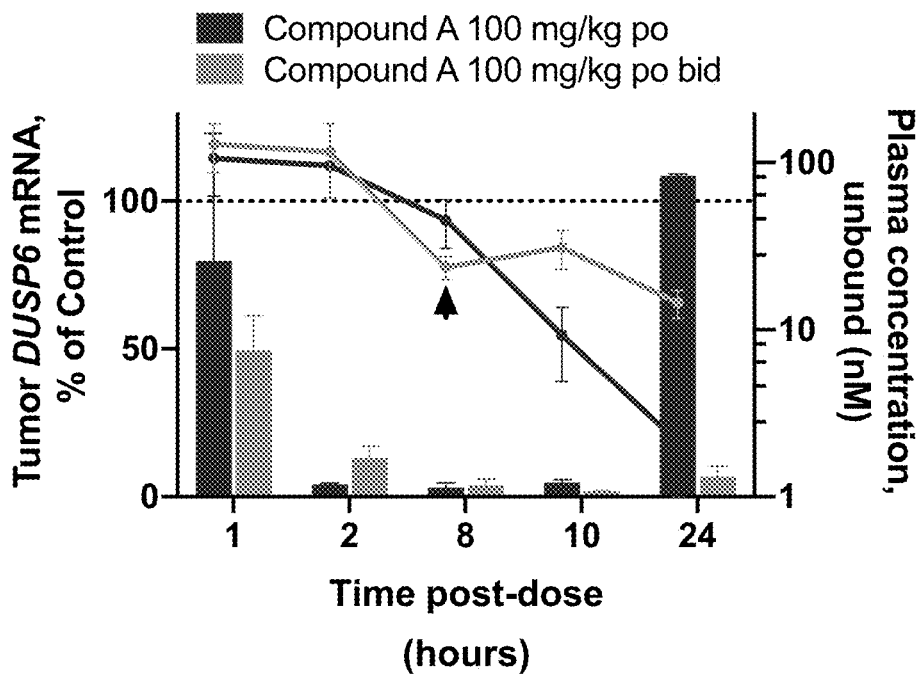
FIG. 1A: A compound of the present invention, Compound A, exhibits PK-dependent RAS pathway modulation in a Capan-2 CDX model (PDAC, KRAS G12V/WT). Single dose compared to twice administered PK/PD measurement of Compound A. Second dose of Compound A delivered 8 hours following first dose, depicted by black arrow. All dose levels well tolerated. Tumor DUSP6 mRNA expression as percent of control graphed as bars on left y-axis. Dotted line indicates return to control level of DUSP6. Unbound plasma PK (nM) graphed as lines, plotted in Log 10 scale on right y-axis. N=3/time point. Error bars represent standard error of the mean.

In this application, unless otherwise clear from context, (i) the term "a" means "one or more"; (ii) the term "or" is used to mean "and/or" unless explicitly indicated to refer to alternatives only or the alternative are mutually exclusive, although the disclosure supports a definition that refers to only alternatives and "and/or"; (iii) the terms "comprising" and "including" are understood to encompass itemized components or steps whether presented by themselves or together with one or more additional components or steps; and (iv) where ranges are provided, endpoints are included.

As used herein, the term "about" is used to indicate that a value includes the standard deviation of error for the device or method being employed to determine the value. In certain embodiments, the term "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of a stated value, unless otherwise stated or otherwise evident from the context (e.g., where such number would exceed 100% of a possible value).

As used herein, the term "adjacent" in the context of describing adjacent atoms refers to bivalent atoms that are directly connected by a covalent bond.

A "compound of the present invention" and similar terms as used herein, whether explicitly noted or not, refers to Ras inhibitors described herein, including compounds of Formula I and subformula thereof, and compounds of Table 1 and Table 2, as well as salts (e.g., pharmaceutically acceptable salts), solvates, hydrates, stereoisomers (including atropisomers), and tautomers thereof.

The term "wild-type" refers to an entity having a structure or activity as found in nature in a "normal" (as contrasted with mutant, diseased, altered, etc) state or context. Those of ordinary skill in the art will appreciate that wild-type genes and polypeptides often exist in multiple different forms (e.g., alleles).

Those skilled in the art will appreciate that certain compounds described herein can exist in one or more different isomeric (e.g., stereoisomers, geometric isomers, atropisomers, tautomers) or isotopic (e.g., in which one or more atoms has been substituted with a different isotope of the atom, such as hydrogen substituted for deuterium) forms. Unless otherwise indicated or clear from context, a depicted structure can be understood to represent any such isomeric or isotopic form, individually or in combination.

Compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

In some embodiments, one or more compounds depicted herein may exist in different tautomeric forms. As will be clear from context, unless explicitly excluded, references to such compounds encompass all such tautomeric forms. In some embodiments, tautomeric forms result from the swapping of a single bond with an adjacent double bond and the concomitant migration of a proton. In certain embodiments, a tautomeric form may be a prototropic tautomer, which is an isomeric protonation states having the same empirical formula and total charge as a reference form. Examples of moieties with prototropic tautomeric forms are ketone—enol pairs, amide—imidic acid pairs, lactam—lactim pairs, amide—imidic acid pairs, enamine—imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. In some embodiments, tautomeric forms can be in equilibrium or sterically locked into one form by appropriate substitution. In certain embodiments, tautomeric forms result from acetal interconversion.

Unless otherwise stated, structures depicted herein are also meant to include compounds that differ only in the presence of one or more isotopically enriched atoms. Exemplary isotopes that can be incorporated into compounds of the present invention include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Isotopically-labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$)) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, one or more hydrogen atoms are replaced by $^{2}H$ or $^{3}H$, or one or more carbon atoms are replaced by $^{13}C$- or $^{14}C$-enriched carbon. Positron emitting isotopes such as $^{15}O$, $^{13}N$, $^{11}C$, and $^{18}F$ are useful for positron emission tomography (PET) studies to examine substrate receptor occupancy. Preparations of isotopically labelled compounds are known to those of skill in the art. For example, isotopically labeled compounds can generally be prepared by following procedures analogous to those disclosed for compounds of the present invention described herein, by substituting an isotopically labeled reagent for a non-isotopically labeled reagent.

As is known in the art, many chemical entities can adopt a variety of different solid forms such as, for example, amorphous forms or crystalline forms (e.g., polymorphs, hydrates, solvate). In some embodiments, compounds of the present invention may be utilized in any such form, including in any solid form. In some embodiments, compounds described or depicted herein may be provided or utilized in hydrate or solvate form.

At various places in the present specification, substituents of compounds of the present disclosure are disclosed in groups or in ranges. It is specifically intended that the present disclosure include each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl. Furthermore, where a compound includes a plurality of positions at which substituents are disclosed in groups or in ranges, unless otherwise indicated, the present disclosure is intended to cover individual compounds and groups of compounds (e.g., genera and subgenera) containing each and every individual subcombination of members at each position.

The term "optionally substituted X" (e.g., "optionally substituted alkyl") is intended to be equivalent to "X, wherein X is optionally substituted" (e.g., "alkyl, wherein said alkyl is optionally substituted"). It is not intended to mean that the feature "X" (e.g., alkyl) per se is optional. As described herein, certain compounds of interest may contain one or more "optionally substituted" moieties. In general, the term "substituted", whether preceded by the term "optionally" or not, means that one or more hydrogens of the designated moiety are replaced with a suitable substituent, e.g., any of the substituents or groups described herein. Unless otherwise indicated, an "optionally substituted" group may have a suitable substituent at each substitutable position of the group, and when more than one position in any given structure may be substituted with more than one substituent selected from a specified group, the substituent may be either the same or different at every position. For example, in the term "optionally substituted $C_1$-$C_6$ alkyl-$C_2$-$C_9$ heteroaryl," the alkyl portion, the heteroaryl portion, or both, may be optionally substituted. Combinations of substituents envisioned by the present disclosure are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group may be, independently, deuterium; halogen; $-(CH_2)_{0-4}R^\circ$; $-(CH_2)_{0-4}OR^\circ$; $-O(CH_2)_{0-4}R^\circ$; $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; 4-8 membered saturated or unsaturated heterocycloalkyl (e.g., pyridyl); 3-8 membered saturated or unsaturated cycloalkyl (e.g., cyclopropyl, cyclobutyl, or cyclopentyl); $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ{}_2$; $-N(R^\circ)C(S)NR^\circ{}_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ{}_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}-C(O)-N(R^\circ)_2$; $-(CH_2)_{0-4}-C(O)-N(R^\circ)-S(O)_2-R^\circ$; $-C(NCN)NR^\circ{}_2$; $-(CH_2)_{0-4}C(O)SR^\circ$; $-(CH_2)_{0-4}C(O)OSiR^\circ{}_3$; $-(CH_2)_{0-4}OC(O)R^\circ$; $-OC(O)(CH_2)_{0-4}SR^\circ$; $-SC(S)SR^\circ$; $-(CH_2)_{0-4}SC(O)R^\circ$; $-(CH_2)_{0-4}C(O)NR^\circ{}_2$; $-C(S)NR^\circ{}_2$; $-C(S)SR^\circ$; $-(CH_2)_{0-4}OC(O)$ $NR^\circ{}_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ{}_2$; $-(CH_2)_{0-4}S(O)R^\circ$; $-N(R^\circ)S(O)_2NR^\circ{}_2$; $-N(R^\circ)S(O)_2R^\circ$; $-N(OR^\circ)R^\circ$; $-C(NOR^\circ)NR^\circ{}_2$; $-C(NH)NR^\circ{}_2$; $-P(O)_2R^\circ$; $-P(O)R^\circ{}_2$; $-P(O)(OR^\circ)_2$; $-OP(O)R^\circ{}_2$; $-OP(O)(OR^\circ)_2$; $-OP(O)(OR^\circ)R^\circ$, $-SiR^\circ{}_3$; $-(C_{1-4}$ straight or branched alkylene)$O-N(R^\circ)_2$; or $-(C_{1-4}$ straight or branched alkylene)$C(O)O-N(R^\circ)_2$, wherein each $R^\circ$ may be substituted as defined below and is independently hydrogen, $-C_{1-6}$ aliphatic, $-CH_2Ph$, $-O(CH_2)_{0-1}Ph$, $-CH_2$-(5-6 membered heteroaryl ring), or a 3-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), may be, independently, halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet{}_2$, $-NO_2$, $-SiR^\bullet{}_3$, $-OSiR^\bullet{}_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*{}_2$, $=NNHC(O)R^*$, $=NNHC(O)OR^*$, $=NNHS(O)_2R^*$, $=NR^*$, $=NOR^*$, $-O(C(R^*{}_2))_{2-3}O-$, or $-S(C(R^*{}_2))_{2-3}S-$, wherein each independent occurrence of $R^*$ is selected from hydrogen, $C_1$-6 aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*{}_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^\bullet$ include halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet{}_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger{}_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger{}_2$, $-C(S)NR^\dagger{}_2$, $-C(NH)NR^\dagger{}_2$, or $-N(R^\dagger)S(O)_2R^\dagger$; wherein each $R^\dagger$ is independently hydrogen, $C_1$-6 aliphatic which may be substituted as defined below, unsubstituted $-OPh$, or an unsubstituted 3-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on an aliphatic group of $R^\dagger$ are independently halogen, $-R^\bullet$, -(haloR$^\bullet$), $-OH$, $-OR^\bullet$, —O(haloR*), —CN, —C(O)OH, —C(O)OR*, —NH$_2$, —NHR*, —NR*$_2$, or —NO$_2$, wherein each R* is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R† include =O and =S.

The term "acetyl," as used herein, refers to the group —C(O)CH$_3$.

The term "alkoxy," as used herein, refers to a —O—C$_1$-C$_{20}$ alkyl group, wherein the alkoxy group is attached to the remainder of the compound through an oxygen atom.

The term "alkyl," as used herein, refers to a saturated, straight or branched monovalent hydrocarbon group containing from 1 to 20 (e.g., from 1 to 10 or from 1 to 6) carbons. In some embodiments, an alkyl group is unbranched (i.e., is linear); in some embodiments, an alkyl group is branched. Alkyl groups are exemplified by, but not limited to, methyl, ethyl, n- and iso-propyl, n-, sec-, iso- and tert-butyl, and neopentyl.

The term "alkylene," as used herein, represents a saturated divalent hydrocarbon group derived from a straight or branched chain saturated hydrocarbon by the removal of two hydrogen atoms, and is exemplified by methylene, ethylene, isopropylene, and the like. The term "C$_x$-C$_y$ alkylene" represents alkylene groups having between x and y carbons. Exemplary values for x are 1, 2, 3, 4, 5, and 6, and exemplary values for y are 2, 3, 4, 5, 6, 7, 8, 9, 10, 12, 14, 16, 18, or 20 (e.g., C$_1$-C$_6$, C$_1$-C$_{10}$, C$_2$-C$_{20}$, C$_2$-C$_6$, C$_2$-C$_{10}$, or C$_2$-C$_{20}$ alkylene). In some embodiments, the alkylene can be further substituted with 1, 2, 3, or 4 substituent groups as defined herein.

The term "alkenyl," as used herein, represents monovalent straight or branched chain groups of, unless otherwise specified, from 2 to 20 carbons (e.g., from 2 to 6 or from 2 to 10 carbons) containing one or more carbon-carbon double bonds and is exemplified by ethenyl, 1-propenyl, 2-propenyl, 2-methyl-1-propenyl, 1-butenyl, and 2-butenyl. Alkenyls include both cis and trans isomers. The term "alkenylene," as used herein, represents a divalent straight or branched chain groups of, unless otherwise specified, from 2 to 20 carbons (e.g., from 2 to 6 or from 2 to 10 carbons) containing one or more carbon-carbon double bonds.

The term "alkynyl," as used herein, represents monovalent straight or branched chain groups from 2 to 20 carbon atoms (e.g., from 2 to 4, from 2 to 6, or from 2 to 10 carbons) containing a carbon-carbon triple bond and is exemplified by ethynyl, and 1-propynyl.

The term "alkynyl sulfone," as used herein, represents a group comprising the structure

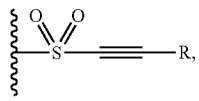

wherein R is any chemically feasible substituent described herein.

The term "amino," as used herein, represents —N(R†)$_2$, e.g., —NH$_2$ and —N(CH$_3$)$_2$.

The term "aminoalkyl," as used herein, represents an alkyl moiety substituted on one or more carbon atoms with one or more amino moieties.

The term "amino acid," as described herein, refers to a molecule having a side chain, an amino group, and an acid group (e.g., —CO$_2$H or —SO$_3$H), wherein the amino acid is attached to the parent molecular group by the side chain, amino group, or acid group (e.g., the side chain). As used herein, the term "amino acid" in its broadest sense, refers to any compound or substance that can be incorporated into a polypeptide chain, e.g., through formation of one or more peptide bonds. In some embodiments, an amino acid has the general structure H$_2$N—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. Exemplary amino acids include alanine, arginine, asparagine, aspartic acid, cysteine, glutamic acid, glutamine, glycine, histidine, optionally substituted hydroxylnorvaline, isoleucine, leucine, lysine, methionine, norvaline, ornithine, phenylalanine, proline, pyrrolysine, selenocysteine, serine, taurine, threonine, tryptophan, tyrosine, and valine.

The term "aryl," as used herein, represents a monovalent monocyclic, bicyclic, or multicyclic ring system formed by carbon atoms, wherein the ring attached to the pendant group is aromatic. Examples of aryl groups are phenyl, naphthyl, phenanthrenyl, and anthracenyl. An aryl ring can be attached to its pendant group at any heteroatom or carbon ring atom that results in a stable structure and any of the ring atoms can be optionally substituted unless otherwise specified.

The term "C$_0$," as used herein, represents a bond. For example, part of the term —N(C(O))—(C$_0$-C$_5$ alkylene-H)— includes —N(C(O))—(C$_0$ alkylene-H)—, which is also represented by —N(C(O))—H)—.

The terms "carbocyclic" and "carbocyclyl," as used herein, refer to a monovalent, optionally substituted C$_3$-C$_{12}$ monocyclic, bicyclic, or tricyclic ring structure, which may be bridged, fused or spirocyclic, in which all the rings are formed by carbon atoms and at least one ring is non-aromatic. Carbocyclic structures include cycloalkyl, cycloalkenyl, and cycloalkynyl groups. Examples of carbocyclyl groups are cyclohexyl, cyclohexenyl, cyclooctynyl, 1,2-dihydronaphthyl, 1,2,3,4-tetrahydronaphthyl, fluorenyl, indenyl, indanyl, decalinyl, and the like. A carbocyclic ring can be attached to its pendant group at any ring atom that results in a stable structure and any of the ring atoms can be optionally substituted unless otherwise specified.

The term "carbonyl," as used herein, represents a C(O) group, which can also be represented as c=O.

The term "carboxyl," as used herein, means —CO$_2$H, (C=O)(OH), COOH, or C(O)OH or the unprotonated counterparts.

The term "cyano," as used herein, represents a —CN group.

The term "cycloalkyl," as used herein, represents a monovalent saturated cyclic hydrocarbon group, which may be bridged, fused or spirocyclic having from three to eight ring carbons, unless otherwise specified, and is exemplified by cyclopropyl, cyclobutyl, cyclopentyl, cyclohexyl, cycloheptyl, and cycloheptyl.

The term "cycloalkenyl," as used herein, represents a monovalent, non-aromatic, saturated cyclic hydrocarbon group, which may be bridged, fused or spirocyclic having from three to eight ring carbons, unless otherwise specified, and containing one or more carbon-carbon double bonds.

The term "diastereomer," as used herein, means stereoisomers that are not mirror images of one another and are non-superimposable on one another.

The term "enantiomer," as used herein, means each individual optically active form of a compound of the invention, having an optical purity or enantiomeric excess (as determined by methods standard in the art) of at least 80% (i.e., at least 90% of one enantiomer and at most 10% of the other enantiomer), preferably at least 90% and more preferably at least 98%.

The term "guanidinyl," refers to a group having the structure:

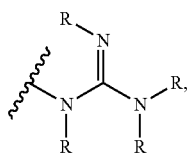

wherein each R is, independently, any any chemically feasible substituent described herein.

The term "guanidinoalkyl alkyl," as used herein, represents an alkyl moiety substituted on one or more carbon atoms with one or more guanidinyl moieties.

The term "haloacetyl," as used herein, refers to an acetyl group wherein at least one of the hydrogens has been replaced by a halogen.

The term "haloalkyl," as used herein, represents an alkyl moiety substituted on one or more carbon atoms with one or more of the same of different halogen moieties.

The term "halogen," as used herein, represents a halogen selected from bromine, chlorine, iodine, or fluorine.

The term "heteroalkyl" as used herein, refers to SET "alkyl" group, as defined herein, in which at least one carbon atom has been replaced with a heteroatom (e.g., an O, N, or S atom). The heteroatom may appear in the middle or at the end of the radical.

The term "heteroaryl," as used herein, represents a monovalent, monocyclic or polycyclic ring structure that contains at least one fully aromatic ring: i.e., they contain 4n+2 µl electrons within the monocyclic or polycyclic ring system and contains at least one ring heteroatom selected from N, O, or S in that aromatic ring. Exemplary unsubstituted heteroaryl groups are of 1 to 12 (e.g., 1 to 11, 1 to 10, 1 to 9, 2 to 12, 2 to 11, 2 to 10, or 2 to 9) carbons. The term "heteroaryl" includes bicyclic, tricyclic, and tetracyclic groups in which any of the above heteroaromatic rings is fused to one or more, aryl or carbocyclic rings, e.g., a phenyl ring, or a cyclohexane ring. Examples of heteroaryl groups include, but are not limited to, pyridyl, pyrazolyl, benzooxazolyl, benzoimidazolyl, benzothiazolyl, imidazolyl, thiazolyl, quinolinyl, tetrahydroquinolinyl, and 4-azaindolyl. A heteroaryl ring can be attached to its pendant group at any ring atom that results in a stable structure and any of the ring atoms can be optionally substituted unless otherwise specified. In some embodiment, the heteroaryl is substituted with 1, 2, 3, or 4 substituents groups.

The term "heterocycloalkyl," as used herein, represents a monovalent monocyclic, bicyclic or polycyclic ring system, which may be bridged, fused or spirocyclic, wherein at least one ring is non-aromatic and wherein the non-aromatic ring contains one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocycloalkyl groups are of 1 to 12 (e.g., 1 to 11, 1 to 10, 1 to 9, 2 to 12, 2 to 11, 2 to 10, or 2 to 9) carbons. The term "heterocycloalkyl" also represents a heterocyclic compound having a bridged multicyclic structure in which one or more carbons or heteroatoms bridges two non-adjacent members of a monocyclic ring, e.g., a quinuclidinyl group. The term "heterocycloalkyl" includes bicyclic, tricyclic, and tetracyclic groups in which any of the above heterocyclic rings is fused to one or more aromatic, carbocyclic, heteroaromatic, or heterocyclic rings, e.g., an aryl ring, a cyclohexane ring, a cyclohexene ring, a cyclopentane ring, a cyclopentene ring, a pyridine ring, or a pyrrolidine ring. Examples of heterocycloalkyl groups are pyrrolidinyl, piperidinyl, 1,2,3,4-tetrahydroquinolinyl, decahydroquinolinyl, dihydropyrrolopyridine, and decahydronapthyridinyl. A heterocycloalkyl ring can be attached to its pendant group at any ring atom that results in a stable structure and any of the ring atoms can be optionally substituted unless otherwise specified.

The term "hydroxy," as used herein, represents a —OH group.

The term "hydroxyalkyl," as used herein, represents an alkyl moiety substituted on one or more carbon atoms with one or more —OH moieties.

The term "isomer," as used herein, means any tautomer, stereoisomer, atropiosmer, enantiomer, or diastereomer of any compound of the invention. It is recognized that the compounds of the invention can have one or more chiral centers or double bonds and, therefore, exist as stereoisomers, such as double-bond isomers (i.e., geometric E/Z isomers) ordiastereomers (e.g., enantiomers (i.e., (+) or (−)) or cis/trans isomers). According to the invention, the chemical structures depicted herein, and therefore the compounds of the invention, encompass all the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

As used herein, the term "linker" refers to a divalent organic moiety connecting moiety B to moiety W in a compound of Formula I, such that the resulting compound is capable of achieving an IC50 of 2 uM or less in the Ras-RAF disruption assay protocol provided in the Examples below, and provided here:

The purpose of this biochemical assay is to measure the ability of test compounds to facilitate ternary complex formation between a nucleotide-loaded Ras isoform and cyclophilin A; the resulting ternary complex disrupts binding to a BRAF$^{RBD}$ construct, inhibiting Ras signaling through a RAF effector.

In assay buffer containing 25 mM HEPES pH 7.3, 0.002% Tween20, 0.1% BSA, 100 mM NaCl and 5 mM MgCl$_2$, tagless Cyclophilin A, His6-K-Ras-GMPPNP (or other Ras variant), and GST-BRAF$^{RBD}$ are combined in a 384-well assay plate at final concentrations of 25 µM, 12.5 nM and 50 nM, respectively. Compound is present in plate wells as a 10-point 3-fold dilution series starting at a final concentration of 30 µM. After incubation at 25° C. for 3 hours, a mixture of Anti-His Eu-W1024 and anti-GST allophycocyanin is then added to assay sample wells at final concentrations of 10 nM and 50 nM, respectively, and the reaction incubated for an additional 1.5 hours. TR-FRET signal is read on a microplate reader (Ex 320 nm, Em 665/615 nm). Compounds that facilitate disruption of a Ras:RAF complex are identified as those eliciting a decrease in the TR-FRET ratio relative to DMSO control wells.

In some embodiments, the linker comprises 20 or fewer linear atoms. In some embodiments, the linker comprises 15 or fewer linear atoms. In some embodiments, the linker comprises 10 or fewer linear atoms. In some embodiments, the linker has a molecular weight of under 500 g/mol. In some embodiments, the linker has a molecular weight of under 400 g/mol. In some embodiments, the linker has a molecular weight of under 300 g/mol. In some embodiments, the linker has a molecular weight of under 200 g/mol. In some embodiments, the linker has a molecular weight of under 100 g/mol. In some embodiments, the linker has a molecular weight of under 50 g/mol.

As used herein, a "monovalent organic moiety" is less than 500 kDa. In some embodiments, a "monovalent organic moiety" is less than 400 kDa. In some embodiments, a "monovalent organic moiety" is less than 300 kDa. In some embodiments, a "monovalent organic moiety" is less than 200 kDa. In some embodiments, a "monovalent organic moiety" is less than 100 kDa. In some embodiments, a "monovalent organic moiety" is less than 50 kDa. In some embodiments, a "monovalent organic moiety" is less than 25 kDa. In some embodiments, a "monovalent organic moiety" is less than 20 kDa. In some embodiments, a "monovalent organic moiety" is less than 15 kDa. In some embodiments, a "monovalent organic moiety" is less than 10 kDa. In some embodiments, a "monovalent organic moiety" is less than 1 kDa. In some embodiments, a "monovalent organic moiety" is less than 500 g/mol. In some embodiments, a "monovalent organic moiety" ranges between 500 g/mol and 500 kDa.

The term "stereoisomer," as used herein, refers to all possible different isomeric as well as conformational forms which a compound may possess (e.g., a compound of any formula described herein), in particular all possible stereochemically and conformationally isomeric forms, all diastereomers, enantiomers or conformers of the basic molecular structure, including atropisomers. Some compounds of the present invention may exist in different tautomeric forms, all of the latter being included within the scope of the present invention.

The term "sulfonyl," as used herein, represents an —S(O)$_2$— group.

The term "thiocarbonyl," as used herein, refers to a —C(S)— group.

The term "vinyl ketone," as used herein, refers to a group comprising a carbonyl group directly connected to a carbon-carbon double bond.

The term "vinyl sulfone," as used herein, refers to a group comprising a sulfonyl group directed connected to a carbon-carbon double bond.

The term "ynone," as used herein, refers to a group comprising the structure

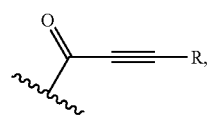

wherein R is any any chemically feasible substituent described herein.

Those of ordinary skill in the art, reading the present disclosure, will appreciate that certain compounds described herein may be provided or utilized in any of a variety of forms such as, for example, salt forms, protected forms, pro-drug forms, ester forms, isomeric forms (e.g., optical or structural isomers), isotopic forms, etc. In some embodiments, reference to a particular compound may relate to a specific form of that compound. In some embodiments, reference to a particular compound may relate to that compound in any form. In some embodiments, for example, a preparation of a single stereoisomer of a compound may be considered to be a different form of the compound than a racemic mixture of the compound; a particular salt of a compound may be considered to be a different form from another salt form of the compound; a preparation containing one conformational isomer ((Z) or (E)) of a double bond may be considered to be a different form from one containing the other conformational isomer ((E) or (Z)) of the double bond; a preparation in which one or more atoms is a different isotope than is present in a reference preparation may be considered to be a different form.

DETAILED DESCRIPTION

Compounds

Provided herein are Ras inhibitors. The approach described herein entails formation of a high affinity three-component complex between a synthetic ligand and two intracellular proteins which do not interact under normal physiological conditions: the target protein of interest (e.g., Ras), and a widely expressed cytosolic chaperone (presenter protein) in the cell (e.g., cyclophilin A). More specifically, in some embodiments, the inhibitors of Ras described herein induce a new binding pocket in Ras by driving formation of a high affinity tri-complex between the Ras protein and the widely expressed cytosolic chaperone, cyclophilin A (CYPA). Without being bound by theory, the inventors believe that one way the inhibitory effect on Ras is effected by compounds of the invention and the complexes they form is by steric occlusion of the interaction site between Ras and downstream effector molecules, such as RAF, which are required for propagating the oncogenic signal.

Without being bound by theory, the inventors postulate that non-covalent interactions of a compound of the present invention with Ras and the chaperone protein (e.g., cyclophilin A) may contribute to the inhibition of Ras activity. For example, van der Waals, hydrophobic, hydrophilic and hydrogen bond interactions, and combinations thereof, may contribute to the ability of the compounds of the present invention to form complexes and act as Ras inhibitors. Accordingly, a variety of Ras proteins may be inhibited by compounds of the present invention (e.g., K-Ras, N-Ras, H-Ras, and mutants thereof at positions 12, 13 and 61, such as G12C, G12D, G12V, G12S, G13C, G13D, and Q61L, and others described herein).

Accordingly, provided herein is a compound, or pharmaceutically acceptable salt thereof, having the structure of Formula 00:

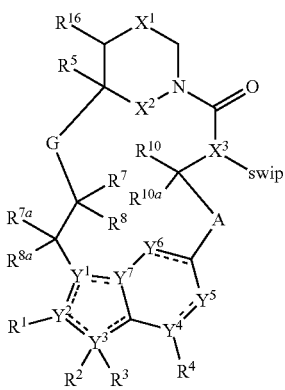

Formula 00 wherein the dotted lines represent zero, one, two, three, or four non-adjacent double bonds;

A is —N(H or $CH_3$)C(O)—($CH_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 10-membered heteroarylene;

G is optionally substituted $C_1$-$C_4$ alkylene, optionally substituted $C_1$-$C_4$ alkenylene, optionally substituted $C_1$-$C_4$ heteroalkylene, —C(O)O—CH($R^6$)— where C is bound to —C($R^7R^8$)—, —C(O)NH—CH($R^6$)— where C is bound to —C($R^7R^8$)—, optionally substituted $C_1$-$C_4$ heteroalkylene, or 3 to 8-membered heteroarylene;

swlp (Switch 1/P-loop) refers to an organic moiety that non-covalently binds to both the Switch 1 binding pocket and residues 12 or 13 of the P-loop of a Ras protein (see, e.g., Johnson et al., 292:12981-12993 (2017), incorporated herein by reference);

$X^1$ is optionally substituted $C_1$-$C_2$ alkylene, NR, O, or $S(O)_n$;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ is CH, $CH_2$, or N;

$Y^6$ is C(O), CH, $CH_2$, or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl, or $R^1$ and $R^2$ combine with the atoms to which they are attached to form an optionally substituted 3 to 14-membered heterocycloalkyl;

$R^2$ is absent, hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl;

$R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=C$R^{7'}R^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7a}$ and $R^{8a}$ are, independently, hydrogen, halo, optionally substituted $C_1$-$C_3$ alkyl, or combine with the carbon to which they are attached to form a carbonyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^{10}$ is hydrogen, halo, hydroxy, $C_1$-$C_3$ alkoxy, or $C_1$-$C_3$ alkyl;

$R^{10a}$ is hydrogen or halo; and $R^{16}$ is hydrogen or $C_1$-$C_3$ alkyl (e.g., methyl). In some embodiments, the resulting compound is capable of achieving an IC50 of 2 uM or less (e.g., 1.5 uM, 1 uM, 500 nM, or 100 nM or less) in the Ras-RAF disruption assay protocol described herein.

Accordingly, provided herein is a compound, or pharmaceutically acceptable salt thereof, having the structure of Formula I:

Formula I

[Chemical structure of Formula I showing a complex molecule with substituents $R^{16}$, $R^5$, $X^1$, $X^2$, $X^3$, G, $R^7$, $R^{7a}$, $R^8$, $R^{8a}$, $R^{10}$, $R^{10a}$, A, $R^{11}$, B, L, W, $Y^1$-$Y^7$, $R^1$, $R^2$, $R^3$, $R^4$]

wherein the dotted lines represent zero, one, two, three, or four non-adjacent double bonds;

A is —N(H or $CH_3$)C(O)—($CH_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 10-membered heteroarylene;

B is absent, —CH($R^9$)—, or >C=$CR^9R^{9'}$ where the carbon is bound to the carbonyl carbon of —N($R^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

G is optionally substituted $C_1$-$C_4$ alkylene, optionally substituted $C_1$-$C_4$ alkenylene, optionally substituted $C_1$-$C_4$ heteroalkylene, —C(O)O—CH($R^6$)— where C is bound to —C($R^7R^8$)—, —C(O)NH—CH($R^6$)— where C is bound to —C($R^7R^8$)—, optionally substituted $C_1$-$C_4$ heteroalkylene, or 3 to 8-membered heteroarylene; L is absent or a linker;

W is hydrogen, cyano, S(O)$_2$R', optionally substituted amino, optionally substituted amido, optionally substituted $C_1$-$C_4$ alkoxy, optionally substituted $C_1$-$C_4$ hydroxyalkyl, optionally substituted $C_1$-$C_4$ aminoalkyl, optionally substituted $C_1$-$C_4$ haloalkyl, optionally substituted $C_1$-$C_4$ alkyl, optionally substituted $C_1$-$C_4$ guanidinoalkyl, $C_0$-$C_4$ alkyl optionally substituted 3 to 11-membered heterocycloalkyl, optionally substituted 3 to 8-membered cycloalkyl, or optionally substituted 3 to 8-membered heteroaryl;

$X^1$ is optionally substituted $C_1$-$C_2$ alkylene, NR, O, or S(O)$_n$;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ is CH, $CH_2$, or N;

$Y^6$ is C(O), CH, $CH_2$, or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl, or $R^1$ and $R^2$ combine with the atoms to which they are attached to form an optionally substituted 3 to 14-membered heterocycloalkyl;

$R^2$ is absent, hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl;

$R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=$CR^{7'}R^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7a}$ and $R^{8a}$ are, independently, hydrogen, halo, optionally substituted $C_1$-$C_3$ alkyl, or combine with the carbon to which they are attached to form a carbonyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is hydrogen, F, optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl, or $R^9$ and L combine with the atoms to which they are attached to form an optionally substituted 3 to 14-membered heterocycloalkyl;

$R^{9'}$ is hydrogen or optionally substituted $C_1$-$C_6$ alkyl;

$R^{10}$ is hydrogen, halo, hydroxy, $C_1$-$C_3$ alkoxy, or $C_1$-$C_3$ alkyl;

$R^{10a}$ is hydrogen or halo;

$R^{11}$ is hydrogen or $C_1$-$C_3$ alkyl;

$R^{16}$ is hydrogen or $C_1$-$C_3$ alkyl (e.g., methyl).

In some embodiments, the disclosure features a compound, or pharmaceutically acceptable salt thereof, of structural Formula Ia:

Formula Ia

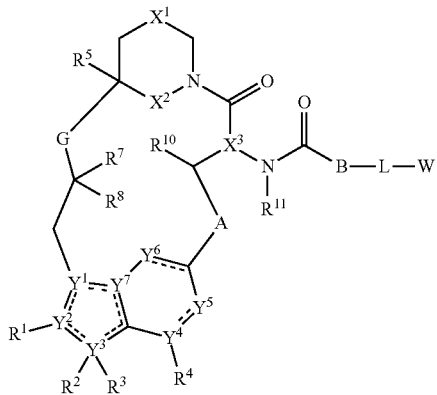

wherein the dotted lines represent zero, one, two, three, or four non-adjacent double bonds;

A is —N(H or CH$_3$)C(O)—(CH$_2$)— where the amino nitrogen is bound to the carbon atom of —CH(R$^{10}$)—, optionally substituted 3 to 6-membered cycloalkylene, optionally substituted 3 to 6-membered heterocycloalkylene, optionally substituted 6-membered arylene, or optionally substituted 5 to 10-membered heteroarylene;

B is —CH(R$^9$)— or >C=CR$^9$R$^{9'}$ where the carbon is bound to the carbonyl carbon of —N(R$^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene; G is optionally substituted C$_1$-C$_4$ alkylene, optionally substituted C$_1$-C$_4$ alkenylene, optionally substituted C$_1$-C$_4$ heteroalkylene, —C(O)O—CH(R$^6$)— where C is bound to —C(R$^7$R$^8$)—, —C(O)NH—CH(R$^6$)— where C is bound to —C(R$^7$R$^8$)—, optionally substituted C$_1$-C$_4$ heteroalkylene, or 3 to 8-membered heteroarylene;

L is absent or a linker;

W is hydrogen, optionally substituted amino, optionally substituted C$_1$-C$_4$ alkoxy, optionally substituted C$_1$-C$_4$ hydroxyalkyl, optionally substituted C$_1$-C$_4$ aminoalkyl, optionally substituted C$_1$-C$_4$ haloalkyl, optionally substituted C$_1$-C$_4$ alkyl, optionally substituted C$_1$-C$_4$ guanidinoalkyl, C$_0$-C$_4$ alkyl optionally substituted 3 to 11-membered heterocycloalkyl, optionally substituted 3 to 8-membered cycloalkyl, or optionally substituted 3 to 8-membered heteroaryl;

X$^1$ is optionally substituted C$_1$-C$_2$ alkylene, NR, O, or S(O)$_n$;

X$^2$ is O or NH;

X$^3$ is N or CH;

n is 0, 1, or 2;

R is hydrogen, cyano, optionally substituted C$_1$-C$_4$ alkyl, optionally substituted C$_2$-C$_4$ alkenyl, optionally substituted C$_2$-C$_4$ alkynyl, C(O)R', C(O)OR', C(O)N(R')$_2$, S(O)R', S(O)$_2$R', or S(O)$_2$N(R')$_2$;

each R' is, independently, H or optionally substituted C$_1$-C$_4$ alkyl;

Y$^1$ is C, CH, or N;

Y$^2$, Y$^3$, Y$^4$, and Y$^7$ are, independently, C or N;

Y$^5$ is CH, CH$_2$, or N;

Y$^6$ is C(O), CH, CH$_2$, or N;

R$^1$ is cyano, optionally substituted C$_1$-C$_6$ alkyl, optionally substituted C$_1$-C$_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl, or R$^1$ and R$^2$ combine with the atoms to which they are attached to form an optionally substituted 3 to 14-membered heterocycloalkyl;

R$^2$ is absent, hydrogen, optionally substituted C$_1$-C$_6$ alkyl, optionally substituted C$_2$-C$_6$ alkenyl, optionally substituted C$_2$-C$_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl;

R$^3$ is absent, or

R$^2$ and R$^3$ combine with the atom to which they are attached to form an optionally substituted 3 to 8-membered cycloalkyl or optionally substituted 3 to 14-membered heterocycloalkyl;

R$^4$ is absent, hydrogen, halogen, cyano, or methyl optionally substituted with 1 to 3 halogens;

R$^5$ is hydrogen, C$_1$-C$_4$ alkyl optionally substituted with halogen, cyano, hydroxy, or C$_1$-C$_4$ alkoxy, cyclopropyl, or cyclobutyl;

R$^6$ is hydrogen or methyl; R$^7$ is hydrogen, halogen, or optionally substituted C$_1$-C$_3$ alkyl, or R$^6$ and R$^7$ combine with the carbon atoms to which they are attached to form an optionally substituted 3 to 6-membered cycloalkyl or optionally substituted 3 to 7-membered heterocycloalkyl;

R$^8$ is hydrogen, halogen, hydroxy, cyano, optionally substituted C$_1$-C$_3$ alkoxy, optionally substituted C$_1$-C$_3$ alkyl, optionally substituted C$_2$-C$_6$ alkenyl, optionally substituted C$_2$-C$_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or R$^7$ and R$^8$ combine with the carbon atom to which they are attached to form C=CR$^{7'}$R$^{8'}$; C=N(OH), C=N(O—C$_1$-C$_3$ alkyl), C=O, C=S, C=NH, optionally substituted 3 to 6-membered cycloalkyl, or optionally substituted 3 to 7-membered heterocycloalkyl;

R$^{7a}$ and R$^{8a}$ are, independently, hydrogen, halo, optionally substituted C$_1$-C$_3$ alkyl, or combine with the carbon to which they are attached to form a carbonyl;

R$^{7'}$ is hydrogen, halogen, or optionally substituted C$_1$-C$_3$ alkyl; R$^{8'}$ is hydrogen, halogen, hydroxy, cyano, optionally substituted C$_1$-C$_3$ alkoxy, optionally substituted C$_1$-C$_3$ alkyl, optionally substituted C$_2$-C$_6$ alkenyl, optionally substituted C$_2$-C$_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or R$^{7'}$ and R$^{8'}$ combine with the carbon atom to which they are attached to form optionally substituted 3 to 6-membered cycloalkyl or optionally substituted 3 to 7-membered heterocycloalkyl;

R$^9$ is optionally substituted C$_1$-C$_6$ alkyl, optionally substituted C$_1$-C$_6$ heteroalkyl, optionally substituted 3 to 6-membered cycloalkyl, or optionally substituted 3 to 7-membered heterocycloalkyl, or R$^9$ and L combine with the atoms to which they are attached to form an optionally substituted 3 to 14-membered heterocycloalkyl;

$R^{9'}$ is hydrogen or optionally substituted $C_1$-$C_6$ alkyl;
$R^{10}$ is hydrogen, halo, hydroxy, $C_1$-$C_3$ alkoxy, or $C_1$-$C_3$ alkyl;
$R^{10a}$ is hydrogen or halo; and
$R^{11}$ is hydrogen or $C_1$-$C_3$ alkyl.

In some embodiments, the disclosure features a compound, or pharmaceutically acceptable salt thereof, of structural Formula Ib:

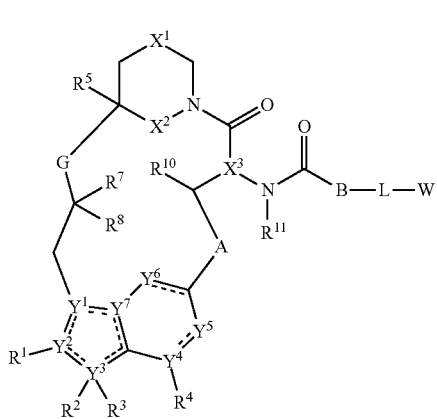

Formula Ib wherein the dotted lines represent zero, one, two, three, or four non-adjacent double bonds;

A is —N(H or CH$_3$)C(O)—(CH$_2$)— where the amino nitrogen is bound to the carbon atom of —CH(R$^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH(R$^9$)— where the carbon is bound to the carbonyl carbon of —N(R$^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

G is optionally substituted $C_1$-$C_4$ alkylene, optionally substituted $C_1$-$C_4$ alkenylene, optionally substituted $C_1$-$C_4$ heteroalkylene, —C(O)O—CH(R$^6$)— where C is bound to —C(R$^7$R$^8$)—, —C(O)NH—CH(R$^6$)— where C is bound to —C(R$^7$R$^8$)—, optionally substituted $C_1$-$C_4$ heteroalkylene, or 3 to 8-membered heteroarylene;

L is absent or a linker;

W is hydrogen, optionally substituted amino, optionally substituted $C_1$-$C_4$ alkoxy, optionally substituted $C_1$-$C_4$ hydroxyalkyl, optionally substituted $C_1$-$C_4$ aminoalkyl, optionally substituted $C_1$-$C_4$ haloalkyl, optionally substituted $C_1$-$C_4$ alkyl, optionally substituted $C_1$-$C_4$ guanidinoalkyl, $C_0$-$C_4$ alkyl optionally substituted 3 to 11-membered heterocycloalkyl, optionally substituted 3 to 8-membered cycloalkyl, or optionally substituted 3 to 8-membered heteroaryl;

$X^1$ is optionally substituted $C_1$-$C_2$ alkylene, NR, O, or S(O)$_n$;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$R', or S(O)$_2$N(R')$_2$; each R' is, independently, H or optionally substituted $C_1$-$C_4$ alkyl;

$Y^1$ is C, CH, or N;
$Y^2$, $Y^3$, $Y^4$, and $Y^7$ are, independently, C or N;
$Y^5$ and $Y^6$ are, independently, CH or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

$R^2$ is hydrogen, optionally substituted $C_1$-$C_6$ alkyl, optionally substituted $C_2$-$C_6$ alkenyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=CR$^{7'}$R$^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl;

$R^{10}$ is hydrogen, hydroxy, $C_1$-$C_3$ alkoxy, or $C_1$-$C_3$ alkyl; and $R^{11}$ is hydrogen or $C_1$-$C_3$ alkyl.

In some embodiments of compounds of the present invention, G is optionally substituted $C_1$-$C_4$ heteroalkylene.

In some embodiments, a compound of the present invention has the structure of Formula Ic, or a pharmaceutically acceptable salt thereof:

Formula Ic

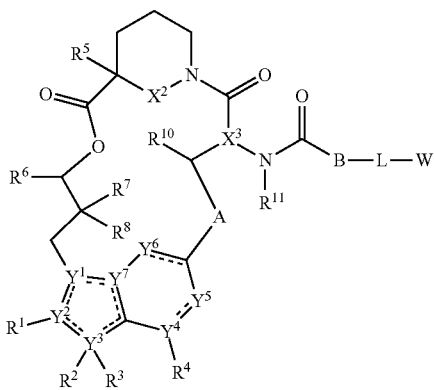

wherein the dotted lines represent zero, one, two, three, or four non-adjacent double bonds;

A is —N(H or $CH_3$)C(O)—($CH_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —N($R^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is hydrogen, optionally substituted amino, optionally substituted $C_1$-$C_4$ alkoxy, optionally substituted $C_1$-$C_4$ hydroxyalkyl, optionally substituted $C_1$-$C_4$ aminoalkyl, optionally substituted $C_1$-$C_4$ haloalkyl, optionally substituted $C_1$-$C_4$ alkyl, optionally substituted $C_1$-$C_4$ guanidinoalkyl, $C_0$-$C_4$ alkyl optionally substituted 3 to 11-membered heterocycloalkyl, optionally substituted 3 to 8-membered cycloalkyl, or optionally substituted 3 to 8-membered heteroaryl;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$R', or S(O)$_2$N(R')$_2$; each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ and $Y^6$ are, independently, CH or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

$R^2$ is hydrogen, optionally substituted $C_1$-$C_6$ alkyl, optionally substituted $C_2$-$C_6$ alkenyl, optionally substituted 3 to 6-membered cycloalkyl, optionally substituted 3 to 7-membered heterocycloalkyl, optionally substituted 6-membered aryl, optionally substituted 5 or 6-membered heteroaryl;

$R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=CR$^{7'}$R$^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl;

$R^{10}$ is hydrogen, hydroxy, $C_1$-$C_3$ alkoxy, or $C_1$-$C_3$ alkyl; and $R^{11}$ is hydrogen or $C_1$-$C_3$ alkyl.

In some embodiments of compounds of the present invention, $X^2$ is NH. In some embodiments, $X^3$ is CH.

In some embodiments of compounds of the present invention, $R^{11}$ is hydrogen. In some embodiments, $R^{11}$ is $C_1$-$C_3$ alkyl. In some embodiments, $R^{11}$ is methyl.

In some embodiments, a compound of the present invention has the structure of Formula Id, or a pharmaceutically acceptable salt thereof:

Formula Id

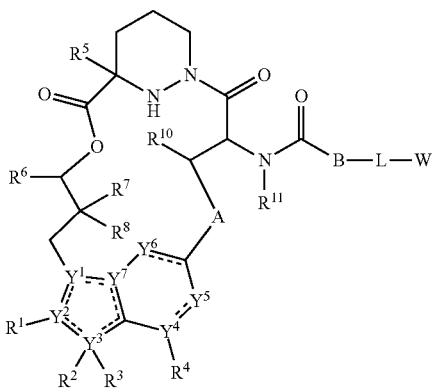

wherein the dotted lines represent zero, one, two, three, or four non-adjacent double bonds;

A is —N(H or CH$_3$)C(O)—(CH$_2$)— where the amino nitrogen is bound to the carbon atom of —CH(R$^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH(R$^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is hydrogen, optionally substituted amino, optionally substituted C$_1$-C$_4$ alkoxy, optionally substituted C$_1$-C$_4$ hydroxyalkyl, optionally substituted C$_1$-C$_4$ aminoalkyl, optionally substituted C$_1$-C$_4$ haloalkyl, optionally substituted C$_1$-C$_4$ alkyl, optionally substituted C$_1$-C$_4$ guanidinoalkyl, C$_0$-C$_4$ alkyl optionally substituted 3 to 11-membered heterocycloalkyl, optionally substituted 3 to 8-membered cycloalkyl, or optionally substituted 3 to 8-membered heteroaryl;

n is 0, 1, or 2;

R is hydrogen, cyano, optionally substituted C$_1$-C$_4$ alkyl, optionally substituted C$_2$-C$_4$ alkenyl, optionally substituted C$_2$-C$_4$ alkynyl, C(O)R', C(O)OR', C(O)N(R')$_2$, S(O)R', S(O)$_2$R', or S(O)$_2$N(R')$_2$;

each R' is, independently, H or optionally substituted C$_1$-C$_4$ alkyl;

Y$^1$ is C, CH, or N;

Y$^2$, Y$^3$, Y$^4$, and Y$^7$ are, independently, C or N;

Y$^5$ and Y$^6$ are, independently, CH or N;

R$^1$ is cyano, optionally substituted C$_1$-C$_6$ alkyl, optionally substituted C$_1$-C$_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

R$^2$ is hydrogen, optionally substituted C$_1$-C$_6$ alkyl, optionally substituted C$_2$-C$_6$ alkenyl, optionally substituted 3 to 6-membered cycloalkyl, optionally substituted 3 to 7-membered heterocycloalkyl, optionally substituted 6-membered aryl, optionally substituted 5 or 6-membered heteroaryl; R$^3$ is absent, or R$^2$ and R$^3$ combine with the atom to which they are attached to form an optionally substituted 3 to 8-membered cycloalkyl or optionally substituted 3 to 14-membered heterocycloalkyl;

R$^4$ is absent, hydrogen, halogen, cyano, or methyl optionally substituted with 1 to 3 halogens;

R$^5$ is hydrogen, C$_1$-C$_4$ alkyl optionally substituted with halogen, cyano, hydroxy, or C$_1$-C$_4$ alkoxy, cyclopropyl, or cyclobutyl;

R$^6$ is hydrogen or methyl; R$^7$ is hydrogen, halogen, or optionally substituted C$_1$-C$_3$ alkyl, or R$^6$ and R$^7$ combine with the carbon atoms to which they are attached to form an optionally substituted 3 to 6-membered cycloalkyl or optionally substituted 3 to 7-membered heterocycloalkyl;

R$^8$ is hydrogen, halogen, hydroxy, cyano, optionally substituted C$_1$-C$_3$ alkoxy, optionally substituted C$_1$-C$_3$ alkyl, optionally substituted C$_2$-C$_6$ alkenyl, optionally substituted C$_2$-C$_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or R$^7$ and R$^8$ combine with the carbon atom to which they are attached to form C=CR$^{7'}$R$^{8'}$; C=N(OH), C=N(O—C$_1$-C$_3$ alkyl), C=O, C=S, C=NH, optionally substituted 3 to 6-membered cycloalkyl, or optionally substituted 3 to 7-membered heterocycloalkyl;

R$^{7'}$ is hydrogen, halogen, or optionally substituted C$_1$-C$_3$ alkyl; R$^{8'}$ is hydrogen, halogen, hydroxy, cyano, optionally substituted C$_1$-C$_3$ alkoxy, optionally substituted C$_1$-C$_3$ alkyl, optionally substituted C$_2$-C$_6$ alkenyl, optionally substituted C$_2$-C$_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or R$^{7'}$ and R$^{8'}$ combine with the carbon atom to which they are attached to form optionally substituted 3 to 6-membered cycloalkyl or optionally substituted 3 to 7-membered heterocycloalkyl;

R$^9$ is optionally substituted C$_1$-C$_6$ alkyl, optionally substituted C$_1$-C$_6$ heteroalkyl, optionally substituted 3 to 6-membered cycloalkyl, or optionally substituted 3 to 7-membered heterocycloalkyl; and R$^{10}$ is hydrogen, hydroxy, C$_1$-C$_3$ alkoxy, or C$_1$-C$_3$ alkyl.

In some embodiments of compounds of the present invention, X$^1$ is optionally substituted C$_1$-C$_2$ alkylene. In some embodiments, X$^1$ is methylene. In some embodiments, X$^1$ is methylene substituted with a C$_1$-C$_6$ alkyl group or a halogen. In some embodiments, X$^1$ is —CH(Br)—. In some embodiments, X$^1$ is —CH(CH$_3$)—.

In some embodiments of compounds of the present invention, R$^3$ is absent.

In some embodiments of compounds of the present invention, R$^4$ is hydrogen.

In some embodiments of compounds of the present invention, R$^5$ is hydrogen. In some embodiments, R$^5$ is C$_1$-C$_4$ alkyl optionally substituted with halogen. In some embodiments, R$^5$ is methyl.

In some embodiments of compounds of the present invention, Y$^4$ is C. In some embodiments, Y$^5$ is CH. In some embodiments, Y$^6$ is CH. In some embodiments, Y$^1$ is C. In some embodiments, Y$^2$ is C. In some embodiments, Y$^3$ is N. In some embodiments, Y$^7$ is C.

In some embodiments, a compound of the present invention has the structure of Formula Ie, or a pharmaceutically acceptable salt thereof:

Formula Ie

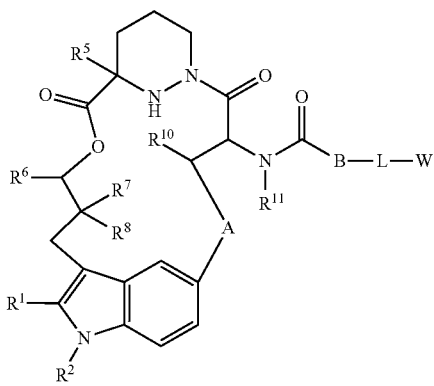

wherein A is —N(H or CH₃)C(O)—(CH₂)— where the amino nitrogen is bound to the carbon atom of —CH (R¹⁰)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH(R⁹)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is hydrogen, optionally substituted amino, optionally substituted C₁-C₄ alkoxy, optionally substituted C₁-C₄ hydroxyalkyl, optionally substituted C₁-C₄ aminoalkyl, optionally substituted C₁-C₄ haloalkyl, optionally substituted C₁-C₄ alkyl, optionally substituted C₁-C₄ guanidinoalkyl, C₀-C₄ alkyl optionally substituted 3 to 11-membered heterocycloalkyl, optionally substituted 3 to 8-membered cycloalkyl, or optionally substituted 3 to 8-membered heteroaryl;

R¹ is cyano, optionally substituted C₁-C₆ alkyl, optionally substituted C₁-C₆ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

R² is hydrogen, optionally substituted C₁-C₆ alkyl, optionally substituted C₂-C₆ alkenyl, optionally substituted 3 to 6-membered cycloalkyl, optionally substituted 3 to 7-membered heterocycloalkyl, optionally substituted 6-membered aryl, optionally substituted 5 or 6-membered heteroaryl; R³ is absent, or R² and R³ combine with the atom to which they are attached to form an optionally substituted 3 to 8-membered cycloalkyl or optionally substituted 3 to 14-membered heterocycloalkyl;

R⁵ is hydrogen, C₁-C₄ alkyl optionally substituted with halogen, cyano, hydroxy, or C₁-C₄ alkoxy, cyclopropyl, or cyclobutyl;

R⁶ is hydrogen or methyl; R⁷ is hydrogen, halogen, or optionally substituted C₁-C₃ alkyl, or R⁶ and R⁷ combine with the carbon atoms to which they are attached to form an optionally substituted 3 to 6-membered cycloalkyl or optionally substituted 3 to 7-membered heterocycloalkyl;

R⁸ is hydrogen, halogen, hydroxy, cyano, optionally substituted C₁-C₃ alkoxy, optionally substituted C₁-C₃ alkyl, optionally substituted C₂-C₆ alkenyl, optionally substituted C₂-C₆ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or R⁷ and R⁸ combine with the carbon atom to which they are attached to form C=CR⁷'R⁸'; C=N(OH), C=N(O—C₁-C₃ alkyl), C=O, C=S, C=NH, optionally substituted 3 to 6-membered cycloalkyl, or optionally substituted 3 to 7-membered heterocycloalkyl;

R⁷' is hydrogen, halogen, or optionally substituted C₁-C₃ alkyl; R⁸' is hydrogen, halogen, hydroxy, cyano, optionally substituted C₁-C₃ alkoxy, optionally substituted C₁-C₃ alkyl, optionally substituted C₂-C₆ alkenyl, optionally substituted C₂-C₆ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or R⁷' and R⁸' combine with the carbon atom to which they are attached to form optionally substituted 3 to 6-membered cycloalkyl or optionally substituted 3 to 7-membered heterocycloalkyl;

R⁹ is optionally substituted C₁-C₆ alkyl, optionally substituted C₁-C₆ heteroalkyl, optionally substituted 3 to 6-membered cycloalkyl, or optionally substituted 3 to 7-membered heterocycloalkyl; and R¹⁰ is hydrogen, hydroxy, C₁-C₃ alkoxy, or C₁-C₃ alkyl.

In some embodiments of compounds of the present invention, R⁶ is hydrogen.

In some embodiments of compounds of the present invention, R² is hydrogen, cyano, optionally substituted C₁-C₆ alkyl, optionally substituted 3 to 6-membered cycloalkyl, or optionally substituted 3 to 6-membered heterocycloalkyl. In some embodiments, R² is optionally substituted C₁-C₆ alkyl, such as ethyl. In some embodiments, R² is fluoro C₁-C₆ alkyl, such as —CH₂CH₂F, —CH₂CHF₂, or —CH₂CF₃.

In some embodiments of compounds of the present invention, R⁷ is optionally substituted C₁-C₃ alkyl. In some embodiments, R⁷ is C₁-C₃ alkyl.

In some embodiments of compounds of the present invention, R⁸ is optionally substituted C₁-C₃ alkyl. In some embodiments, R⁸ is C₁-C₃ alkyl, such as methyl.

In some embodiments, a compound of the present invention has the structure of Formula If, or a pharmaceutically acceptable salt thereof:

Formula If

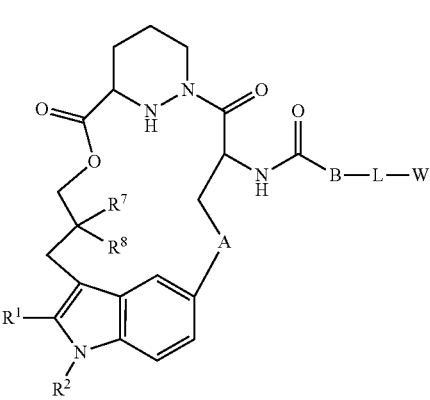

wherein A optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH(R⁹)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is hydrogen, optionally substituted amino, optionally substituted $C_1$-$C_4$ alkoxy, optionally substituted $C_1$-$C_4$ hydroxyalkyl, optionally substituted $C_1$-$C_4$ aminoalkyl, optionally substituted $C_1$-$C_4$ haloalkyl, optionally substituted $C_1$-$C_4$ alkyl, optionally substituted $C_1$-$C_4$ guanidinoalkyl, $C_0$-$C_4$ alkyl optionally substituted 3 to 11-membered heterocycloalkyl, optionally substituted 3 to 8-membered cycloalkyl, or optionally substituted 3 to 8-membered heteroaryl;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

$R^2$ is $C_1$-$C_6$ alkyl or 3 to 6-membered cycloalkyl;

$R^7$ is $C_1$-$C_3$ alkyl;

$R^8$ is $C_1$-$C_3$ alkyl; and $R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl.

In some embodiments of compounds of the present invention, $R^1$ is 5 to 10-membered heteroaryl. In some embodiments, $R^1$ is optionally substituted 6-membered aryl or optionally substituted 6-membered heteroaryl.

In some embodiments of compounds of the present invention, $R_1$ is

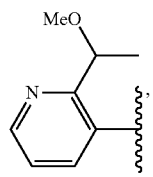
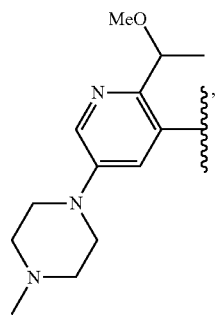
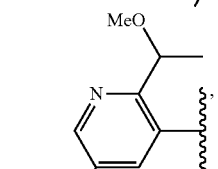
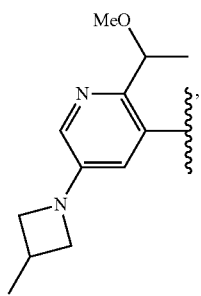

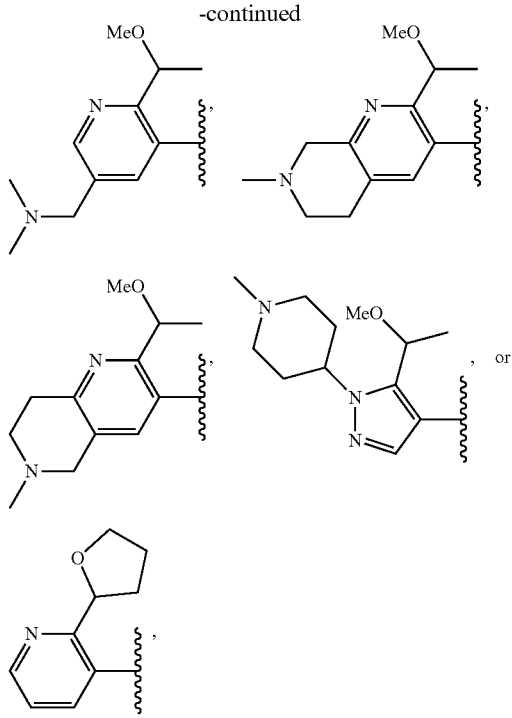

or a stereoisomer thereof. In some embodiments, $R_1$ is

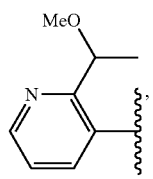 [SMILES: *c1cccnc1C(C)OC]

or a stereoisomer thereof. In some embodiments, $R_1$ is

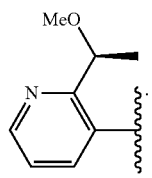 [SMILES: *c1cccnc1[C@H](C)OC]

In some embodiments, $R_1$ is

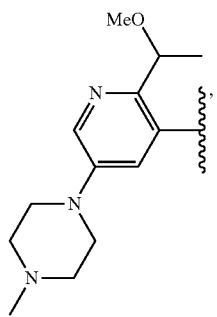 [SMILES: *c1cc(N2CCN(C)CC2)cnc1C(C)OC]

or a stereoisomer thereof. In some embodiments, R₁ is

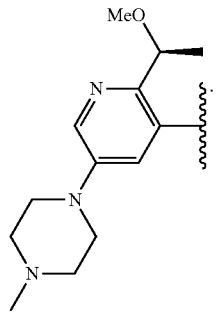 [SMILES: *c1cc(N2CCN(C)CC2)cnc1[C@H](C)OC]

In some embodiments, a compound of the present invention has the structure of Formula Ig, or a pharmaceutically acceptable salt thereof:

Formula Ig

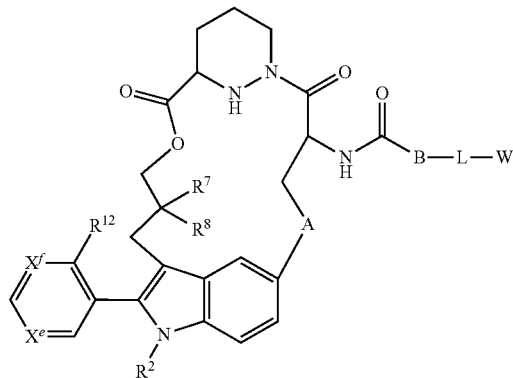

wherein A is optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH(R⁹)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is hydrogen, optionally substituted amino, optionally substituted $C_1$-$C_4$ alkoxy, optionally substituted $C_1$-$C_4$ hydroxyalkyl, optionally substituted $C_1$-$C_4$ aminoalkyl, optionally substituted $C_1$-$C_4$ haloalkyl, optionally substituted $C_1$-$C_4$ alkyl, optionally substituted $C_1$-$C_4$ guanidinoalkyl, $C_0$-$C_4$ alkyl optionally substituted 3 to 11-membered heterocycloalkyl, optionally substituted 3 to 8-membered cycloalkyl, or optionally substituted 3 to 8-membered heteroaryl;

R² is $C_1$-$C_6$ alkyl or 3 to 6-membered cycloalkyl;
R⁷ is $C_1$-$C_3$ alkyl;
R⁸ is $C_1$-$C_3$ alkyl;
R⁹ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl;
$X^e$ is N, CH, or CR¹⁷;
$X^f$ is N or CH;
R¹² is optionally substituted $C_1$-$C_6$ alkyl or optionally substituted $C_1$-$C_6$ heteroalkyl; and R¹⁷ is optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl.

In some embodiments of compounds of the present invention, $X^e$ is N and $X^f$ is CH. In some embodiments, $X^e$ is CH and $X^f$ is N. In some embodiments, $X^e$ is CR¹⁷ and $X^f$ is N.

In some embodiments of compounds of the present invention, R¹² is optionally substituted $C_1$-$C_6$ heteroalkyl. In some embodiments, R¹² is

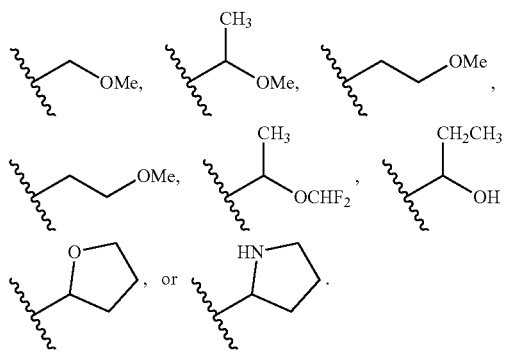

In some embodiments, a compound of the present invention has the structure of Formula Ih, or a pharmaceutically acceptable salt thereof:

Formula Ih

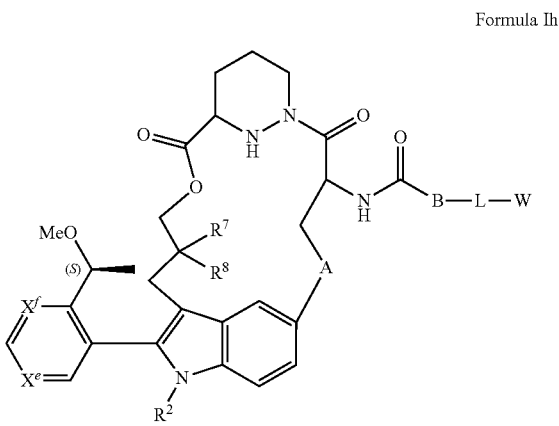

wherein A is optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH(R⁹)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is hydrogen, optionally substituted amino, optionally substituted $C_1$-$C_4$ alkoxy, optionally substituted $C_1$-$C_4$ hydroxyalkyl, optionally substituted $C_1$-$C_4$ aminoalkyl, optionally substituted $C_1$-$C_4$ haloalkyl, optionally substituted $C_1$-$C_4$ alkyl, optionally substituted $C_1$-$C_4$ guanidinoalkyl, $C_0$-$C_4$ alkyl optionally substituted 3 to 11-membered heterocycloalkyl, optionally substituted 3 to 8-membered cycloalkyl, or optionally substituted 3 to 8-membered heteroaryl;

$R^2$ is $C_1$-$C_6$ alkyl or 3 to 6-membered cycloalkyl;
$R^7$ is $C_1$-$C_3$ alkyl;
$R^8$ is $C_1$-$C_3$ alkyl;
$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl;
$X^e$ is CH, or $CR^{17}$; and
$R^{17}$ is optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl.

In some embodiments, a compound of the present invention has the structure of Formula Ii, or a pharmaceutically acceptable salt thereof:

Formula Ii

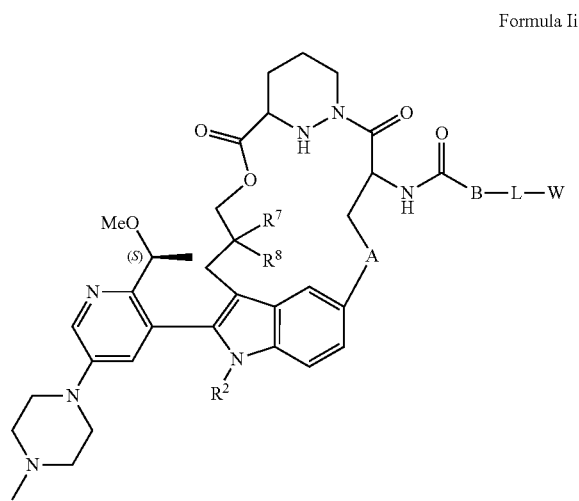

wherein A is optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is hydrogen, optionally substituted amino, optionally substituted $C_1$-$C_4$ alkoxy, optionally substituted $C_1$-$C_4$ hydroxyalkyl, optionally substituted $C_1$-$C_4$ aminoalkyl, optionally substituted $C_1$-$C_4$ haloalkyl, optionally substituted $C_1$-$C_4$ alkyl, optionally substituted $C_1$-$C_4$ guanidinoalkyl, $C_0$-$C_4$ alkyl optionally substituted 3 to 11-membered heterocycloalkyl, optionally substituted 3 to 8-membered cycloalkyl, or optionally substituted 3 to 8-membered heteroaryl;

$R^2$ is $C_1$-$C_6$ alkyl or 3 to 6-membered cycloalkyl;
$R^7$ is $C_1$-$C_3$ alkyl;
$R^8$ is $C_1$-$C_3$ alkyl; and
$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl.

In some embodiments of compounds of the present invention, A is optionally substituted 6-membered arylene. In some embodiments, A has the structure:

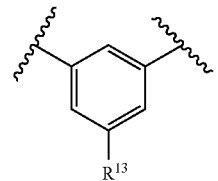

wherein $R^{13}$ is hydrogen, hydroxy, amino, cyano, optionally substituted $C_1$-$C_6$ alkyl, or optionally substituted $C_1$-$C_6$ heteroalkyl. In some embodiments, $R^{13}$ is hydrogen. In some embodiments, $R^{13}$ is hydroxy. In some embodiments, A is an optionally substituted 5 to 10-membered heteroarylene. In some embodiments, A is:

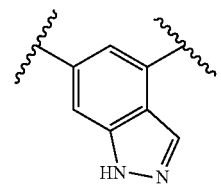

In some embodiments, A is optionally substituted 5 to 6-membered heteroarylene. In some embodiments, A is

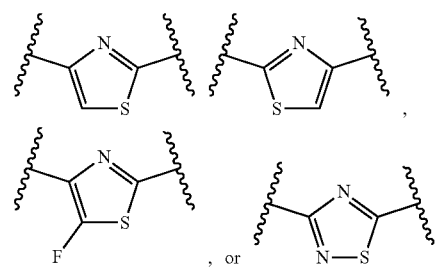

In some embodiments, A is

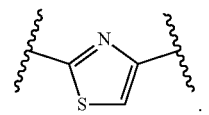

In some embodiments of compounds of the present invention, B is —$CHR^9$—. In some embodiments, $R^9$ is optionally substituted $C_1$-$C_6$ alkyl or optionally substituted 3 to 6-membered cycloalkyl. In some embodiments, $R^9$ is:

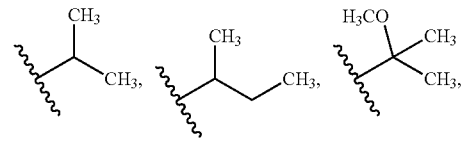

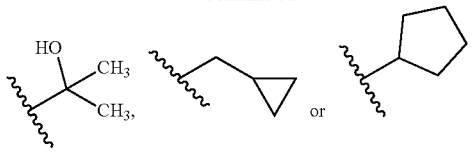 .

In some embodiments, $R^9$ is:

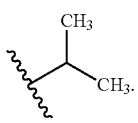

In some embodiments, $R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl.

In some embodiments, B is optionally substituted 6-membered arylene.

In some embodiments, B is 6-membered arylene. In some embodiments, B is:

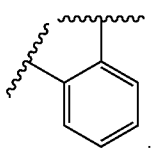 [SMILES: *c1ccccc1*]

In some embodiments B is absent.

In some embodiments of compounds of the present invention, $R^7$ is methyl.

In some embodiments of compounds of the present invention, $R^8$ is methyl.

In some embodiments of compounds of the present invention, $R^{16}$ is hydrogen.

In some embodiments of compounds of the present invention, the linker is the structure of Formula II:

$$A^1\text{-}(B^1)_f\text{---}(C^1)_g\text{---}(B^2)_h\text{-}(D^1)\text{-}(B^3)_i\text{---}(C^2)_j\text{---}(B^4)_k\text{-}A^2 \qquad \text{Formula II}$$

where $A^1$ is a bond between the linker and B; $A^2$ is a bond between W and the linker; $B^1$, $B^2$, $B^3$, and $B^4$ each, independently, is selected from optionally substituted $C_1$-$C_2$ alkylene, optionally substituted $C_1$-$C_3$ heteroalkylene, O, S, and $NR^N$; $R^N$ is hydrogen, optionally substituted $C_1$-$C_4$ alkyl, optionally substituted $C_1$-$C_3$ cycloalkyl, optionally substituted $C_2$-$C_4$ alkenyl, optionally substituted $C_2$-$C_4$ alkynyl, optionally substituted 3 to 14-membered heterocycloalkyl, optionally substituted 6 to 10-membered aryl, or optionally substituted $C_1$-$C_7$ heteroalkyl; $C^1$ and $C^2$ are each, independently, selected from carbonyl, thiocarbonyl, sulphonyl, or phosphoryl; f, g, h, i, j, and k are each, independently, 0 or 1; and $D^1$ is optionally substituted $C_1$-$C_{10}$ alkylene, optionally substituted $C_2$-$C_{10}$ alkenylene, optionally substituted $C_2$-$C_{10}$ alkynylene, optionally substituted 3 to 14-membered heterocycloalkylene, optionally substituted 5 to 10-membered heteroarylene, optionally substituted 3 to 8-membered cycloalkylene, optionally substituted 6 to 10-membered arylene, optionally substituted $C_2$-$C_{10}$ polyethylene glycolene, or optionally substituted $C_1$-$C_{10}$ heteroalkylene, or a chemical bond linking $A^1$-$(B^1)_f$---$(C^1)_g$---$(B^2)_h$- to ---$(B^3)_i$---$(C^2)_j$---$(B^4)_k$-$A^2$. In some embodiments, the linker is acyclic. In some embodiments, the linker has the structure of Formula IIa:

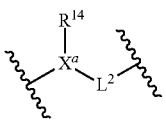

Formula IIa wherein $X^a$ is absent or N;

$R^{14}$ is absent, hydrogen or optionally substituted $C_1$-$C_6$ alkyl or optionally substituted $C_1$-$C_3$ cycloalkyl; and $L^2$ is absent, ---C(O)---, ---SO$_2$---, optionally substituted $C_1$-$C_4$ alkylene or optionally substituted $C_1$-$C_4$ heteroalkylene, wherein at least one of $X^a$, $R^{14}$, or $L^2$ is present. In some embodiments, the linker has the structure:

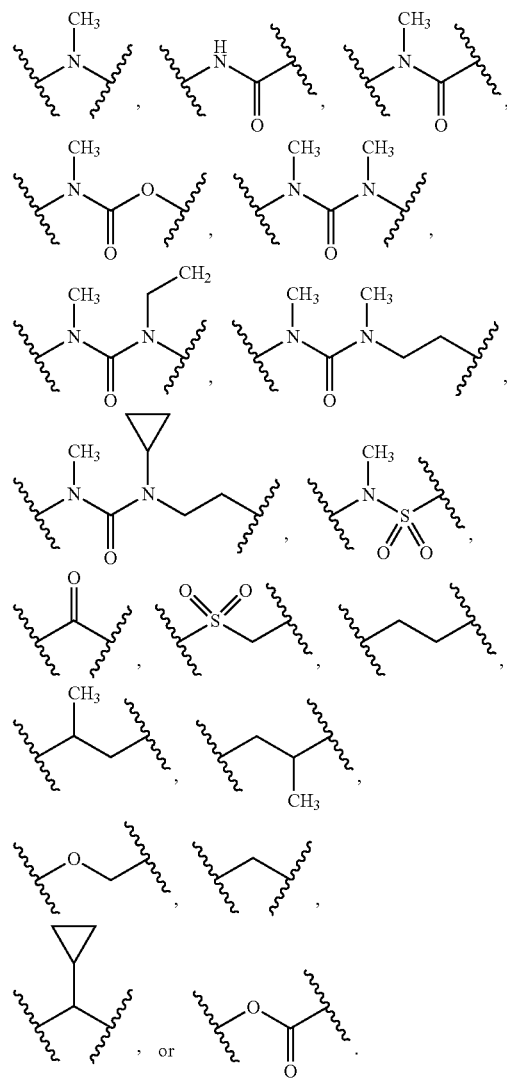

In some embodiments, L is

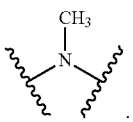

In some embodiments, L is

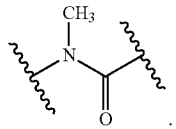

In some embodiments, linker is or comprises a cyclic group. In some embodiments, linker has the structure of Formula IIb:

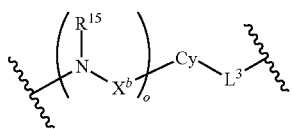

Formula IIb wherein o is 0 or 1;

$X^b$ is C(O) or $SO_2$;

$R^{15}$ is hydrogen or optionally substituted $C_1$-$C_6$ alkyl;

Cy is optionally substituted 3 to 8-membered cycloalkylene, optionally substituted 3 to 8-membered heterocycloalkylene, optionally substituted 6-10 membered arylene, or optionally substituted 5 to 10-membered heteroarylene; and $L^3$ is absent, —C(O)—, —$SO_2$—, optionally substituted $C_1$-$C_4$ alkylene or optionally substituted $C_1$-$C_4$ heteroalkylene. In some embodiments, linker has the structure:

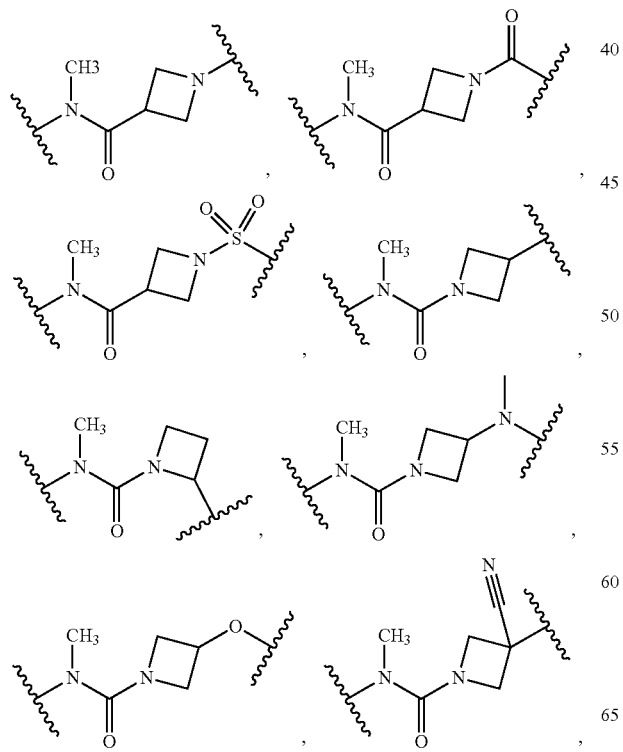

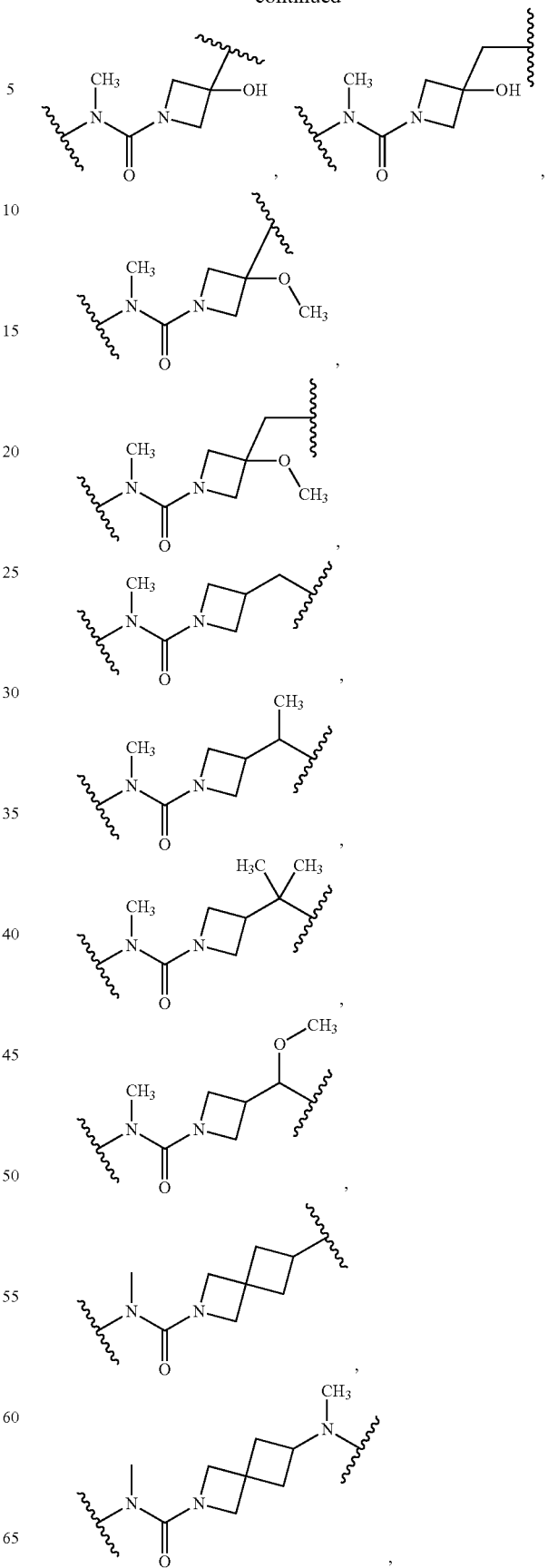

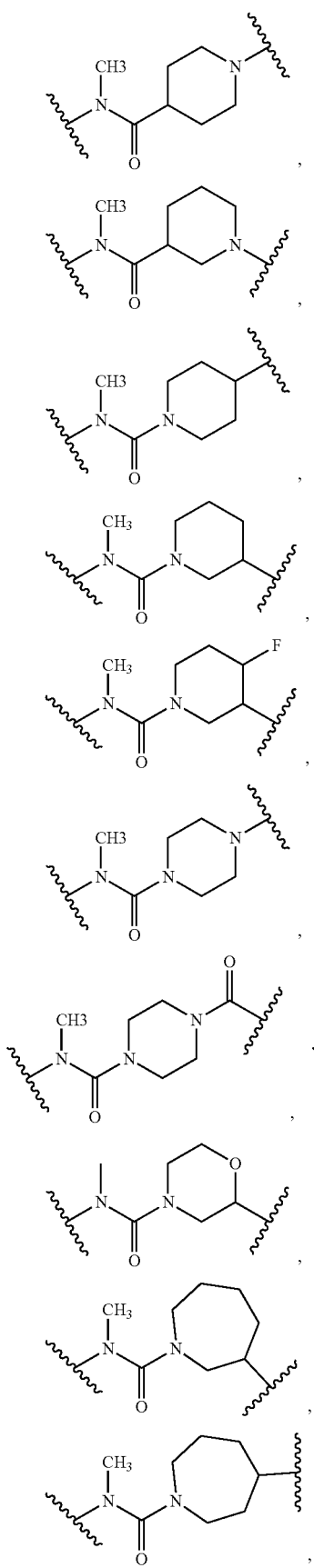
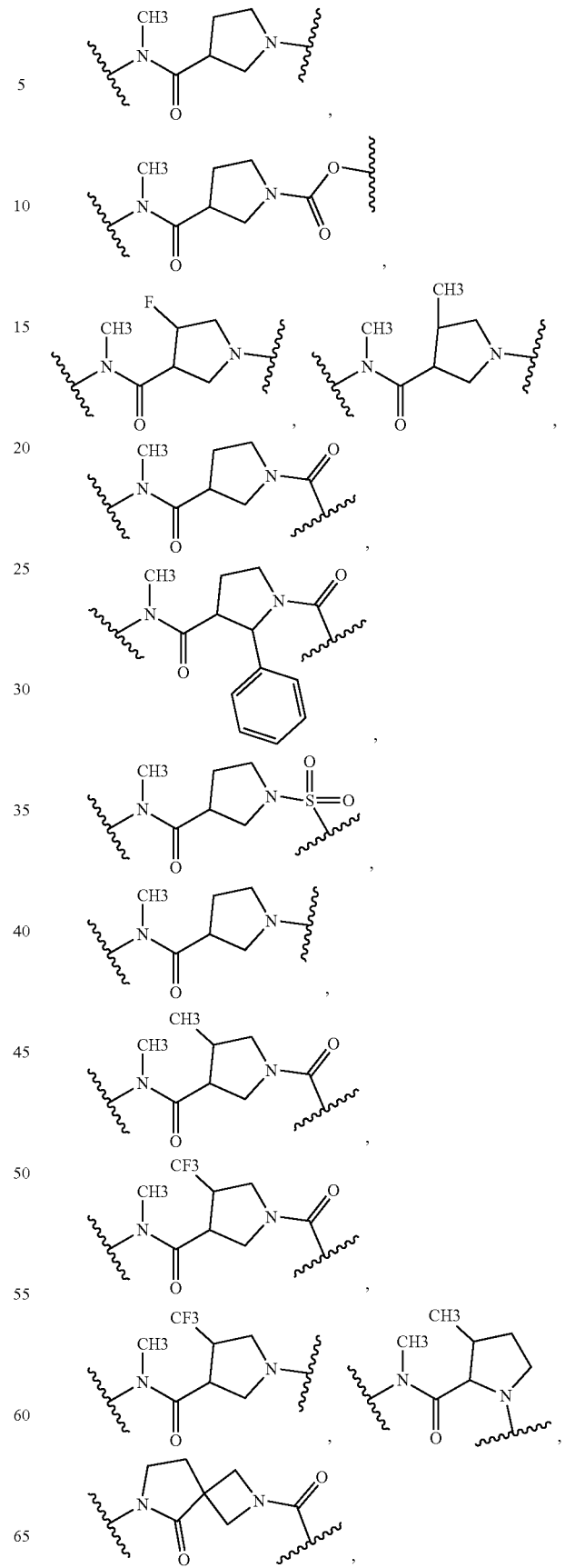

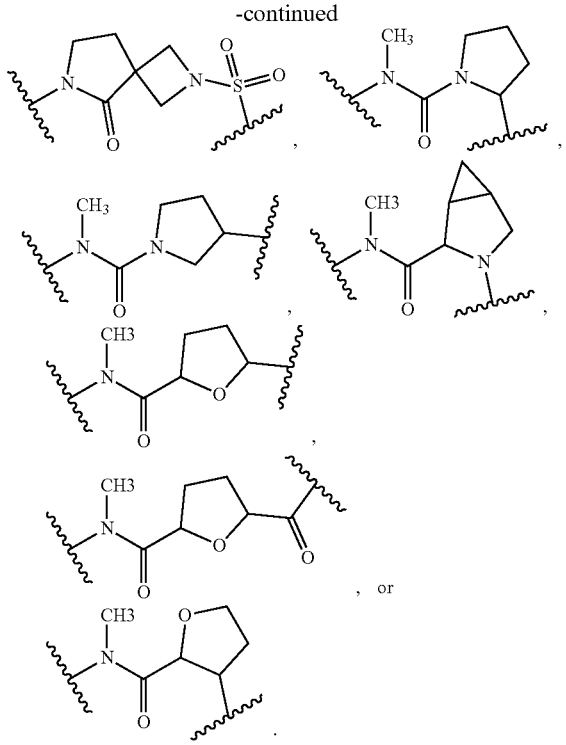

In some embodiments of compounds of the present invention, W is hydrogen, optionally substituted amino, optionally substituted $C_1$-$C_4$ alkoxy, optionally substituted $C_1$-$C_4$ hydroxyalkyl, optionally substituted $C_1$-$C_4$ aminoalkyl, optionally substituted $C_1$-$C_4$ haloalkyl, optionally substituted $C_1$-$C_4$ alkyl, optionally substituted $C_1$-$C_4$ guanidinoalkyl, $C_0$-$C_4$ alkyl optionally substituted 3 to 8-membered heterocycloalkyl, optionally substituted 3 to 8-membered cycloalkyl, or 3 to 8-membered heteroaryl. In some embodiments of compounds of the present invention, W is hydrogen. In some embodiments, W is optionally substituted amino. In some embodiments, W is —NHCH$_3$ or —N(CH$_3$)$_2$. In some embodiments, W is optionally substituted $C_1$-$C_4$ alkoxy. In some embodiments, W is methoxy or iso-propoxy. In some embodiments, W is optionally substituted $C_1$-$C_4$ alkyl. In some embodiments, W is methyl, ethyl, iso-propyl, tert-butyl, or benzyl. In some embodiments, W is optionally substituted amido. In some embodiments, W is

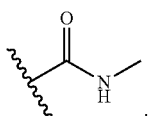

in some embodiments, W is optionally substituted amido. In some embodiments, W is

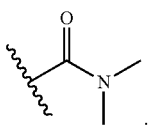 [SMILES: *C(=O)N(C)C]

In some embodiments, W is optionally substituted $C_1$-$C_4$ hydroxyalkyl. In some embodiments, W is

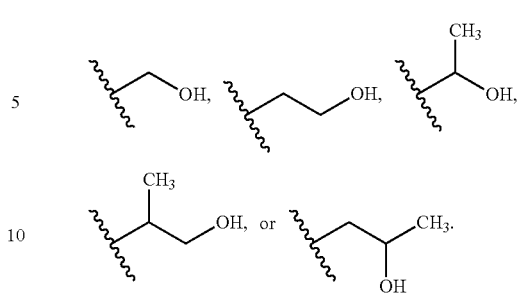

In some embodiments, W is optionally substituted $C_1$-$C_4$ aminoalkyl. In some embodiments, W is

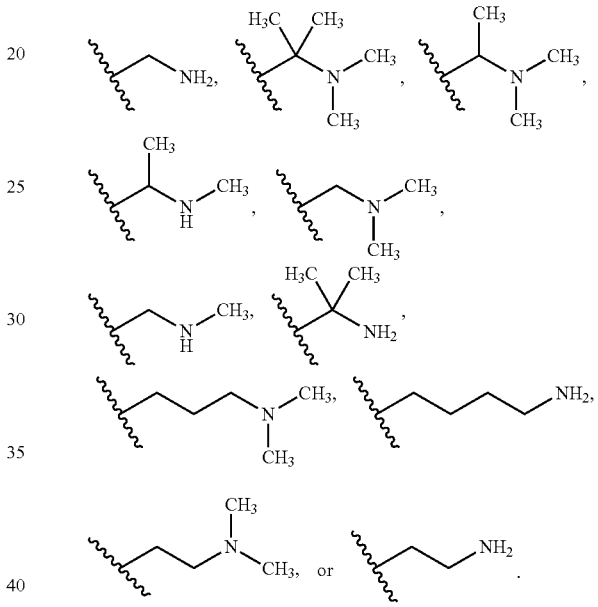

In some embodiments, W is optionally substituted $C_1$-$C_4$ haloalkyl. In some embodiments, W is

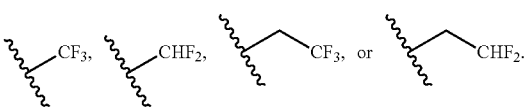

In some embodiments, W is optionally substituted $C_1$-$C_4$ guanidinoalkyl. In some embodiments, W is

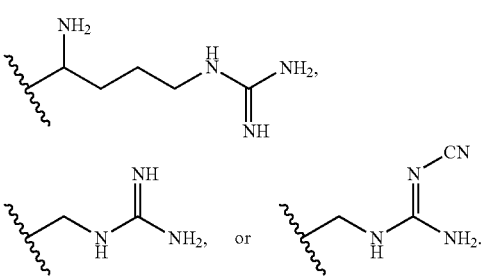

In some embodiments, W is $C_0$-$C_4$ alkyl optionally substituted 3 to 11-membered heterocycloalkyl. In some embodiments, W is
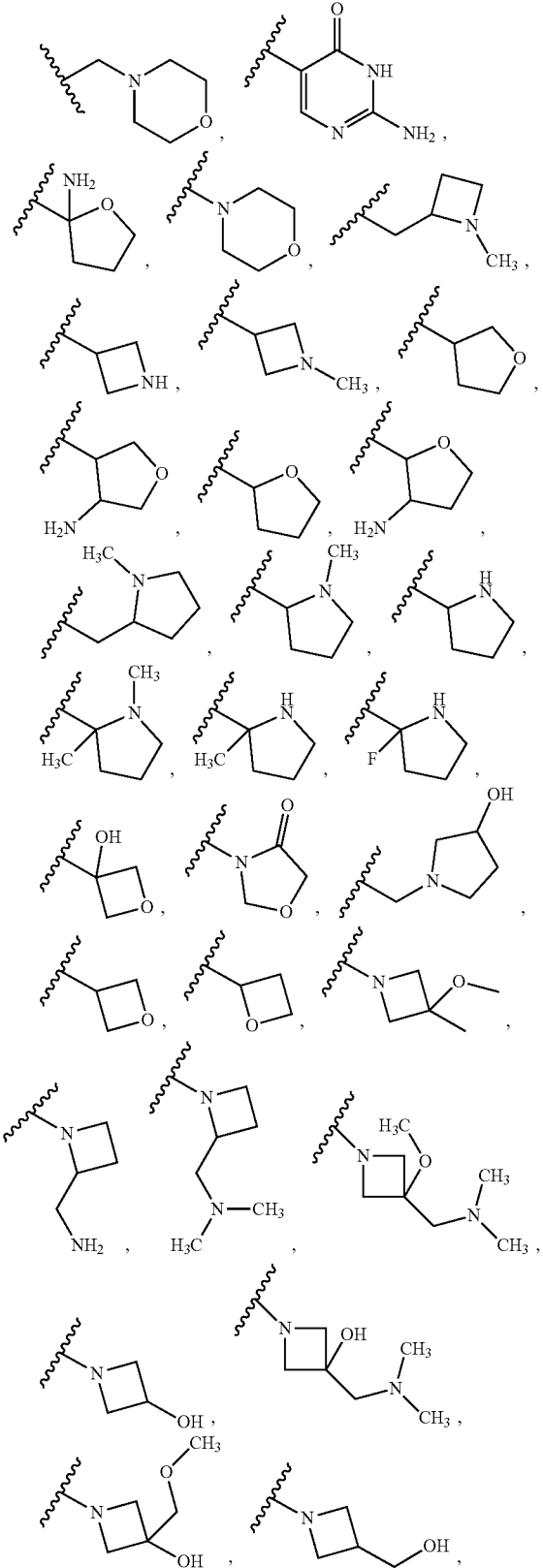
-continued
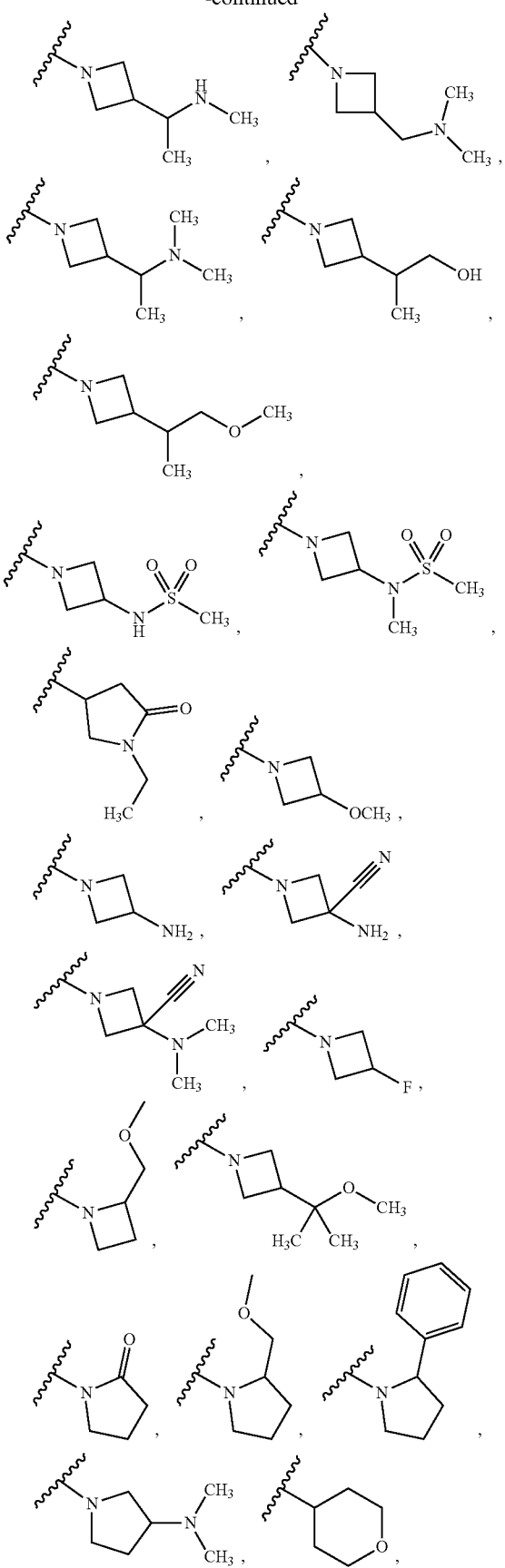

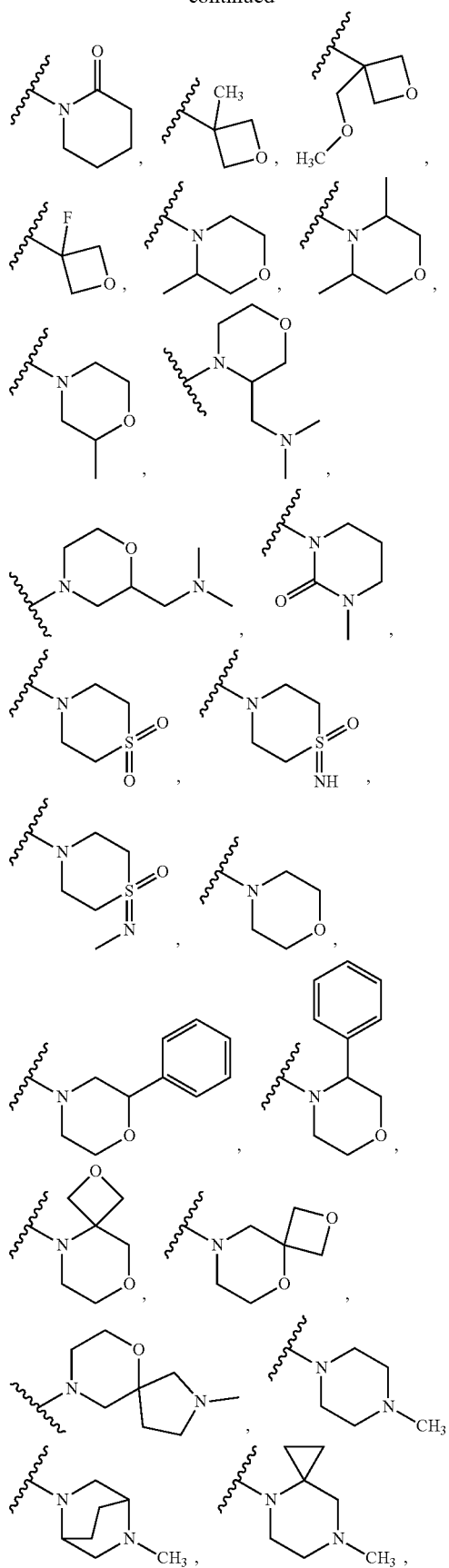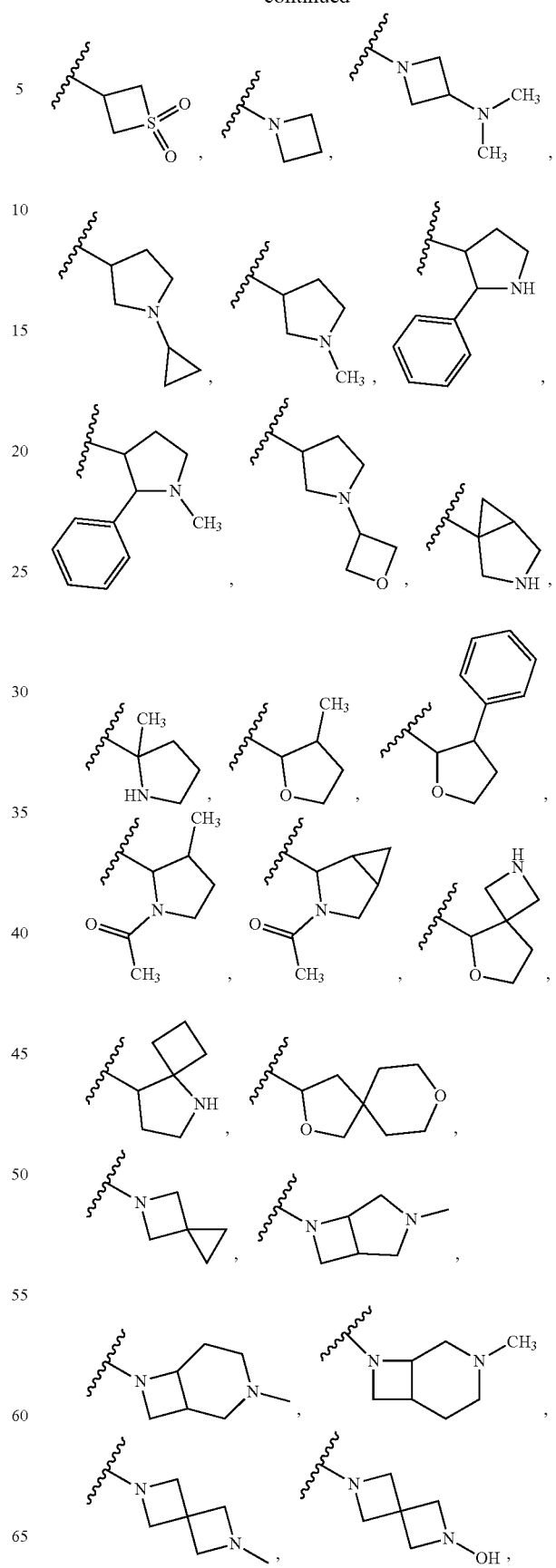

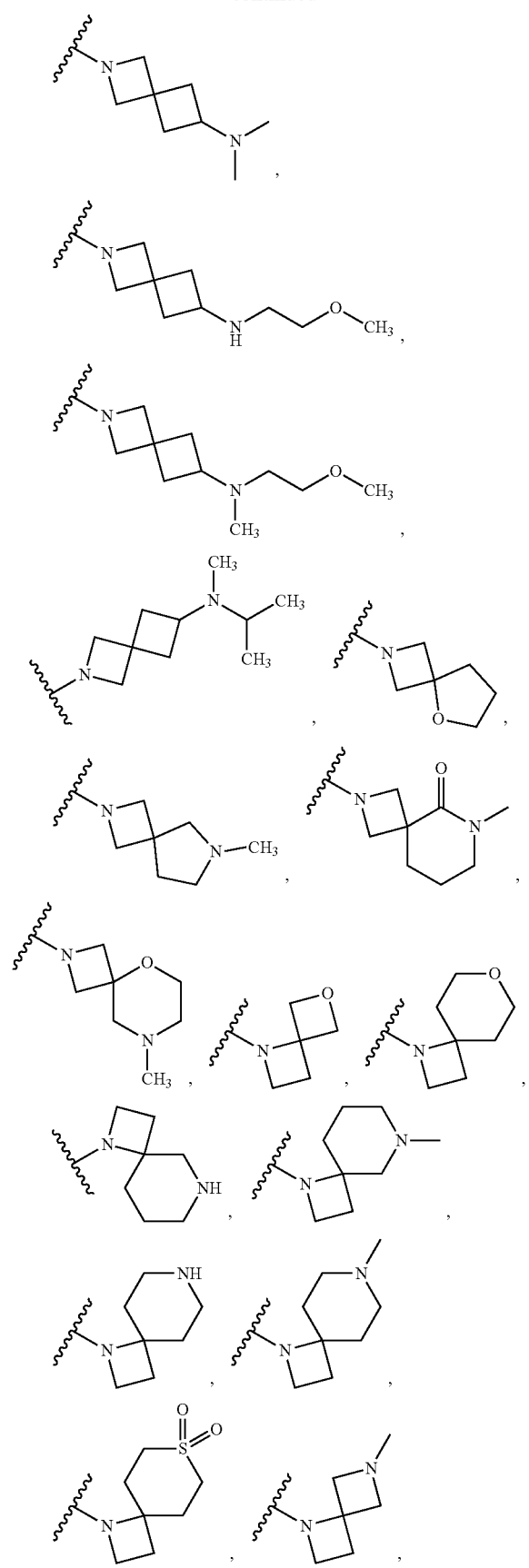
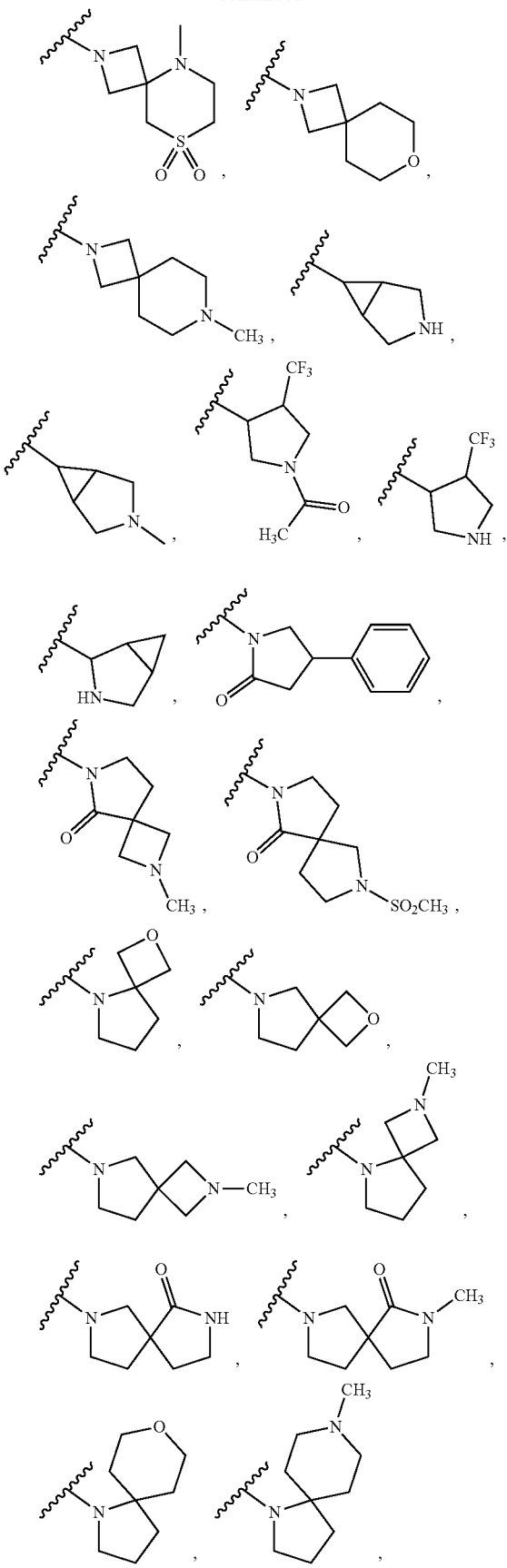

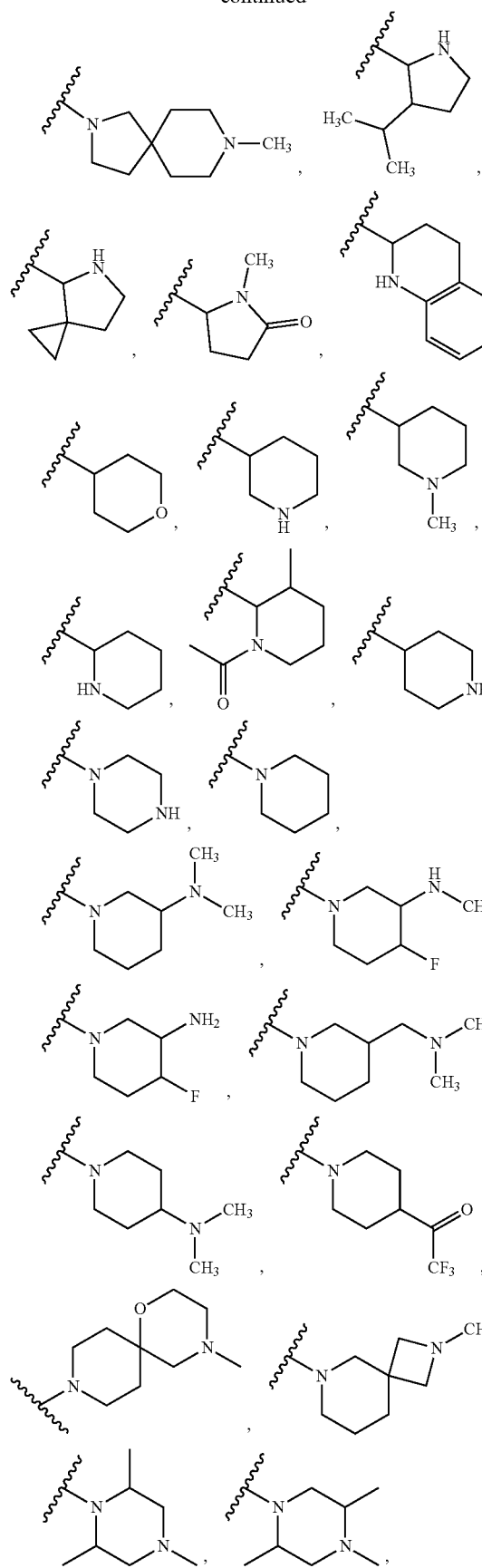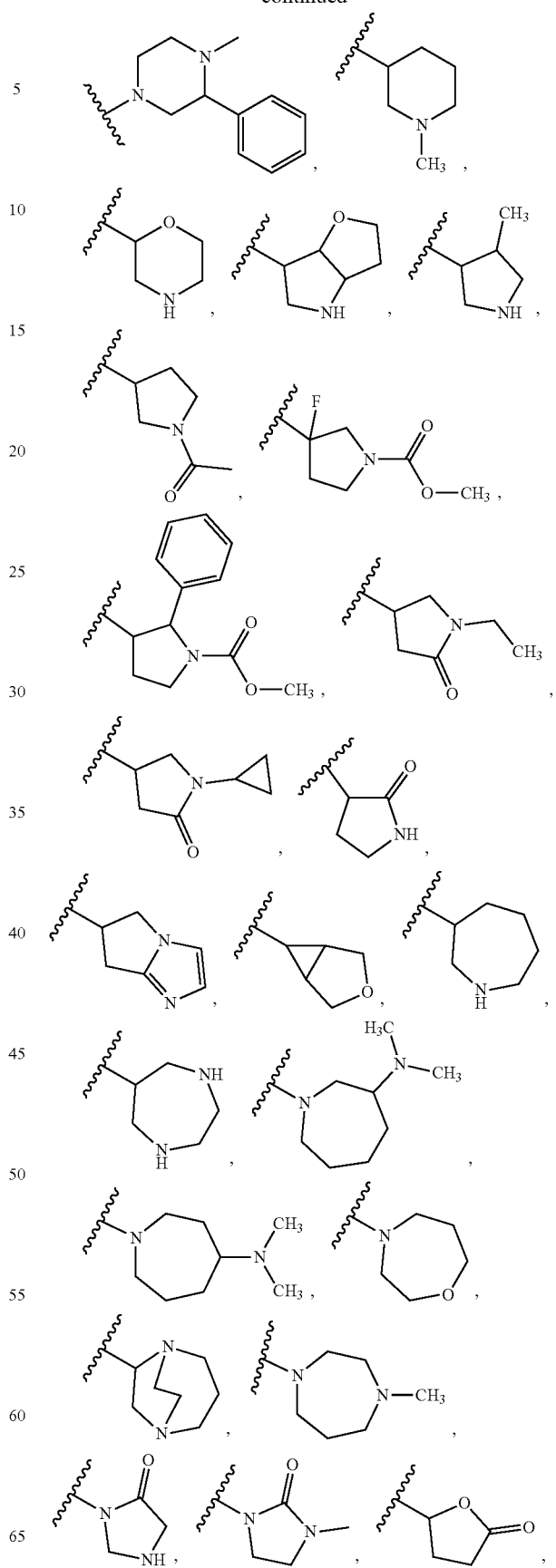

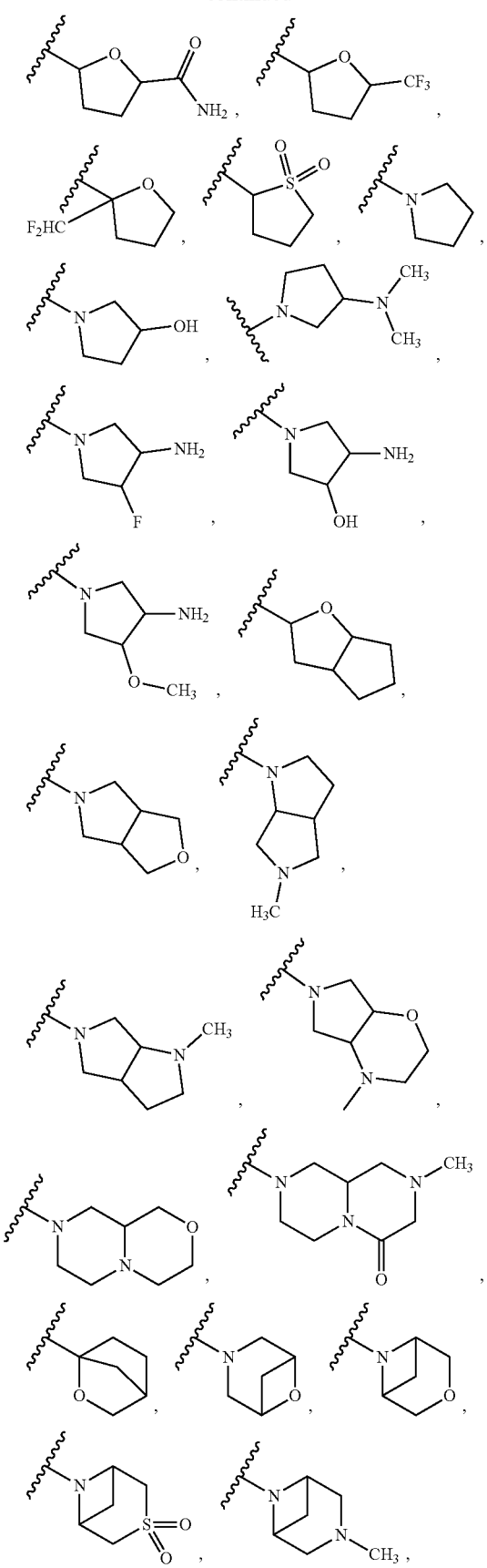
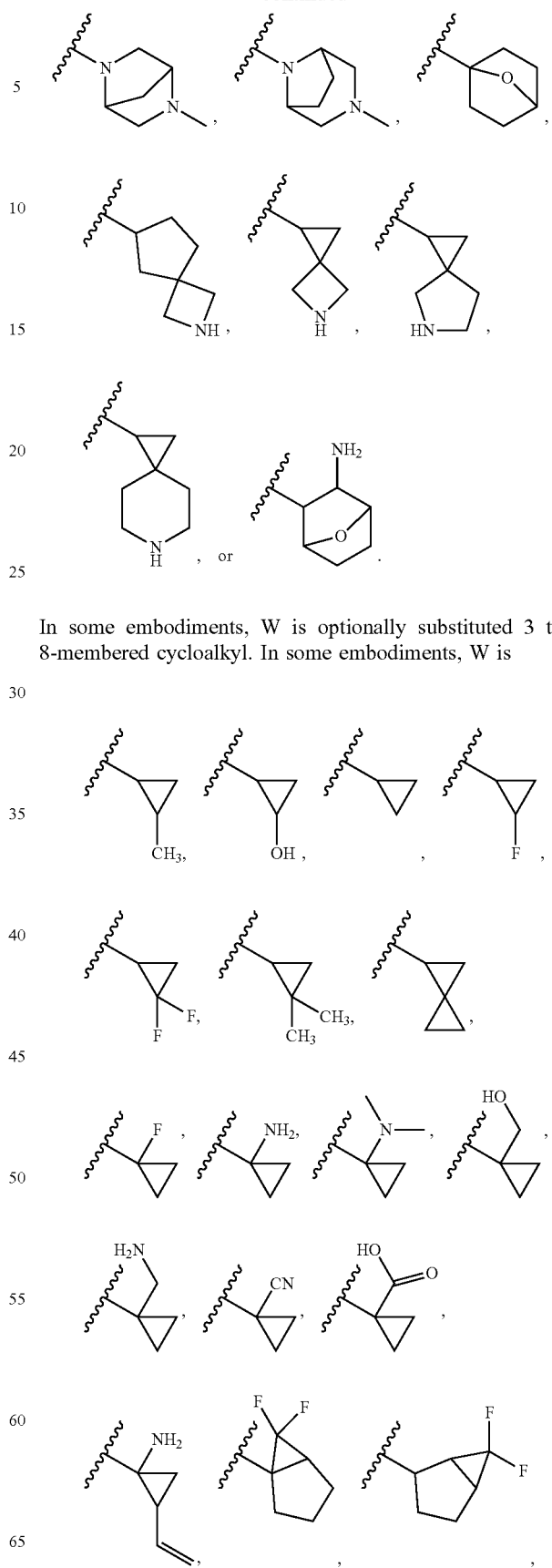
In some embodiments, W is optionally substituted 3 to 8-membered cycloalkyl. In some embodiments, W is

53

-continued

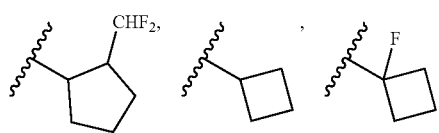

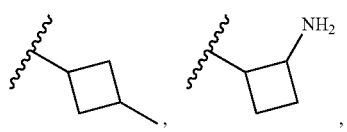

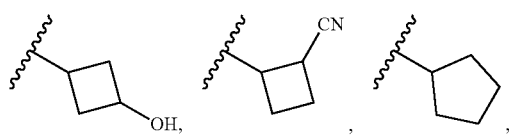

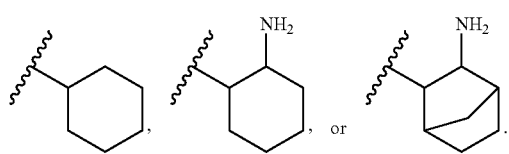

In some embodiments, W is optionally substituted 3 to 8-membered heteroaryl. In some embodiments, W is

54

-continued

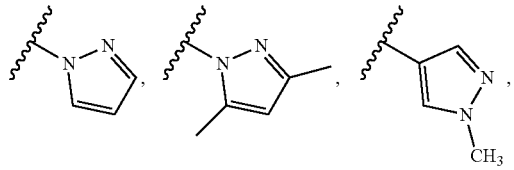

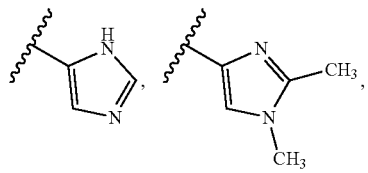

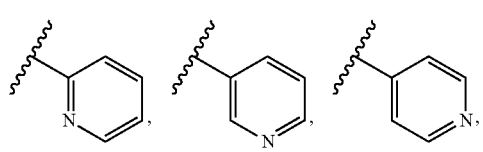

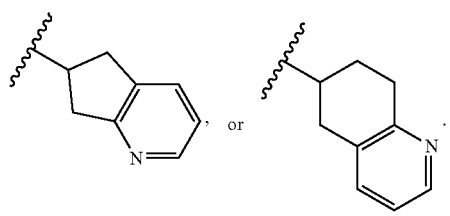

In some embodiments, W is optionally substituted 6- to 10-membered aryl (e.g., phenyl, 4-hydroxy-phenyl, or 2,4-methoxy-phenyl).

In some embodiments, a compound of the present invention is selected from Table 1, or a pharmaceutically acceptable salt or stereoisomer thereof. In some embodiments, a compound of the present invention is selected from Table 1, or a pharmaceutically acceptable salt or atropisomer thereof.

TABLE 1

Certain Compounds of the Present Invention

| Ex# | Structure |
|---|---|
| A1 | 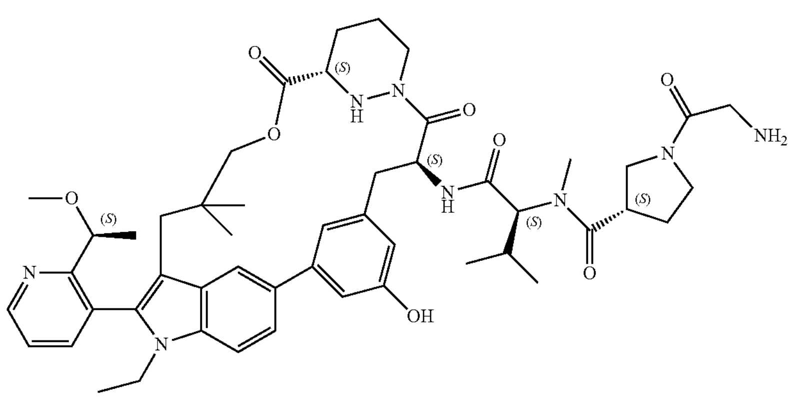 |

TABLE 1-continued
Certain Compounds of the Present Invention
| Ex# | Structure |
|---|---|
| A2 | 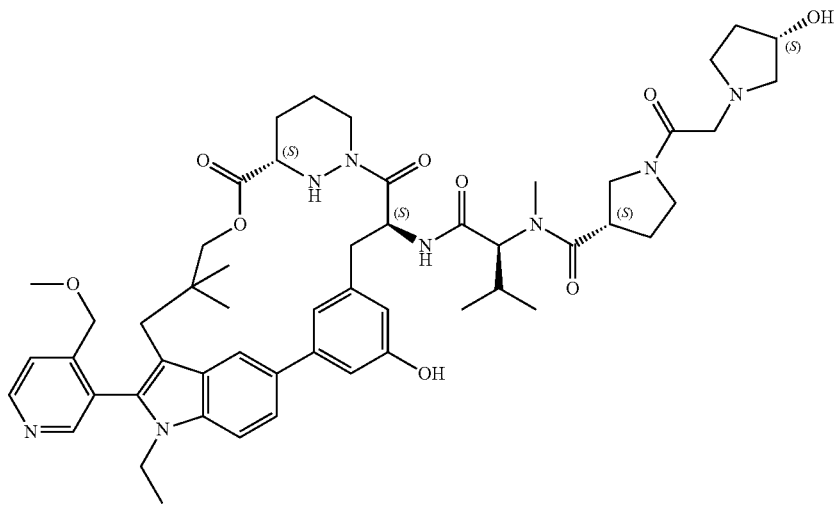 |
| A3 | 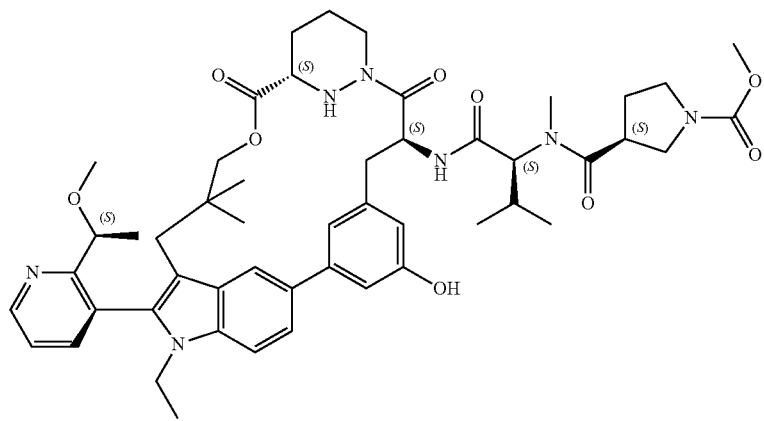 |
| A4 | 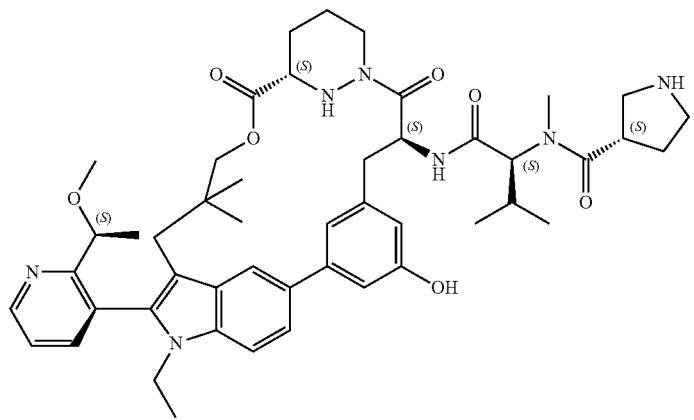 |

TABLE 1-continued
Certain Compounds of the Present Invention
| Ex# | Structure |
|---|---|
| A5 | 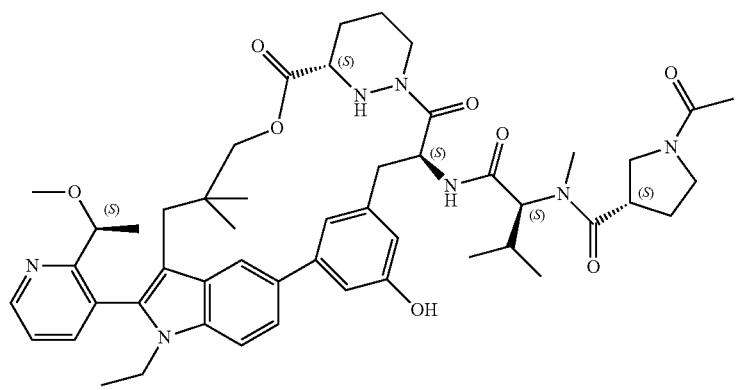 |
| A6 | 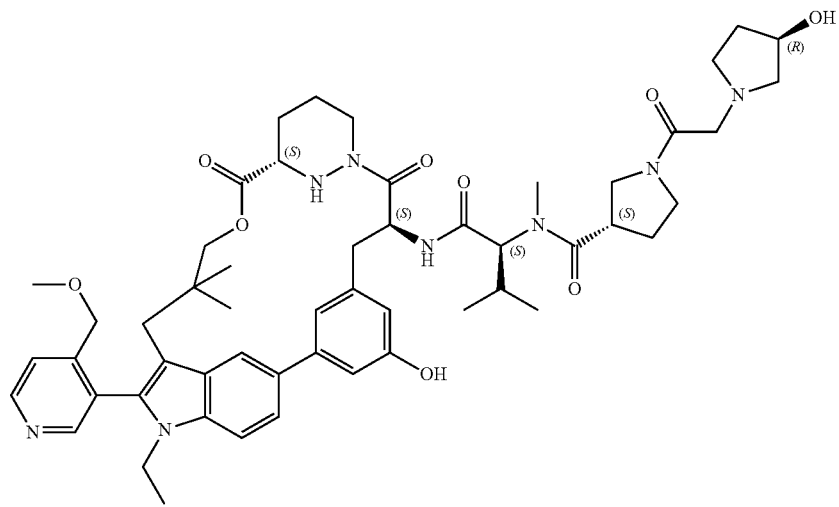 |
| A7 | 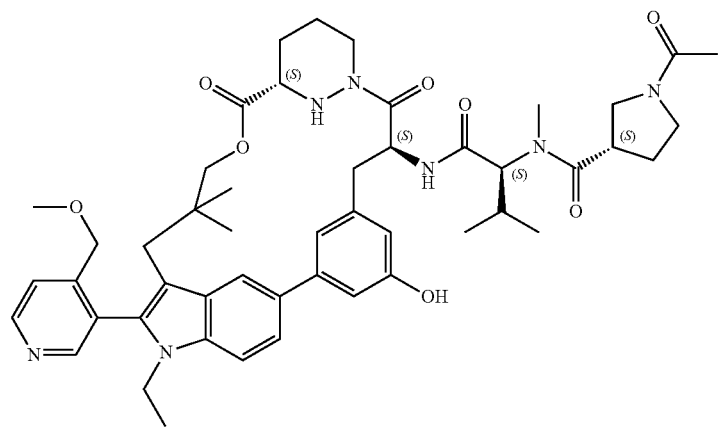 |

TABLE 1-continued
Certain Compounds of the Present Invention
| Ex# | Structure |
|---|---|
| A8 | 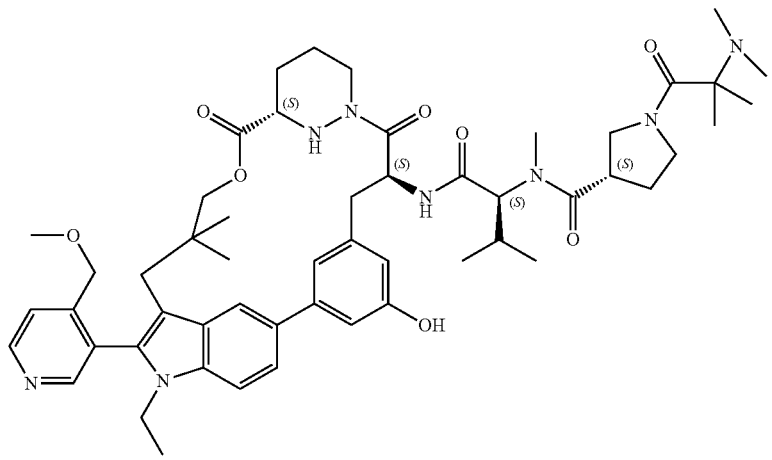 |
| A9 | 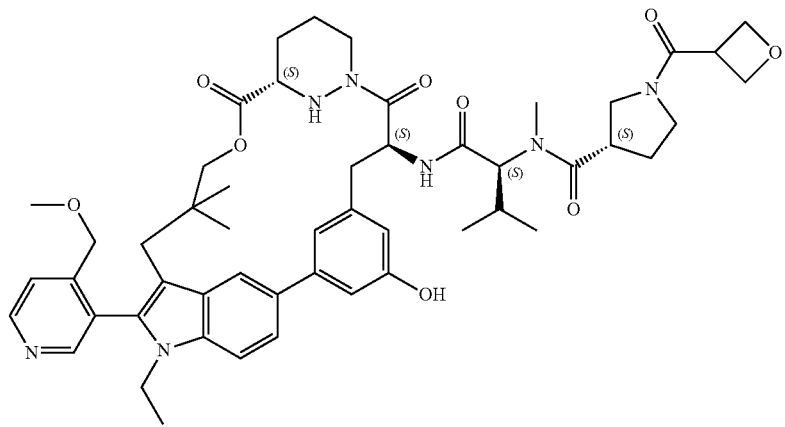 |
| A10 | 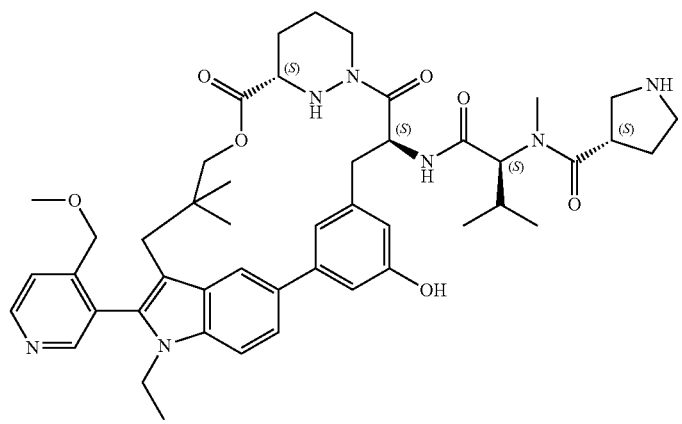 |

TABLE 1-continued
Certain Compounds of the Present Invention
| Ex# | Structure |
|---|---|
| A11 | 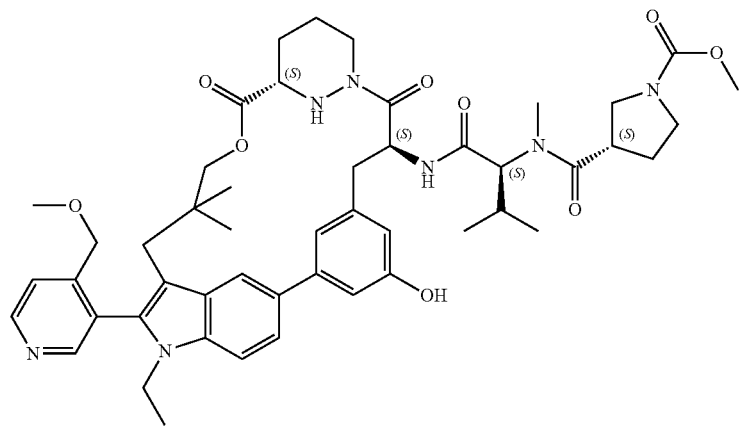 |
| A12 | 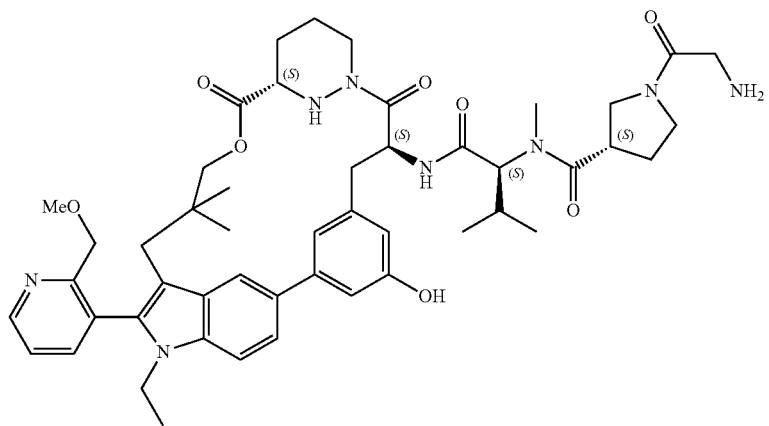 |
| A13 | 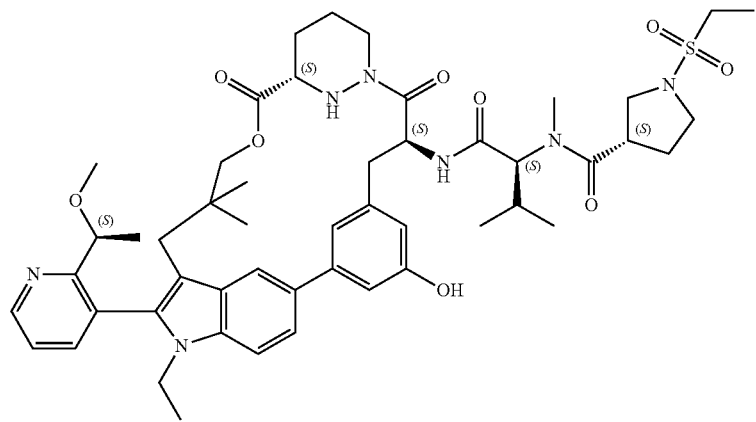 |

TABLE 1-continued
Certain Compounds of the Present Invention
| Ex# | Structure |
|---|---|
| A14 | 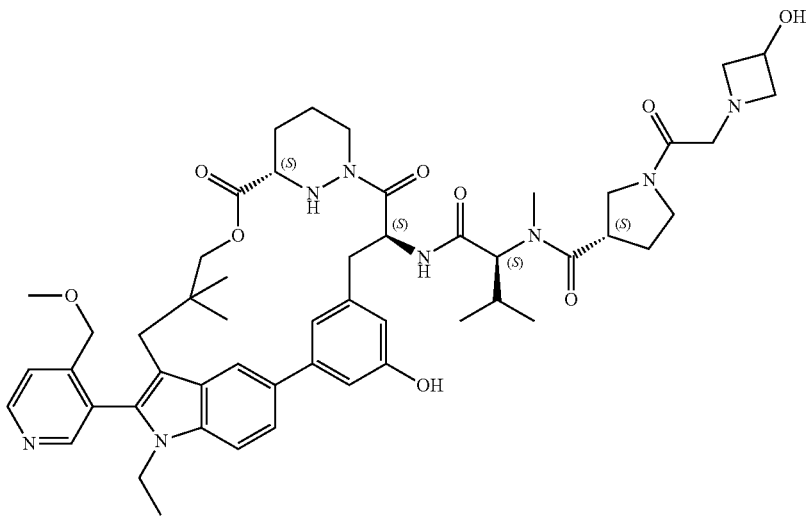 |
| A15 | 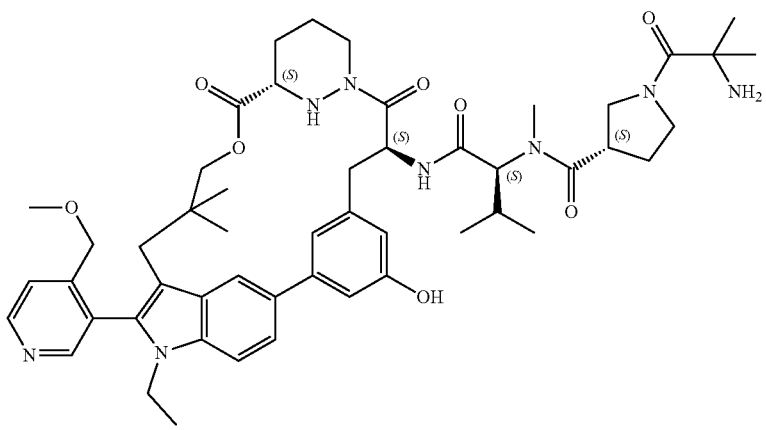 |
| A16 | 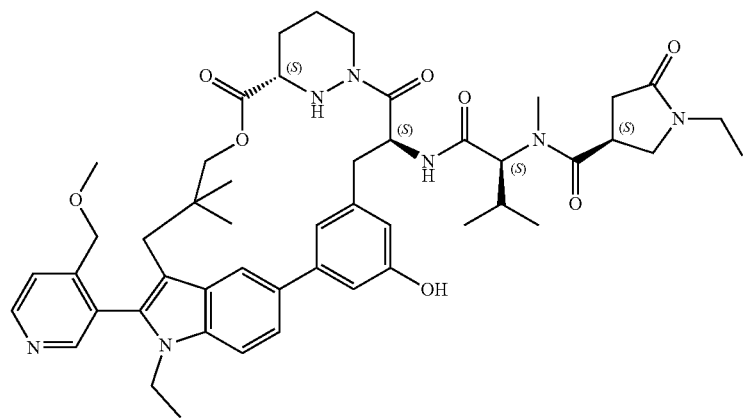 |

TABLE 1-continued

Certain Compounds of the Present Invention

| Ex# | Structure |
|---|---|
| A17 | 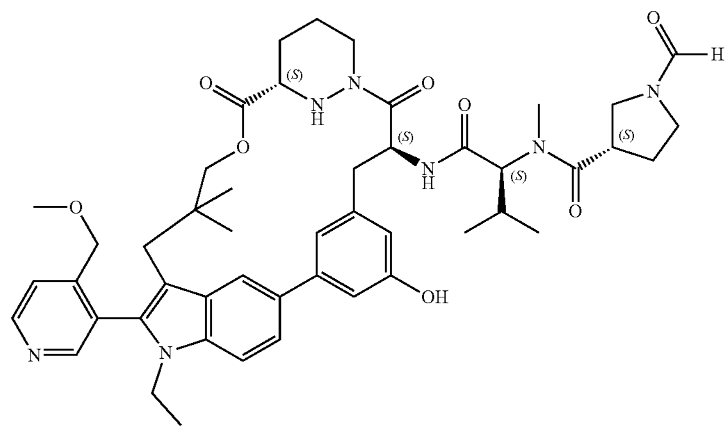 |
| A18 | 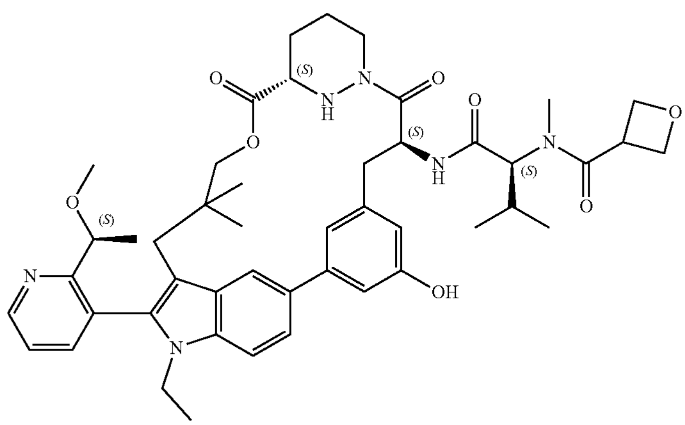 |
| A19 | 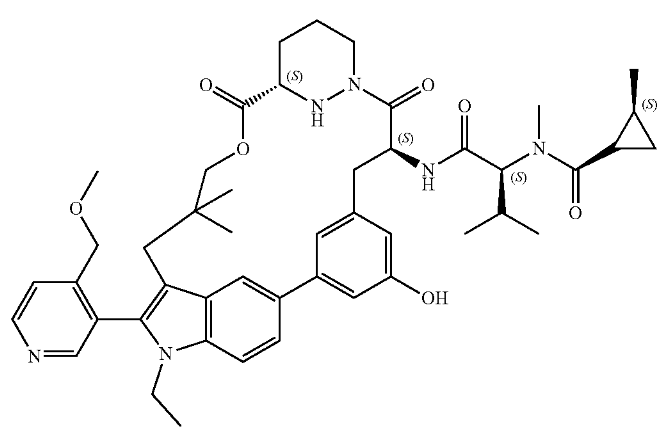 |

TABLE 1-continued

Certain Compounds of the Present Invention

| Ex# | Structure |
|---|---|
| A20 | 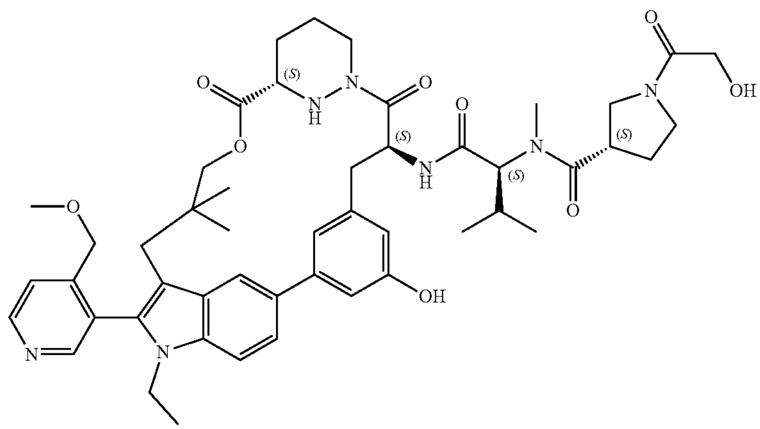 |
| A21 | 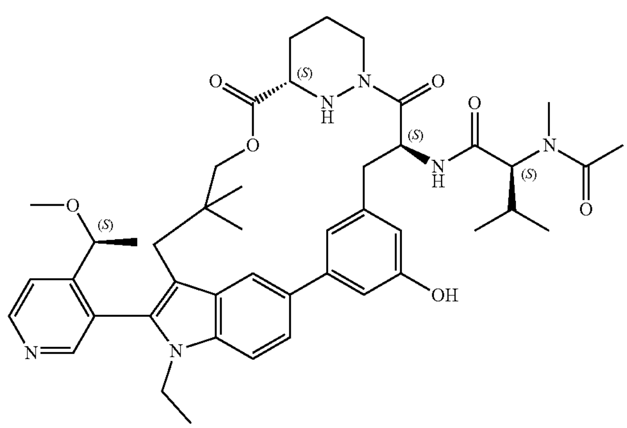 |
| A22 | 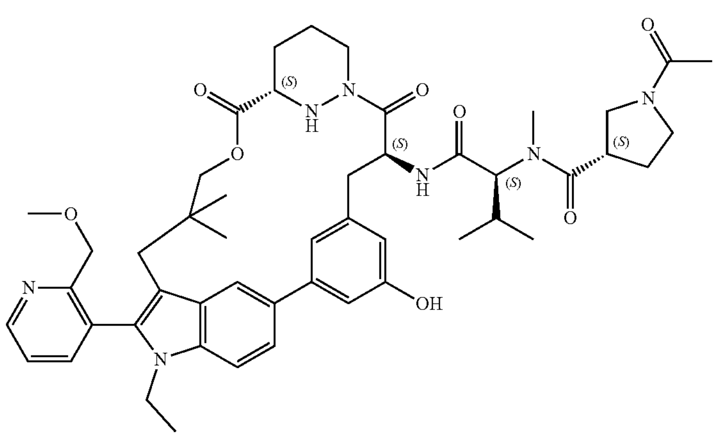 |

TABLE 1-continued

Certain Compounds of the Present Invention

| Ex# | Structure |
| --- | --- |
| A23 | 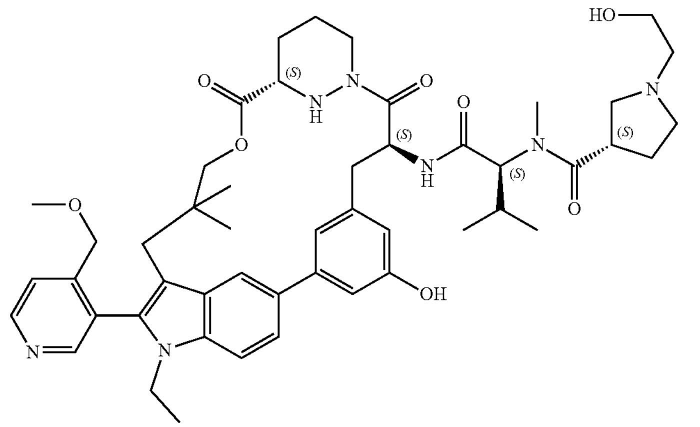 |
| A24 | 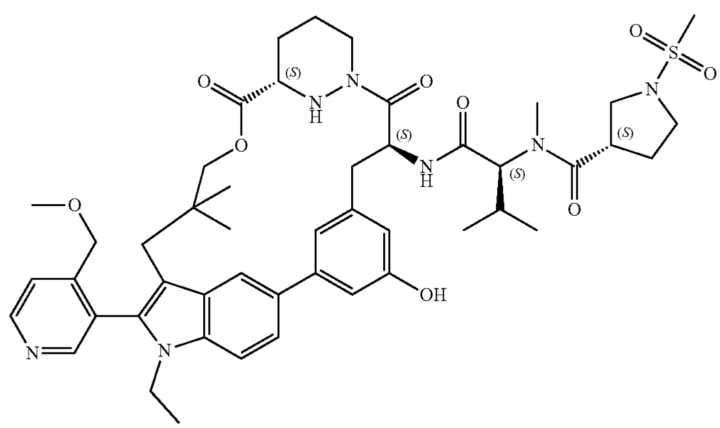 |
| A25 | 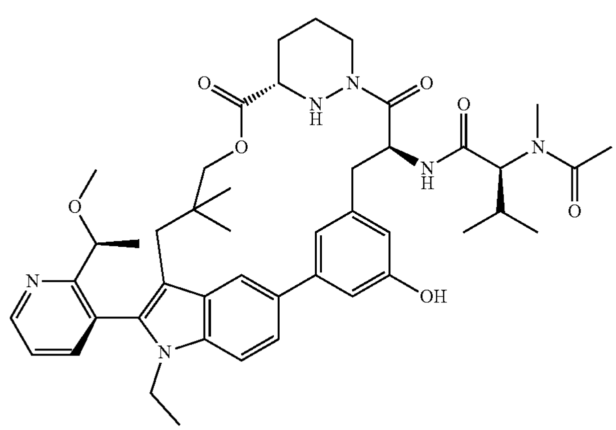 |

TABLE 1-continued
Certain Compounds of the Present Invention
| Ex# | Structure |
|---|---|
| A26 | 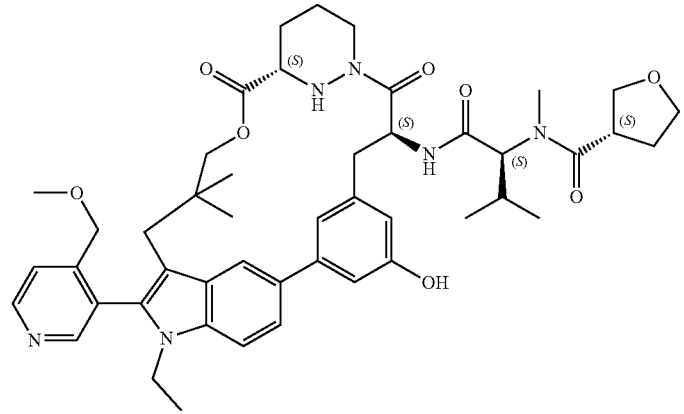 |
| A27 | 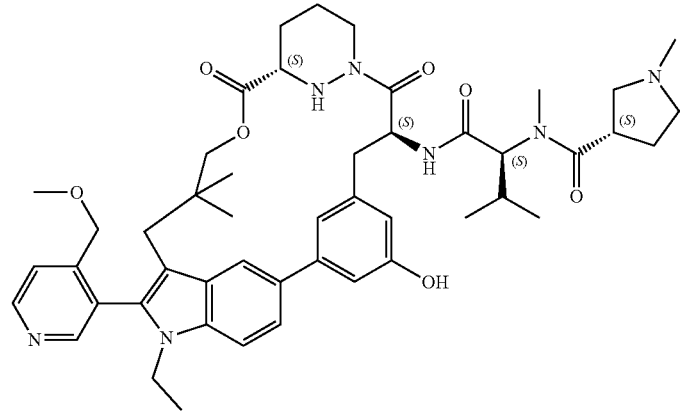 |
| A28 | 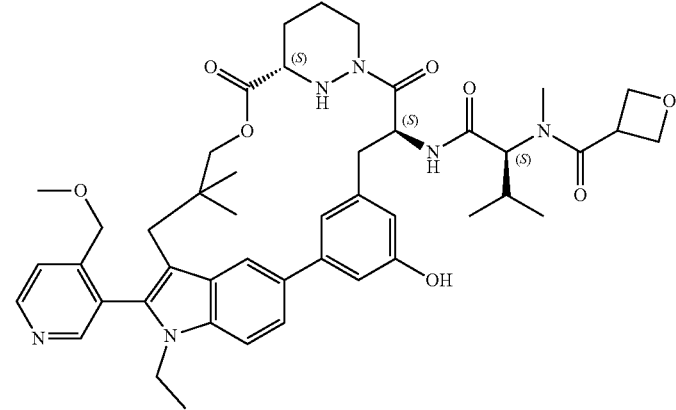 |

TABLE 1-continued
Certain Compounds of the Present Invention
| Ex# | Structure |
|---|---|
| A29 | 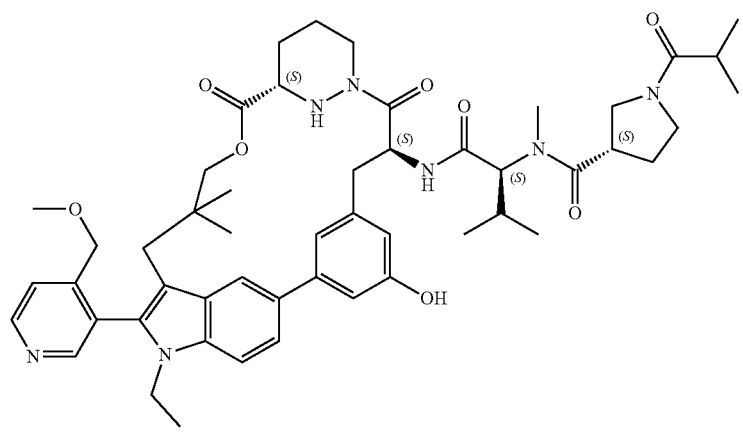 |
| A30 | 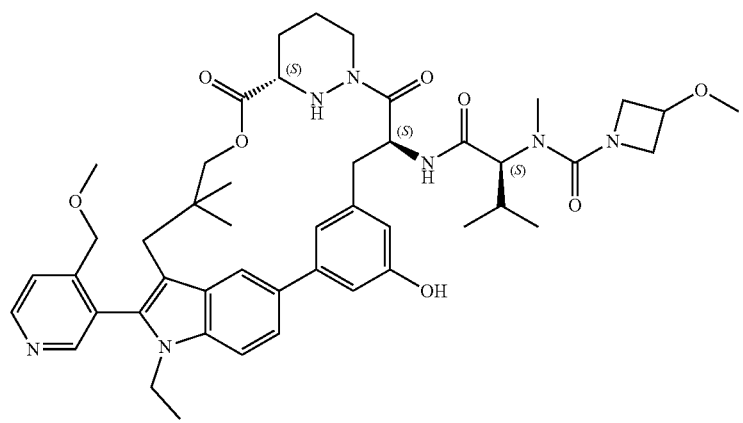 |
| A31 | 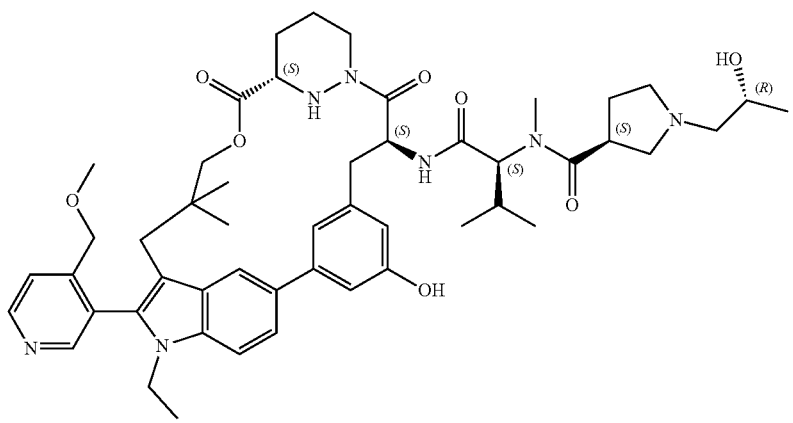 |

TABLE 1-continued
Certain Compounds of the Present Invention
| Ex# | Structure |
|---|---|
| A32 | 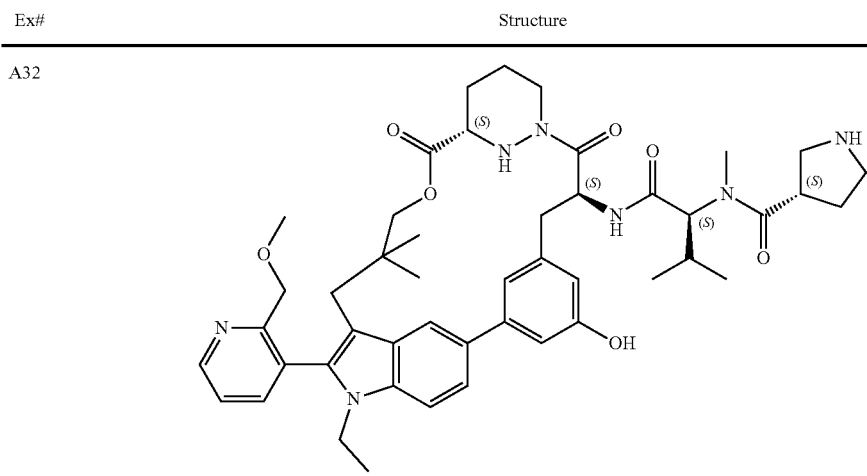 |
| A33 | 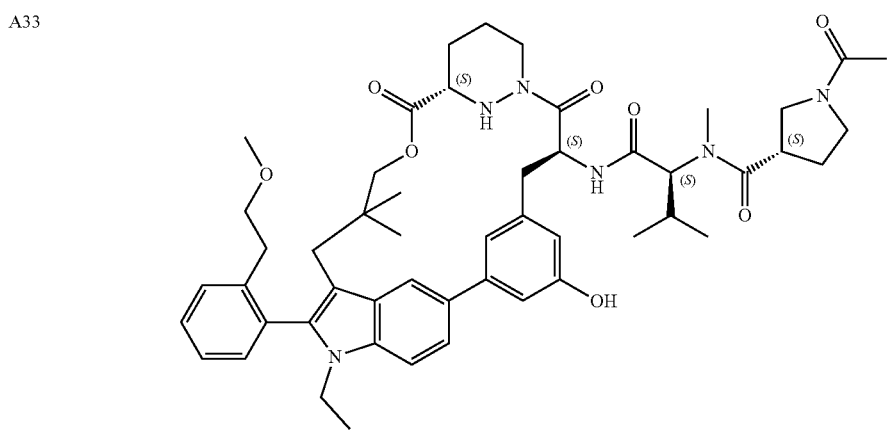 |
| A34 | 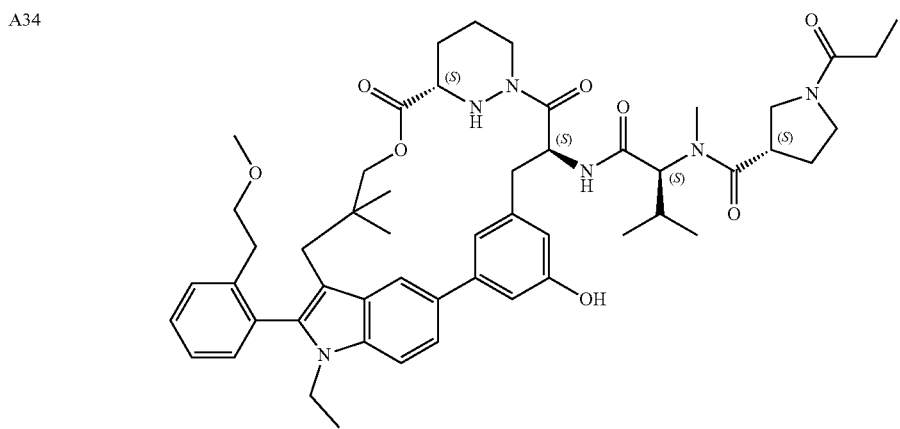 |

TABLE 1-continued

Certain Compounds of the Present Invention

| Ex# | Structure |
|---|---|
| A35 | 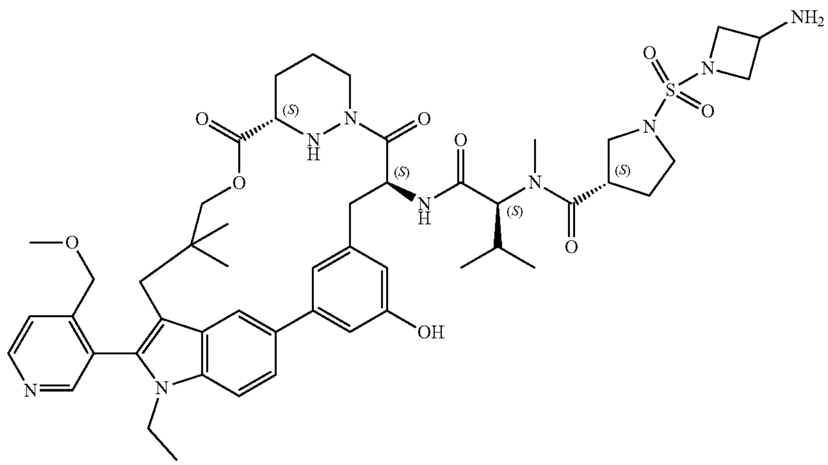 |
| A36 | 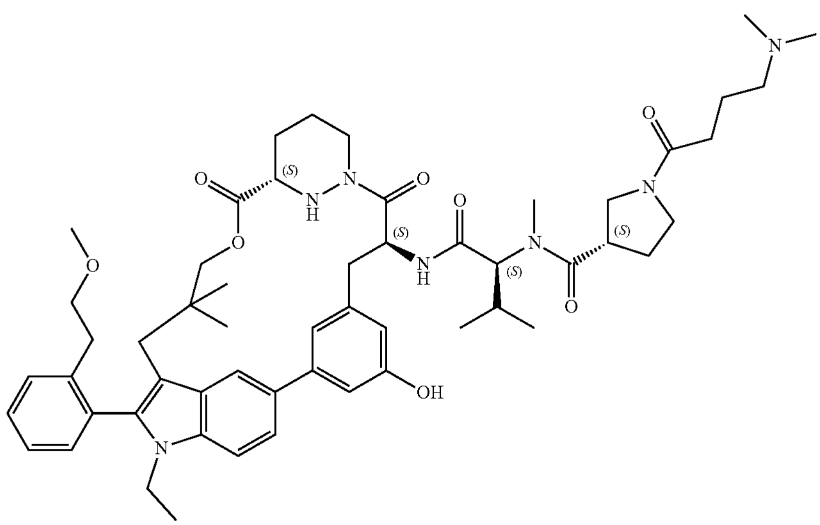 |
| A37 | 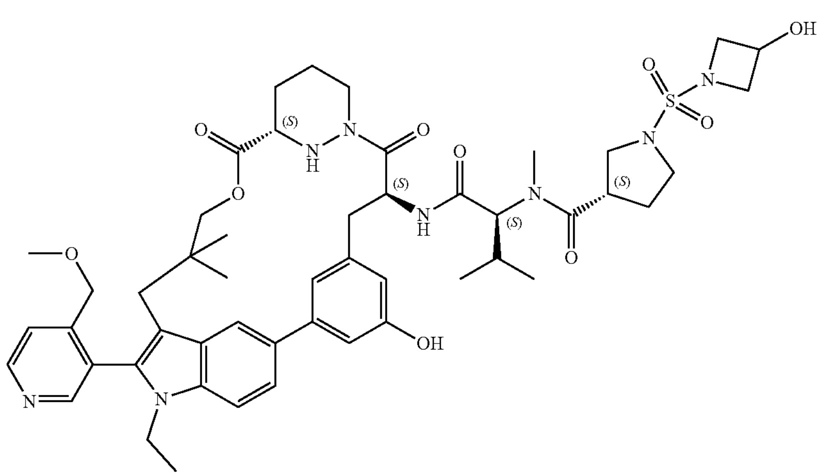 |

TABLE 1-continued
Certain Compounds of the Present Invention
| Ex# | Structure |
|---|---|
| A38 | 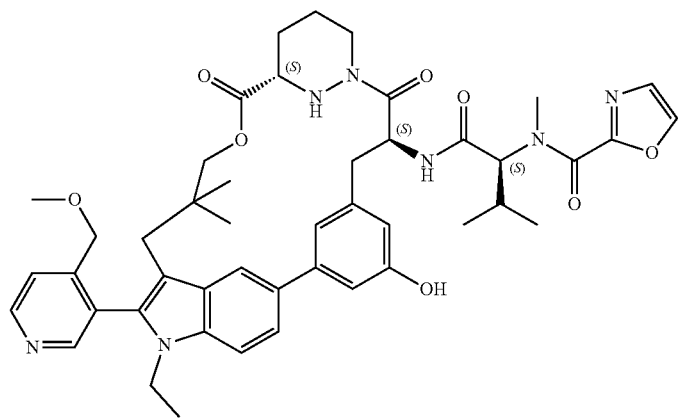 |
| A39 | 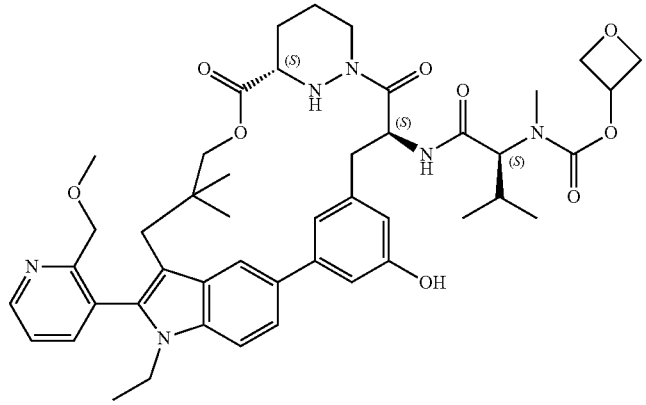 |
| A40 | 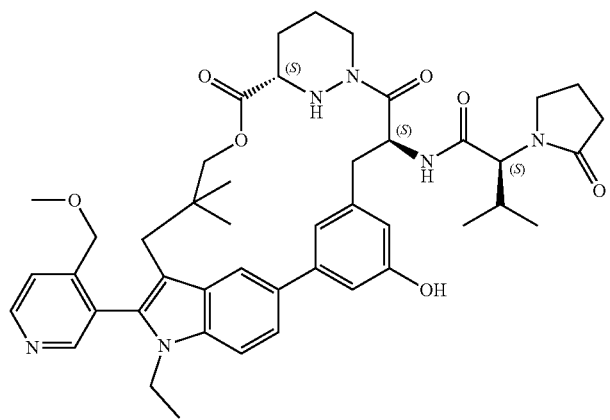 |

US 11,608,346 B2
TABLE 1-continued
Certain Compounds of the Present Invention
| Ex# | Structure |
|---|---|
| A41 | 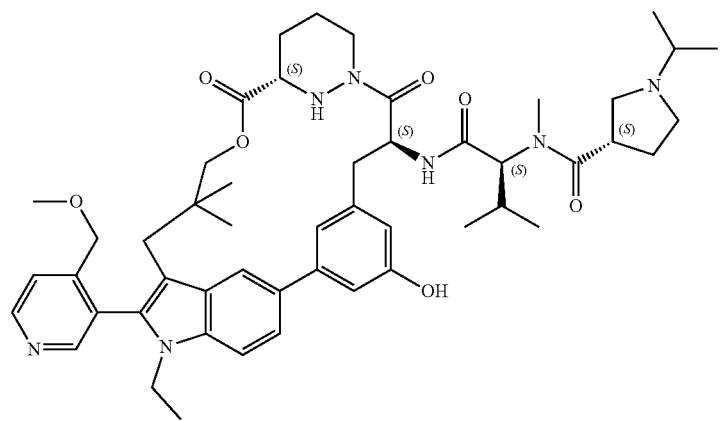 |
| A42 | 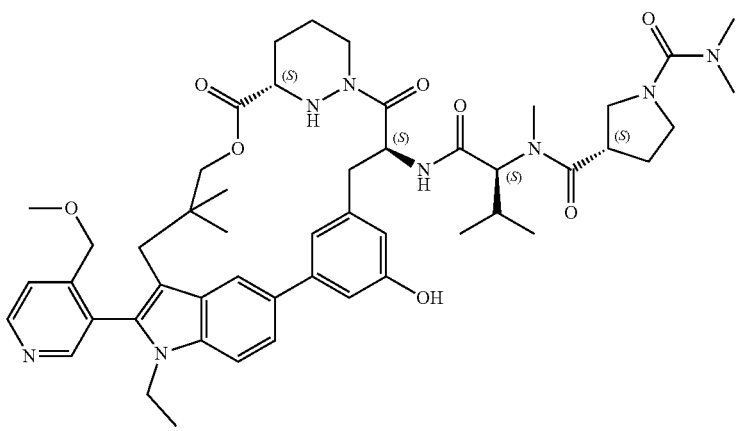 |
| A43 | 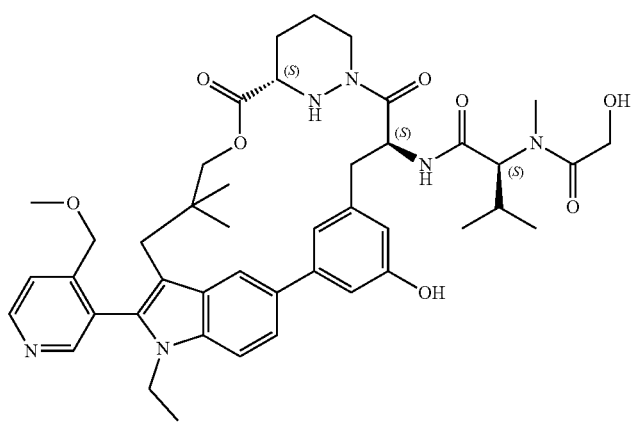 |

TABLE 1-continued
Certain Compounds of the Present Invention
| Ex# | Structure |
|---|---|
| A44 | 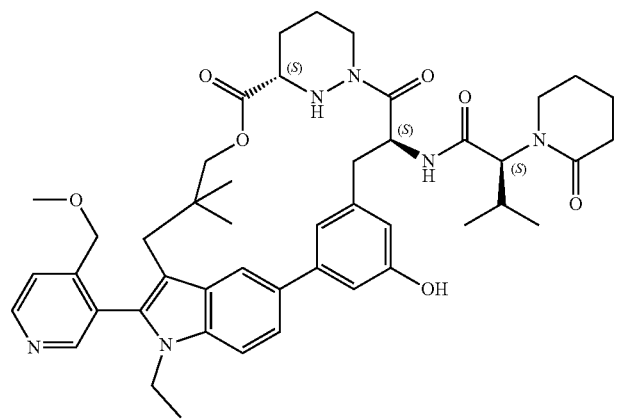 |
| A45 | 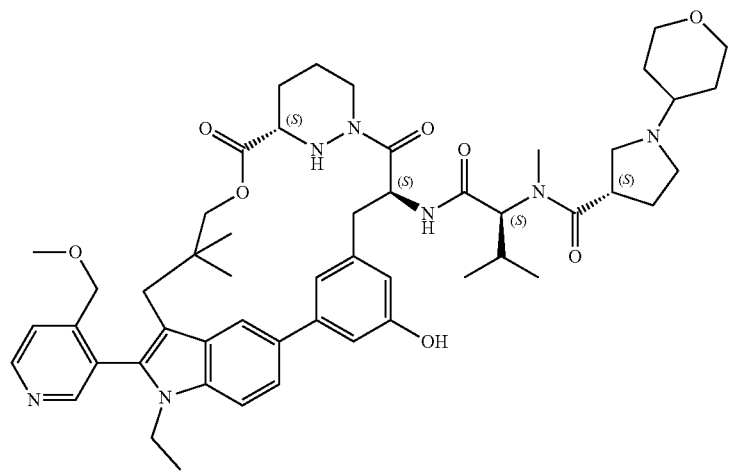 |
| A46 | 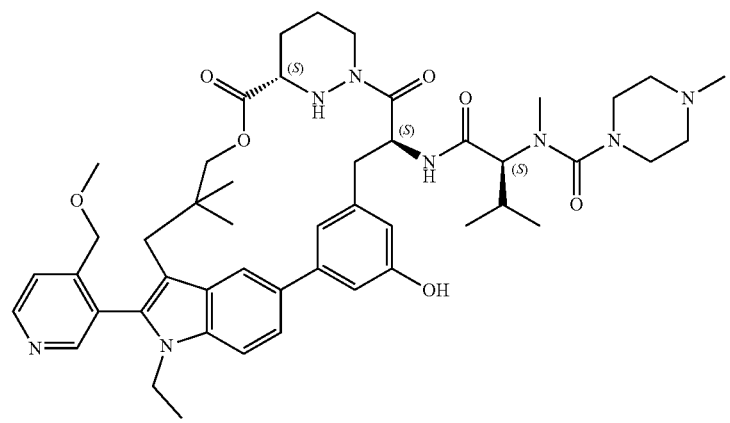 |

TABLE 1-continued

Certain Compounds of the Present Invention

| Ex# | Structure |
|---|---|
| A47 | 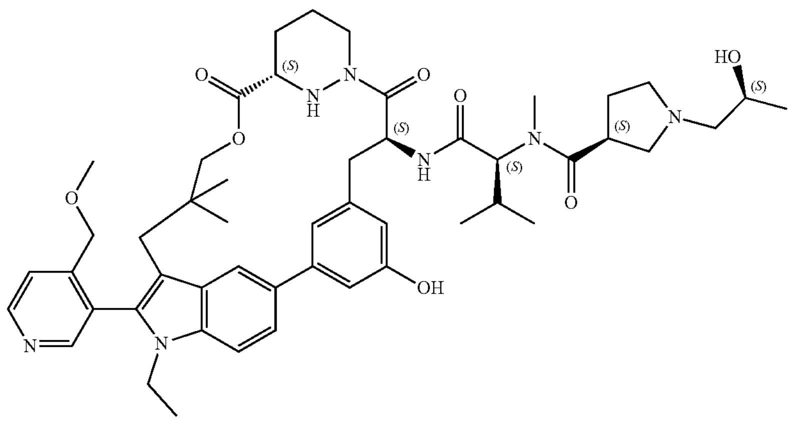 |
| A48 | 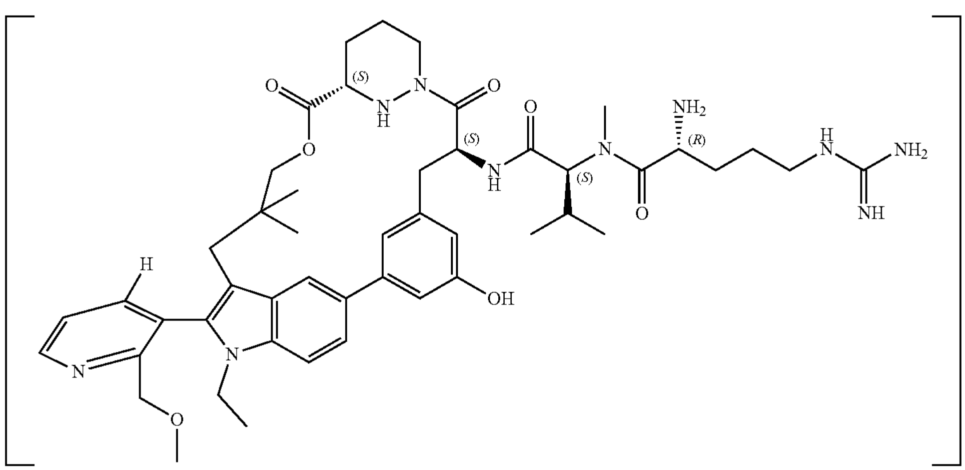 |
| A49 | 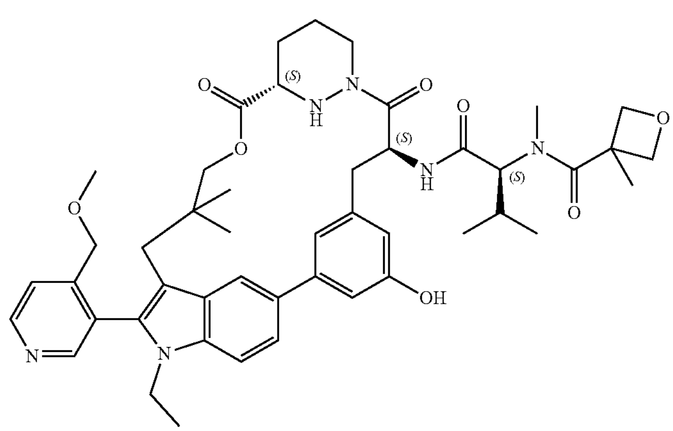 |

TABLE 1-continued
Certain Compounds of the Present Invention
| Ex# | Structure |
|---|---|
| A50 | 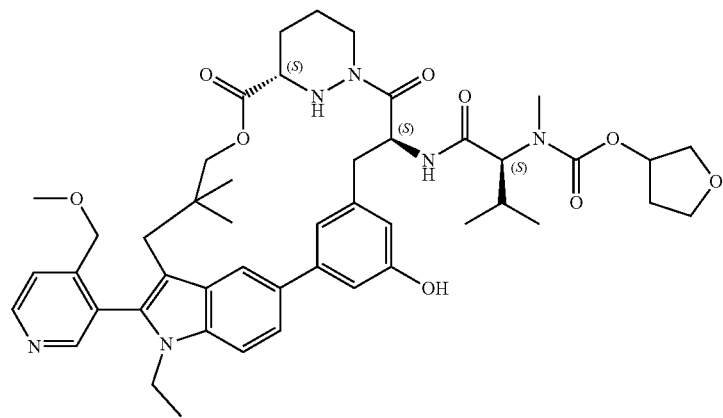 |
| A51 | 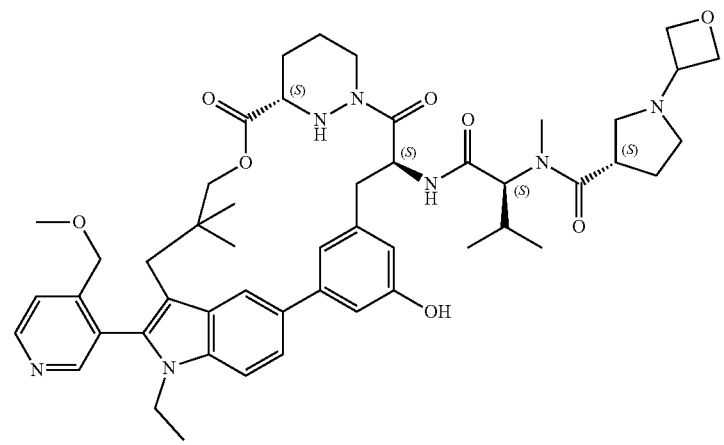 |
| A52 | 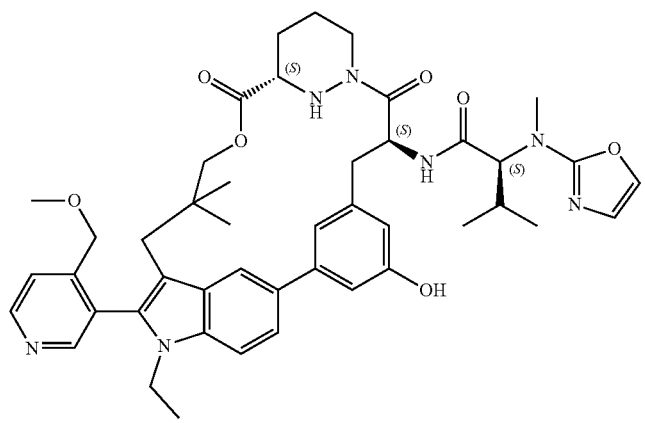 |

TABLE 1-continued
Certain Compounds of the Present Invention
| Ex# | Structure |
|---|---|
| A53 | 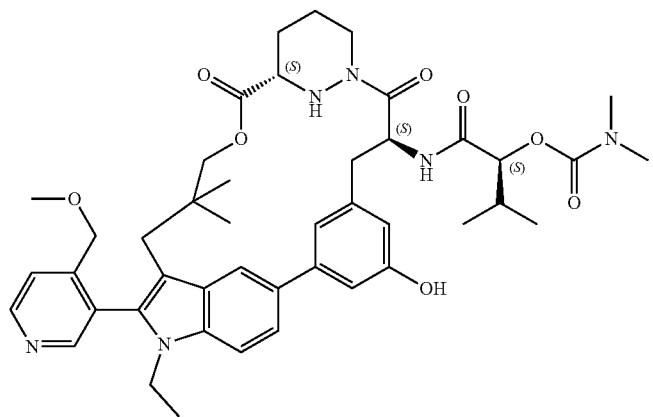 |
| A54 | 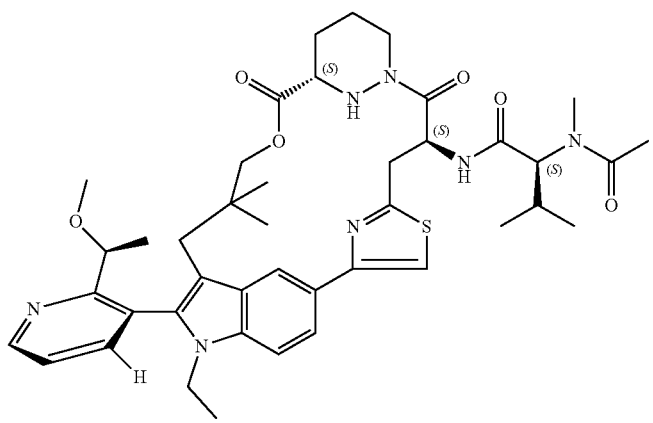 |
| A55 | 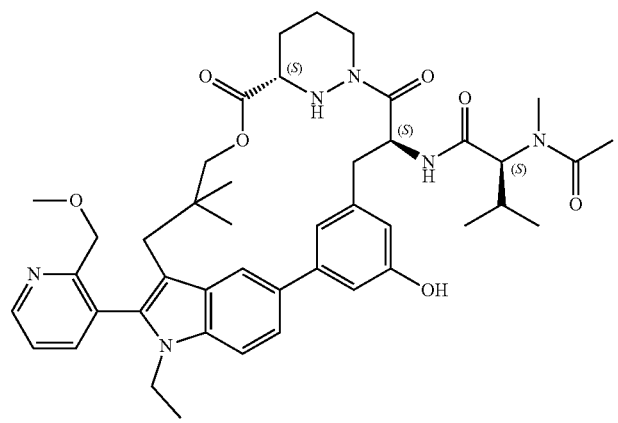 |

TABLE 1-continued
Certain Compounds of the Present Invention
| Ex# | Structure |
|---|---|
| A56 | 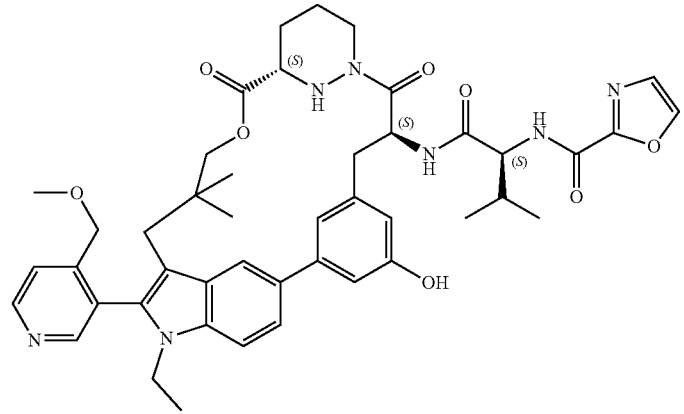 |
| A57 | 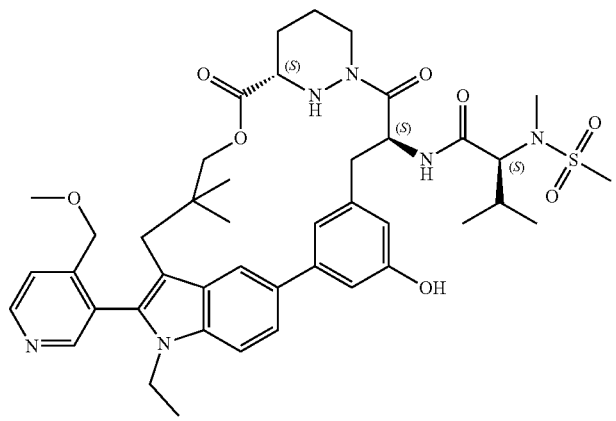 |
| A58 | 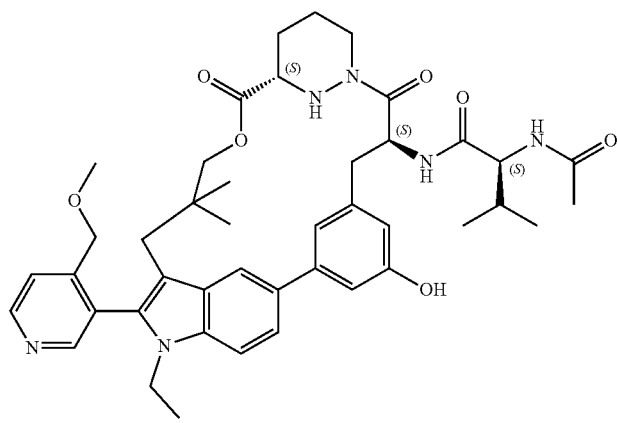 |

TABLE 1-continued
Certain Compounds of the Present Invention
| Ex# | Structure |
|---|---|
| A59 | 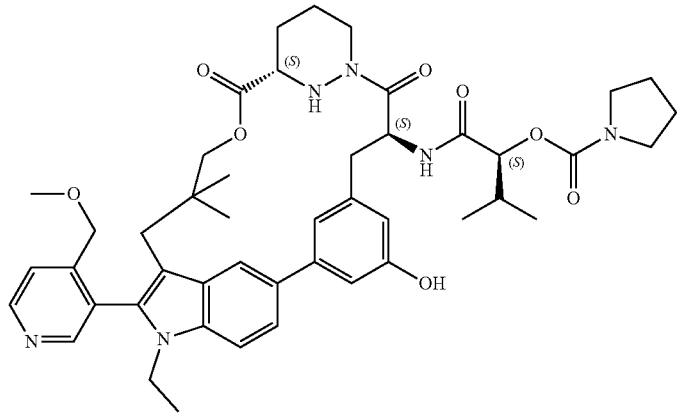 |
| A60 | 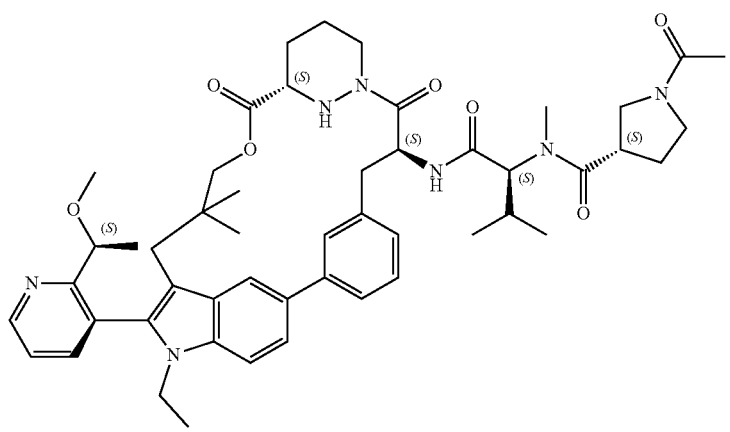 |
| A61 | 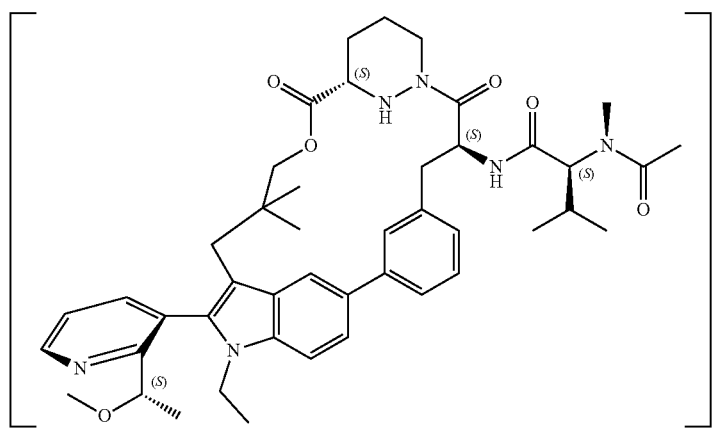 |

TABLE 1-continued
Certain Compounds of the Present Invention
| Ex# | Structure |
|---|---|
| A62 | 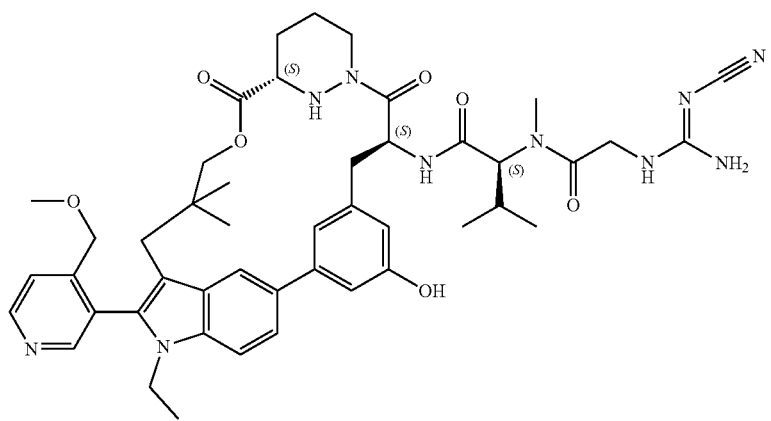 |
| A63 | 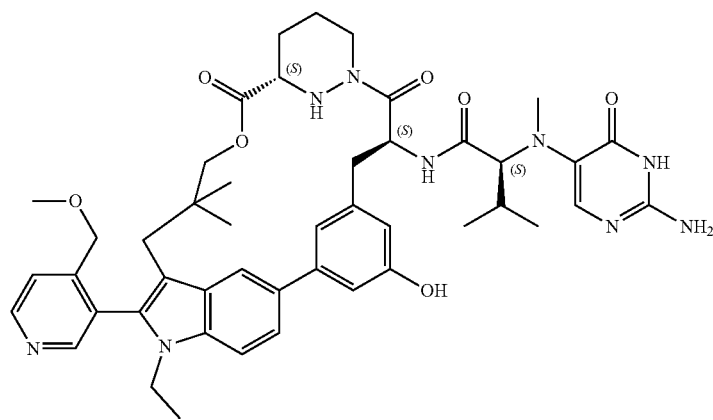 |
| A64 | 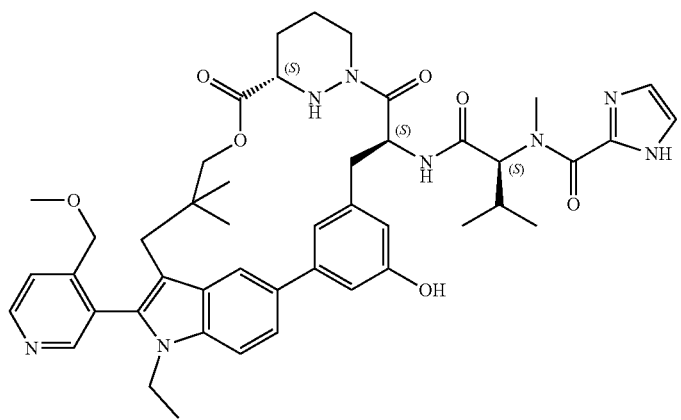 |

TABLE 1-continued
Certain Compounds of the Present Invention
| Ex# | Structure |
|---|---|
| A65 | 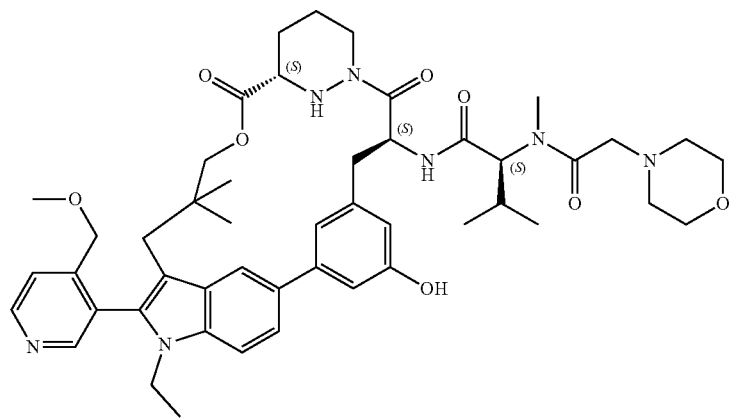 |
| A66 | 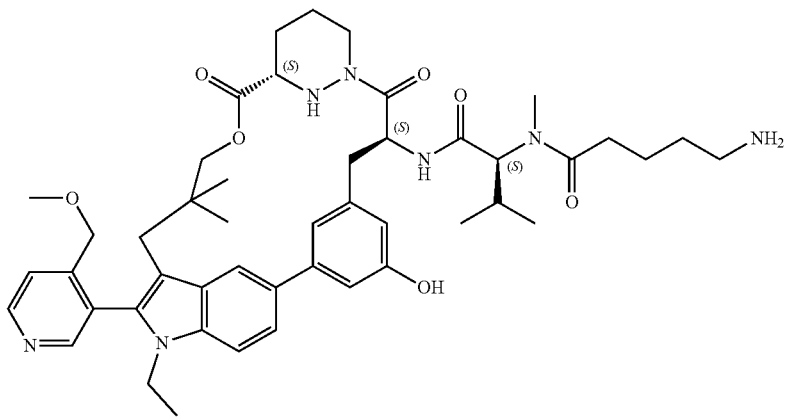 |
| A67 | 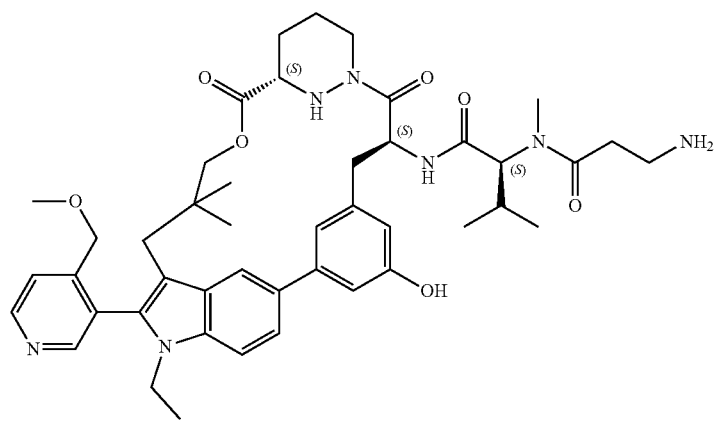 |

TABLE 1-continued
Certain Compounds of the Present Invention
| Ex# | Structure |
|---|---|
| A68 | 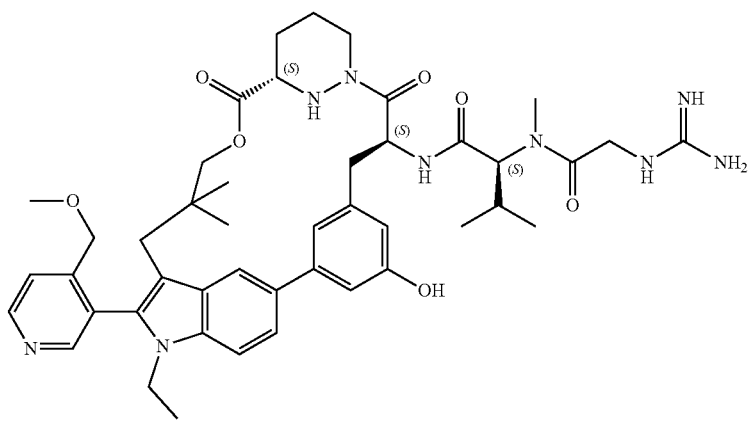 |
| A69 | 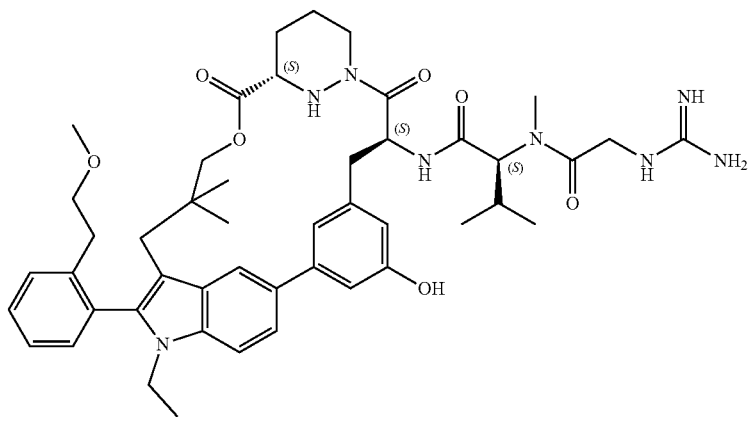 |
| A70 | 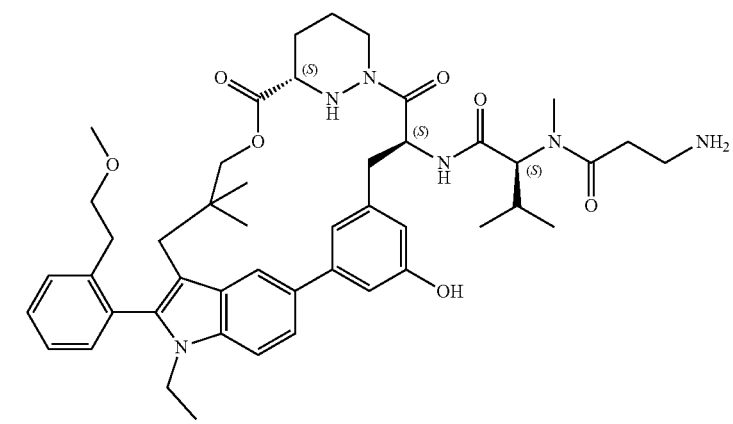 |

TABLE 1-continued
Certain Compounds of the Present Invention
| Ex# | Structure |
|---|---|
| A71 | 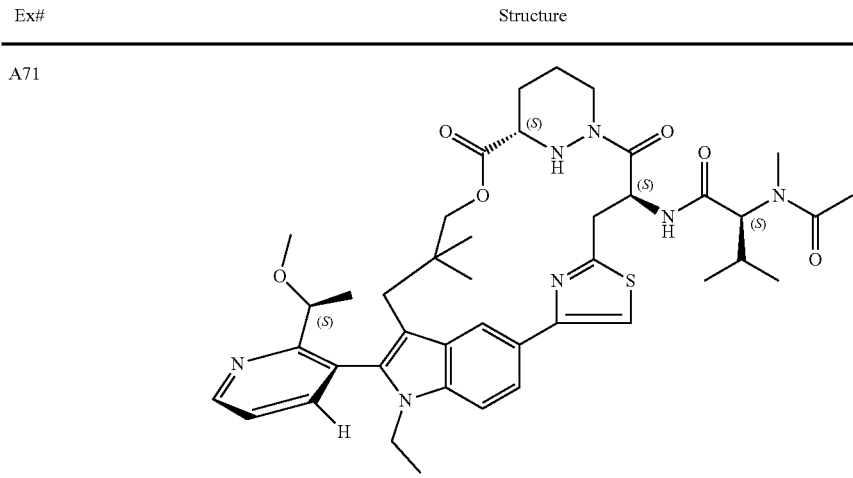 |
| A72 | 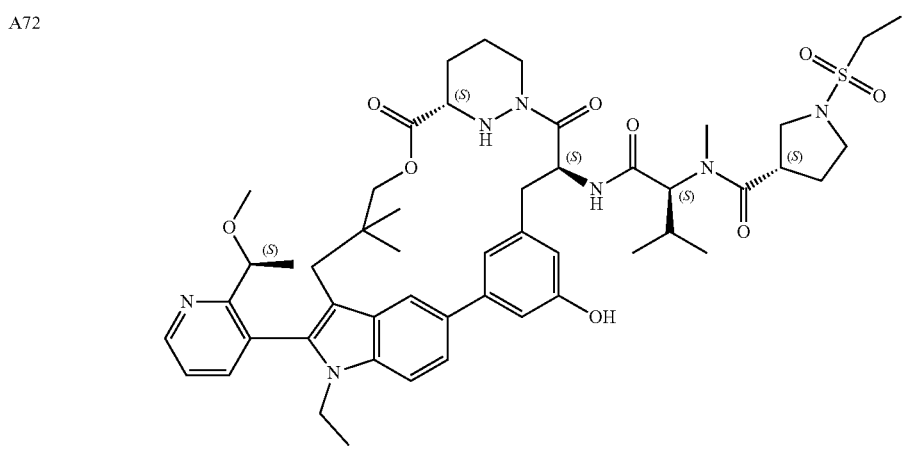 |
| A73 | 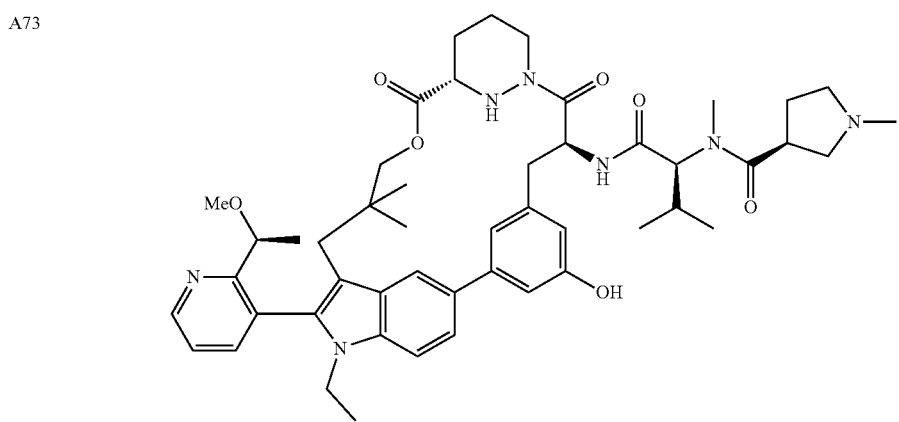 |
Molecular Weight: 864.10

TABLE 1-continued
Certain Compounds of the Present Invention
| Ex# | Structure |
|---|---|
| A74 | 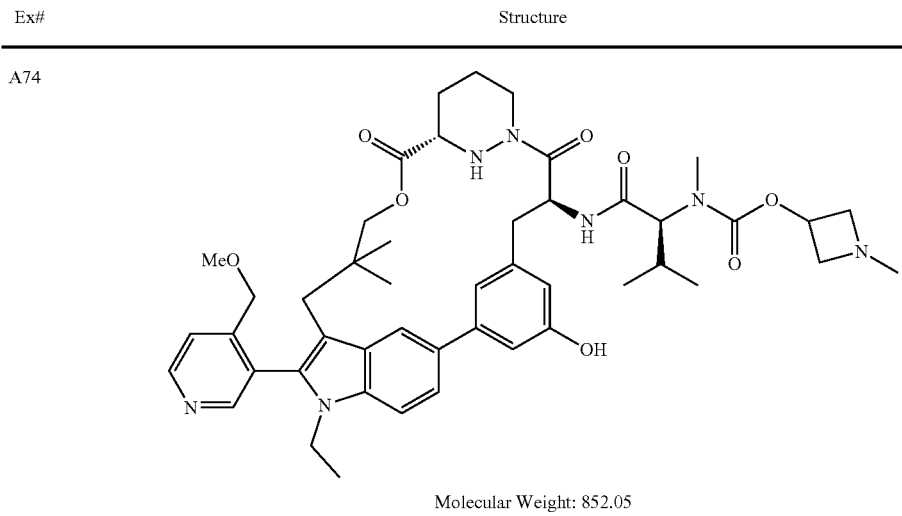<br>Molecular Weight: 852.05 |
| A75 | 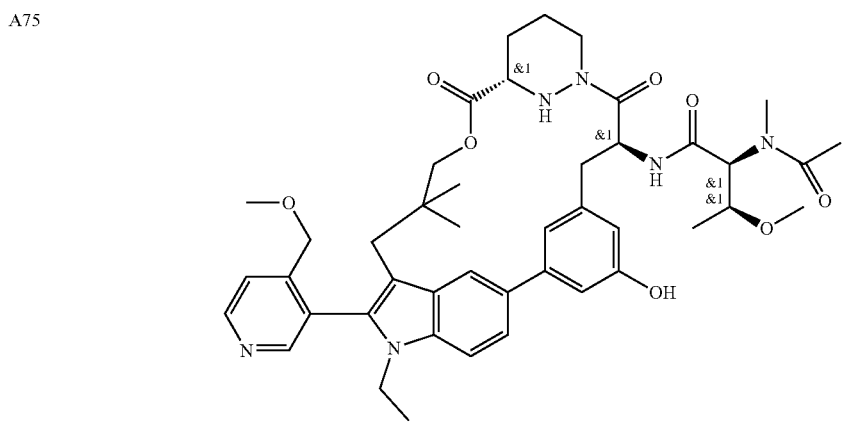 |
| A76 | 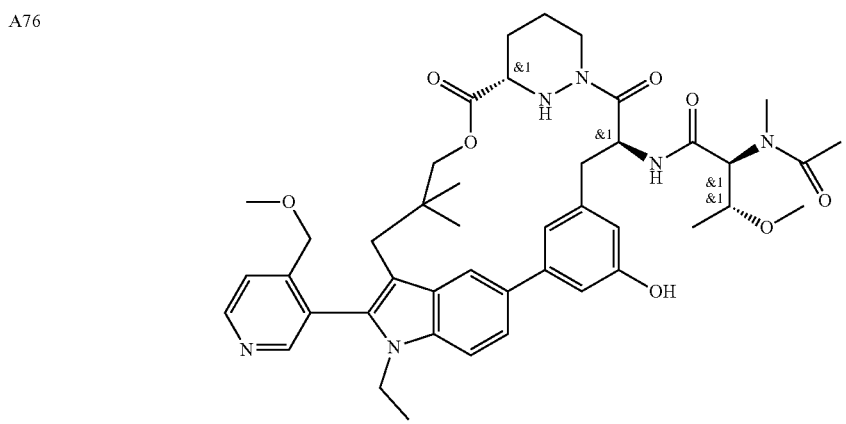 |

TABLE 1-continued

Certain Compounds of the Present Invention

| Ex# | Structure |
|---|---|
| A77 | 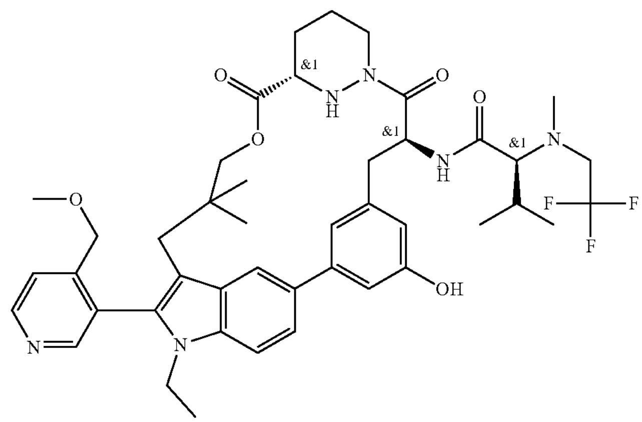 [SMILES: CCn1c(-c2cnccc2COC)c2c3cc(ccc31)-c1cc(O)cc(c1)C[C@H](NC(=O)[C@H](C(C)C)N(C)CC(F)(F)F)C(=O)N1CCC[C@H](N1)C(=O)OCC(C)(C)C2] |
| A78 | 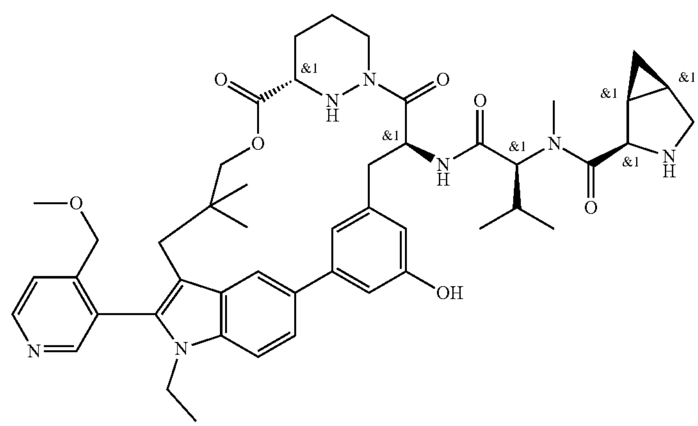 [SMILES: CCn1c(-c2cnccc2COC)c2c3cc(ccc31)-c1cc(O)cc(c1)C[C@H](NC(=O)[C@H](C(C)C)N(C)C(=O)[C@@H]1NC[C@@H]3C[C@@H]31)C(=O)N1CCC[C@H](N1)C(=O)OCC(C)(C)C2] |
| A79 | 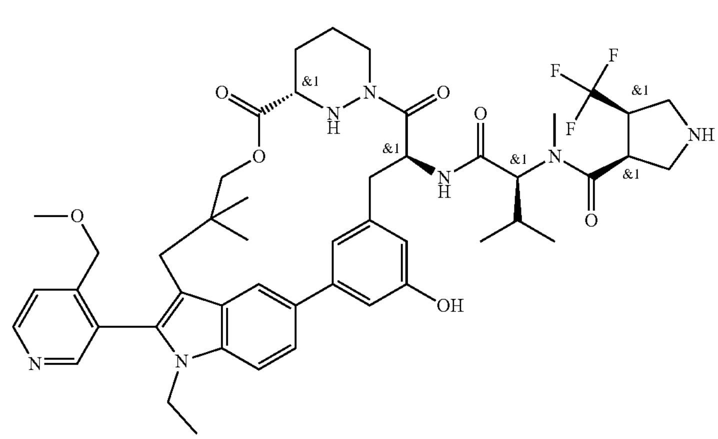 [SMILES: CCn1c(-c2cnccc2COC)c2c3cc(ccc31)-c1cc(O)cc(c1)C[C@H](NC(=O)[C@H](C(C)C)N(C)C(=O)[C@@H]1CNC[C@@H]1C(F)(F)F)C(=O)N1CCC[C@H](N1)C(=O)OCC(C)(C)C2] |

TABLE 1-continued

Certain Compounds of the Present Invention

| Ex# | Structure |
|---|---|
| A80 | 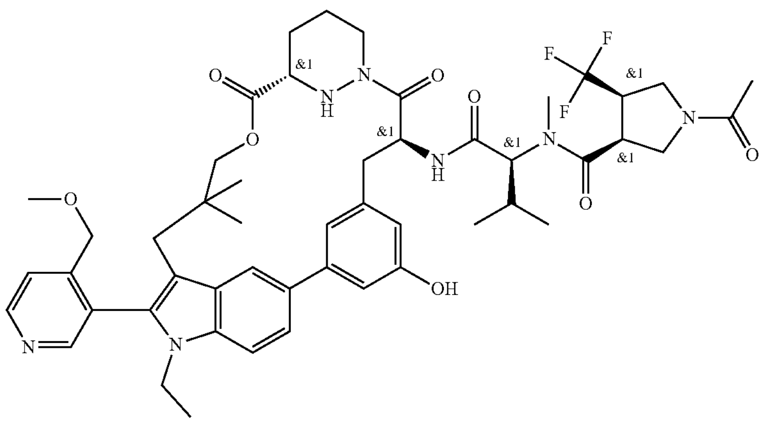 [SMILES: CCn1c(-c2cnccc2COC)c2c3cc(ccc31)-c1cc(O)cc(c1)C[C@H](NC(=O)[C@H](C(C)C)N(C)C(=O)[C@@H]1CN(C(C)=O)C[C@@H]1C(F)(F)F)C(=O)N1CCC[C@H](N1)C(=O)OCC(C)(C)C2] |
| A81 | 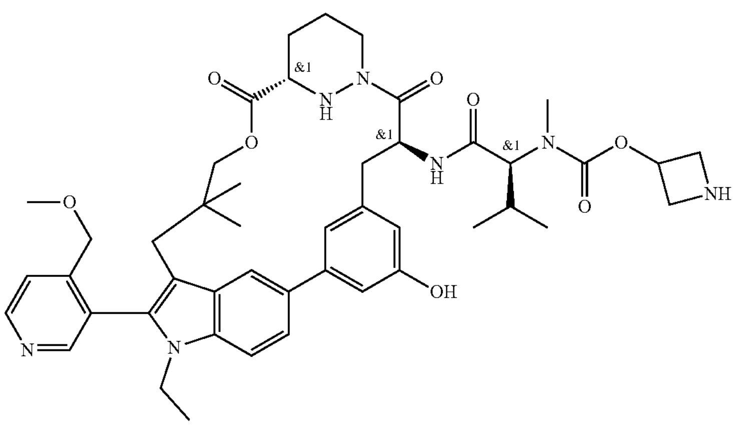 [SMILES: CCn1c(-c2cnccc2COC)c2c3cc(ccc31)-c1cc(O)cc(c1)C[C@H](NC(=O)[C@H](C(C)C)N(C)C(=O)OC1CNC1)C(=O)N1CCC[C@H](N1)C(=O)OCC(C)(C)C2] |
| A82 | 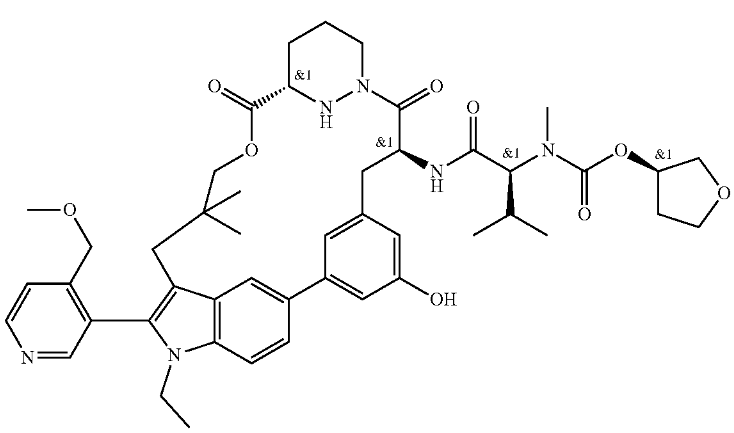 [SMILES: CCn1c(-c2cnccc2COC)c2c3cc(ccc31)-c1cc(O)cc(c1)C[C@H](NC(=O)[C@H](C(C)C)N(C)C(=O)O[C@@H]1CCOC1)C(=O)N1CCC[C@H](N1)C(=O)OCC(C)(C)C2] |

TABLE 1-continued

Certain Compounds of the Present Invention

| Ex# | Structure |
|---|---|
| A83 | 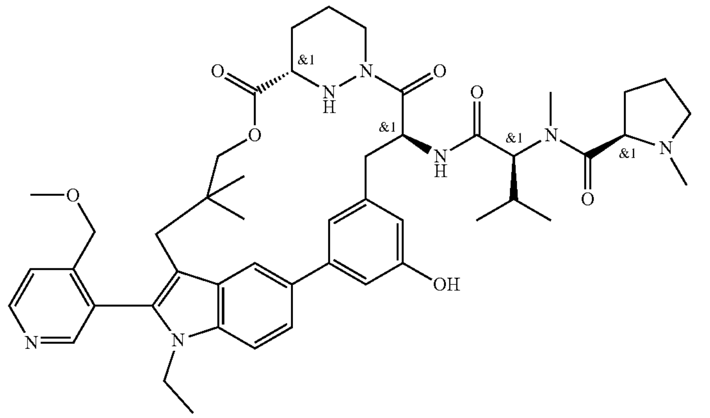 [SMILES: CCn1c(-c2cnccc2COC)c2c3cc(ccc31)-c1cc(O)cc(c1)C[C@H](NC(=O)[C@H](C(C)C)N(C)C(=O)[C@H]1CCCN1C)C(=O)N1CCC[C@H](N1)C(=O)OCC(C)(C)C2] |
| A84 | 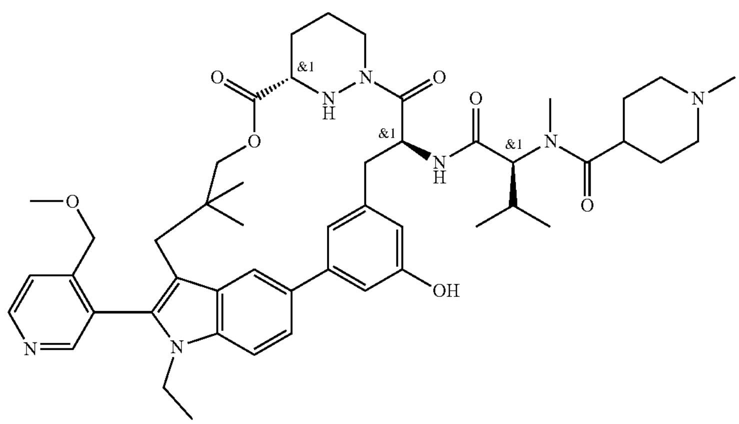 [SMILES: CCn1c(-c2cnccc2COC)c2c3cc(ccc31)-c1cc(O)cc(c1)C[C@H](NC(=O)[C@H](C(C)C)N(C)C(=O)C1CCN(C)CC1)C(=O)N1CCC[C@H](N1)C(=O)OCC(C)(C)C2] |
| A85 | 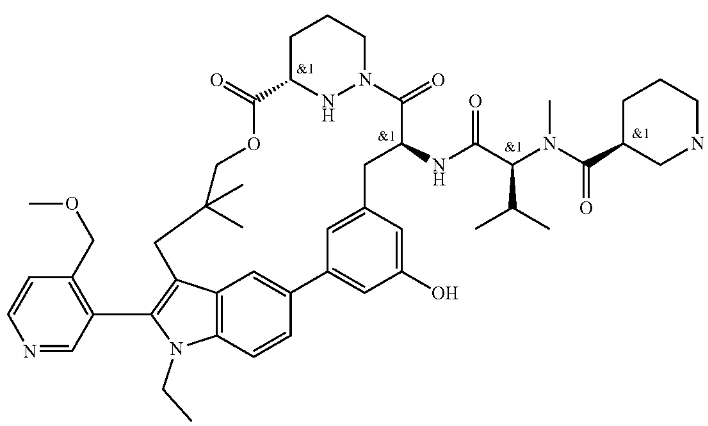 [SMILES: CCn1c(-c2cnccc2COC)c2c3cc(ccc31)-c1cc(O)cc(c1)C[C@H](NC(=O)[C@H](C(C)C)N(C)C(=O)[C@H]1CCCNC1)C(=O)N1CCC[C@H](N1)C(=O)OCC(C)(C)C2] |

TABLE 1-continued

Certain Compounds of the Present Invention

| Ex# | Structure |
|---|---|
| A86 | 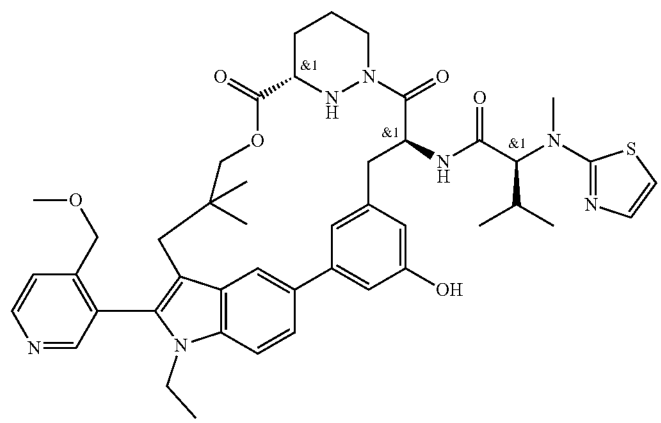 [SMILES: CCn1c(-c2cnccc2COC)c2c3cc(ccc31)-c1cc(O)cc(c1)C[C@H](NC(=O)[C@H](C(C)C)N(C)c1nccs1)C(=O)N1CCC[C@H](N1)C(=O)OCC(C)(C)C2] |
| A87 | 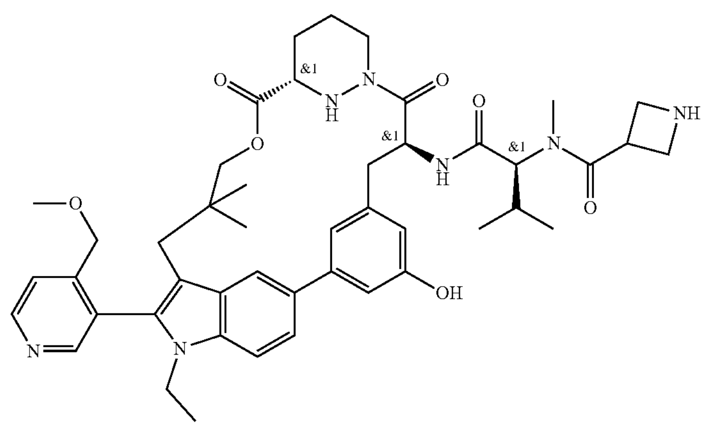 [SMILES: CCn1c(-c2cnccc2COC)c2c3cc(ccc31)-c1cc(O)cc(c1)C[C@H](NC(=O)[C@H](C(C)C)N(C)C(=O)C1CNC1)C(=O)N1CCC[C@H](N1)C(=O)OCC(C)(C)C2] |
| A88 | 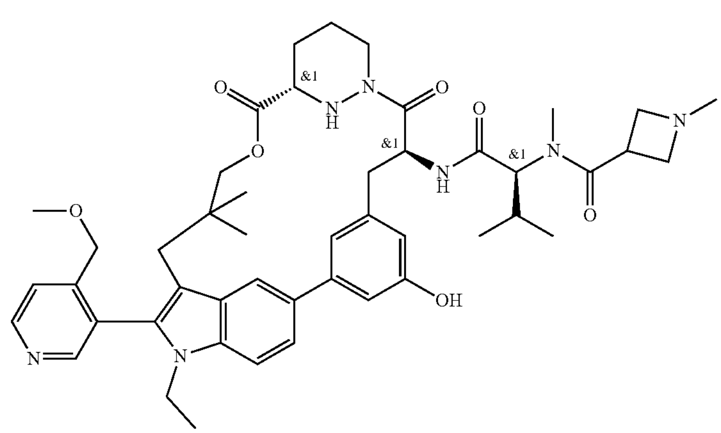 [SMILES: CCn1c(-c2cnccc2COC)c2c3cc(ccc31)-c1cc(O)cc(c1)C[C@H](NC(=O)[C@H](C(C)C)N(C)C(=O)C1CN(C)C1)C(=O)N1CCC[C@H](N1)C(=O)OCC(C)(C)C2] |

TABLE 1-continued
Certain Compounds of the Present Invention
| Ex# | Structure |
|---|---|
| A89 | 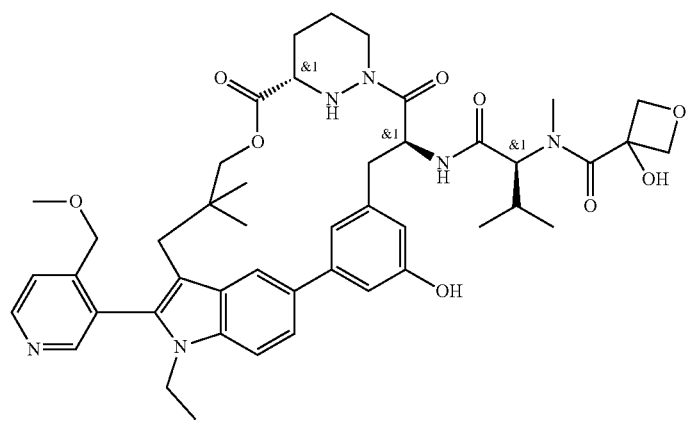 [SMILES: CCn1c(-c2cnccc2COC)c2c3cc(ccc31)-c1cc(O)cc(c1)C[C@H](NC(=O)[C@H](C(C)C)N(C)C(=O)C1(O)COC1)C(=O)N1CCC[C@H](N1)C(=O)OCC(C)(C)C2] |
| A90 | 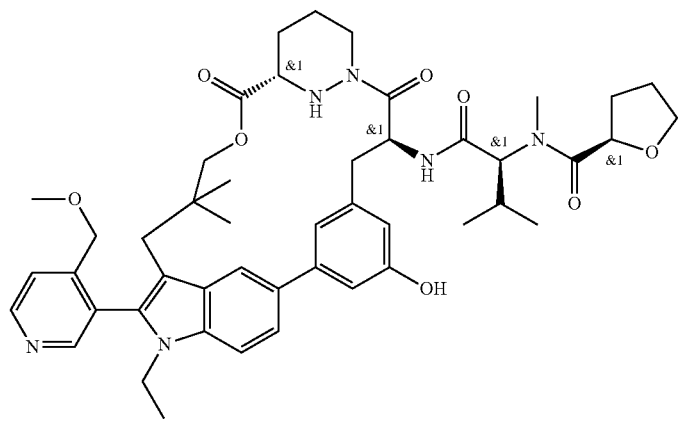 [SMILES: CCn1c(-c2cnccc2COC)c2c3cc(ccc31)-c1cc(O)cc(c1)C[C@H](NC(=O)[C@H](C(C)C)N(C)C(=O)[C@H]1CCCO1)C(=O)N1CCC[C@H](N1)C(=O)OCC(C)(C)C2] |
| A91 | 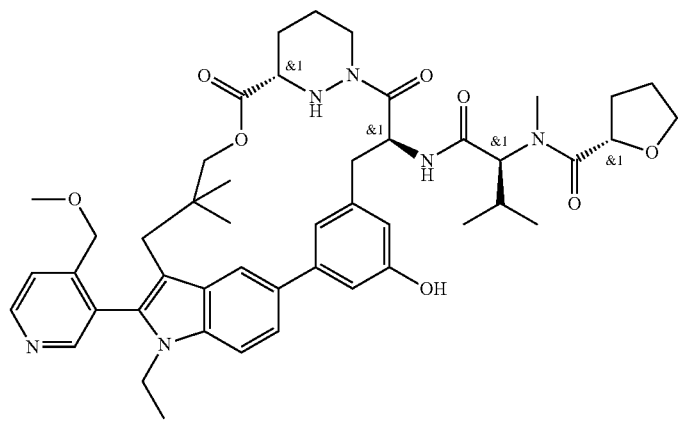 [SMILES: CCn1c(-c2cnccc2COC)c2c3cc(ccc31)-c1cc(O)cc(c1)C[C@H](NC(=O)[C@H](C(C)C)N(C)C(=O)[C@@H]1CCCO1)C(=O)N1CCC[C@H](N1)C(=O)OCC(C)(C)C2] |

TABLE 1-continued
Certain Compounds of the Present Invention
| Ex# | Structure |
|---|---|
| A92 | 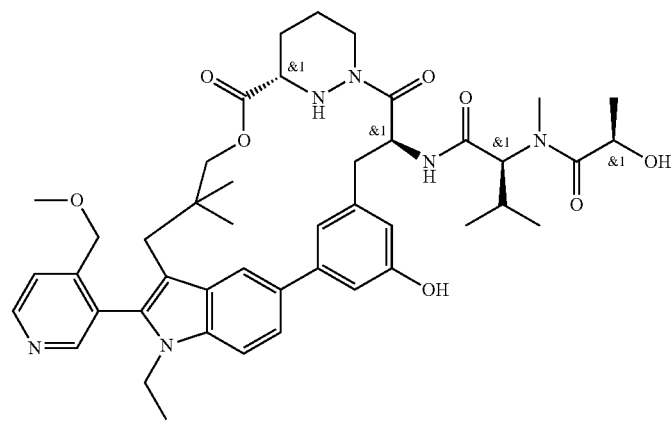 [SMILES: CCn1c(-c2cnccc2COC)c2c3cc(ccc31)-c1cc(O)cc(c1)C[C@H](NC(=O)[C@H](C(C)C)N(C)C(=O)[C@@H](C)O)C(=O)N1CCC[C@H](N1)C(=O)OCC(C)(C)C2] |
| A93 | 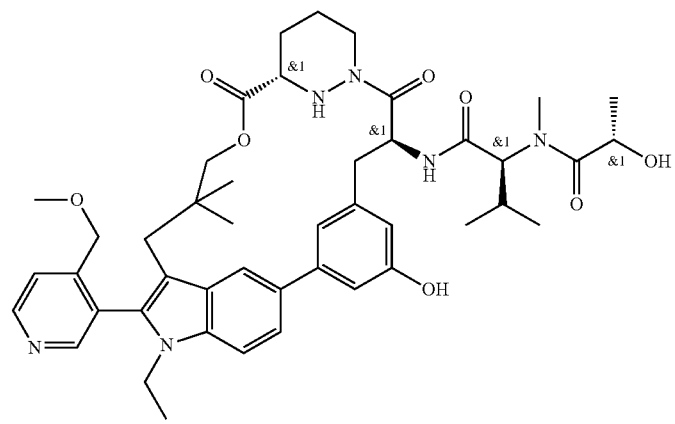 [SMILES: CCn1c(-c2cnccc2COC)c2c3cc(ccc31)-c1cc(O)cc(c1)C[C@H](NC(=O)[C@H](C(C)C)N(C)C(=O)[C@H](C)O)C(=O)N1CCC[C@H](N1)C(=O)OCC(C)(C)C2] |
| A94 | 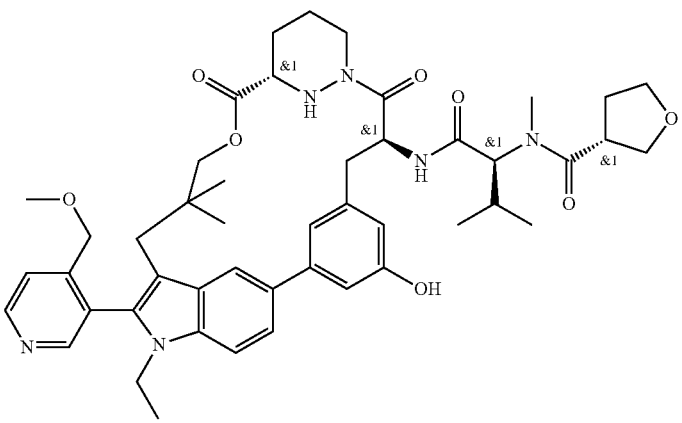 [SMILES: CCn1c(-c2cnccc2COC)c2c3cc(ccc31)-c1cc(O)cc(c1)C[C@H](NC(=O)[C@H](C(C)C)N(C)C(=O)[C@@H]1CCOC1)C(=O)N1CCC[C@H](N1)C(=O)OCC(C)(C)C2] |

TABLE 1-continued
Certain Compounds of the Present Invention
| Ex# | Structure |
|---|---|
| A95 | 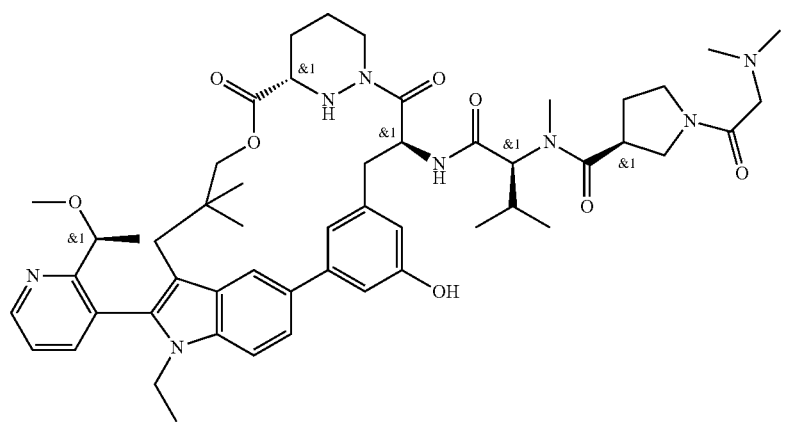 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@H]1CCN(C(=O)CN(C)C)C1)C(=O)N1CCC[C@H](N1)C(=O)OCC(C)(C)C2] |
| A96 | 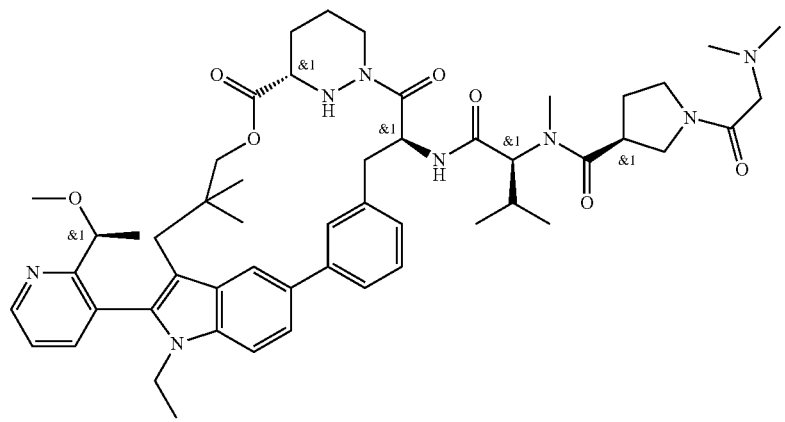 [SMILES: CCn1c(-c2cccnc2[C@H](C)OC)c2c3cc(ccc31)-c1cccc(c1)C[C@H](NC(=O)[C@H](C(C)C)N(C)C(=O)[C@H]1CCN(C(=O)CN(C)C)C1)C(=O)N1CCC[C@H](N1)C(=O)OCC(C)(C)C2] |
| A97 | 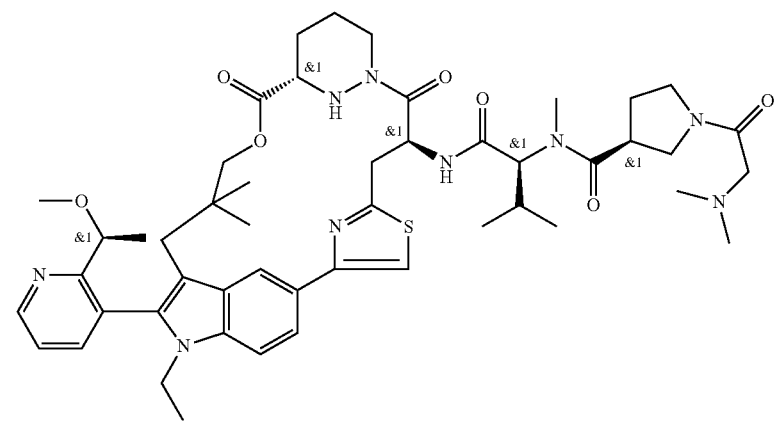 |

TABLE 1-continued

Certain Compounds of the Present Invention

| Ex# | Structure |
|---|---|
| A98 | 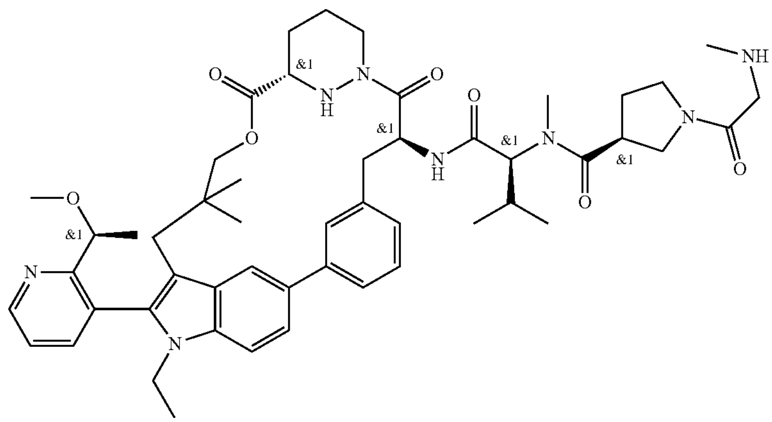 [SMILES: CCn1c(-c2cccnc2[C@H](C)OC)c2c3cc(ccc31)-c1cccc(c1)C[C@H](NC(=O)[C@H](C(C)C)N(C)C(=O)[C@H]1CCN(C(=O)CNC)C1)C(=O)N1CCC[C@H](N1)C(=O)OCC(C)(C)C2] |
| A99 | 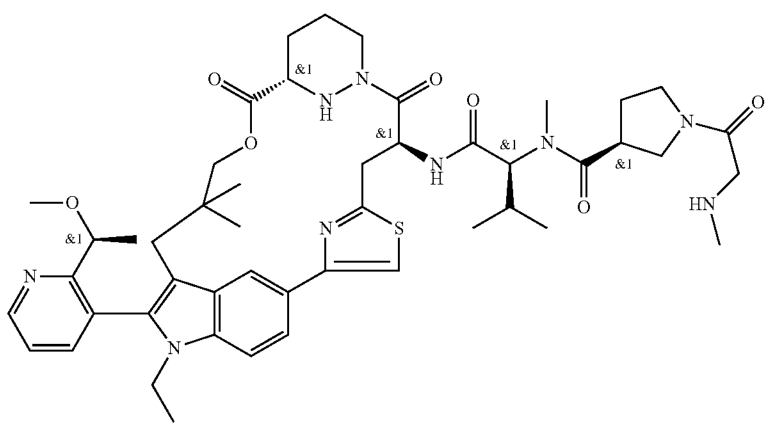 [SMILES: CCn1c(-c2cccnc2[C@H](C)OC)c2c3cc(ccc31)-c1csc(n1)C[C@H](NC(=O)[C@H](C(C)C)N(C)C(=O)[C@H]1CCN(C(=O)CNC)C1)C(=O)N1CCC[C@H](N1)C(=O)OCC(C)(C)C2] |
| A100 | 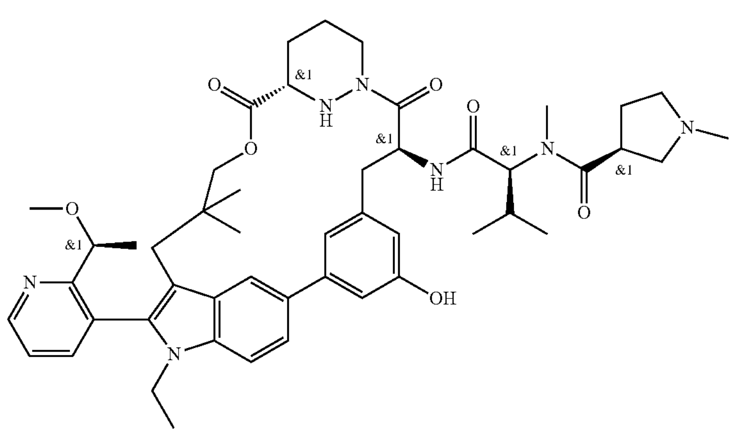 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@H]1CCN(C)C1)C(=O)N1CCC[C@H](N1)C(=O)OCC(C)(C)C2] |

TABLE 1-continued

Certain Compounds of the Present Invention

| Ex# | Structure |
|---|---|
| A101 | 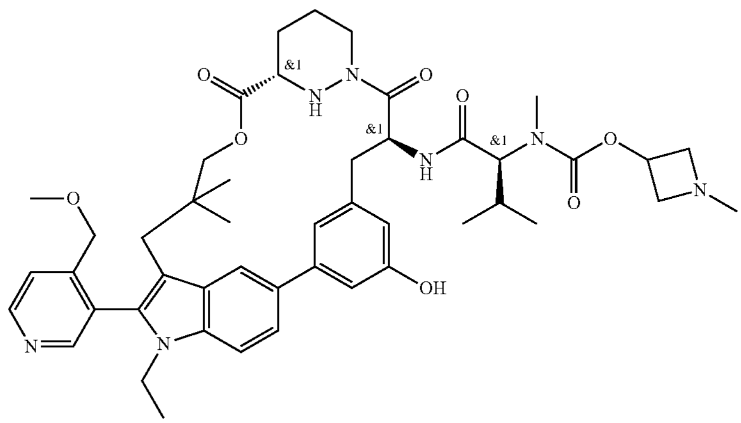 [SMILES: CCn1c(-c2cnccc2COC)c2c3cc(ccc31)-c1cc(O)cc(c1)C[C@H](NC(=O)[C@H](C(C)C)N(C)C(=O)OC1CN(C)C1)C(=O)N1CCC[C@H](N1)C(=O)OCC(C)(C)C2] |
| A102 | 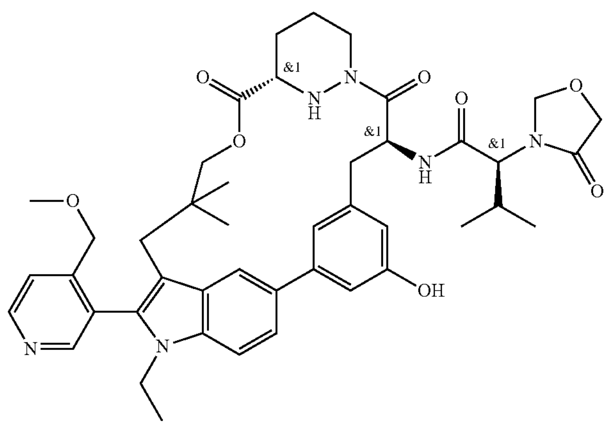 [SMILES: CCn1c(-c2cnccc2COC)c2c3cc(ccc31)-c1cc(O)cc(c1)C[C@H](NC(=O)[C@H](C(C)C)N1COCC1=O)C(=O)N1CCC[C@H](N1)C(=O)OCC(C)(C)C2] |
| A103 | 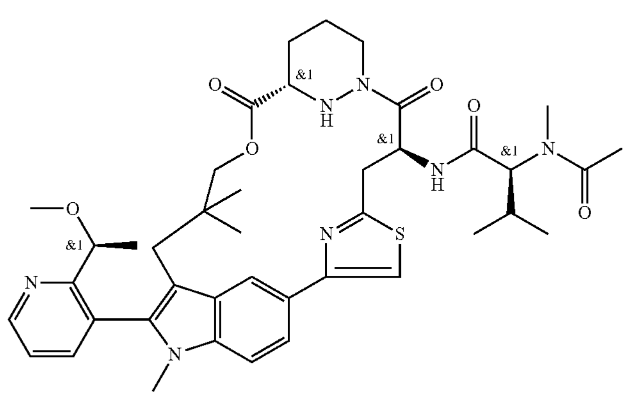 [SMILES: CO[C@@H](C)c1ncccc1-c1c2c3cc(ccc3n1C)-c1csc(n1)C[C@H](NC(=O)[C@H](C(C)C)N(C)C(C)=O)C(=O)N1CCC[C@H](N1)C(=O)OCC(C)(C)C2] |

TABLE 1-continued

Certain Compounds of the Present Invention

| Ex# | Structure |
|---|---|
| A104 | 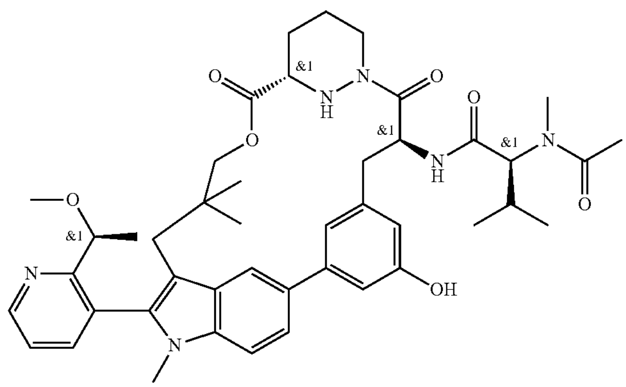 [SMILES: CO[C@@H](C)c1ncccc1-c1c2c3cc(ccc3n1C)-c1cc(O)cc(c1)C[C@H](NC(=O)[C@H](C(C)C)N(C)C(C)=O)C(=O)N1CCC[C@H](N1)C(=O)OCC(C)(C)C2] |
| A105 | 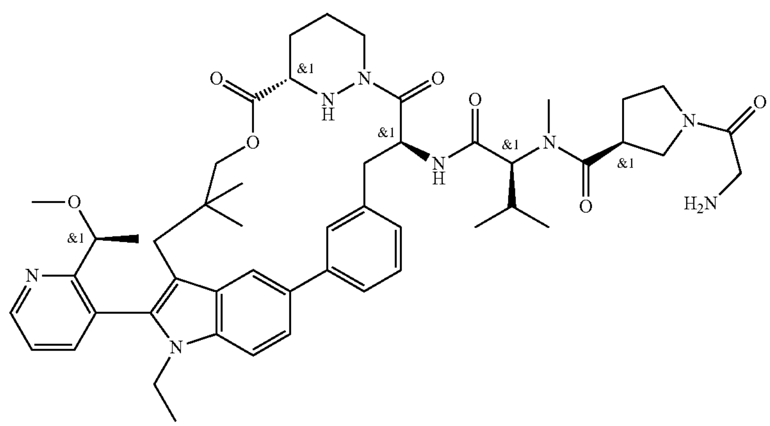 [SMILES: CCn1c(-c2cccnc2[C@H](C)OC)c2c3cc(ccc31)-c1cccc(c1)C[C@H](NC(=O)[C@H](C(C)C)N(C)C(=O)[C@H]1CCN(C(=O)CN)C1)C(=O)N1CCC[C@H](N1)C(=O)OCC(C)(C)C2] |
| A106 | 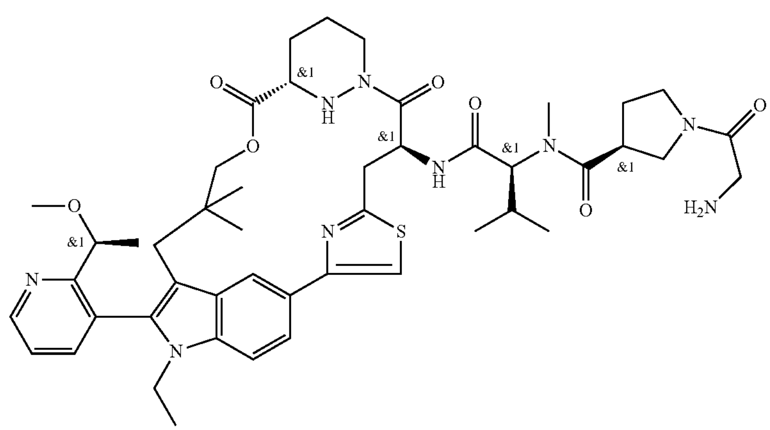 [SMILES: CCn1c(-c2cccnc2[C@H](C)OC)c2c3cc(ccc31)-c1csc(n1)C[C@H](NC(=O)[C@H](C(C)C)N(C)C(=O)[C@H]1CCN(C(=O)CN)C1)C(=O)N1CCC[C@H](N1)C(=O)OCC(C)(C)C2] |

TABLE 1-continued
Certain Compounds of the Present Invention
| Ex# | Structure |
|---|---|
| A107 | 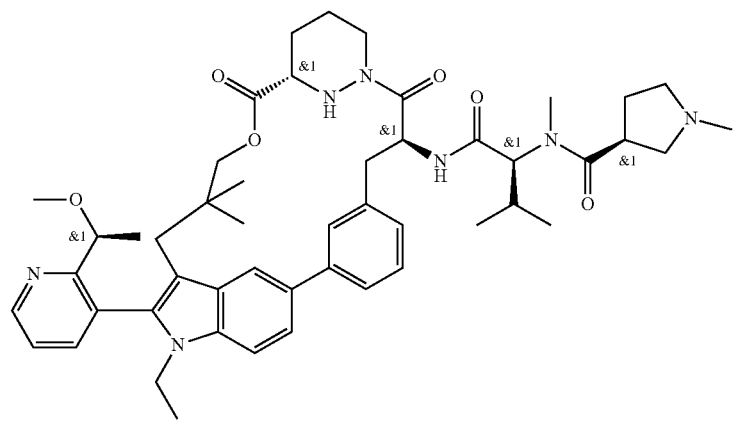 [SMILES: CCn1c(-c2cccnc2[C@H](C)OC)c2c3cc(ccc31)-c1cccc(c1)C[C@H](NC(=O)[C@H](C(C)C)N(C)C(=O)[C@H]1CCN(C)C1)C(=O)N1CCC[C@H](N1)C(=O)OCC(C)(C)C2] |
| A108 | 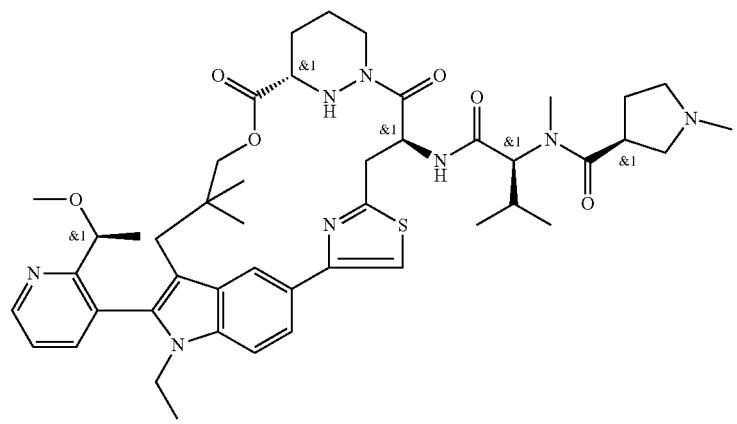 [SMILES: CCn1c(-c2cccnc2[C@H](C)OC)c2c3cc(ccc31)-c1csc(n1)C[C@H](NC(=O)[C@H](C(C)C)N(C)C(=O)[C@H]1CCN(C)C1)C(=O)N1CCC[C@H](N1)C(=O)OCC(C)(C)C2] |
| A109 | 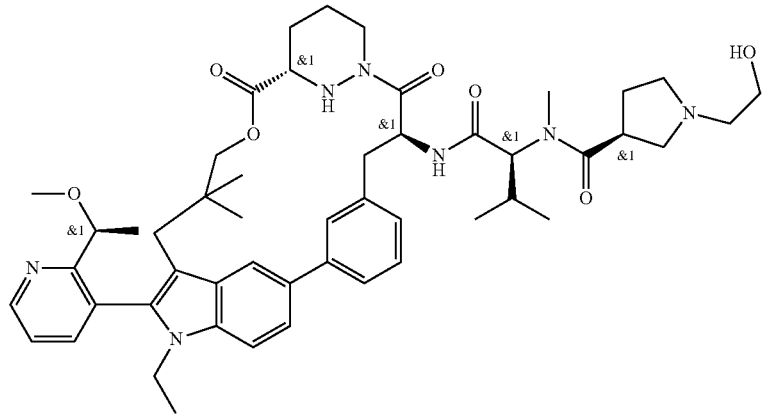 [SMILES: CCn1c(-c2cccnc2[C@H](C)OC)c2c3cc(ccc31)-c1cccc(c1)C[C@H](NC(=O)[C@H](C(C)C)N(C)C(=O)[C@H]1CCN(CCO)C1)C(=O)N1CCC[C@H](N1)C(=O)OCC(C)(C)C2] |

TABLE 1-continued
Certain Compounds of the Present Invention
| Ex# | Structure |
|---|---|
| A110 | 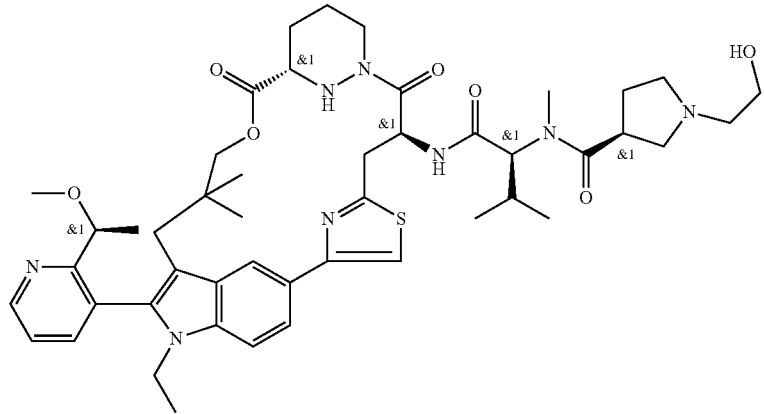 [SMILES: CCn1c(-c2cccnc2[C@H](C)OC)c2c3cc(ccc31)-c1csc(n1)C[C@H](NC(=O)[C@H](C(C)C)N(C)C(=O)[C@H]1CCN(CCO)C1)C(=O)N1CCC[C@H](N1)C(=O)OCC(C)(C)C2] |
| A111 | 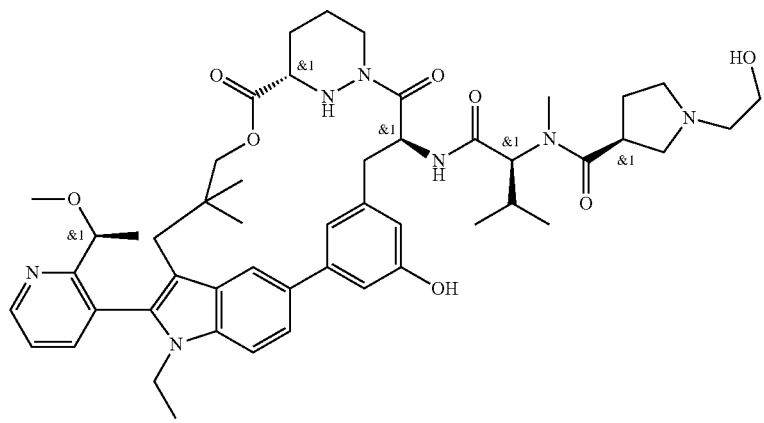 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@H]1CCN(CCO)C1)C(=O)N1CCC[C@H](N1)C(=O)OCC(C)(C)C2] |
| A112 | 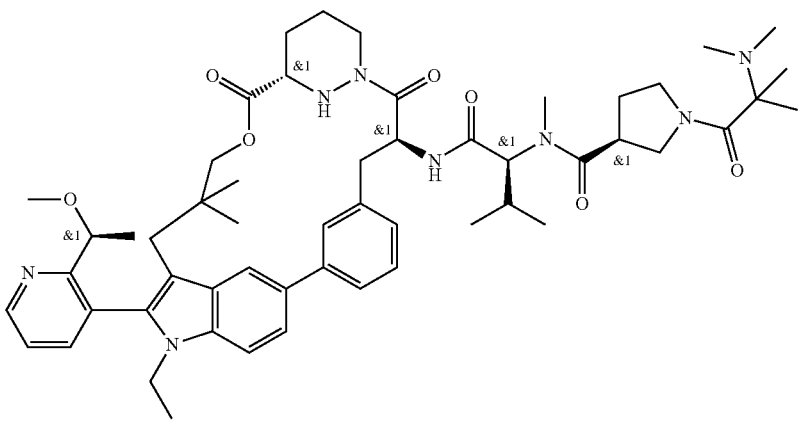 [SMILES: CCn1c(-c2cccnc2[C@H](C)OC)c2c3cc(ccc31)-c1cccc(c1)C[C@H](NC(=O)[C@H](C(C)C)N(C)C(=O)[C@H]1CCN(C(=O)C(C)(C)N(C)C)C1)C(=O)N1CCC[C@H](N1)C(=O)OCC(C)(C)C2] |

TABLE 1-continued
Certain Compounds of the Present Invention
| Ex# | Structure |
|---|---|
| A113 | 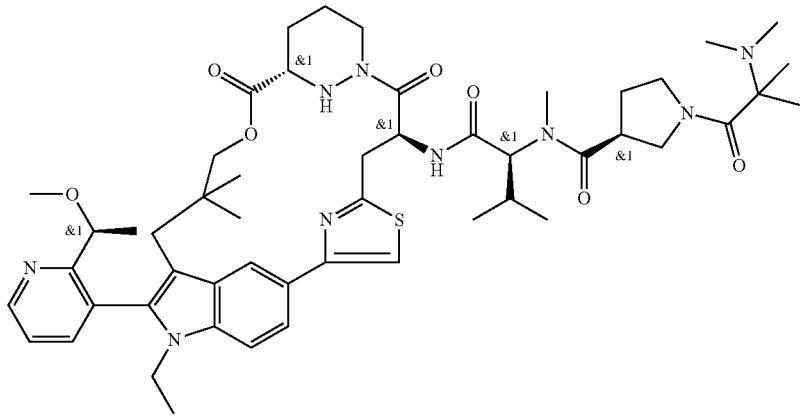 [SMILES: CCn1c(-c2cccnc2[C@H](C)OC)c2c3cc(ccc31)-c1csc(n1)C[C@H](NC(=O)[C@H](C(C)C)N(C)C(=O)[C@H]1CCN(C(=O)C(C)(C)N(C)C)C1)C(=O)N1CCC[C@H](N1)C(=O)OCC(C)(C)C2] |
| A114 | 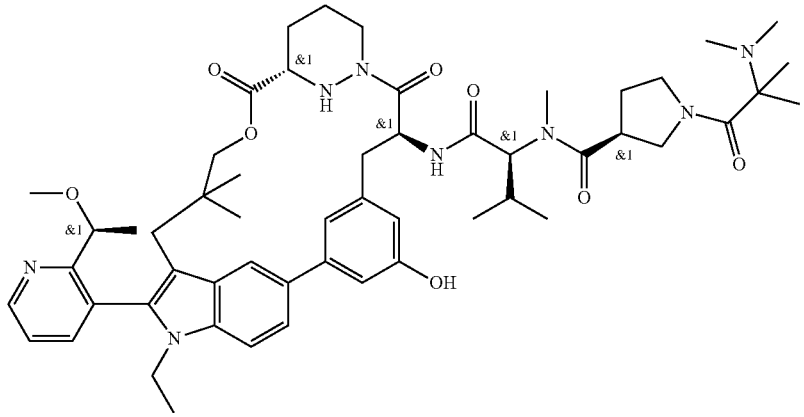 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@H]1CCN(C(=O)C(C)(C)N(C)C)C1)C(=O)N1CCC[C@H](N1)C(=O)OCC(C)(C)C2] |
| A115 | 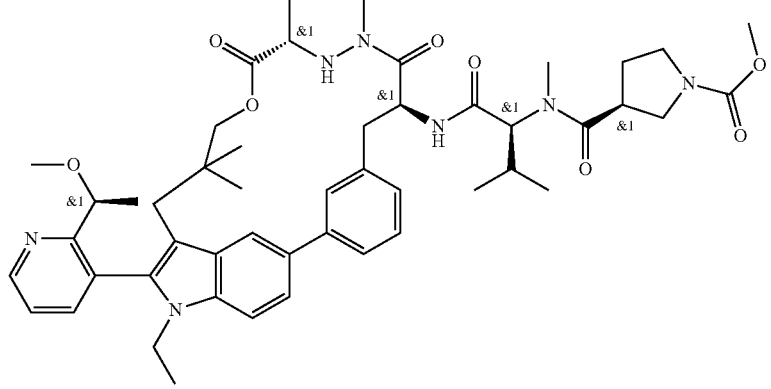 |

TABLE 1-continued
Certain Compounds of the Present Invention
| Ex# | Structure |
|---|---|
| A116 | 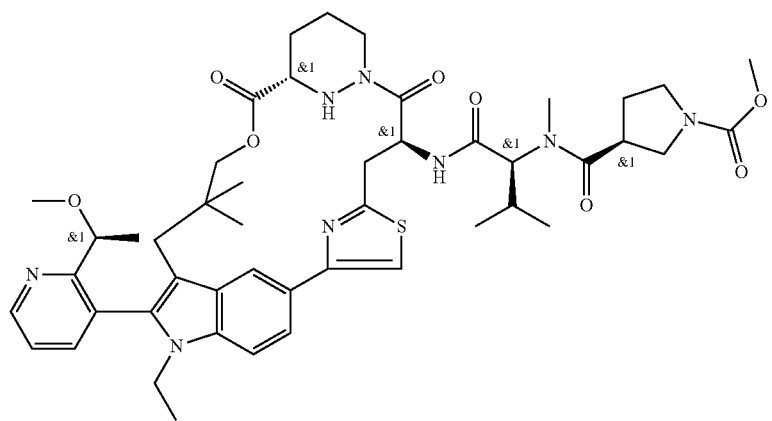 [SMILES: CCn1c(-c2cccnc2[C@H](C)OC)c2c3cc(ccc31)-c1csc(n1)C[C@H](NC(=O)[C@H](C(C)C)N(C)C(=O)[C@H]1CCN(C(=O)OC)C1)C(=O)N1CCC[C@H](N1)C(=O)OCC(C)(C)C2] |
| A117 | 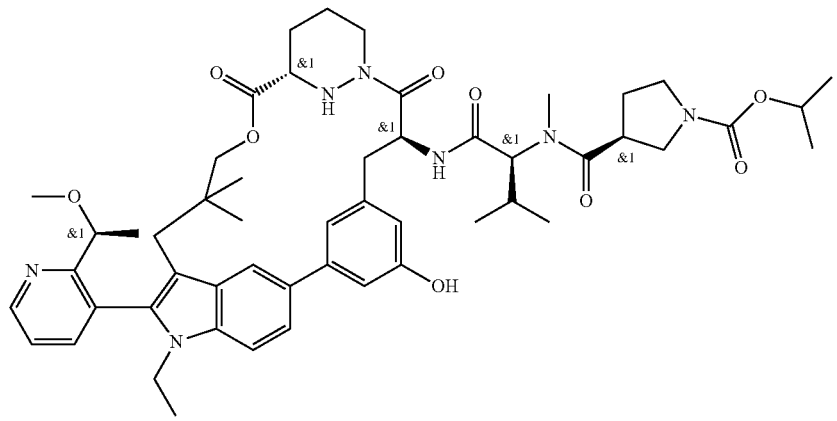 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@H]1CCN(C(=O)OC(C)C)C1)C(=O)N1CCC[C@H](N1)C(=O)OCC(C)(C)C2] |
| A118 | 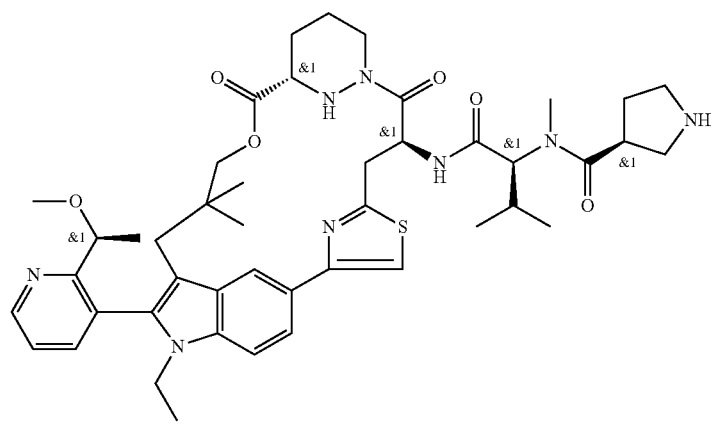 [SMILES: CCn1c(-c2cccnc2[C@H](C)OC)c2c3cc(ccc31)-c1csc(n1)C[C@H](NC(=O)[C@H](C(C)C)N(C)C(=O)[C@H]1CCNC1)C(=O)N1CCC[C@H](N1)C(=O)OCC(C)(C)C2] |

TABLE 1-continued

Certain Compounds of the Present Invention

| Ex# | Structure |
|---|---|
| A119 | 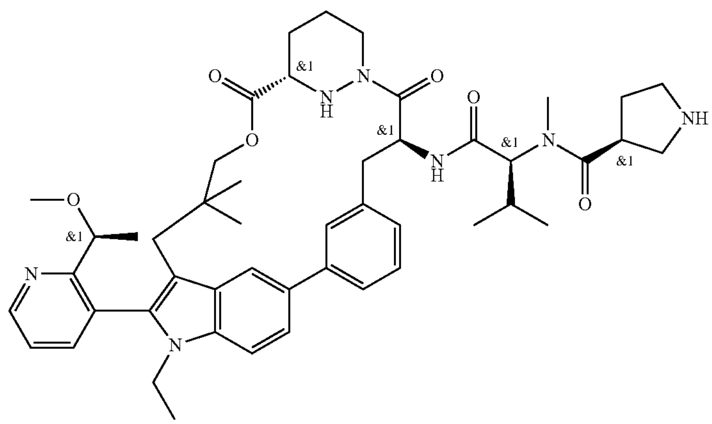 [SMILES: CCn1c(-c2cccnc2[C@H](C)OC)c2c3cc(ccc31)-c1cccc(c1)C[C@H](NC(=O)[C@H](C(C)C)N(C)C(=O)[C@H]1CCNC1)C(=O)N1CCC[C@H](N1)C(=O)OCC(C)(C)C2] |
| A120 | 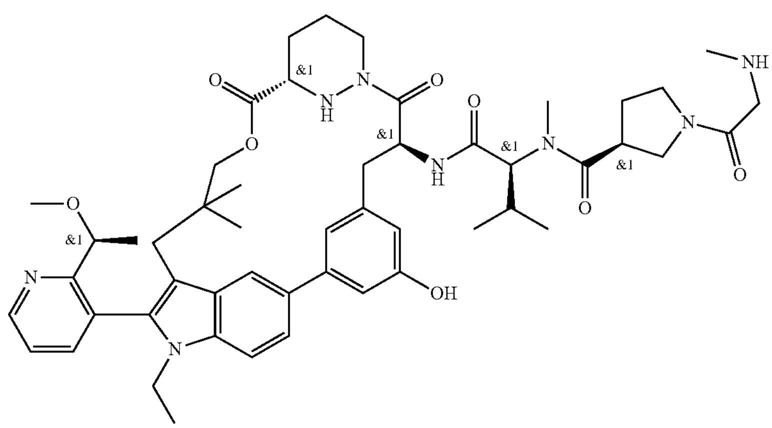 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@H]1CCN(C(=O)CNC)C1)C(=O)N1CCC[C@H](N1)C(=O)OCC(C)(C)C2] |
| A121 | 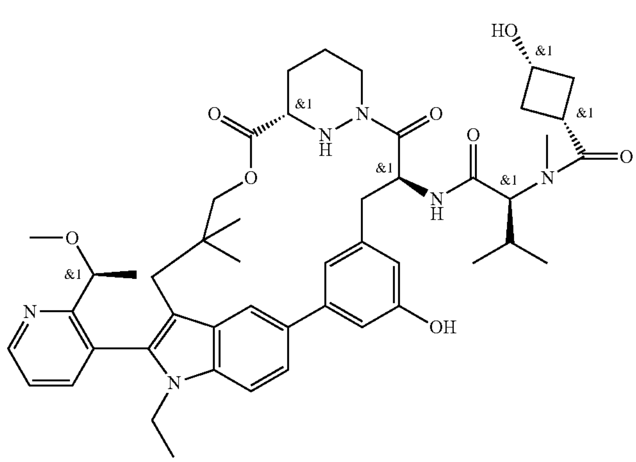 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@H]1C[C@@H](O)C1)C(=O)N1CCC[C@H](N1)C(=O)OCC(C)(C)C2] |

TABLE 1-continued
Certain Compounds of the Present Invention
| Ex# | Structure |
|---|---|
| A122 | 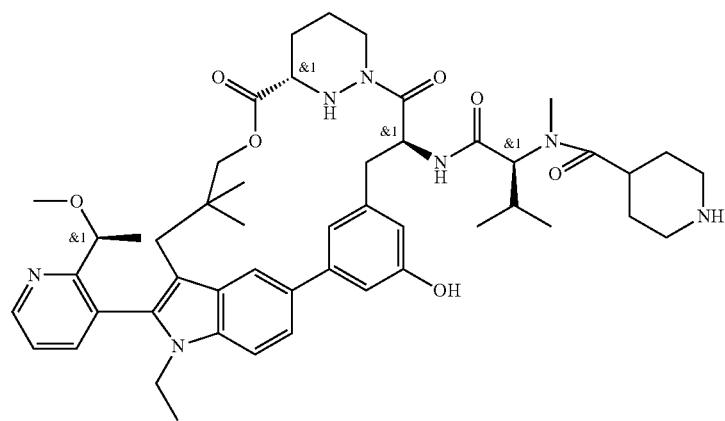 [SMILES: CCn1c(-c2cccnc2[C@H](C)OC)c2c3cc(ccc31)-c1cc(O)cc(c1)C[C@H](NC(=O)[C@H](C(C)C)N(C)C(=O)C1CCNCC1)C(=O)N1CCC[C@H](N1)C(=O)OCC(C)(C)C2] |
| A123 | 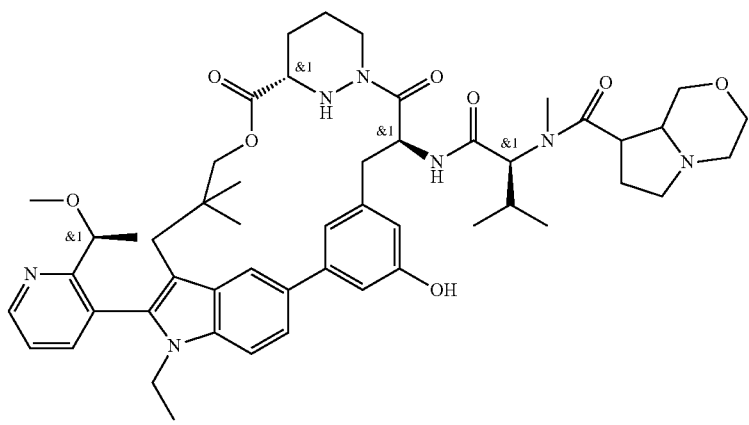 [SMILES: CCn1c(-c2cccnc2[C@H](C)OC)c2c3cc(ccc31)-c1cc(O)cc(c1)C[C@H](NC(=O)[C@H](C(C)C)N(C)C(=O)C1CCN3CCOCC13)C(=O)N1CCC[C@H](N1)C(=O)OCC(C)(C)C2] |
| A124 | 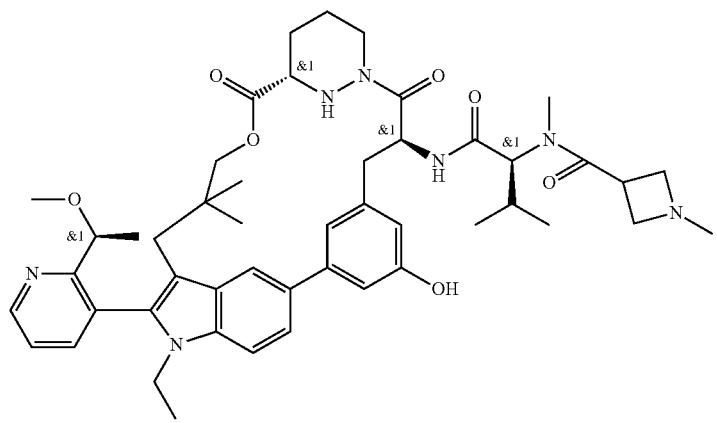 [SMILES: CCn1c(-c2cccnc2[C@H](C)OC)c2c3cc(ccc31)-c1cc(O)cc(c1)C[C@H](NC(=O)[C@H](C(C)C)N(C)C(=O)C1CN(C)C1)C(=O)N1CCC[C@H](N1)C(=O)OCC(C)(C)C2] |

TABLE 1-continued
Certain Compounds of the Present Invention
| Ex# | Structure |
|---|---|
| A125 | 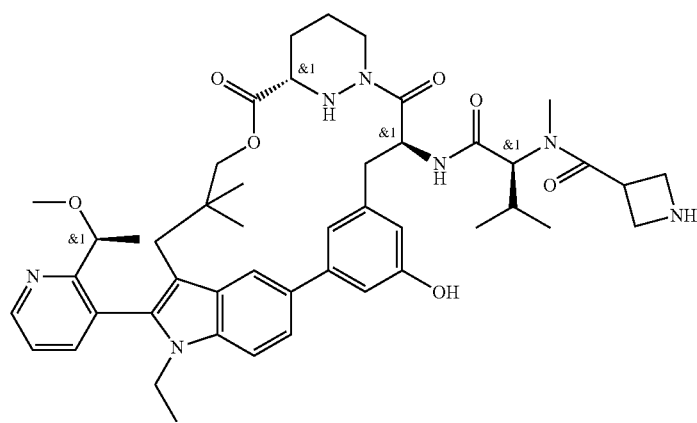 [SMILES: CCn1c(-c2cccnc2[C@H](C)OC)c2c3cc(ccc31)-c1cc(O)cc(c1)C[C@H](NC(=O)[C@H](C(C)C)N(C)C(=O)C1CNC1)C(=O)N1CCC[C@H](N1)C(=O)OCC(C)(C)C2] |
| A126 | 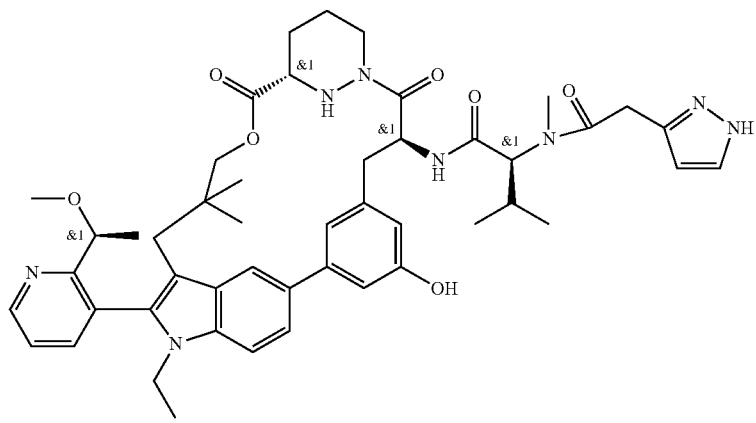 [SMILES: CCn1c(-c2cccnc2[C@H](C)OC)c2c3cc(ccc31)-c1cc(O)cc(c1)C[C@H](NC(=O)[C@H](C(C)C)N(C)C(=O)Cc1cc[nH]n1)C(=O)N1CCC[C@H](N1)C(=O)OCC(C)(C)C2] |
| A127 | 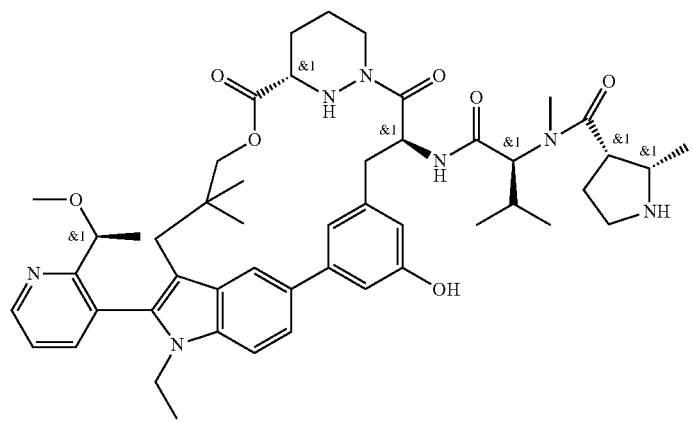 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@H]1CCN[C@H]1C)C(=O)N1CCC[C@H](N1)C(=O)OCC(C)(C)C2] |

TABLE 1-continued
Certain Compounds of the Present Invention
| Ex# | Structure |
|---|---|
| A128 | 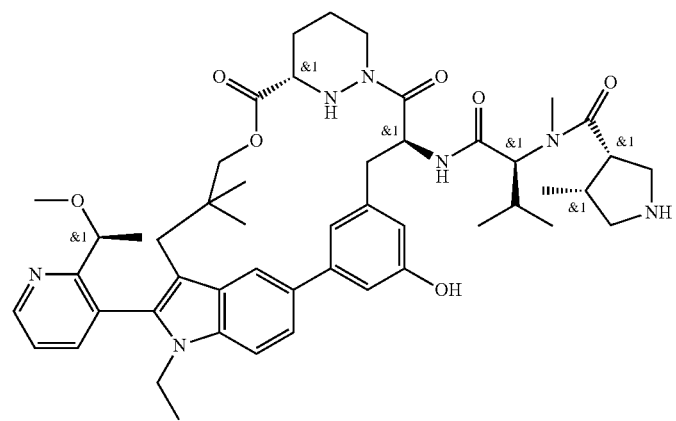 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@@H]1CNC[C@@H]1C)C(=O)N1CCC[C@H](N1)C(=O)OCC(C)(C)C2] |
| A129 | 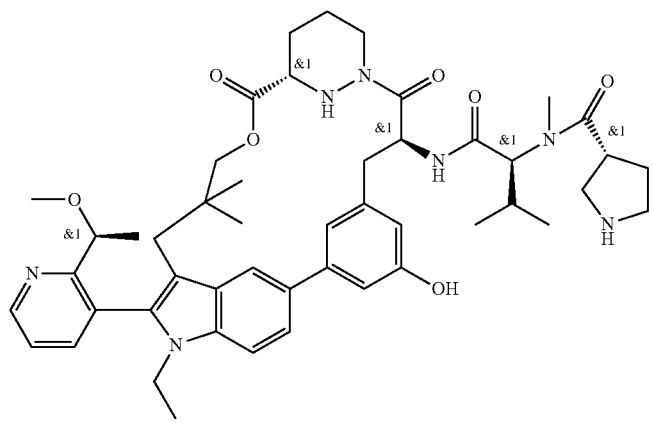 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@@H]1CCNC1)C(=O)N1CCC[C@H](N1)C(=O)OCC(C)(C)C2] |
| A130 | 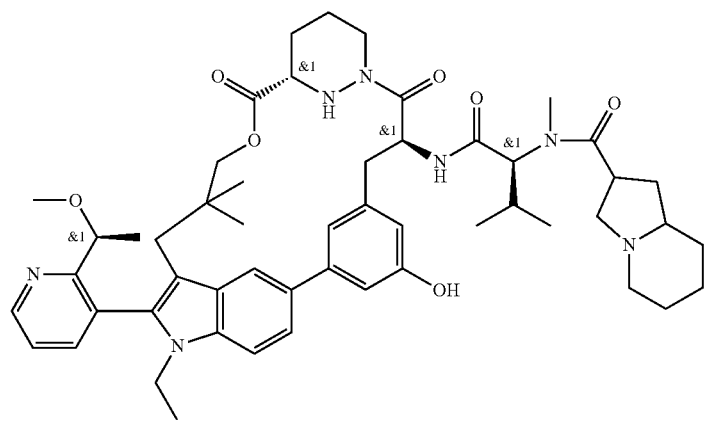 [SMILES: CCn1c(-c2cccnc2[C@H](C)OC)c2c3cc(ccc31)-c1cc(O)cc(c1)C[C@H](NC(=O)[C@H](C(C)C)N(C)C(=O)C1CC3CCCCN3C1)C(=O)N1CCC[C@H](N1)C(=O)OCC(C)(C)C2] |

TABLE 1-continued
Certain Compounds of the Present Invention
| Ex# | Structure |
|---|---|
| A131 | 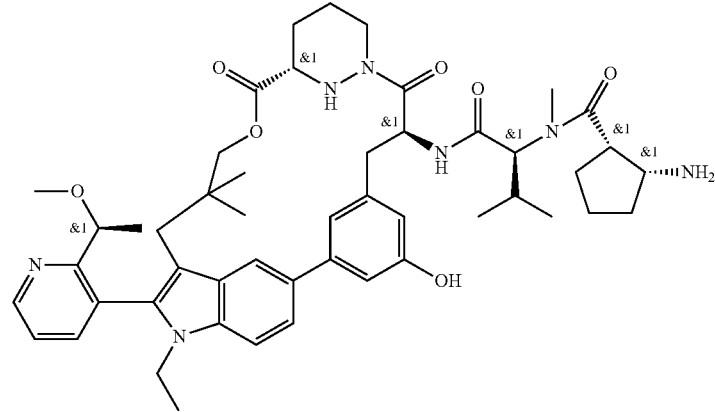 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@H]1CCC[C@H]1N)C(=O)N1CCC[C@H](N1)C(=O)OCC(C)(C)C2] |
| A132 | 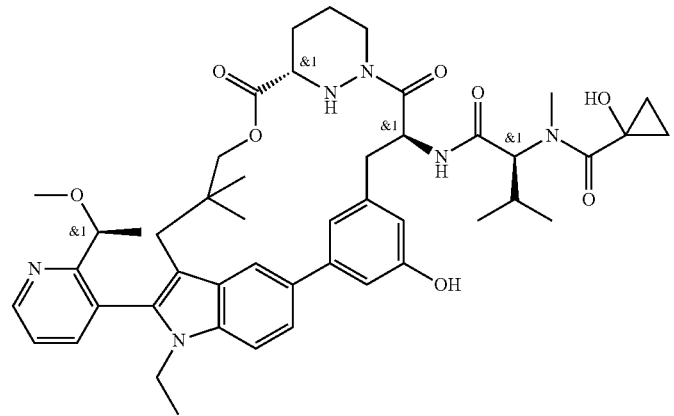 [SMILES: CCn1c(-c2cccnc2[C@H](C)OC)c2c3cc(ccc31)-c1cc(O)cc(c1)C[C@H](NC(=O)[C@H](C(C)C)N(C)C(=O)C1(O)CC1)C(=O)N1CCC[C@H](N1)C(=O)OCC(C)(C)C2] |
| A133 | 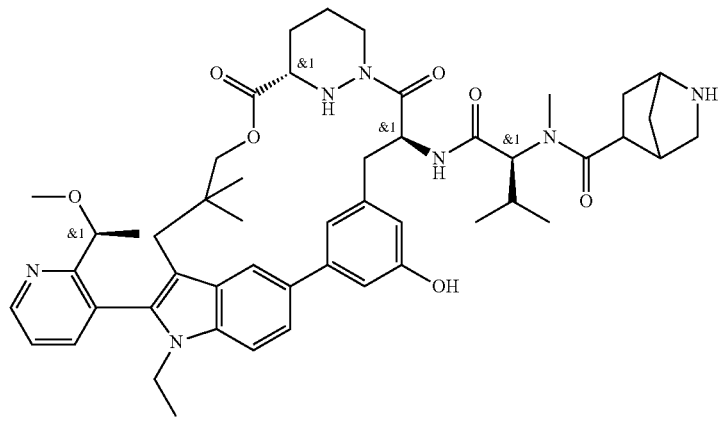 [SMILES: CCn1c(-c2cccnc2[C@H](C)OC)c2c3cc(ccc31)-c1cc(O)cc(c1)C[C@H](NC(=O)[C@H](C(C)C)N(C)C(=O)C1CC3CC1CN3)C(=O)N1CCC[C@H](N1)C(=O)OCC(C)(C)C2] |

TABLE 1-continued
Certain Compounds of the Present Invention
| Ex# | Structure |
|---|---|
| A134 | 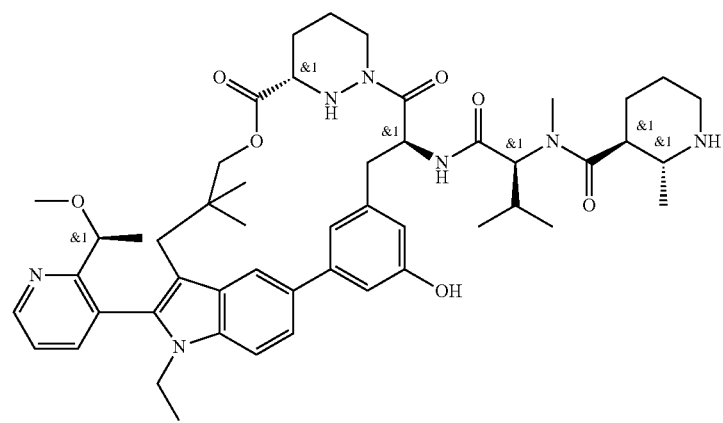 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@H]1CCCN[C@@H]1C)C(=O)N1CCC[C@H](N1)C(=O)OCC(C)(C)C2] |
| A135 | 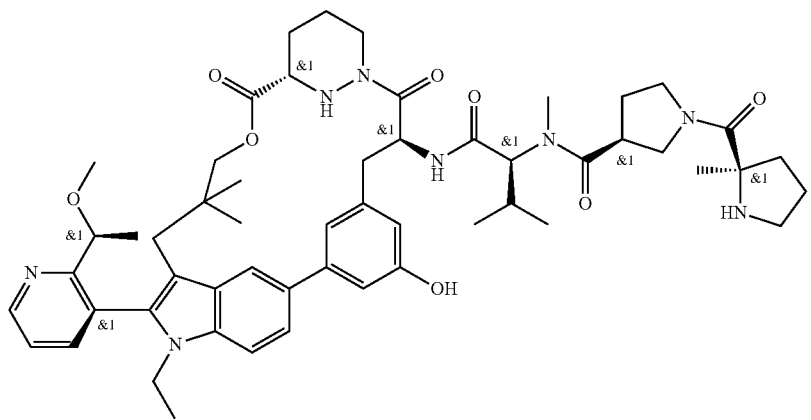 |
| A136 | 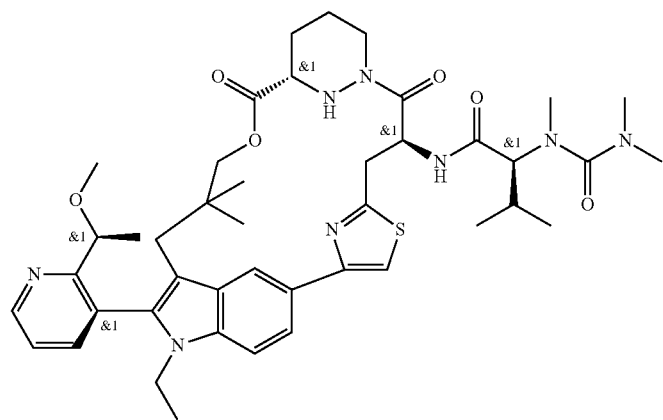 |

TABLE 1-continued

Certain Compounds of the Present Invention

| Ex# | Structure |
|---|---|
| A137 | 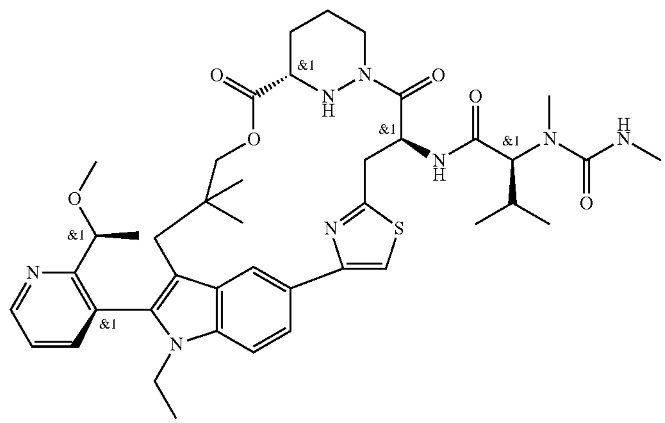 |
| A138 | 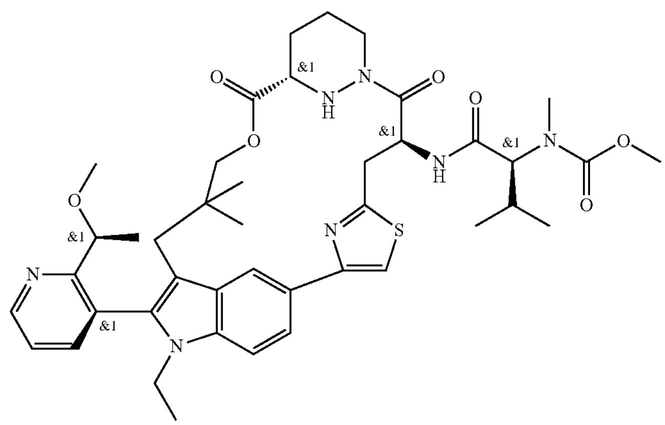 |
| A139 | 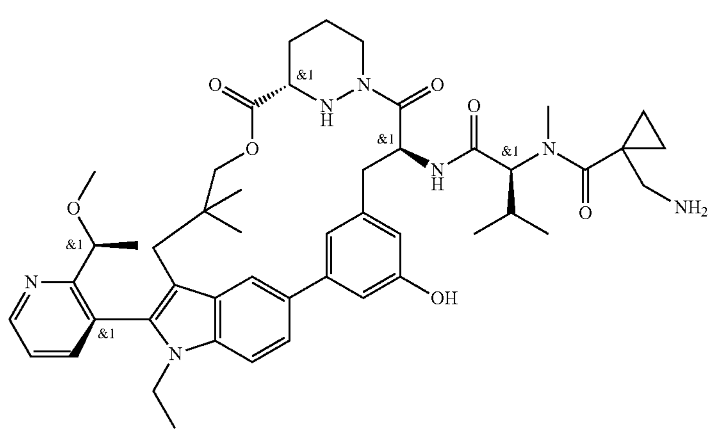 |

148
TABLE 1-continued
Certain Compounds of the Present Invention
| Ex# | Structure |
|---|---|
| A140 | 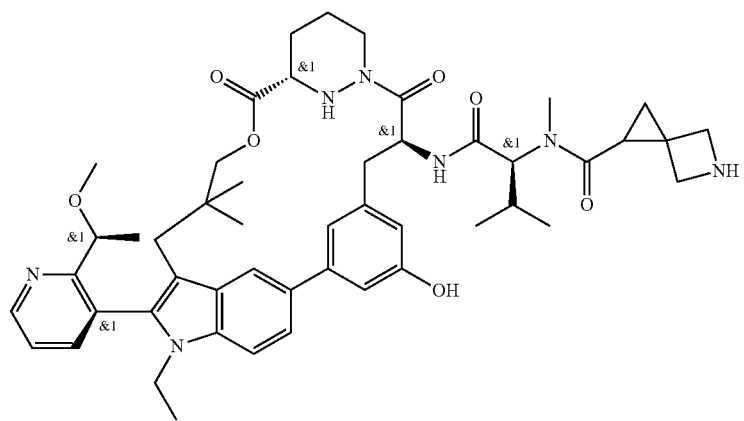 |
| A141 | 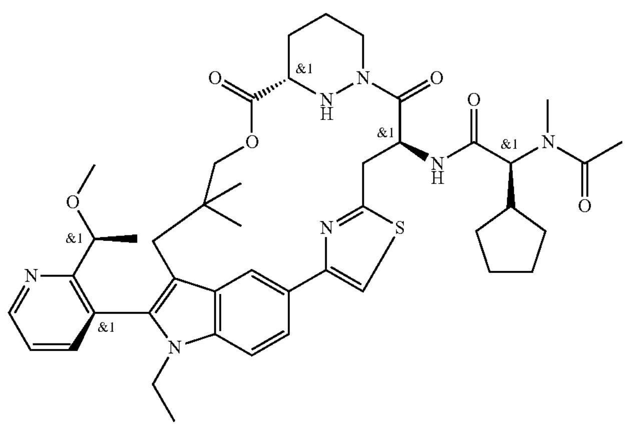 |
| A142 | 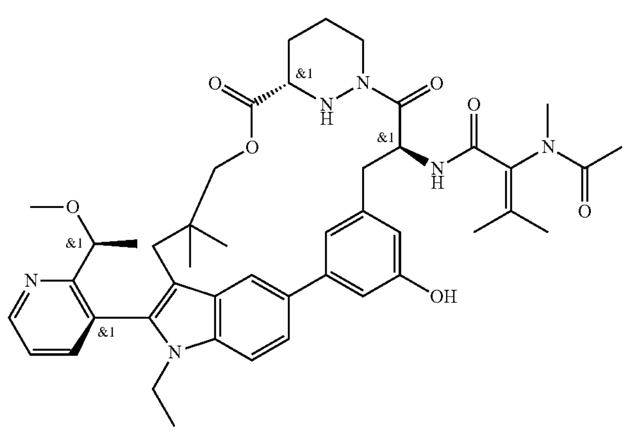 |

TABLE 1-continued

Certain Compounds of the Present Invention

| Ex# | Structure |
| --- | --- |
| A143 | 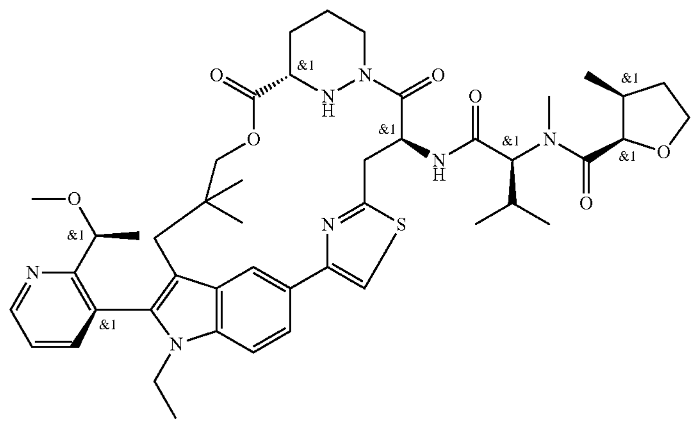 |
| A144 | 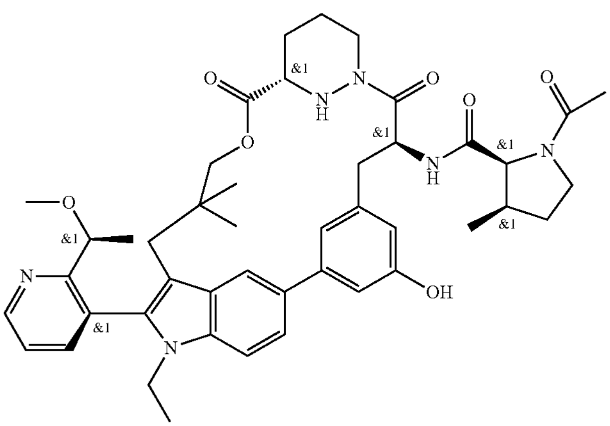 |
| A145 | 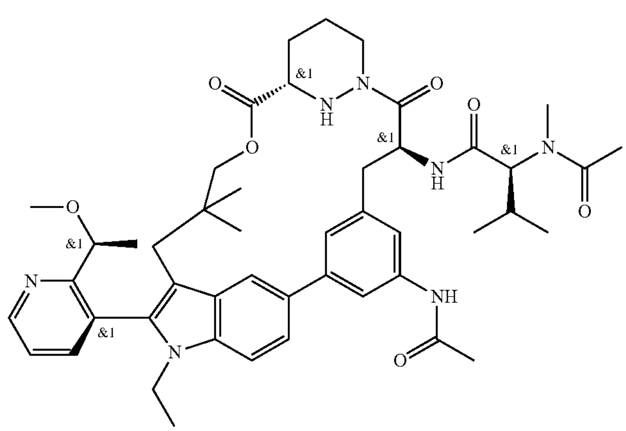 |

TABLE 1-continued
Certain Compounds of the Present Invention
| Ex# | Structure |
|---|---|
| A146 | 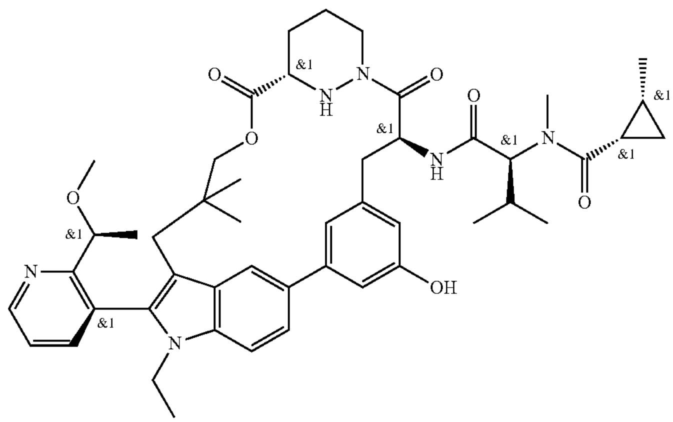 |
| A147 | 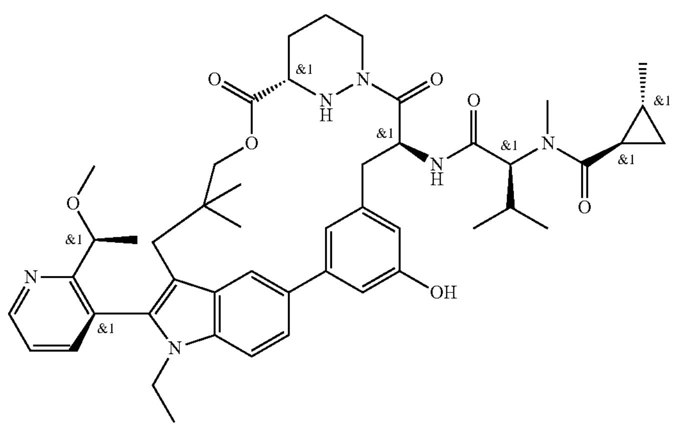 |
| A148 | 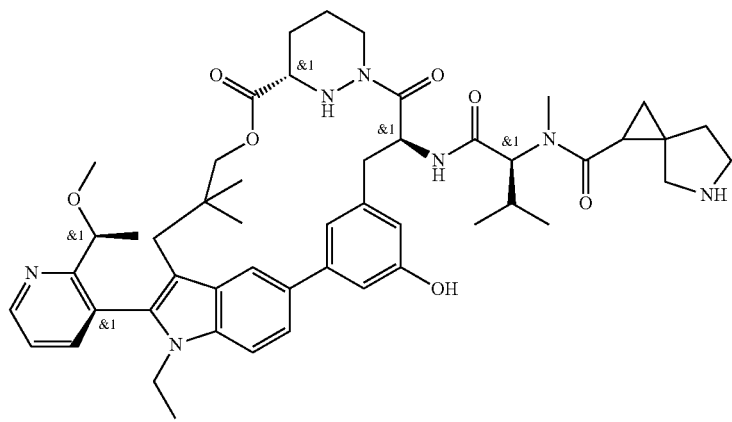 |

TABLE 1-continued
Certain Compounds of the Present Invention
| Ex# | Structure |
|---|---|
| A149 | 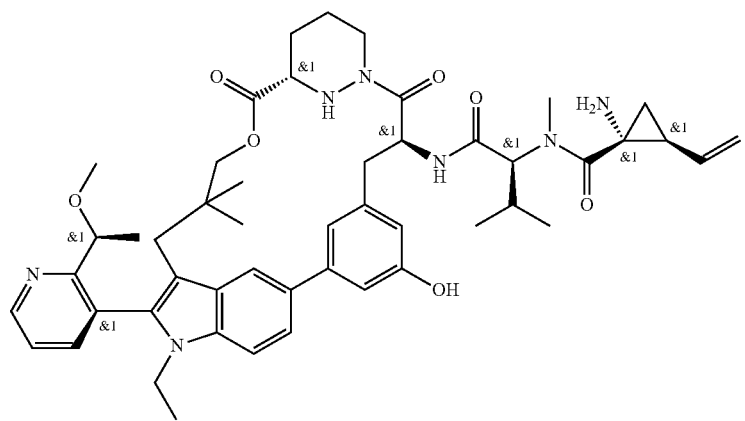 |
| A150 | 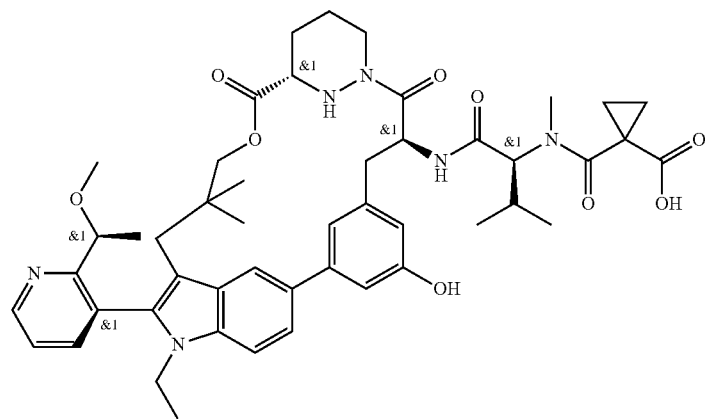 |
| A151 | 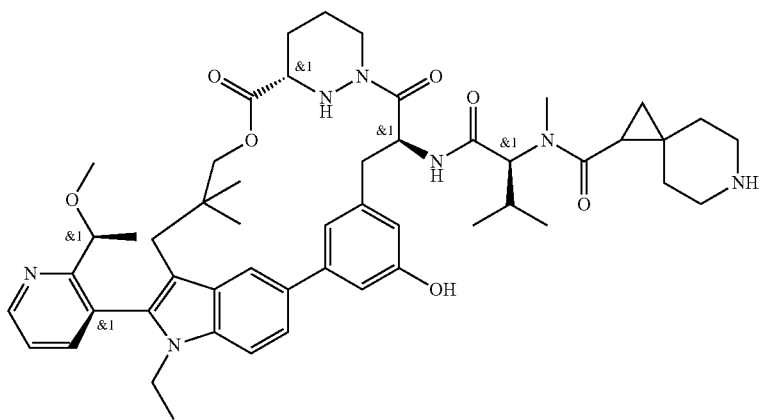 |

TABLE 1-continued

Certain Compounds of the Present Invention

| Ex# | Structure |
|---|---|
| A152 | 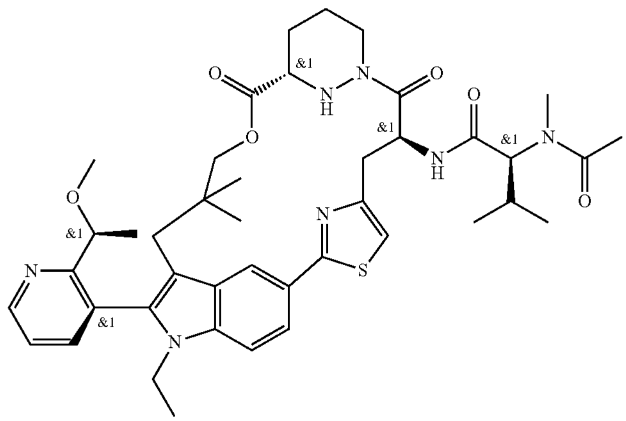 |
| A153 | 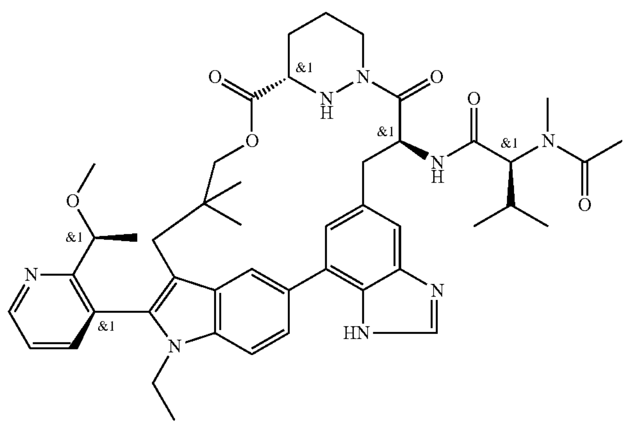 |
| A154 | 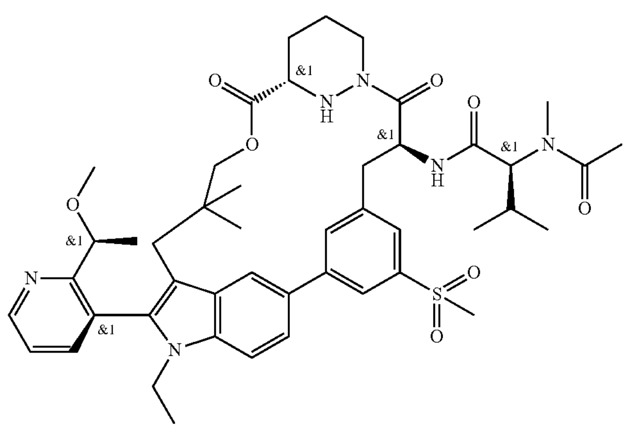 |

TABLE 1-continued
Certain Compounds of the Present Invention
| Ex# | Structure |
|---|---|
| A155 | 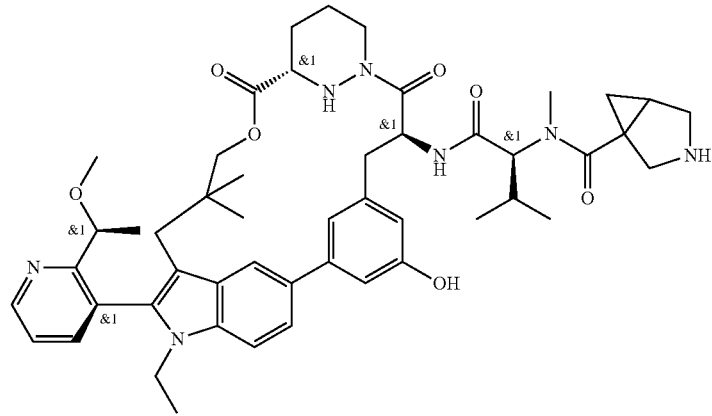 |
| A156 | 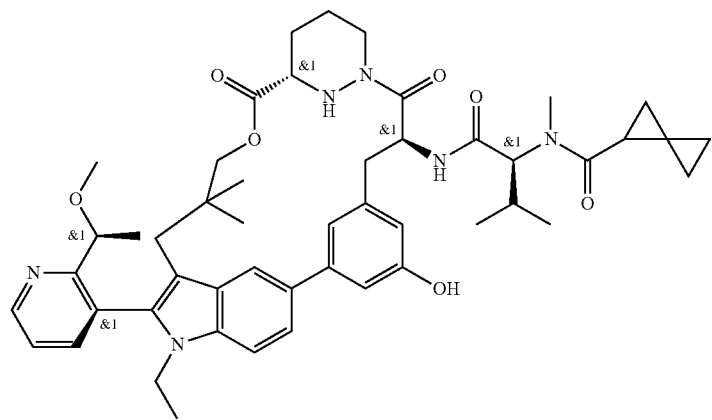 |
| A157 | 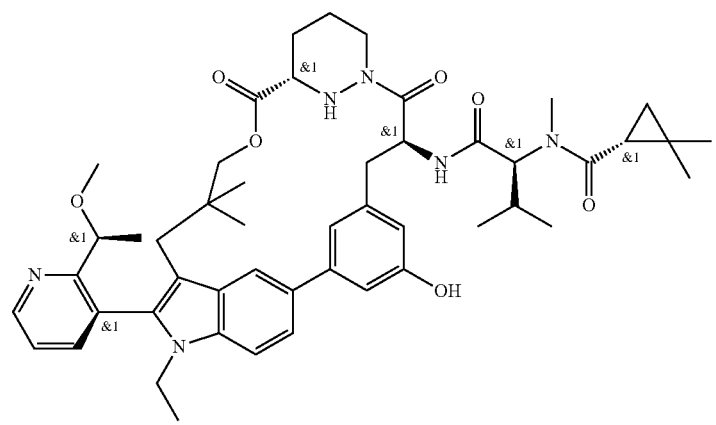 |

TABLE 1-continued
Certain Compounds of the Present Invention
| Ex# | Structure |
|---|---|
| A158 | 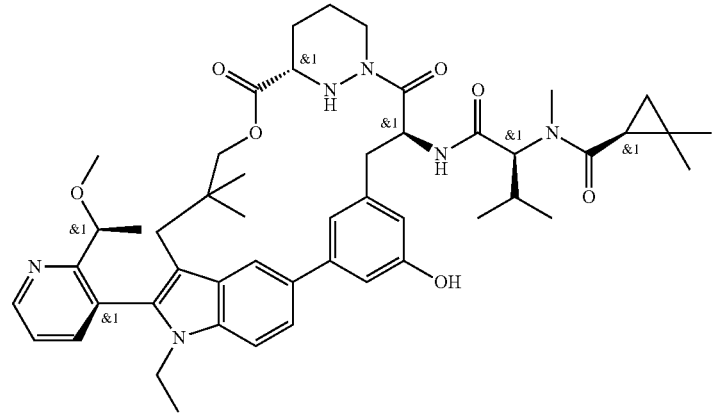 |
| A159 | 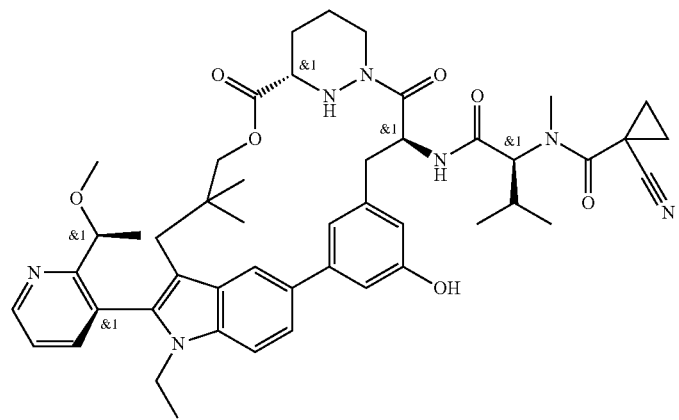 |
| A160 | 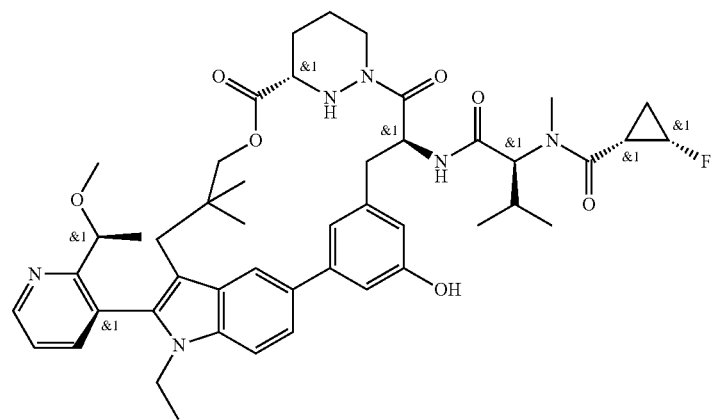 |

TABLE 1-continued
Certain Compounds of the Present Invention
| Ex# | Structure |
|---|---|
| A161 | 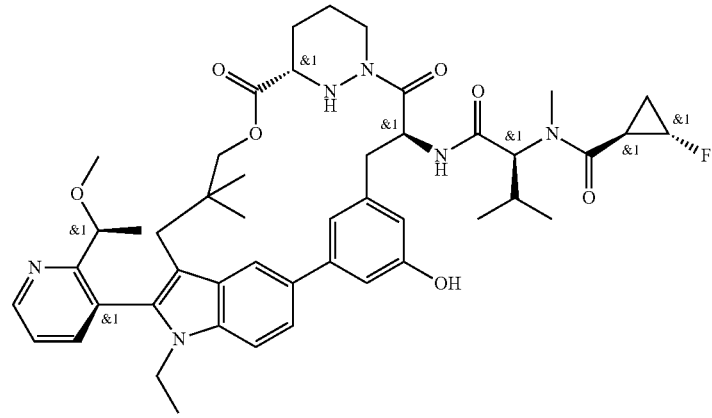 |
| A162 | 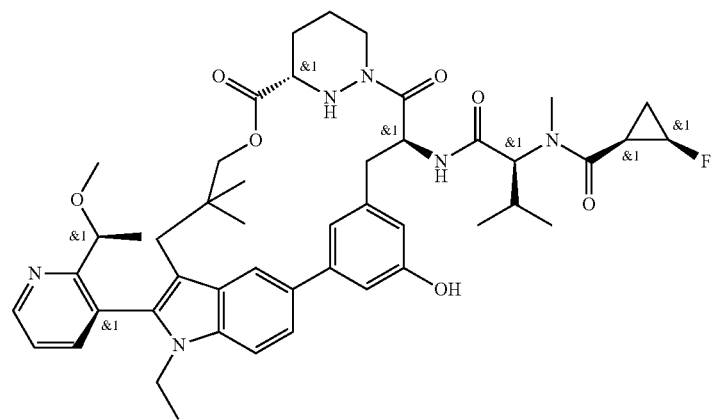 |
| A163 | 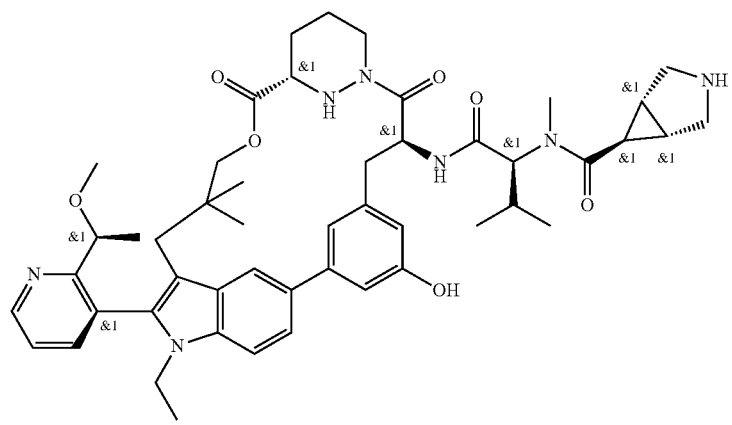 |

TABLE 1-continued
Certain Compounds of the Present Invention
| Ex# | Structure |
|---|---|
| A164 | 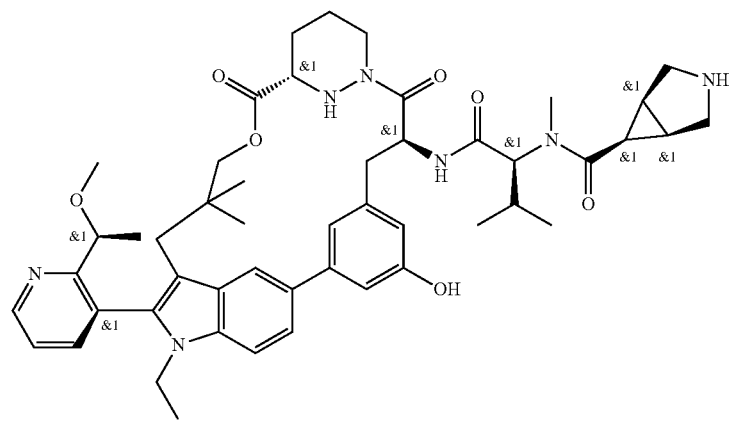 |
| A165 | 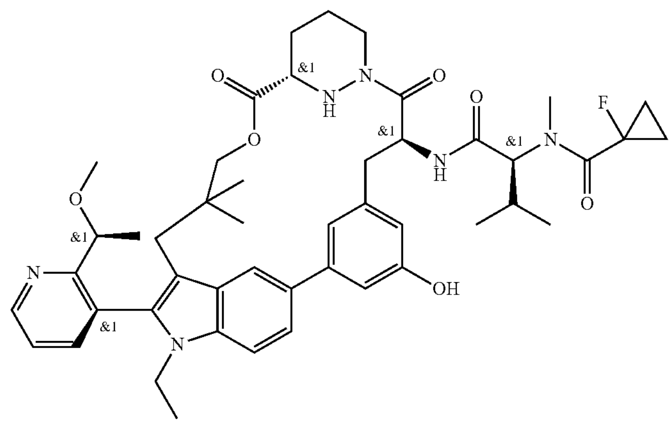 |
| A166 | 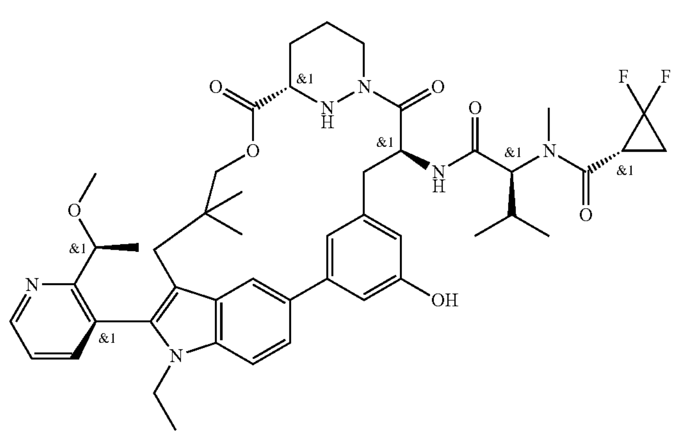 |

TABLE 1-continued
Certain Compounds of the Present Invention
| Ex# | Structure |
|---|---|
| A167 | 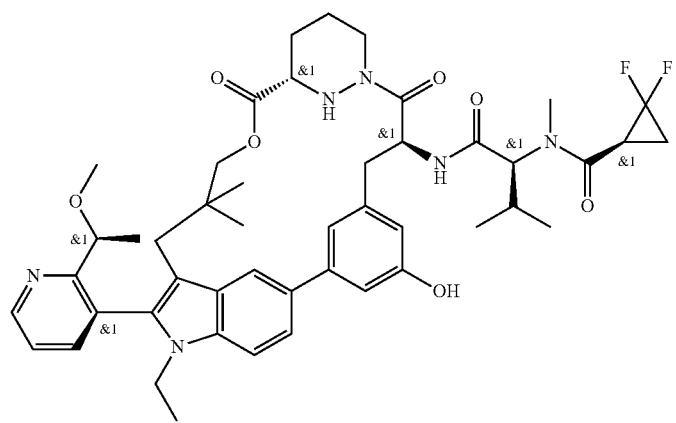 |
| A168 | 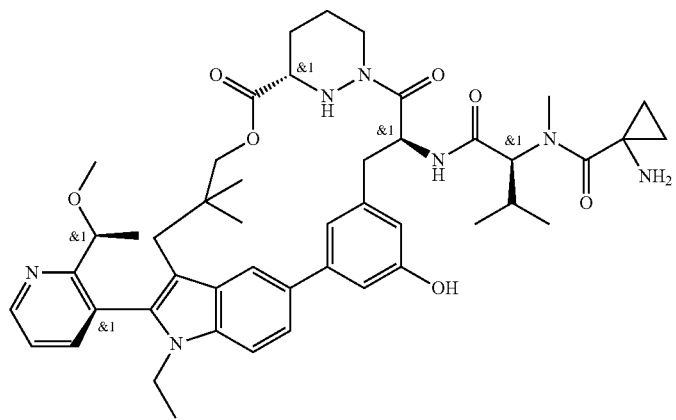 |
| A169 | 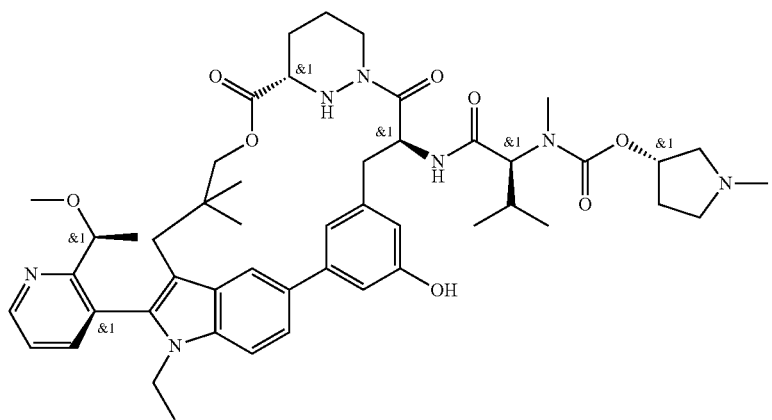 |

TABLE 1-continued
Certain Compounds of the Present Invention
| Ex# | Structure |
|---|---|
| A170 | 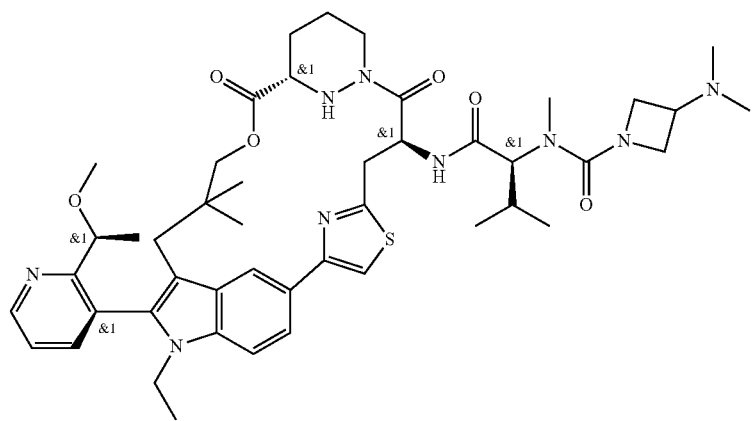 |
| A171 | 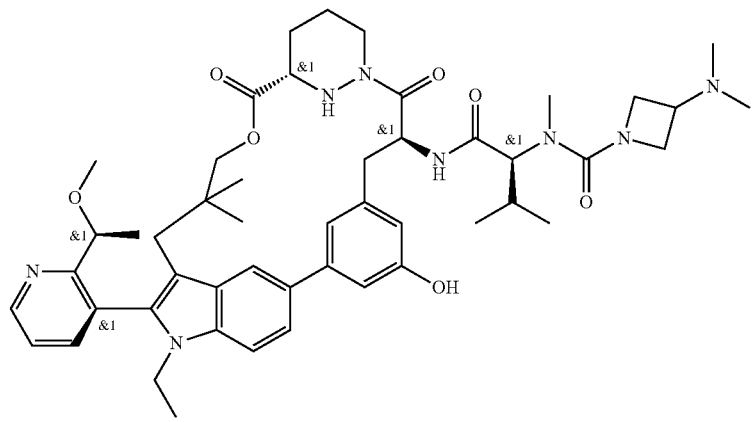 |
| A172 | 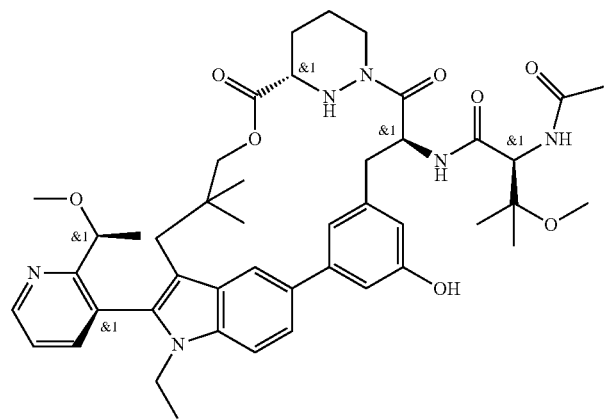 |

TABLE 1-continued
Certain Compounds of the Present Invention
| Ex# | Structure |
|---|---|
| A173 | 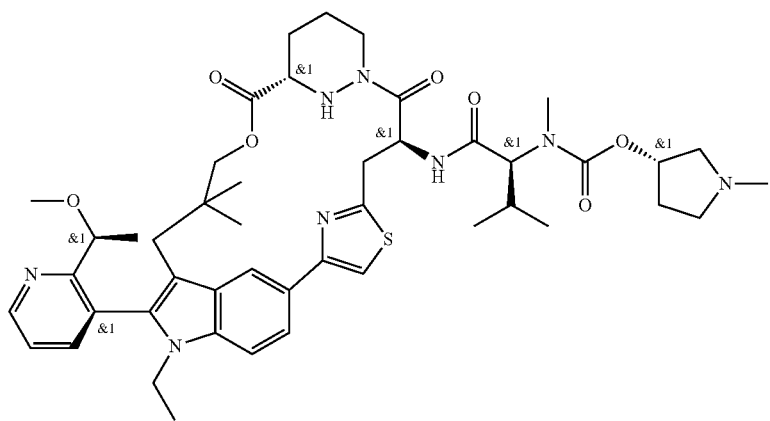 |
| A174 | 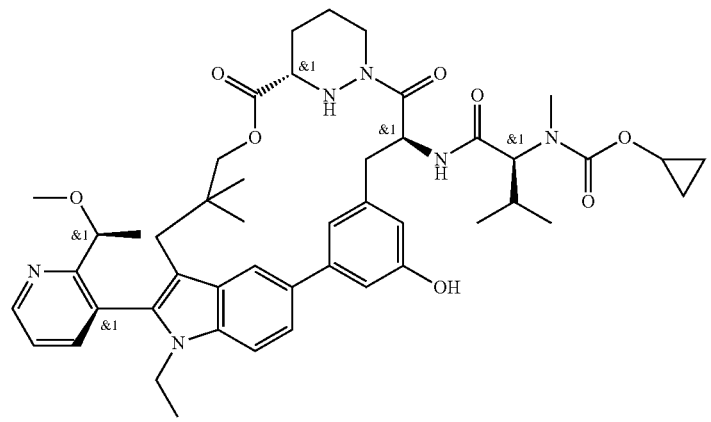 |
| A175 | 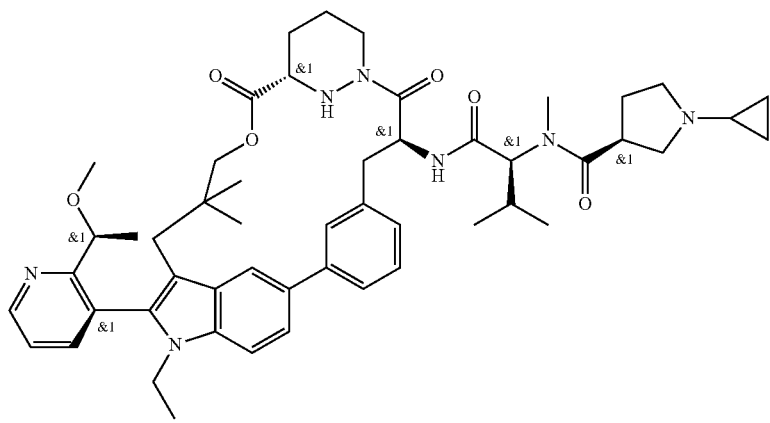 |

TABLE 1-continued

Certain Compounds of the Present Invention

| Ex# | Structure |
|---|---|
| A176 | 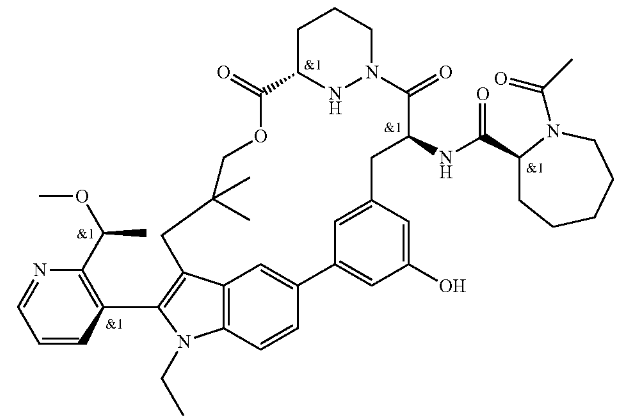 |
| A177 | 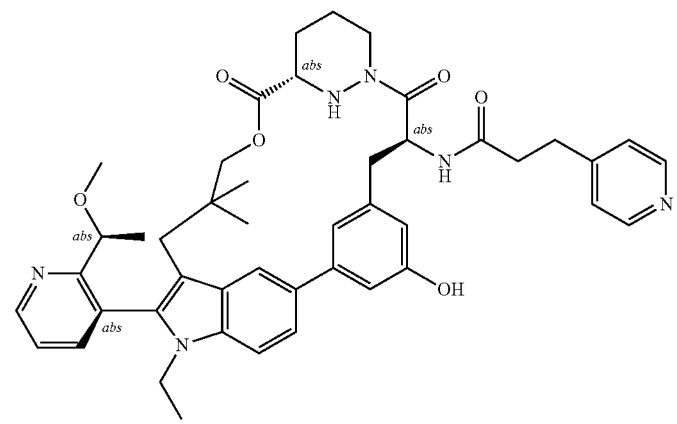 |
| A178 | 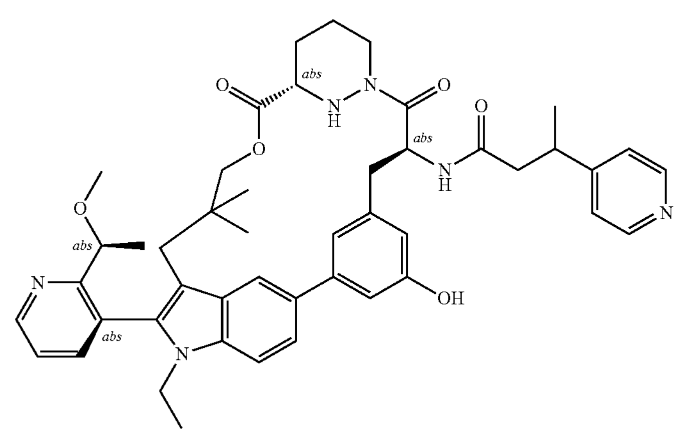 |

TABLE 1-continued
Certain Compounds of the Present Invention
| Ex# | Structure |
|---|---|
| A179 | 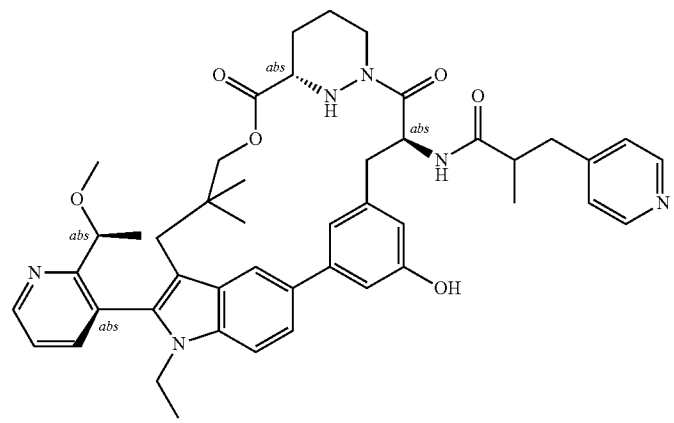 |
| A180 | 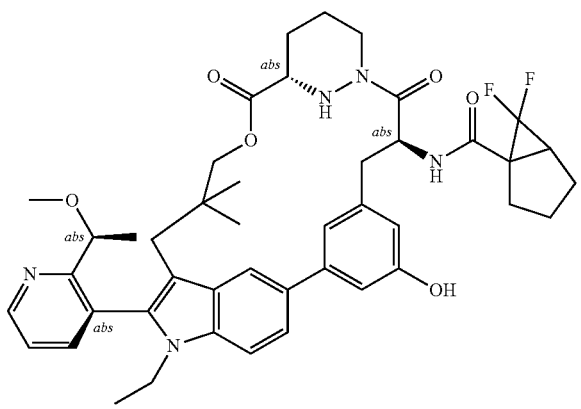 |
| A181 | 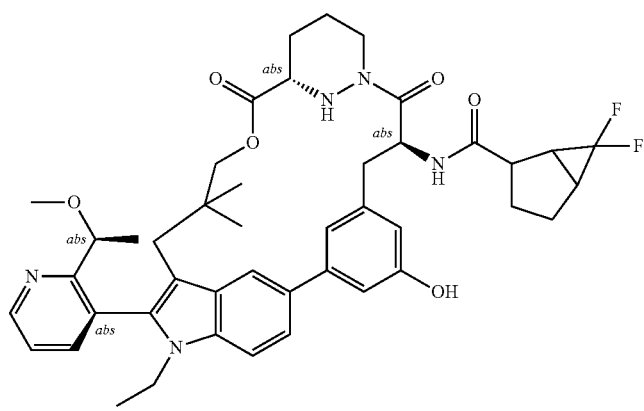 |

TABLE 1-continued

Certain Compounds of the Present Invention

| Ex# | Structure |
|---|---|
| A182 | 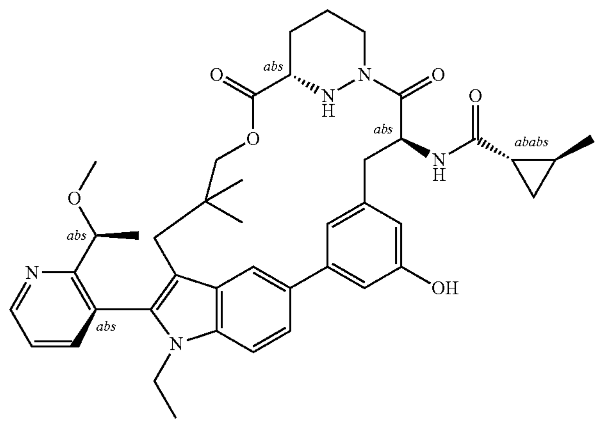 |
| A183 | 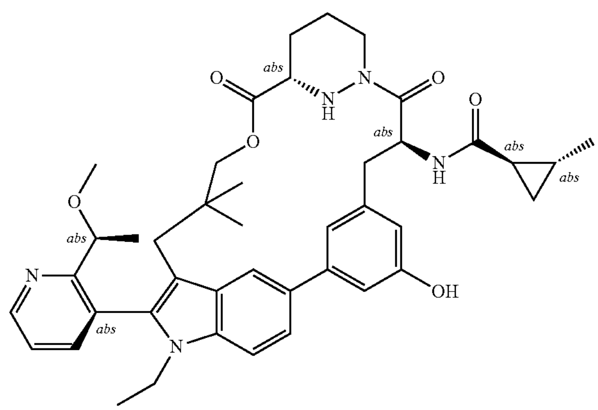 |
| A184 | 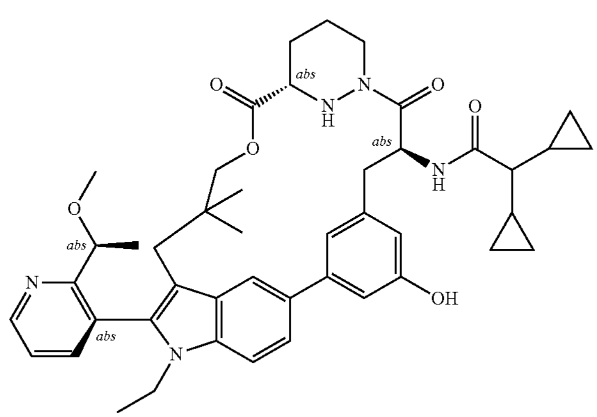 |

TABLE 1-continued

Certain Compounds of the Present Invention

| Ex# | Structure |
|---|---|
| A185 | 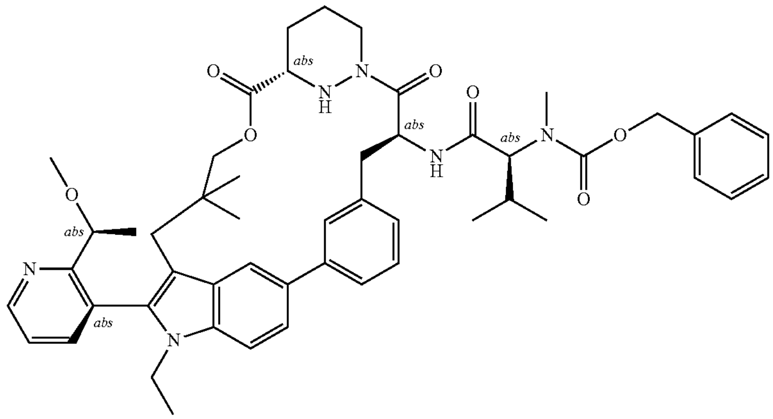 |
| A186 | 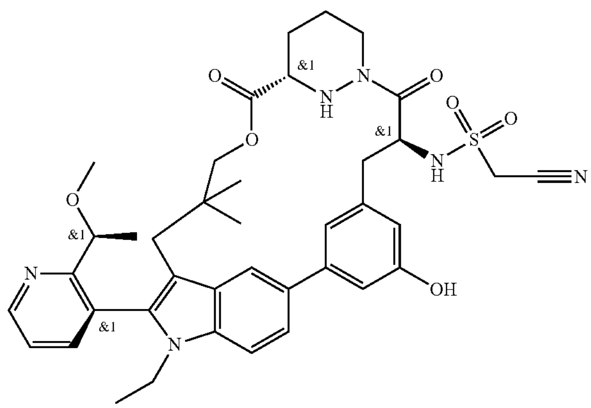 |
| A187 | 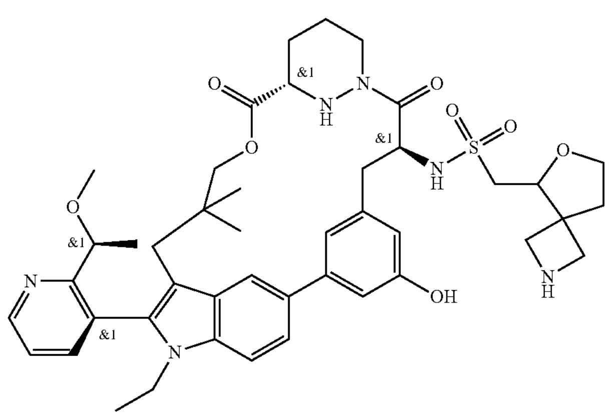 |

TABLE 1-continued
Certain Compounds of the Present Invention
| Ex# | Structure |
|---|---|
| A188 | 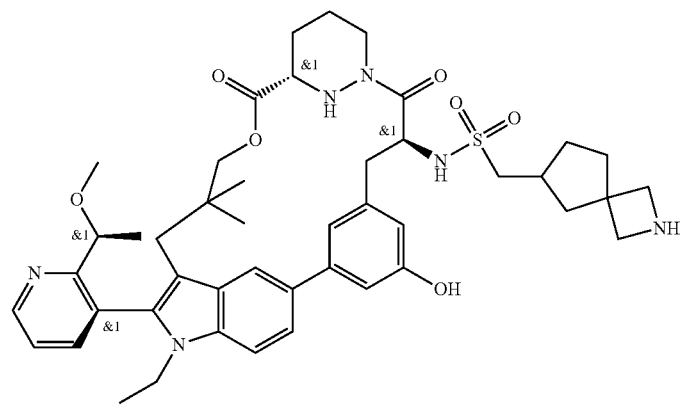 |
| A189 | 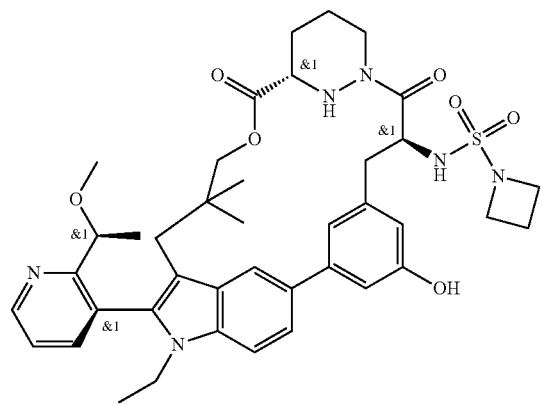 |
| A190 | 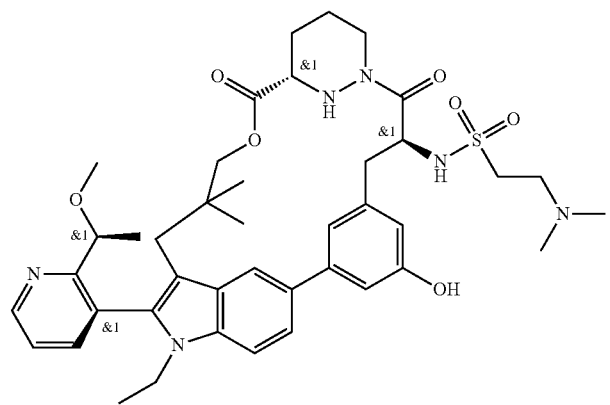 |

TABLE 1-continued
Certain Compounds of the Present Invention
| Ex# | Structure |
|---|---|
| A191 | 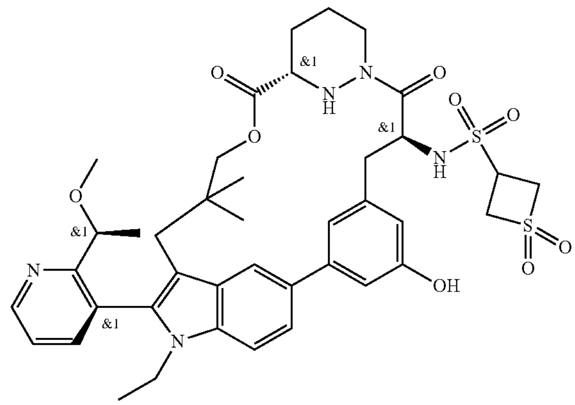 |
| A192 | 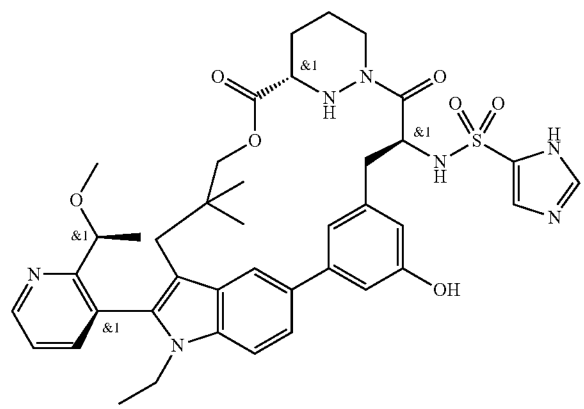 |
| A193 | 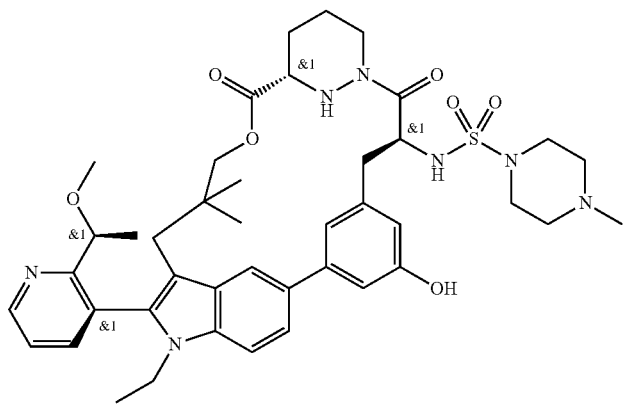 |

TABLE 1-continued
Certain Compounds of the Present Invention
| Ex# | Structure |
|---|---|
| A194 | 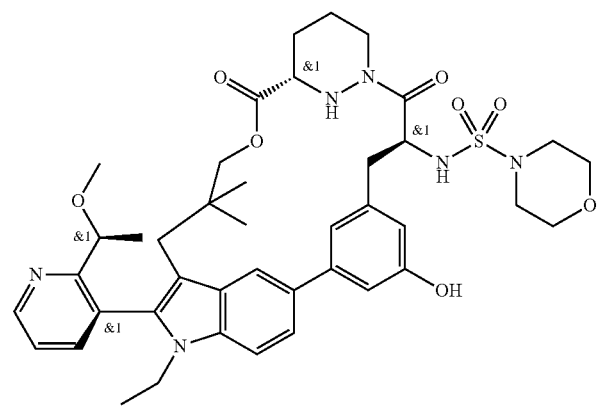 |
| A195 | 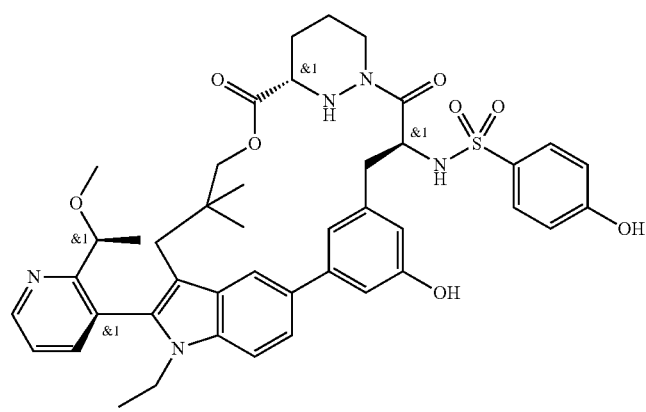 |
| A196 | 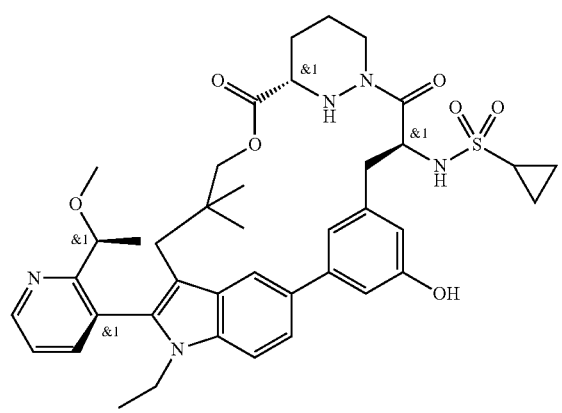 |

TABLE 1-continued
Certain Compounds of the Present Invention
| Ex# | Structure |
|---|---|
| A197 | 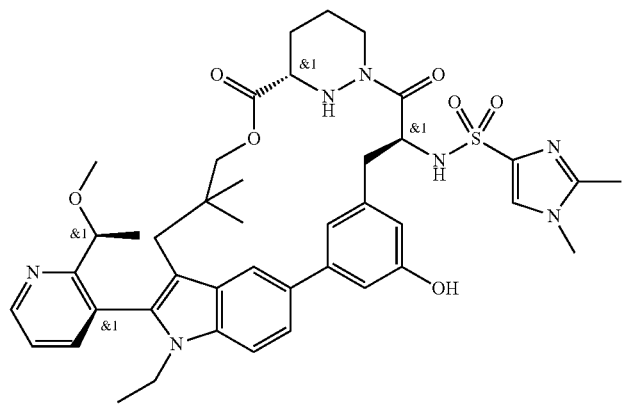 |
| A198 | 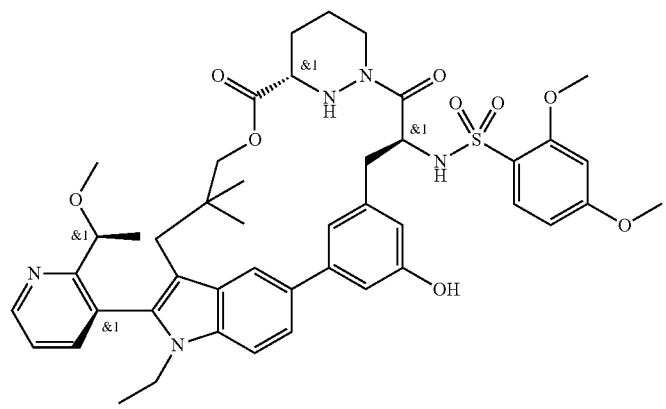 |
| A199 | 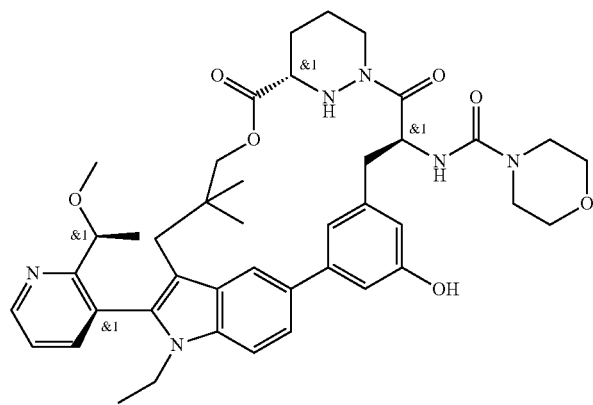 |

TABLE 1-continued
Certain Compounds of the Present Invention
| Ex# | Structure |
|---|---|
| A200 | 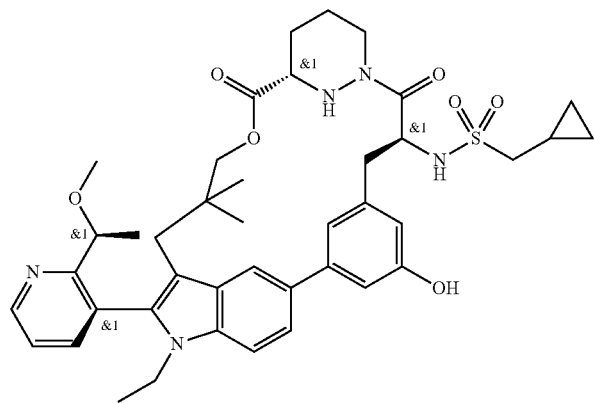 |
| A201 | 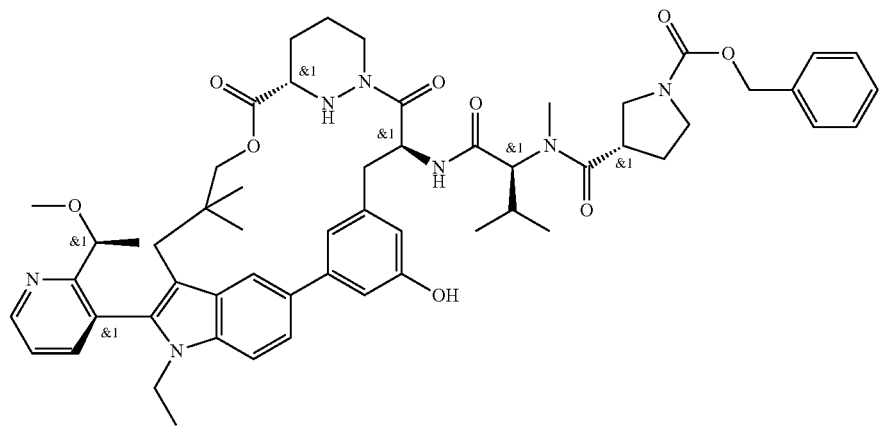 |
| A202 | 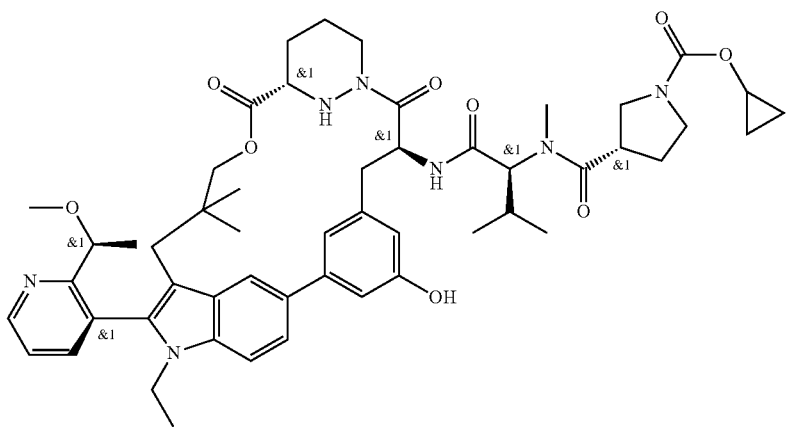 |

TABLE 1-continued

Certain Compounds of the Present Invention

| Ex# | Structure |
|---|---|
| A203 | 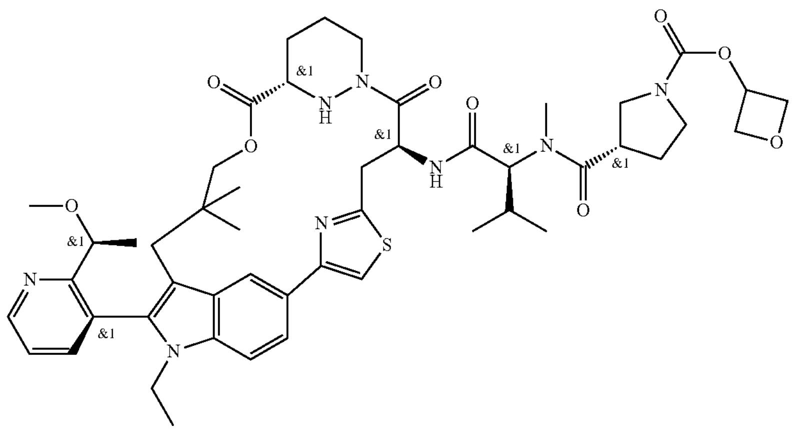 |
| A204 | 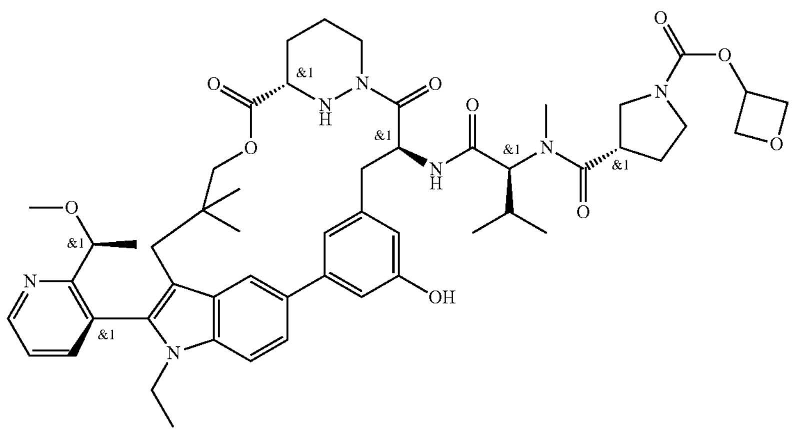 |
| A205 | 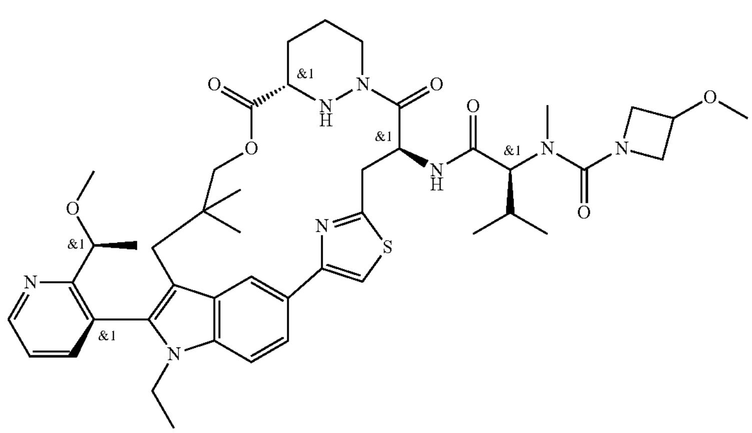 |

TABLE 1-continued

Certain Compounds of the Present Invention

| Ex# | Structure |
|---|---|
| A206 | 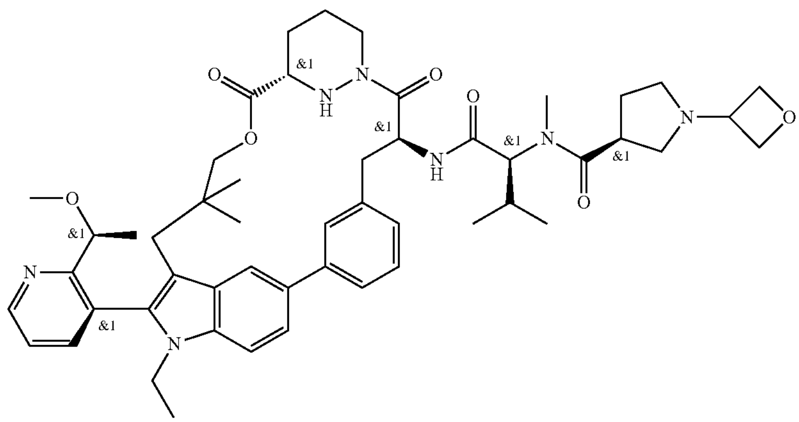 |
| A207 | 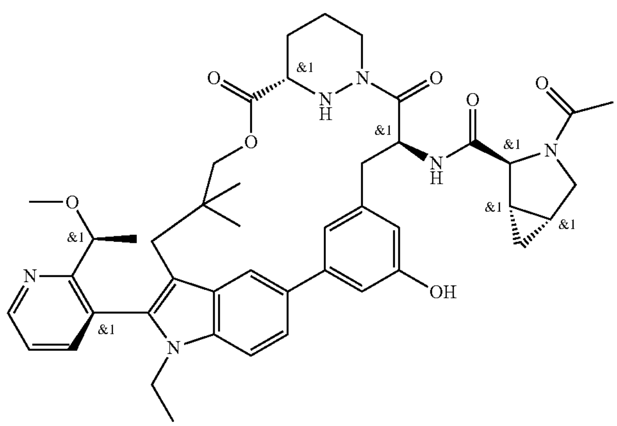 |
| A208 | 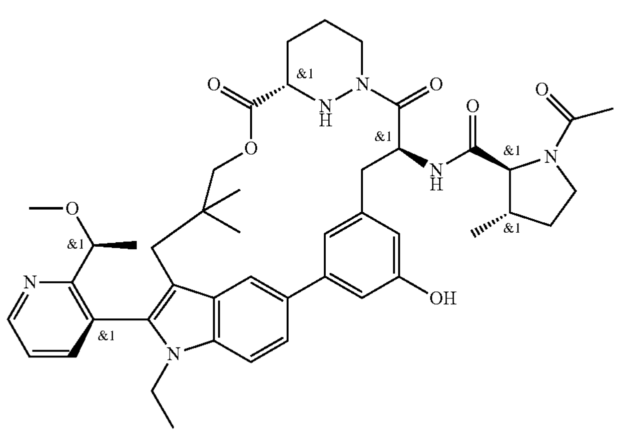 |

TABLE 1-continued
Certain Compounds of the Present Invention
| Ex# | Structure |
|---|---|
| A209 | 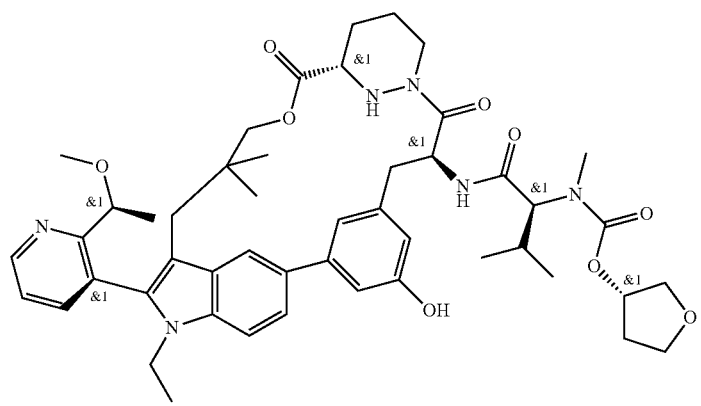 |
| A210 | 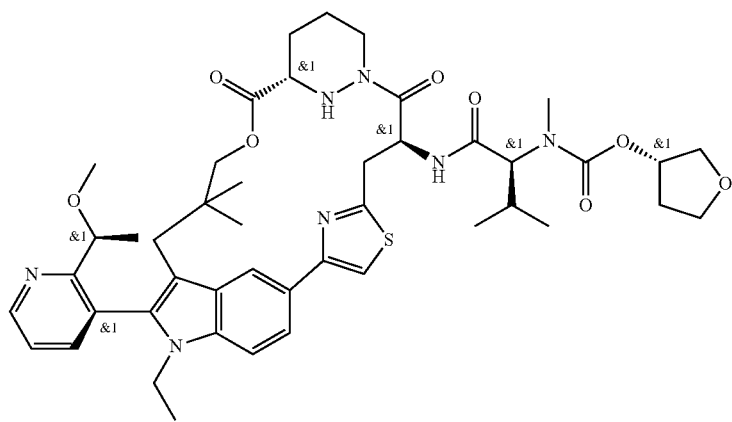 |
| A211 | 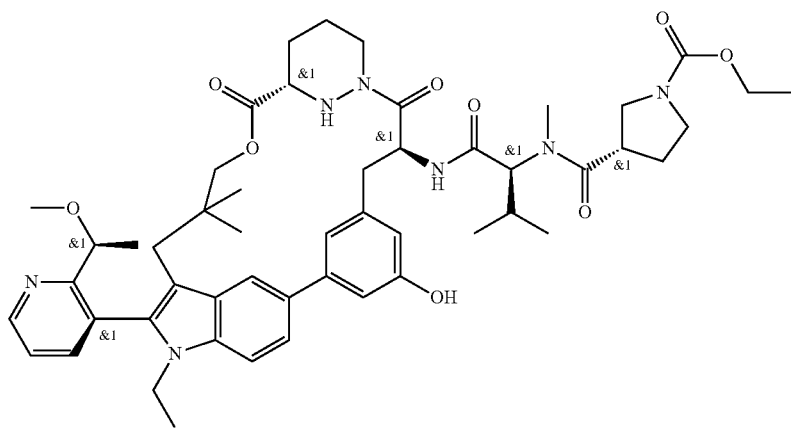 |

TABLE 1-continued

Certain Compounds of the Present Invention

| Ex# | Structure |
|---|---|
| A212 | 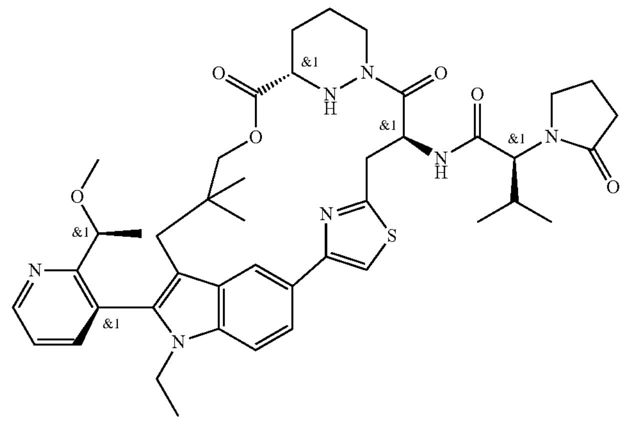 |
| A213 | 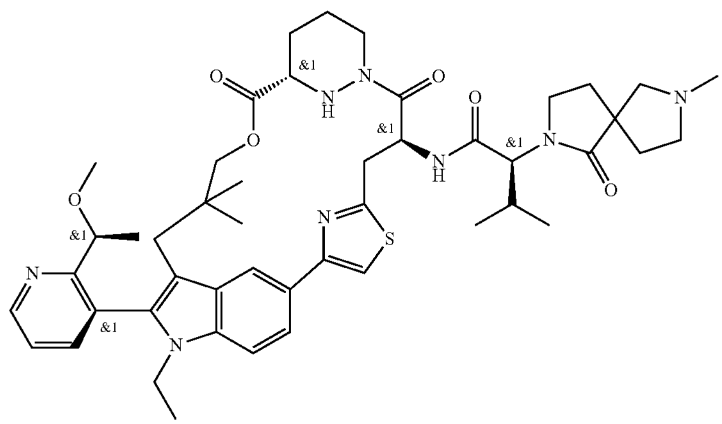 |
| A214 | 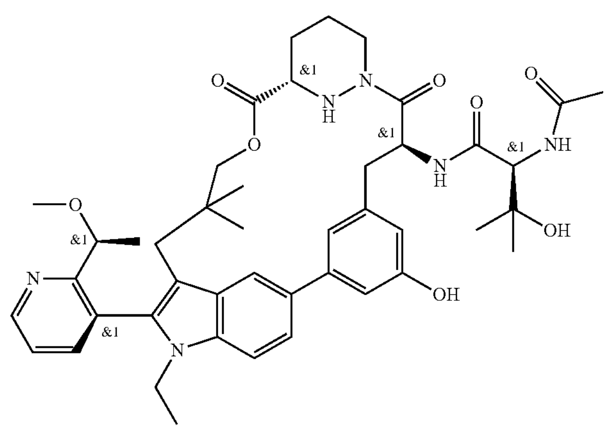 |

TABLE 1-continued
Certain Compounds of the Present Invention
| Ex# | Structure |
|---|---|
| A215 | 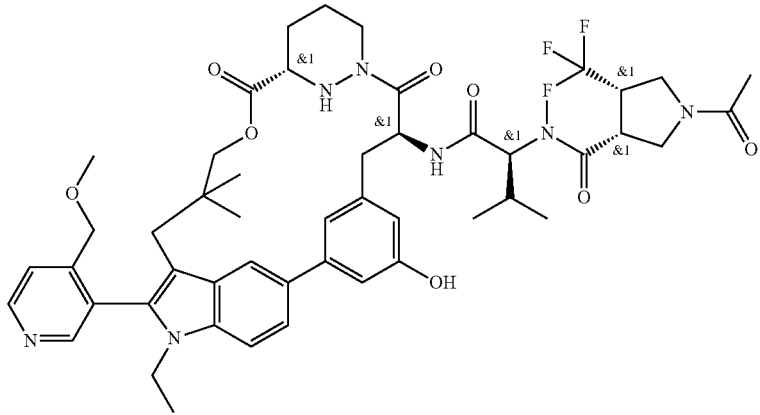 [SMILES: CCn1c(-c2cnccc2COC)c2c3cc(ccc31)-c1cc(O)cc(c1)C[C@H](NC(=O)[C@H](C(C)C)N(C)C(=O)[C@H]1CN(C(C)=O)C[C@H]1C(F)(F)F)C(=O)N1CCC[C@H](N1)C(=O)OCC(C)(C)C2] |
| A216 | 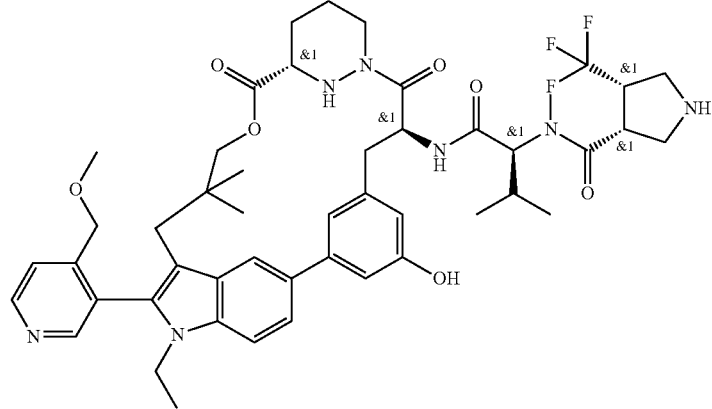 [SMILES: CCn1c(-c2cnccc2COC)c2c3cc(ccc31)-c1cc(O)cc(c1)C[C@H](NC(=O)[C@H](C(C)C)N(C)C(=O)[C@H]1CNC[C@H]1C(F)(F)F)C(=O)N1CCC[C@H](N1)C(=O)OCC(C)(C)C2] |
| A217 | 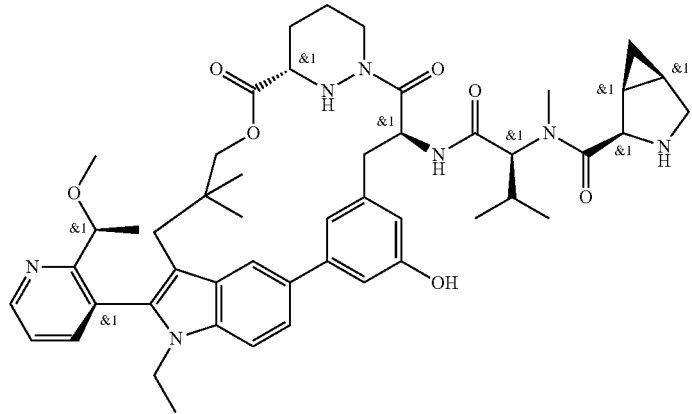 |

TABLE 1-continued
Certain Compounds of the Present Invention
| Ex# | Structure |
|---|---|
| A218 | 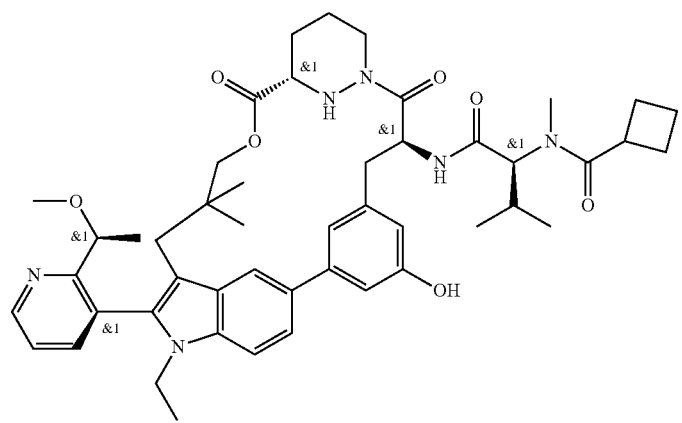 |
| A219 | 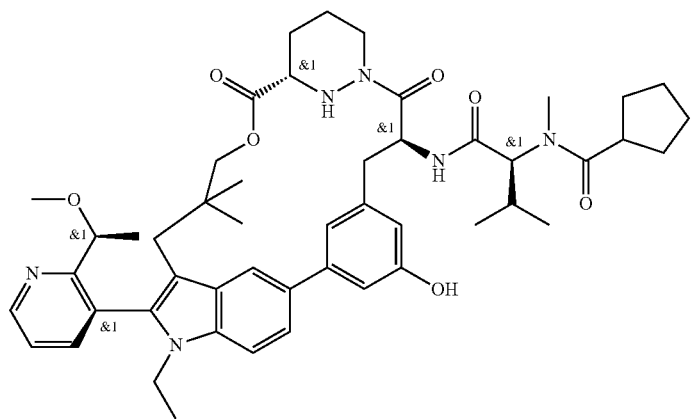 |
| A220 | 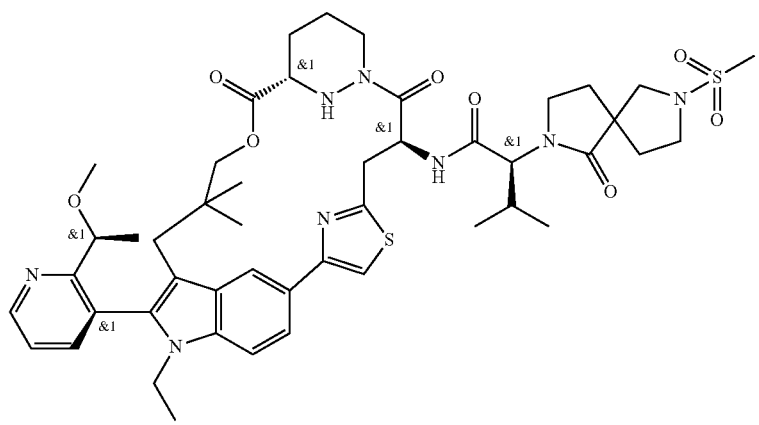 |

TABLE 1-continued
Certain Compounds of the Present Invention
| Ex# | Structure |
|---|---|
| A221 | 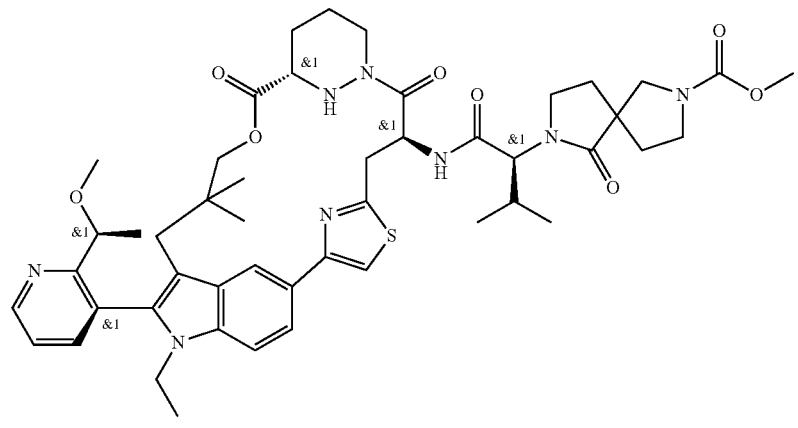 |
| A222 | 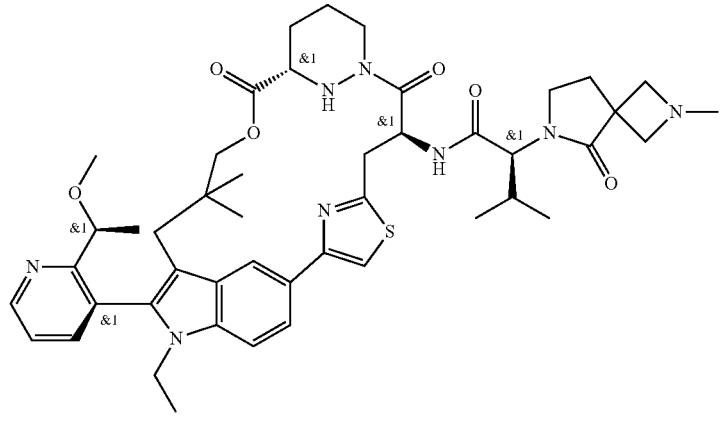 |
| A223 | 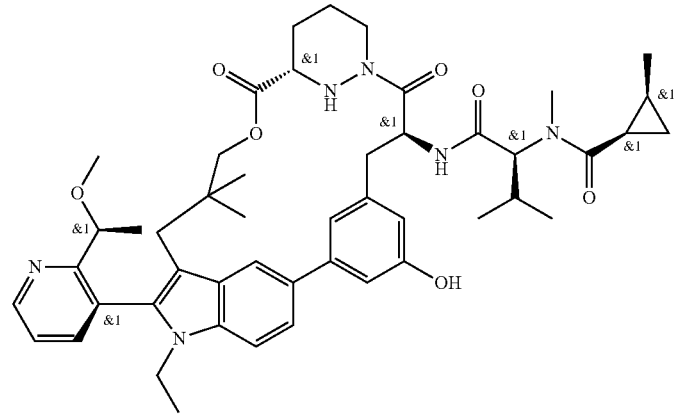 |

TABLE 1-continued

Certain Compounds of the Present Invention

| Ex# | Structure |
|---|---|
| A224 | 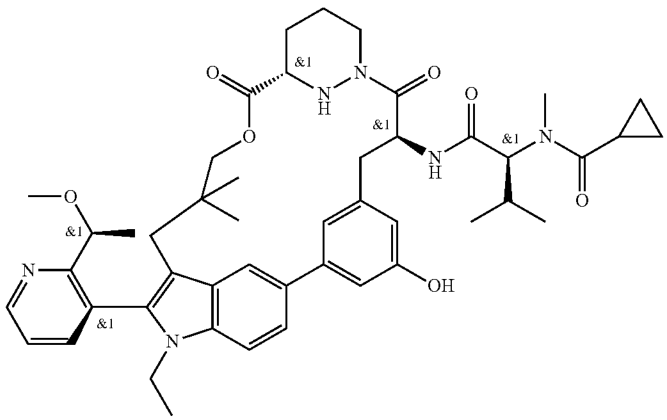 |
| A225 | 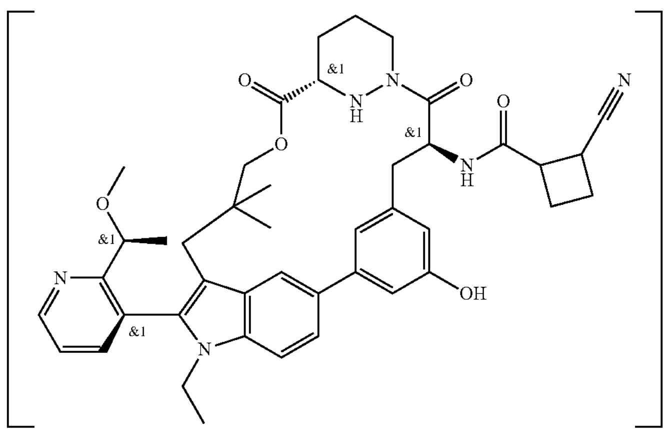 |
| A226 | 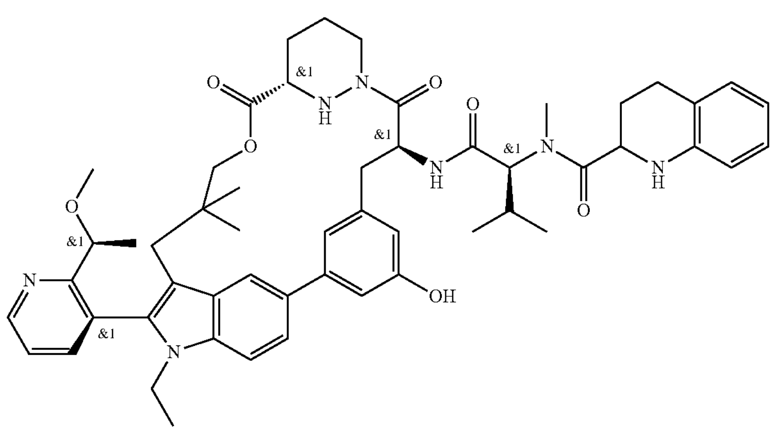 |

TABLE 1-continued
Certain Compounds of the Present Invention
| Ex# | Structure |
|---|---|
| A227 | 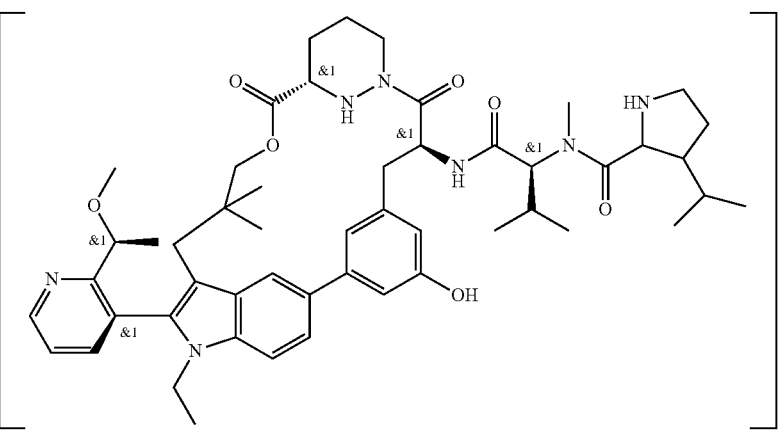 |
| A228 | 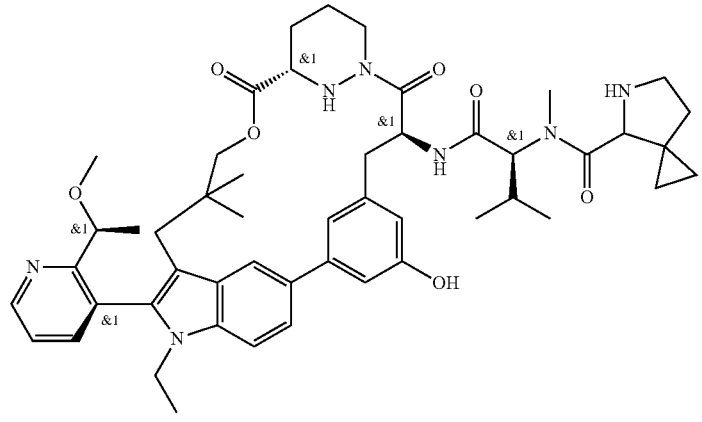 |
| A229 | 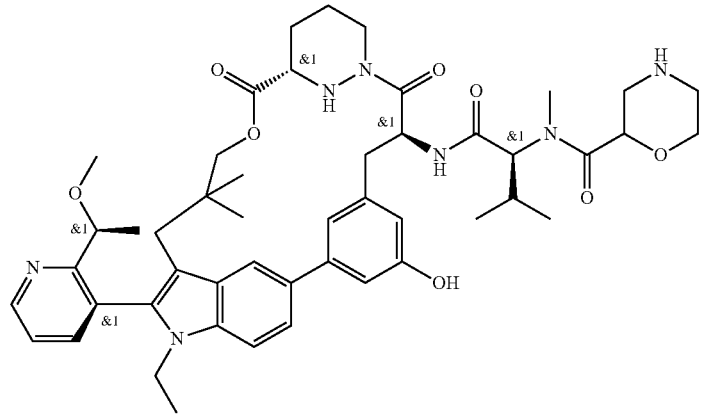 |

TABLE 1-continued
Certain Compounds of the Present Invention
| Ex# | Structure |
|---|---|
| A230 | 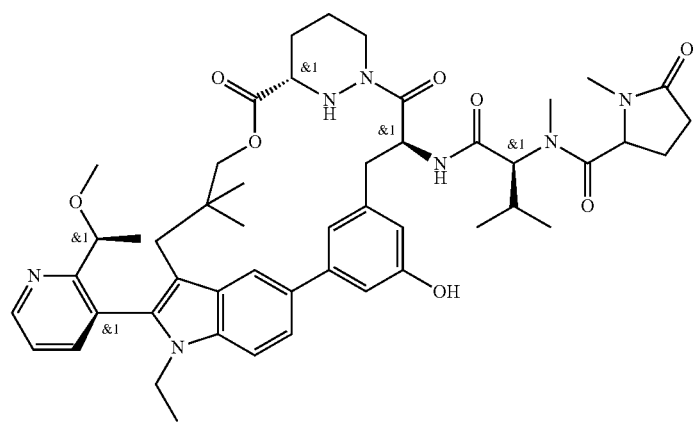 |
| A231 | 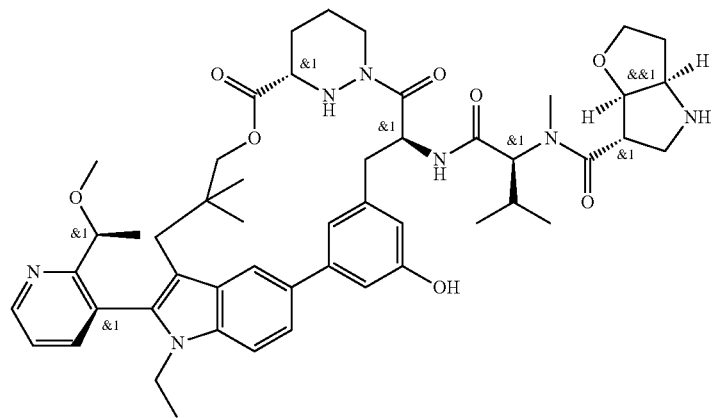 |
| A232 | 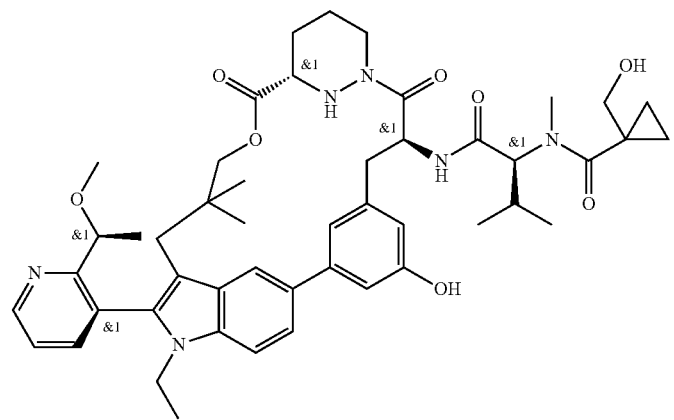 |

US 11,608,346 B2
209                                                                                          210
TABLE 1-continued
Certain Compounds of the Present Invention
| Ex# | Structure |
|---|---|
| A233 | 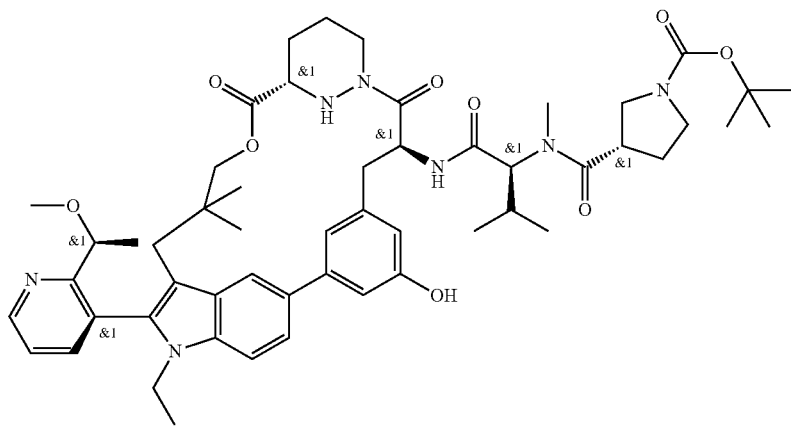 |
| A234 | 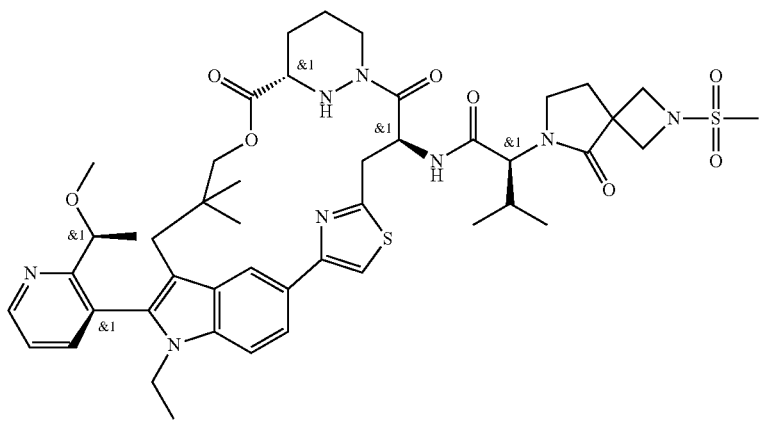 |
| A235 | 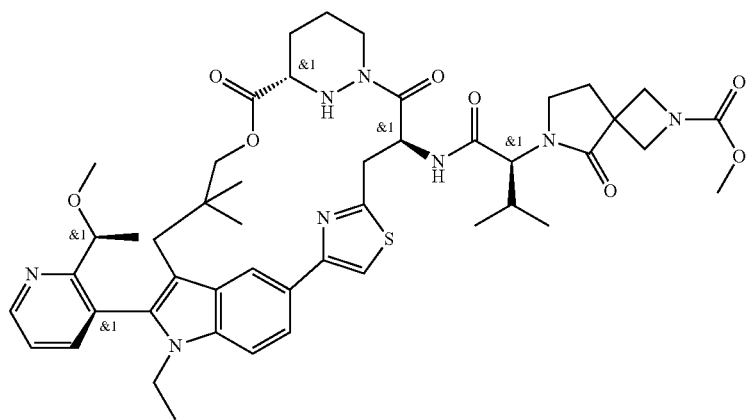 |

TABLE 1-continued
Certain Compounds of the Present Invention
| Ex# | Structure |
|---|---|
| A236 | 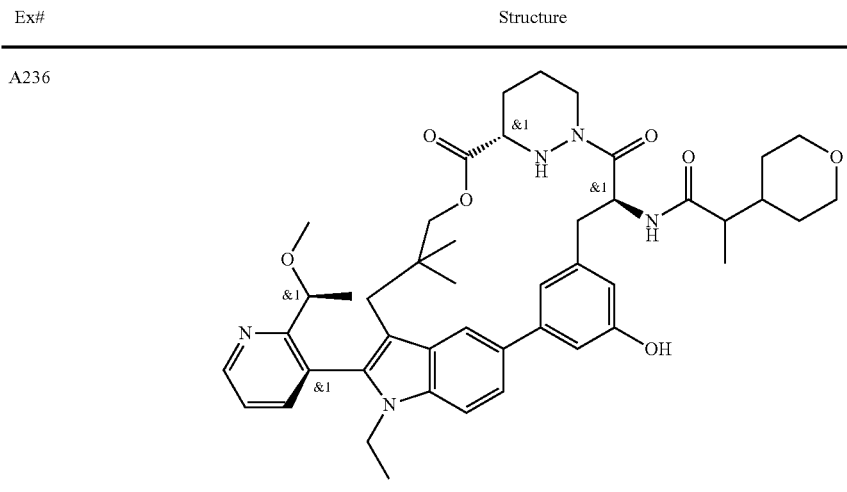 |
| A237 | 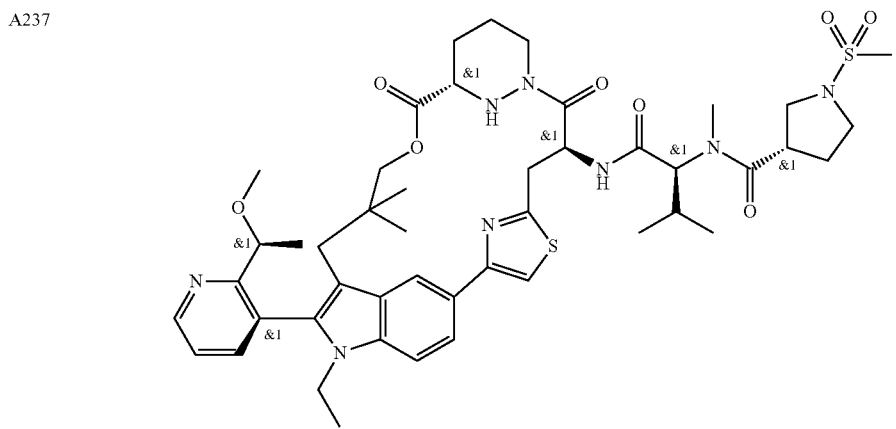 |
| A238 | 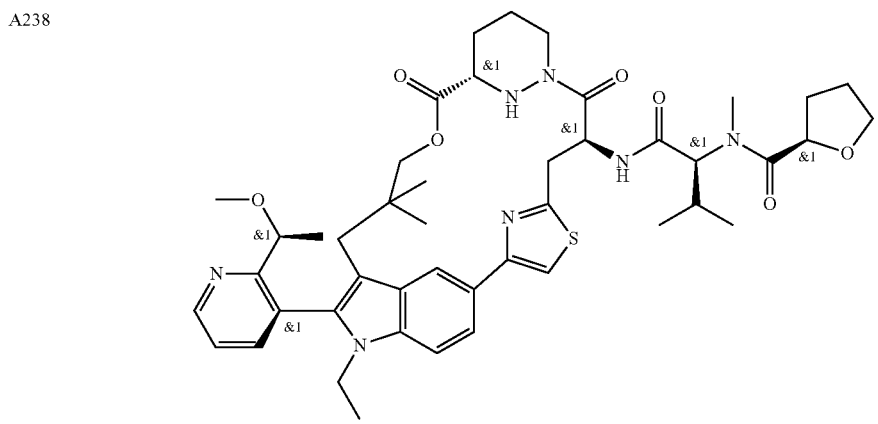 |

TABLE 1-continued
Certain Compounds of the Present Invention
| Ex# | Structure |
|---|---|
| A239 | 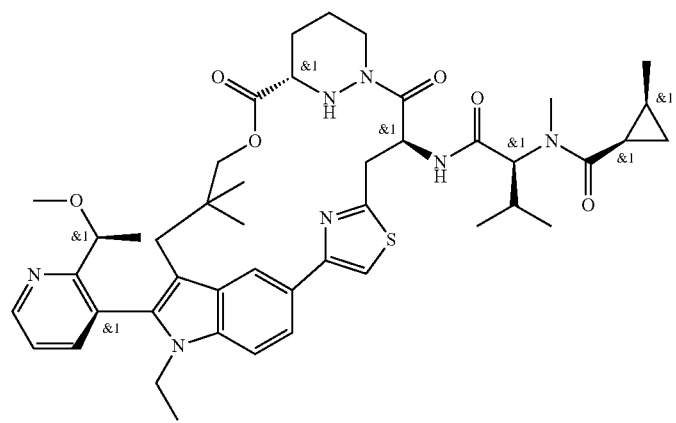 |
| A240 | 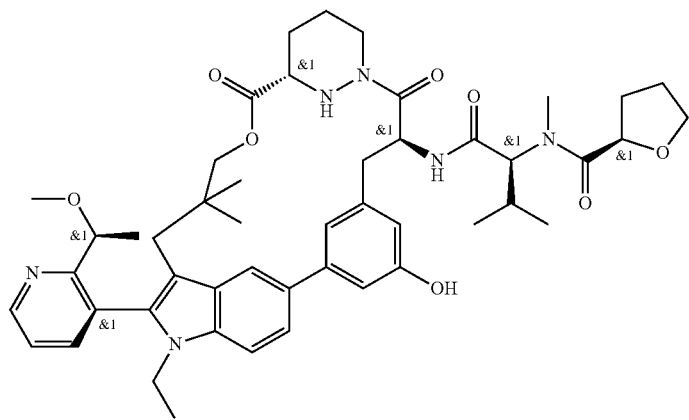 |
| A241 | 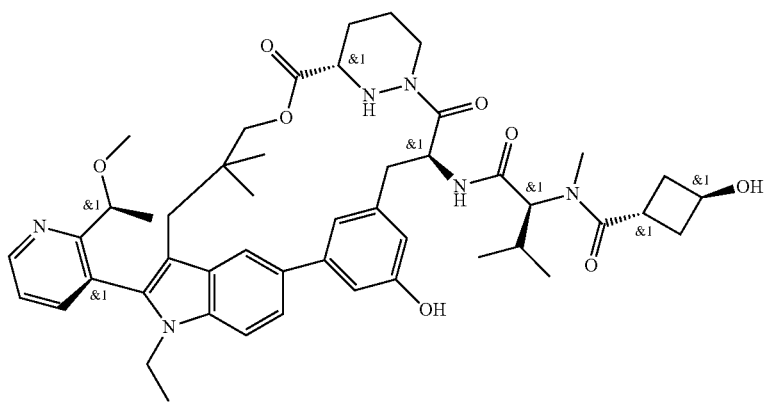 |

TABLE 1-continued
Certain Compounds of the Present Invention
| Ex# | Structure |
|---|---|
| A242 | 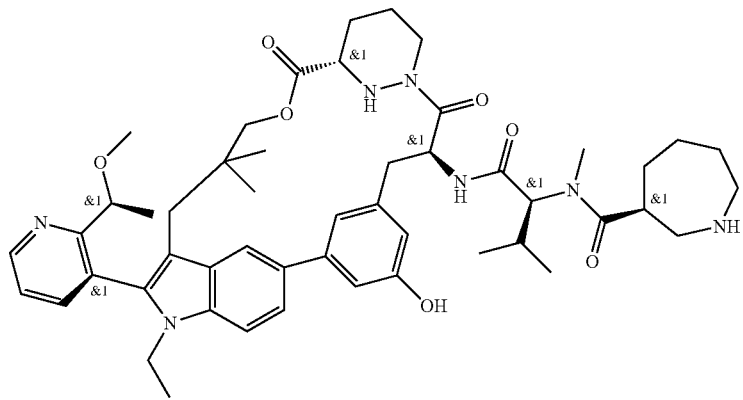 |
| A243 | 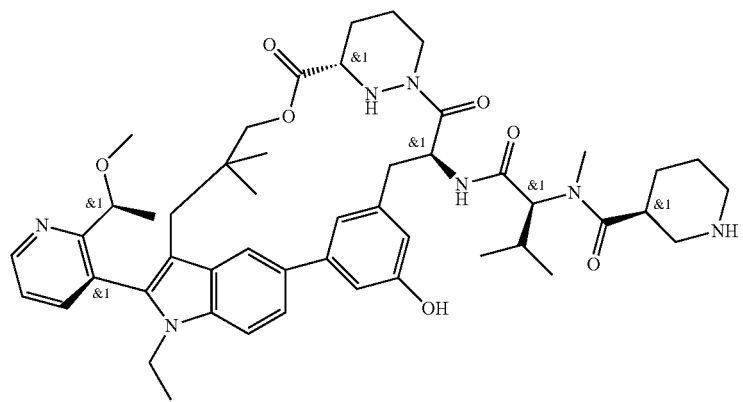 |
| A244 | 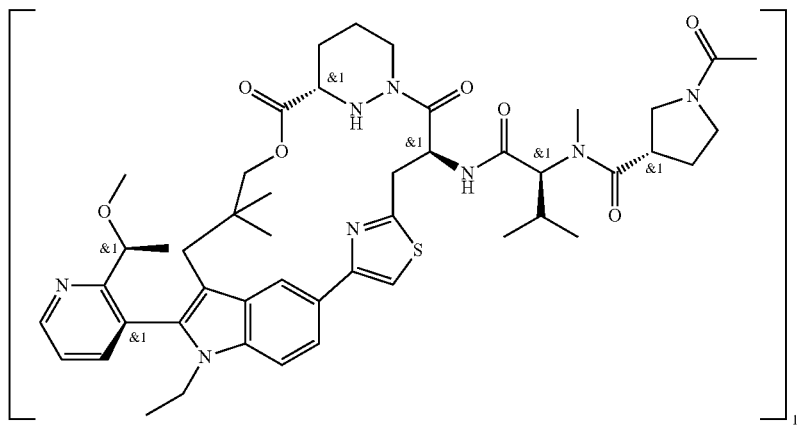 |

TABLE 1-continued
Certain Compounds of the Present Invention
| Ex# | Structure |
|---|---|
| A245 | 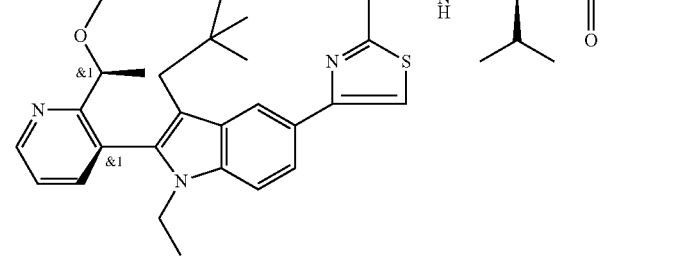 |
| A246 | 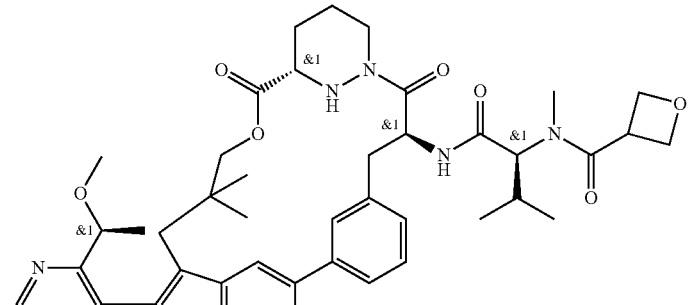 |
| A247 | 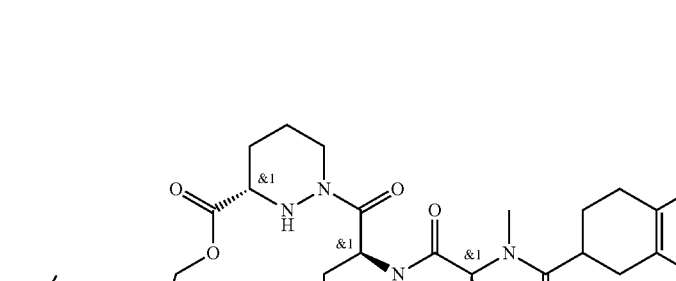 |

TABLE 1-continued
Certain Compounds of the Present Invention
| Ex# | Structure |
|---|---|
| A248 | 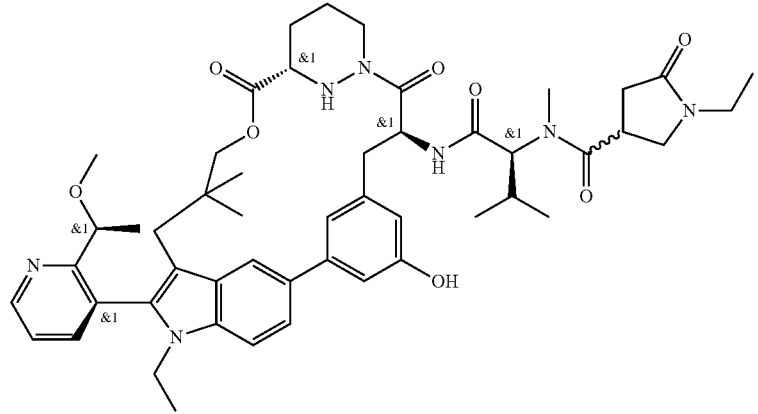 |
| A249 | 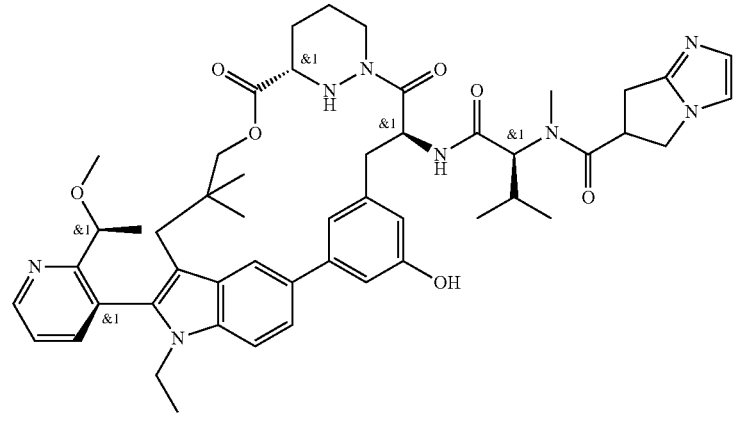 |
| A250 | 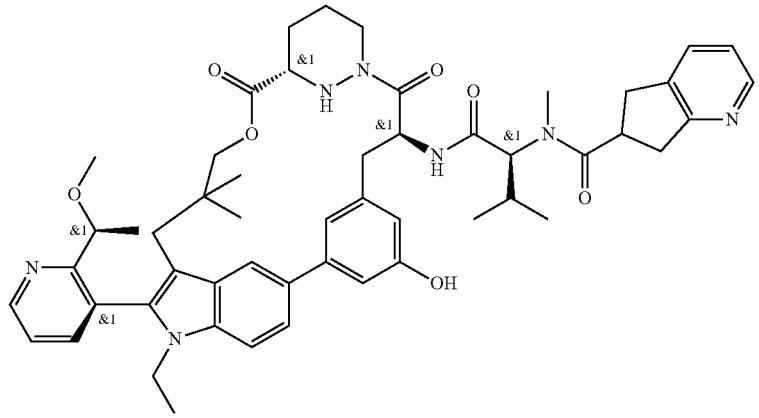 |

TABLE 1-continued
Certain Compounds of the Present Invention
| Ex# | Structure |
|---|---|
| A251 | 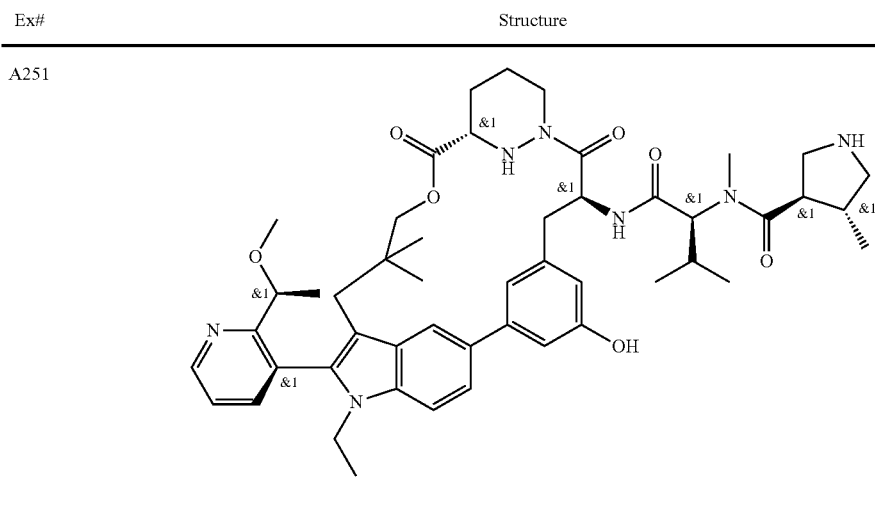 |
| A252 | 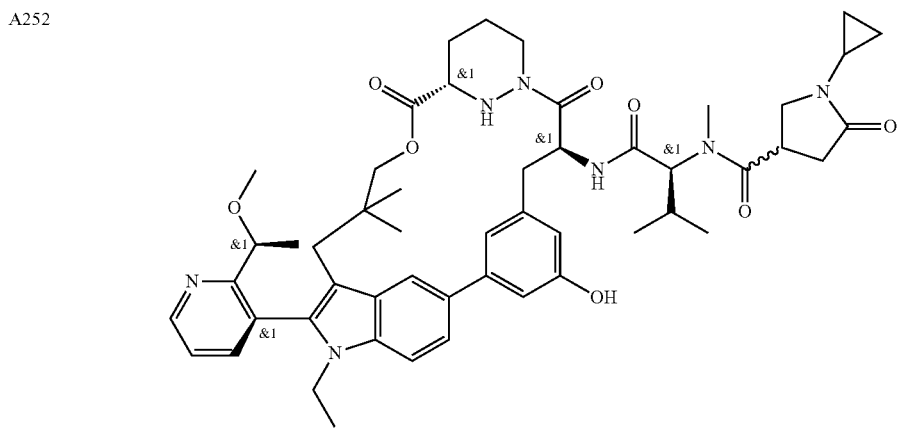 |
| A253 | 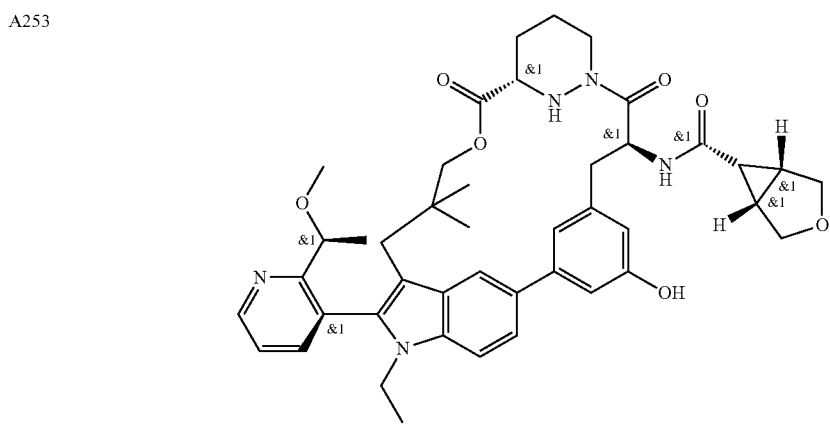 |

TABLE 1-continued
Certain Compounds of the Present Invention
| Ex# | Structure |
|---|---|
| A254 | 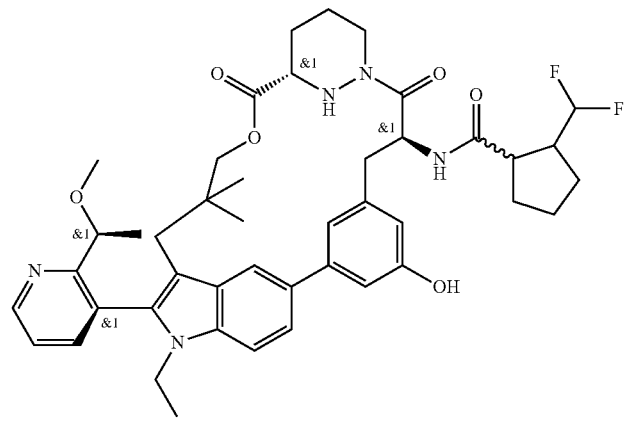 |
| A255 | 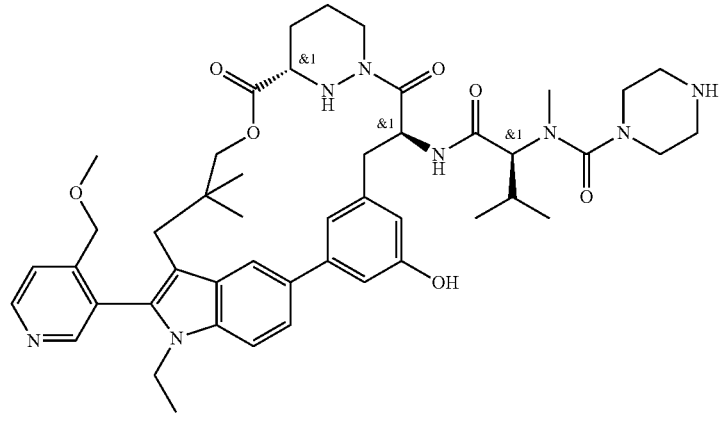 [SMILES: CCn1c(-c2cnccc2COC)c2c3cc(ccc31)-c1cc(O)cc(c1)C[C@H](NC(=O)[C@H](C(C)C)N(C)C(=O)N1CCNCC1)C(=O)N1CCC[C@H](N1)C(=O)OCC(C)(C)C2] |
| A256 | 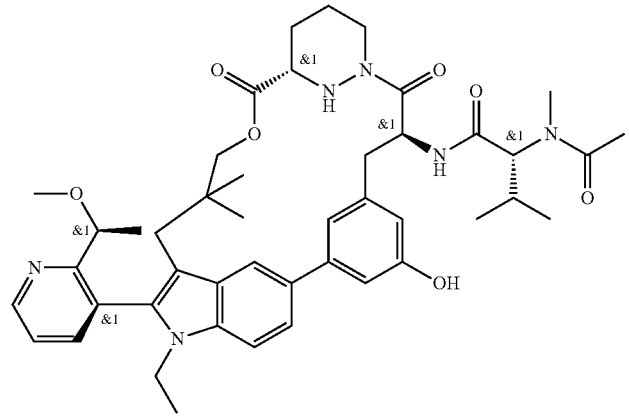 |

TABLE 1-continued

Certain Compounds of the Present Invention

| Ex# | Structure |
|---|---|
| A257 | 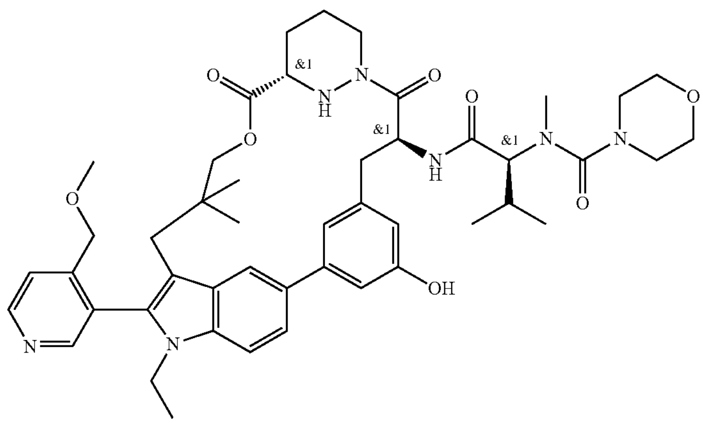 [SMILES: CCn1c(-c2cnccc2COC)c2c3cc(ccc31)-c1cc(O)cc(c1)C[C@H](NC(=O)[C@H](C(C)C)N(C)C(=O)N1CCOCC1)C(=O)N1CCC[C@H](N1)C(=O)OCC(C)(C)C2] |
| A258 | 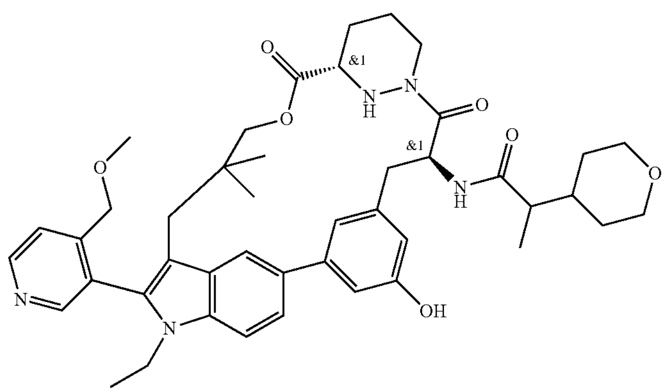 [SMILES: CCn1c(-c2cnccc2COC)c2c3cc(ccc31)-c1cc(O)cc(c1)C[C@H](NC(=O)C(C)C1CCOCC1)C(=O)N1CCC[C@H](N1)C(=O)OCC(C)(C)C2] |
| A259 | 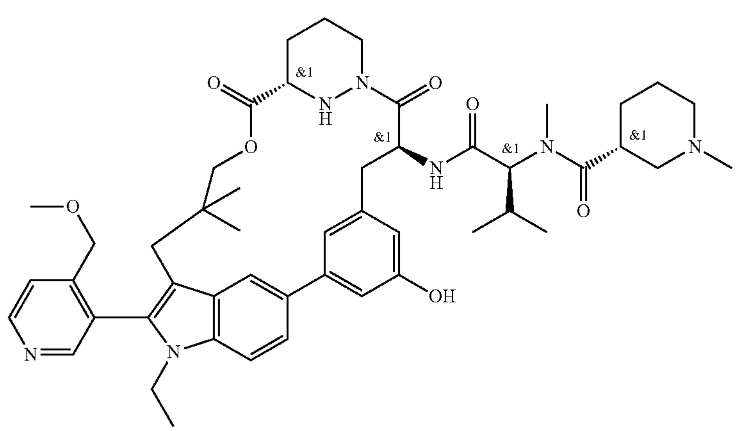 [SMILES: CCn1c(-c2cnccc2COC)c2c3cc(ccc31)-c1cc(O)cc(c1)C[C@H](NC(=O)[C@H](C(C)C)N(C)C(=O)[C@@H]1CCCN(C)C1)C(=O)N1CCC[C@H](N1)C(=O)OCC(C)(C)C2] |

TABLE 1-continued
Certain Compounds of the Present Invention
| Ex# | Structure |
|---|---|
| A260 | 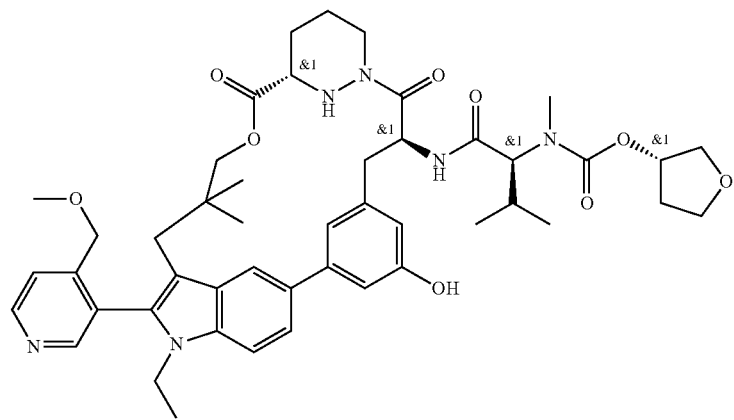 [SMILES: CCn1c(-c2cnccc2COC)c2c3cc(ccc31)-c1cc(O)cc(c1)C[C@H](NC(=O)[C@H](C(C)C)N(C)C(=O)O[C@H]1CCOC1)C(=O)N1CCC[C@H](N1)C(=O)OCC(C)(C)C2] |
| A261 | 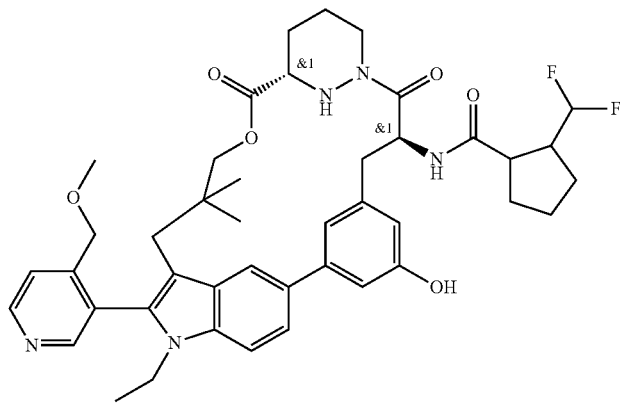 [SMILES: CCn1c(-c2cnccc2COC)c2c3cc(ccc31)-c1cc(O)cc(c1)C[C@H](NC(=O)C1CCCC1C(F)F)C(=O)N1CCC[C@H](N1)C(=O)OCC(C)(C)C2] |
| A262 | 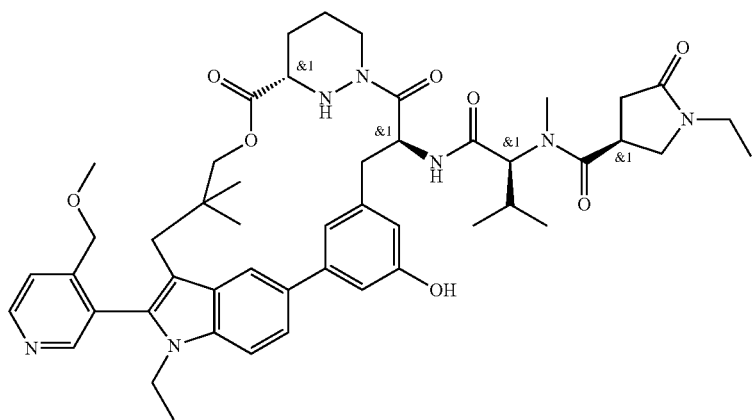 [SMILES: CCN1C[C@@H](C(=O)N(C)[C@H](C(=O)N[C@H]2Cc3cc(O)cc(c3)-c3ccc4c(c3)c(c(-c3cnccc3COC)n4CC)CC(C)(C)COC(=O)[C@@H]3CCCN(N3)C2=O)C(C)C)CC1=O] |

TABLE 1-continued
Certain Compounds of the Present Invention
| Ex# | Structure |
|---|---|
| A263 | 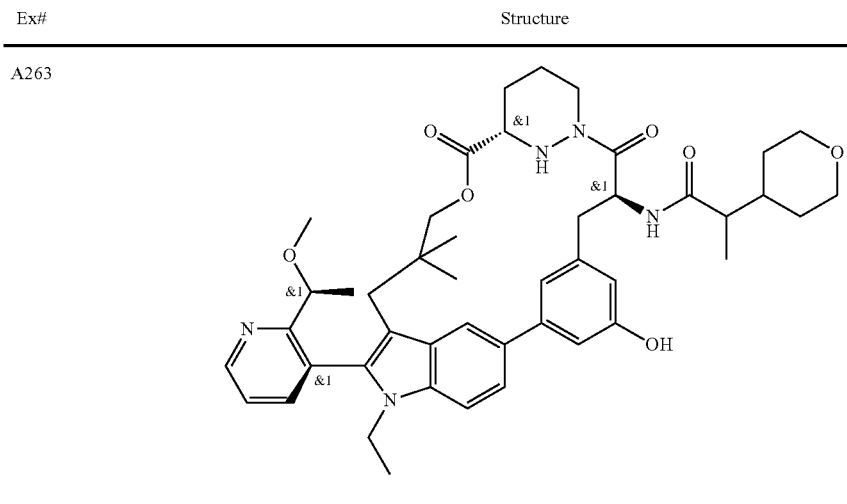 |
| A264 | 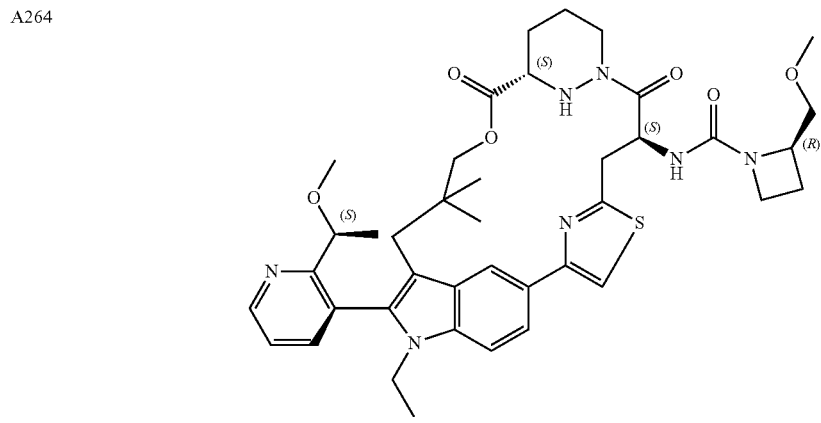 |
| A265 | 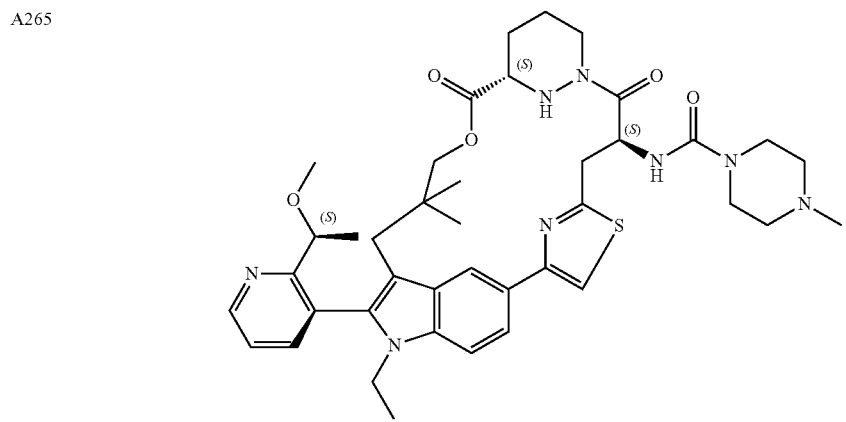 |

TABLE 1-continued
Certain Compounds of the Present Invention
| Ex# | Structure |
|---|---|
| A266 | 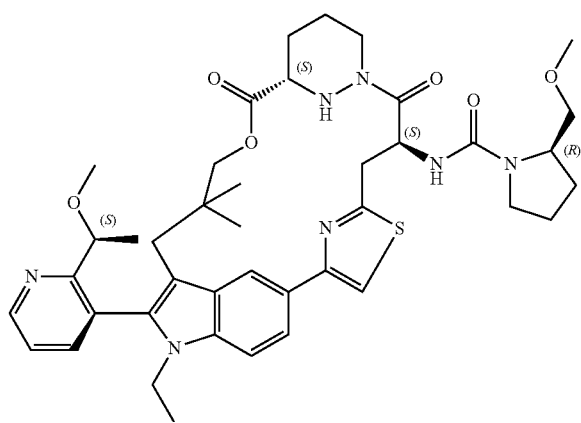 |
| A267 | 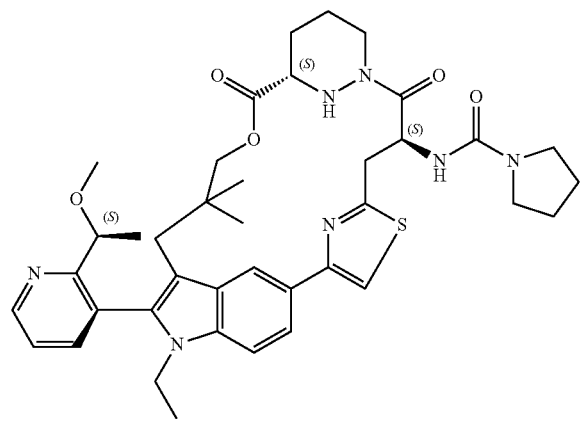 |
| A268 | 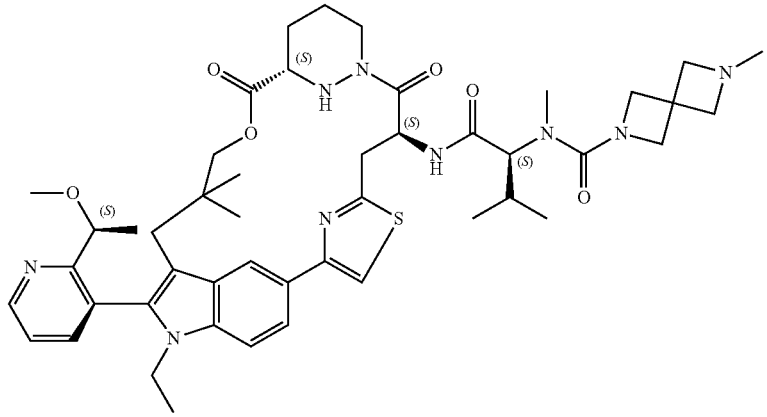 |

TABLE 1-continued
Certain Compounds of the Present Invention
| Ex# | Structure |
|---|---|
| A270 | 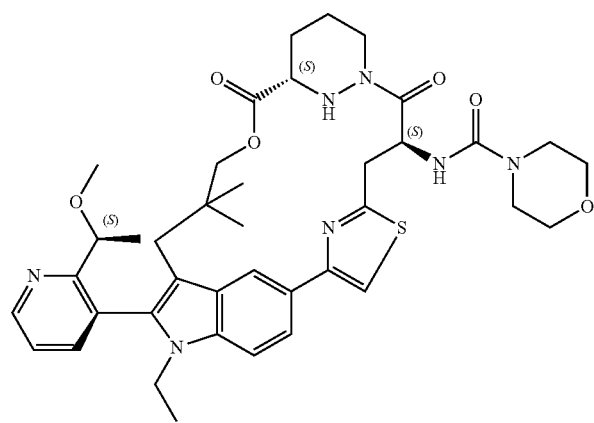 |
| A271 | 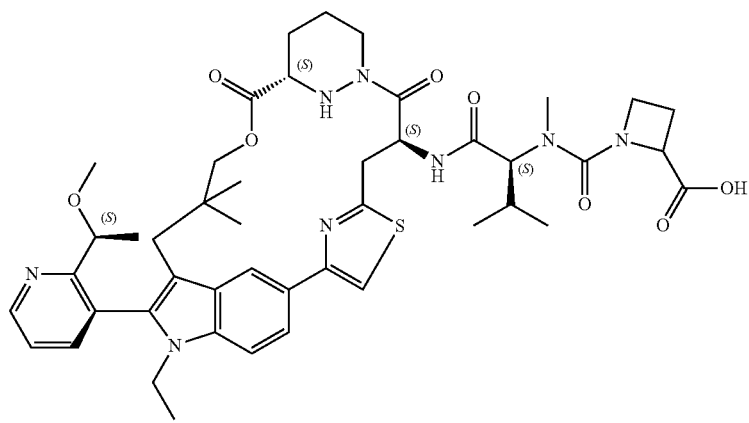 |
| A272 | 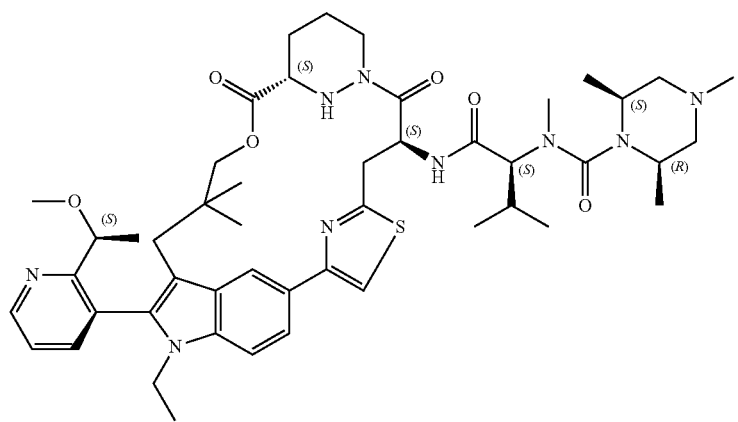 |

TABLE 1-continued
Certain Compounds of the Present Invention
| Ex# | Structure |
|---|---|
| A273 | 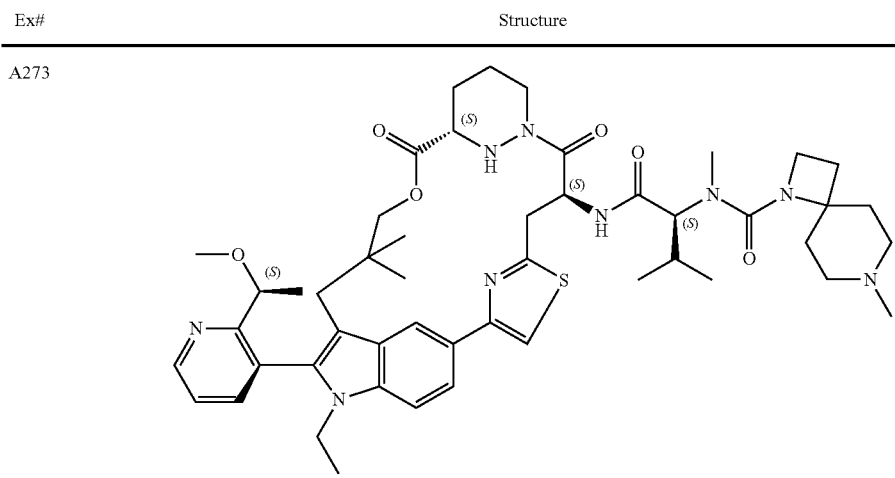 |
| A274 | 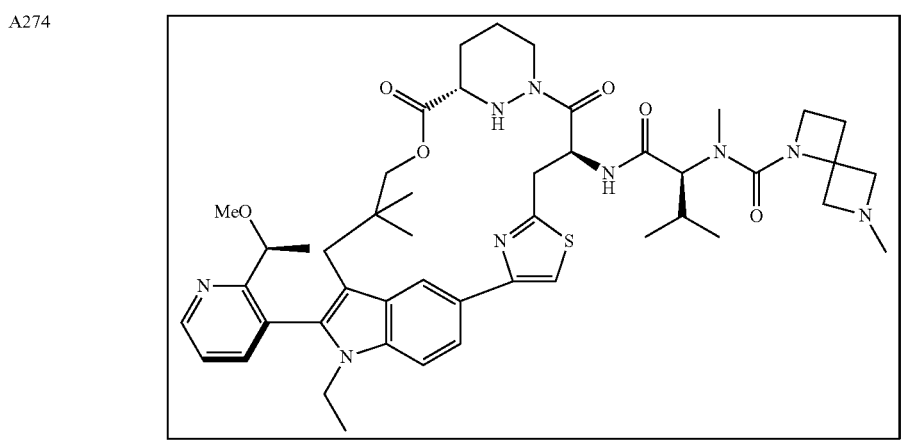 |
| A275 | 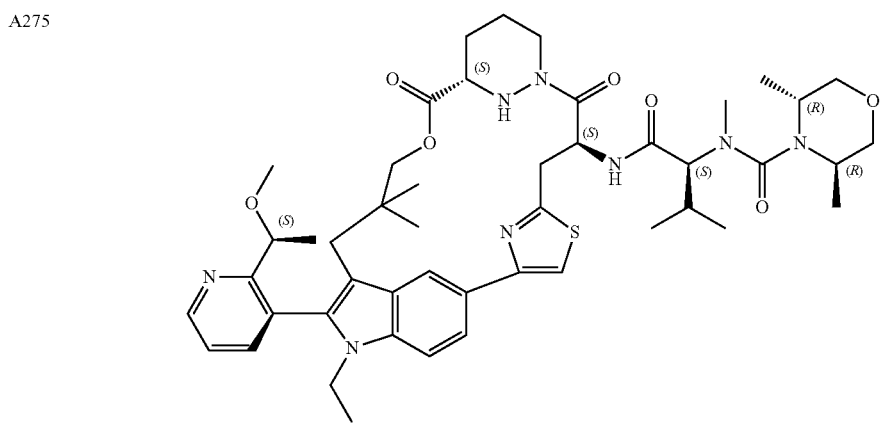 |

TABLE 1-continued

Certain Compounds of the Present Invention

| Ex# | Structure |
|---|---|
| A276 | 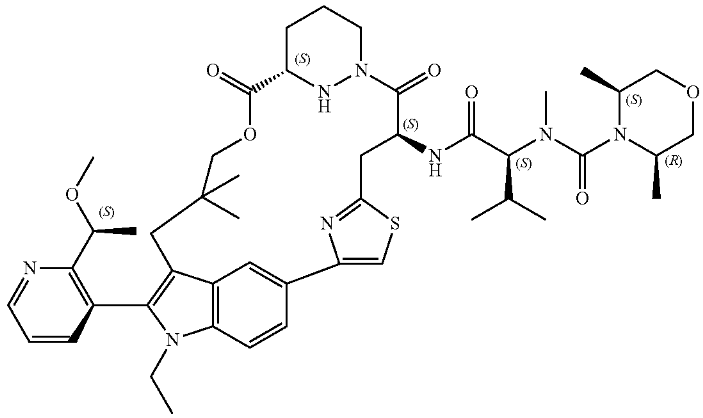 |
| A277 | 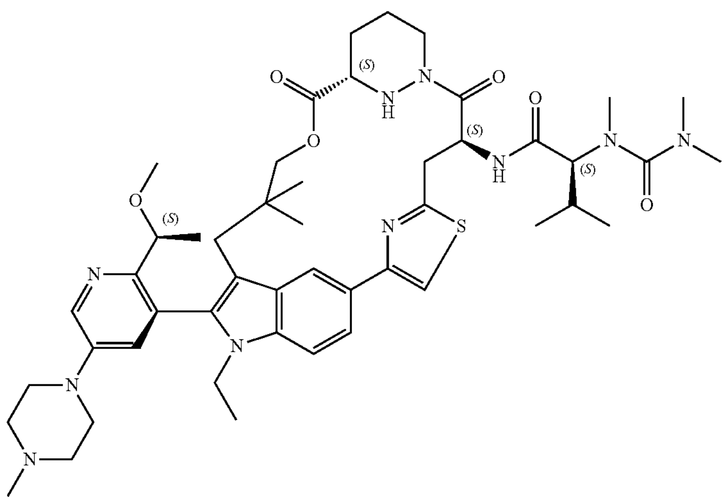 |
| A278 | 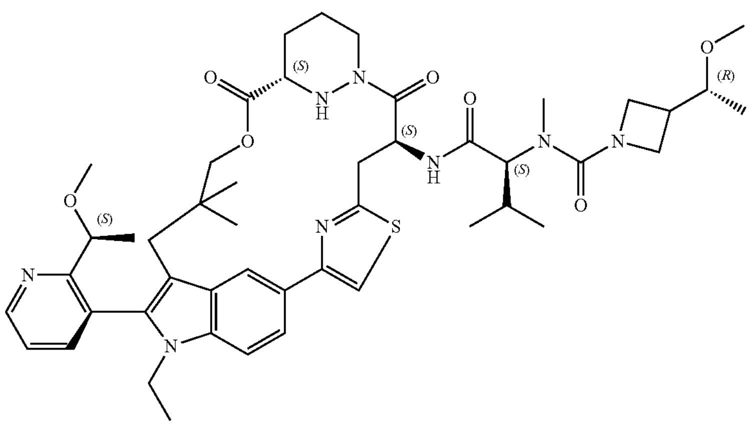 |

TABLE 1-continued

Certain Compounds of the Present Invention

| Ex# | Structure |
|---|---|
| A279 | 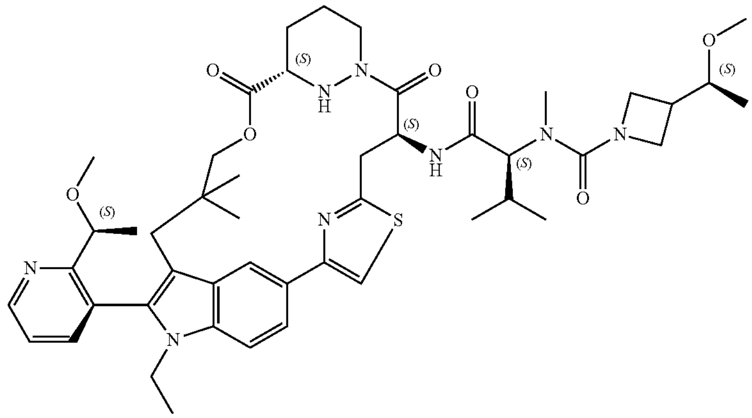 |
| A280 | 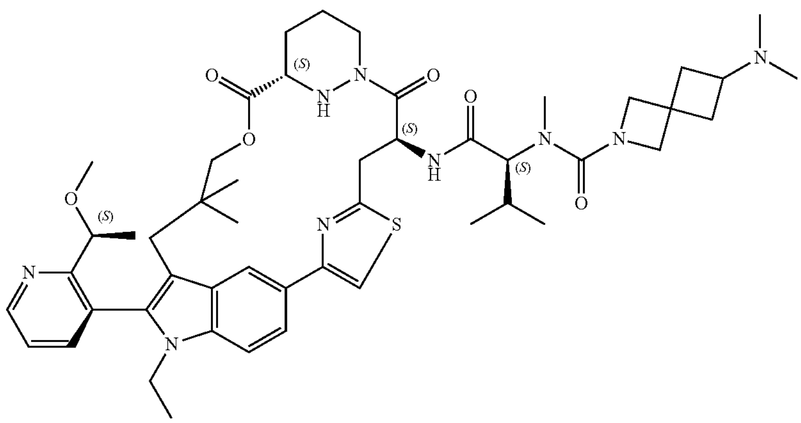 |
| A281 | 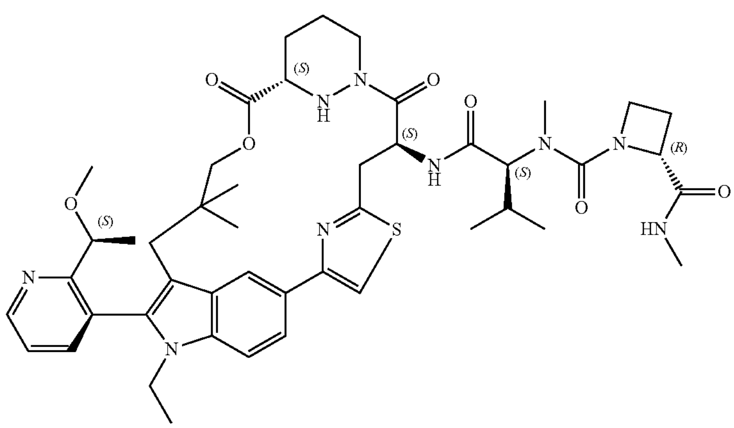 |

TABLE 1-continued

Certain Compounds of the Present Invention

| Ex# | Structure |
|---|---|
| A282 | 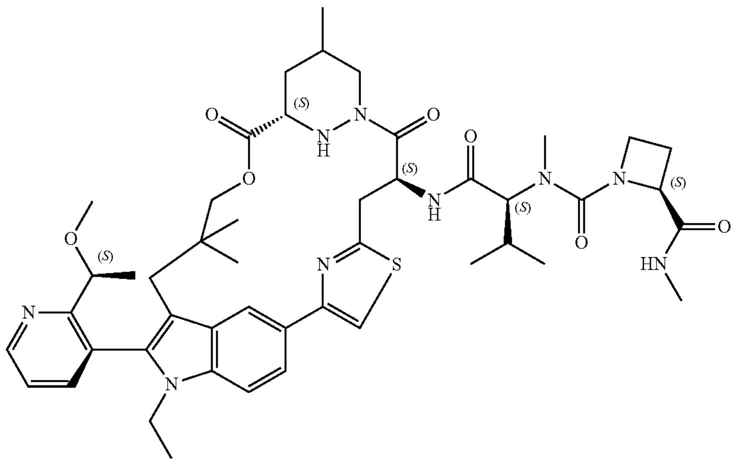 |
| A283 | 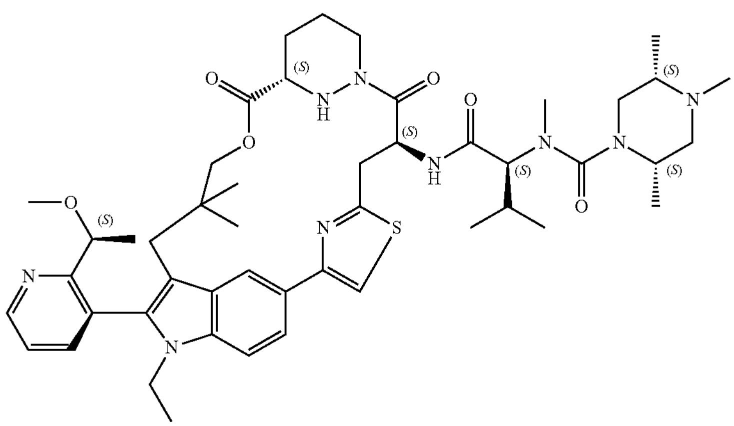 |
| A284 | 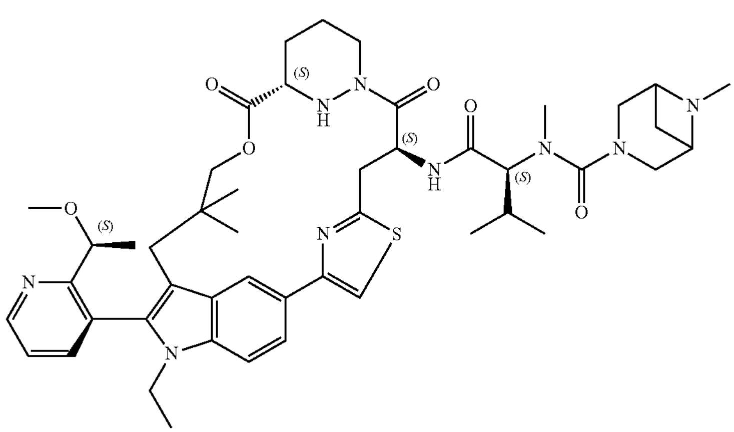 |

TABLE 1-continued

Certain Compounds of the Present Invention

| Ex# | Structure |
|---|---|
| A285 | 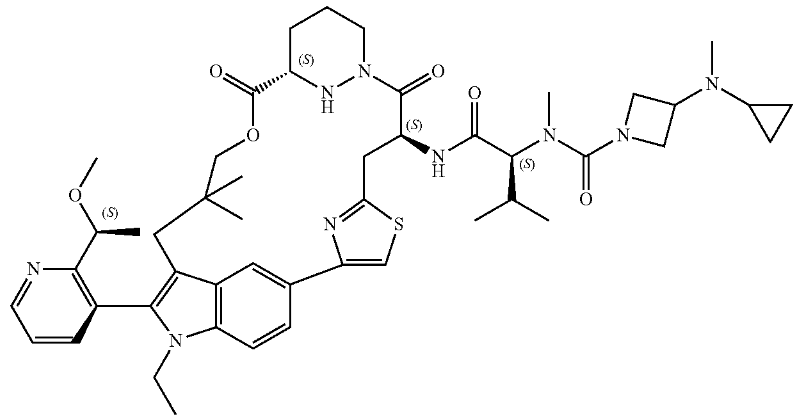 |
| A286 | 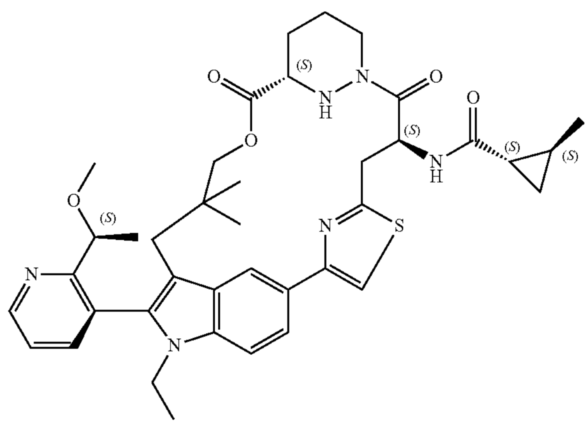 |
| A287 | 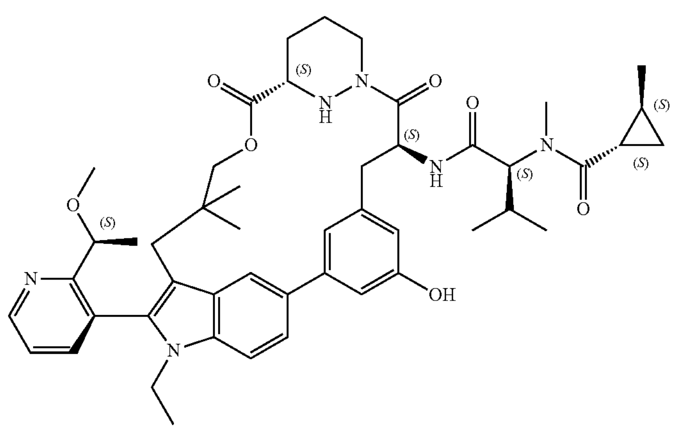 |

TABLE 1-continued
Certain Compounds of the Present Invention
| Ex# | Structure |
|---|---|
| A288 | 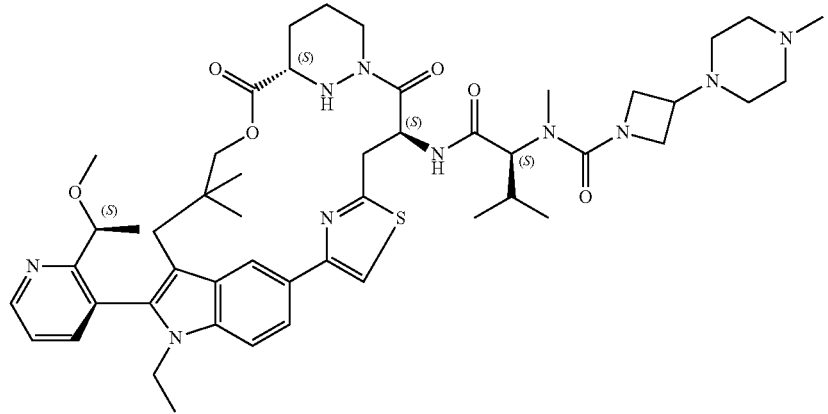 |
| A289 | 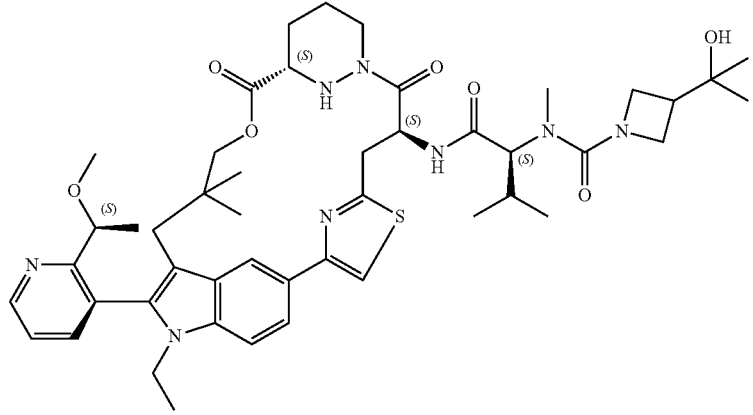 |
| A290 | 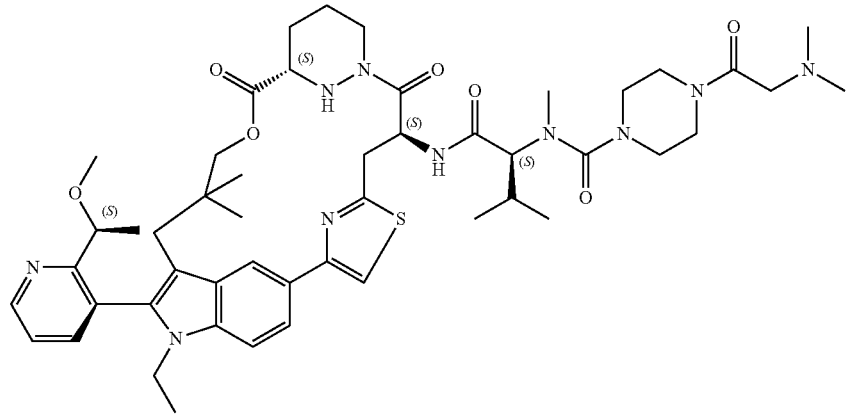 |

TABLE 1-continued

Certain Compounds of the Present Invention

| Ex# | Structure |
|---|---|
| A291 | 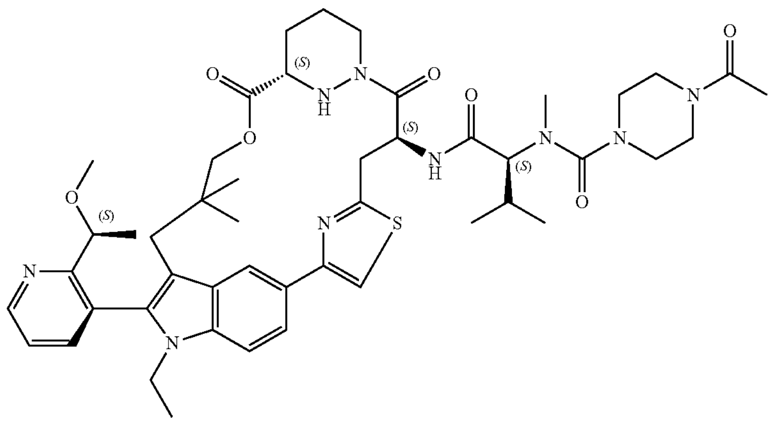 |
| A292 | 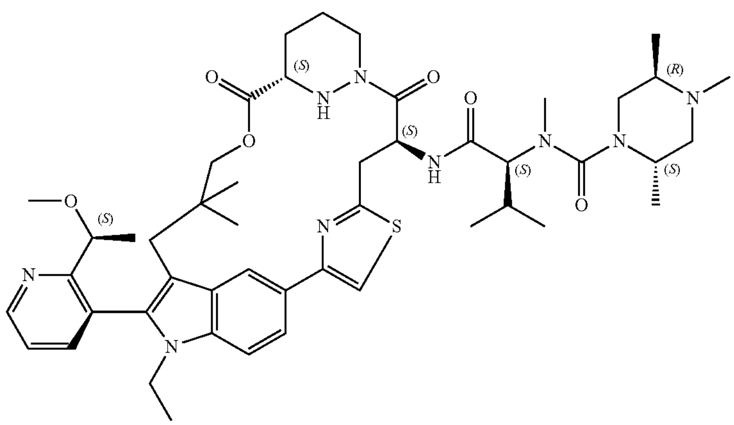 |
| A293 | 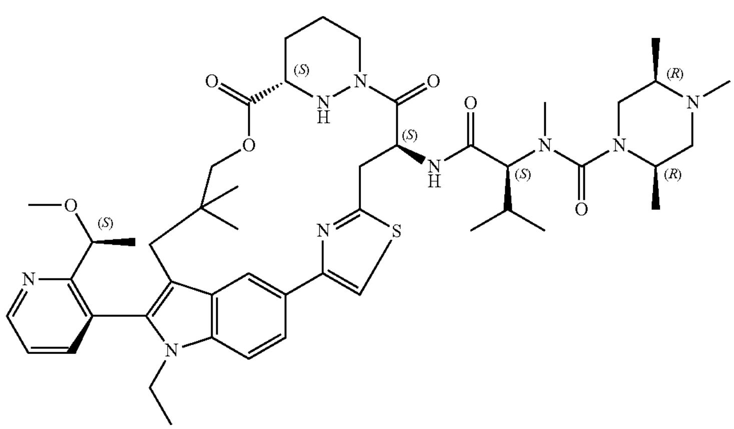 |

TABLE 1-continued
Certain Compounds of the Present Invention
| Ex# | Structure |
| --- | --- |
| A294 | 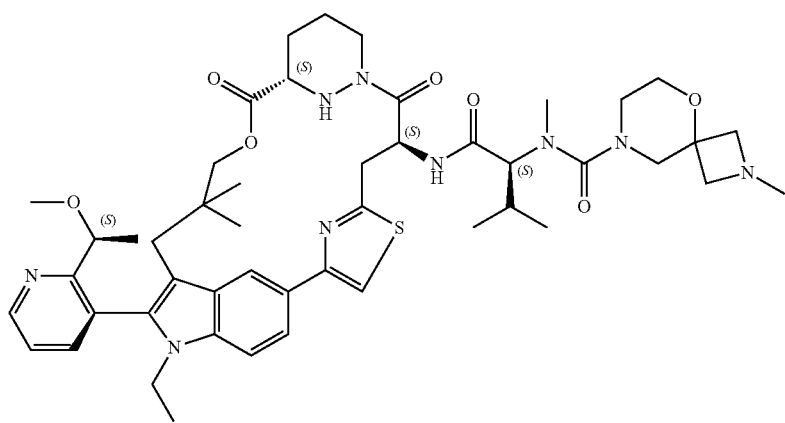 |
| A295 | 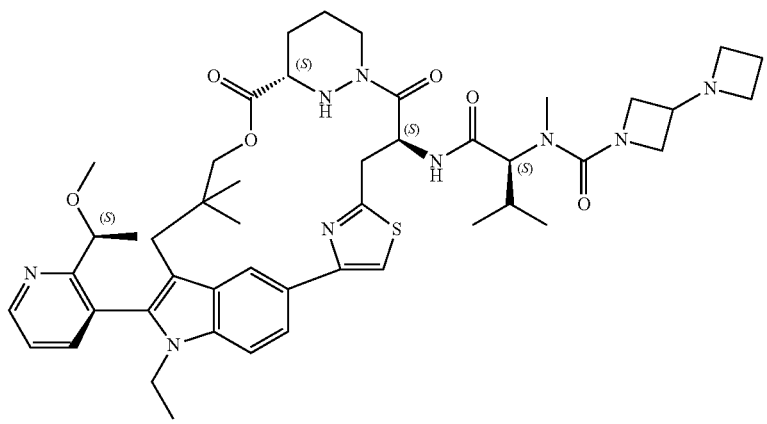 |
| A296 | 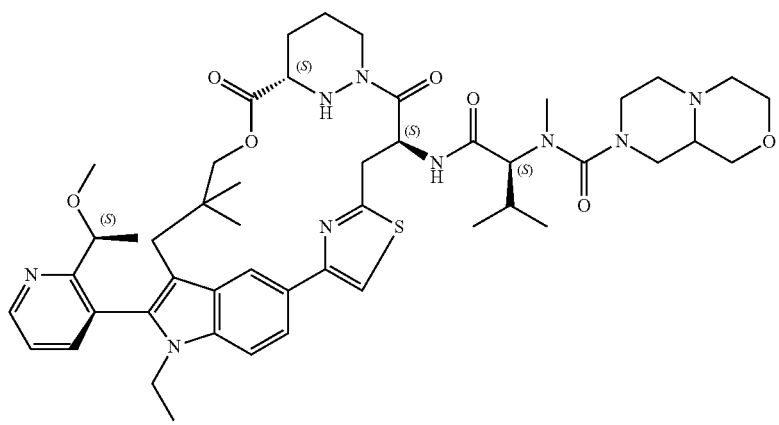 |

US 11,608,346 B2
251　　252
TABLE 1-continued
Certain Compounds of the Present Invention
| Ex# | Structure |
|---|---|
| A297 | 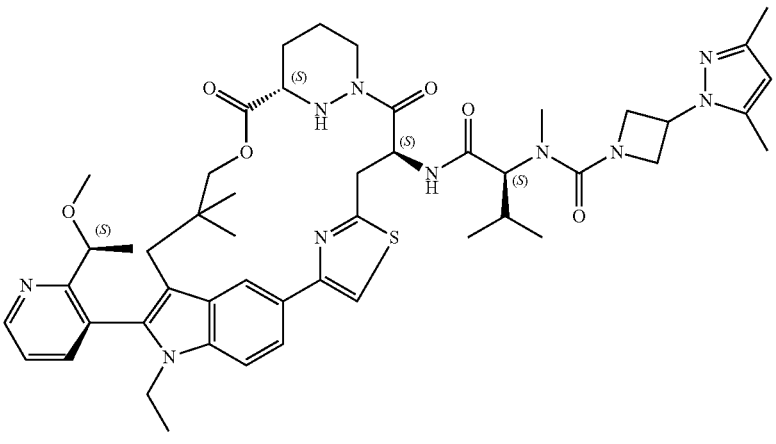 |
| A298 | 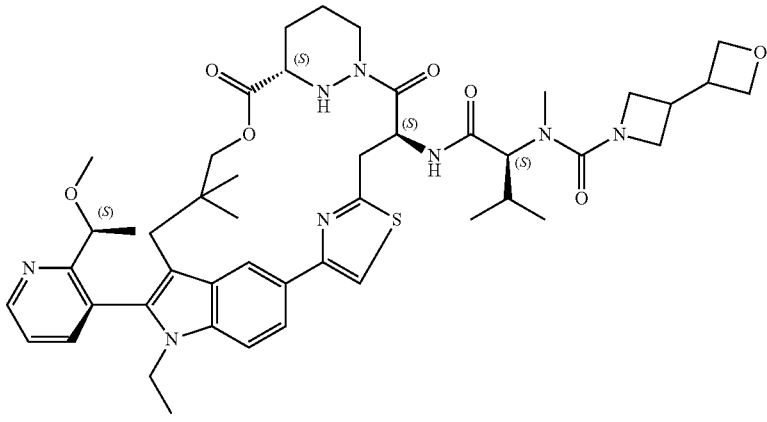 |
| A299 | 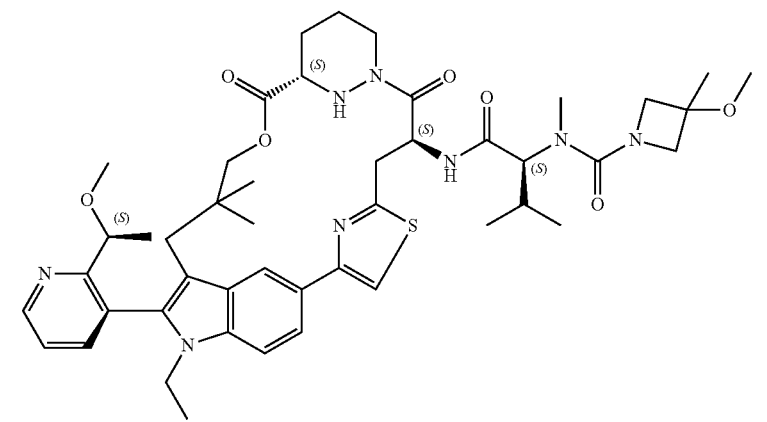 |

US 11,608,346 B2
253                                                                                                                      254
TABLE 1-continued
Certain Compounds of the Present Invention
| Ex# | Structure |
|---|---|
| A300 | 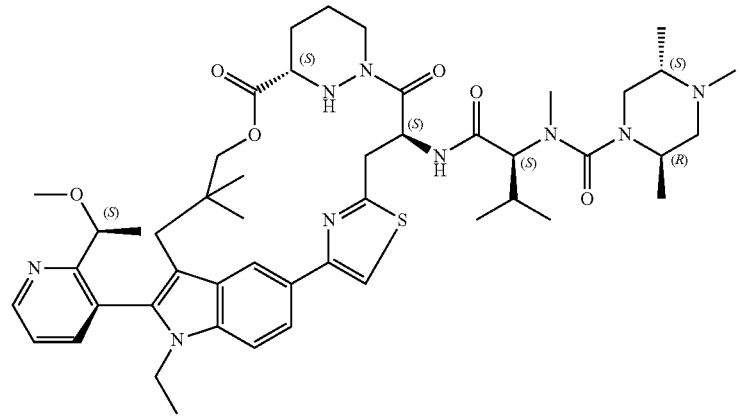 |
| A301 | 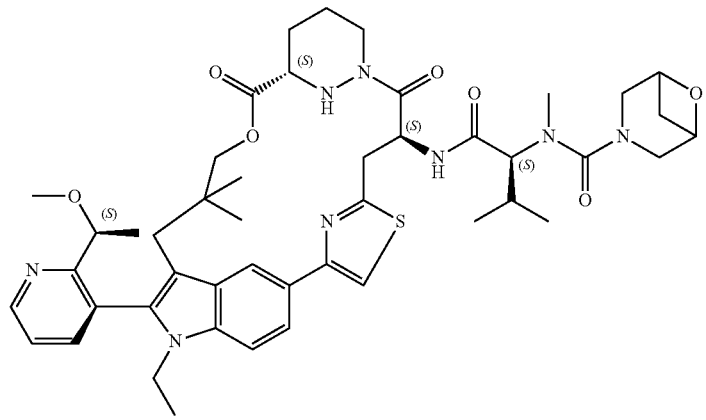 |
| A302 | 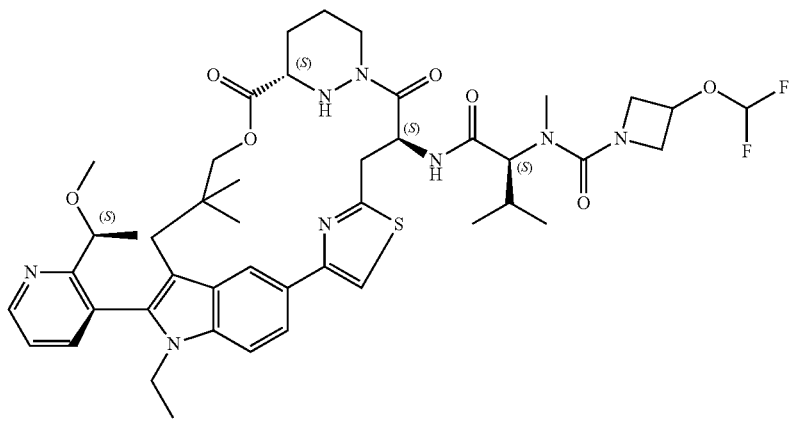 |

TABLE 1-continued
Certain Compounds of the Present Invention
| Ex# | Structure |
| --- | --- |
| A303 | 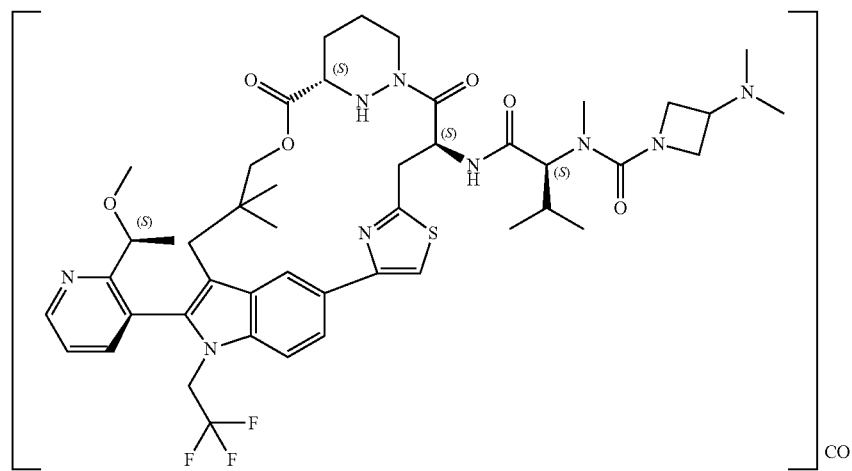 |
| A304 | 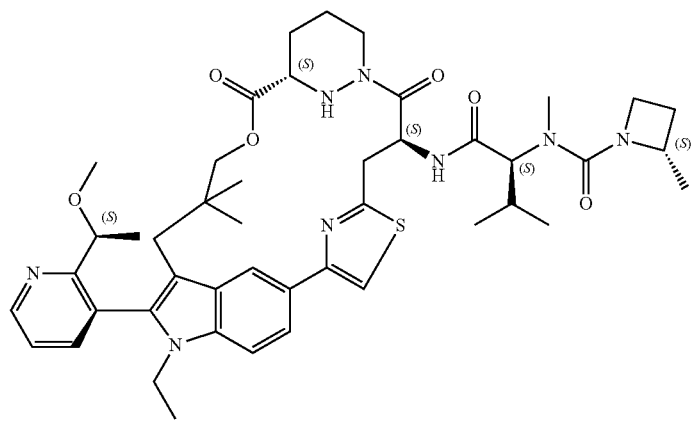 |
| A305 | 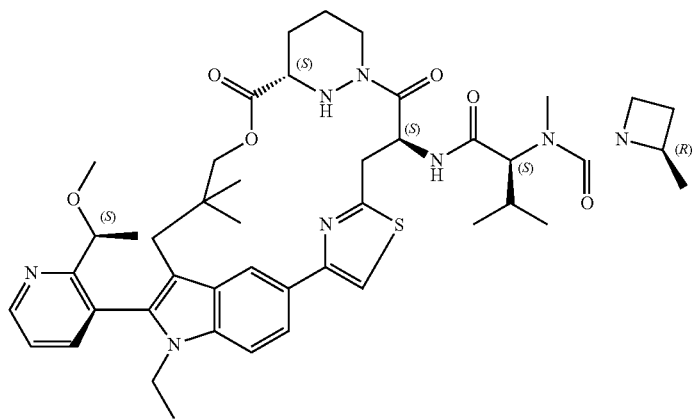 |

TABLE 1-continued

Certain Compounds of the Present Invention

| Ex# | Structure |
|---|---|
| A306 | 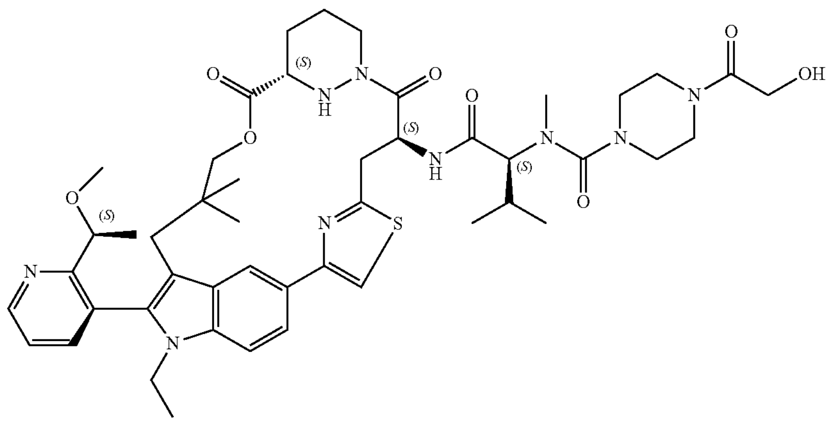 |
| A307 | 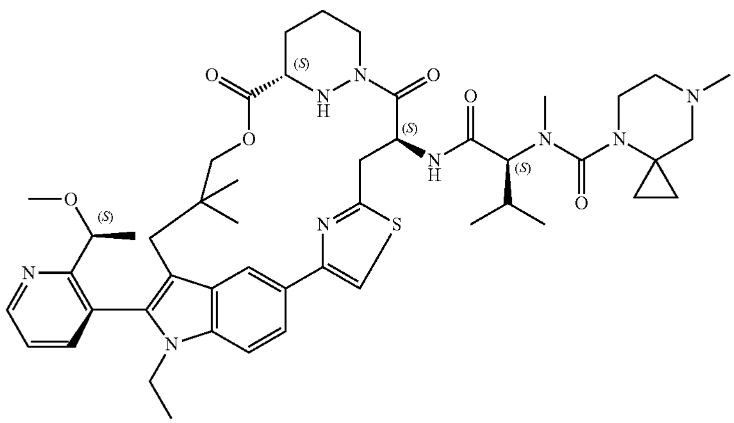 |
| A308 | 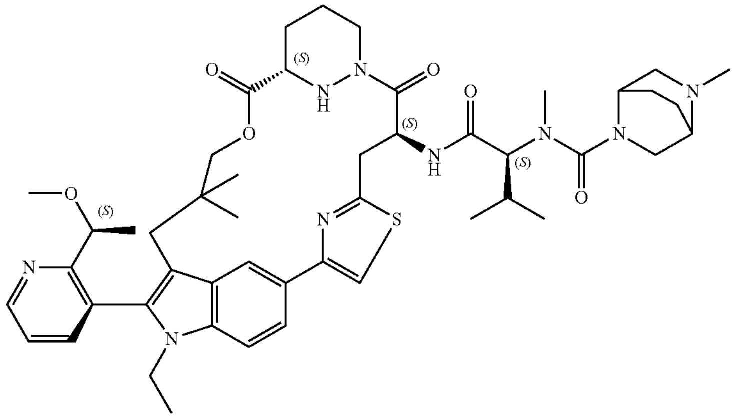 |

TABLE 1-continued

Certain Compounds of the Present Invention

| Ex# | Structure |
|---|---|
| A309 | 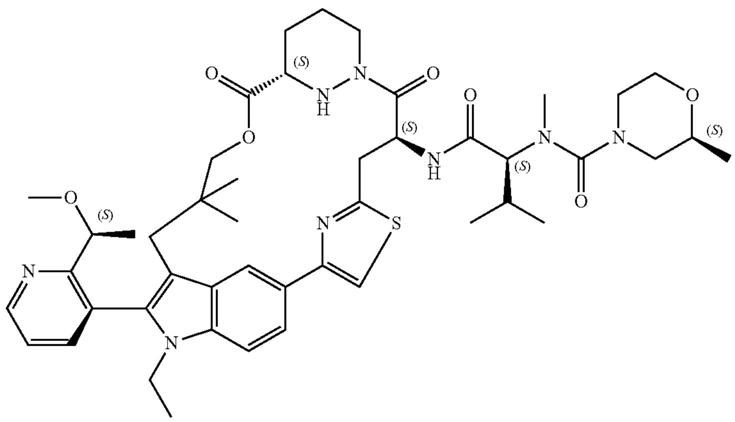 |
| A310 | 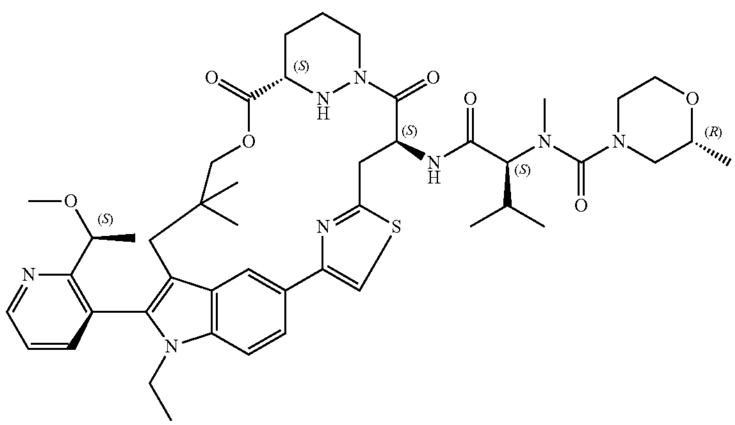 |
| A311 | 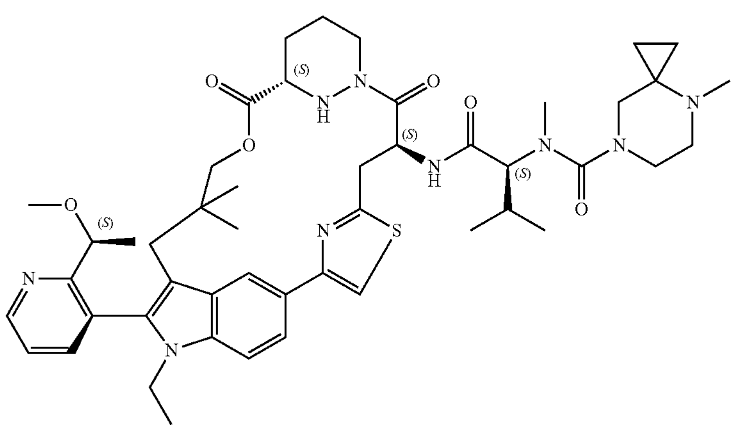 |

TABLE 1-continued
Certain Compounds of the Present Invention
| Ex# | Structure |
|---|---|
| A312 | 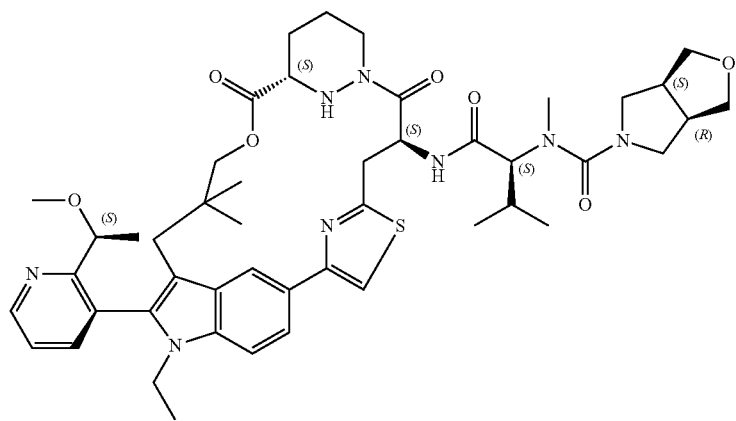 |
| A313 | 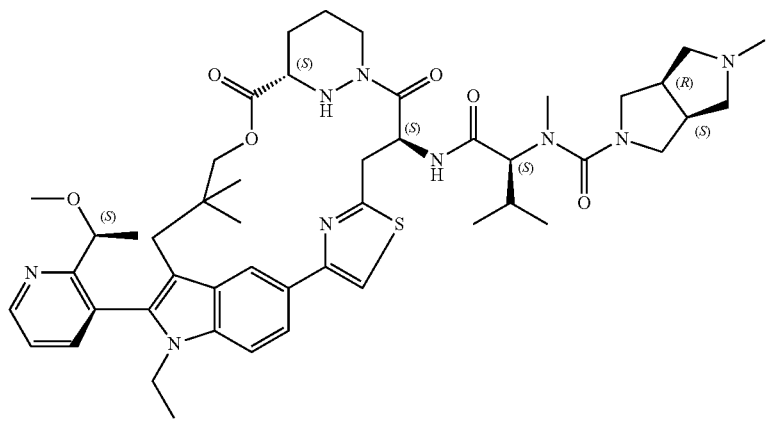 |
| A314 | 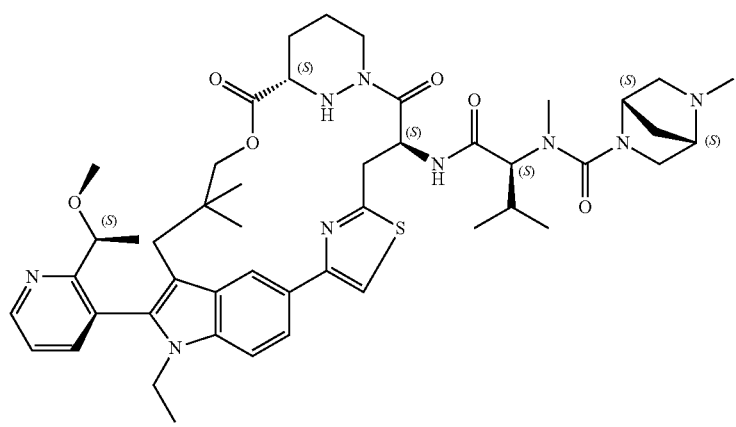 |

TABLE 1-continued
Certain Compounds of the Present Invention
| Ex# | Structure |
|---|---|
| A315 | 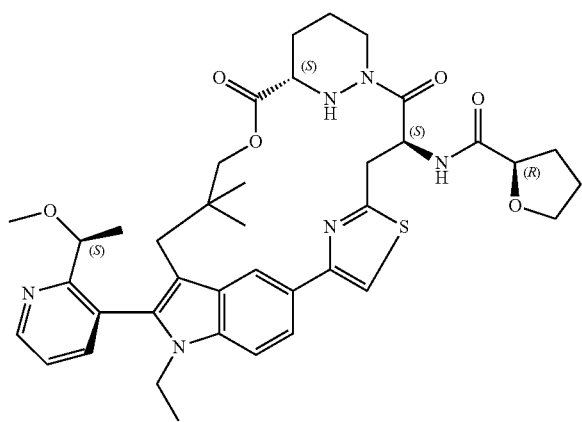 |
| A316 | 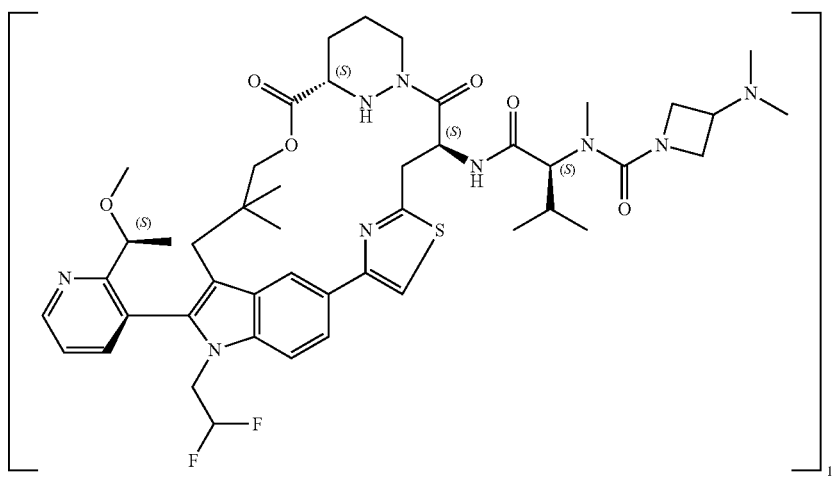 |
| A317 | 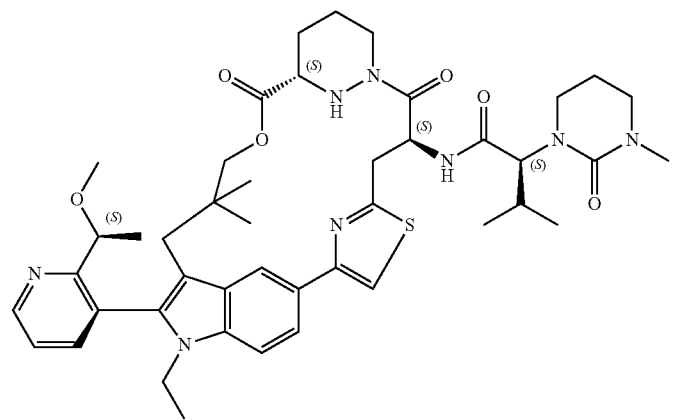 |

TABLE 1-continued
Certain Compounds of the Present Invention
| Ex# | Structure |
|---|---|
| A318 | 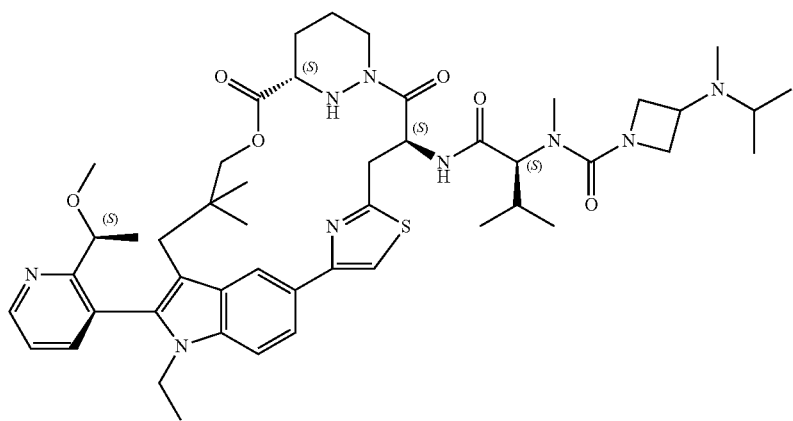 |
| A319 | 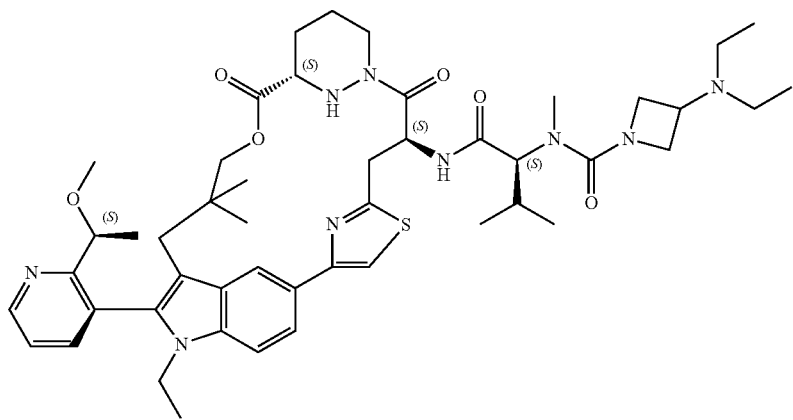 |
| A320 | 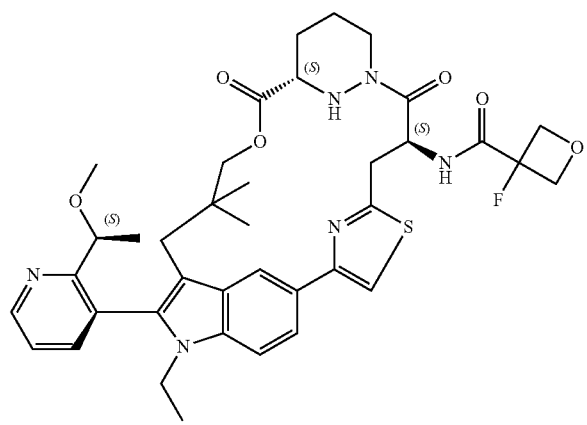 |

TABLE 1-continued
Certain Compounds of the Present Invention
| Ex# | Structure |
|---|---|
| A321 | 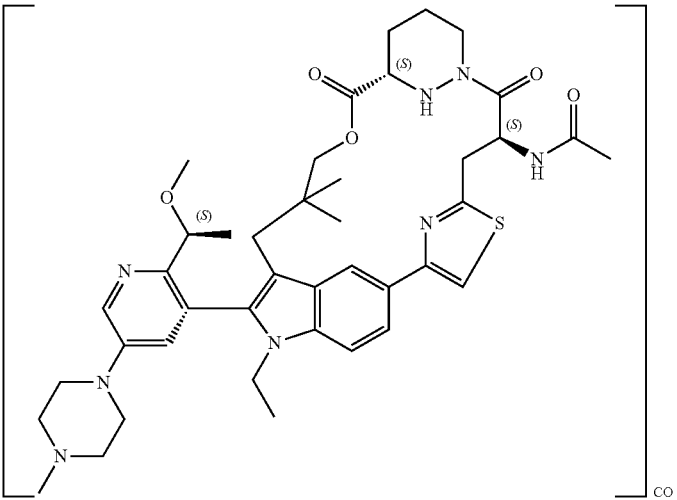 |
| A322 | 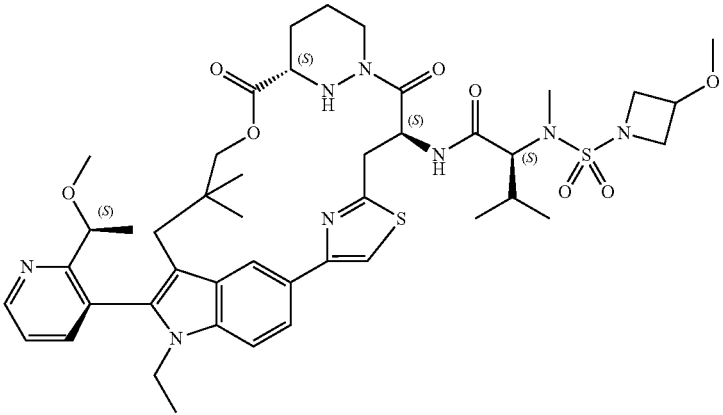 |
| A323 | 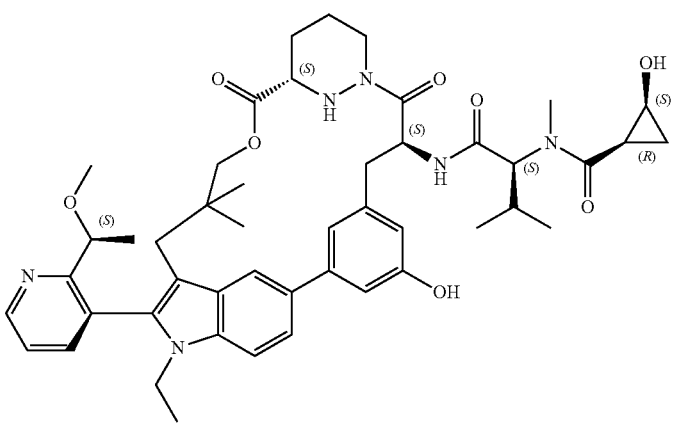 |

TABLE 1-continued

Certain Compounds of the Present Invention

| Ex# | Structure |
|---|---|
| A324 | 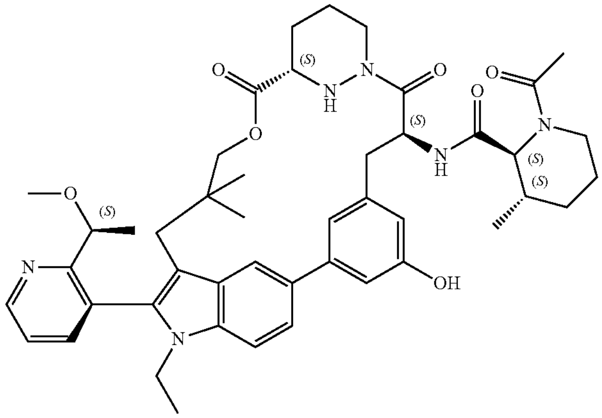 |
| A325 | 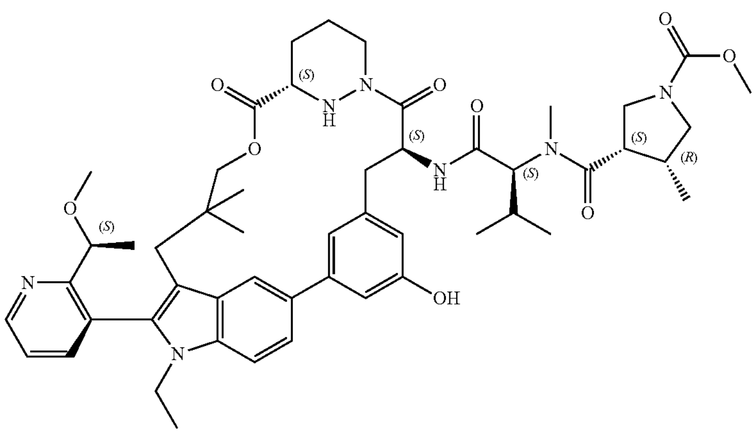 |
| A326 | 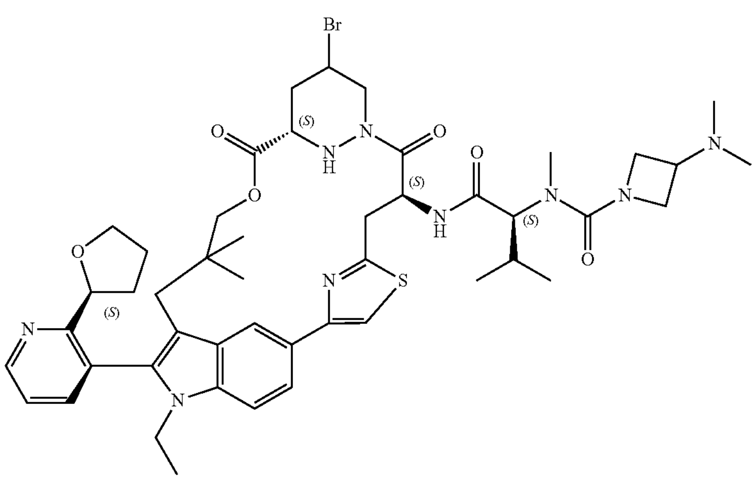 |

TABLE 1-continued

Certain Compounds of the Present Invention

| Ex# | Structure |
|---|---|
| A327 | 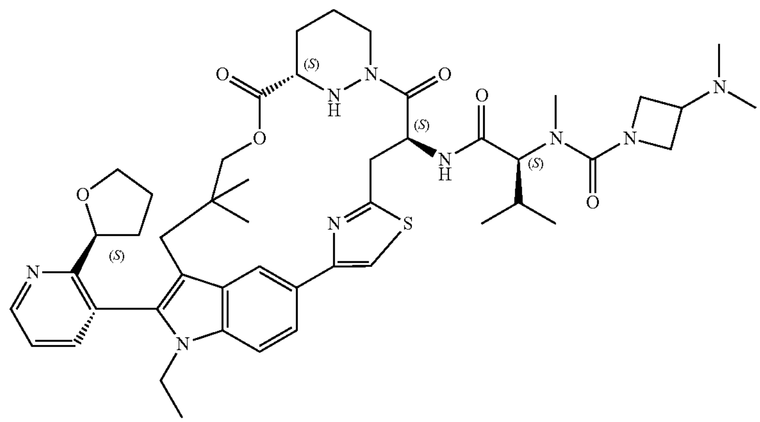 |
| A328 | 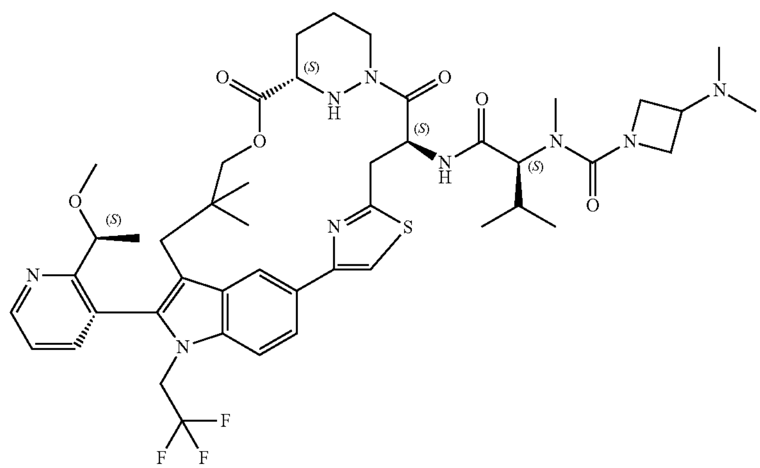 |
| A329 | 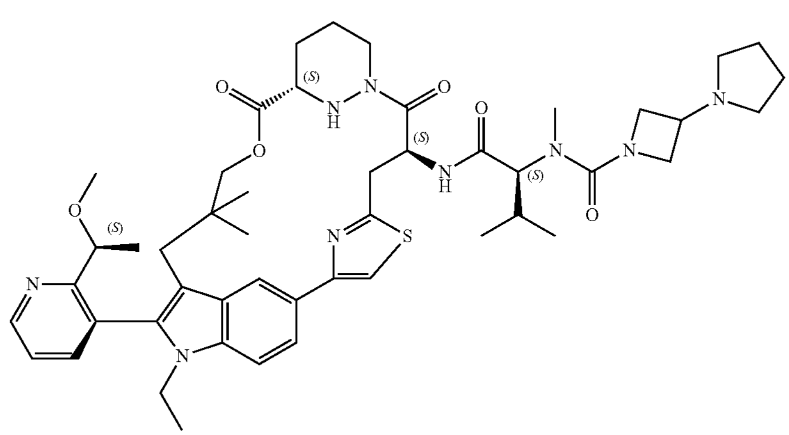 |

TABLE 1-continued
Certain Compounds of the Present Invention
| Ex# | Structure |
|---|---|
| A330 | 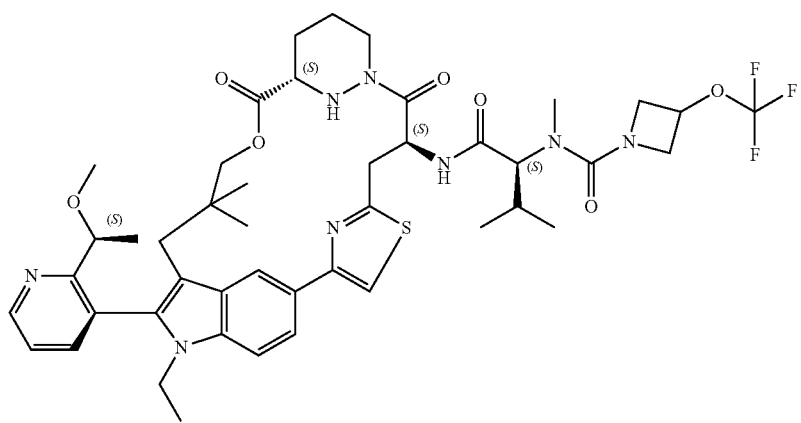 |
| A331 | 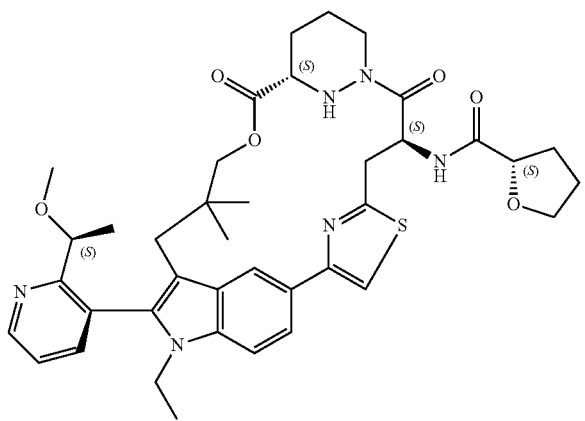 |
| A332 | 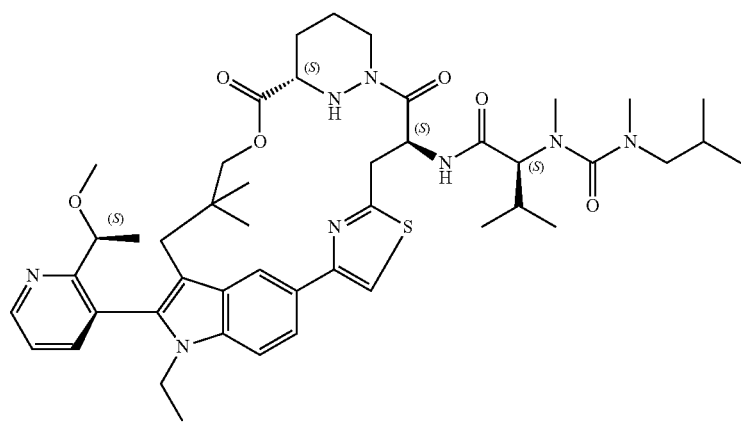 |

TABLE 1-continued

Certain Compounds of the Present Invention

| Ex# | Structure |
|---|---|
| A333 | 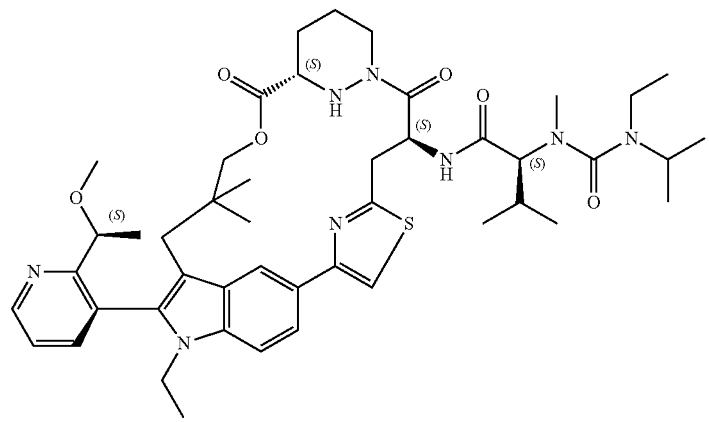 |
| A334 | 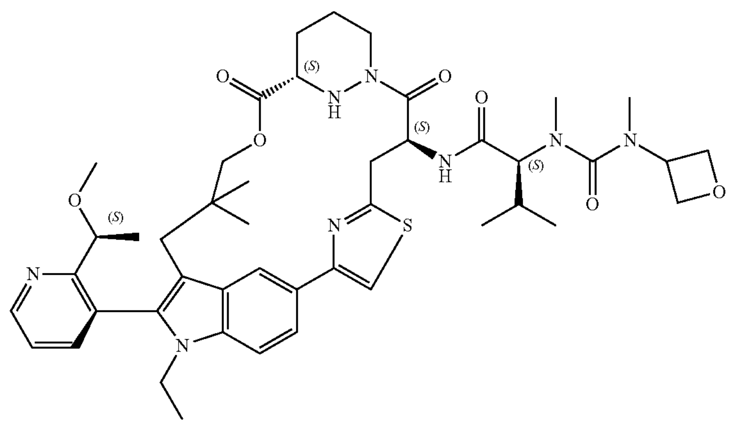 |
| A335 | 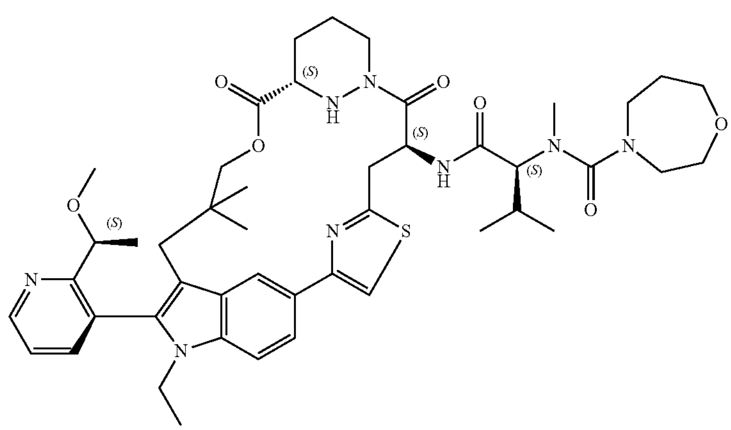 |

TABLE 1-continued

Certain Compounds of the Present Invention

| Ex# | Structure |
|---|---|
| A336 | 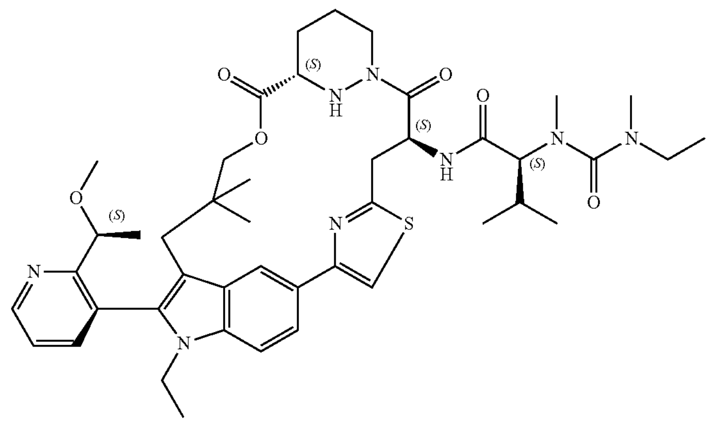 |
| A337 | 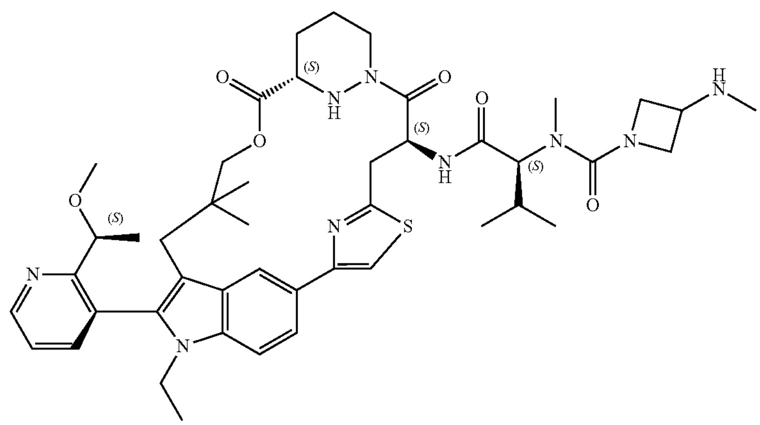 |
| A338 | 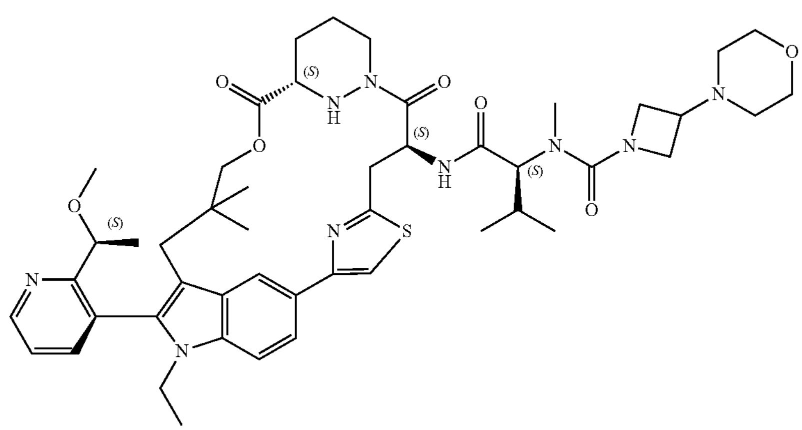 |

TABLE 1-continued
Certain Compounds of the Present Invention
| Ex# | Structure |
|---|---|
| A339 | 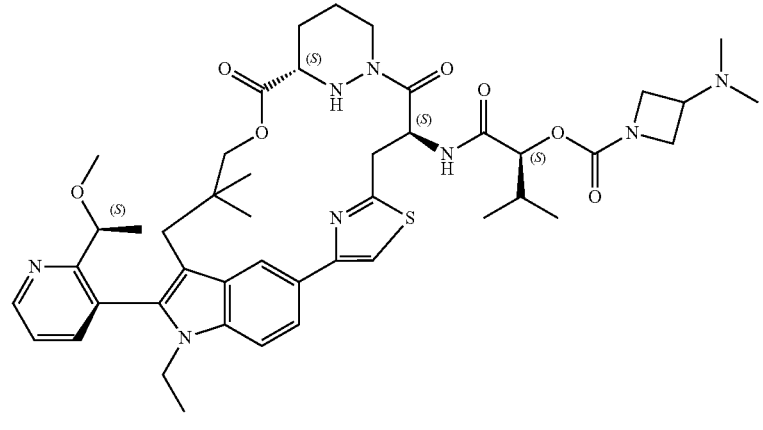 |
| A340 | 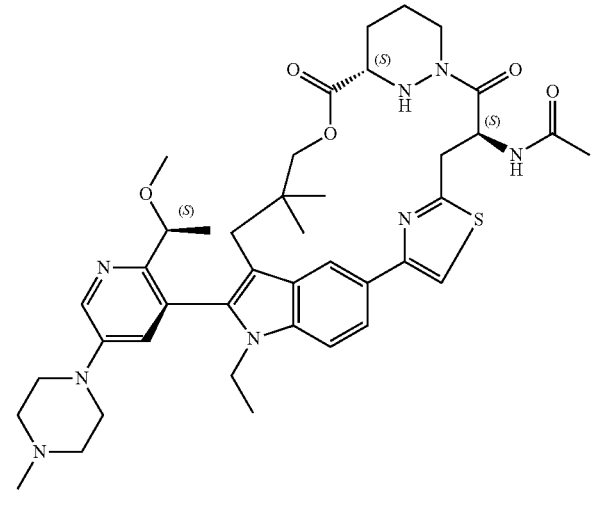 |
| A341 | 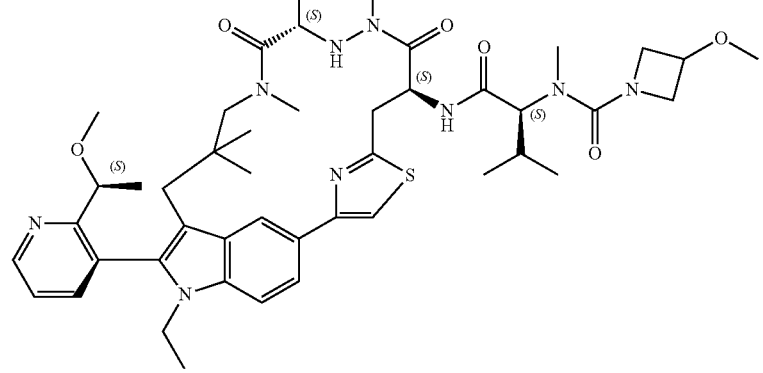 |

TABLE 1-continued
Certain Compounds of the Present Invention
| Ex# | Structure |
|---|---|
| A342 | 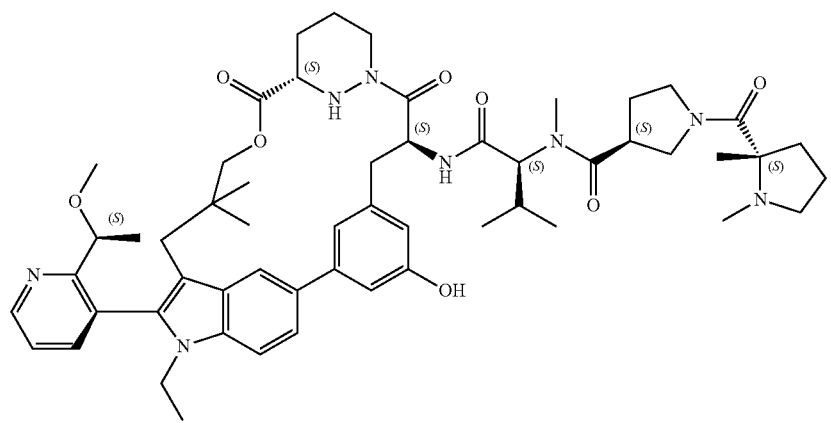 |
| A343 | 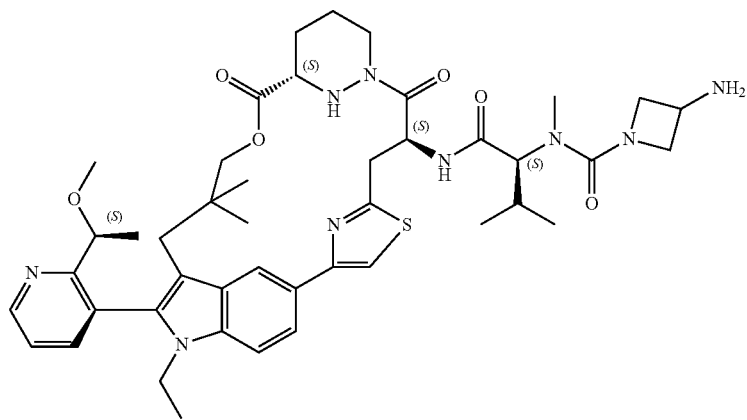 |
| A344 | 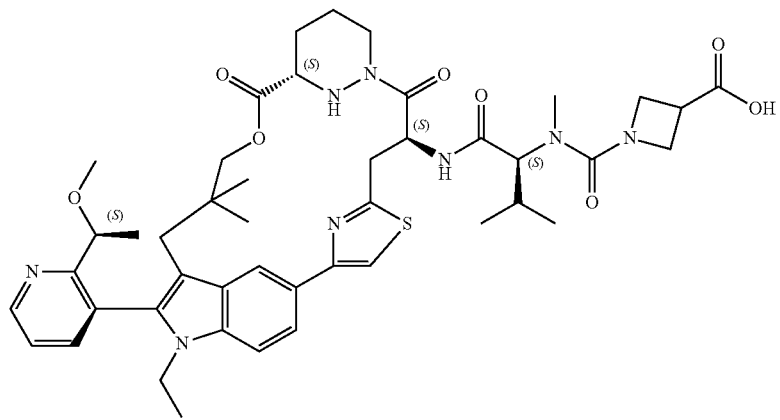 |

TABLE 1-continued

Certain Compounds of the Present Invention

| Ex# | Structure |
|---|---|
| A345 | 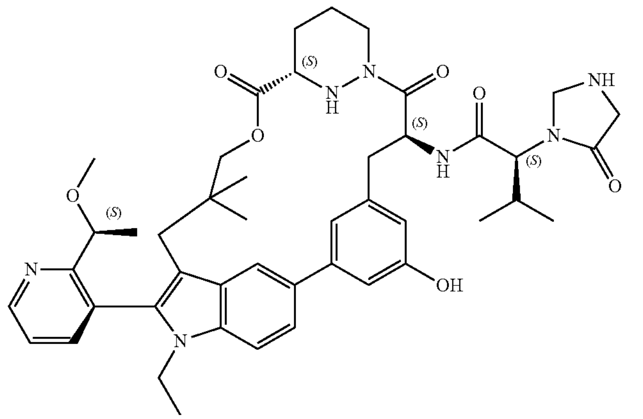 |
| A346 | 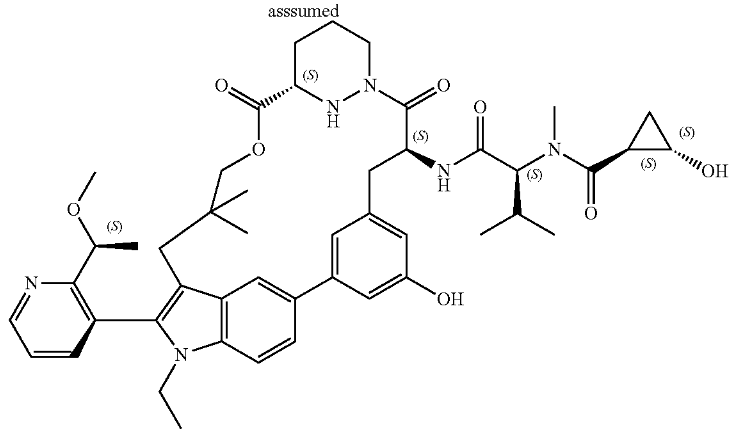 |
| A347 | 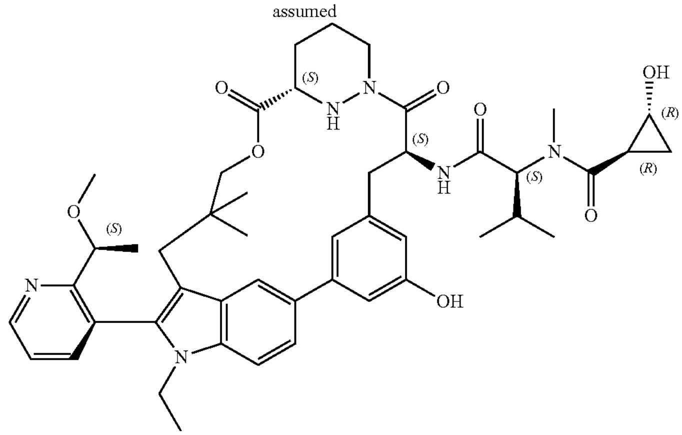 |

TABLE 1-continued
Certain Compounds of the Present Invention
| Ex# | Structure |
|---|---|
| A348 | 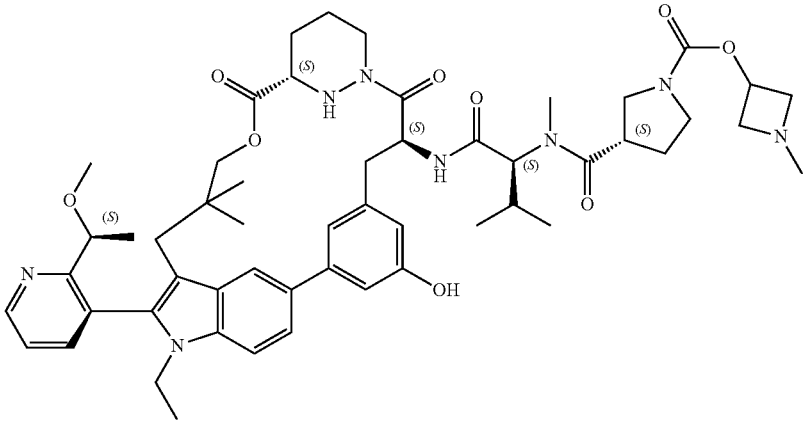 |
| A349 | 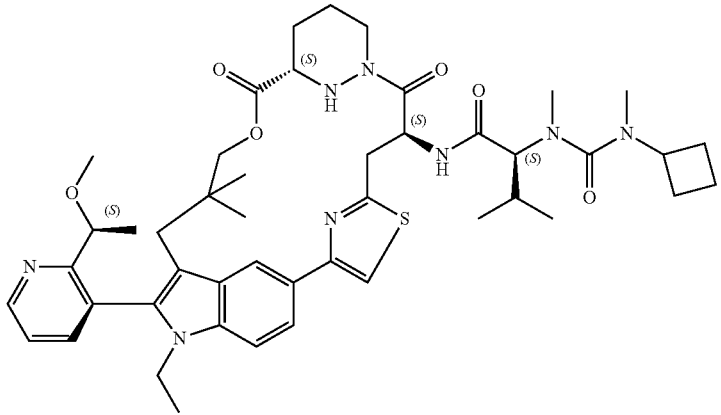 |
| A350 | 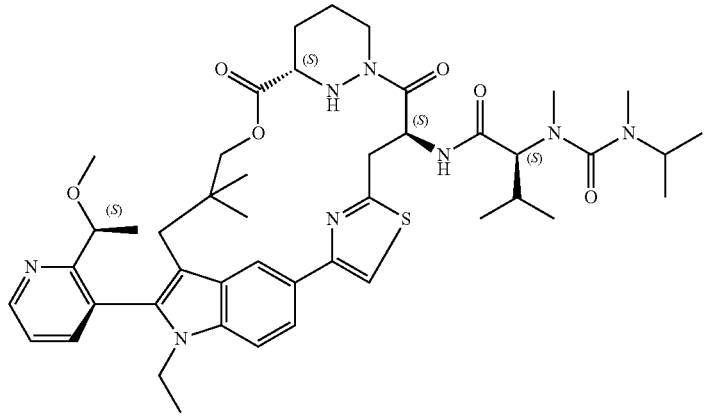 |

TABLE 1-continued
Certain Compounds of the Present Invention
| Ex# | Structure |
|---|---|
| A351 | 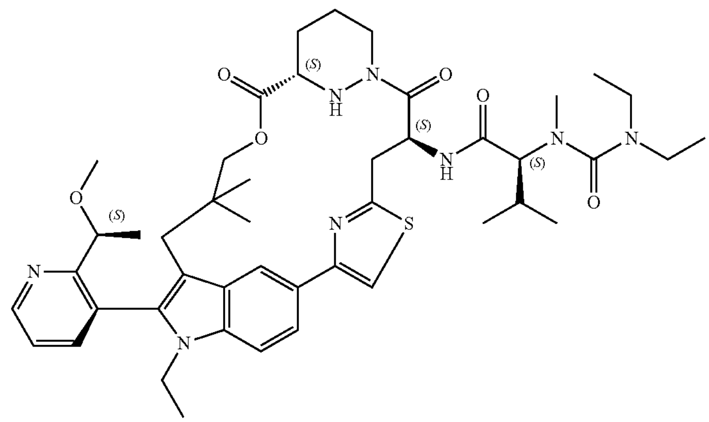 |
| A352 | 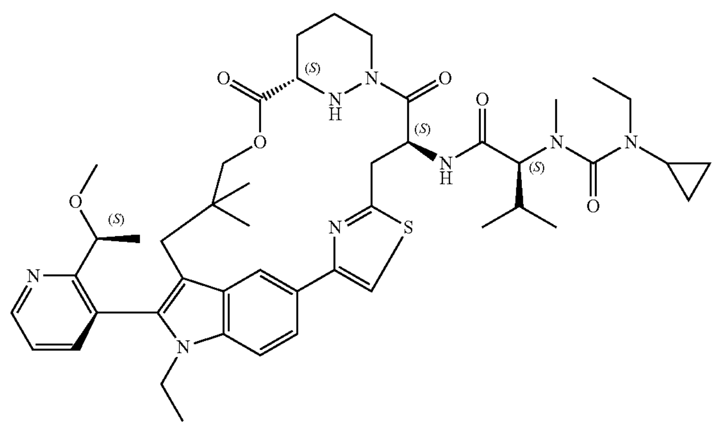 |
| A353 | 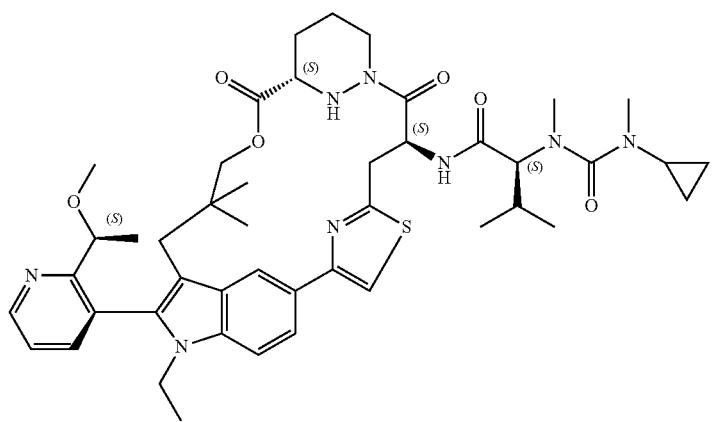 |

TABLE 1-continued
Certain Compounds of the Present Invention
| Ex# | Structure |
|---|---|
| A354 | 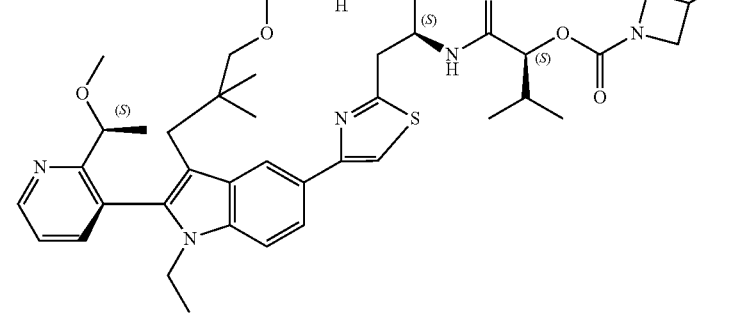 |
| A355 | 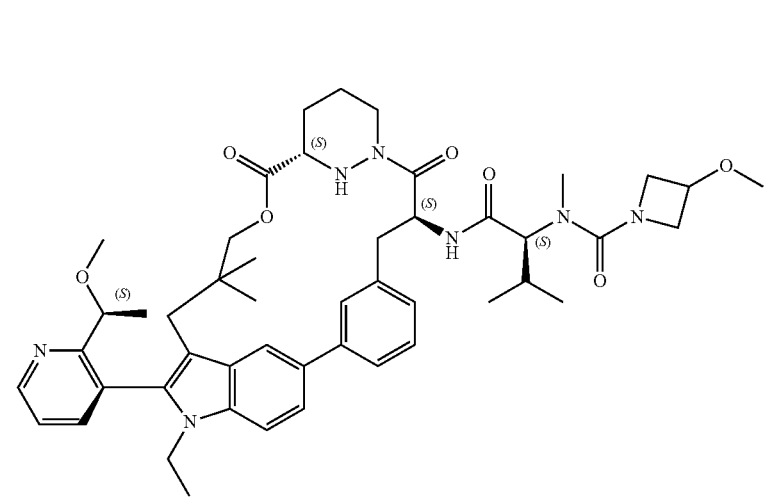 |
| A356 | 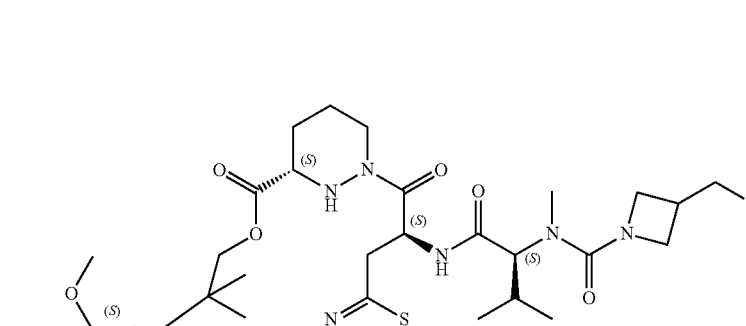 |

TABLE 1-continued

Certain Compounds of the Present Invention

| Ex# | Structure |
|---|---|
| A357 | 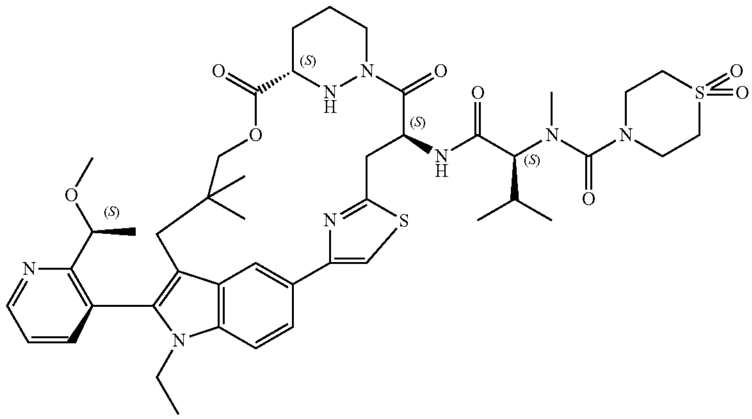 |
| A358 | 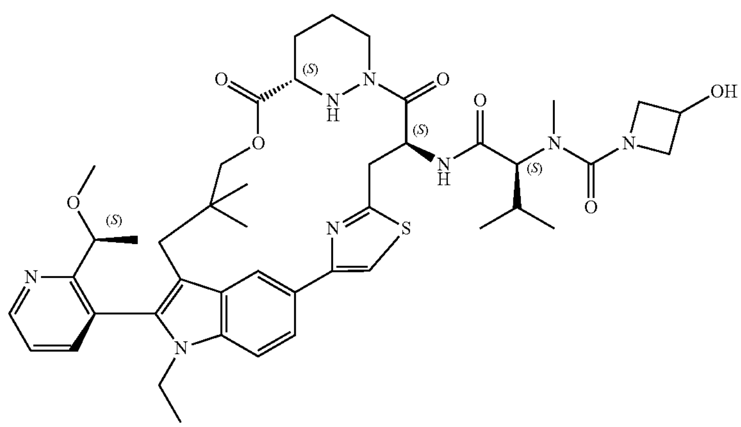 |
| A359 | 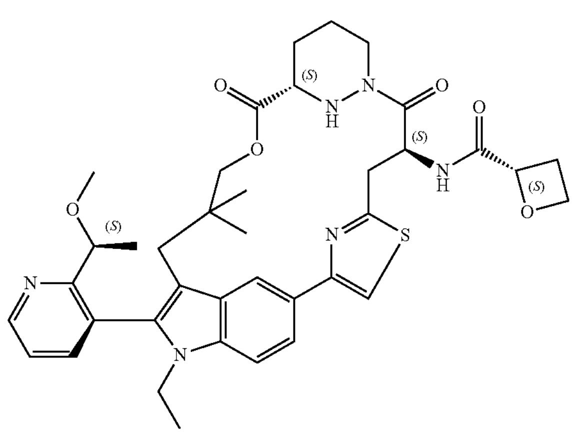 |

TABLE 1-continued
Certain Compounds of the Present Invention
| Ex# | Structure |
|---|---|
| A360 | 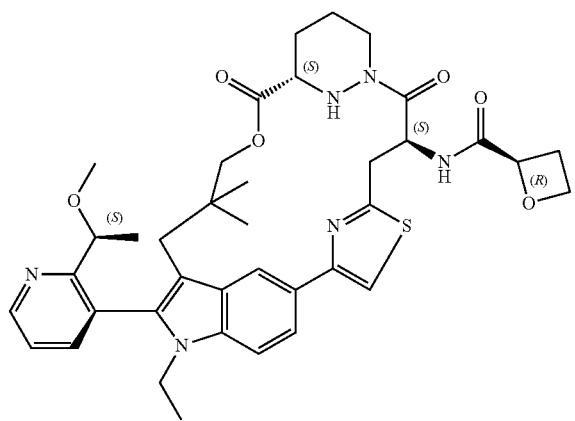 |
| A361 | 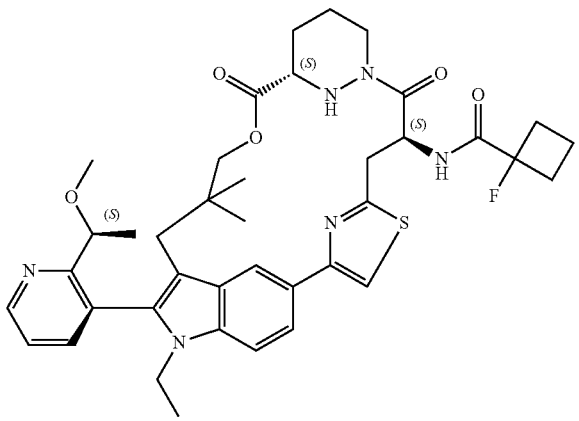 |
| A362 | 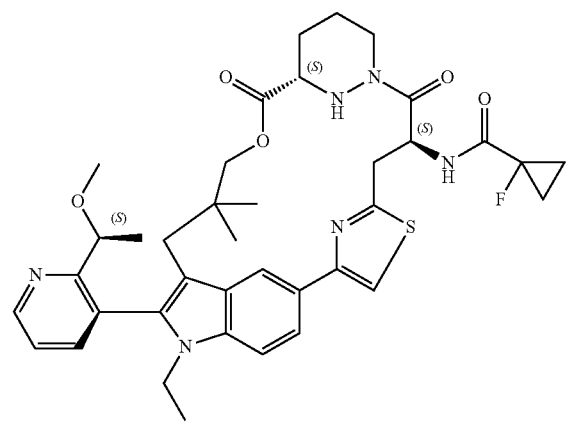 |

TABLE 1-continued

Certain Compounds of the Present Invention

| Ex# | Structure |
|---|---|
| A363 | 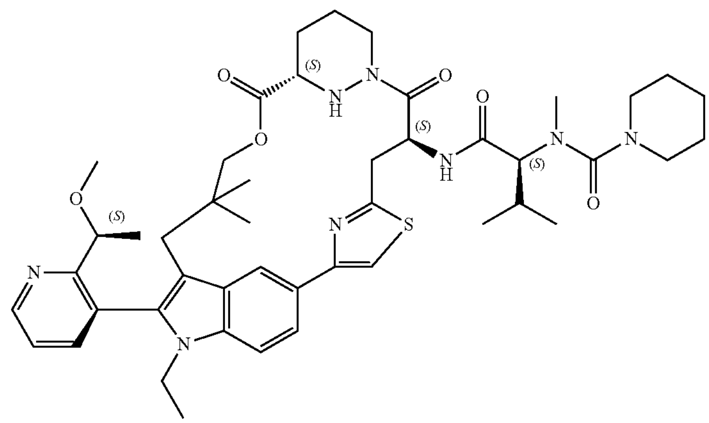 |
| A364 | 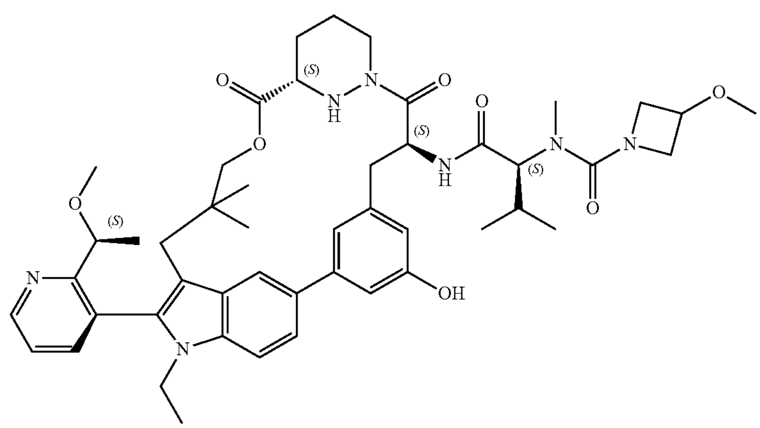 |
| A365 | 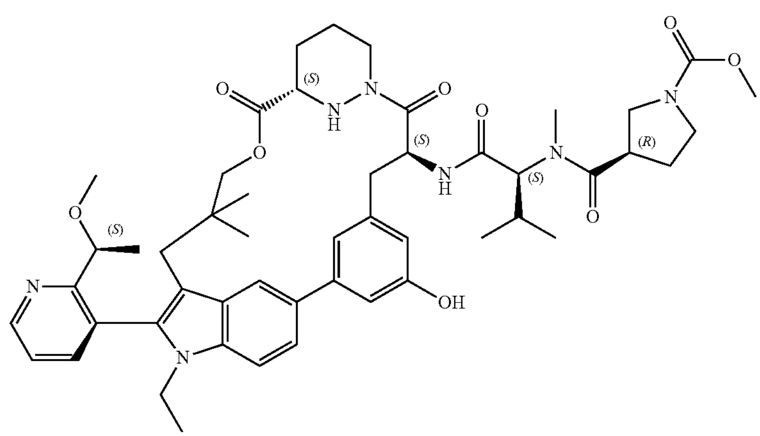 |

TABLE 1-continued

Certain Compounds of the Present Invention

| Ex# | Structure |
|---|---|
| A366 | 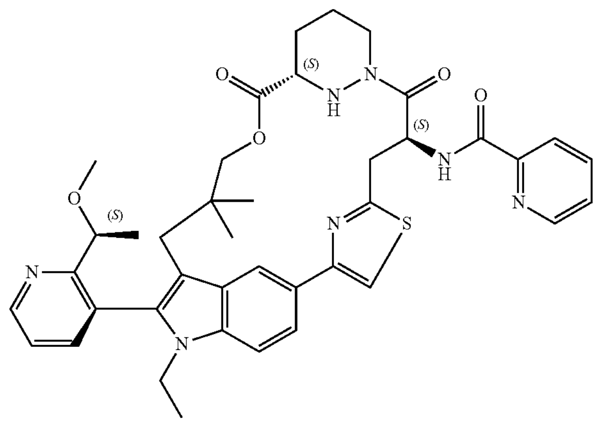 |
| A367 | 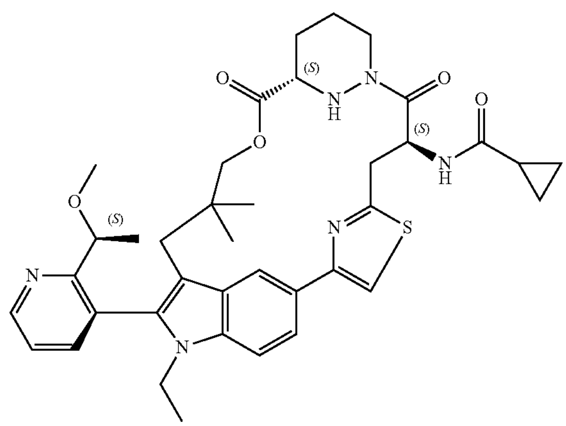 |
| A368 | 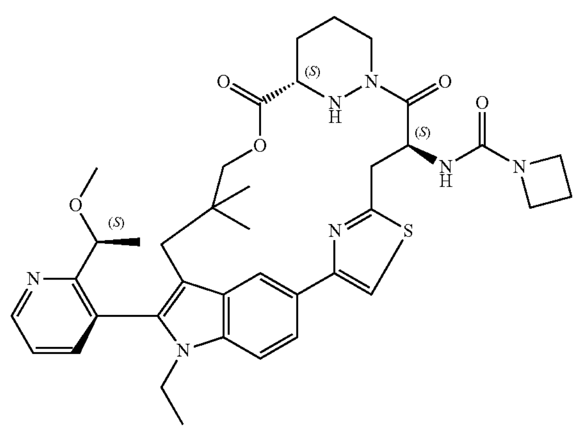 |

TABLE 1-continued
Certain Compounds of the Present Invention
| Ex# | Structure |
|---|---|
| A369 | 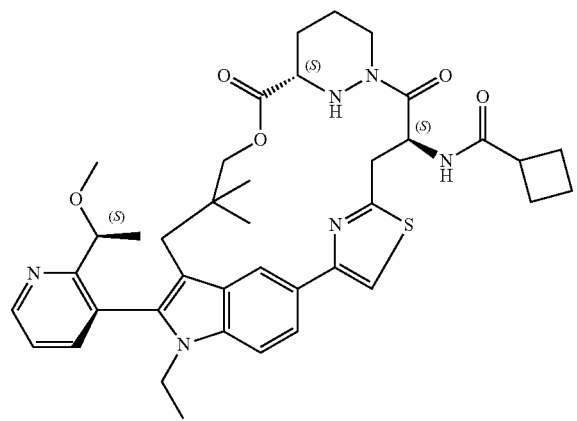 |
| A370 | 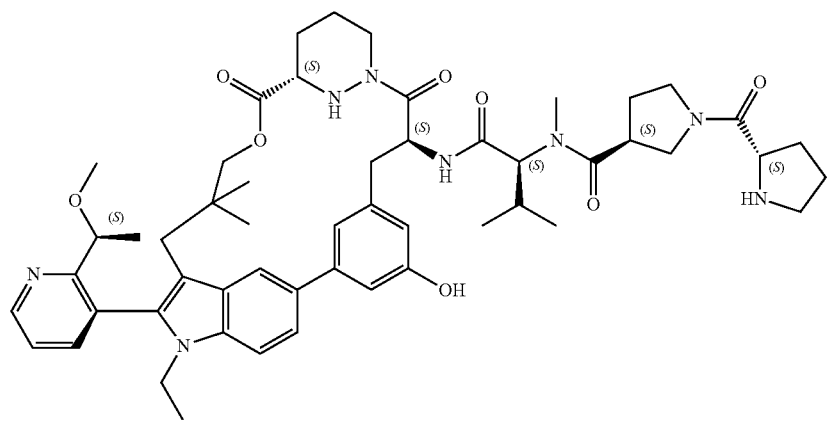 |
| A371 | 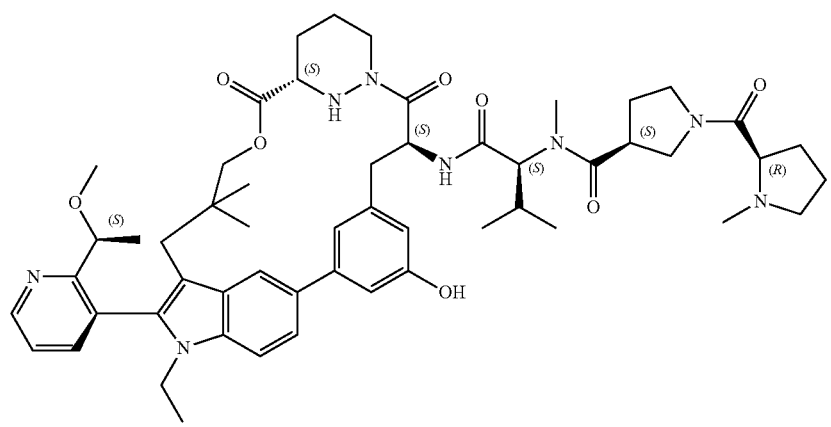 |

TABLE 1-continued

Certain Compounds of the Present Invention

| Ex# | Structure |
|---|---|
| A372 | 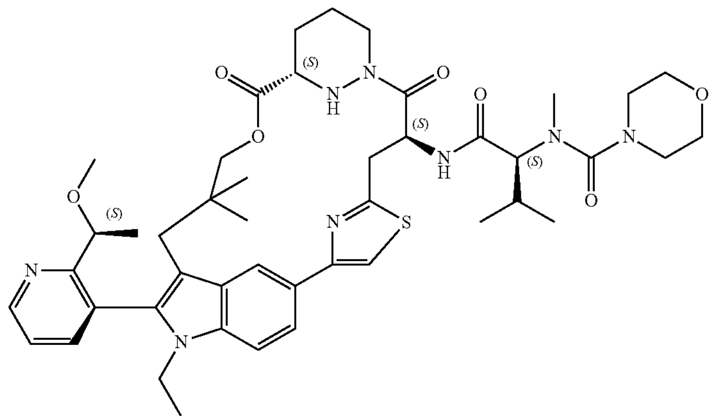 |
| A373 | 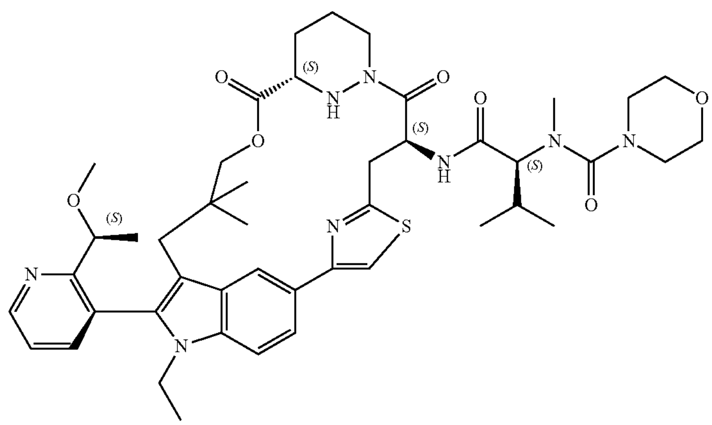 |
| A374 | 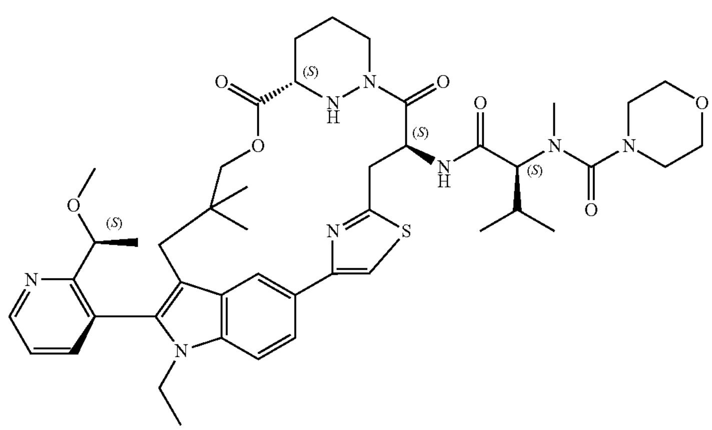 |

US 11,608,346 B2

TABLE 1-continued

Certain Compounds of the Present Invention

| Ex# | Structure |
|---|---|
| A375 | 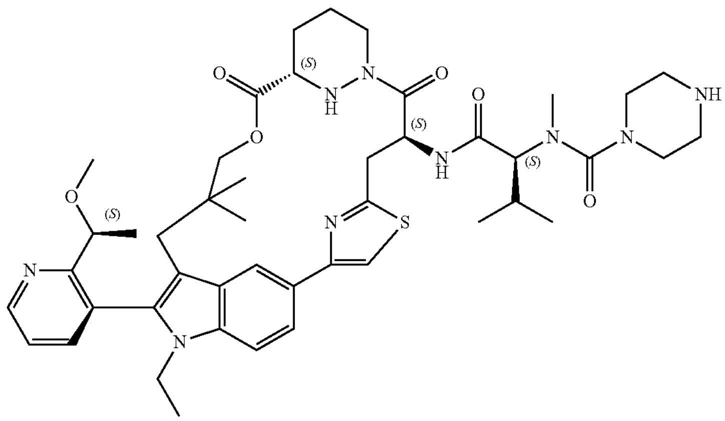 |
| A376 | 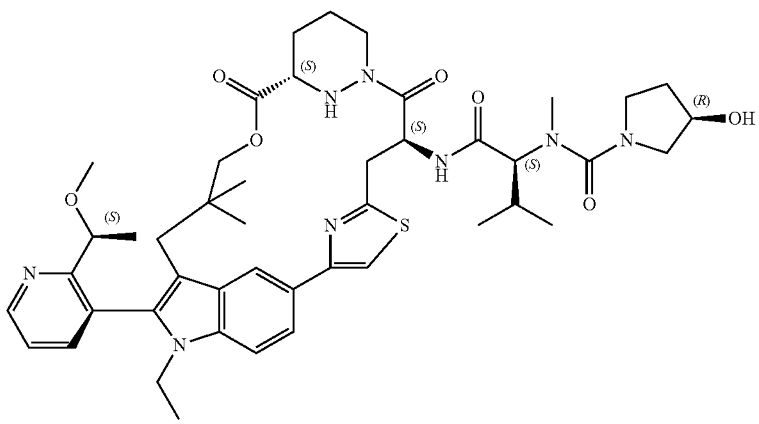 |
| A377 | 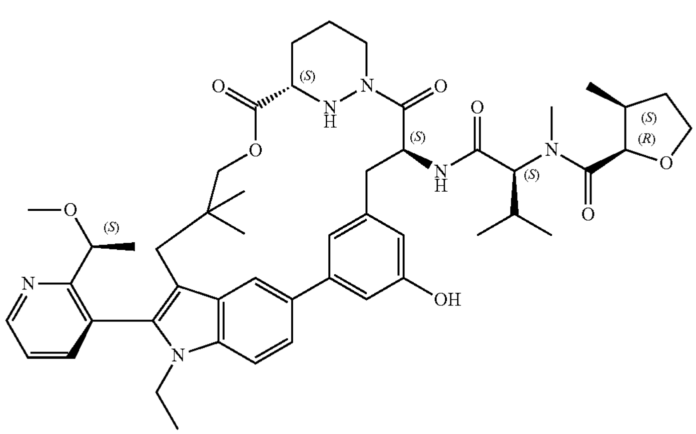 |

TABLE 1-continued
Certain Compounds of the Present Invention
| Ex# | Structure |
|---|---|
| A378 | 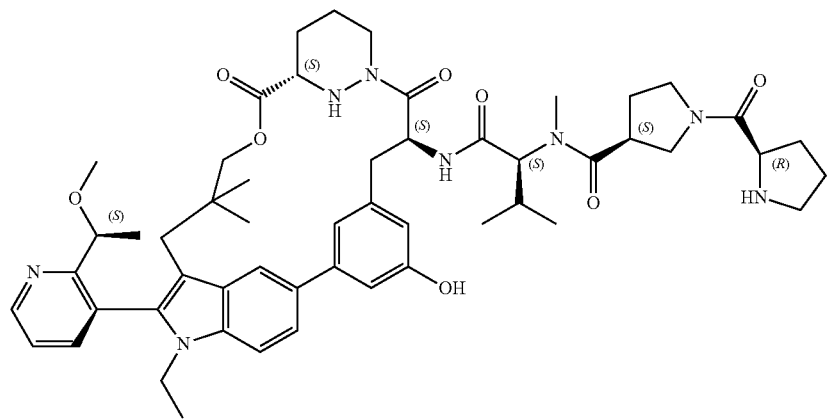 |
| A379 | 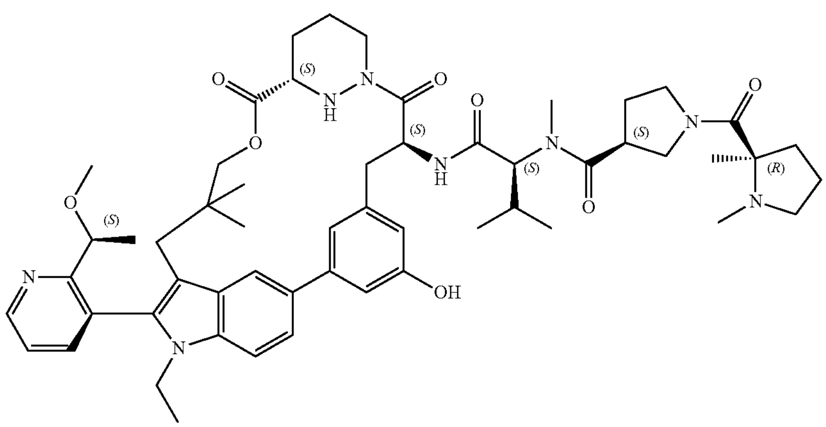 |
| A380 | 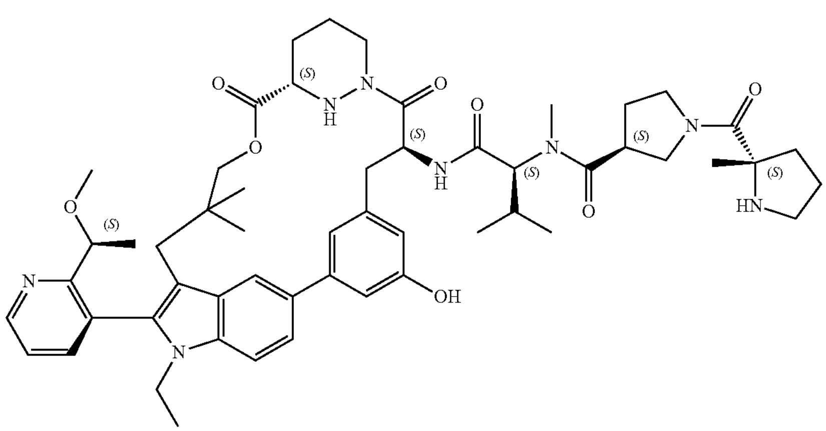 |

TABLE 1-continued
Certain Compounds of the Present Invention
| Ex# | Structure |
|---|---|
| A381 | 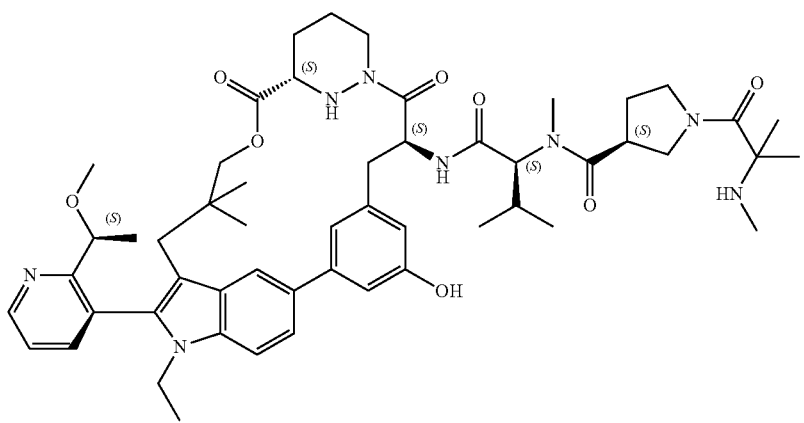 |
| A382 | 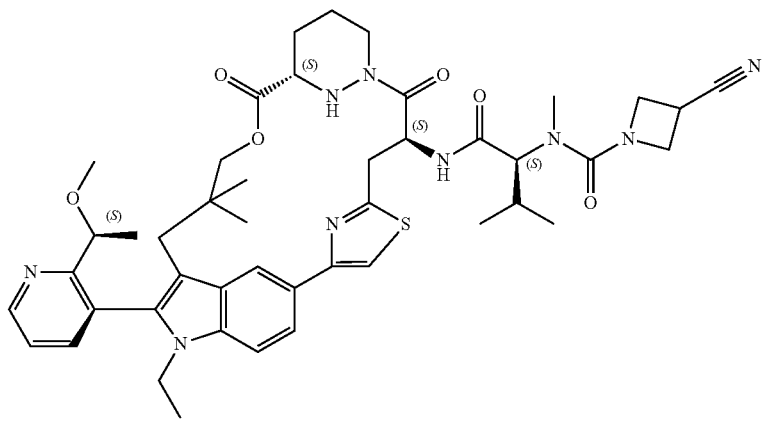 |
| A383 | 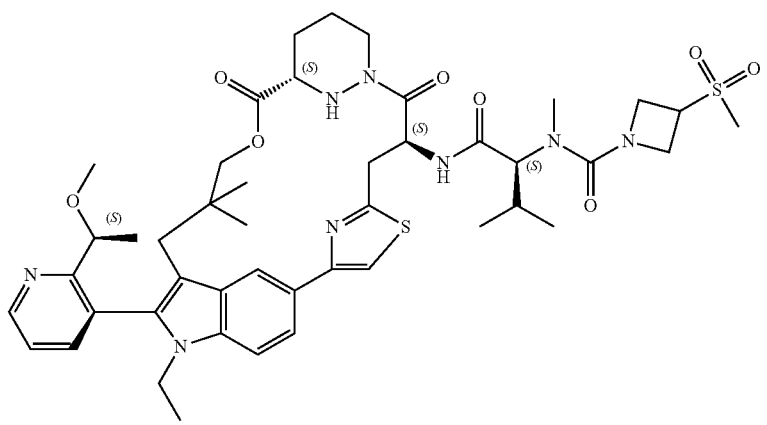 |

TABLE 1-continued
Certain Compounds of the Present Invention
| Ex# | Structure |
| --- | --- |
| A384 | 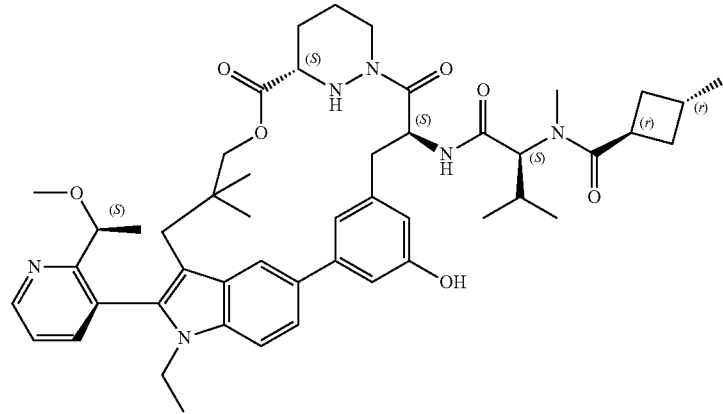 |
| A385 | 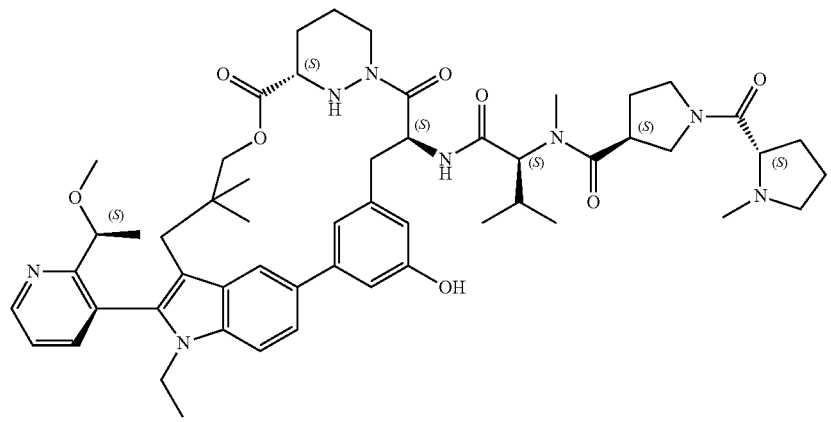 |
| A386 | 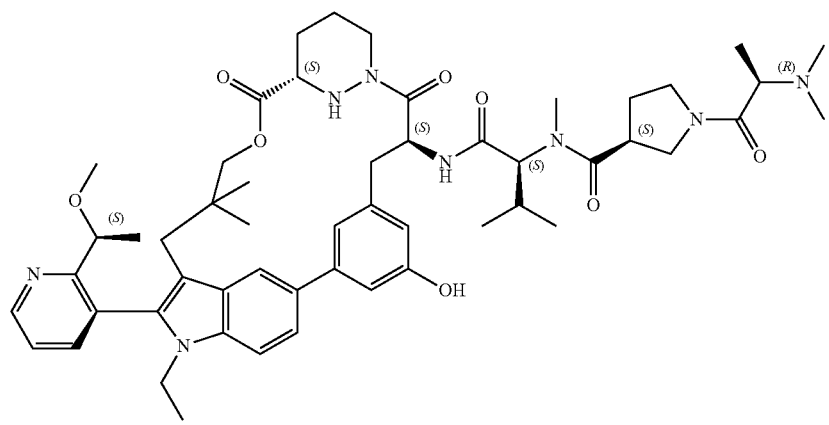 |

TABLE 1-continued
Certain Compounds of the Present Invention
| Ex# | Structure |
|---|---|
| A387 | 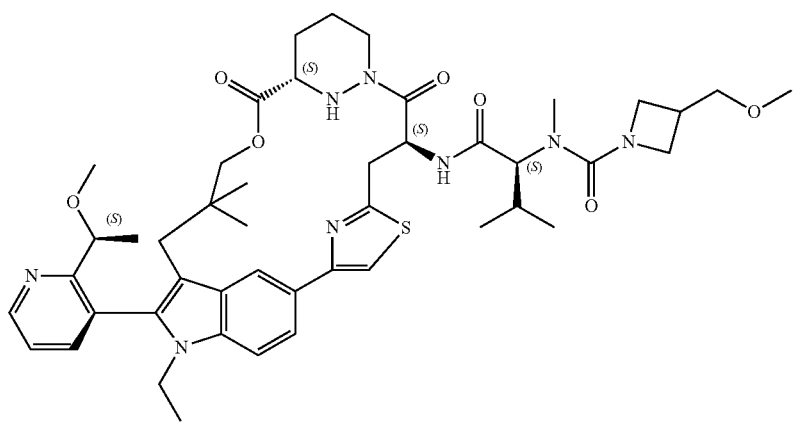 |
| A388 | 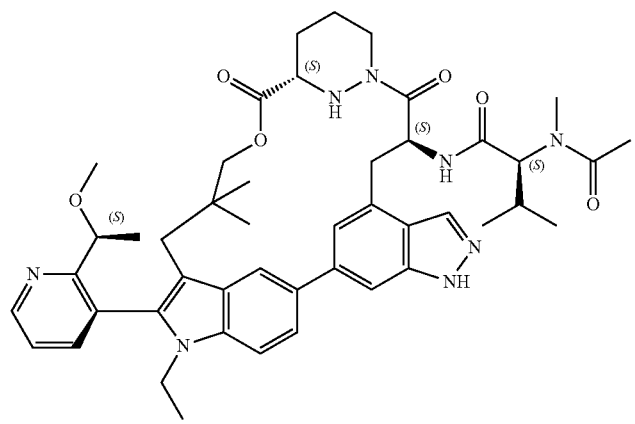 |
| A389 | 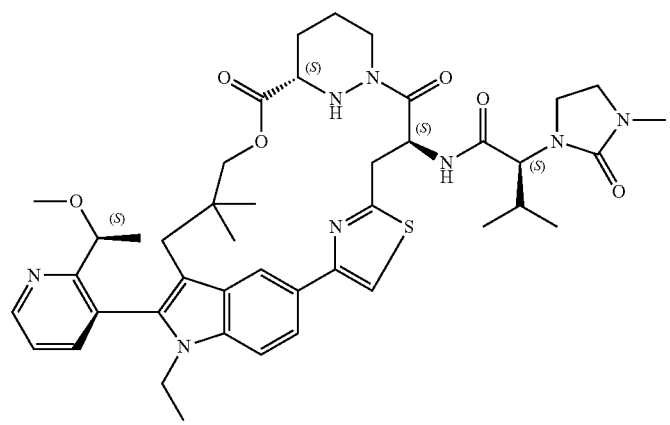 |

TABLE 1-continued
Certain Compounds of the Present Invention
| Ex# | Structure |
|---|---|
| A391 | 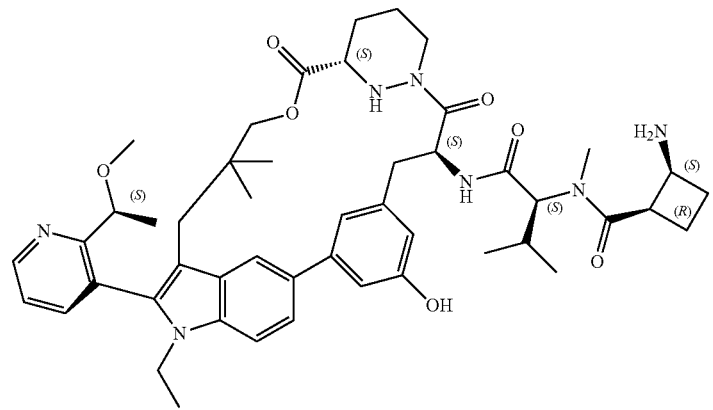 |
| A392 | 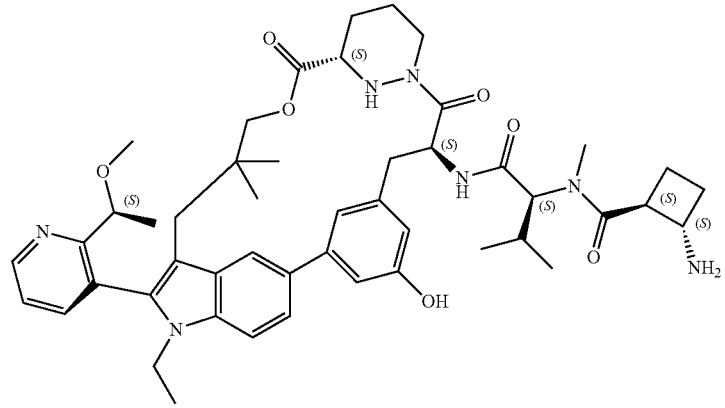 |
| A393 | 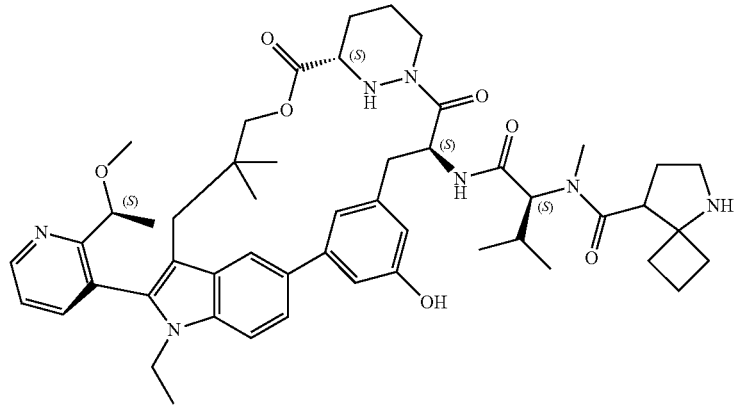 |

315
316
TABLE 1-continued
Certain Compounds of the Present Invention
| Ex# | Structure |
|---|---|
| A394 | 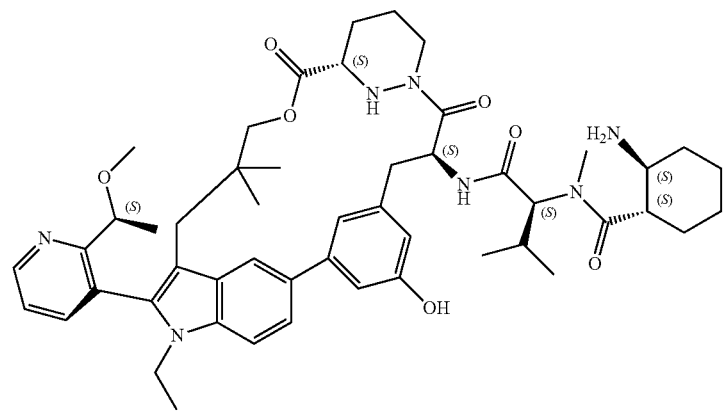 |
| A395 | 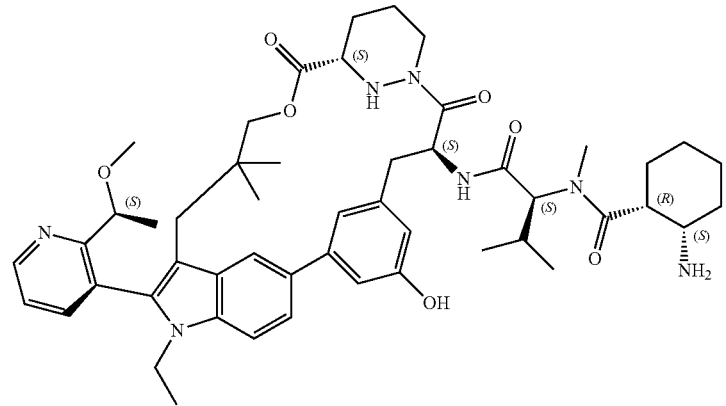 |
| A396 | 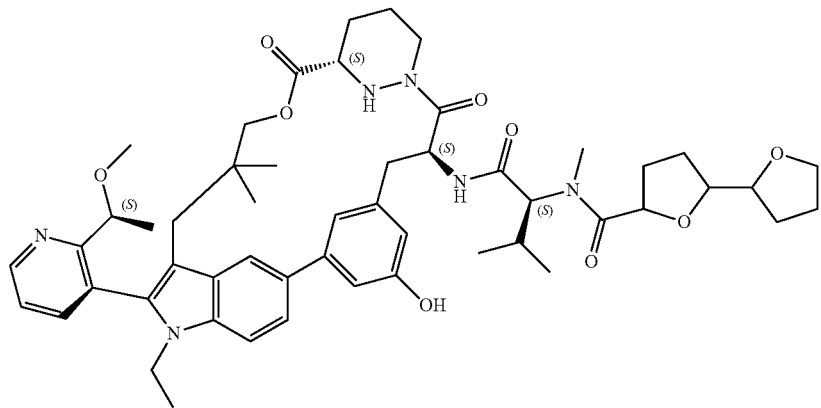 |

TABLE 1-continued
Certain Compounds of the Present Invention
| Ex# | Structure |
|---|---|
| A397 | 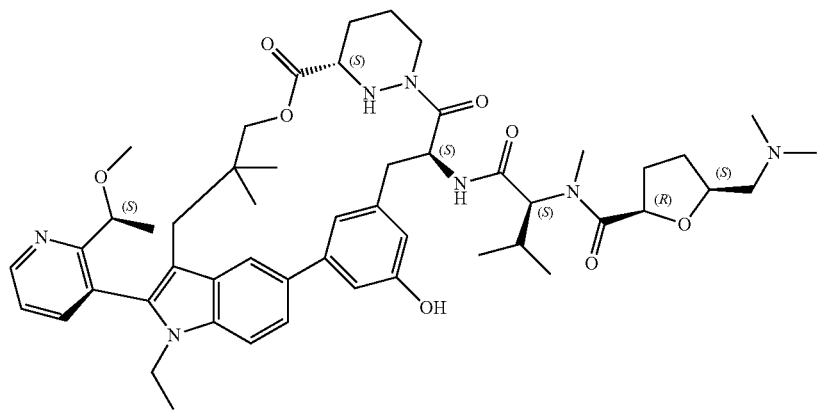 |
| A398 | 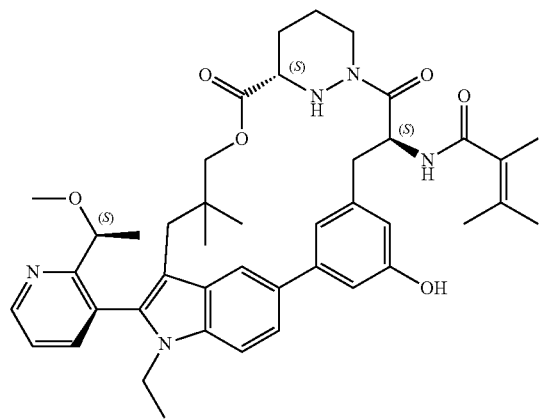 |
| A399 | 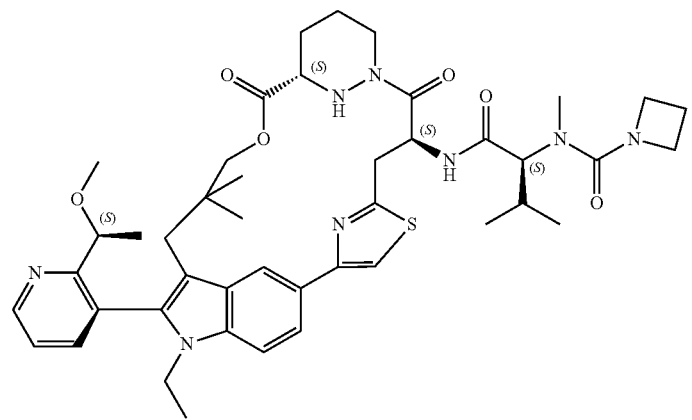 |

TABLE 1-continued
Certain Compounds of the Present Invention
| Ex# | Structure |
|---|---|
| A400 | 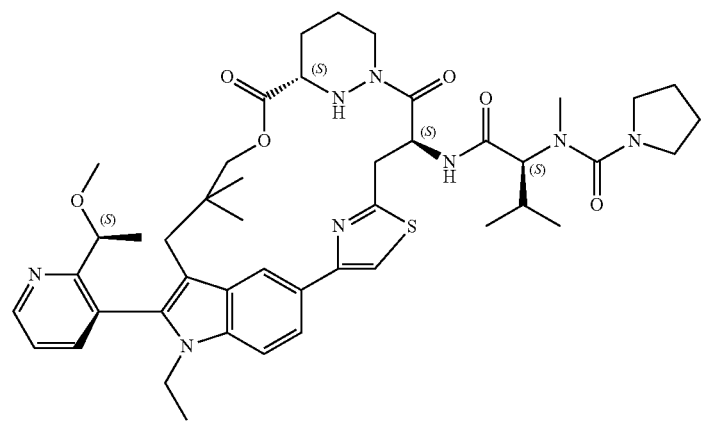 |
| A401 | 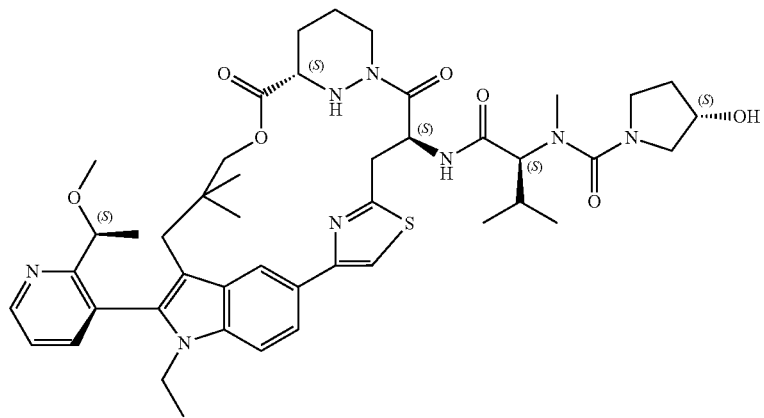 |
| A402 | 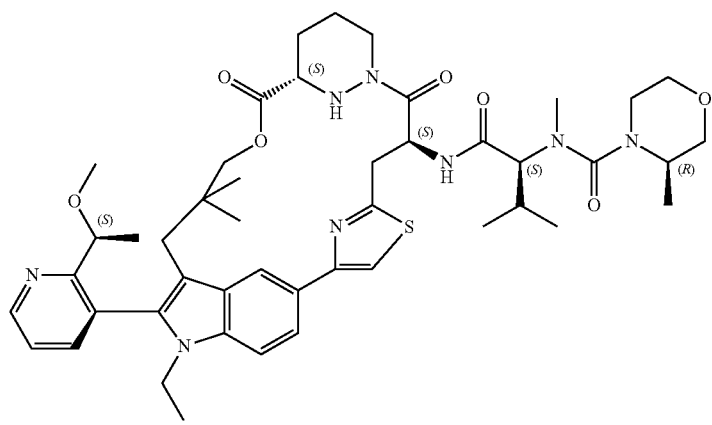 |

TABLE 1-continued
Certain Compounds of the Present Invention
| Ex# | Structure |
|---|---|
| A403 | 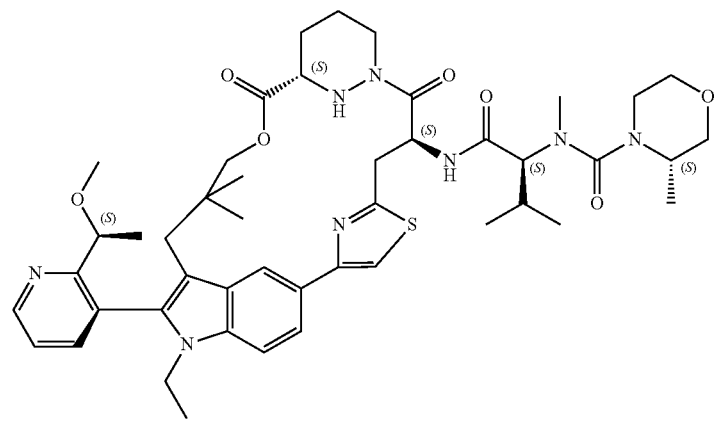 |
| A404 | 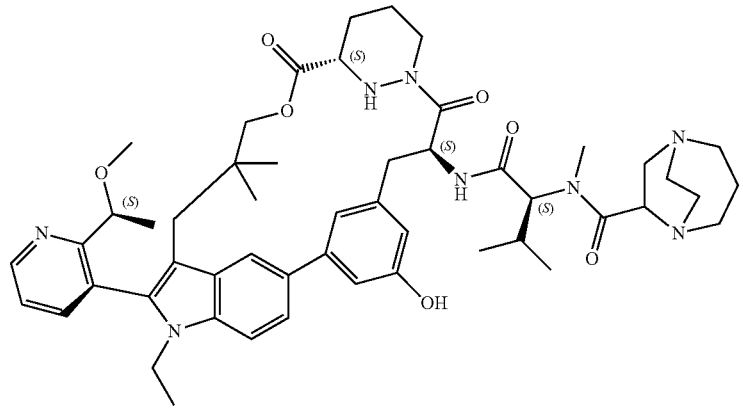 |
| A405 | 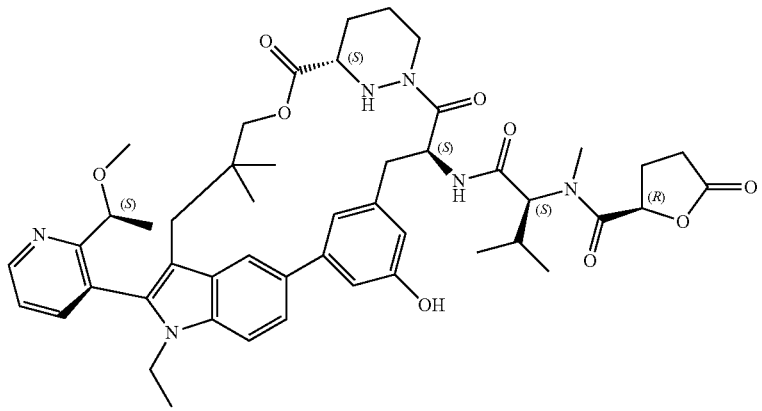 |

TABLE 1-continued
Certain Compounds of the Present Invention
| Ex# | Structure |
|---|---|
| A406 | 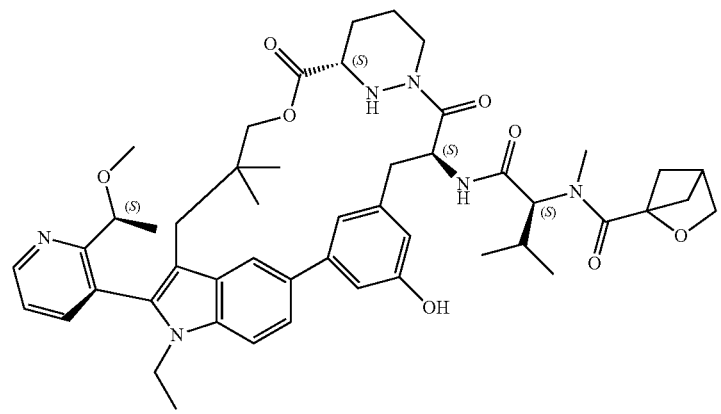 |
| A407 | 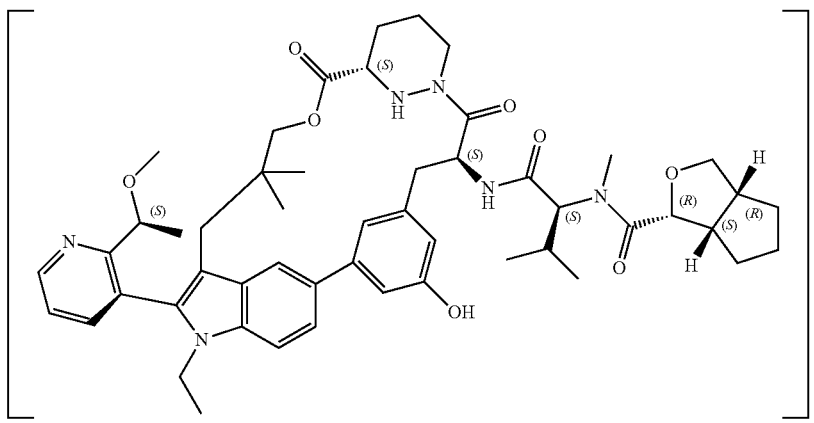 |
| A408 | 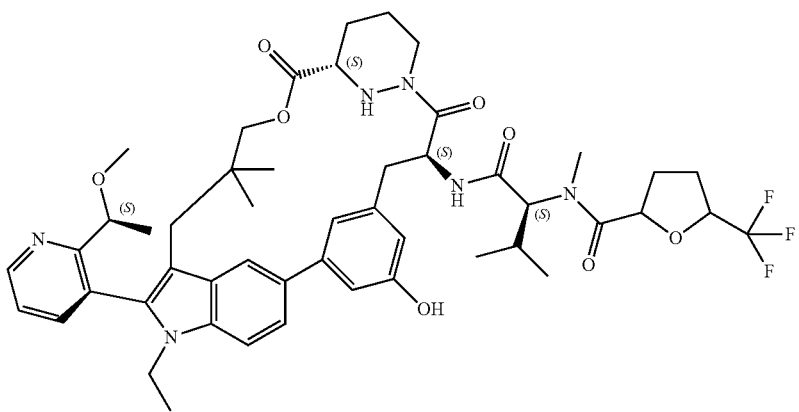 |

TABLE 1-continued
Certain Compounds of the Present Invention
| Ex# | Structure |
|---|---|
| A409 | 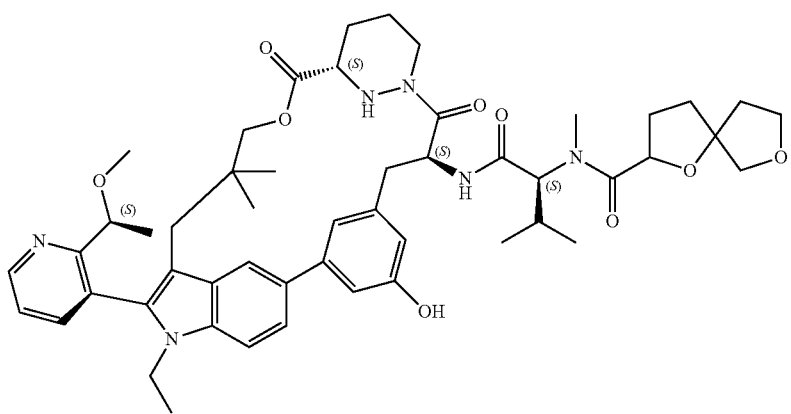 |
| A410 | 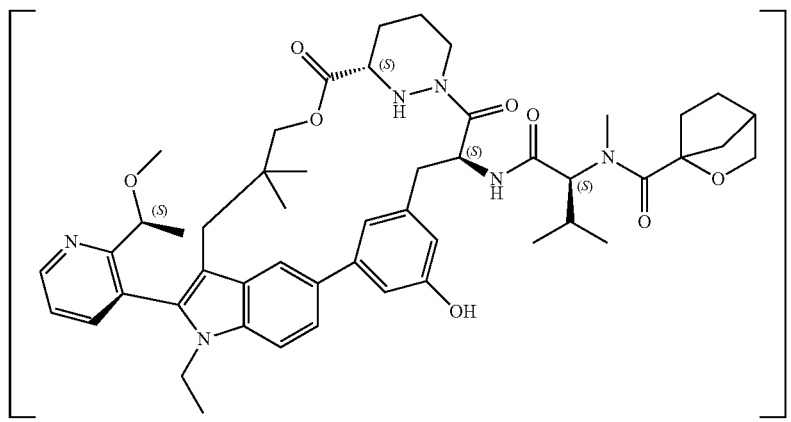 |
| A411 | 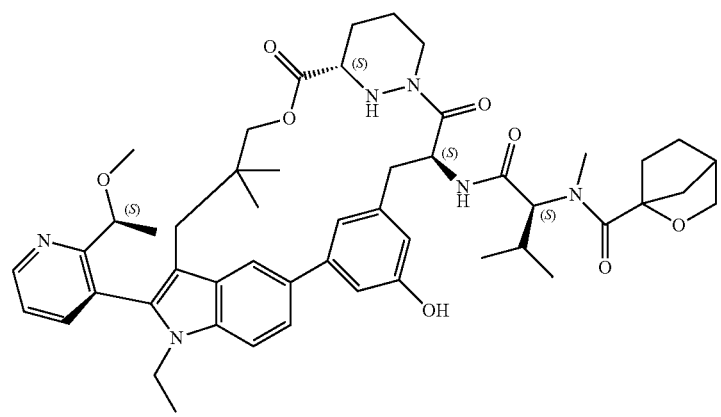 |

TABLE 1-continued
Certain Compounds of the Present Invention
| Ex# | Structure |
|---|---|
| A412 | 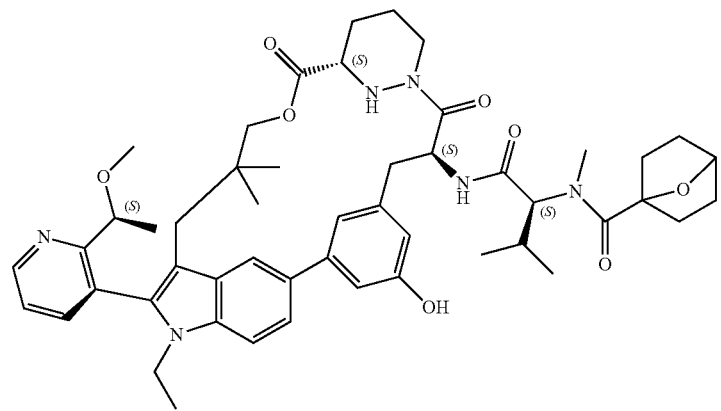 |
| A413 | 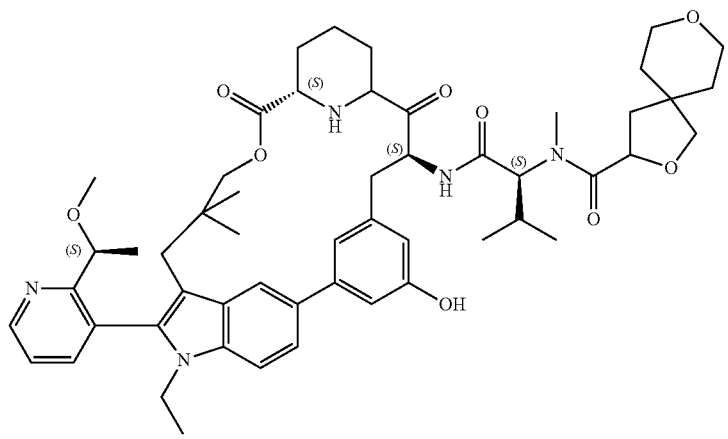 |
| A414 | 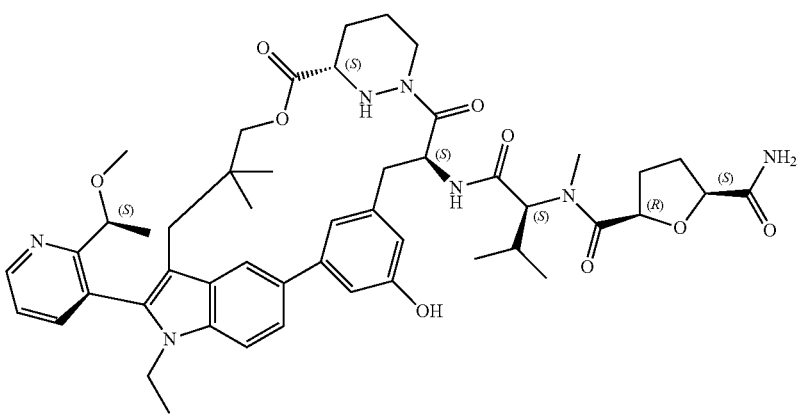 |

TABLE 1-continued

Certain Compounds of the Present Invention

| Ex# | Structure |
|---|---|
| A415 | 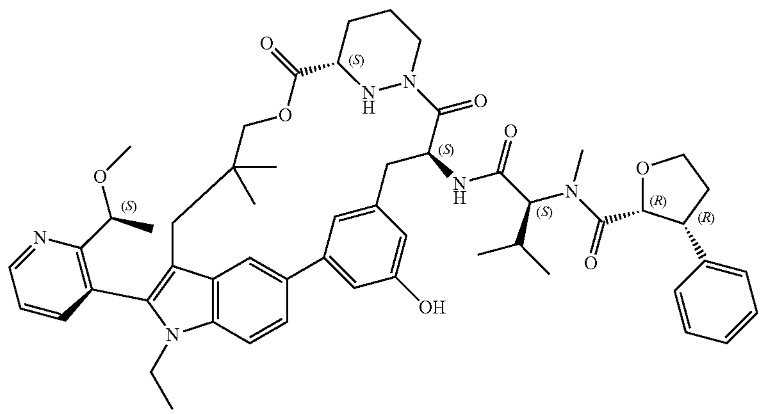 |
| A416 | 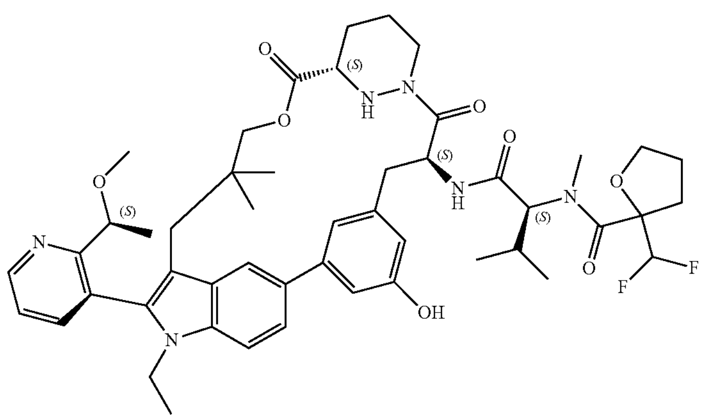 |
| A417 | 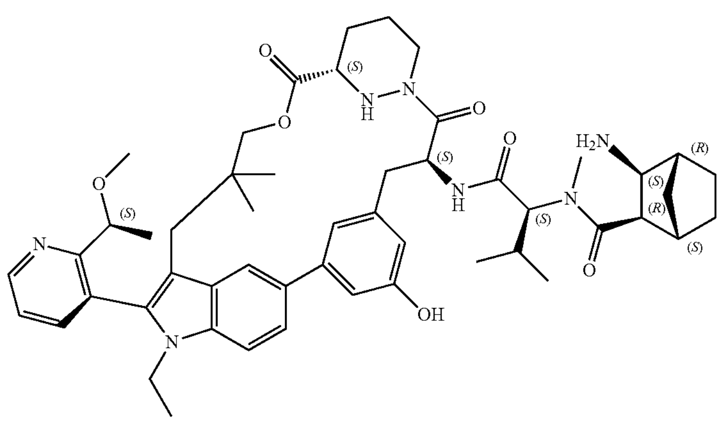 |

TABLE 1-continued

Certain Compounds of the Present Invention

| Ex# | Structure |
|---|---|
| A418 | 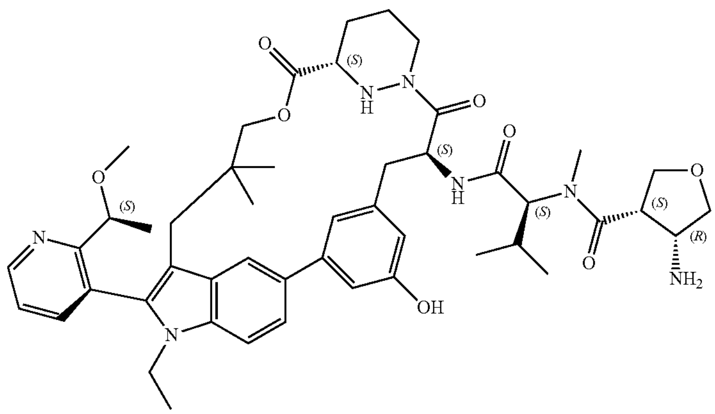 |
| A419 | 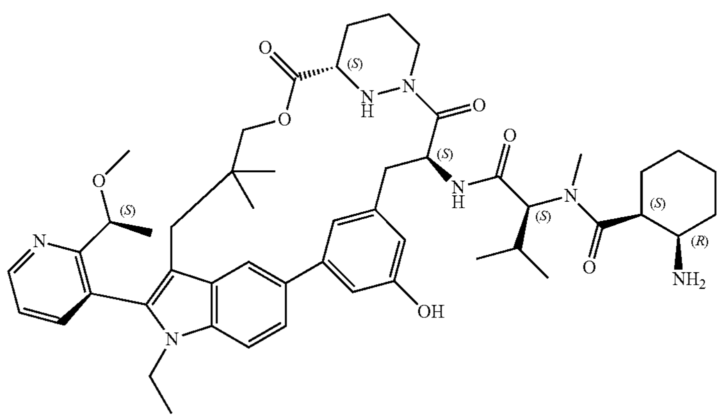 |
| A420 | 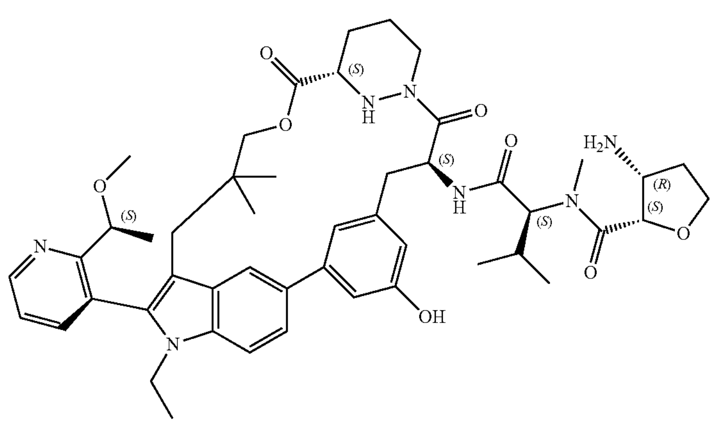 |

TABLE 1-continued
Certain Compounds of the Present Invention
| Ex# | Structure |
|---|---|
| A421 | 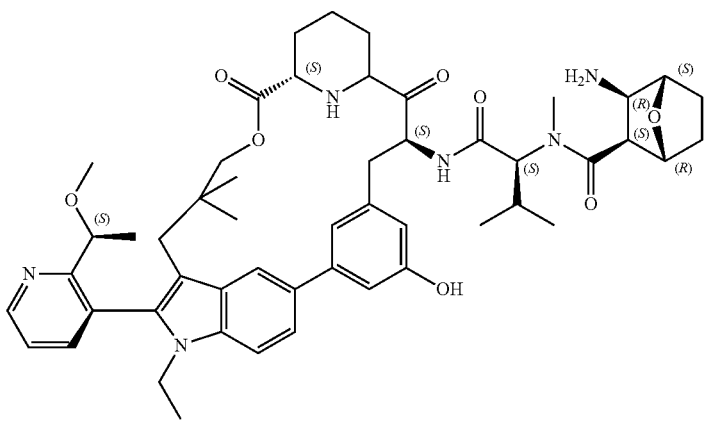 |
| A422 | 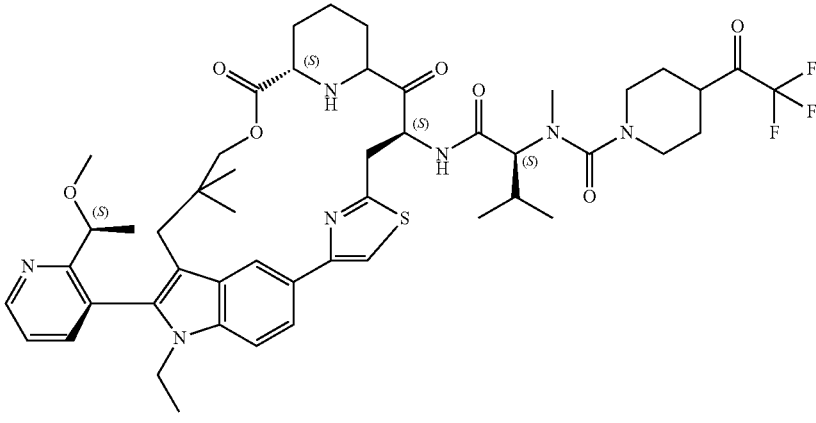 |
| A423 | 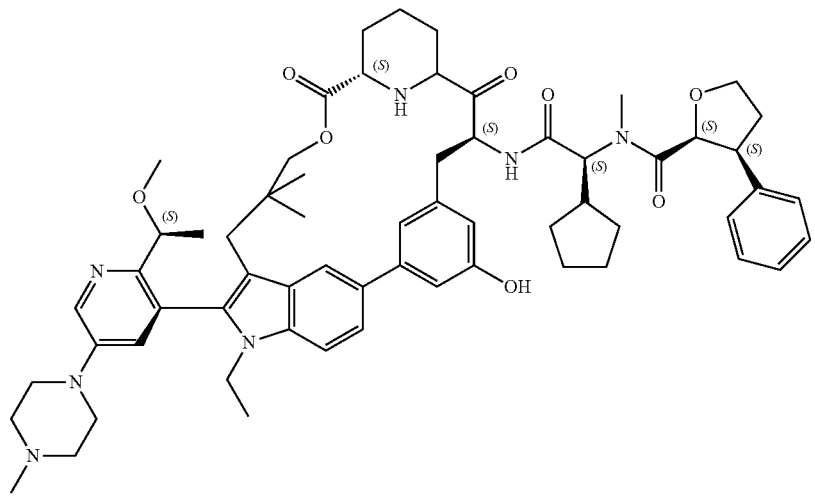 |

TABLE 1-continued
Certain Compounds of the Present Invention
| Ex# | Structure |
|---|---|
| A424 | 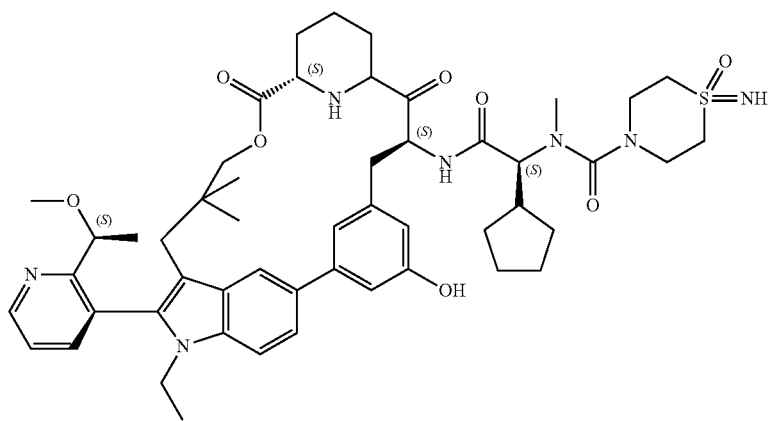 |
| A425 | 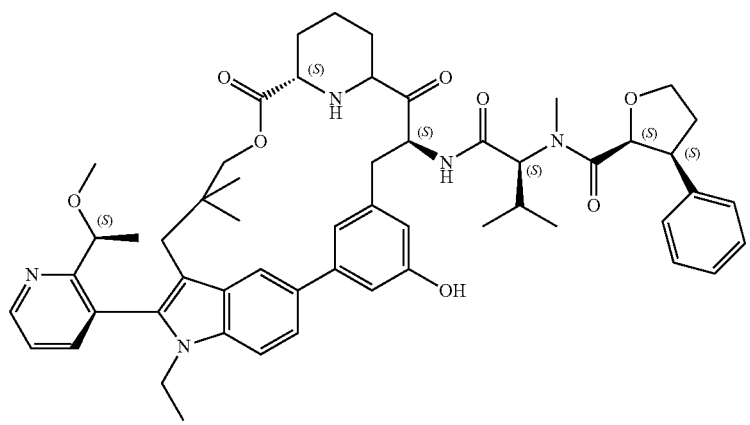 |
| A426 | 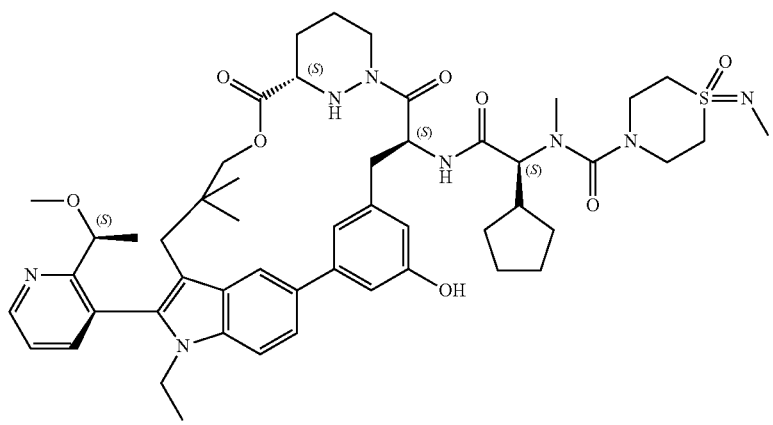 |

TABLE 1-continued
Certain Compounds of the Present Invention
| Ex# | Structure |
|---|---|
| A427 | 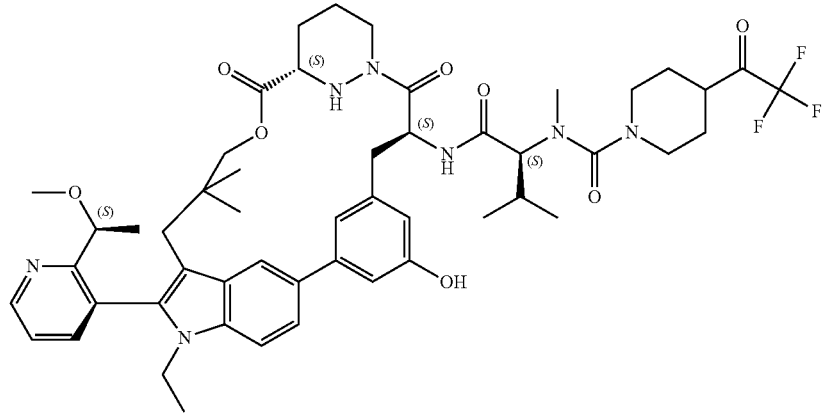 |
| A428 | 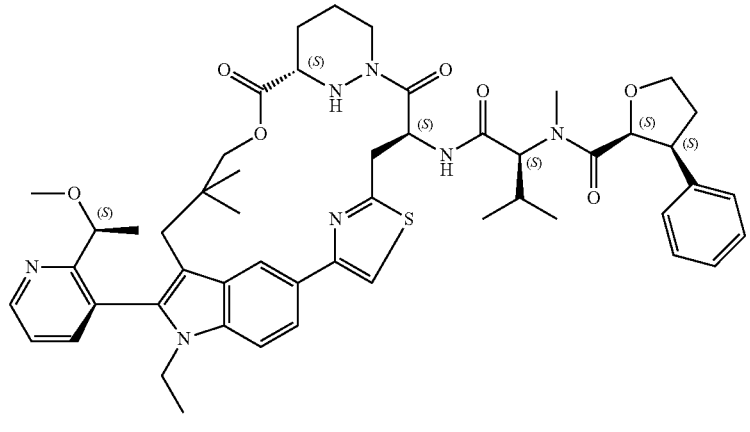 |
| A429 | 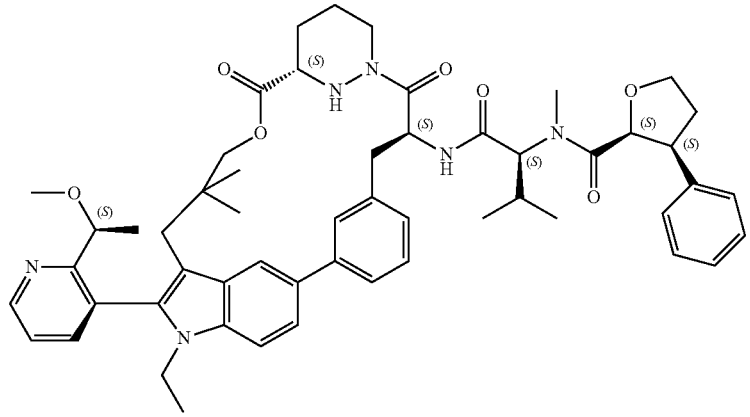 |

TABLE 1-continued
Certain Compounds of the Present Invention
| Ex# | Structure |
|---|---|
| A430 | 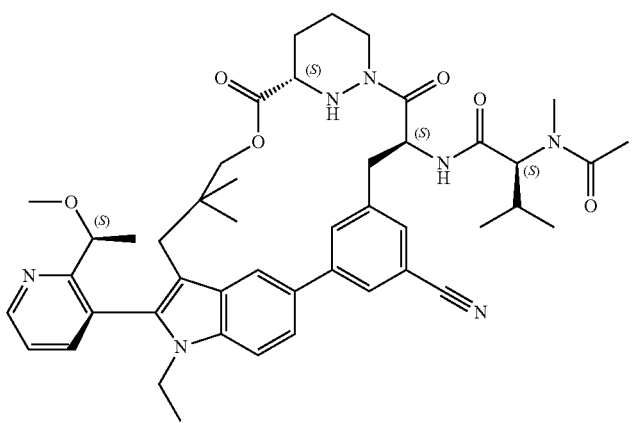 |
| A431 | 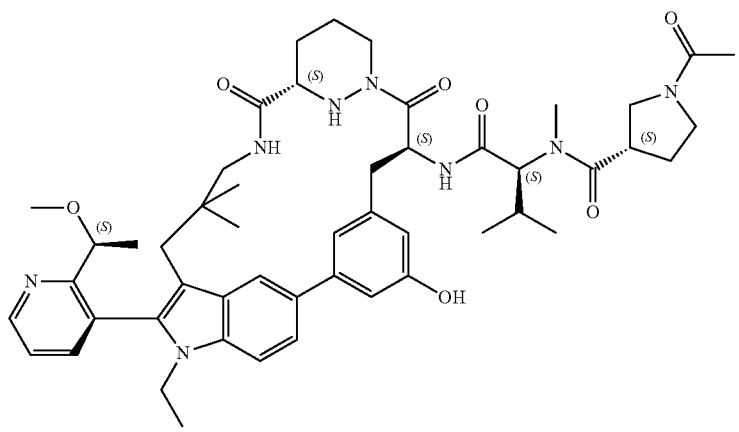 |
| A432 | 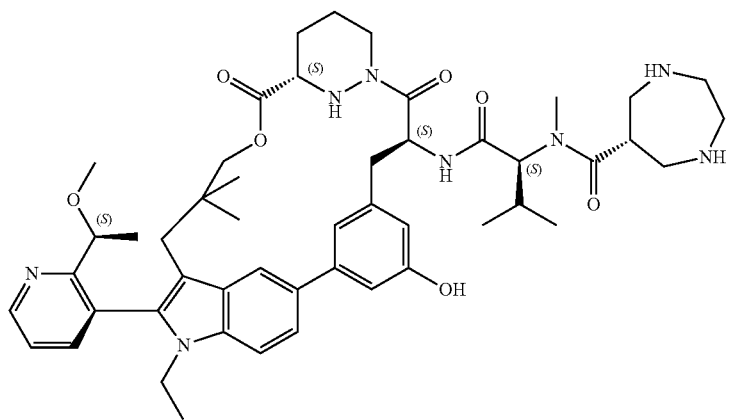 |

TABLE 1-continued
Certain Compounds of the Present Invention
| Ex# | Structure |
|---|---|
| A433 | 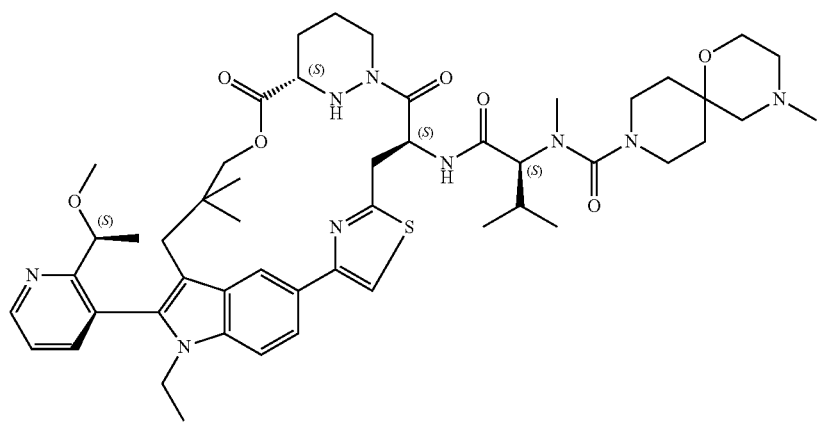 |
| A434 | 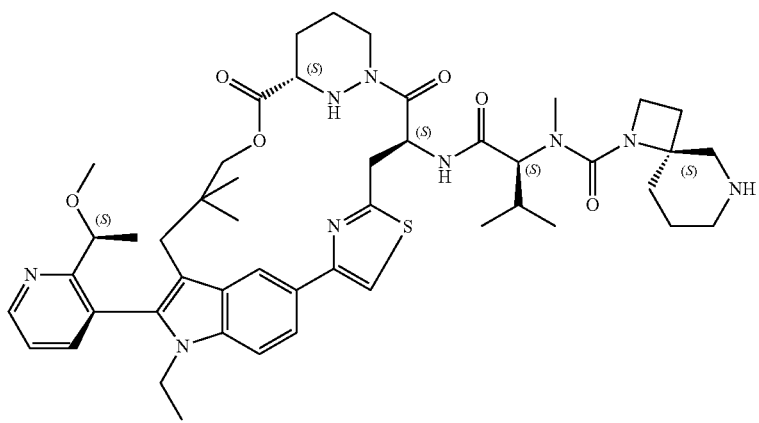 |
| A435 | 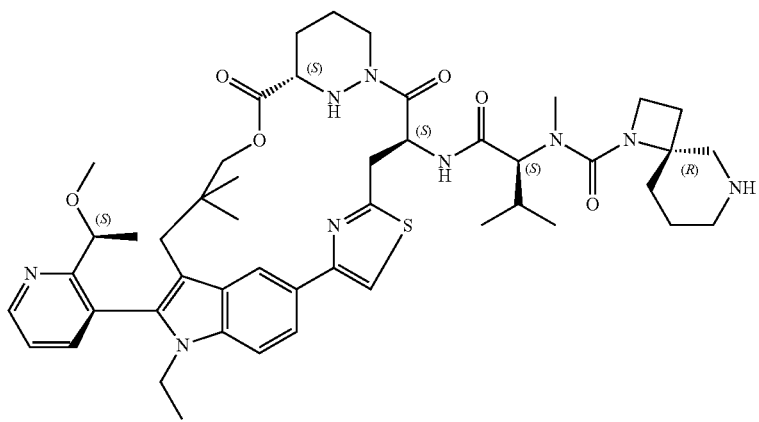 |

TABLE 1-continued
Certain Compounds of the Present Invention
| Ex# | Structure |
|---|---|
| A436 | 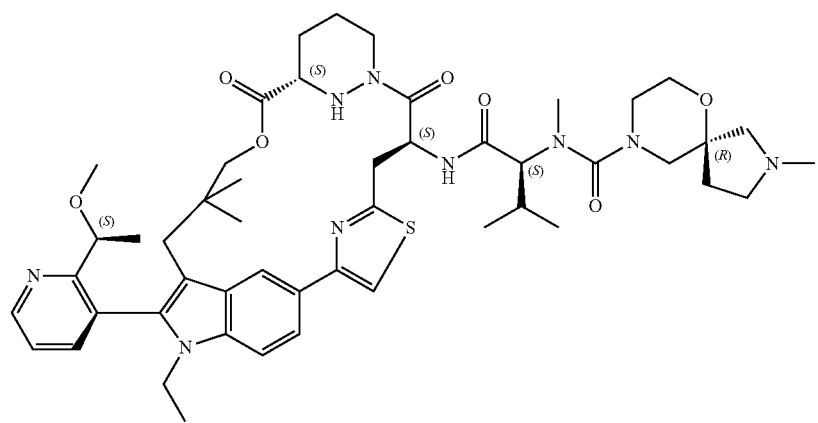 |
| A437 | 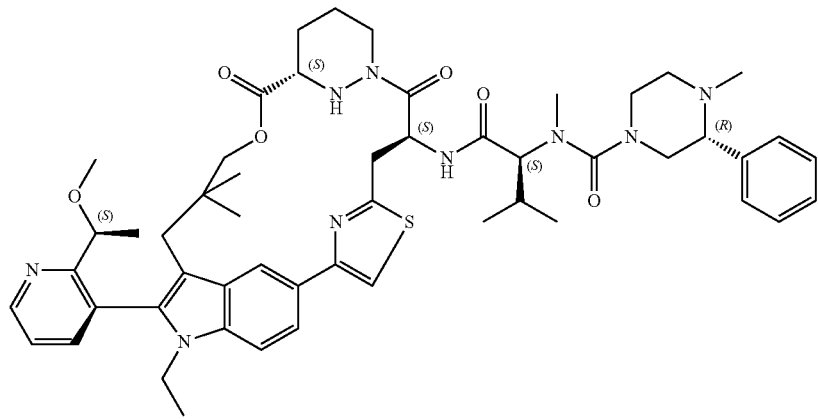 |
| A438 | 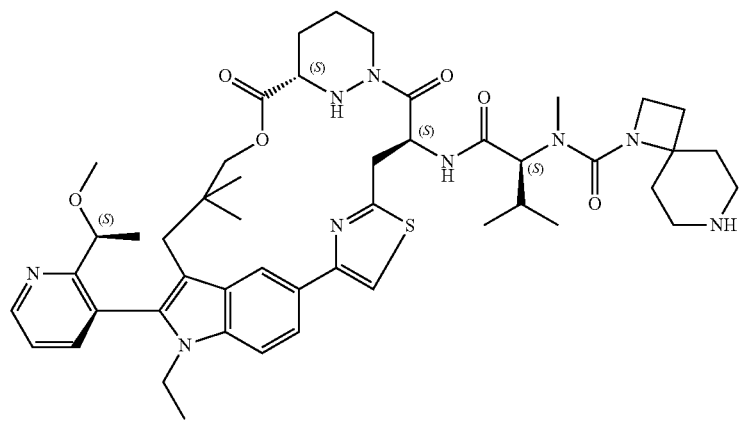 |

TABLE 1-continued
Certain Compounds of the Present Invention
| Ex# | Structure |
|---|---|
| A439 | 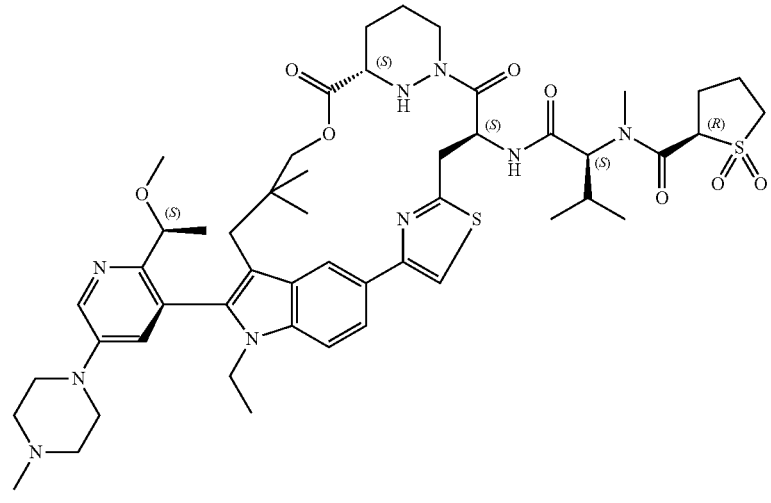 |
| A440 | 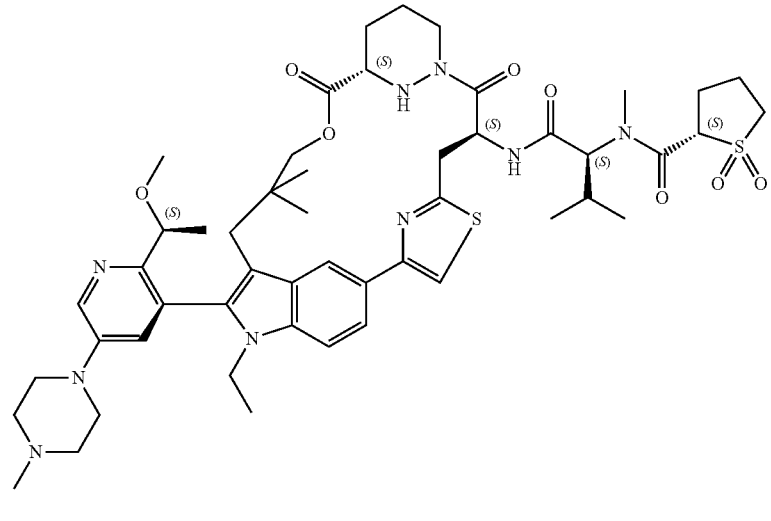 |
| A441 | 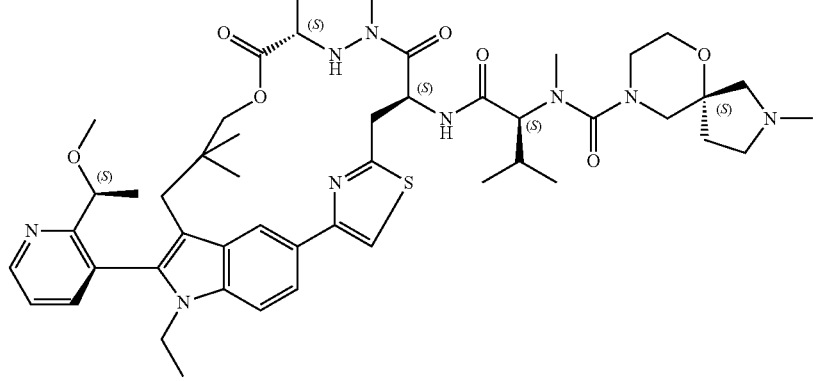 |

TABLE 1-continued

Certain Compounds of the Present Invention

| Ex# | Structure |
|---|---|
| A442 | 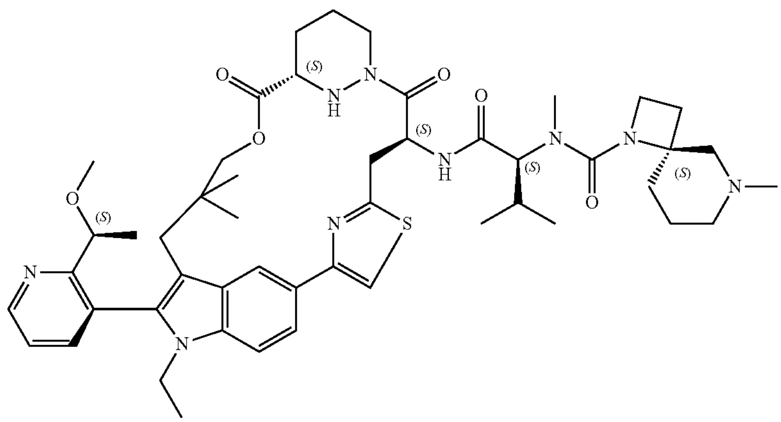 |
| A443 | 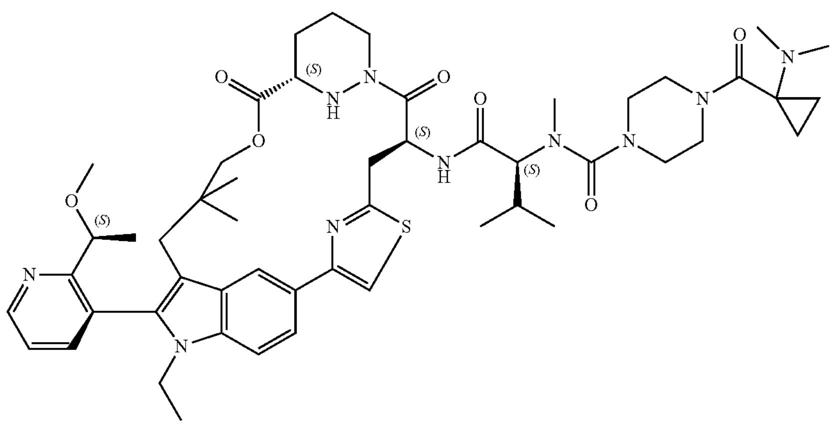 |
| A444 | 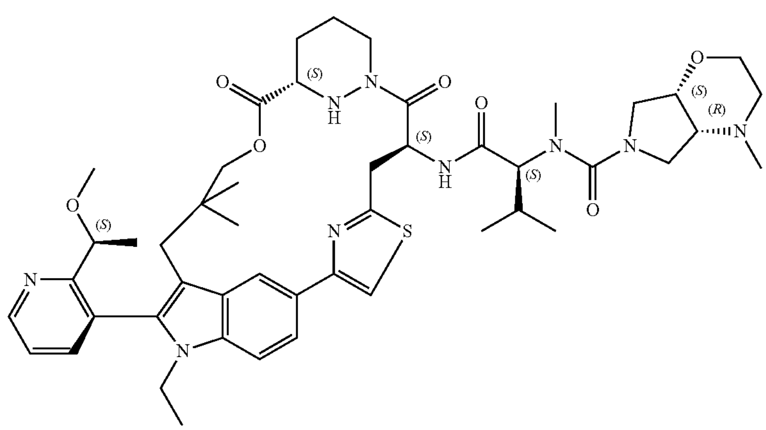 |

TABLE 1-continued
Certain Compounds of the Present Invention
| Ex# | Structure |
|---|---|
| A445 | 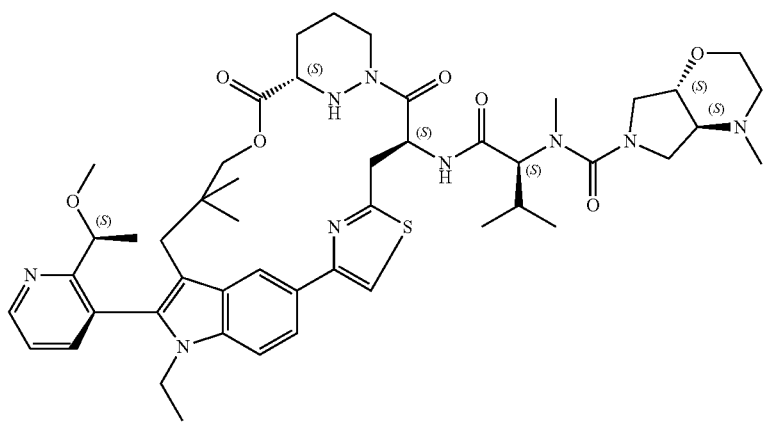 |
| A446 | 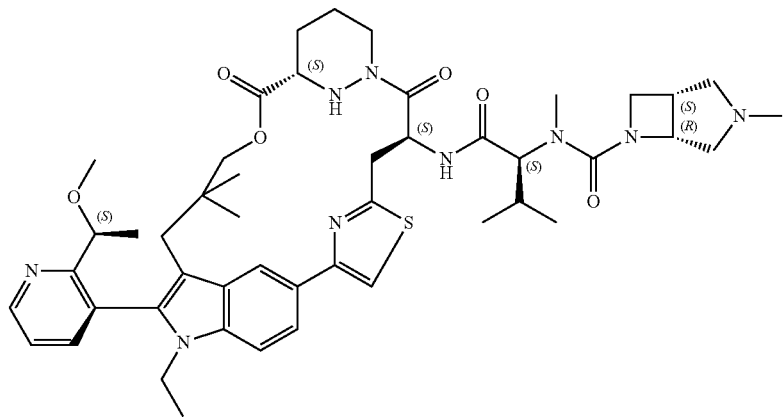 |
| A447 | 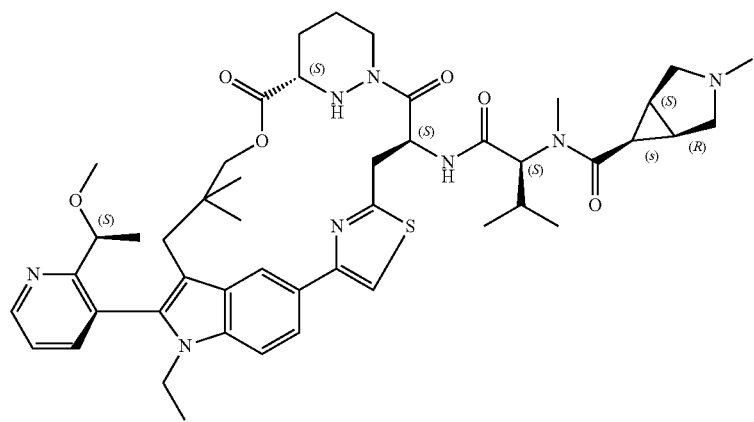 |

TABLE 1-continued
Certain Compounds of the Present Invention
| Ex# | Structure |
|---|---|
| A448 | 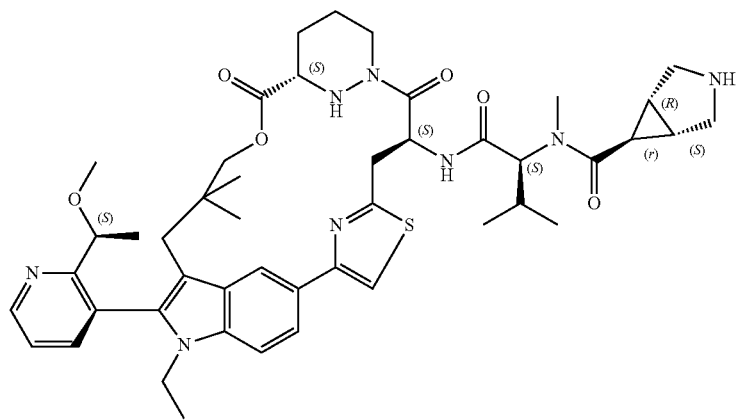 |
| A449 | 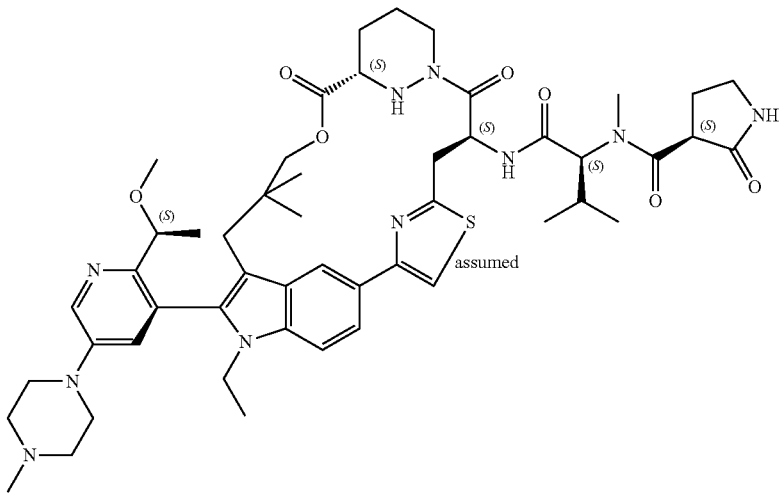 |
| A450 | 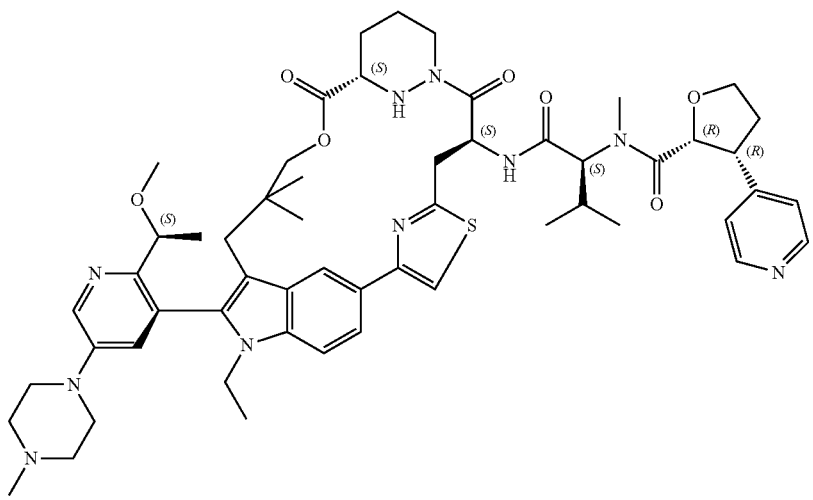 |

TABLE 1-continued
Certain Compounds of the Present Invention
| Ex# | Structure |
|---|---|
| A451 | 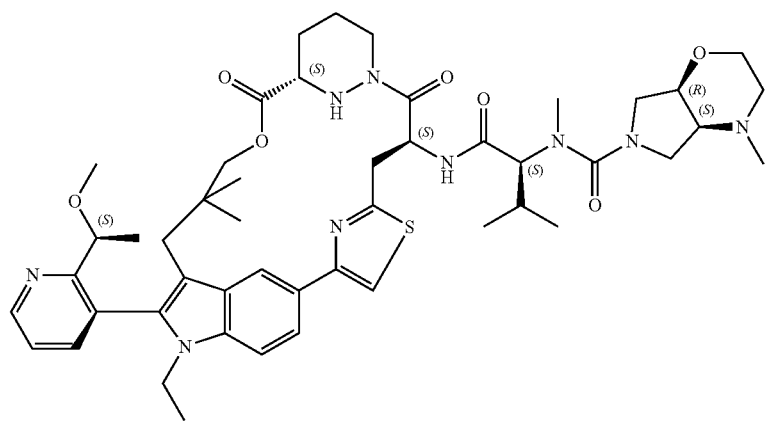 |
| A452 | 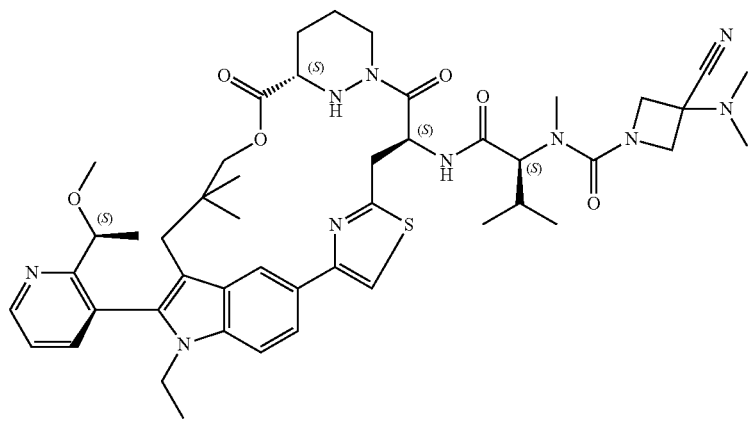 |
| A453 | 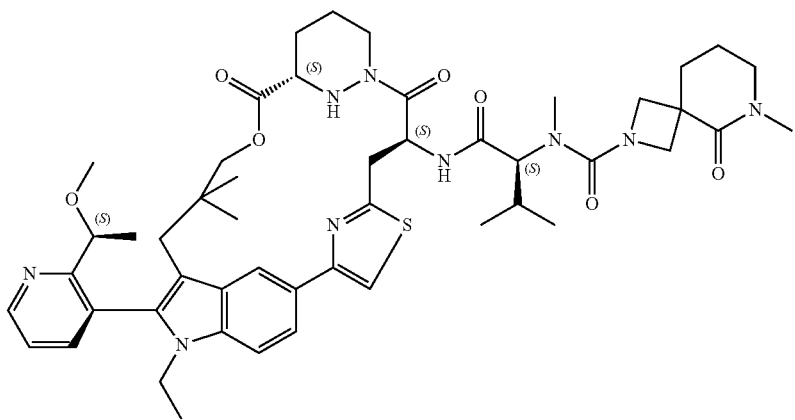 |

| Ex# | Structure |
|---|---|
| A454 | 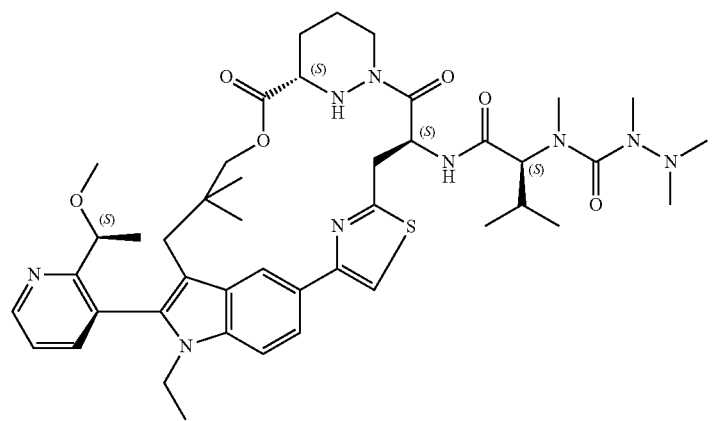 |
| A455 | 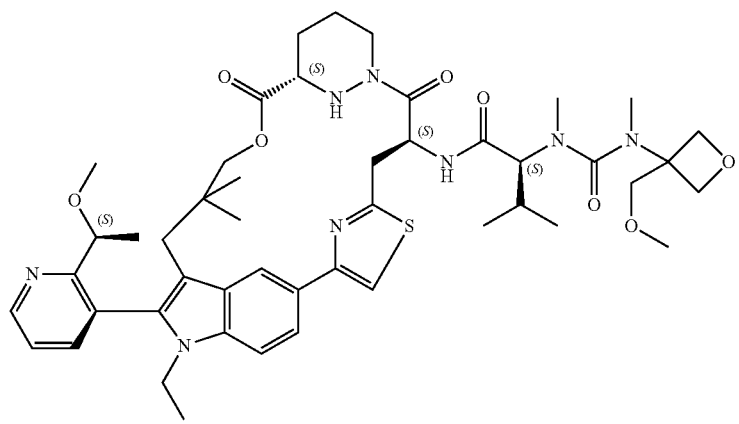 |
| A456 | 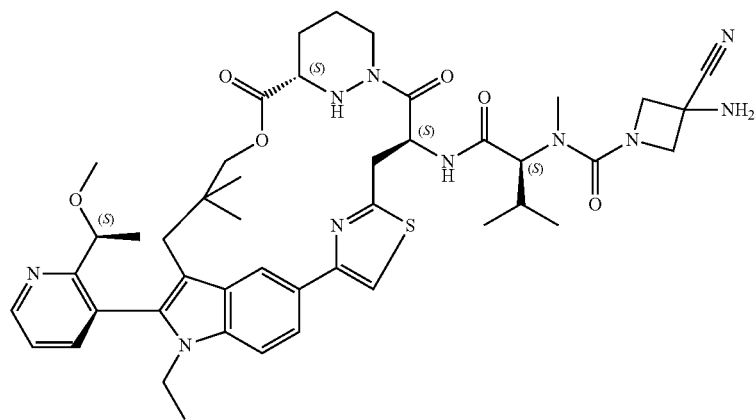 |

TABLE 1-continued

Certain Compounds of the Present Invention

| Ex# | Structure |
|---|---|
| A457 | 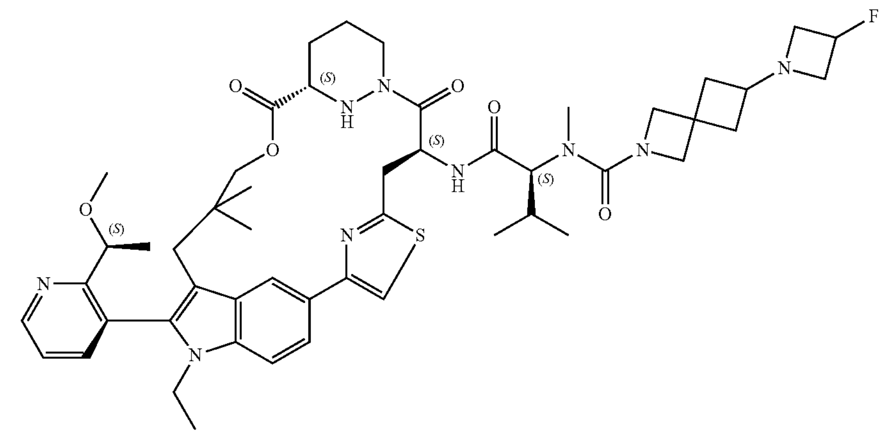 |
| A458 | 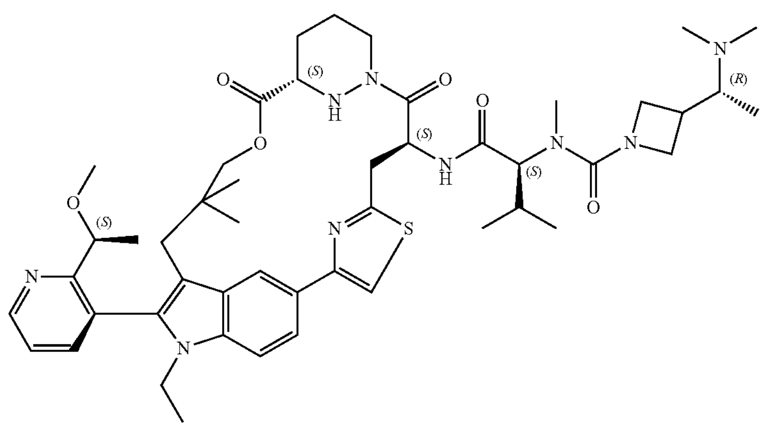 |
| A459 | 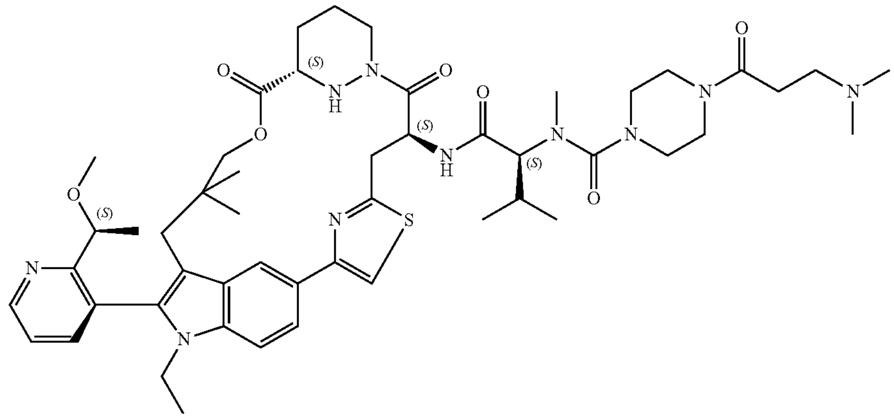 |

TABLE 1-continued
Certain Compounds of the Present Invention
| Ex# | Structure |
|---|---|
| A460 | 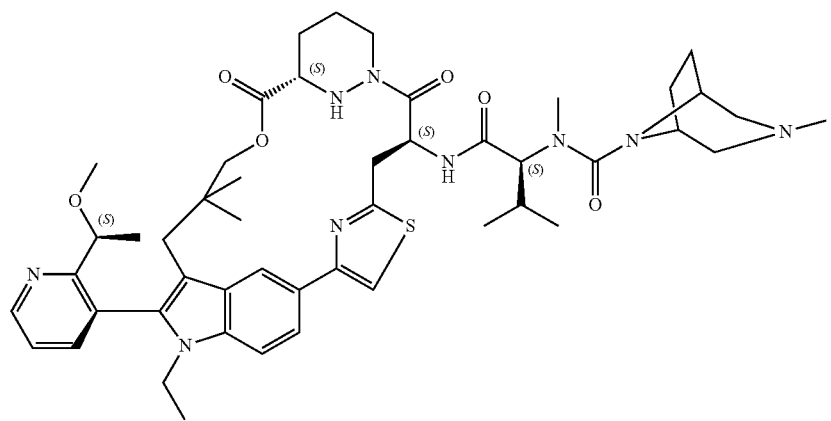 |
| A461 | 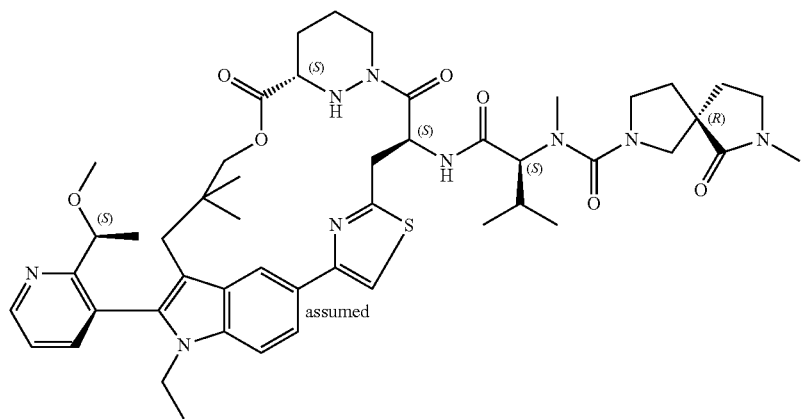 |
| A462 | 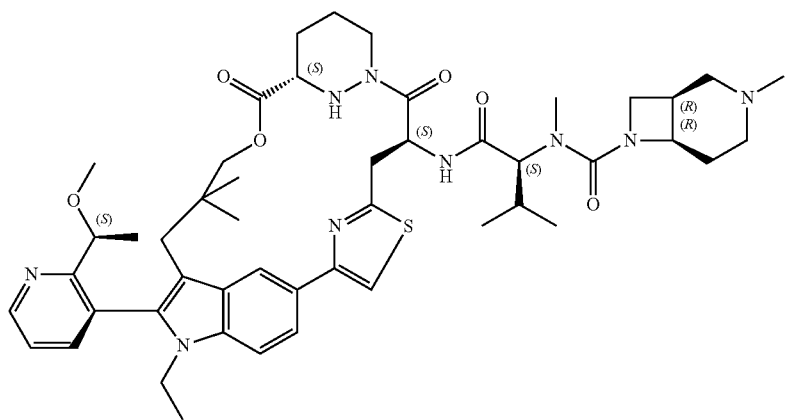 |

TABLE 1-continued
Certain Compounds of the Present Invention
| Ex# | Structure |
|---|---|
| A463 | 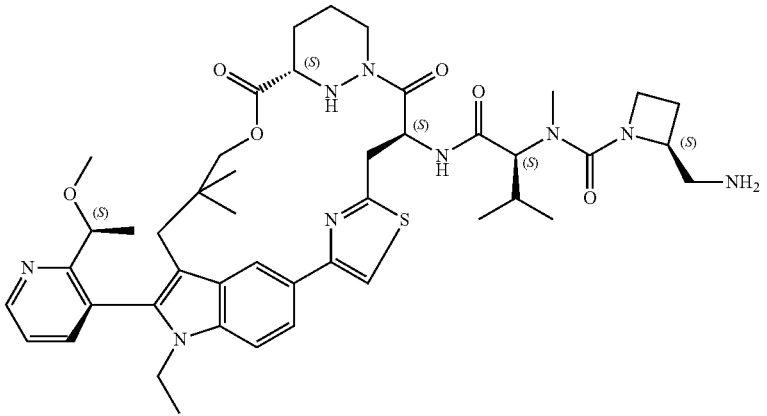 |
| A464 | 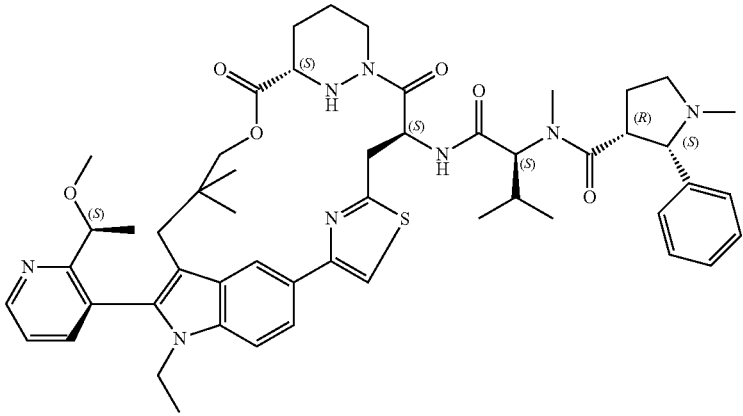 |
| A465 | 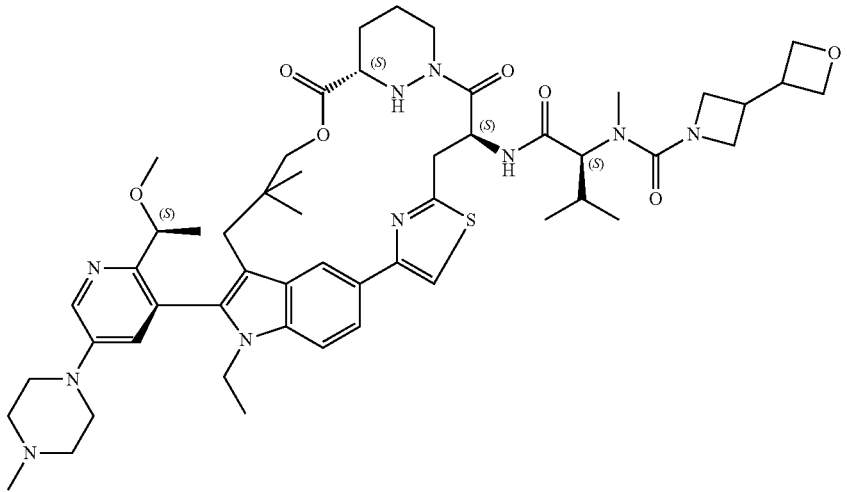 |

TABLE 1-continued

Certain Compounds of the Present Invention

| Ex# | Structure |
|---|---|
| A466 | 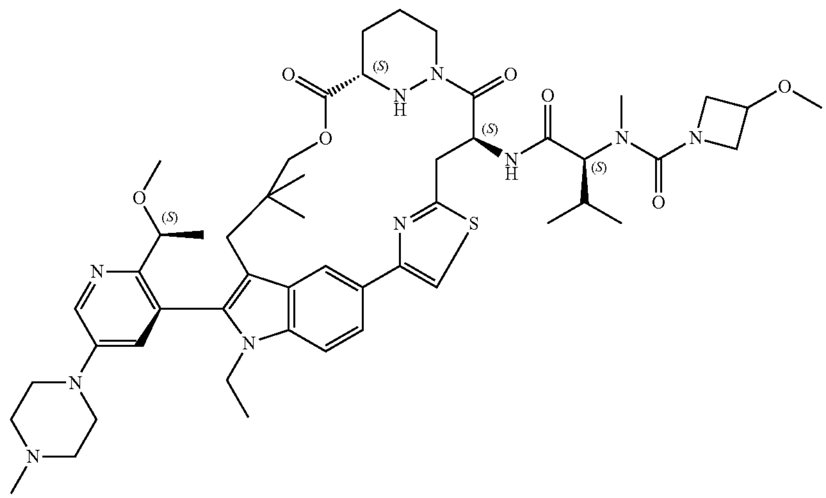 |
| A467 | 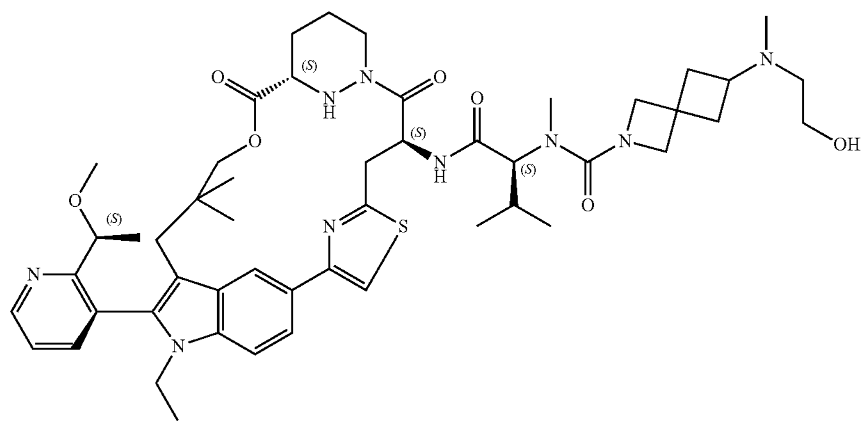 |
| A468 | 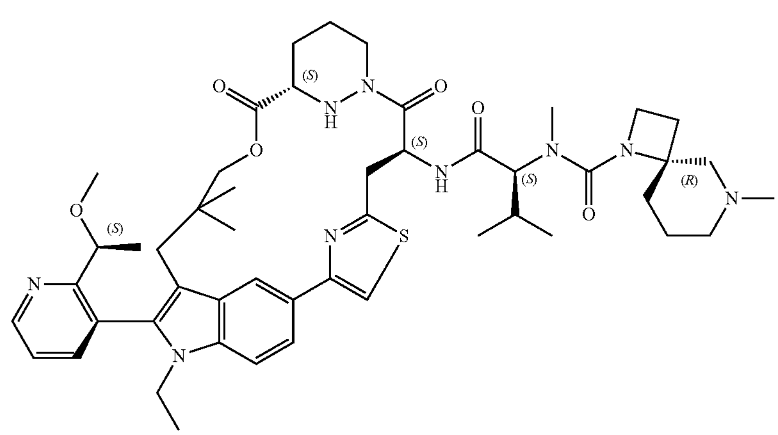 |

TABLE 1-continued

Certain Compounds of the Present Invention

| Ex# | Structure |
|---|---|
| A469 | 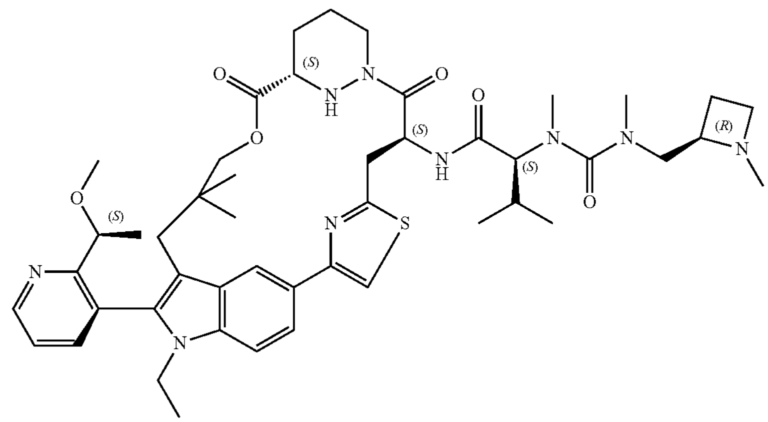 |
| A470 | 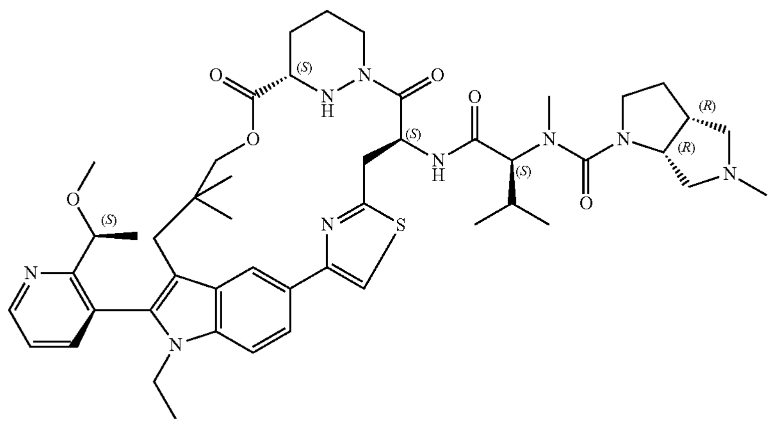 |
| A471 | 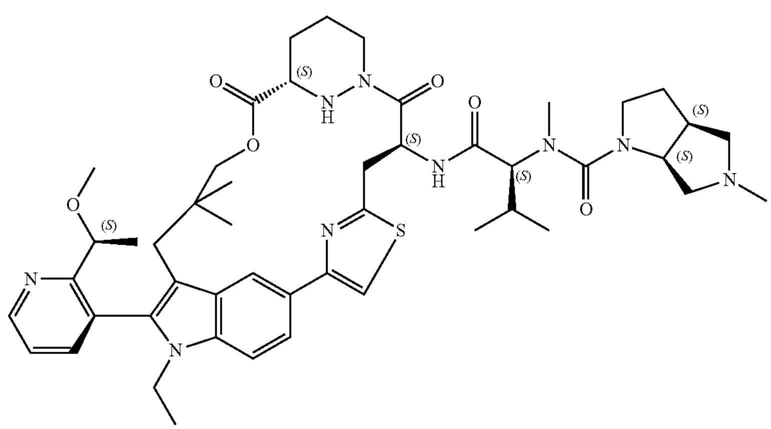 |

TABLE 1-continued
Certain Compounds of the Present Invention
| Ex# | Structure |
|---|---|
| A472 | 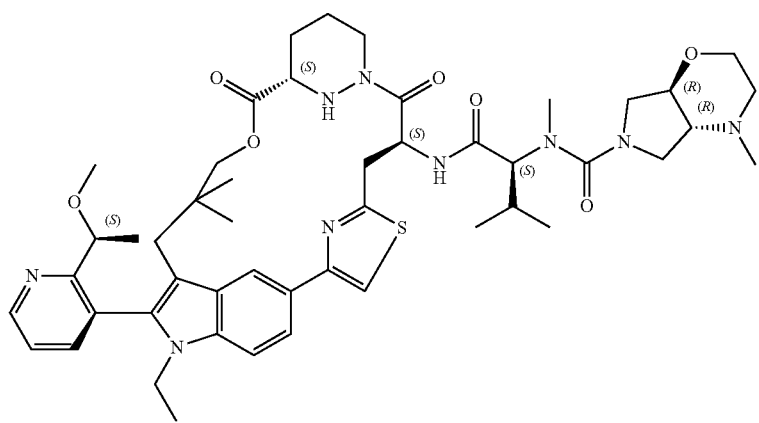 |
| A473 | 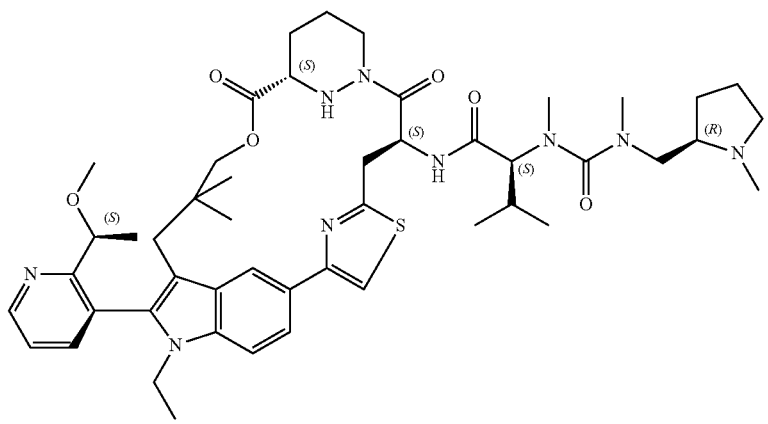 |
| A474 | 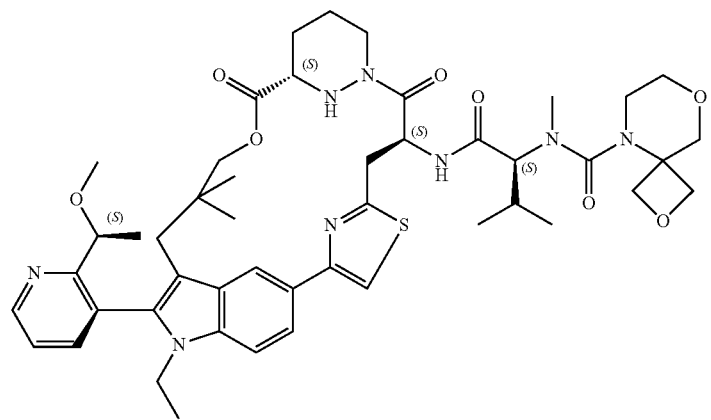 |

TABLE 1-continued
Certain Compounds of the Present Invention
| Ex# | Structure |
|---|---|
| A475 | 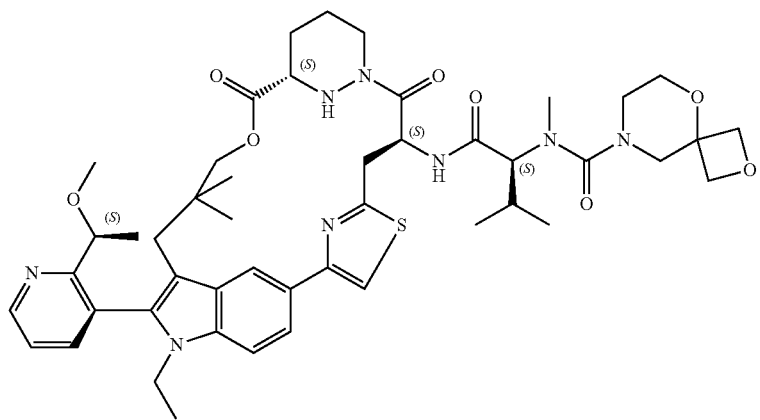 |
| A476 | 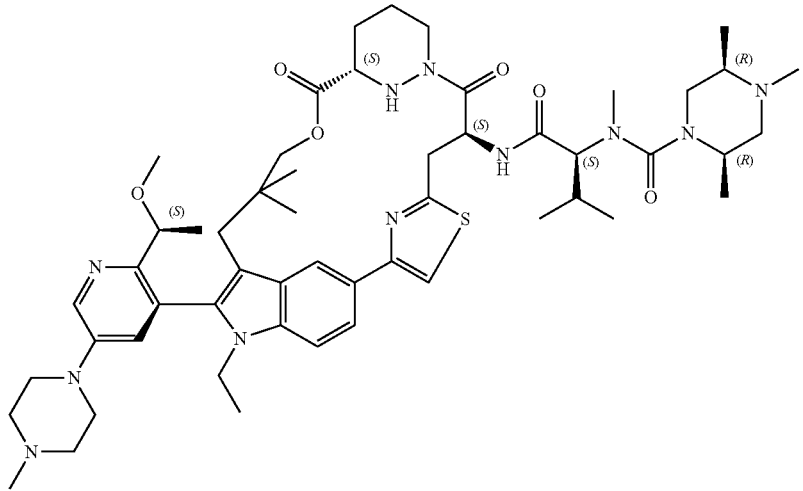 |
| A477 | 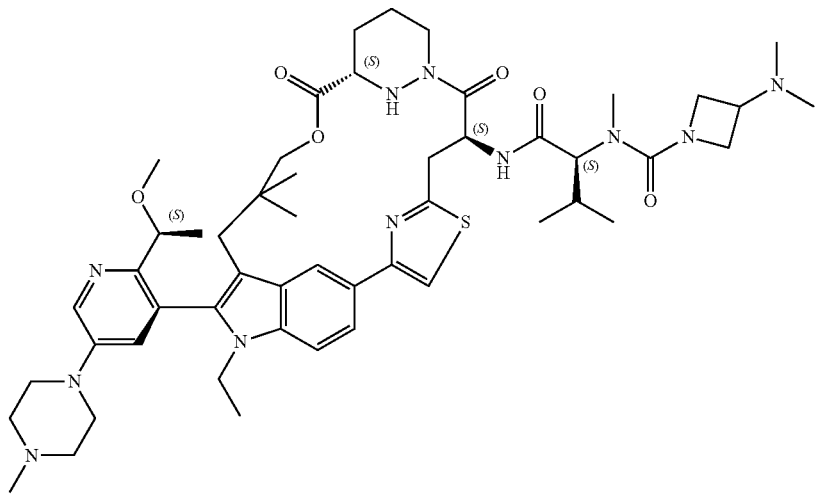 |

TABLE 1-continued
Certain Compounds of the Present Invention
| Ex# | Structure |
|---|---|
| A478 | 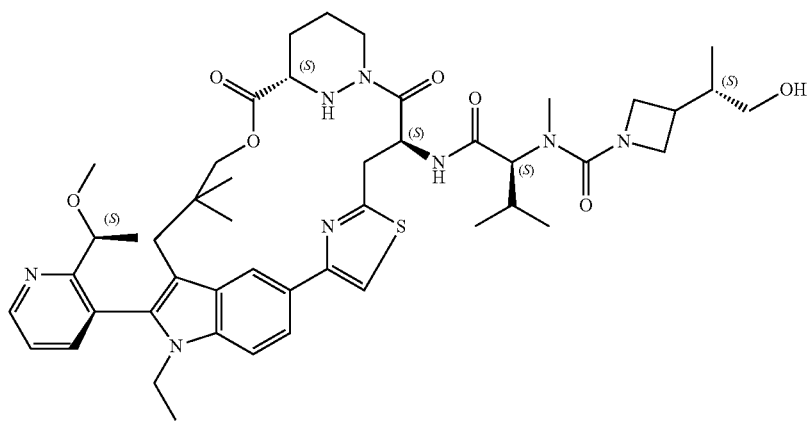 |
| A479 | 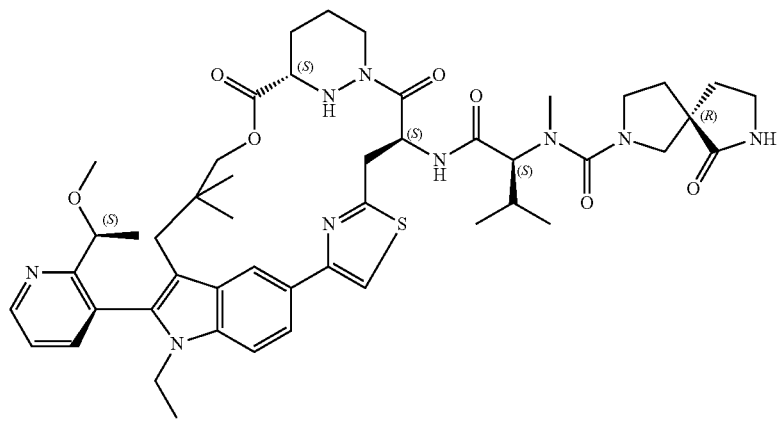 |
| A480 | 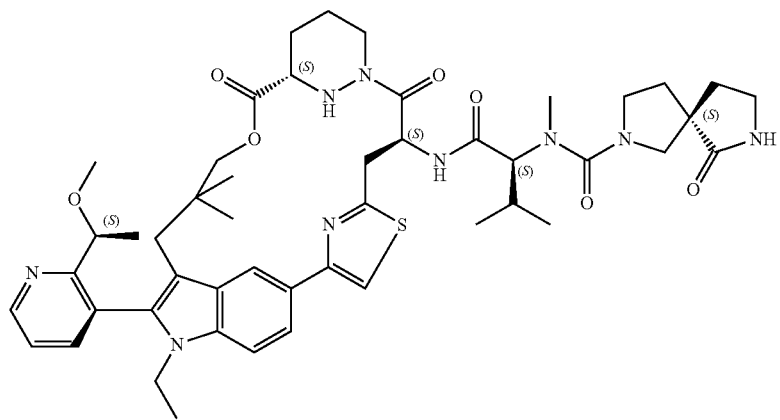 |

TABLE 1-continued
Certain Compounds of the Present Invention
| Ex# | Structure |
|---|---|
| A481 | 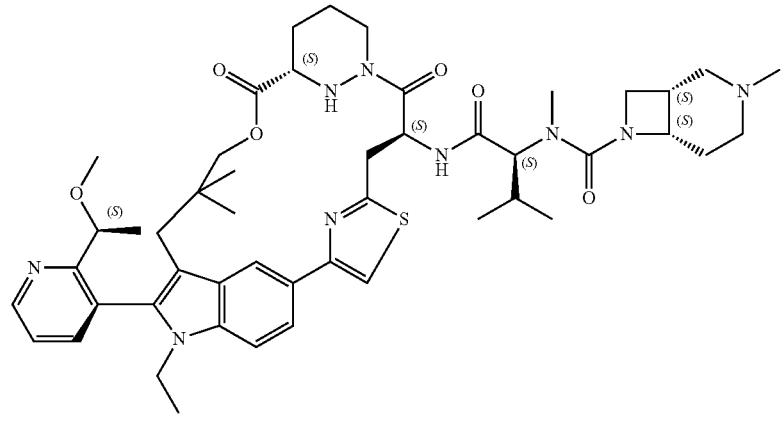 |
| A482 | 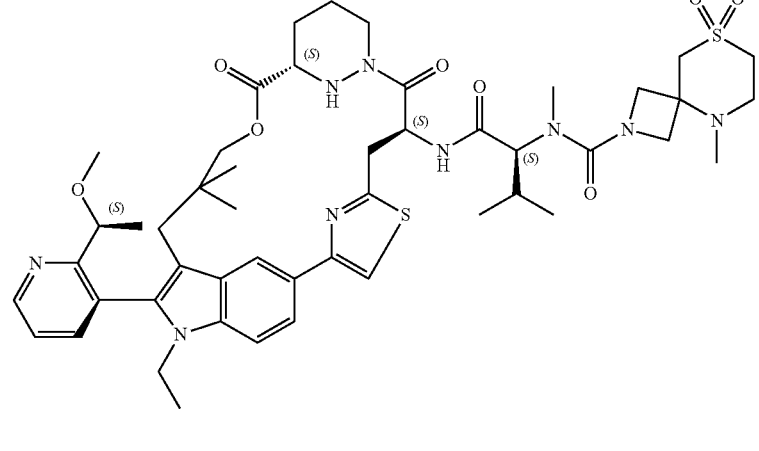 |
| A483 | 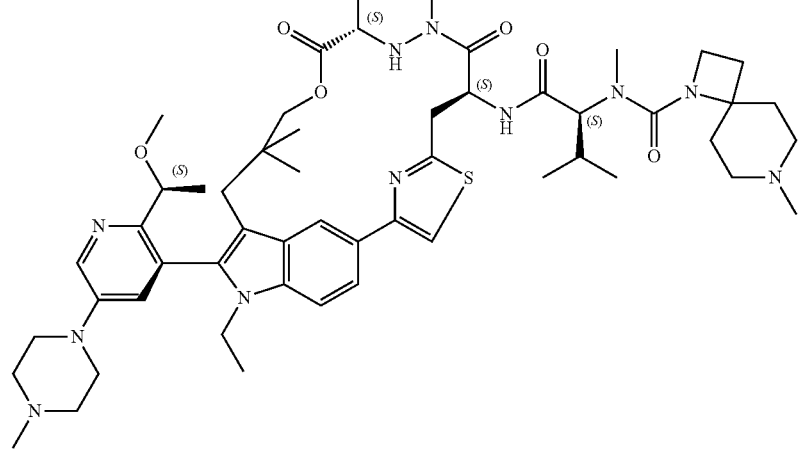 |

TABLE 1-continued

Certain Compounds of the Present Invention

| Ex# | Structure |
|---|---|
| A484 | 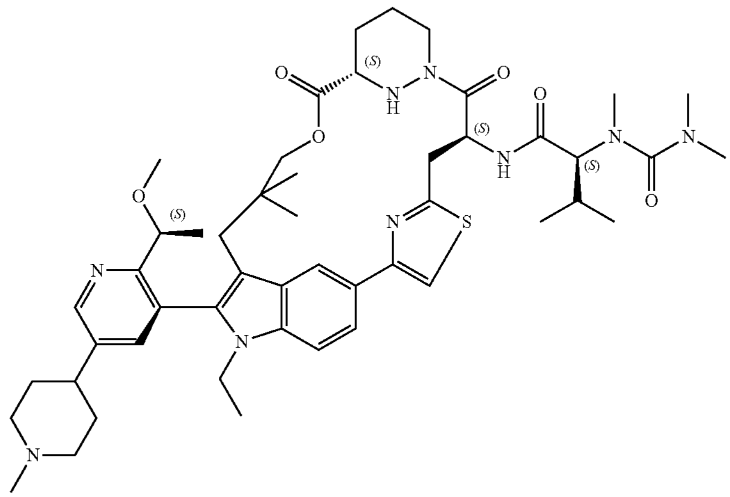 |
| A485 | 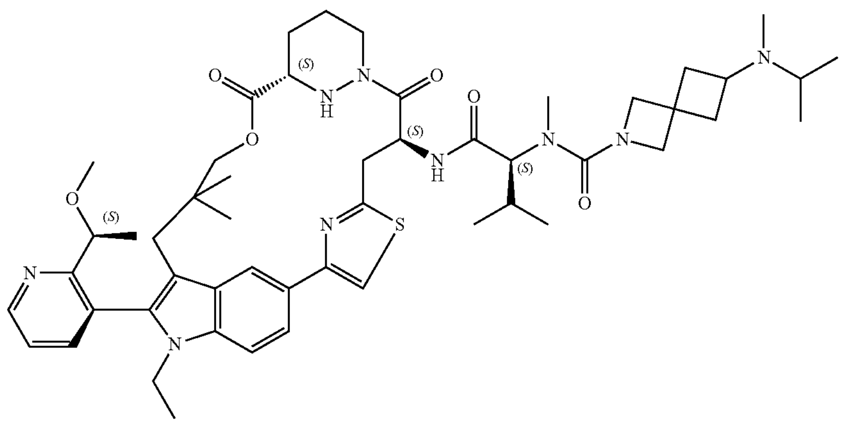 |
| A486 | 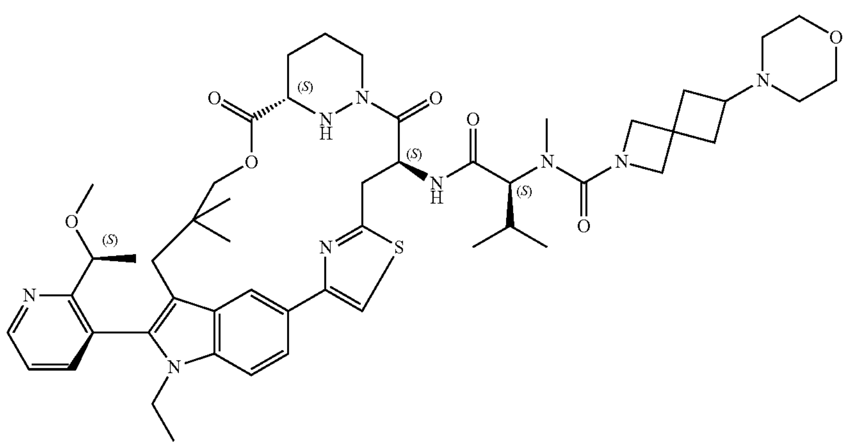 |

TABLE 1-continued
Certain Compounds of the Present Invention
| Ex# | Structure |
| --- | --- |
| A487 | 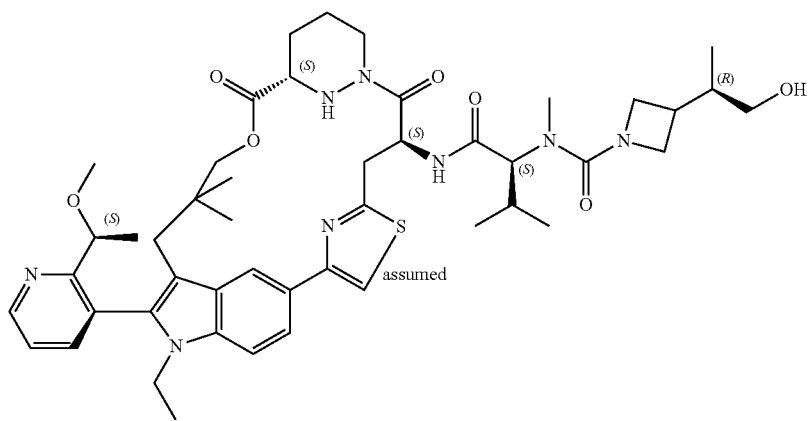 |
| A488 | 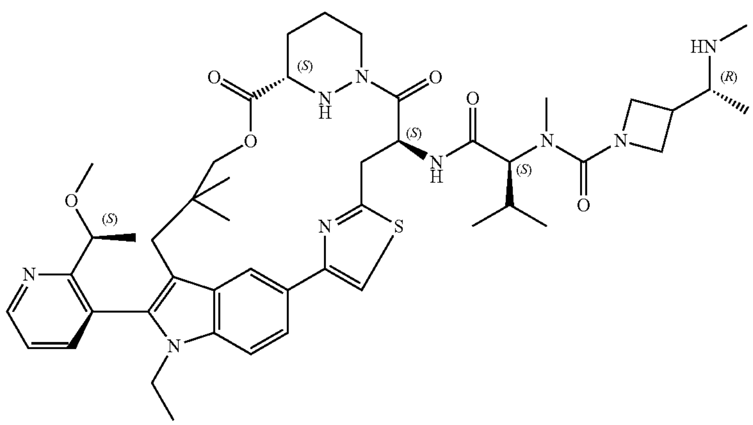 |
| A489 | 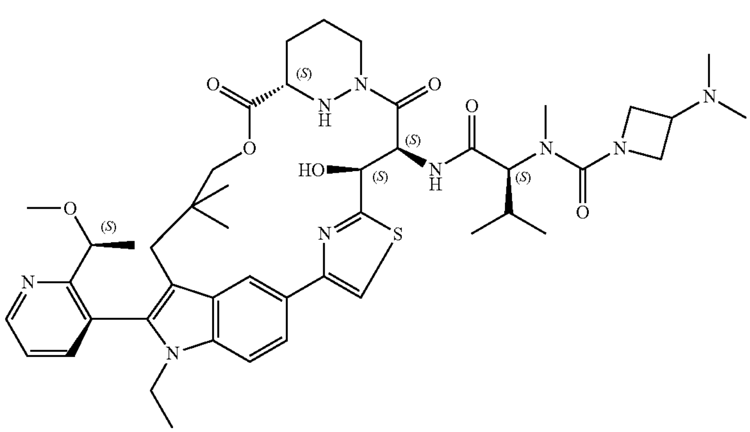 |

//
TABLE 1-continued
Certain Compounds of the Present Invention
| Ex# | Structure |
|---|---|
| A490 | 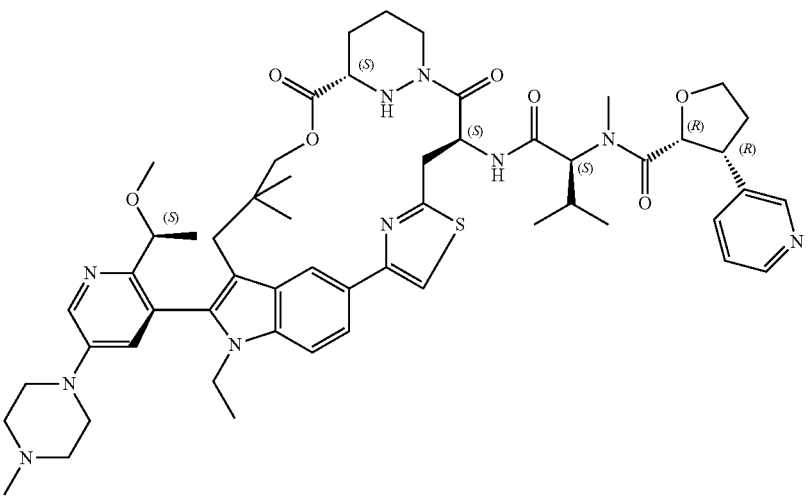 |
| A491 | 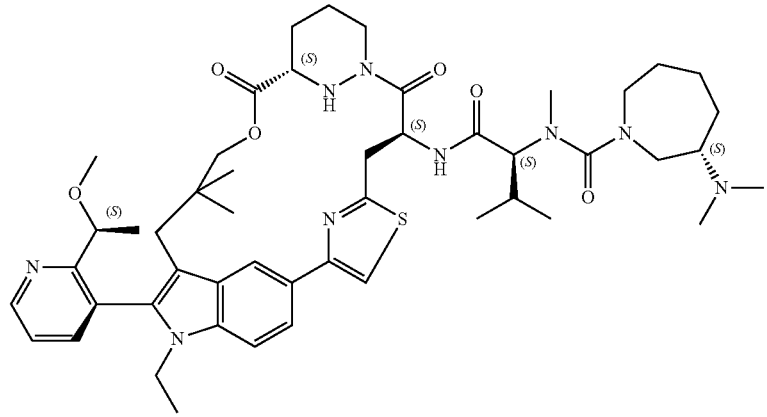 |
| A492 | 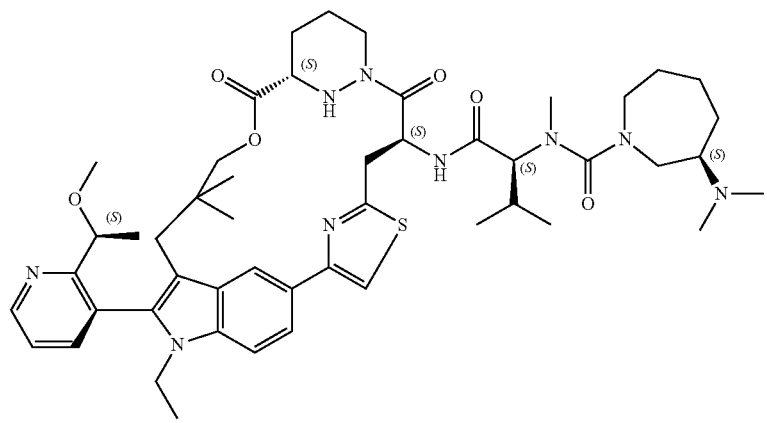 |

TABLE 1-continued
Certain Compounds of the Present Invention
| Ex# | Structure |
|---|---|
| A493 | 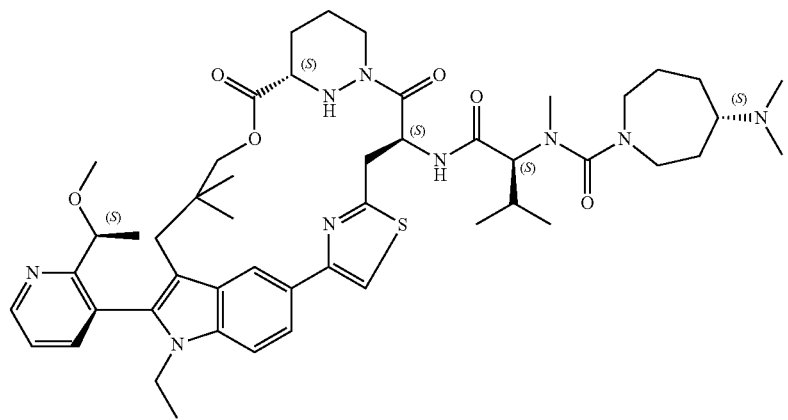 |
| A494 | 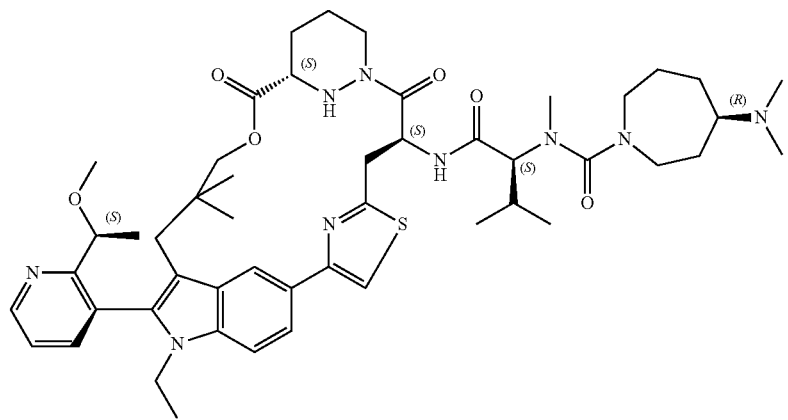 |
| A495 | 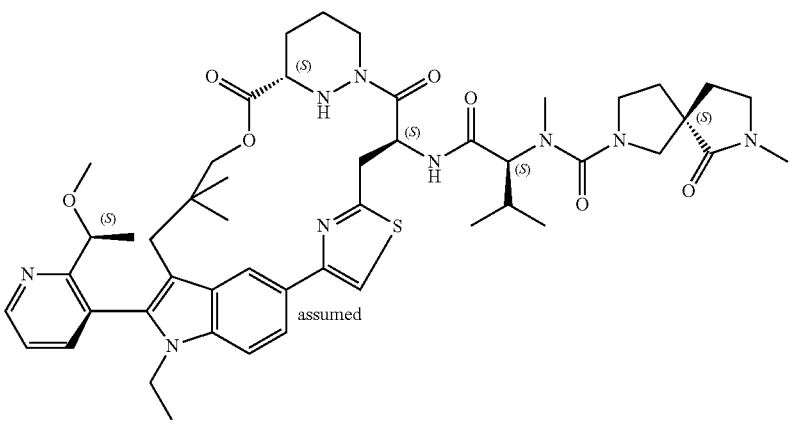 |

TABLE 1-continued
Certain Compounds of the Present Invention
| Ex# | Structure |
|---|---|
| A496 | 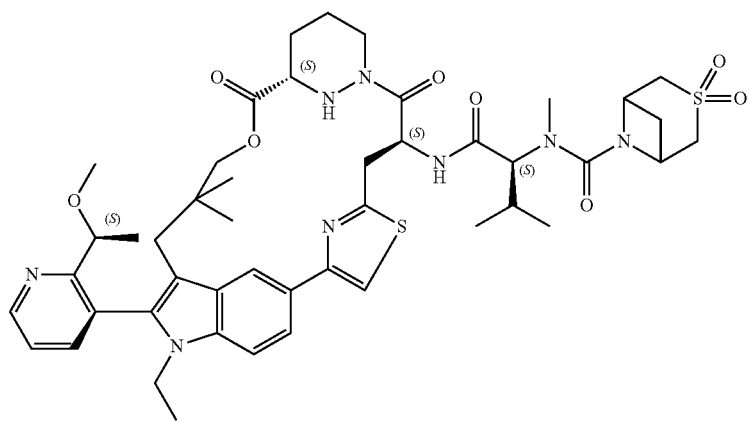 |
| A497 | 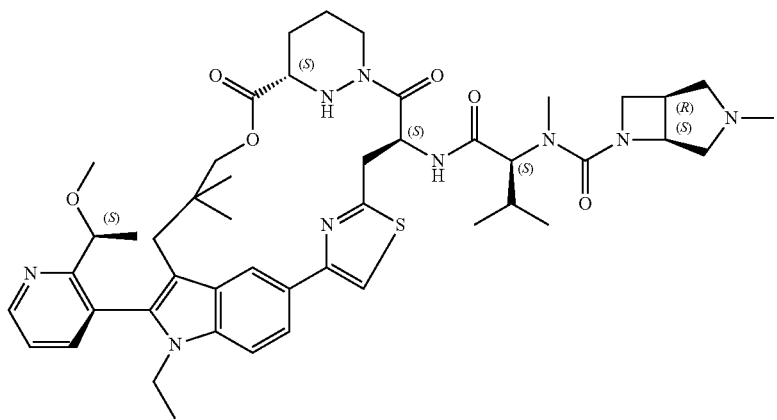 |
| A498 | 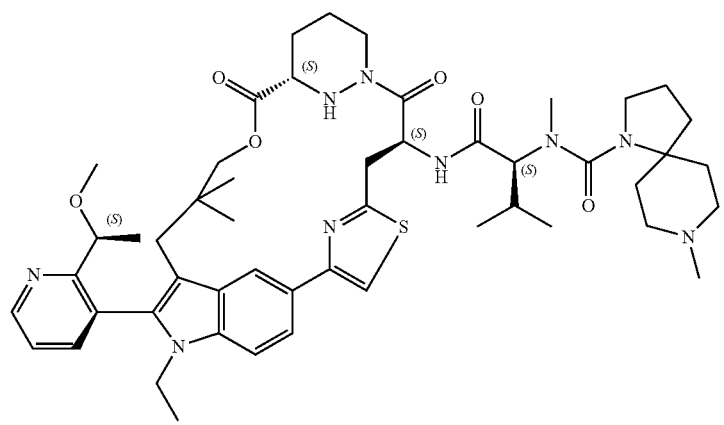 |

TABLE 1-continued
Certain Compounds of the Present Invention
| Ex# | Structure |
|---|---|
| A499 | 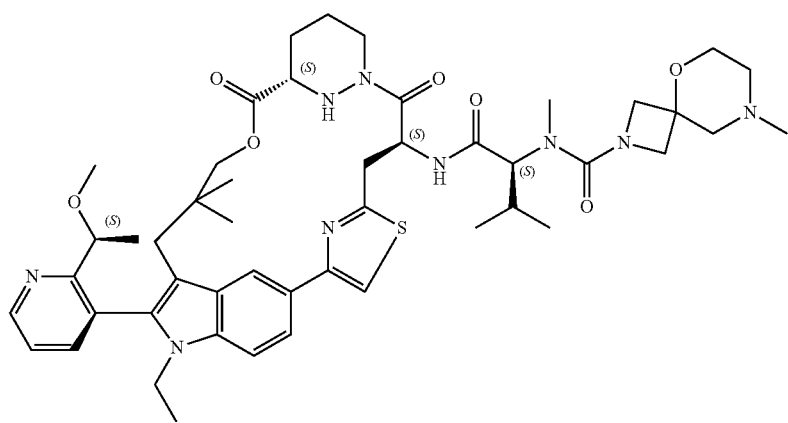 |
| A500 | 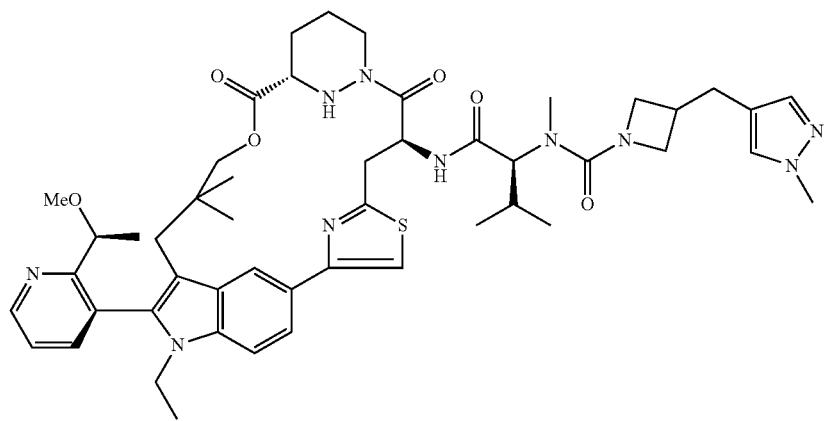 |
| A501 | 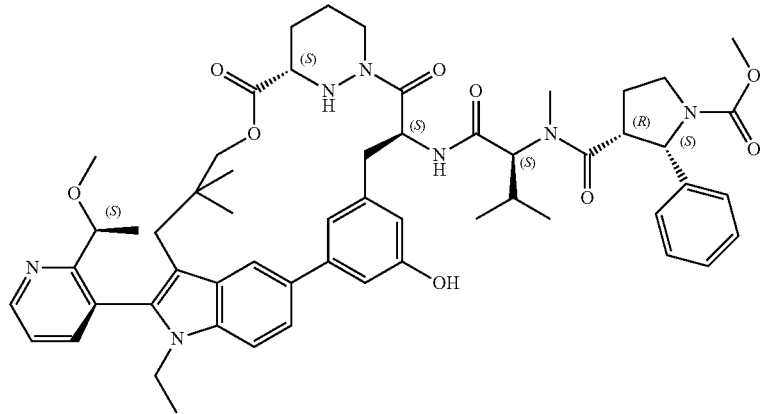 |

TABLE 1-continued
Certain Compounds of the Present Invention
| Ex# | Structure |
|---|---|
| A502 | 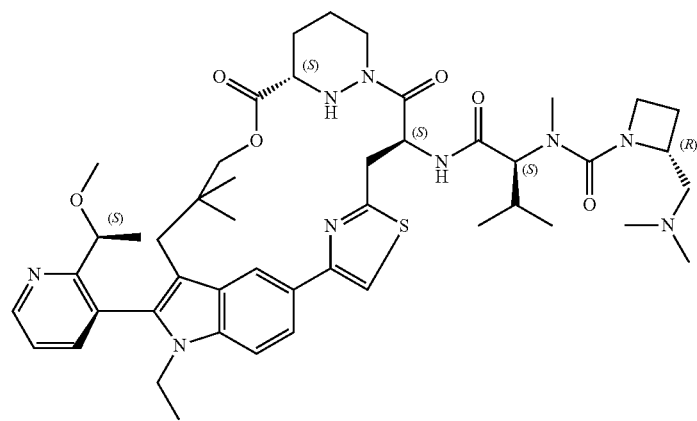 |
| A503 | 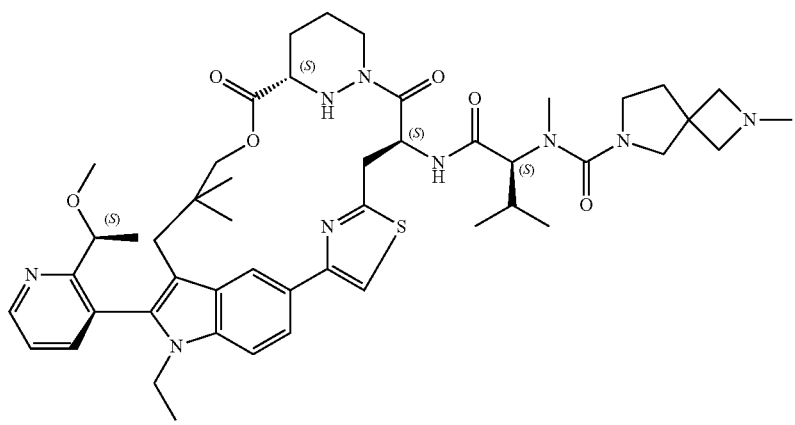 |
| A504 | 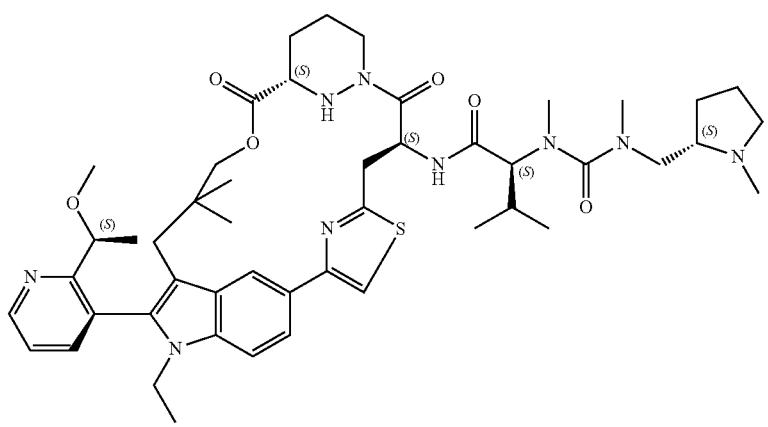 |

TABLE 1-continued

Certain Compounds of the Present Invention

| Ex# | Structure |
|---|---|
| A505 | 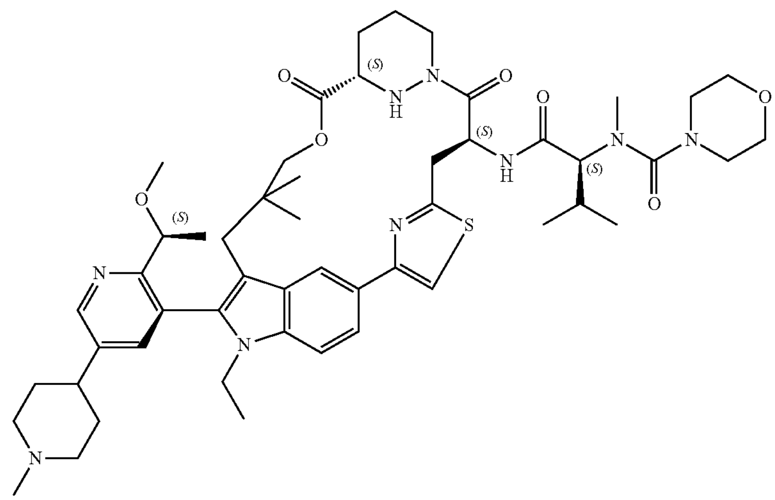 |
| A506 | 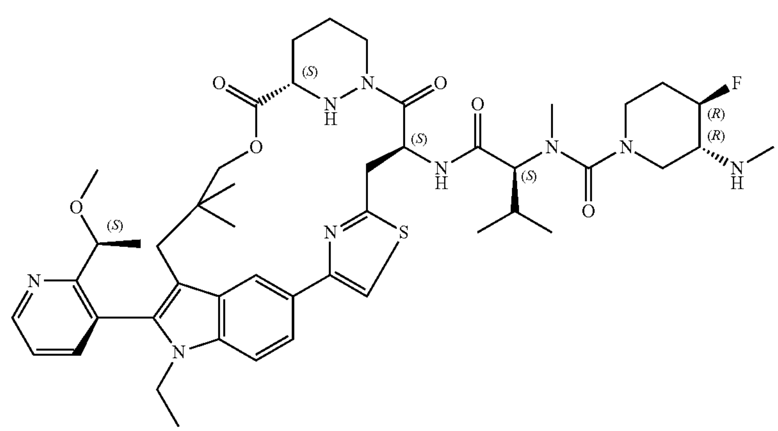 |
| A507 | 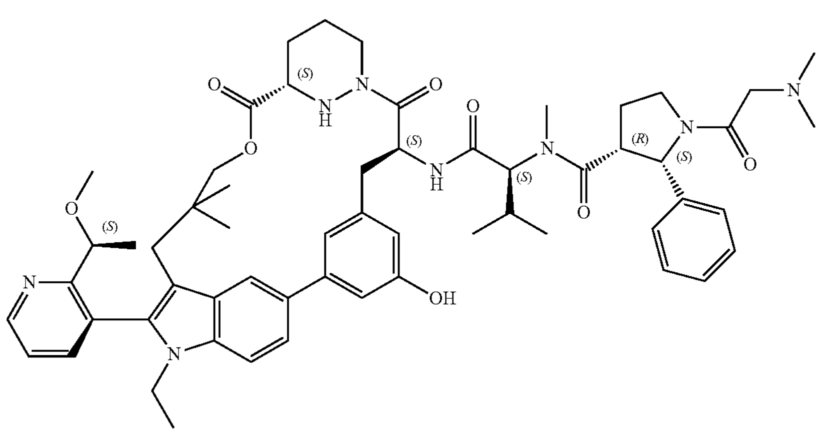 |

TABLE 1-continued
Certain Compounds of the Present Invention
| Ex# | Structure |
| --- | --- |
| A508 | 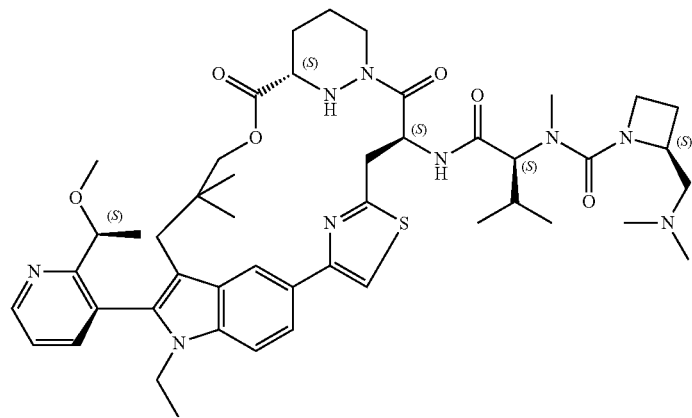 |
| A509 | 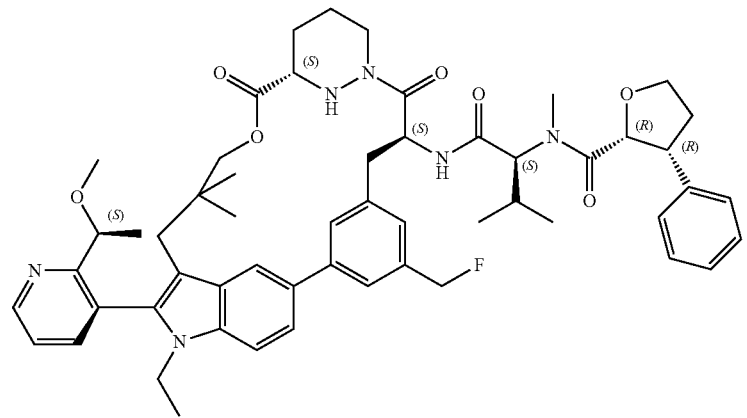 |
| A510 | 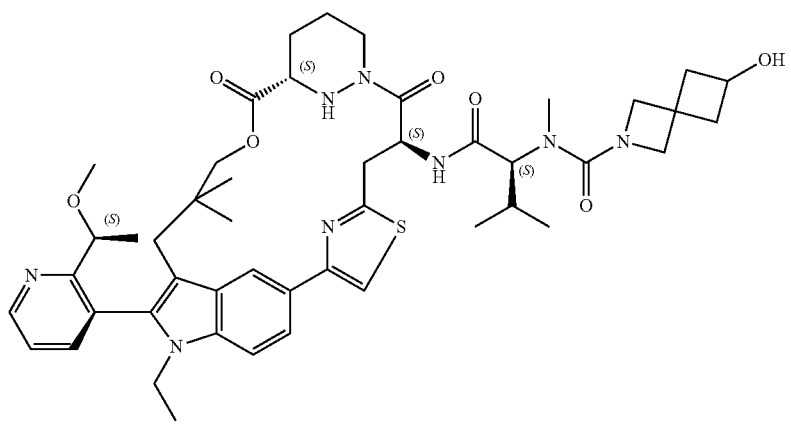 |

TABLE 1-continued
Certain Compounds of the Present Invention
| Ex# | Structure |
|---|---|
| A511 | 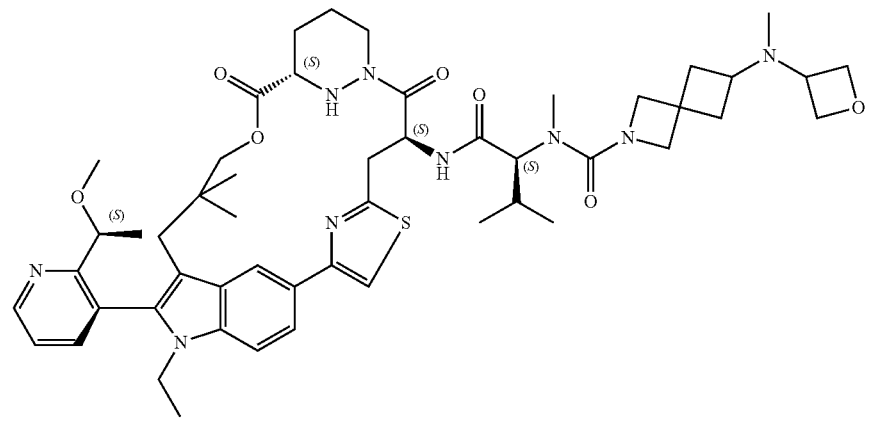 |
| A512 | 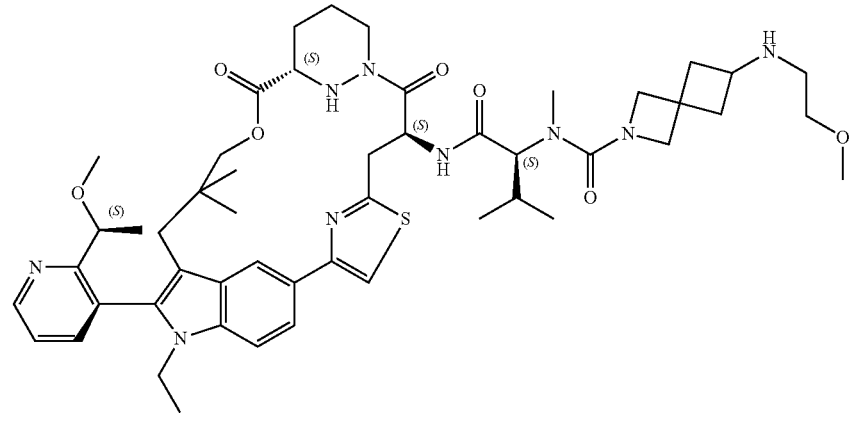 |
| A513 | 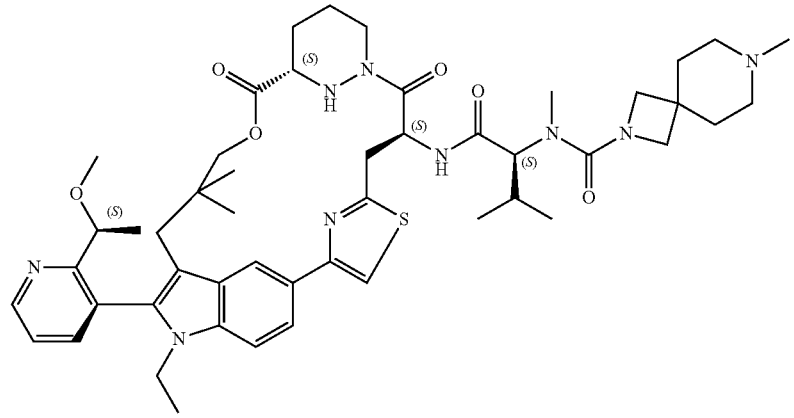 |

TABLE 1-continued

Certain Compounds of the Present Invention

| Ex# | Structure |
| --- | --- |
| A514 | 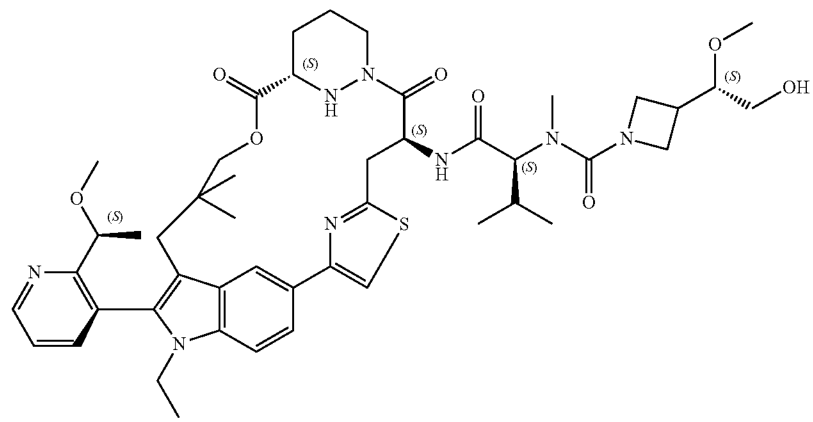 |
| A515 | 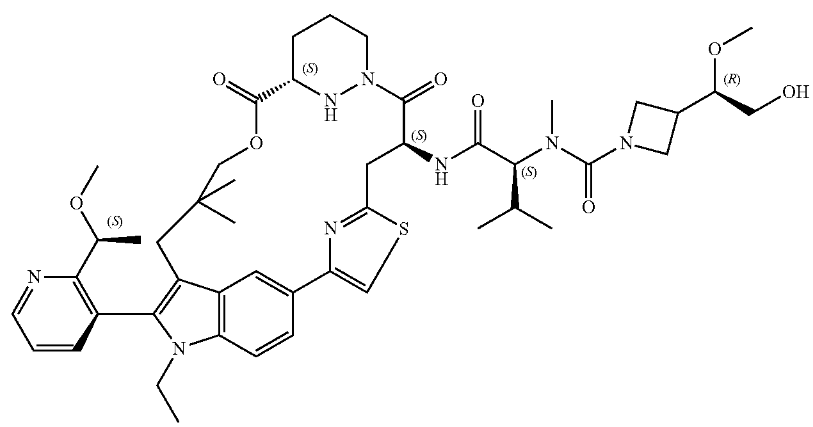 |
| A516 | 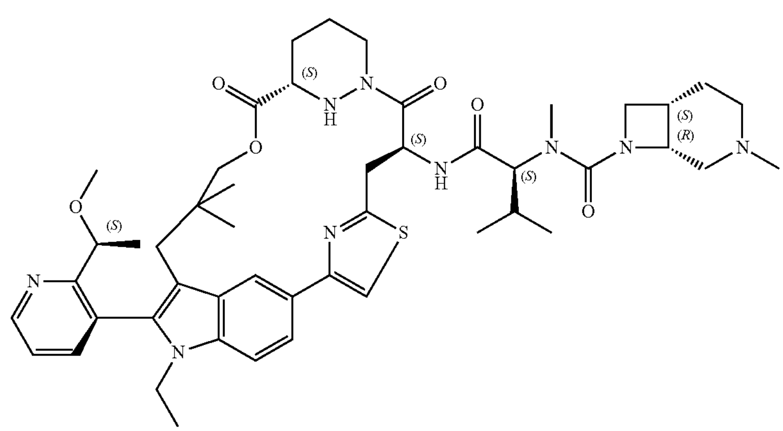 |

TABLE 1-continued
Certain Compounds of the Present Invention
| Ex# | Structure |
|---|---|
| A517 | 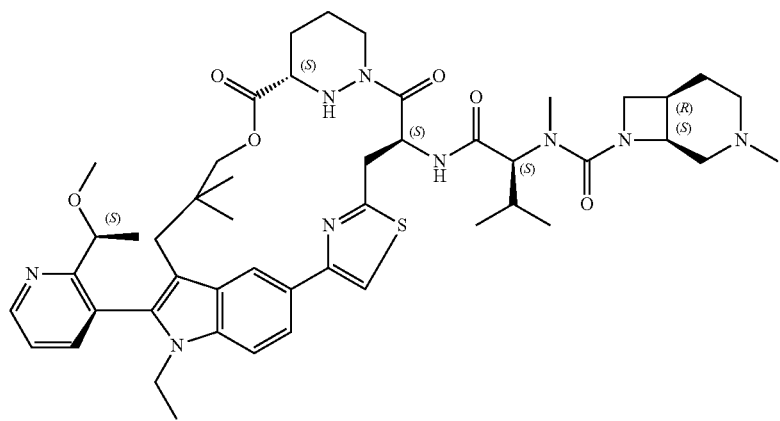 |
| A518 | 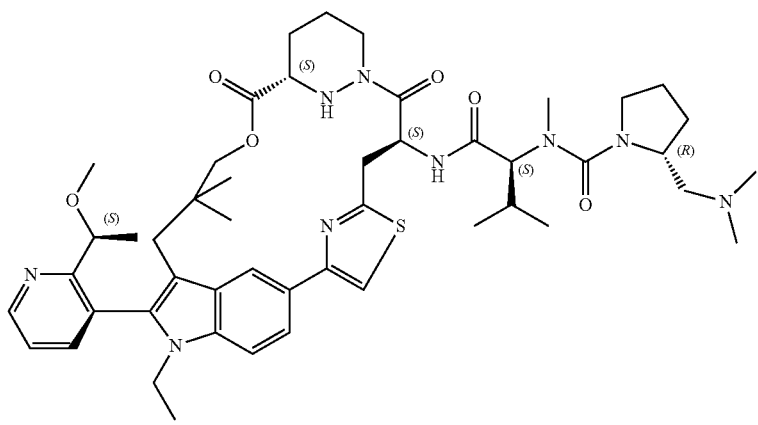 |
| A519 | 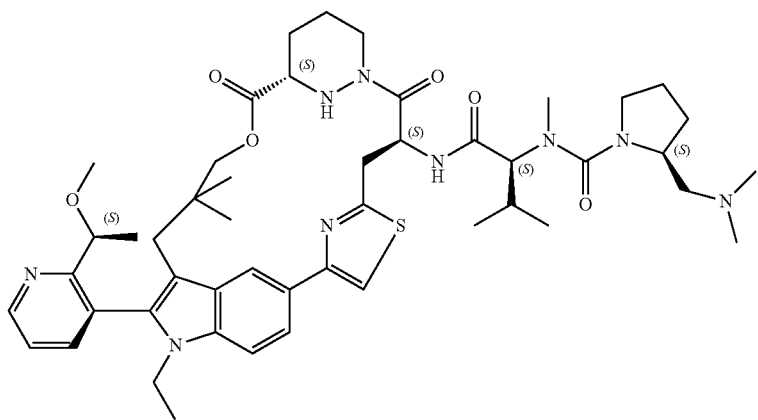 |

TABLE 1-continued
Certain Compounds of the Present Invention
| Ex# | Structure |
|---|---|
| A520 | 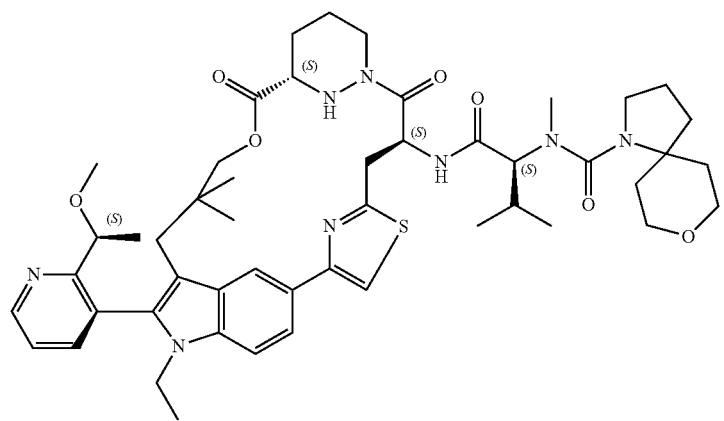 |
| A521 | 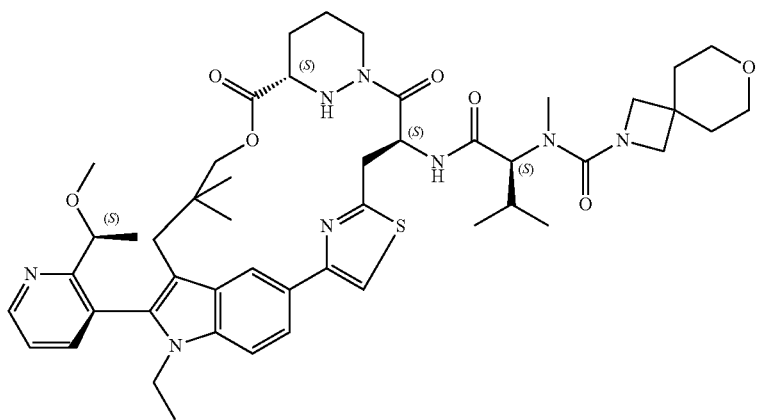 |
| A522 | 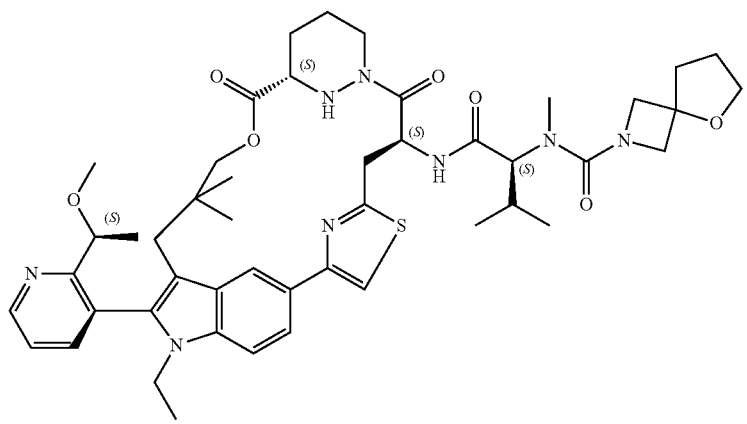 |

TABLE 1-continued
Certain Compounds of the Present Invention
| Ex# | Structure |
|---|---|
| A523 | 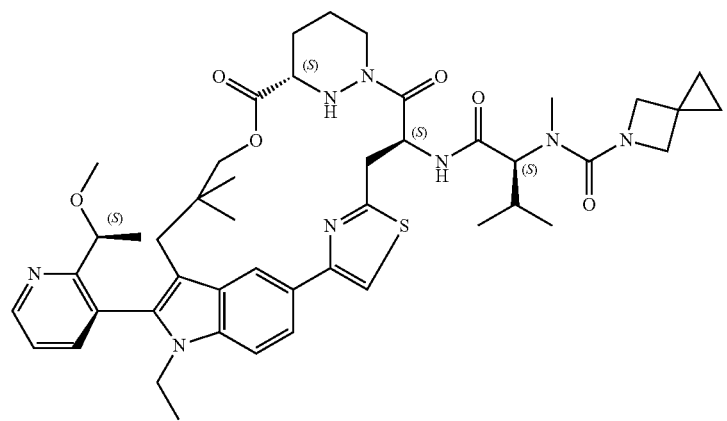 |
| A524 | 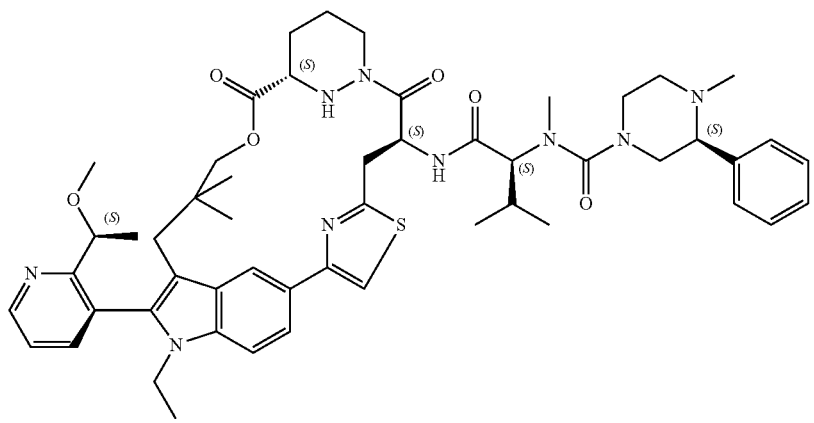 |
| A525 | 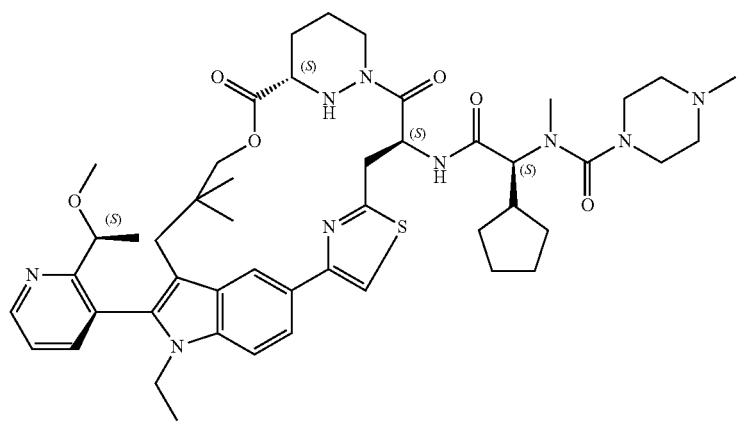 |

TABLE 1-continued

Certain Compounds of the Present Invention

| Ex# | Structure |
|---|---|
| A526 | 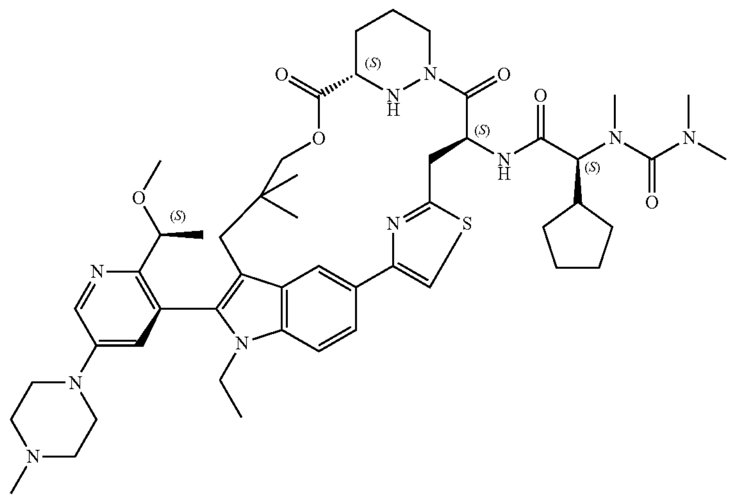 |
| A527 | 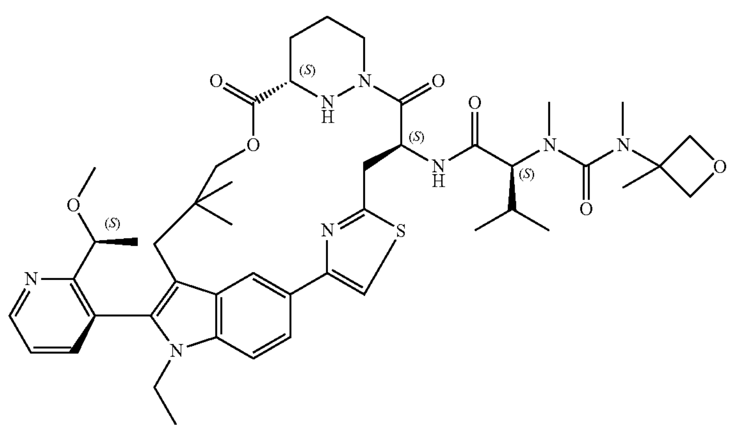 |
| A528 | 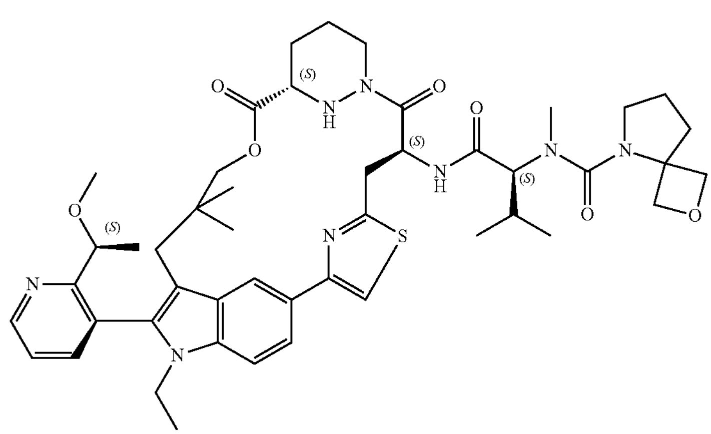 |

TABLE 1-continued

Certain Compounds of the Present Invention

| Ex# | Structure |
|---|---|
| A529 | 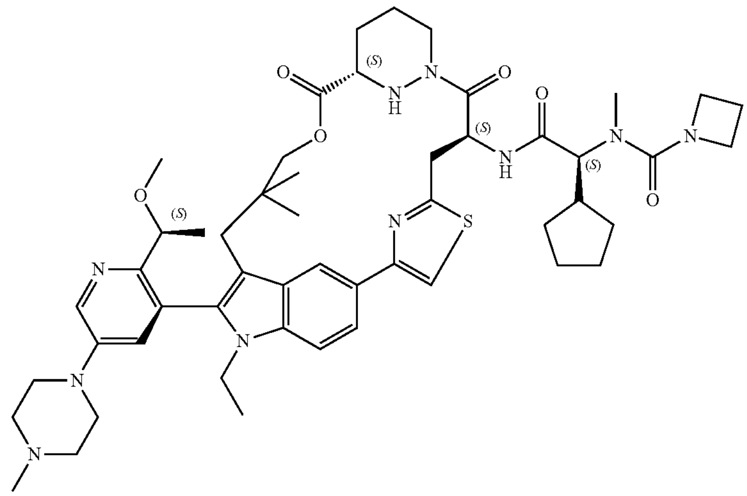 |
| A530 | 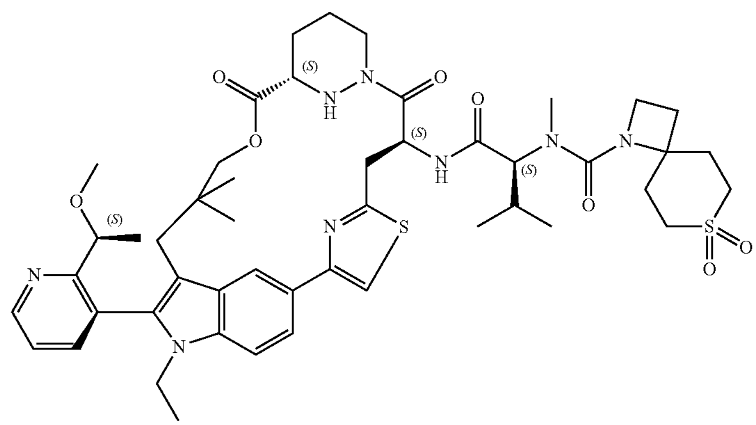 |
| A531 | 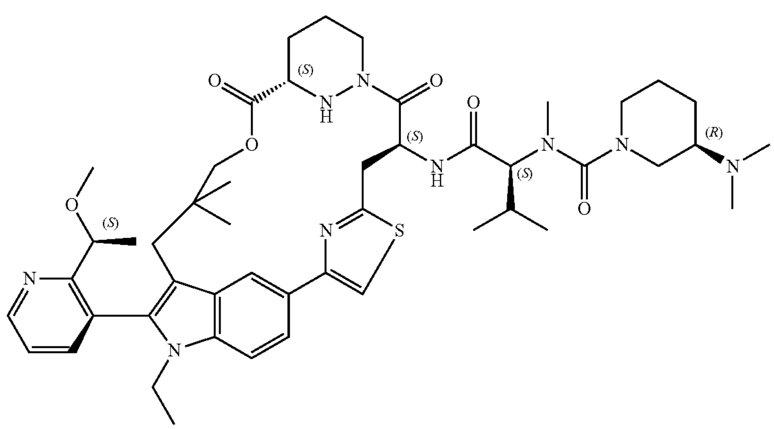 |

TABLE 1-continued
Certain Compounds of the Present Invention
| Ex# | Structure |
|---|---|
| A532 | 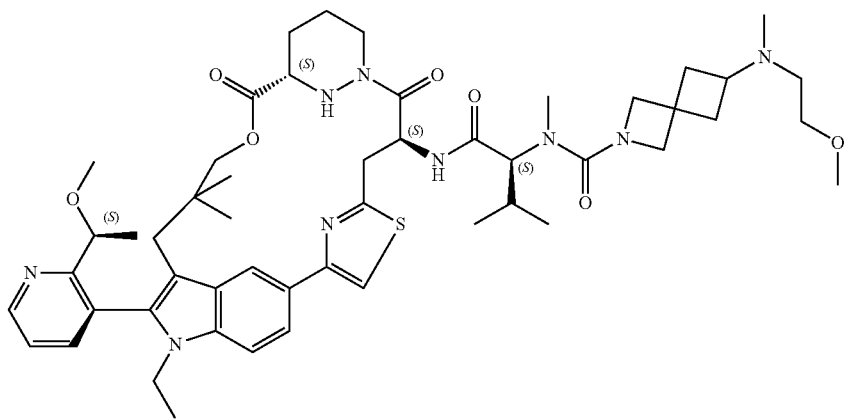 |
| A533 | 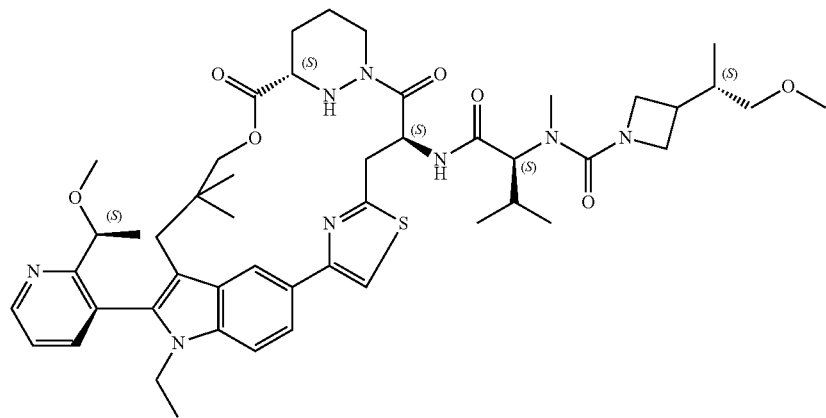 |
| A534 | 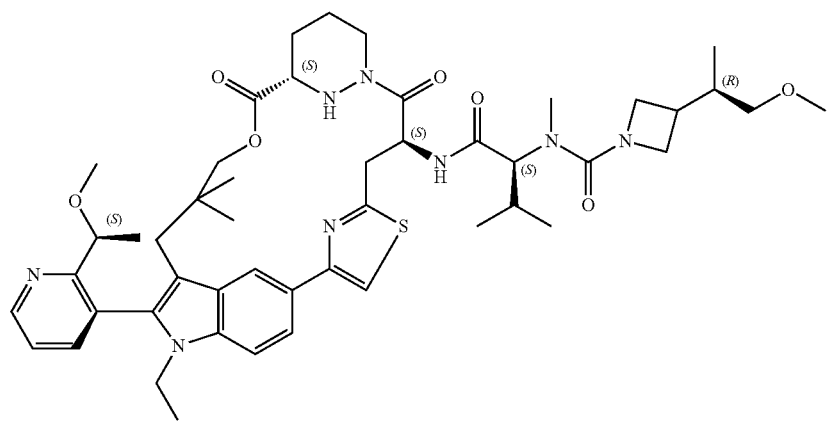 |

TABLE 1-continued
Certain Compounds of the Present Invention
| Ex# | Structure |
| --- | --- |
| A535 | 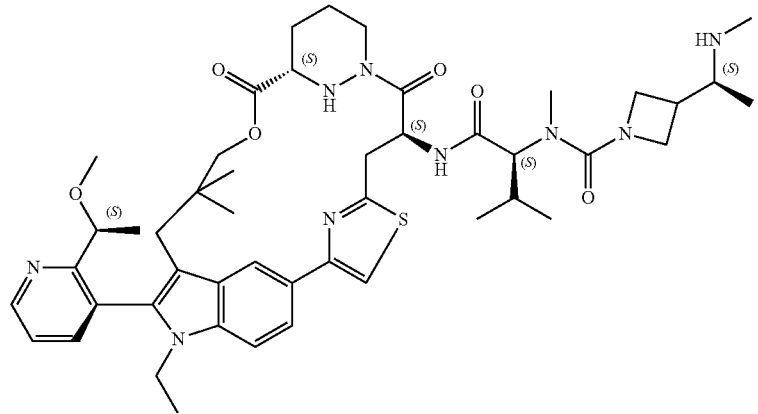 |
| A536 | 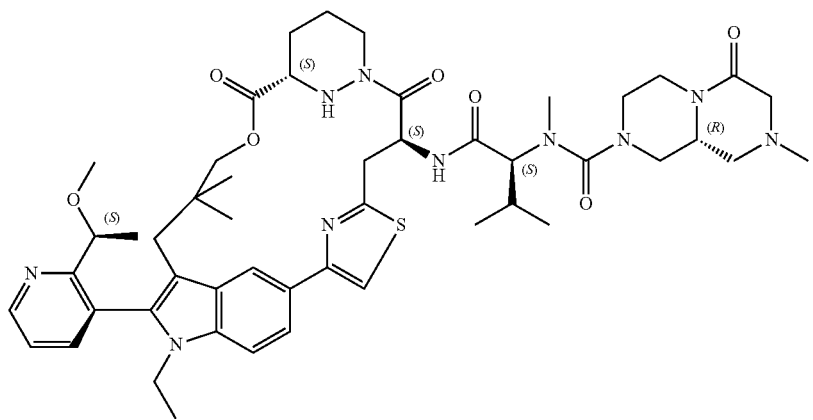 |
| A537 | 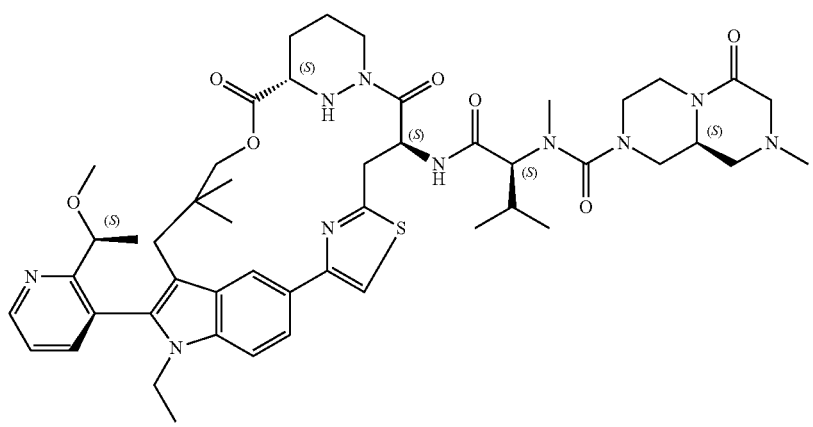 |

TABLE 1-continued
Certain Compounds of the Present Invention
| Ex# | Structure |
|---|---|
| A538 | 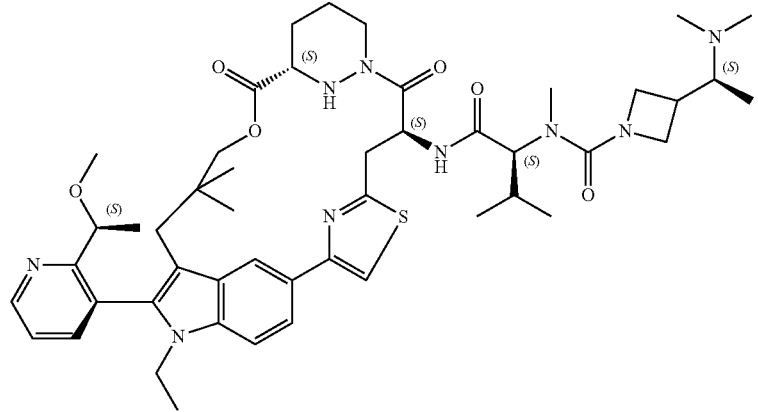 |
| A539 | 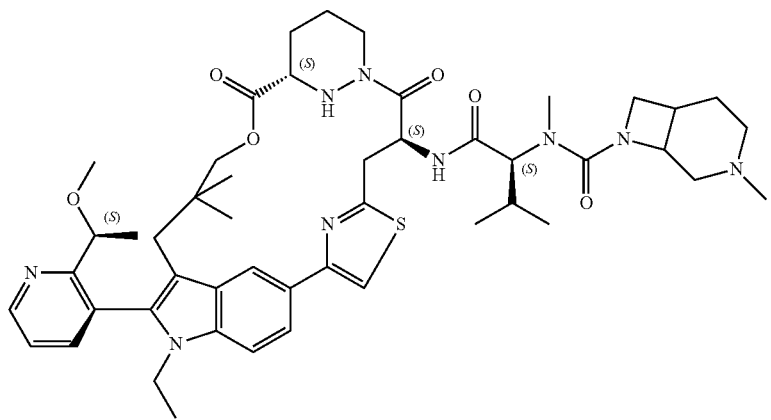 |
| A540 | 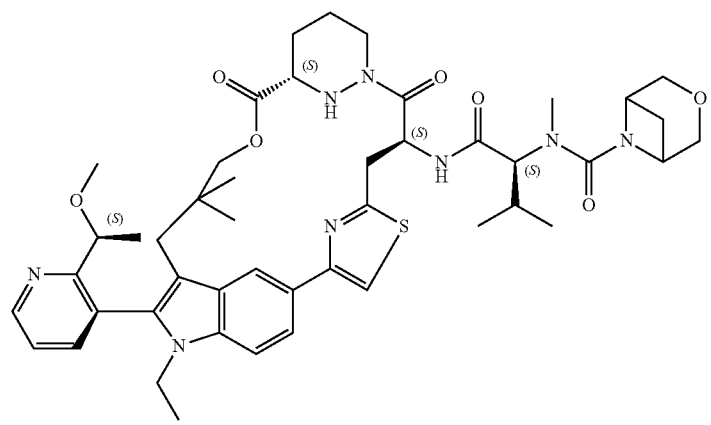 |

TABLE 1-continued

Certain Compounds of the Present Invention

| Ex# | Structure |
|---|---|
| A541 | 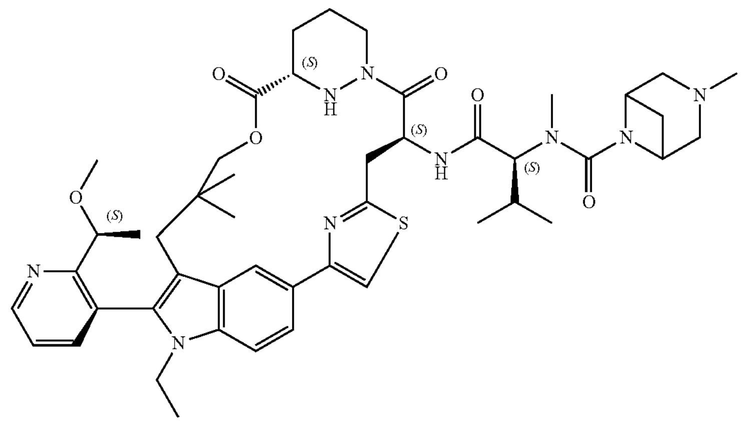 |
| A542 | 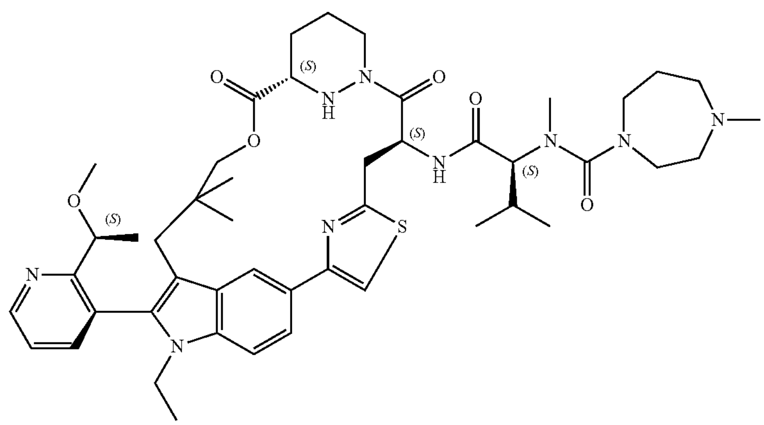 |
| A543 | 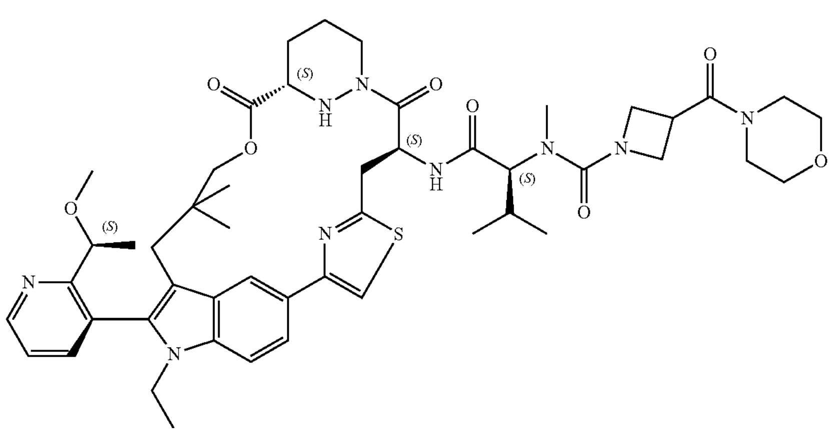 |

TABLE 1-continued

Certain Compounds of the Present Invention

| Ex# | Structure |
|---|---|
| A544 | 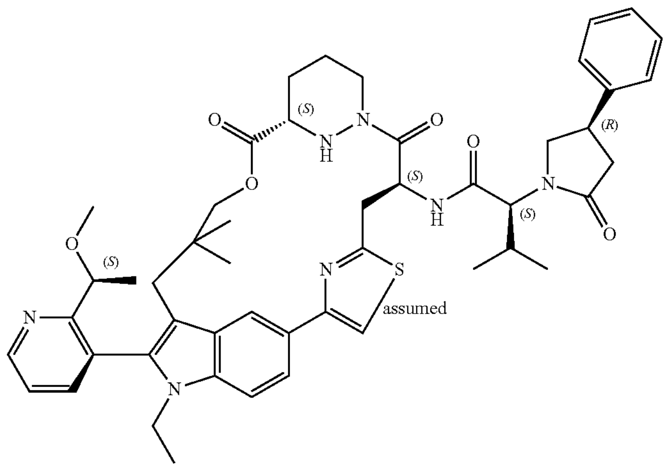 |
| A545 | 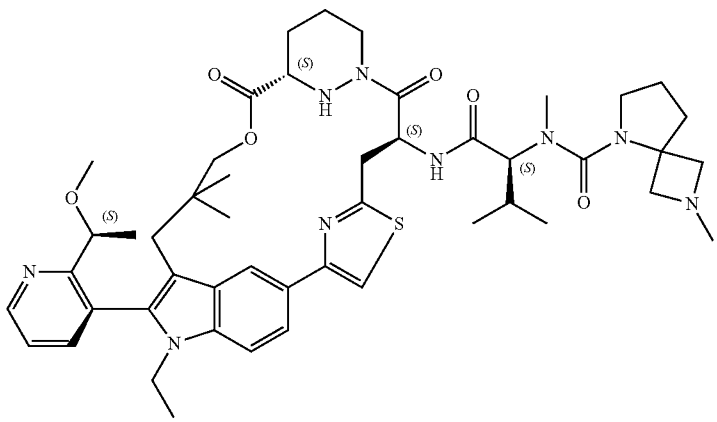 |
| A546 | 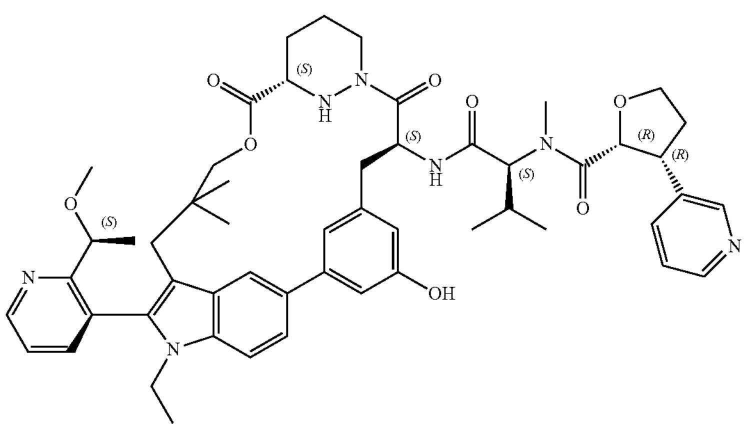 |

US 11,608,346 B2
TABLE 1-continued
Certain Compounds of the Present Invention
| Ex# | Structure |
|---|---|
| A547 | 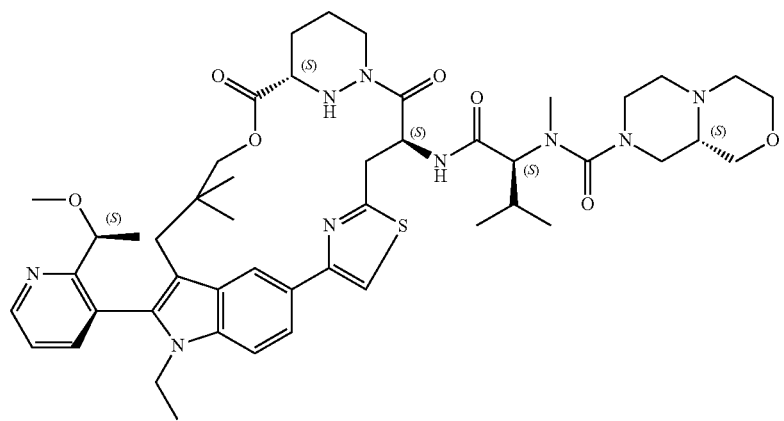 |
| A548 | 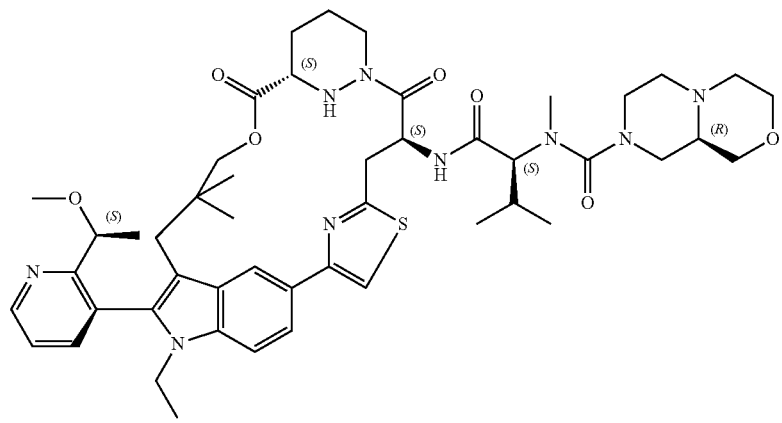 |
| A549 | 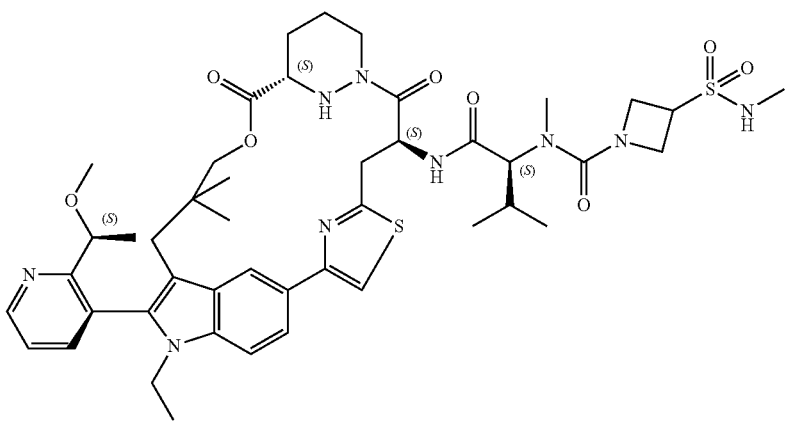 |

TABLE 1-continued
Certain Compounds of the Present Invention
| Ex# | Structure |
|---|---|
| A550 | 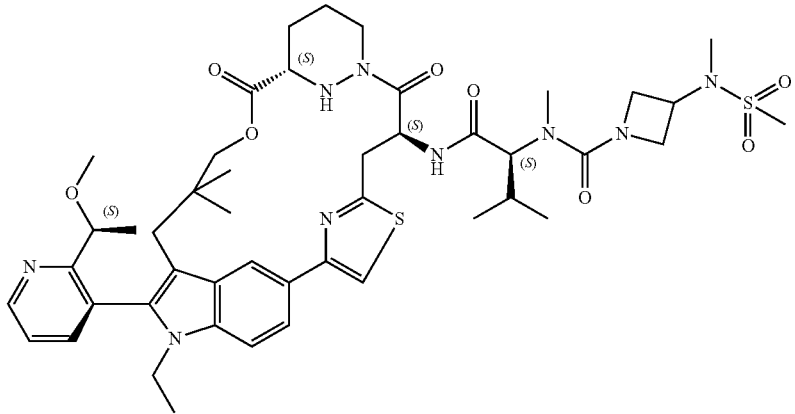 |
| A551 | 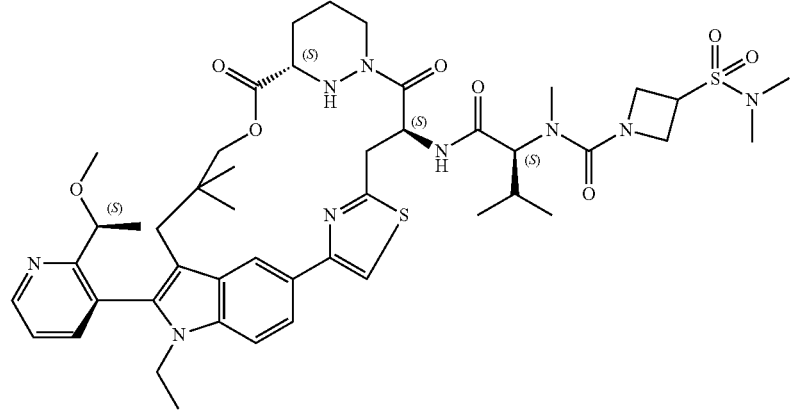 |
| A552 | 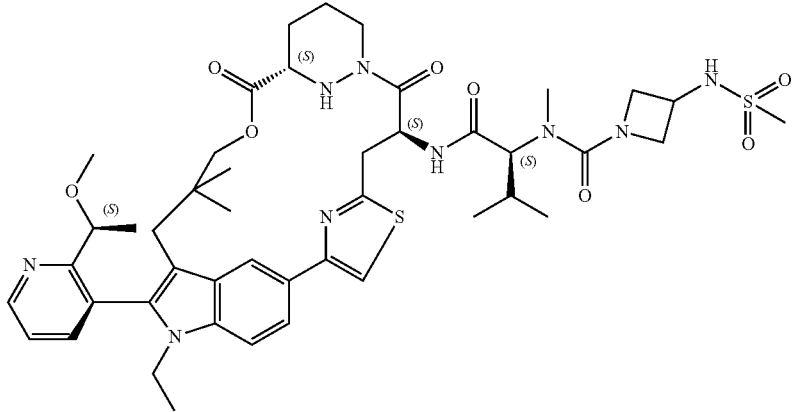 |

TABLE 1-continued
Certain Compounds of the Present Invention
| Ex# | Structure |
|---|---|
| A553 | 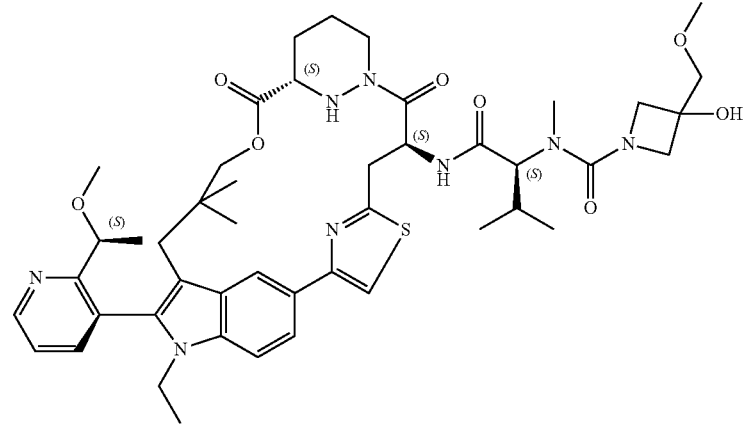 |
| A554 | 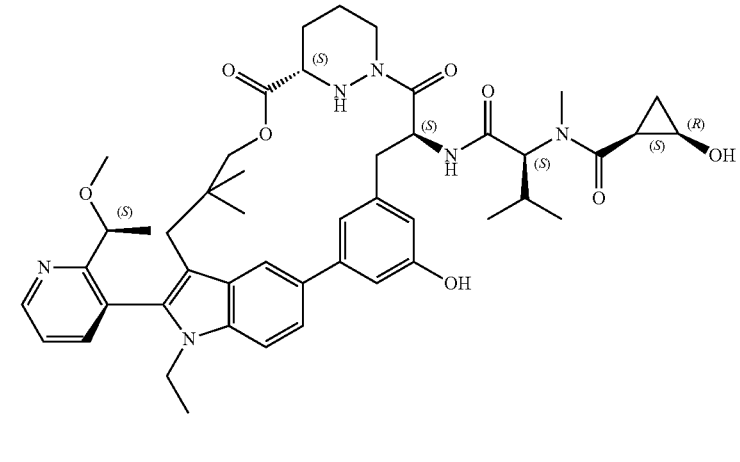 |
| A555 | 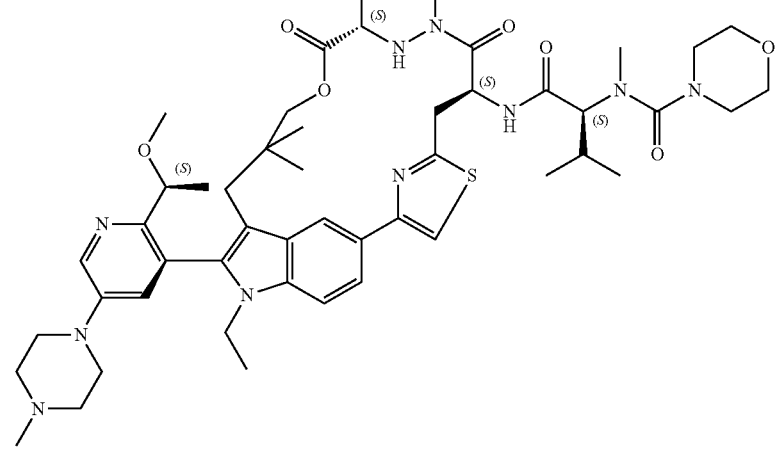 |

TABLE 1-continued
Certain Compounds of the Present Invention
| Ex# | Structure |
|---|---|
| A556 | 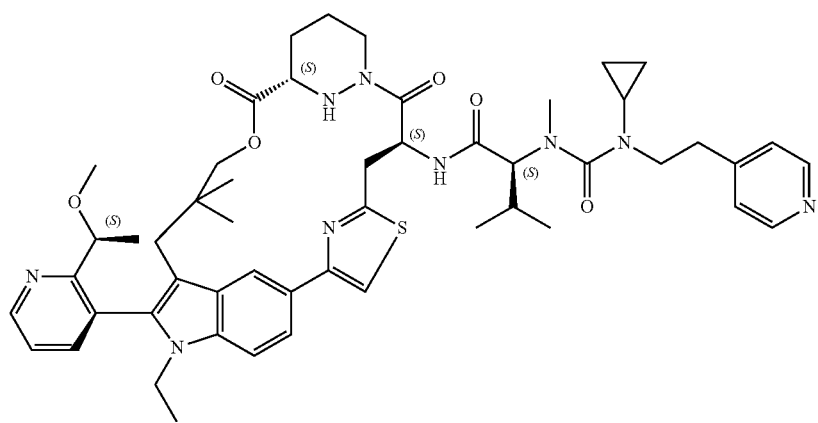 |
| A557 | 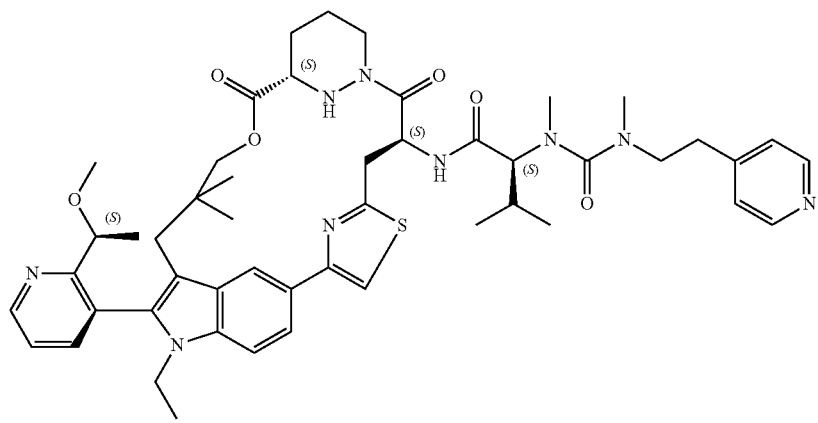 |
| A558 | 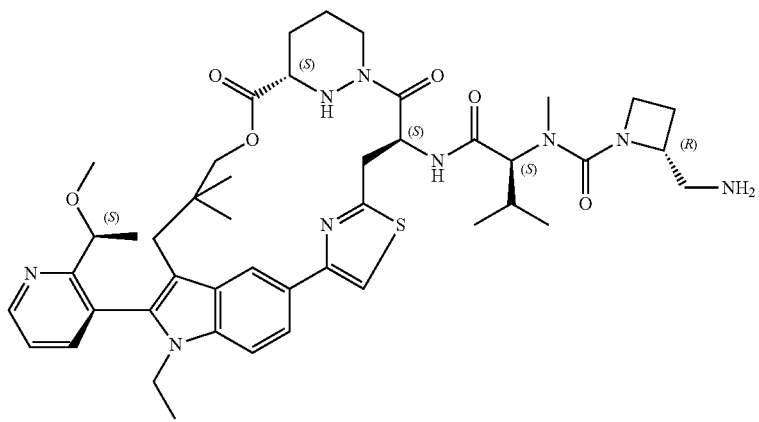 |

TABLE 1-continued

Certain Compounds of the Present Invention

| Ex# | Structure |
|---|---|
| A559 | 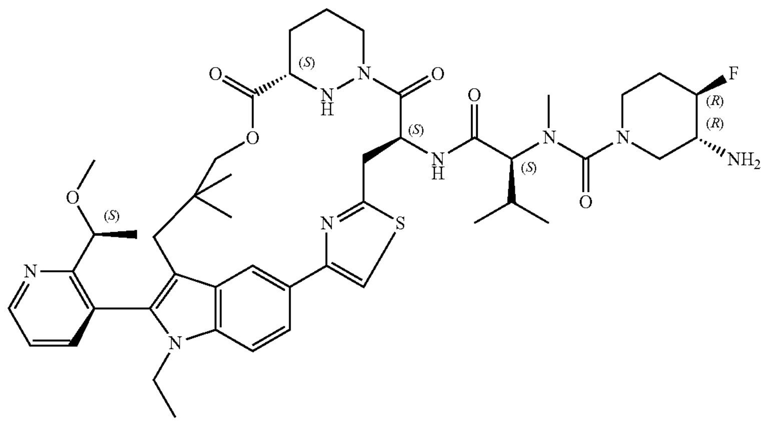 |
| A560 | 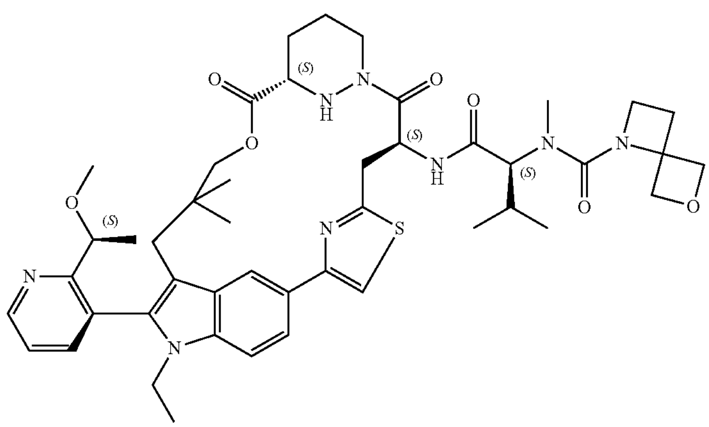 |
| A561 | 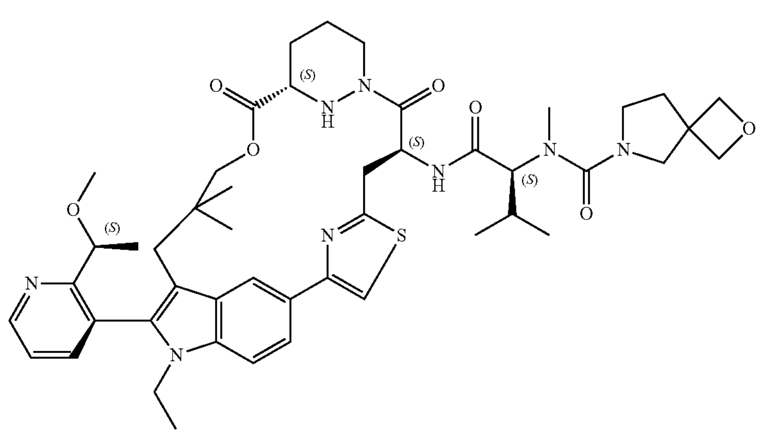 |

TABLE 1-continued

Certain Compounds of the Present Invention

| Ex# | Structure |
|---|---|
| A562 | 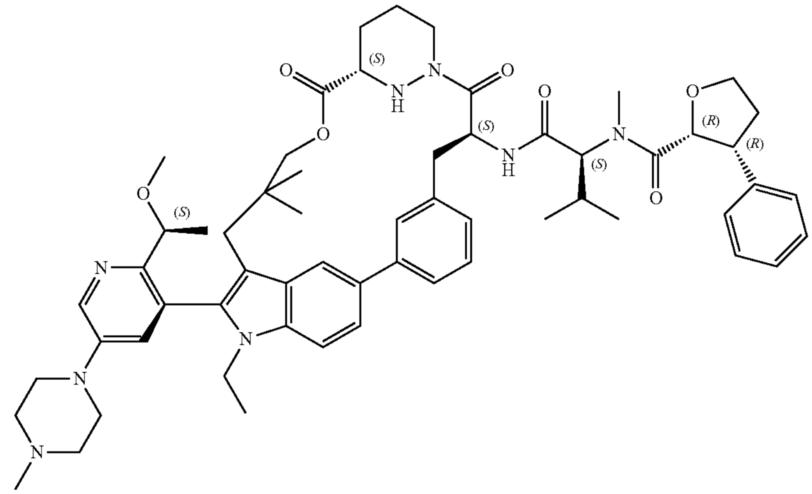 |
| A563 | 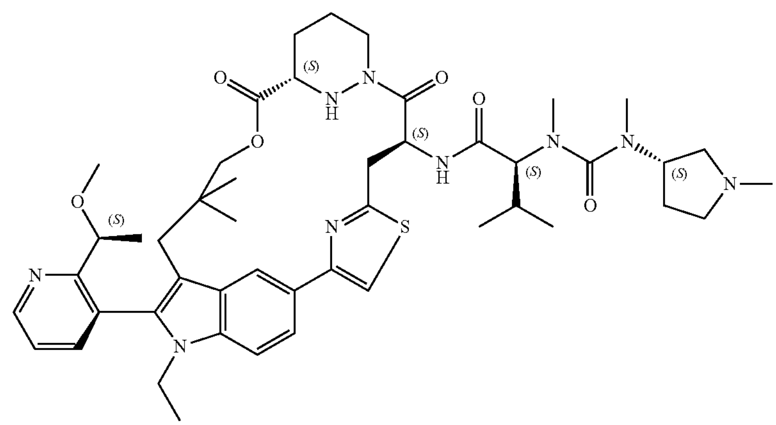 |
| A564 | 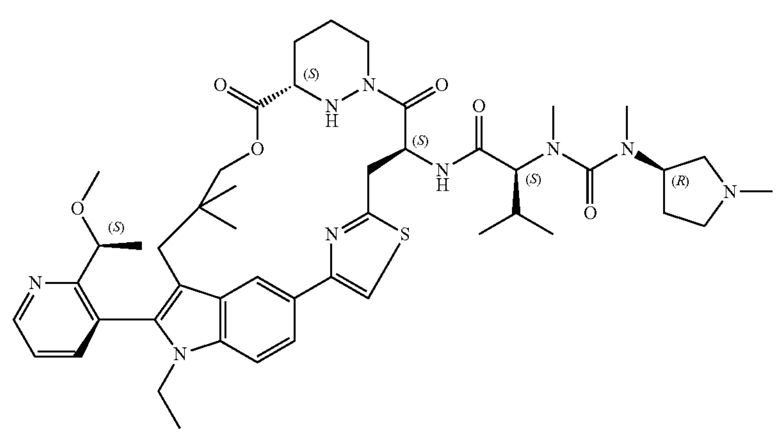 |

| Ex# | Structure |
|---|---|
| A565 | 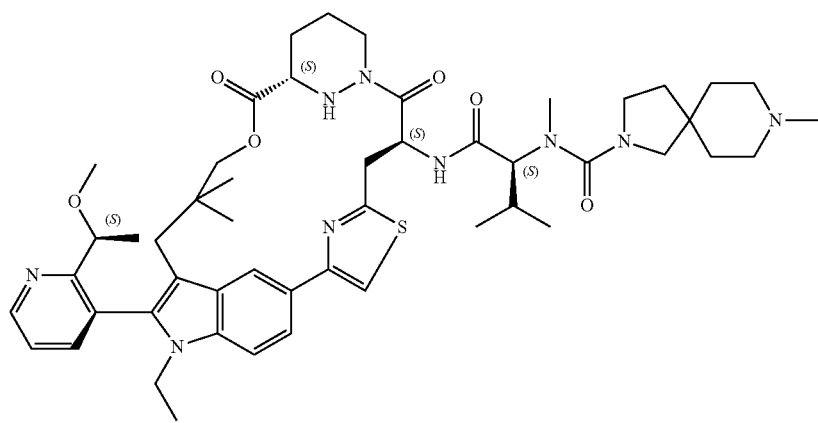 |
| A566 | 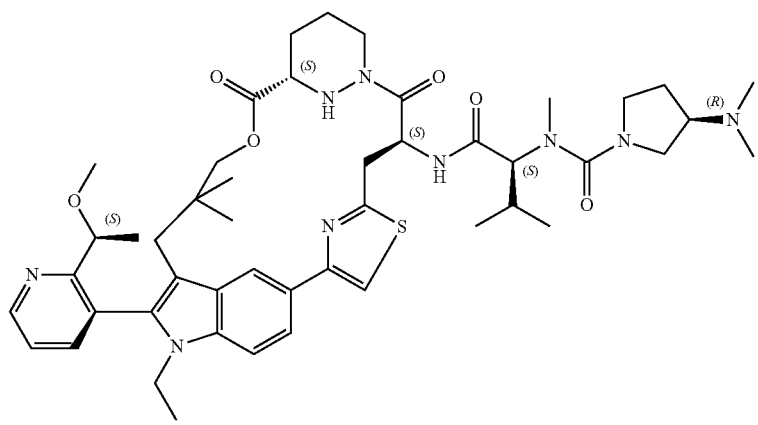 |
| A567 | 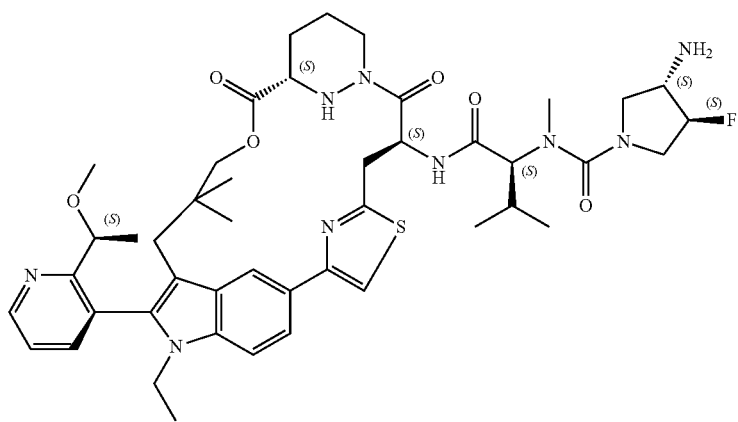 |

TABLE 1-continued
Certain Compounds of the Present Invention
| Ex# | Structure |
|---|---|
| A568 | 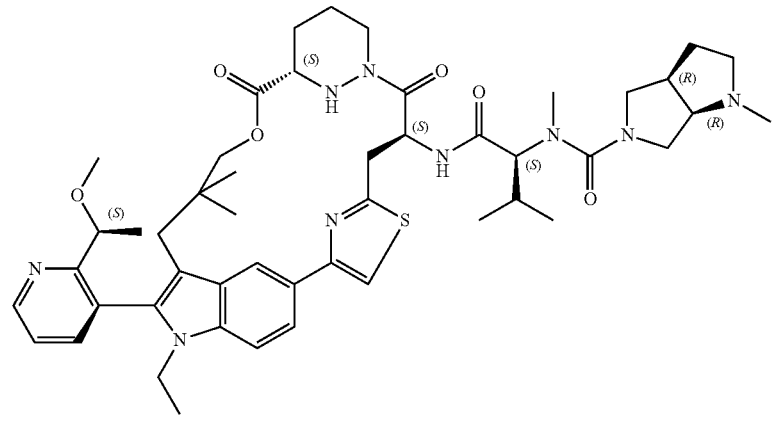 |
| A569 | 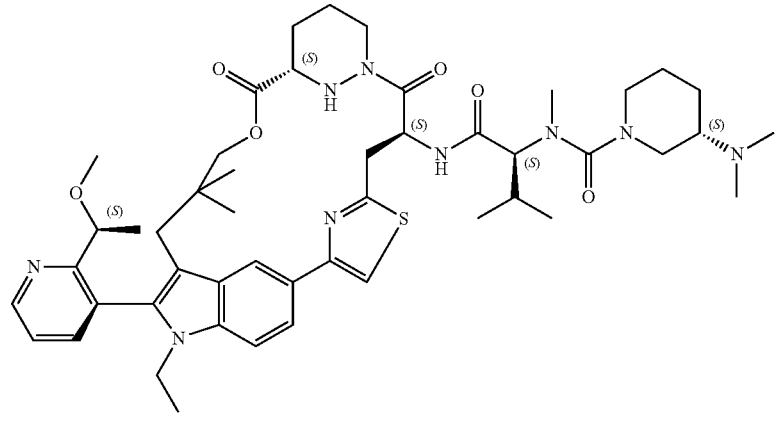 |
| A570 | 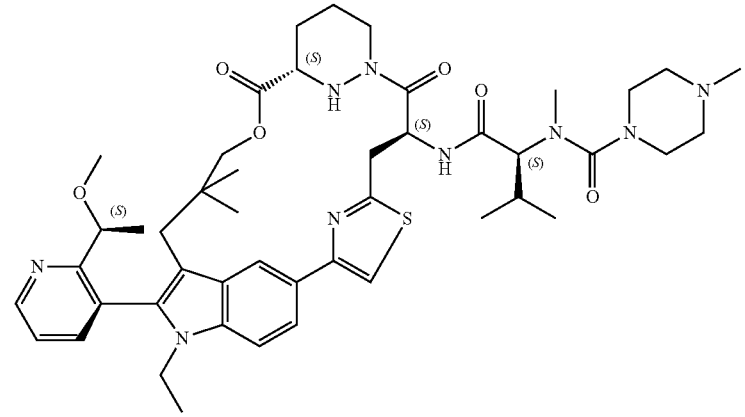 |

TABLE 1-continued
Certain Compounds of the Present Invention
| Ex# | Structure |
|---|---|
| A571 | 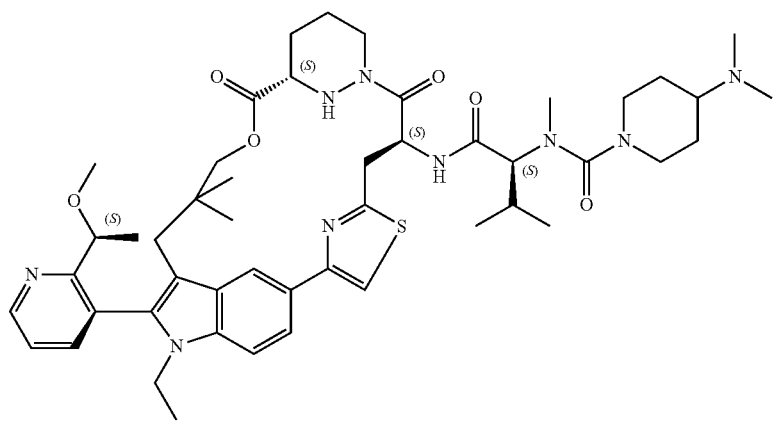 |
| A572 | 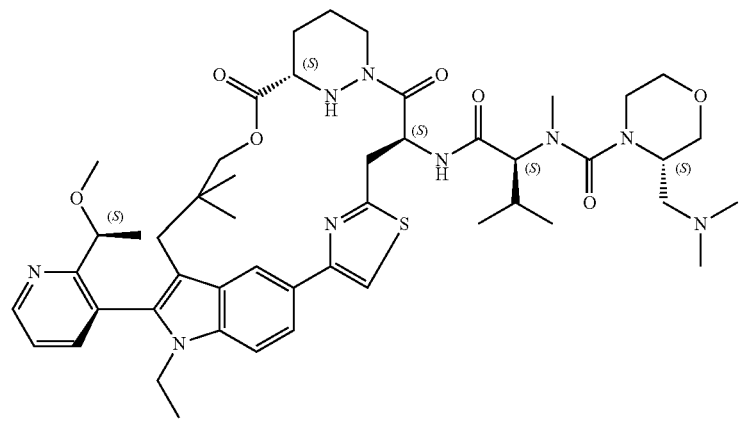 |
| A573 | 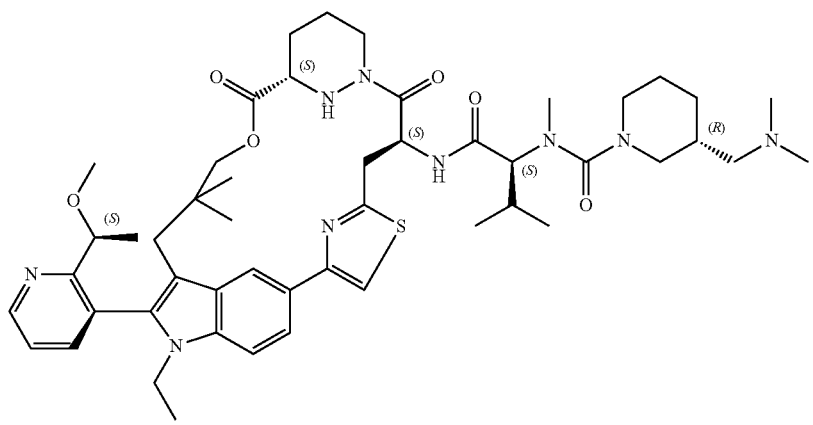 |

US 11,608,346 B2
435                                                                                                              436
TABLE 1-continued
Certain Compounds of the Present Invention
| Ex# | Structure |
|---|---|
| A574 | 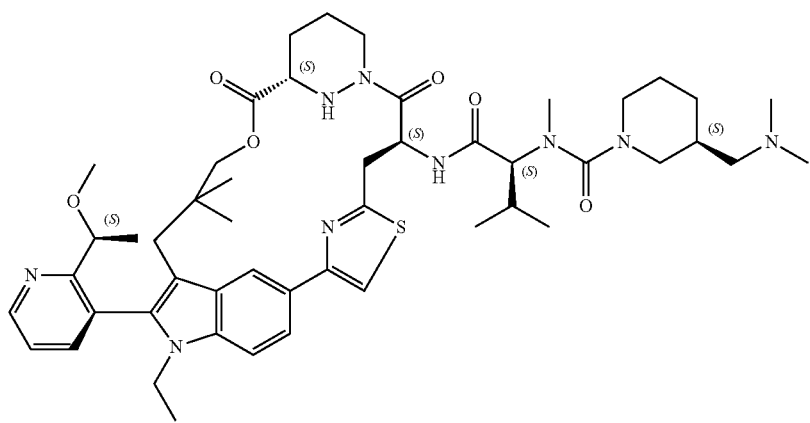 |
| A575 | 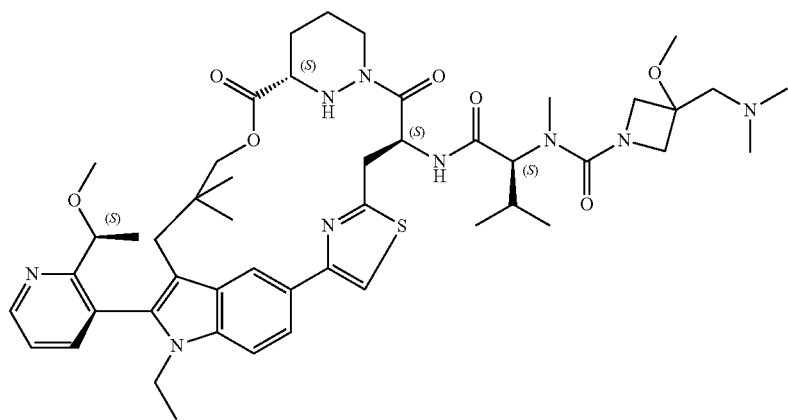 |
| A576 | 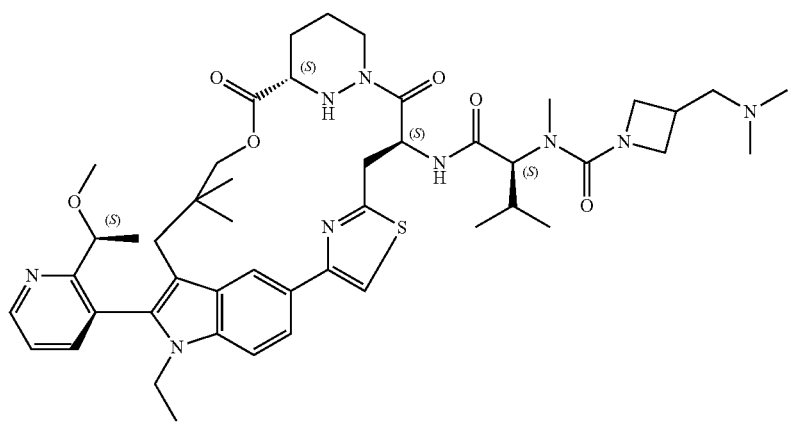 |

TABLE 1-continued

Certain Compounds of the Present Invention

| Ex# | Structure |
|---|---|
| A577 | 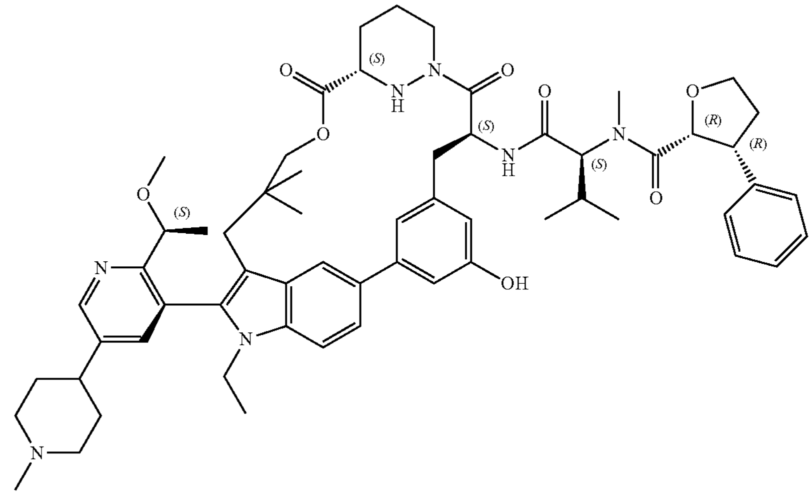 |
| A578 | 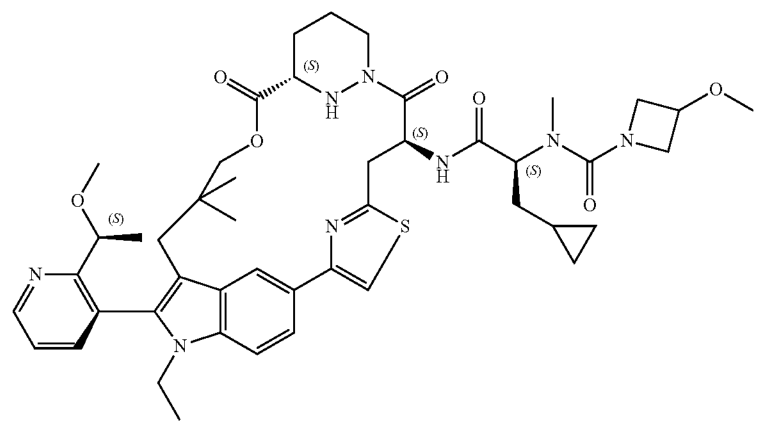 |
| A579 | 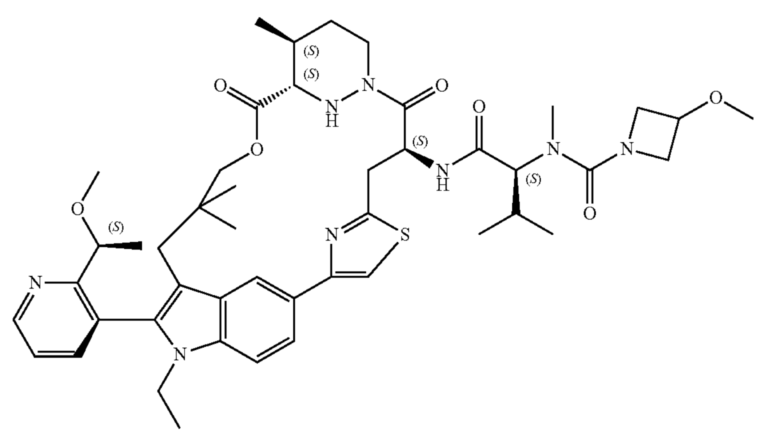 |

TABLE 1-continued
Certain Compounds of the Present Invention
| Ex# | Structure |
|---|---|
| A580 | 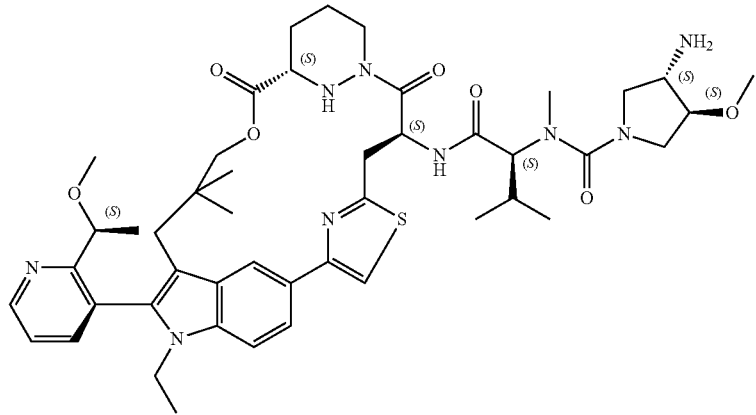 |
| A581 | 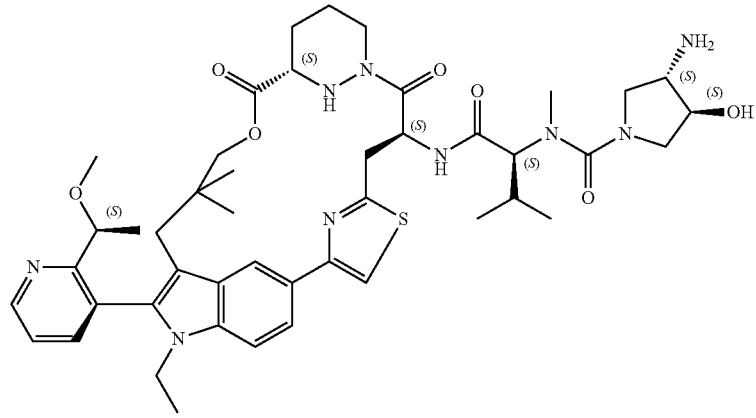 |
| A582 | 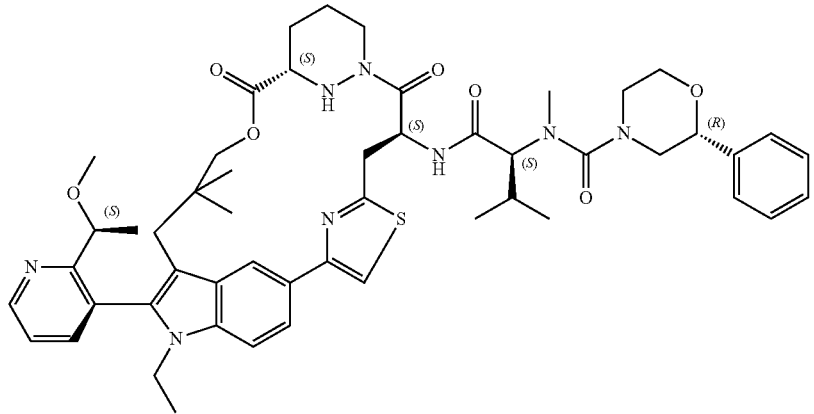 |

TABLE 1-continued

Certain Compounds of the Present Invention

| Ex# | Structure |
|---|---|
| A583 | 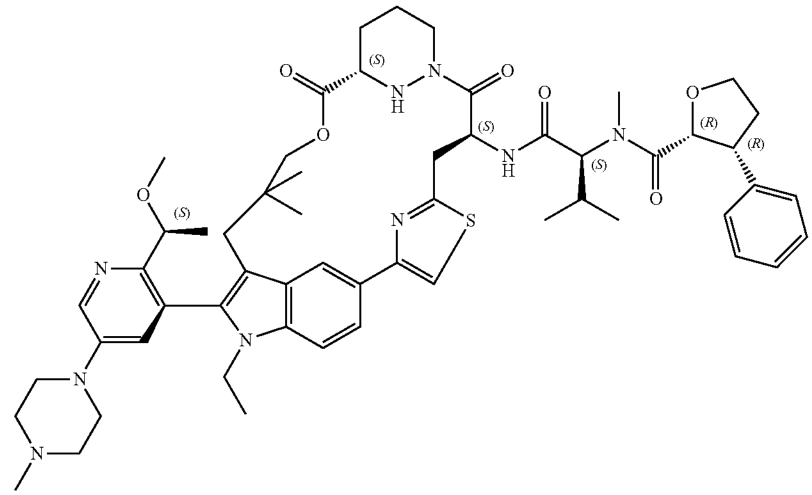 |
| A584 | 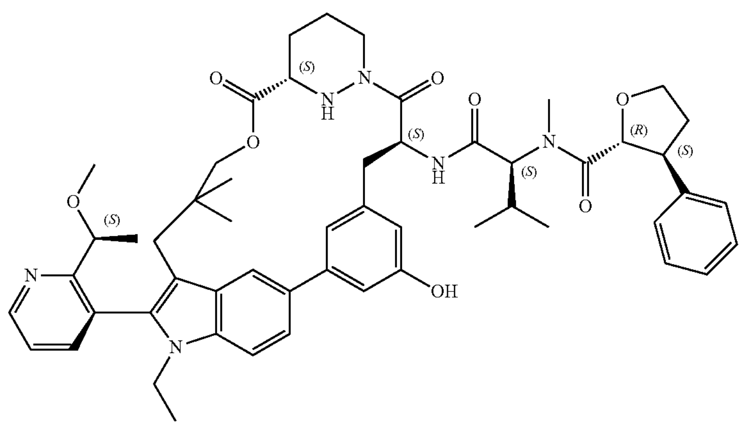 |
| A585 | 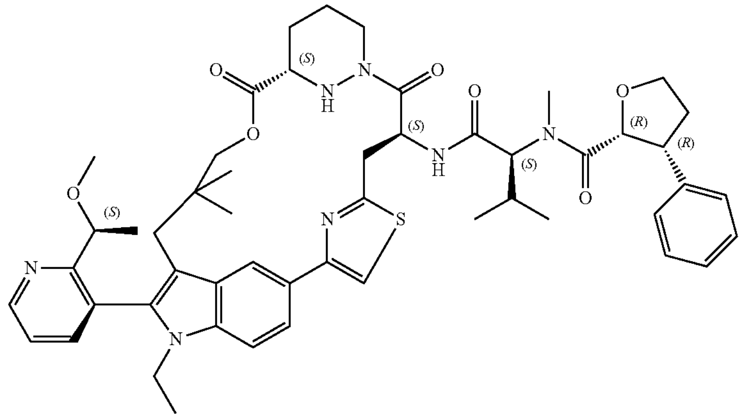 |

US 11,608,346 B2
TABLE 1-continued
Certain Compounds of the Present Invention
| Ex# | Structure |
|---|---|
| A586 | 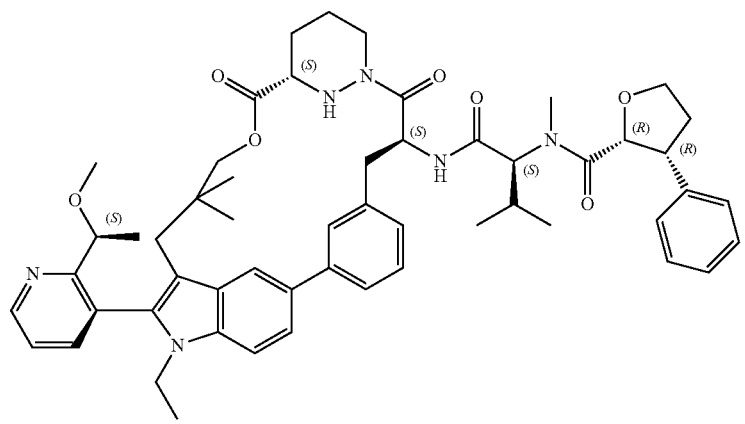 |
| A587 | 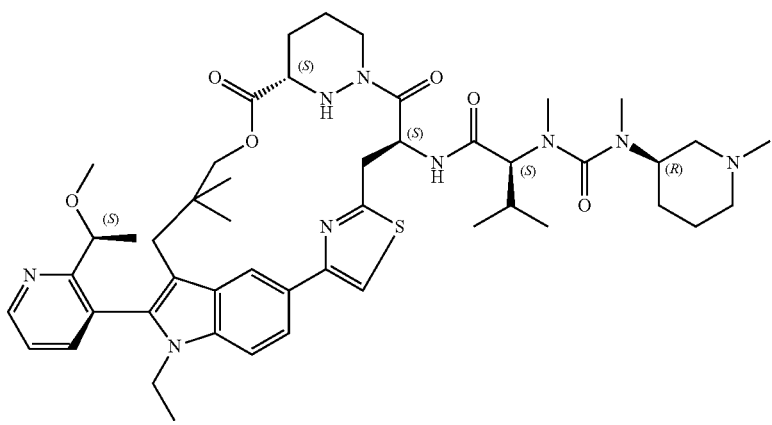 |
| A588 | 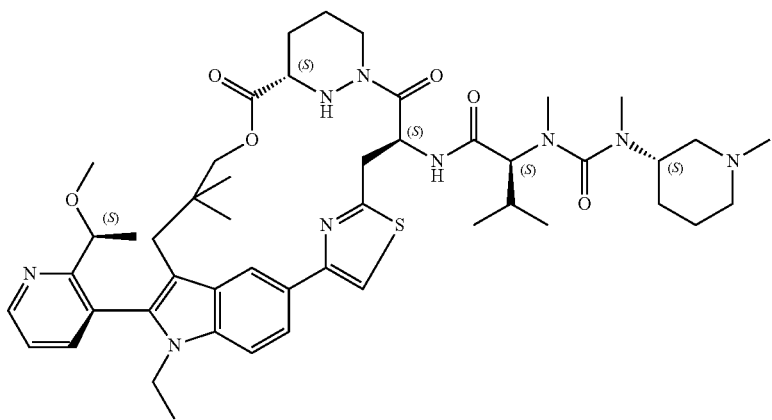 |

TABLE 1-continued
Certain Compounds of the Present Invention
| Ex# | Structure |
|---|---|
| A589 | 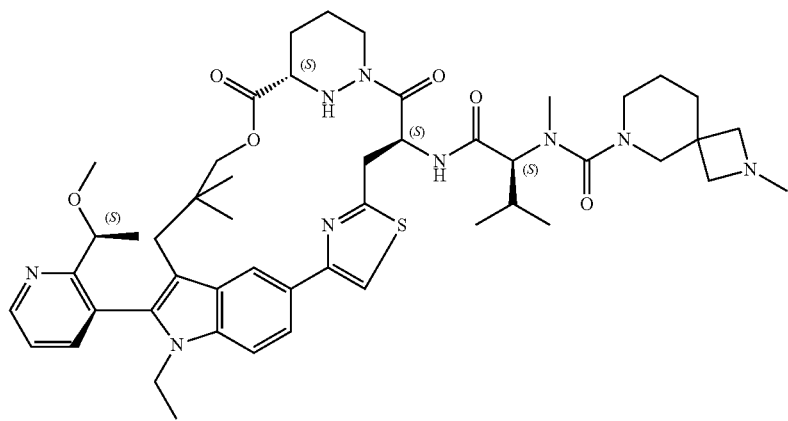 |
| A590 | 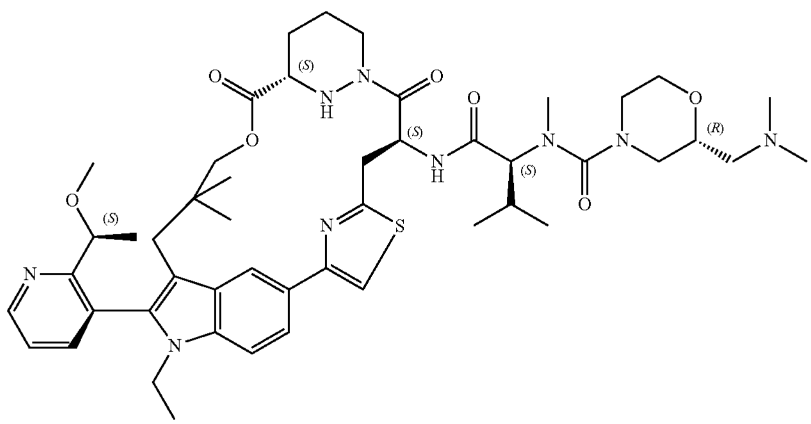 |
| A591 | 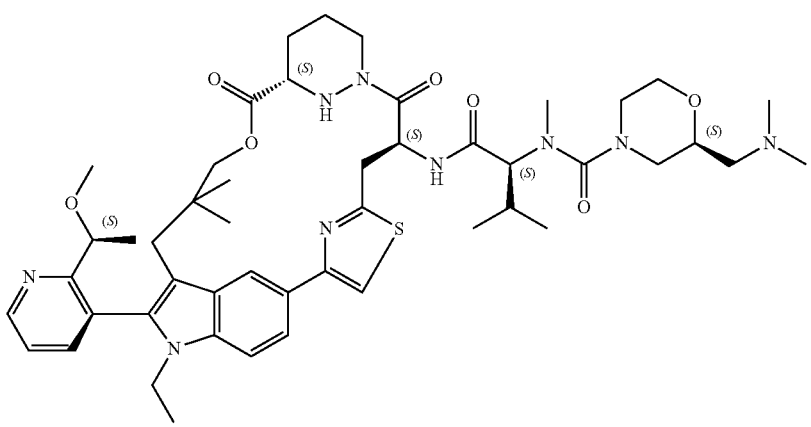 |

TABLE 1-continued
Certain Compounds of the Present Invention
| Ex# | Structure |
|---|---|
| A592 | 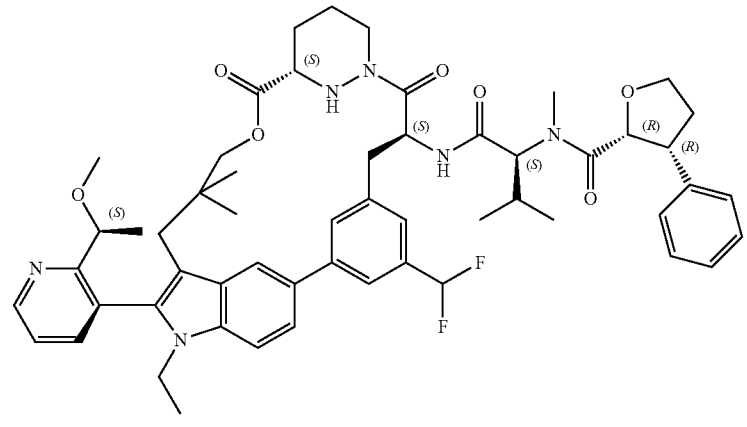 |
| A593 | 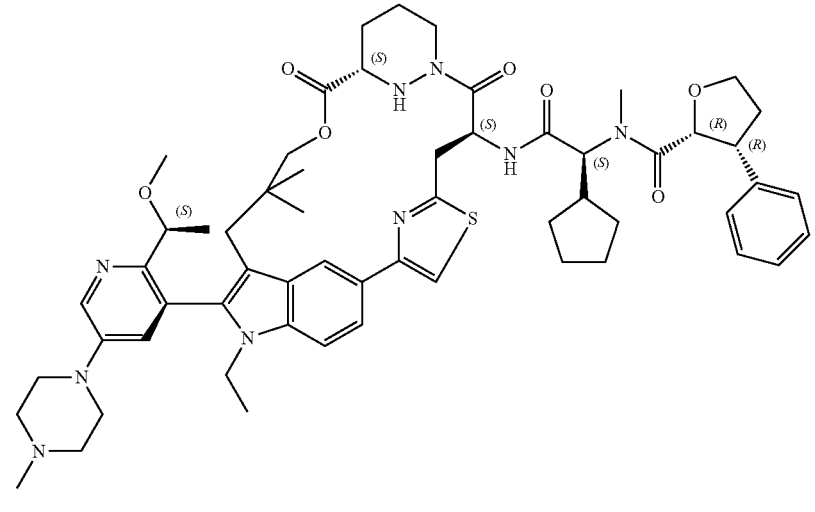 |
| A594 | 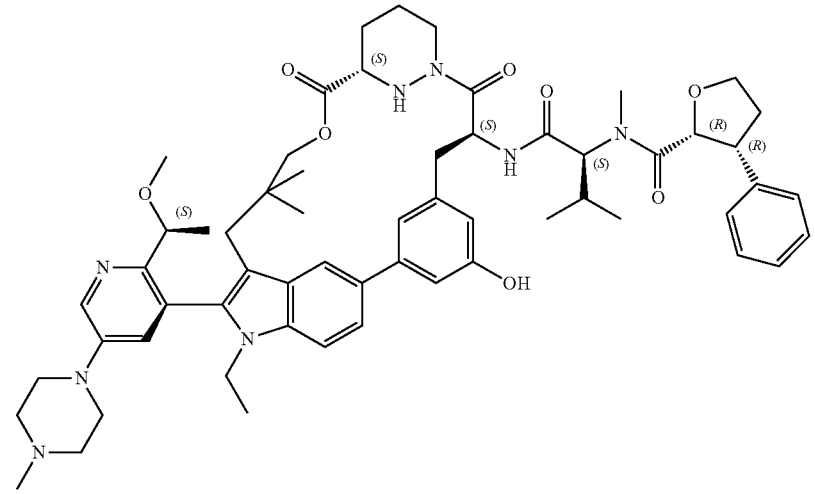 |

TABLE 1-continued

Certain Compounds of the Present Invention

| Ex# | Structure |
|---|---|
| A595 | 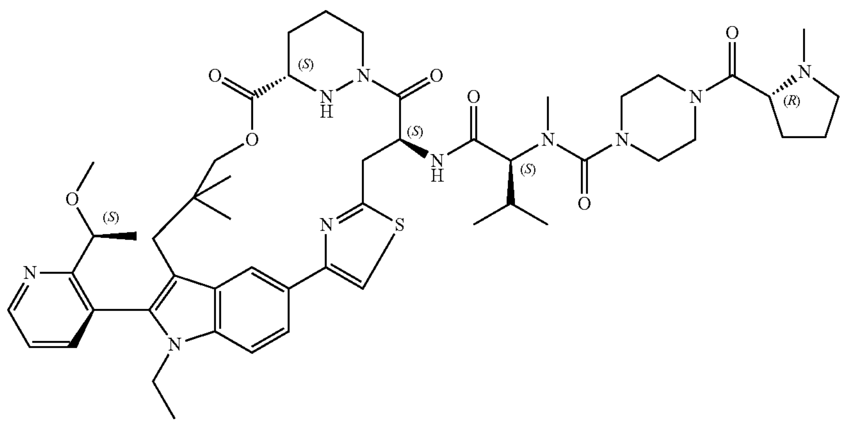 |
| A596 | 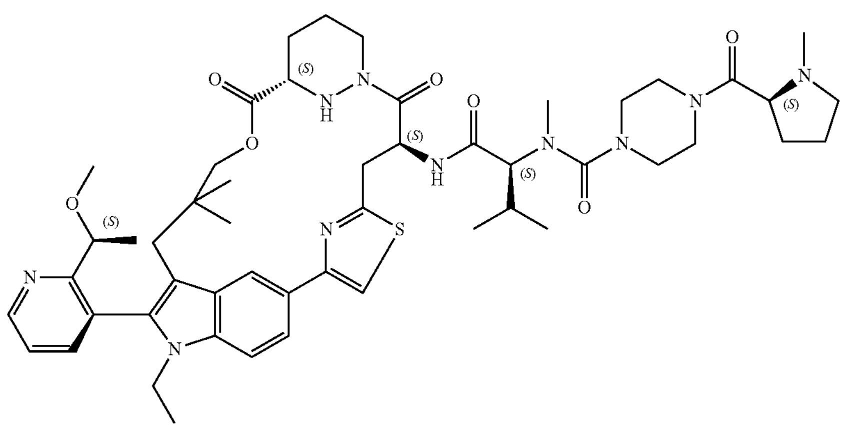 |
| A597 | 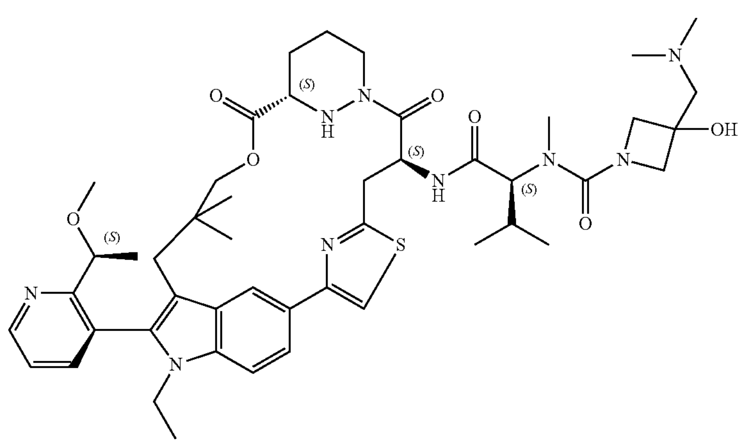 |

TABLE 1-continued
Certain Compounds of the Present Invention
| Ex# | Structure |
|---|---|
| A598 | 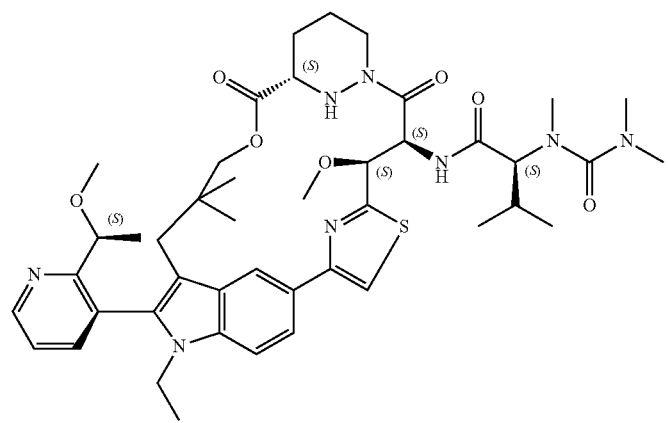 |
| A599 | 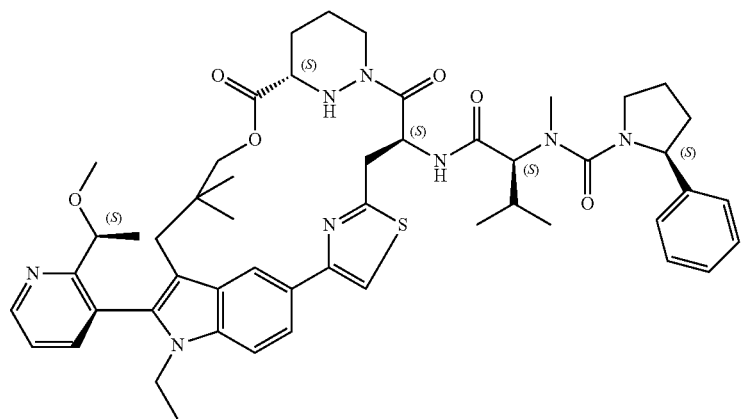 |
| A600 | 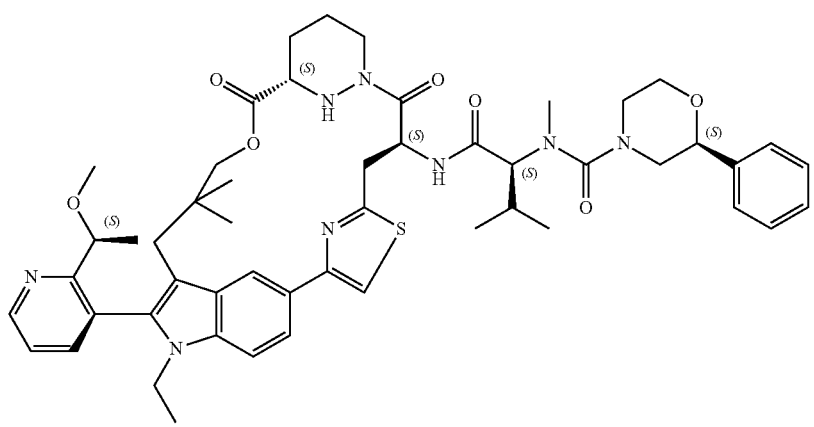 |

TABLE 1-continued
Certain Compounds of the Present Invention
| Ex# | Structure |
|---|---|
| A601 | 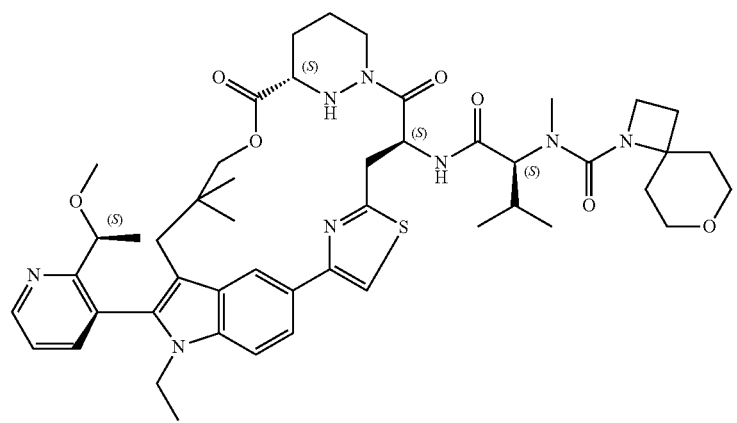 |
| A602 | 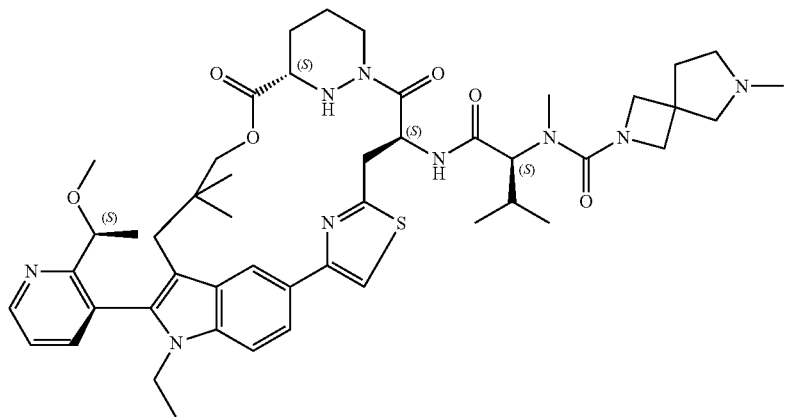 |
| A603 | 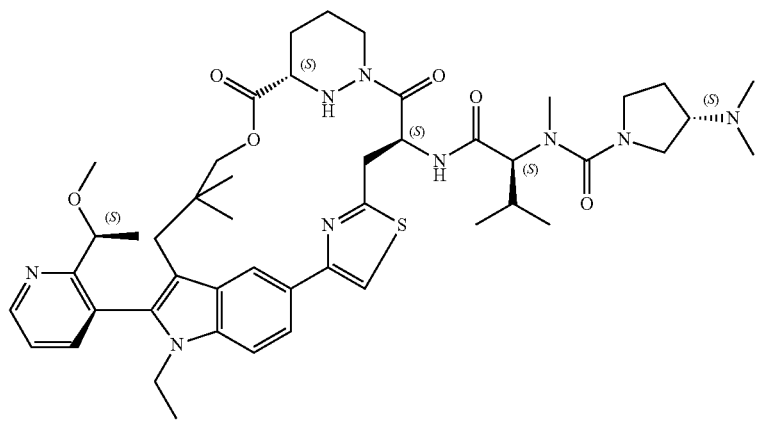 |

TABLE 1-continued
Certain Compounds of the Present Invention
| Ex# | Structure |
|---|---|
| A604 | 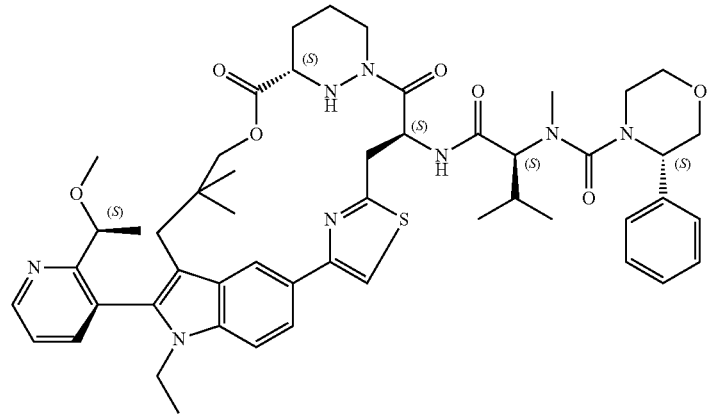 |
| A605 | 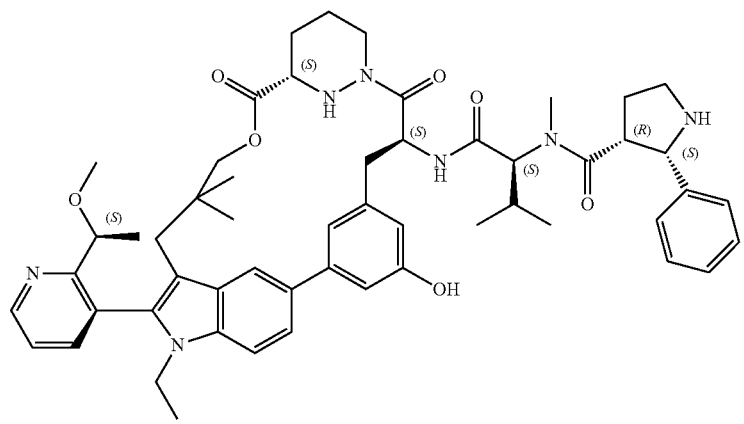 |
| A606 | 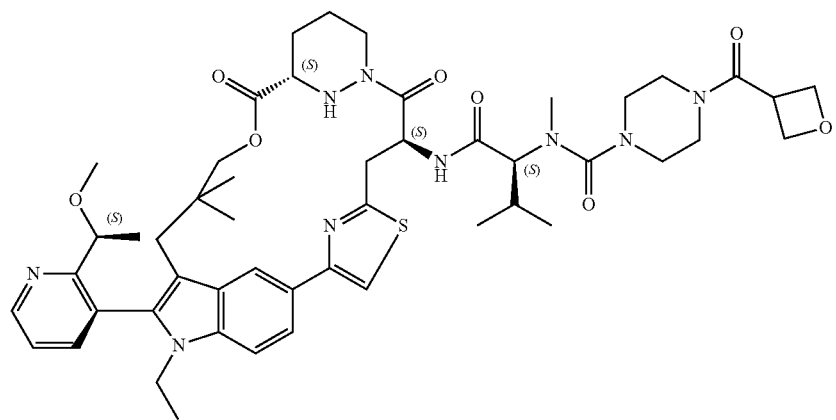 |

TABLE 1-continued
Certain Compounds of the Present Invention
| Ex# | Structure |
|---|---|
| A607 | 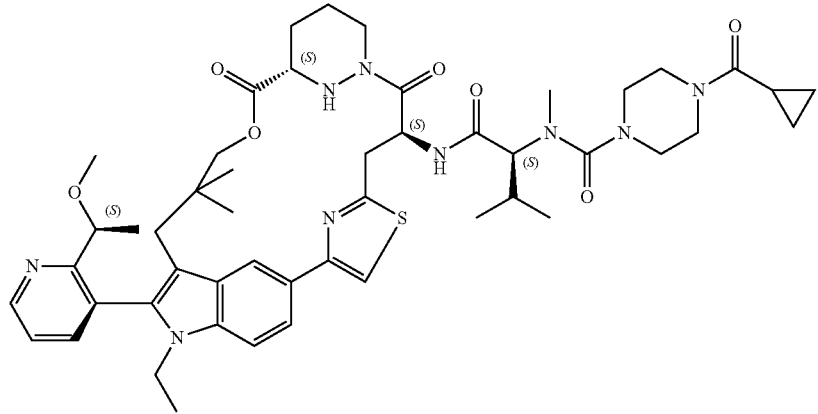 |
| A608 | 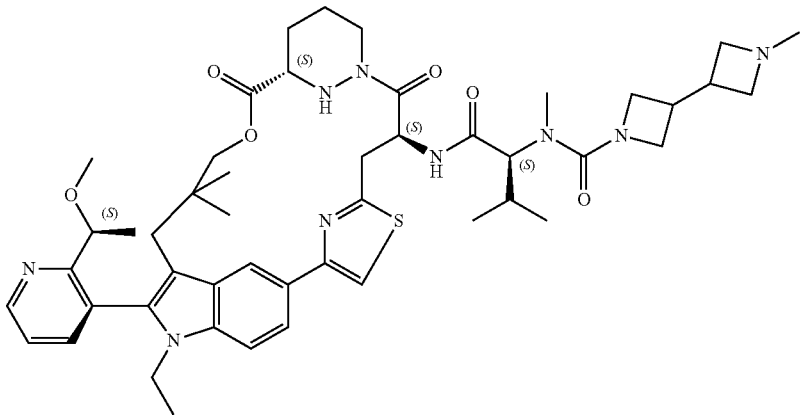 |
| A609 | 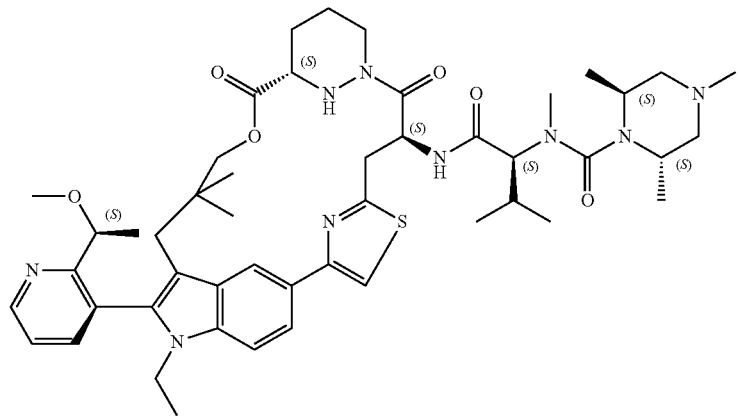 |

TABLE 1-continued
Certain Compounds of the Present Invention
| Ex# | Structure |
|---|---|
| A610 | 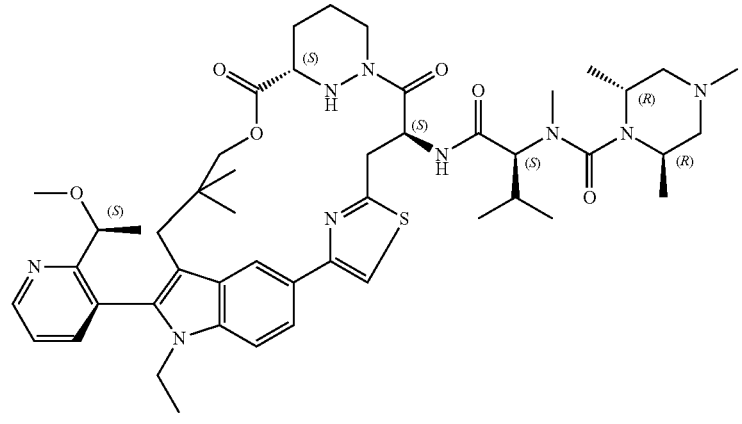 |
| A611 | 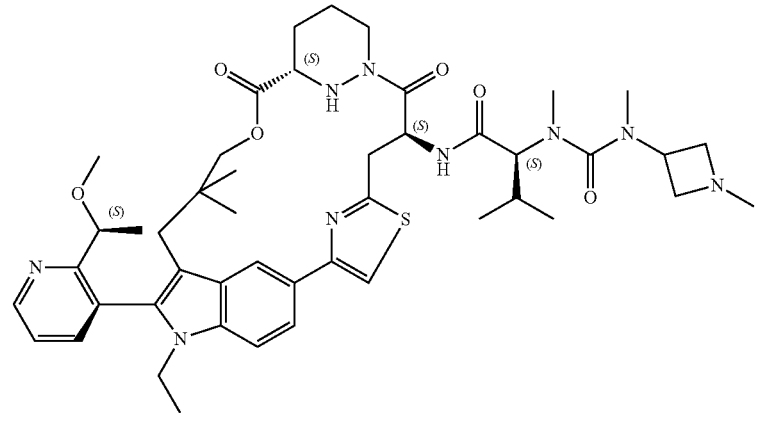 |
| A612 | 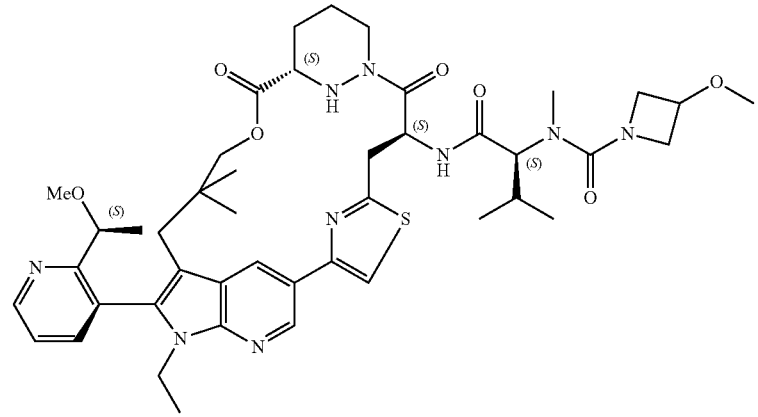 |

TABLE 1-continued
Certain Compounds of the Present Invention
| Ex# | Structure |
|---|---|
| A613 | 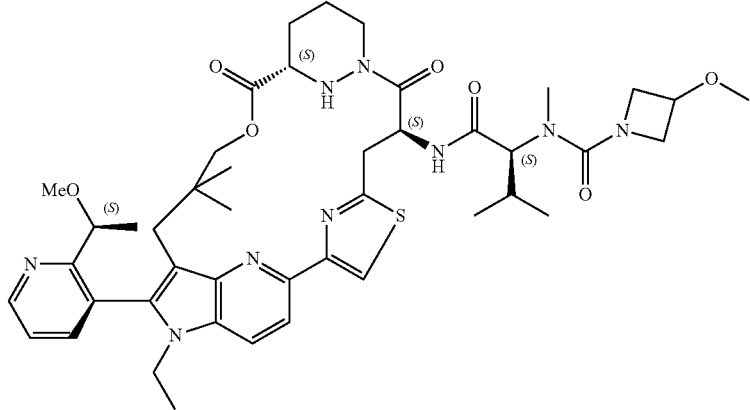 |
| A614 | 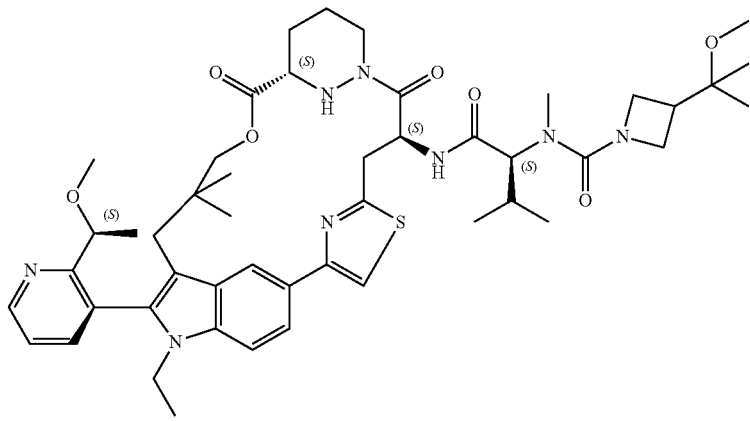 |
| A615 | 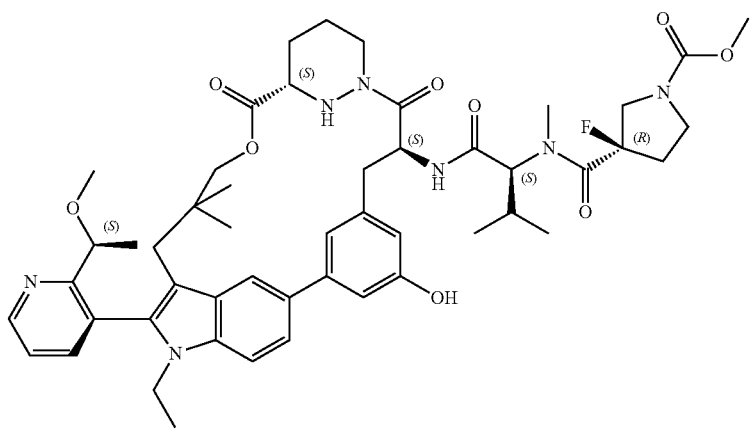 |

TABLE 1-continued

Certain Compounds of the Present Invention

| Ex# | Structure |
|---|---|
| A616 | 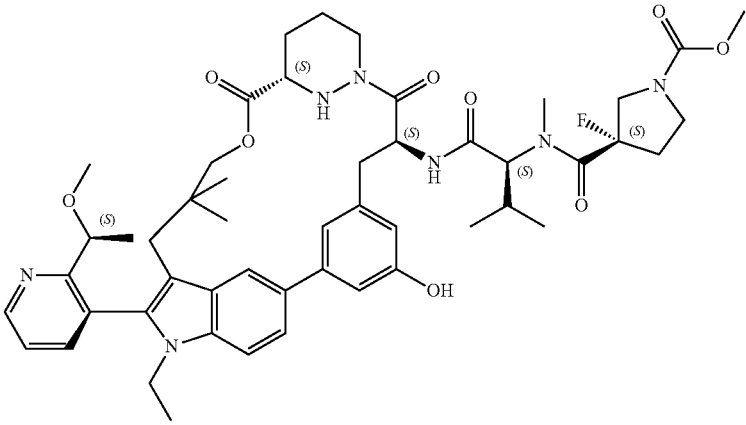 |

Note that some compounds are shown with bonds as flat or wedged. In some instances, the relative stereochemistry of stereoisomers has been determined; in some instances, the absolute stereochemistry has been determined. In some instances, a single Example number corresponds to a mixture of stereoisomers. All stereoisomers of the compounds of the foregoing table are contemplated by the present invention. In particular embodiments, an atropisomer of a compound of the foregoing table is contemplated.
Any compound shown in brackets indicates that the compound is a disastereomer, and the absolute stereochemistry of such diastereomer may not be known.

In some embodiments, a compound of Table 2 is provided, or a pharmaceutically acceptable salt thereof. In some embodiments, a compound of the present invention is selected from Table 2, or a pharmaceutically acceptable salt or atropisomer thereof.

TABLE 2

Certain Compounds of the Present Invention

| Ex# | Structure |
|---|---|
| B4 | 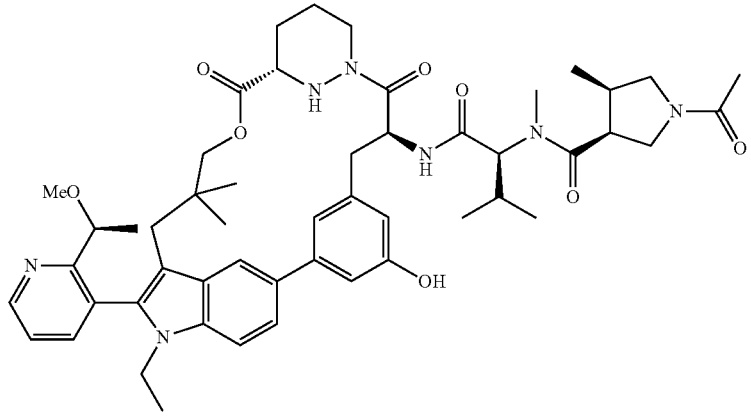 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@@H]1CN(C(C)=O)C[C@@H]1C)C(=O)N1CCC[C@H](N1)C(=O)OCC(C)(C)C2] |

TABLE 2-continued
Certain Compounds of the Present Invention
| Ex# | Structure |
|---|---|
| B5 | 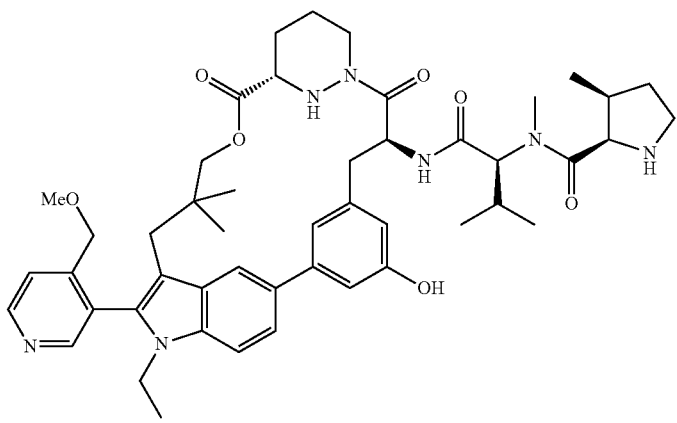 [SMILES: CCn1c(-c2cnccc2COC)c2c3cc(ccc31)-c1cc(O)cc(c1)C[C@H](NC(=O)[C@H](C(C)C)N(C)C(=O)[C@@H]1NCC[C@@H]1C)C(=O)N1CCC[C@H](N1)C(=O)OCC(C)(C)C2] |
| B6 | 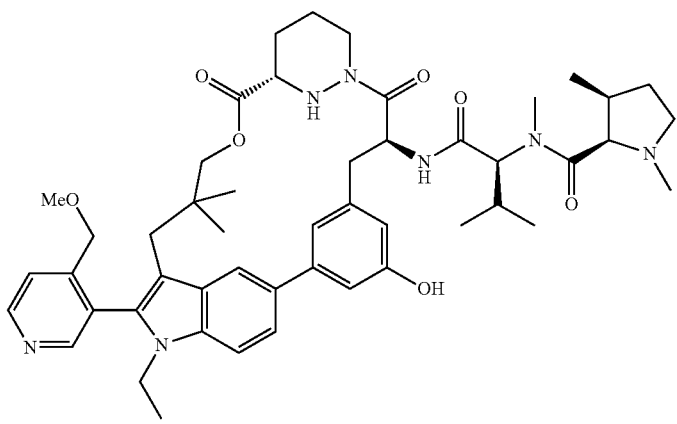 [SMILES: CCn1c(-c2cnccc2COC)c2c3cc(ccc31)-c1cc(O)cc(c1)C[C@H](NC(=O)[C@H](C(C)C)N(C)C(=O)[C@H]1[C@@H](C)CCN1C)C(=O)N1CCC[C@H](N1)C(=O)OCC(C)(C)C2] |
| B8 | 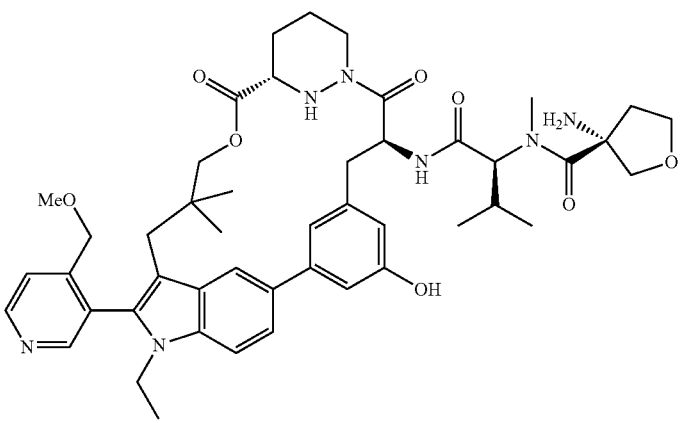 [SMILES: CCn1c(-c2cnccc2COC)c2c3cc(ccc31)-c1cc(O)cc(c1)C[C@H](NC(=O)[C@H](C(C)C)N(C)C(=O)[C@@]1(N)CCOC1)C(=O)N1CCC[C@H](N1)C(=O)OCC(C)(C)C2] |

TABLE 2-continued
Certain Compounds of the Present Invention
| Ex# | Structure |
|---|---|
| B9 | 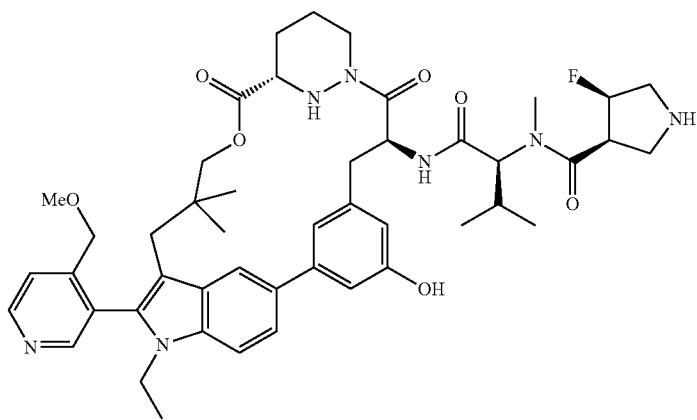 [SMILES: CCn1c(-c2cnccc2COC)c2c3cc(ccc31)-c1cc(O)cc(c1)C[C@H](NC(=O)[C@H](C(C)C)N(C)C(=O)[C@@H]1CNC[C@@H]1F)C(=O)N1CCC[C@H](N1)C(=O)OCC(C)(C)C2] |
| B12 | 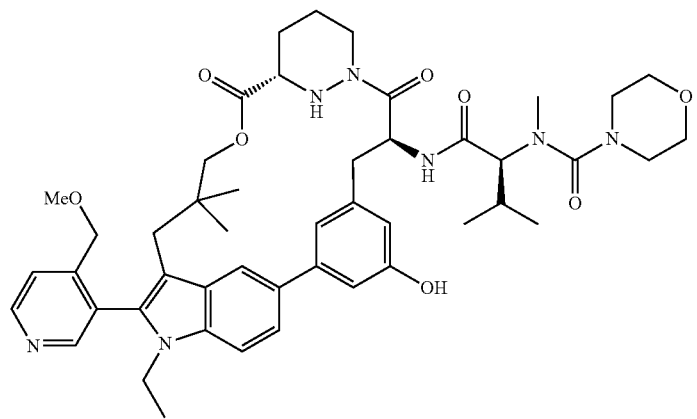 [SMILES: CCn1c(-c2cnccc2COC)c2c3cc(ccc31)-c1cc(O)cc(c1)C[C@H](NC(=O)[C@H](C(C)C)N(C)C(=O)N1CCOCC1)C(=O)N1CCC[C@H](N1)C(=O)OCC(C)(C)C2] |
| B13 | 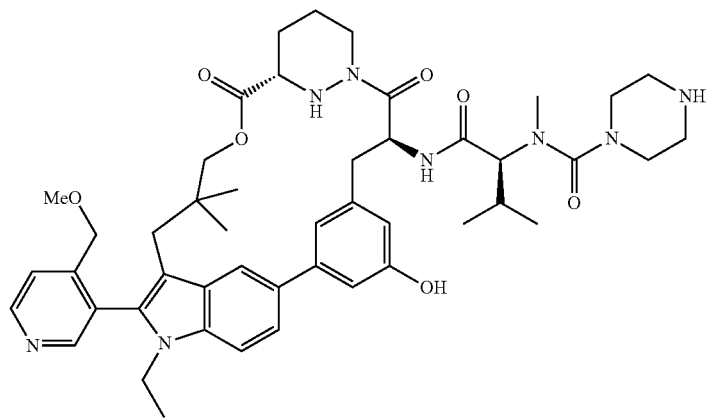 [SMILES: CCn1c(-c2cnccc2COC)c2c3cc(ccc31)-c1cc(O)cc(c1)C[C@H](NC(=O)[C@H](C(C)C)N(C)C(=O)N1CCNCC1)C(=O)N1CCC[C@H](N1)C(=O)OCC(C)(C)C2] |

TABLE 2-continued
Certain Compounds of the Present Invention
| Ex# | Structure |
|---|---|
| B19 | 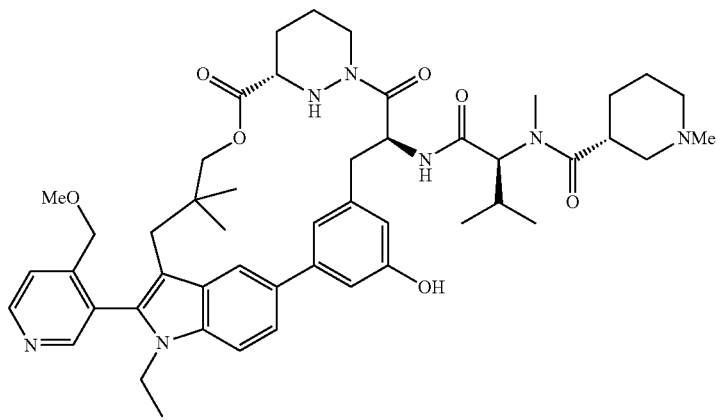 [SMILES: CCn1c(-c2cnccc2COC)c2c3cc(ccc31)-c1cc(O)cc(c1)C[C@H](NC(=O)[C@H](C(C)C)N(C)C(=O)[C@@H]1CCCN(C)C1)C(=O)N1CCC[C@H](N1)C(=O)OCC(C)(C)C2] |
| B44 | 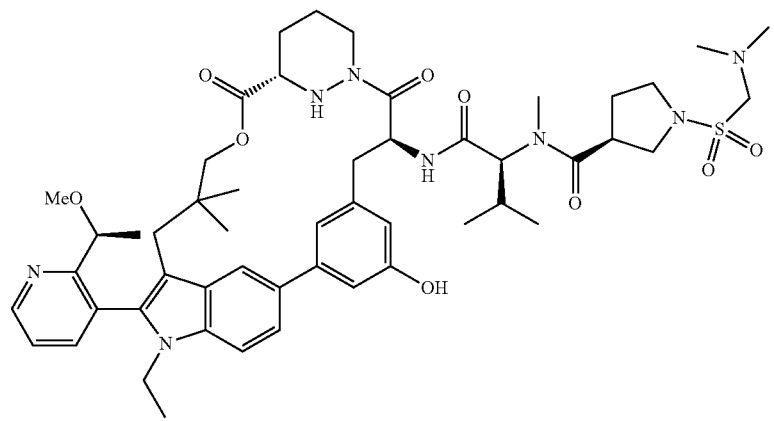 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@H]1CCN(S(=O)(=O)CN(C)C)C1)C(=O)N1CCC[C@H](N1)C(=O)OCC(C)(C)C2] |
| B47 | 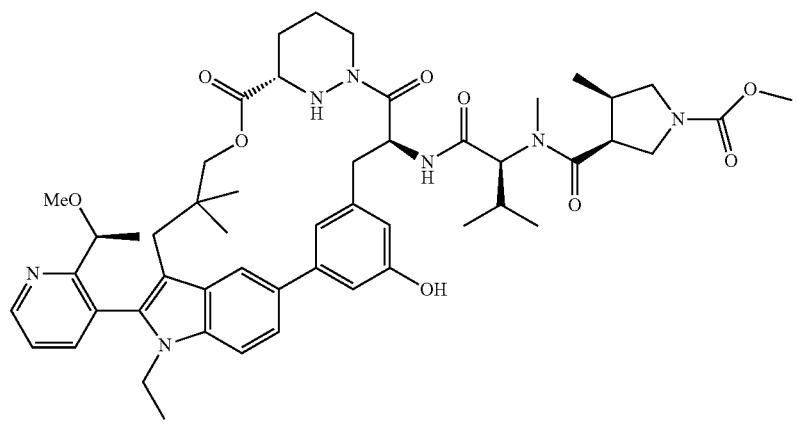 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@@H]1CN(C(=O)OC)C[C@@H]1C)C(=O)N1CCC[C@H](N1)C(=O)OCC(C)(C)C2] |

TABLE 2-continued

Certain Compounds of the Present Invention

| Ex# | Structure |
| --- | --- |
| B57 | 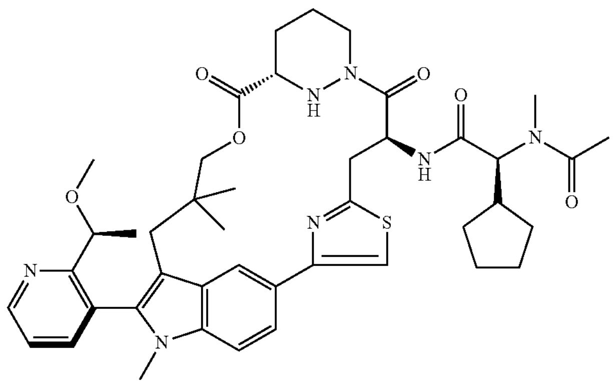 |
| B58 | 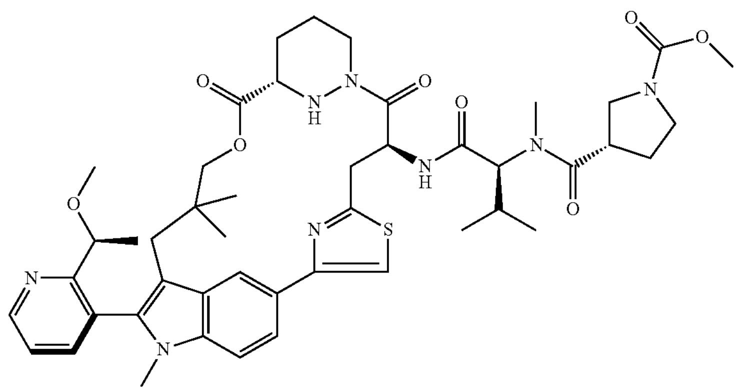 |
| B59 | 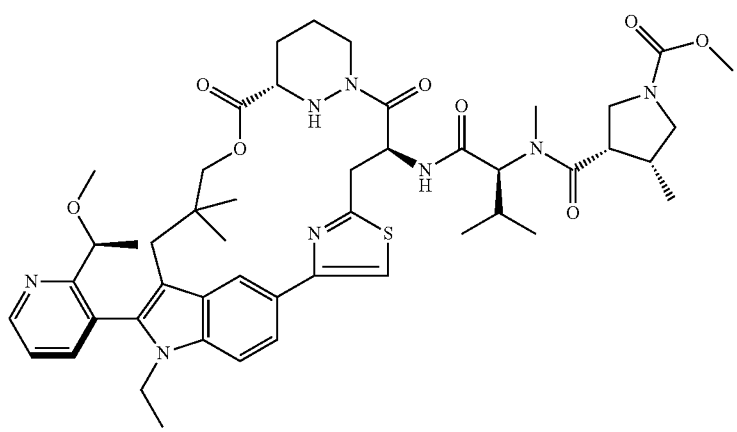 |
| B60 | 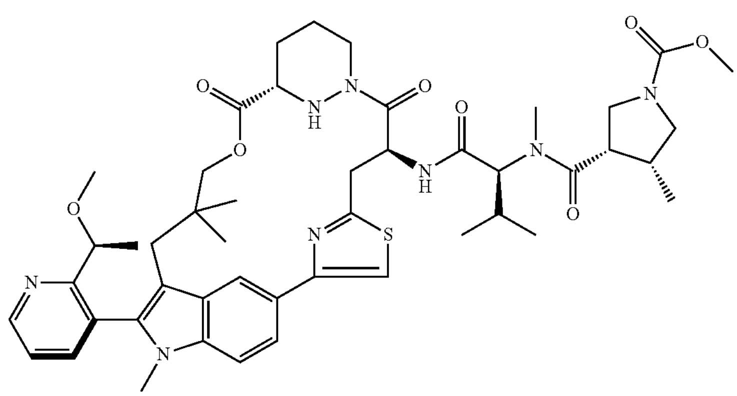 |

TABLE 2-continued

Certain Compounds of the Present Invention

| Ex# | Structure |
|---|---|
| B61 | 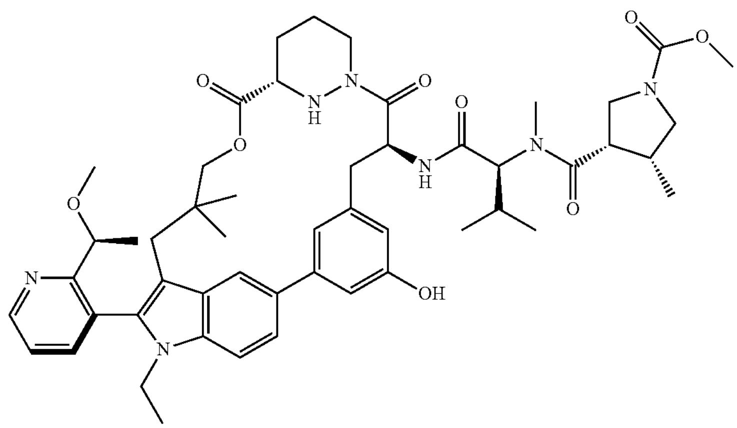 |
| B66 | 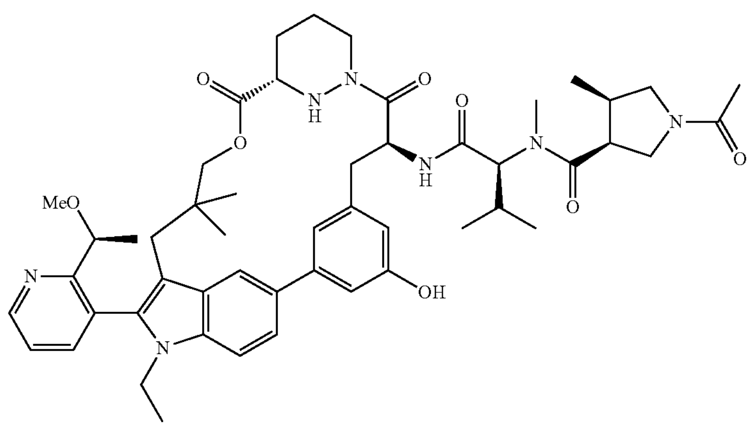 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@@H]1CN(C(C)=O)C[C@@H]1C)C(=O)N1CCC[C@H](N1)C(=O)OCC(C)(C)C2] |
| B67 | 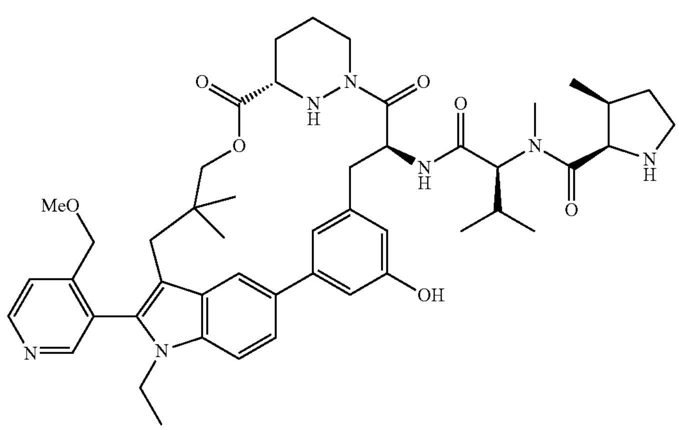 [SMILES: CCn1c(-c2cnccc2COC)c2c3cc(ccc31)-c1cc(O)cc(c1)C[C@H](NC(=O)[C@H](C(C)C)N(C)C(=O)[C@@H]1NCC[C@@H]1C)C(=O)N1CCC[C@H](N1)C(=O)OCC(C)(C)C2] |

TABLE 2-continued
Certain Compounds of the Present Invention
| Ex# | Structure |
|---|---|
| B69 | 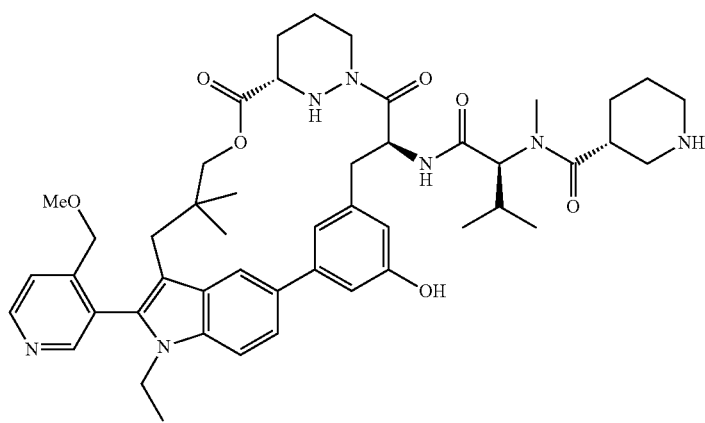 [SMILES: CCn1c(-c2cnccc2COC)c2c3cc(ccc31)-c1cc(O)cc(c1)C[C@H](NC(=O)[C@H](C(C)C)N(C)C(=O)[C@@H]1CCCNC1)C(=O)N1CCC[C@H](N1)C(=O)OCC(C)(C)C2] |
| B71 | 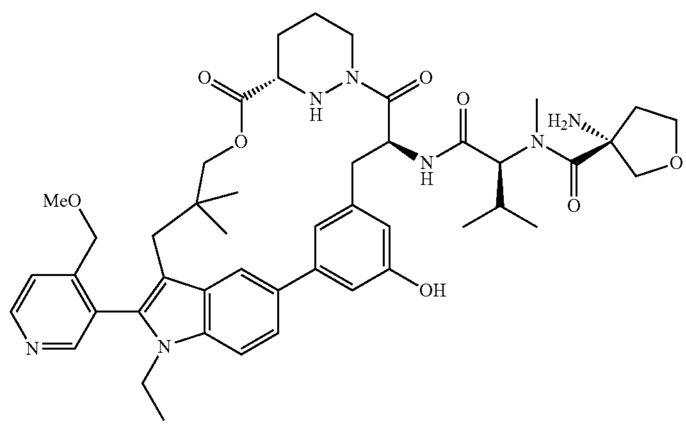 [SMILES: CCn1c(-c2cnccc2COC)c2c3cc(ccc31)-c1cc(O)cc(c1)C[C@H](NC(=O)[C@H](C(C)C)N(C)C(=O)[C@@]1(N)CCOC1)C(=O)N1CCC[C@H](N1)C(=O)OCC(C)(C)C2] |
| B73 | 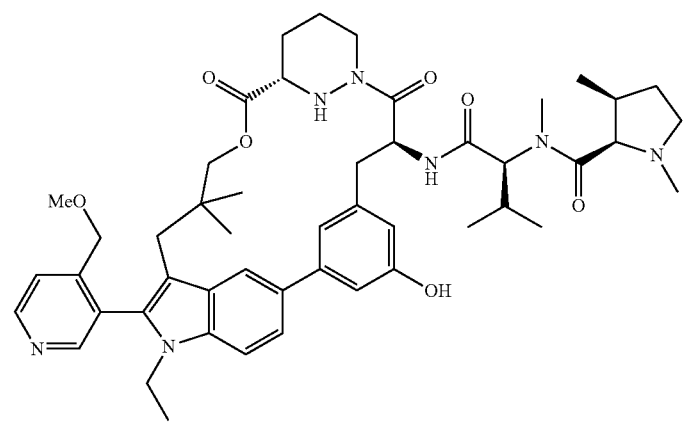 [SMILES: CCn1c(-c2cnccc2COC)c2c3cc(ccc31)-c1cc(O)cc(c1)C[C@H](NC(=O)[C@H](C(C)C)N(C)C(=O)[C@H]1[C@@H](C)CCN1C)C(=O)N1CCC[C@H](N1)C(=O)OCC(C)(C)C2] |

TABLE 2-continued

Certain Compounds of the Present Invention

| Ex# | Structure |
|---|---|
| B74 | 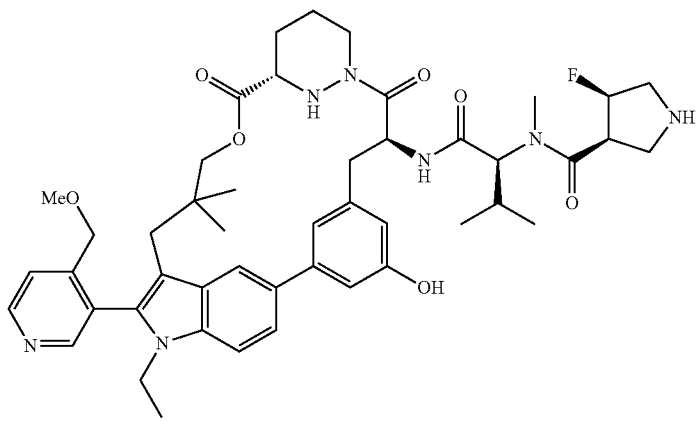 [SMILES: CCn1c(-c2cnccc2COC)c2c3cc(ccc31)-c1cc(O)cc(c1)C[C@H](NC(=O)[C@H](C(C)C)N(C)C(=O)[C@@H]1CNC[C@@H]1F)C(=O)N1CCC[C@H](N1)C(=O)OCC(C)(C)C2] |
| B80 | 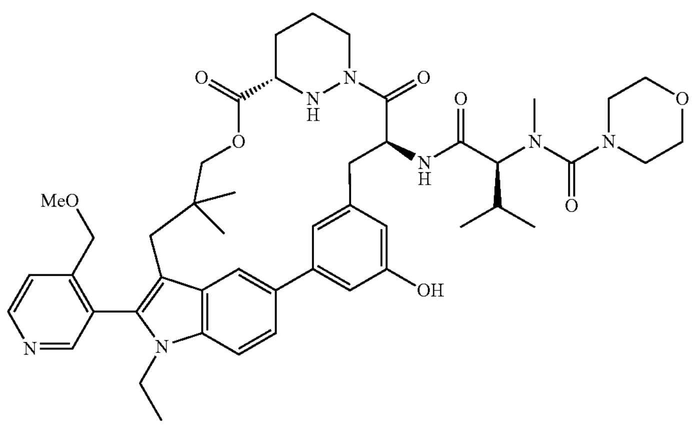 [SMILES: CCn1c(-c2cnccc2COC)c2c3cc(ccc31)-c1cc(O)cc(c1)C[C@H](NC(=O)[C@H](C(C)C)N(C)C(=O)N1CCOCC1)C(=O)N1CCC[C@H](N1)C(=O)OCC(C)(C)C2] |
| B81 | 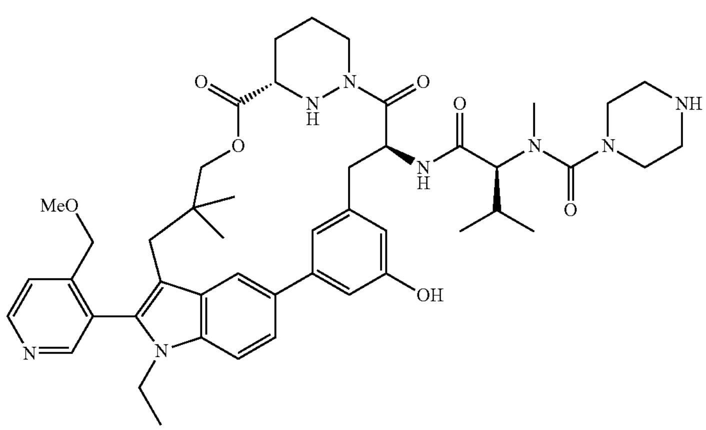 [SMILES: CCn1c(-c2cnccc2COC)c2c3cc(ccc31)-c1cc(O)cc(c1)C[C@H](NC(=O)[C@H](C(C)C)N(C)C(=O)N1CCNCC1)C(=O)N1CCC[C@H](N1)C(=O)OCC(C)(C)C2] |

TABLE 2-continued
Certain Compounds of the Present Invention
| Ex# | Structure |
|---|---|
| B94 | 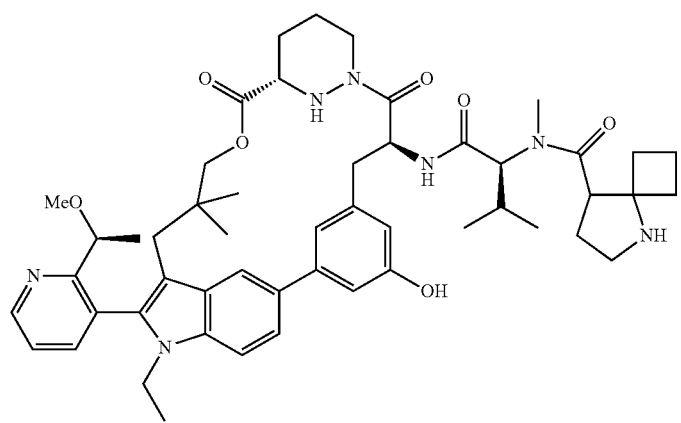 [SMILES: CCn1c(-c2cccnc2[C@H](C)OC)c2c3cc(ccc31)-c1cc(O)cc(c1)C[C@H](NC(=O)[C@H](C(C)C)N(C)C(=O)C1CCNC13CCC3)C(=O)N1CCC[C@H](N1)C(=O)OCC(C)(C)C2] |
| B95 | 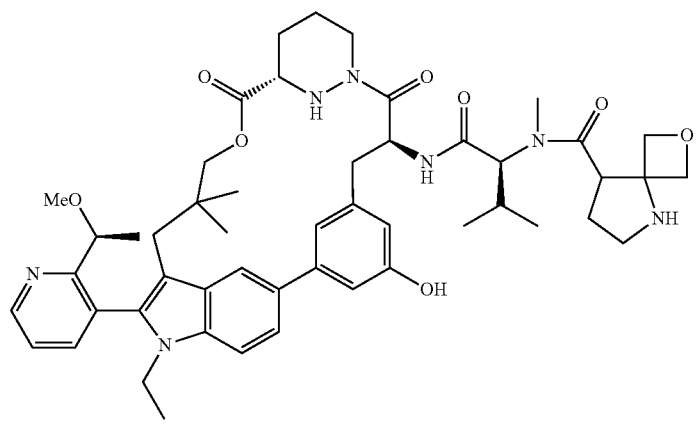 [SMILES: CCn1c(-c2cccnc2[C@H](C)OC)c2c3cc(ccc31)-c1cc(O)cc(c1)C[C@H](NC(=O)[C@H](C(C)C)N(C)C(=O)C1CCNC13COC3)C(=O)N1CCC[C@H](N1)C(=O)OCC(C)(C)C2] |
| B96 | 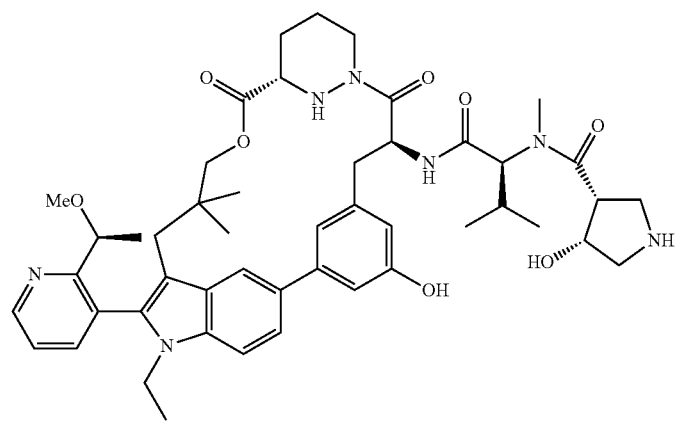 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@@H]1CNC[C@@H]1O)C(=O)N1CCC[C@H](N1)C(=O)OCC(C)(C)C2] |

TABLE 2-continued
Certain Compounds of the Present Invention
| Ex# | Structure |
|---|---|
| B97 | 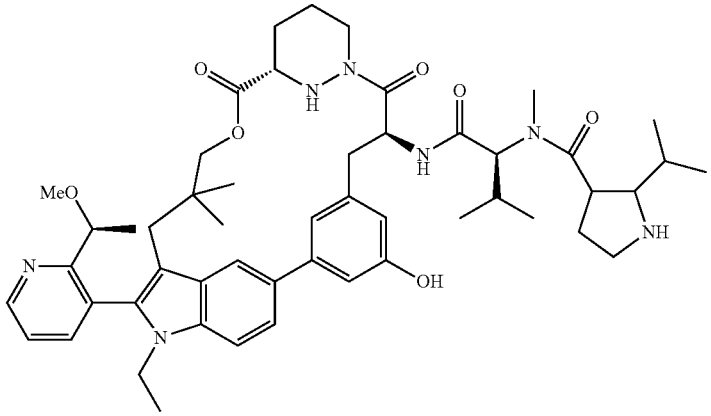 [SMILES: CCn1c(-c2cccnc2[C@H](C)OC)c2c3cc(ccc31)-c1cc(O)cc(c1)C[C@H](NC(=O)[C@H](C(C)C)N(C)C(=O)C1CCNC1C(C)C)C(=O)N1CCC[C@H](N1)C(=O)OCC(C)(C)C2] |
| B99 | 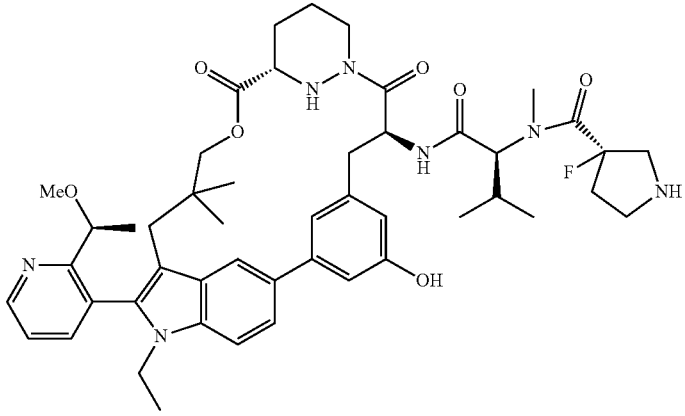 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@@]1(F)CCNC1)C(=O)N1CCC[C@H](N1)C(=O)OCC(C)(C)C2] |
| B100 | 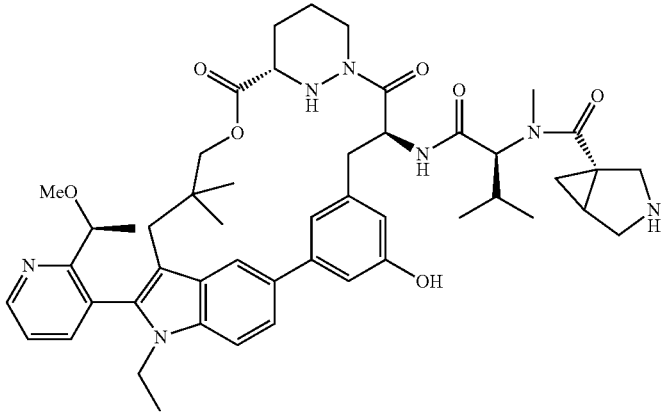 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@]13CNCC1C3)C(=O)N1CCC[C@H](N1)C(=O)OCC(C)(C)C2] |

TABLE 2-continued
Certain Compounds of the Present Invention
| Ex# | Structure |
|---|---|
| B104 | 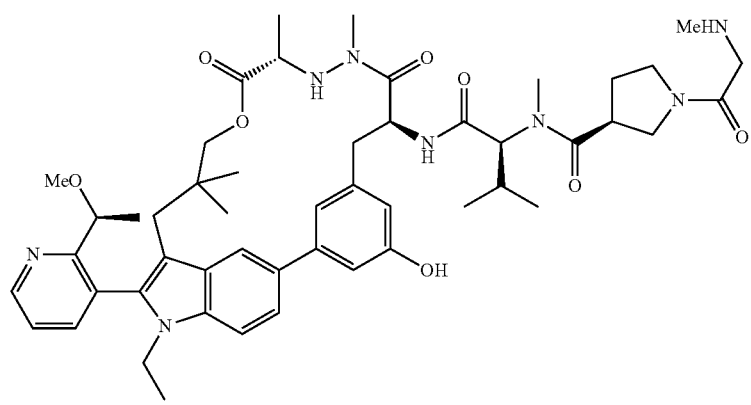 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@H]1CCN(C(=O)CNC)C1)C(=O)N(C)N[C@@H](C)C(=O)OCC(C)(C)C2] |
| B106 | 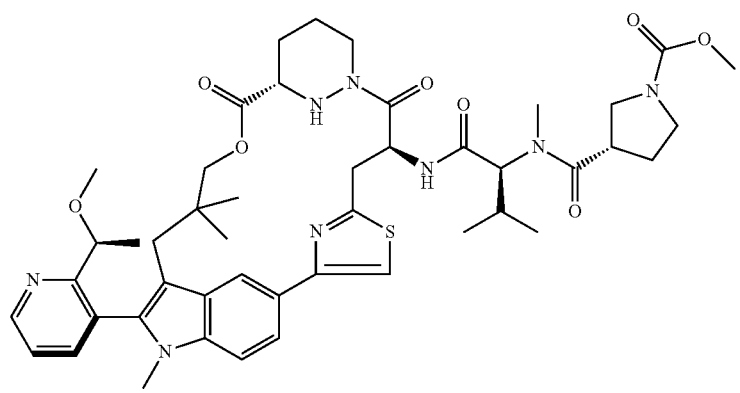 |
| B107 | 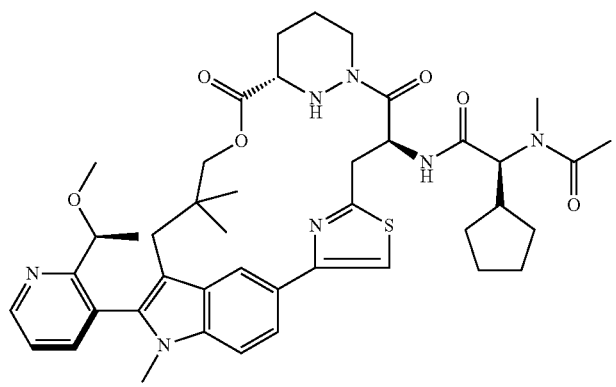 |

TABLE 2-continued

Certain Compounds of the Present Invention

| Ex# | Structure |
|---|---|
| B109 | 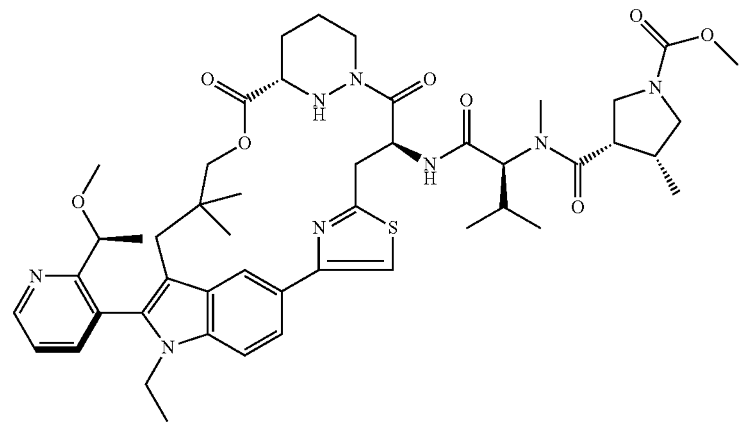 |
| B110 | 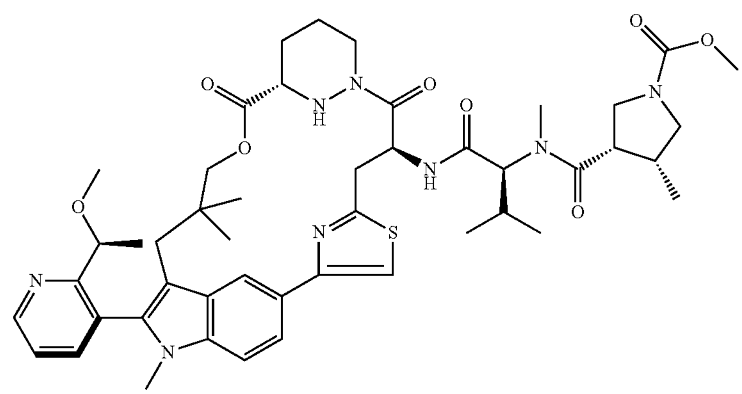 |
| B111 | 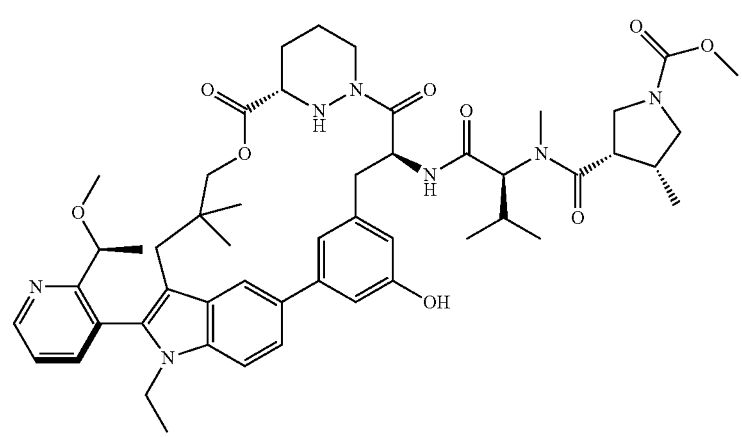 |

TABLE 2-continued
Certain Compounds of the Present Invention
| Ex# | Structure |
|---|---|
| B112 | 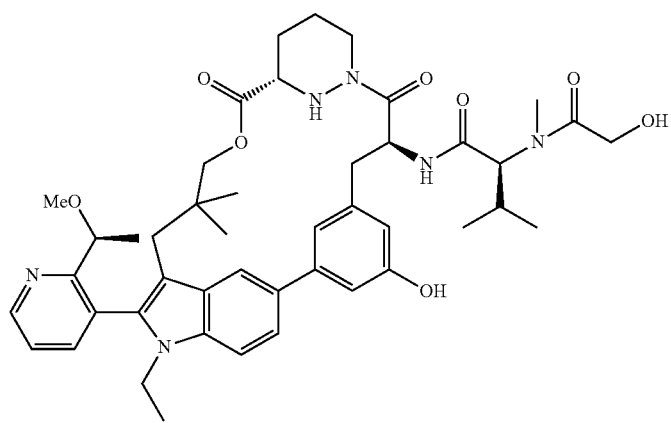 [SMILES: CCn1c(-c2cccnc2[C@H](C)OC)c2c3cc(ccc31)-c1cc(O)cc(c1)C[C@H](NC(=O)[C@H](C(C)C)N(C)C(=O)CO)C(=O)N1CCC[C@H](N1)C(=O)OCC(C)(C)C2] |
| B113 | 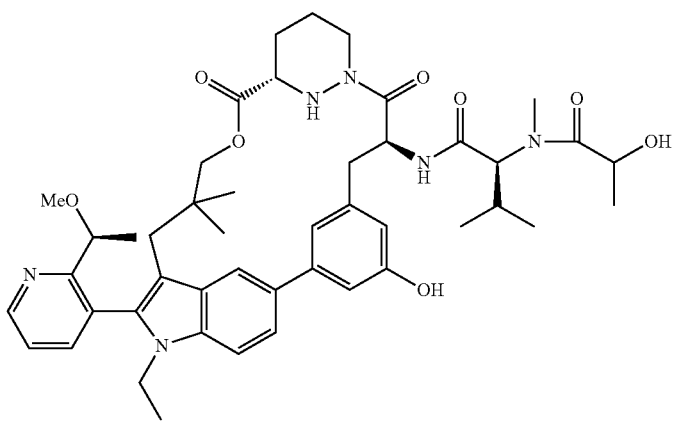 [SMILES: CCn1c(-c2cccnc2[C@H](C)OC)c2c3cc(ccc31)-c1cc(O)cc(c1)C[C@H](NC(=O)[C@H](C(C)C)N(C)C(=O)C(C)O)C(=O)N1CCC[C@H](N1)C(=O)OCC(C)(C)C2] |
| B114 | 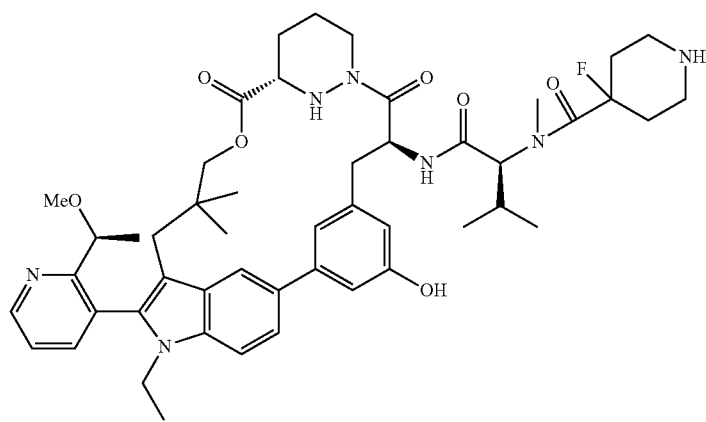 [SMILES: CCn1c(-c2cccnc2[C@H](C)OC)c2c3cc(ccc31)-c1cc(O)cc(c1)C[C@H](NC(=O)[C@H](C(C)C)N(C)C(=O)C1(F)CCNCC1)C(=O)N1CCC[C@H](N1)C(=O)OCC(C)(C)C2] |

TABLE 2-continued

Certain Compounds of the Present Invention

| Ex# | Structure |
| --- | --- |
| B117 | 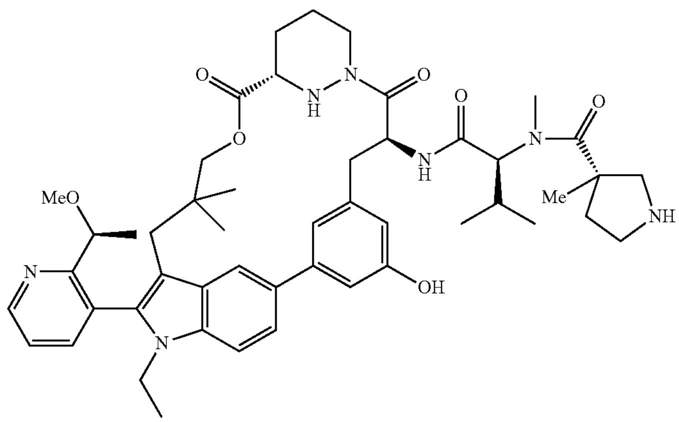 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@@]1(C)CCNC1)C(=O)N1CCC[C@H](N1)C(=O)OCC(C)(C)C2] |
| B119 | 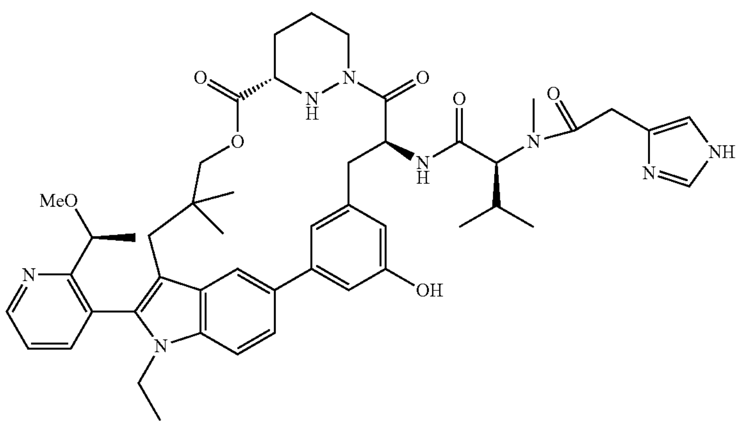 [SMILES: CCn1c(-c2cccnc2[C@H](C)OC)c2c3cc(ccc31)-c1cc(O)cc(c1)C[C@H](NC(=O)[C@H](C(C)C)N(C)C(=O)Cc1c[nH]cn1)C(=O)N1CCC[C@H](N1)C(=O)OCC(C)(C)C2] |
| B122 | 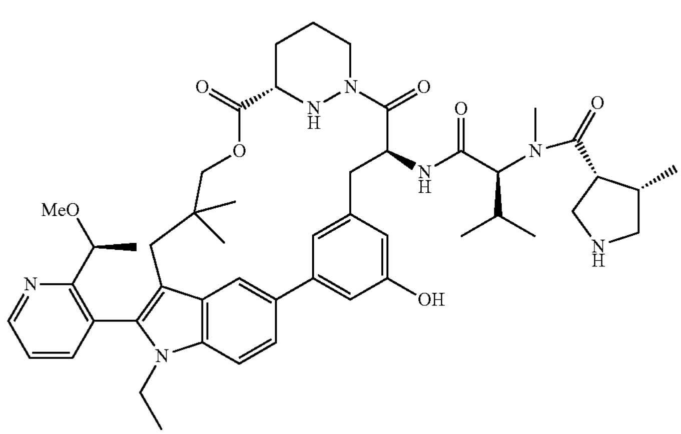 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@H]1CNC[C@H]1C)C(=O)N1CCC[C@H](N1)C(=O)OCC(C)(C)C2] |

TABLE 2-continued

Certain Compounds of the Present Invention

| Ex# | Structure |
|---|---|
| B123 | 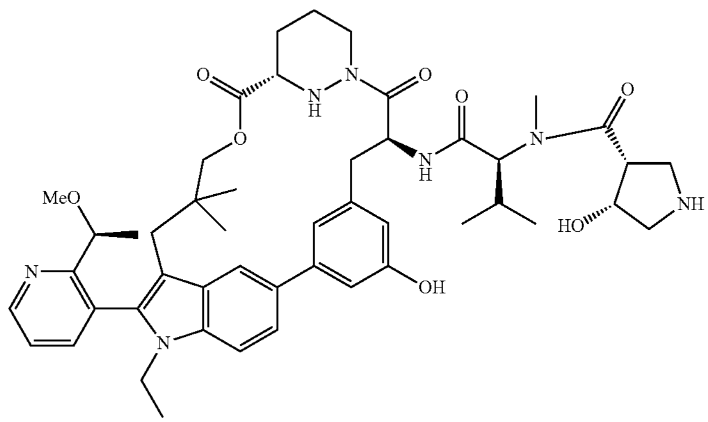 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@@H]1CNC[C@@H]1O)C(=O)N1CCC[C@H](N1)C(=O)OCC(C)(C)C2] |
| B124 | 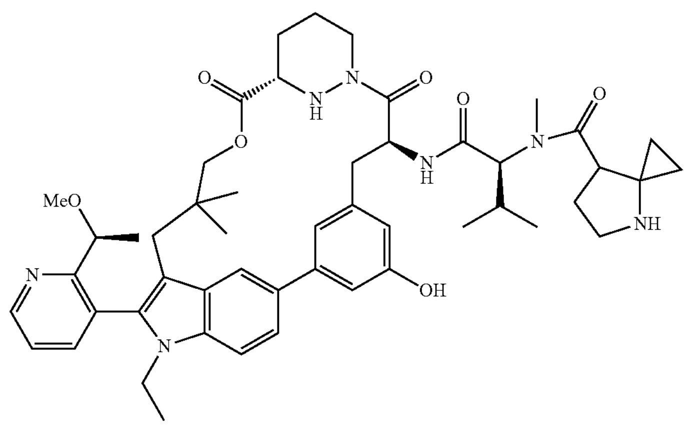 [SMILES: CCn1c(-c2cccnc2[C@H](C)OC)c2c3cc(ccc31)-c1cc(O)cc(c1)C[C@H](NC(=O)[C@H](C(C)C)N(C)C(=O)C1CCNC13CC3)C(=O)N1CCC[C@H](N1)C(=O)OCC(C)(C)C2] |
| B126 | 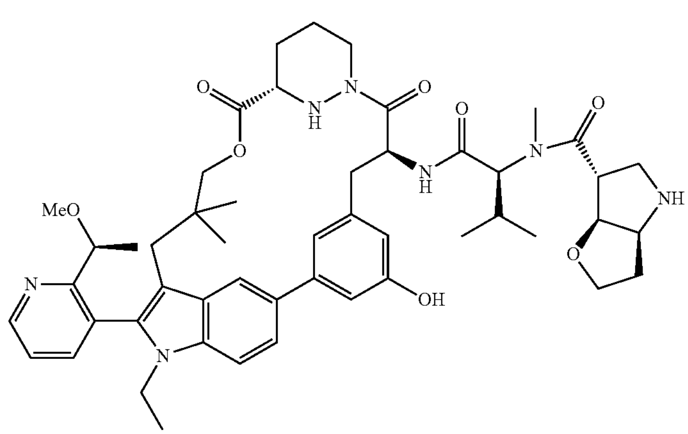 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@@H]1CN[C@H]3CCO[C@H]31)C(=O)N1CCC[C@H](N1)C(=O)OCC(C)(C)C2] |

TABLE 2-continued

Certain Compounds of the Present Invention

| Ex# | Structure |
|---|---|
| B128 | 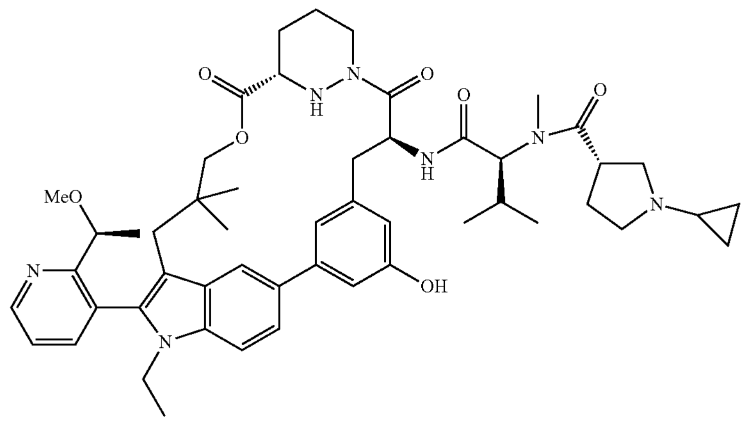 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@H]1CCN(C3CC3)C1)C(=O)N1CCC[C@H](N1)C(=O)OCC(C)(C)C2] |
| B129 | 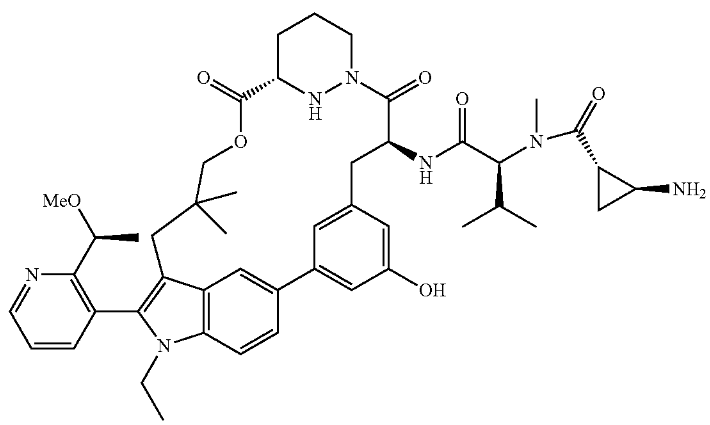 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@H]1C[C@@H]1N)C(=O)N1CCC[C@H](N1)C(=O)OCC(C)(C)C2] |
| B130 | 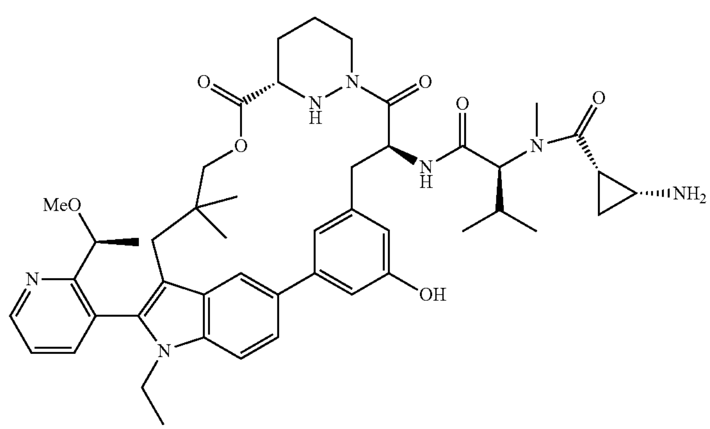 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@H]1C[C@H]1N)C(=O)N1CCC[C@H](N1)C(=O)OCC(C)(C)C2] |

TABLE 2-continued
Certain Compounds of the Present Invention
| Ex# | Structure |
|---|---|
| B133 | 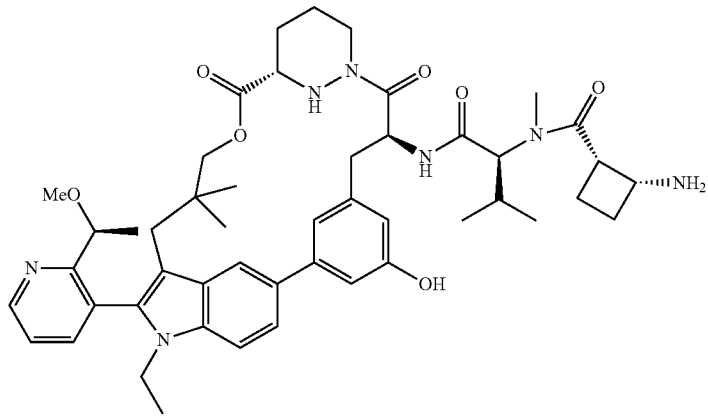 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@H]1CC[C@H]1N)C(=O)N1CCC[C@H](N1)C(=O)OCC(C)(C)C2] |
| B134 | 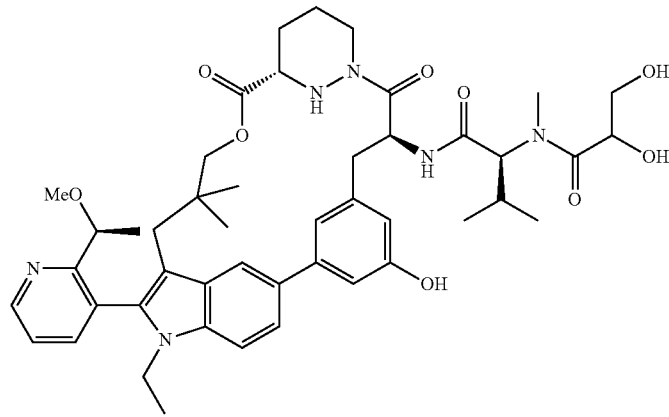 [SMILES: CCn1c(-c2cccnc2[C@H](C)OC)c2c3cc(ccc31)-c1cc(O)cc(c1)C[C@H](NC(=O)[C@H](C(C)C)N(C)C(=O)C(O)CO)C(=O)N1CCC[C@H](N1)C(=O)OCC(C)(C)C2] |
| B135 | 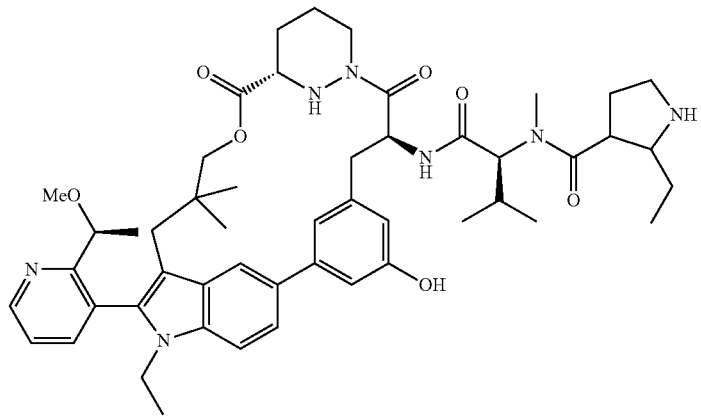 [SMILES: CCC1NCCC1C(=O)N(C)[C@H](C(=O)N[C@H]1Cc2cc(O)cc(c2)-c2ccc3c(c2)c(c(-c2cccnc2[C@H](C)OC)n3CC)CC(C)(C)COC(=O)[C@@H]2CCCN(N2)C1=O)C(C)C] |

TABLE 2-continued
Certain Compounds of the Present Invention
| Ex# | Structure |
|---|---|
| B137 | 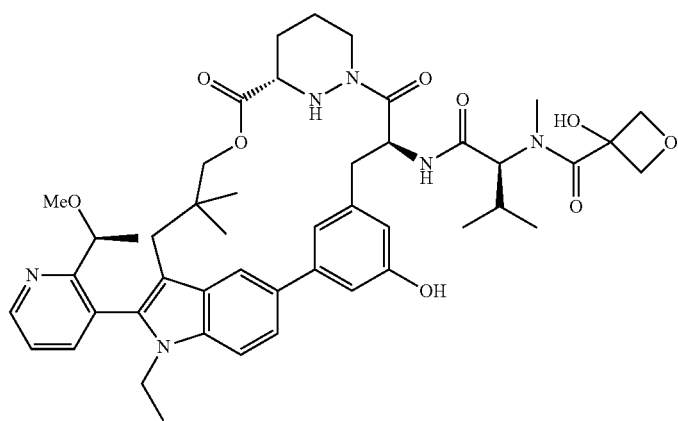 [SMILES: CCn1c(-c2cccnc2[C@H](C)OC)c2c3cc(ccc31)-c1cc(O)cc(c1)C[C@H](NC(=O)[C@H](C(C)C)N(C)C(=O)C1(O)COC1)C(=O)N1CCC[C@H](N1)C(=O)OCC(C)(C)C2] |
| B138 | 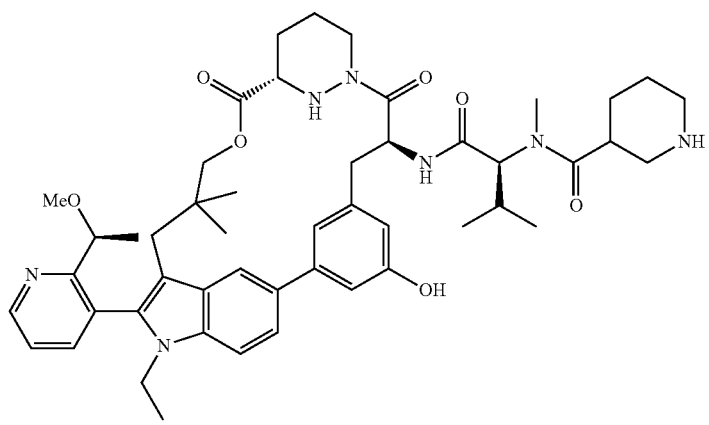 [SMILES: CCn1c(-c2cccnc2[C@H](C)OC)c2c3cc(ccc31)-c1cc(O)cc(c1)C[C@H](NC(=O)[C@H](C(C)C)N(C)C(=O)C1CCCNC1)C(=O)N1CCC[C@H](N1)C(=O)OCC(C)(C)C2] |
| B139 | 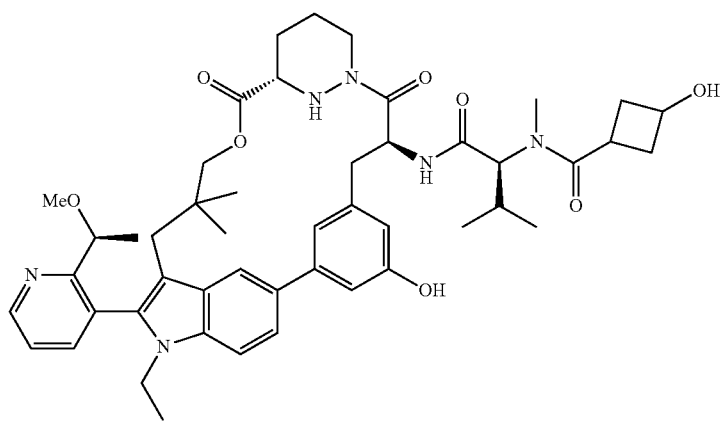 [SMILES: CCn1c(-c2cccnc2[C@H](C)OC)c2c3cc(ccc31)-c1cc(O)cc(c1)C[C@H](NC(=O)[C@H](C(C)C)N(C)C(=O)C1CC(O)C1)C(=O)N1CCC[C@H](N1)C(=O)OCC(C)(C)C2] |

TABLE 2-continued
Certain Compounds of the Present Invention
| Ex# | Structure |
|---|---|
| B141 | 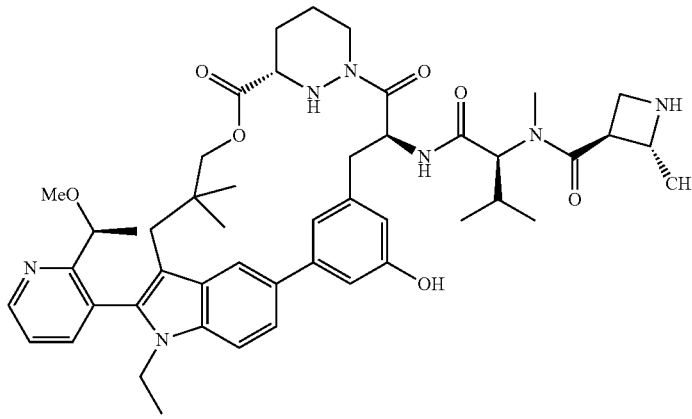 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@H]1CN[C@@H]1C)C(=O)N1CCC[C@H](N1)C(=O)OCC(C)(C)C2] |
| B143 | 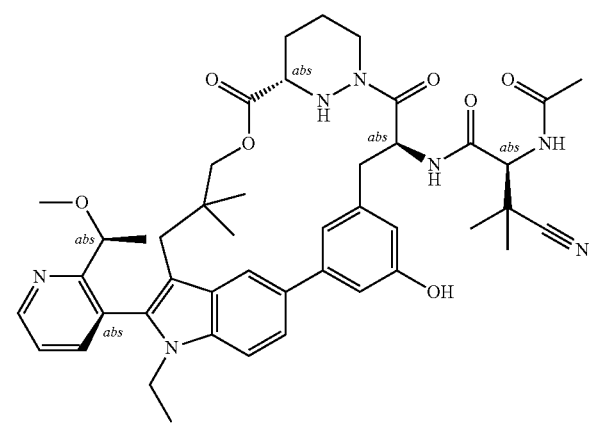 |
| B144 | 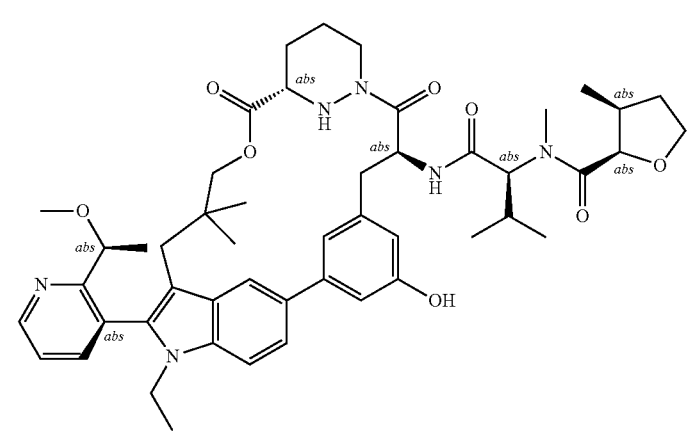 |

TABLE 2-continued
Certain Compounds of the Present Invention
| Ex# | Structure |
|---|---|
| B145 | 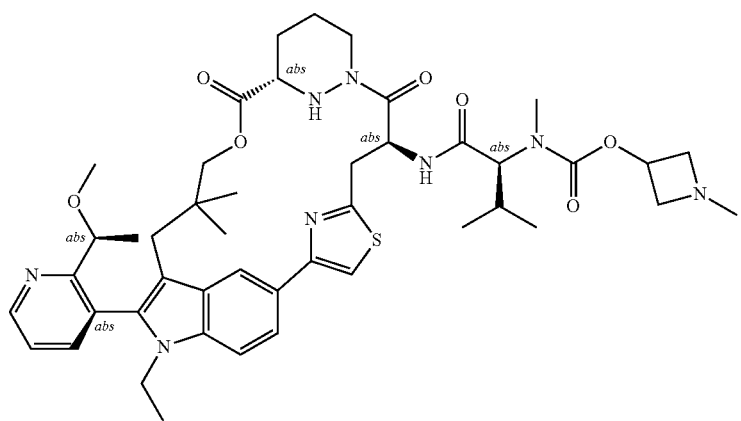 |
| B146 | 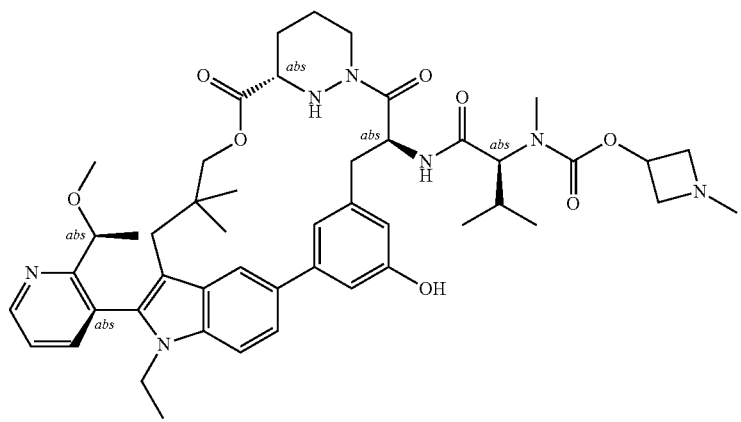 |
| B147 | 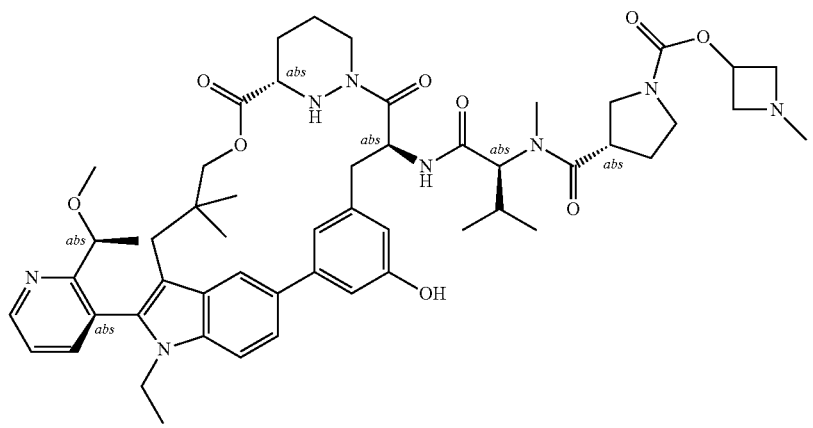 |

TABLE 2-continued

Certain Compounds of the Present Invention

| Ex# | Structure |
|---|---|
| B148 | 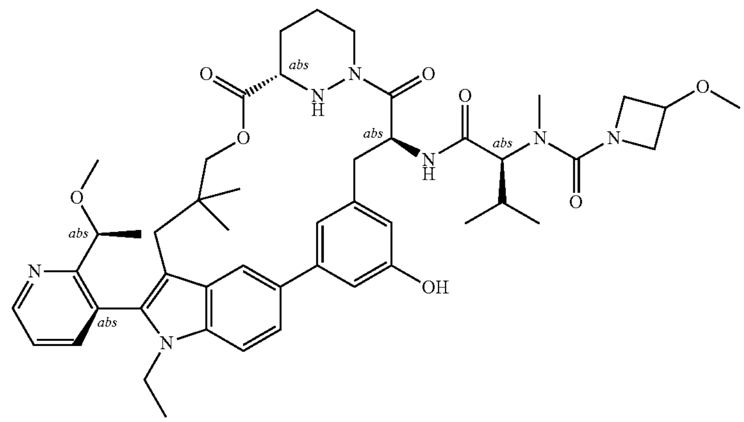 |
| B149 | 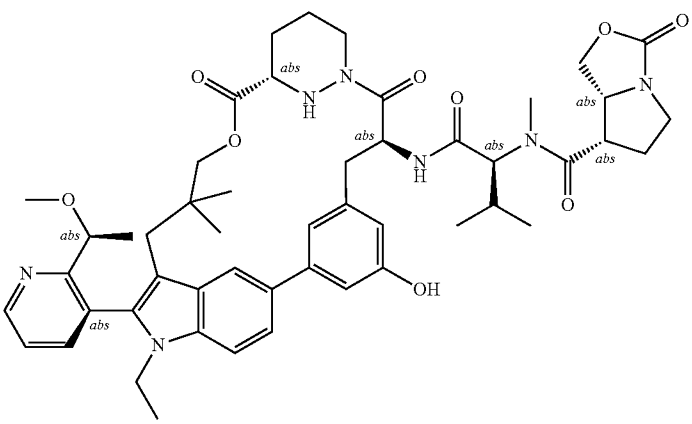 |
| B150 | 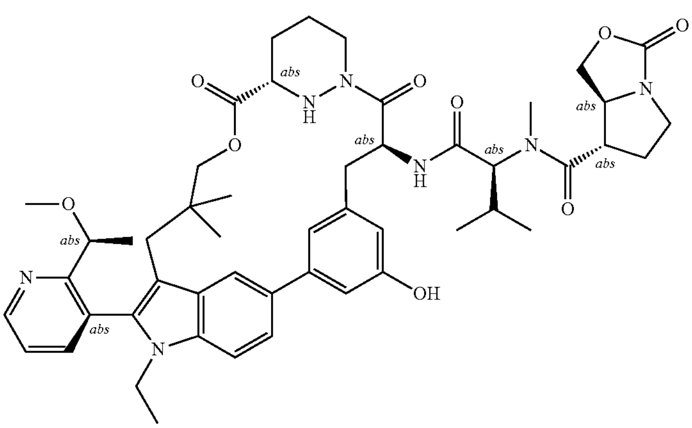 |

TABLE 2-continued
Certain Compounds of the Present Invention
| Ex# | Structure |
|---|---|
| B151 | 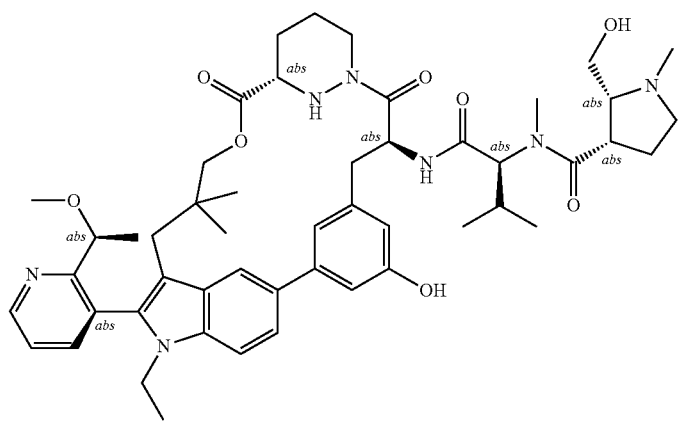 |
| B152 | 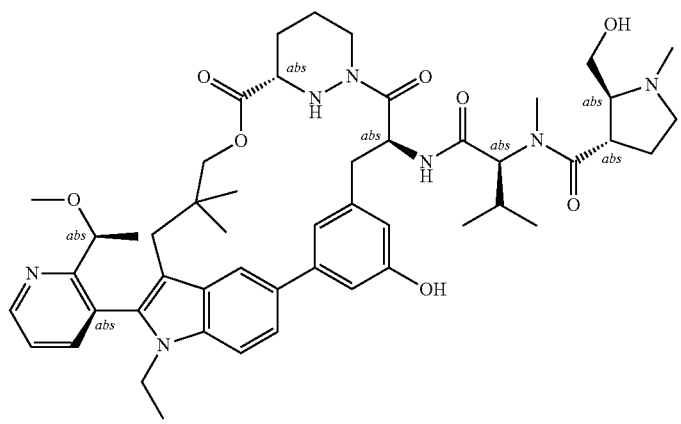 |
| B153 | 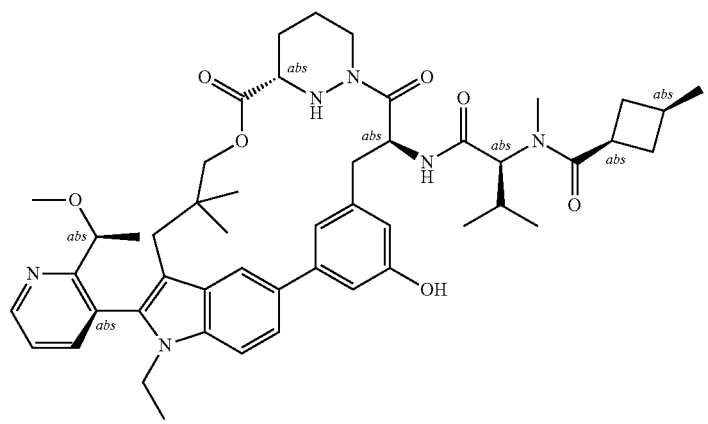 |

TABLE 2-continued

Certain Compounds of the Present Invention

| Ex# | Structure |
|---|---|
| B154 | 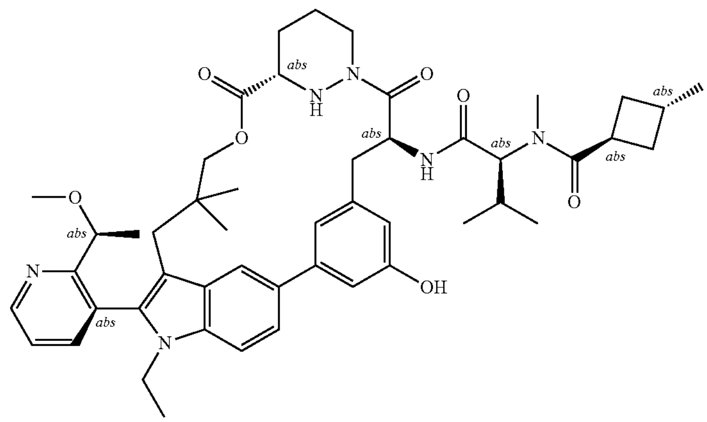 |
| B155 | 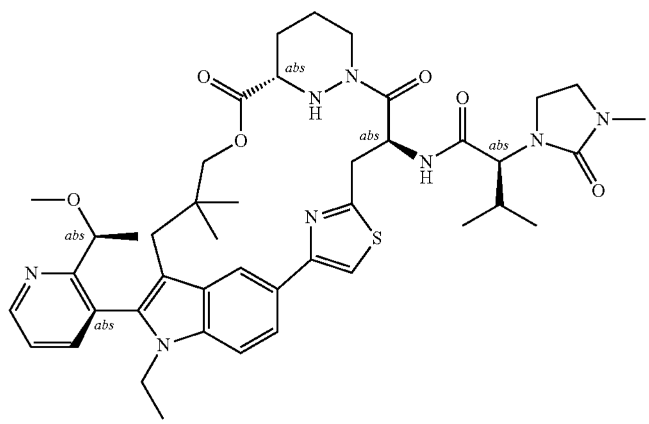 |
| B156 | 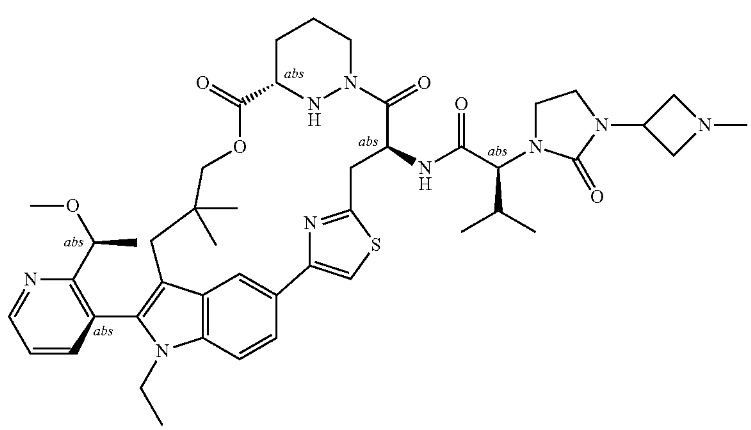 |

TABLE 2-continued

Certain Compounds of the Present Invention

| Ex# | Structure |
|---|---|
| B157 | 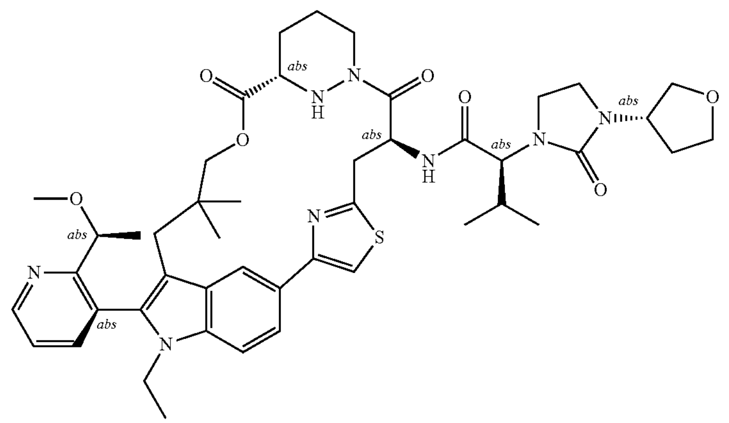 |
| B158 | 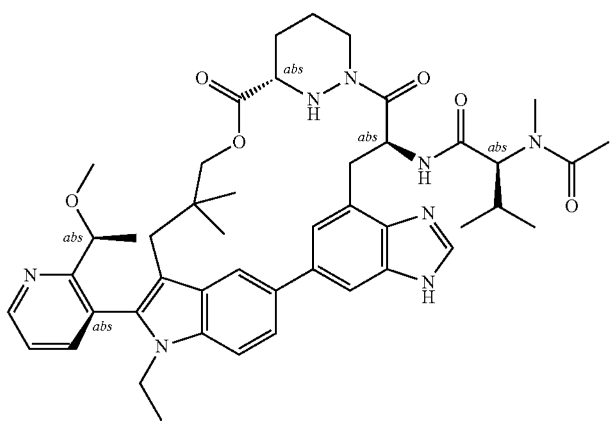 |
| B159 | 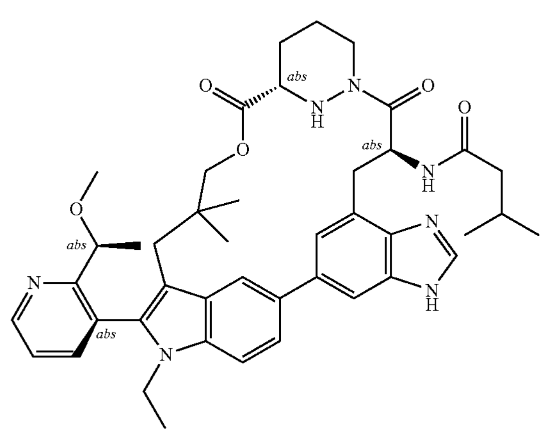 |

TABLE 2-continued
Certain Compounds of the Present Invention
| Ex# | Structure |
|---|---|
| B160 | 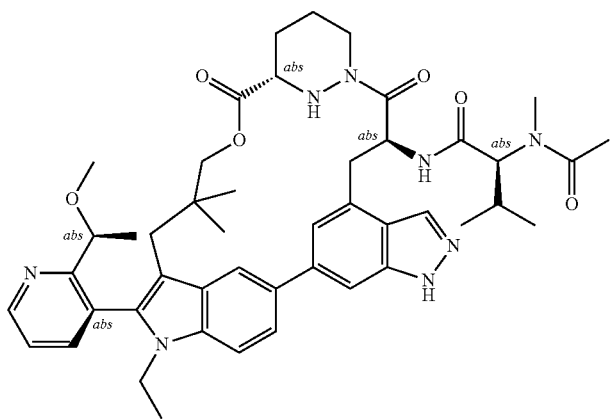 |
| B161 | 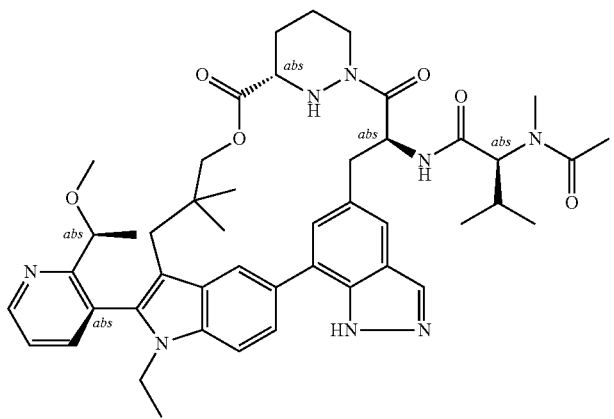 |
| B162 | 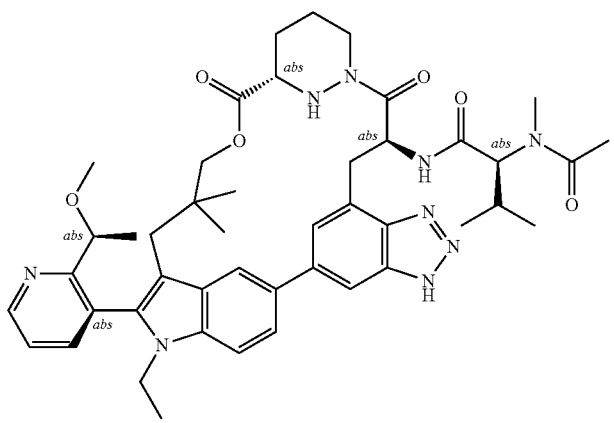 |

TABLE 2-continued
Certain Compounds of the Present Invention
| Ex# | Structure |
|---|---|
| B163 | 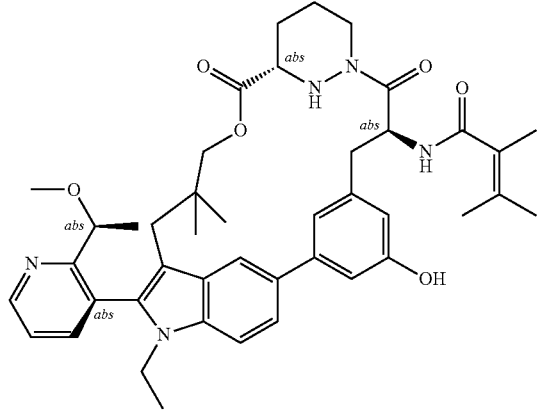 |
| B164 | 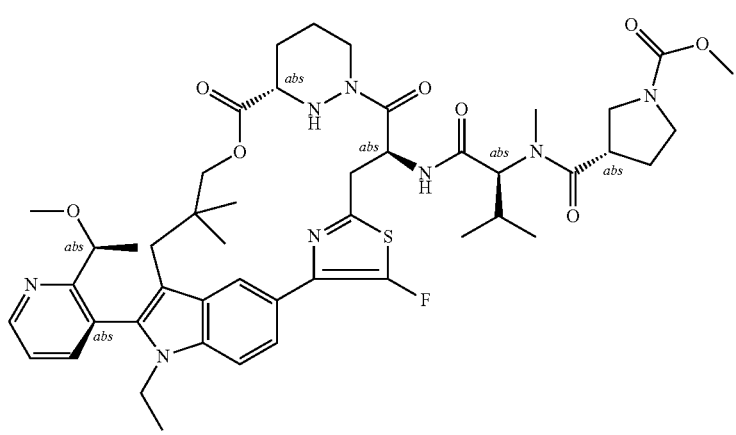 |
| B165 | 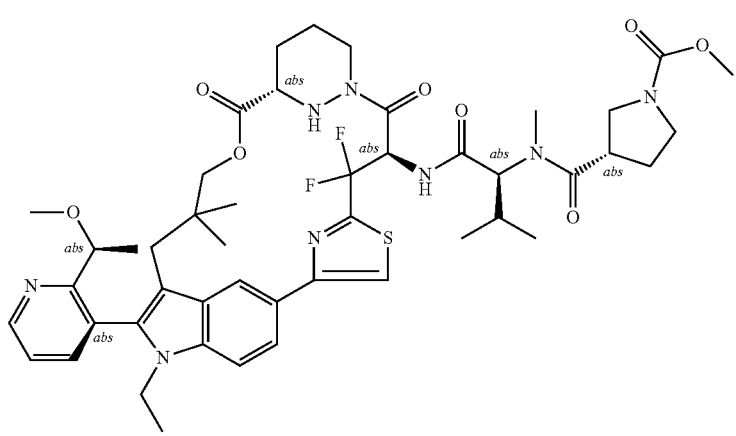 |

TABLE 2-continued

Certain Compounds of the Present Invention

| Ex# | Structure |
|---|---|
| B166 | 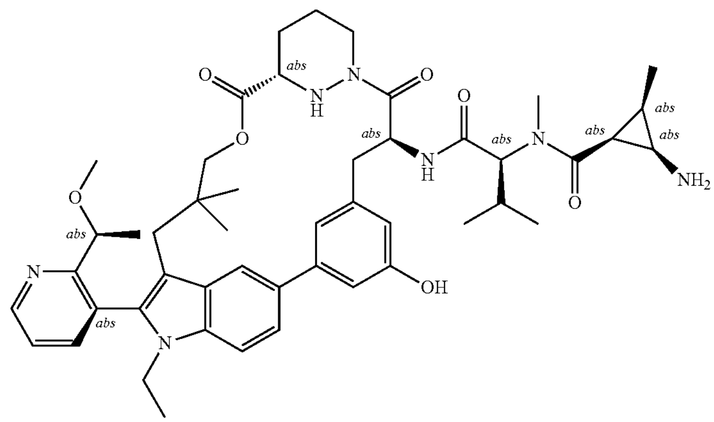 |
| B167 | 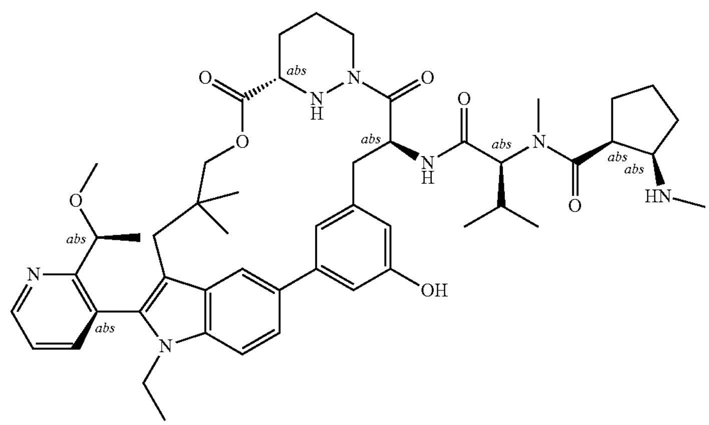 |
| B168 | 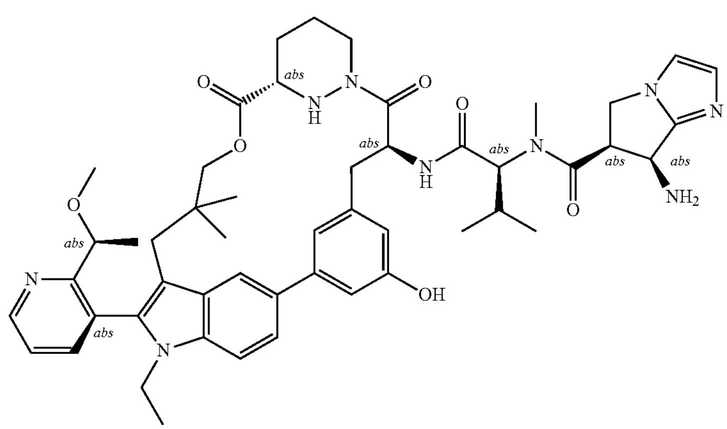 |

TABLE 2-continued

Certain Compounds of the Present Invention

| Ex# | Structure |
|---|---|
| B169 | 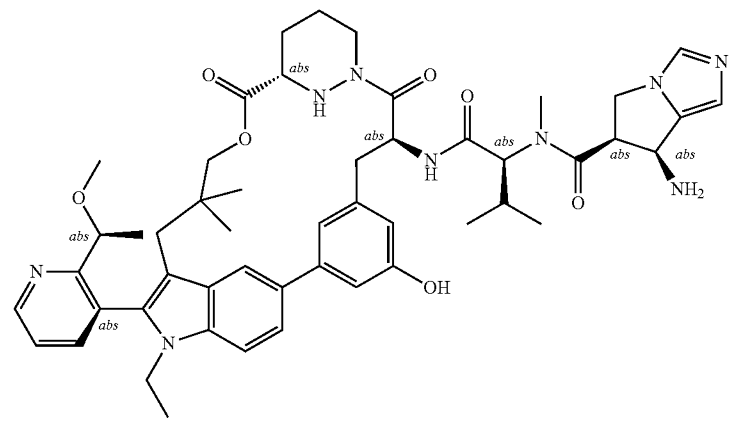 |
| B170 | 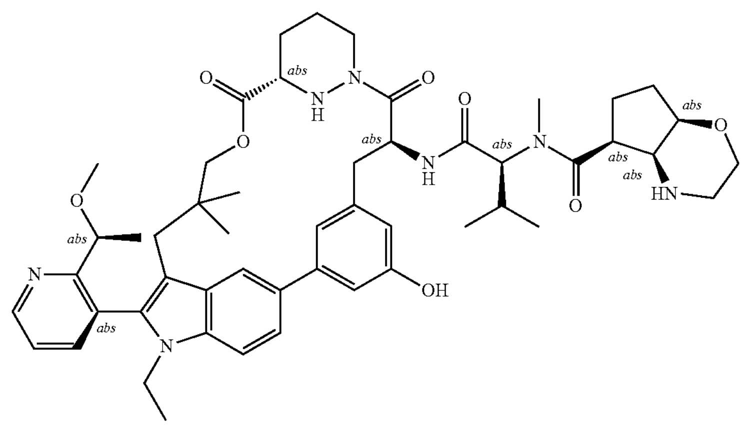 |
| B171 | 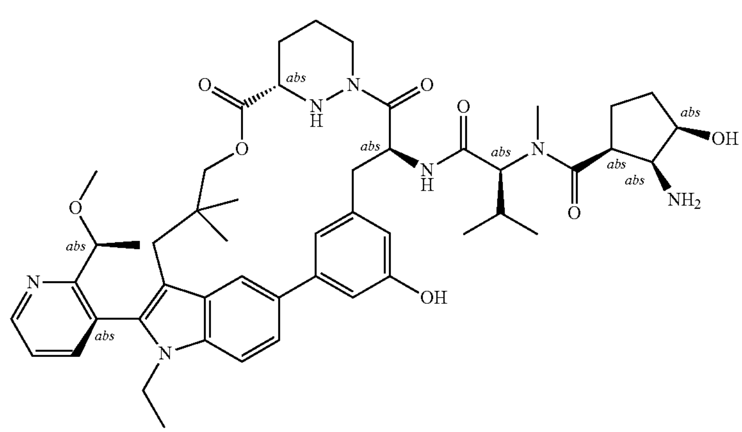 |

TABLE 2-continued
Certain Compounds of the Present Invention
| Ex# | Structure |
|---|---|
| B172 | 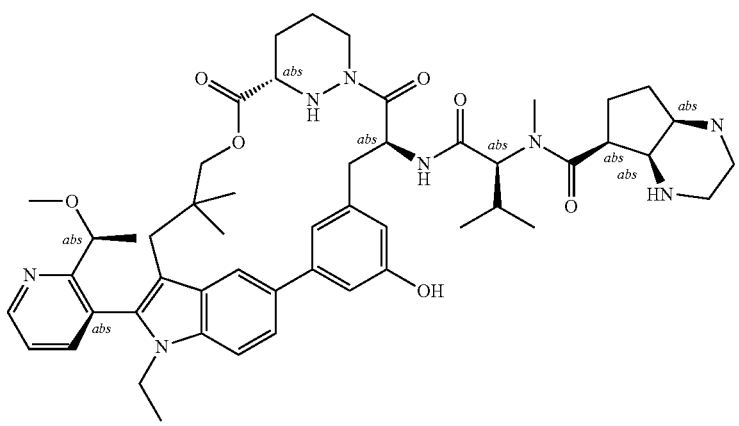 |
| B173 | 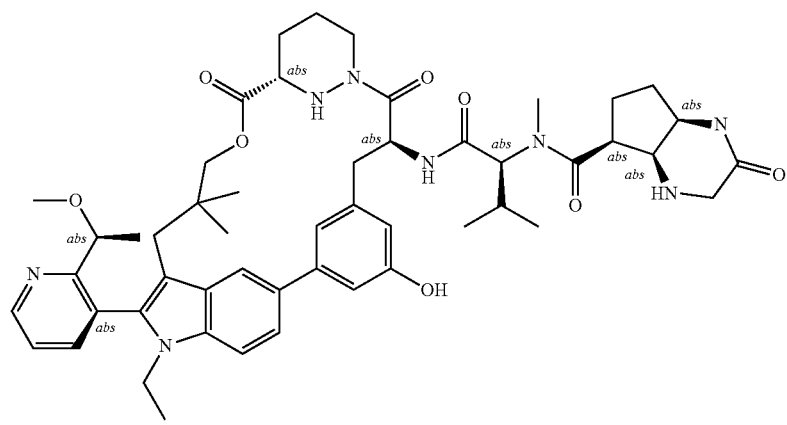 |
| B174 | 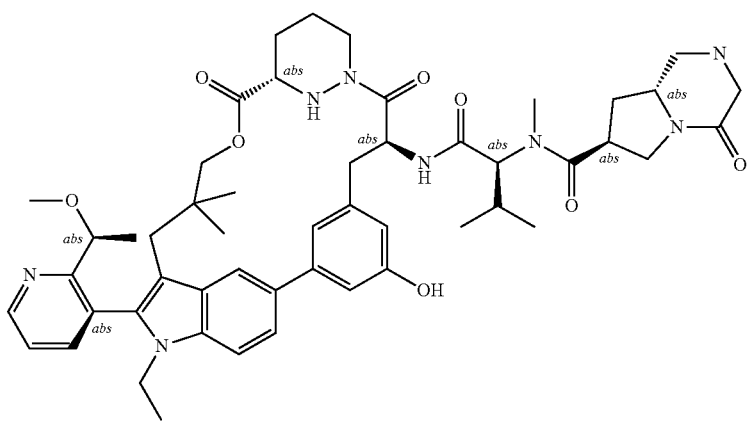 |

521
TABLE 2-continued
Certain Compounds of the Present Invention
| Ex# | Structure |
|---|---|
| B175 | 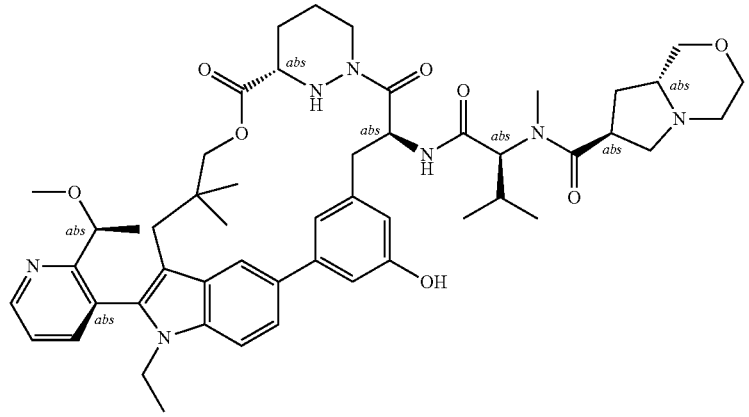 |
| B176 | 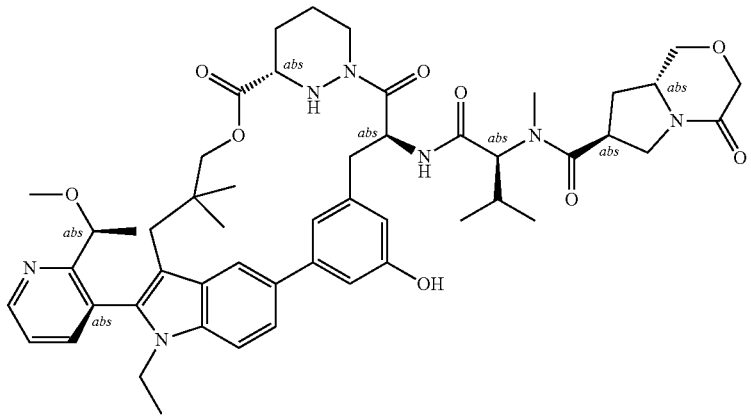 |
| B177 | 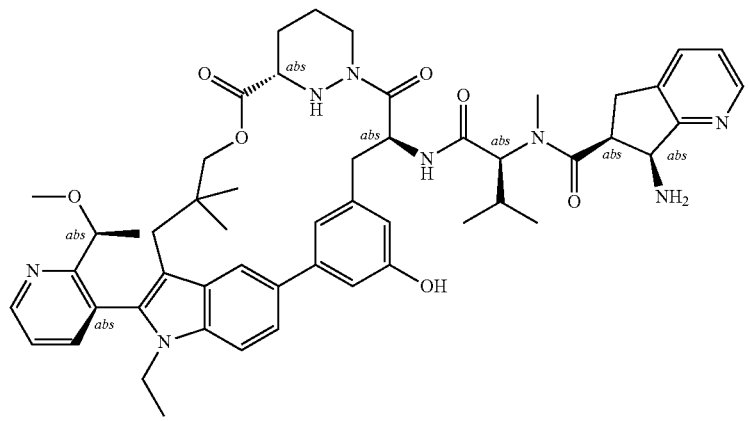 |

TABLE 2-continued
Certain Compounds of the Present Invention
| Ex# | Structure |
|---|---|
| B178 | 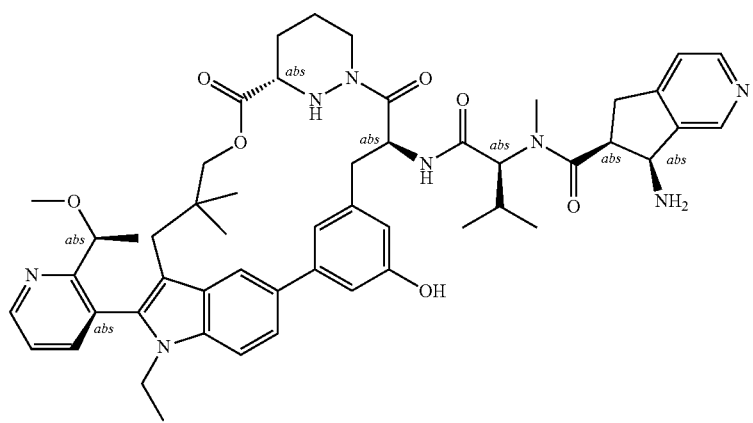 |
| B179 | 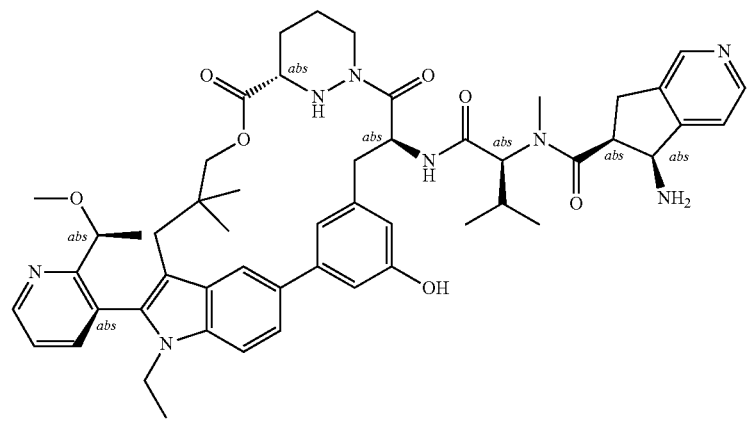 |
| B180 | 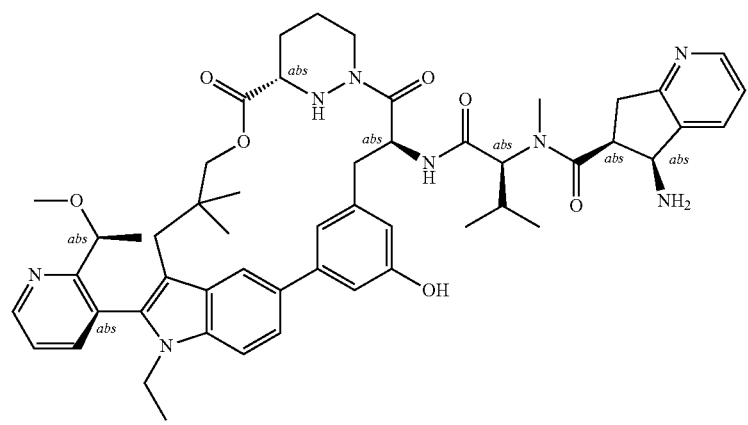 |

TABLE 2-continued

Certain Compounds of the Present Invention

| Ex# | Structure |
|---|---|
| B181 | 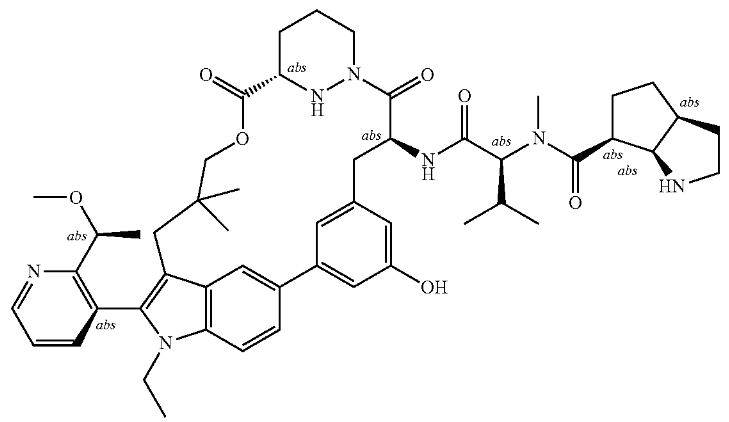 |
| B182 | 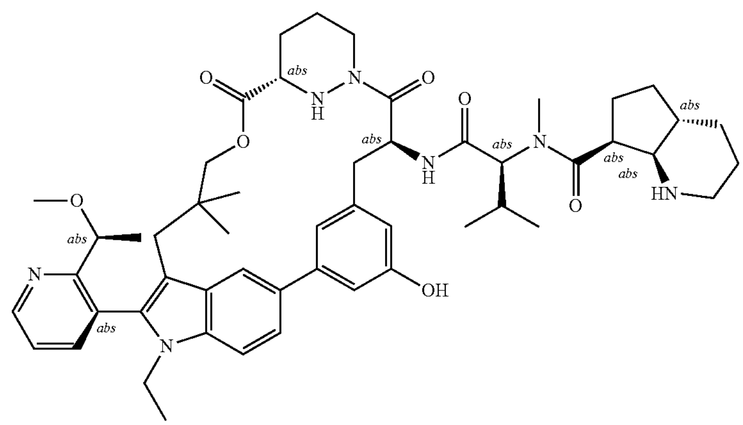 |
| B183 | 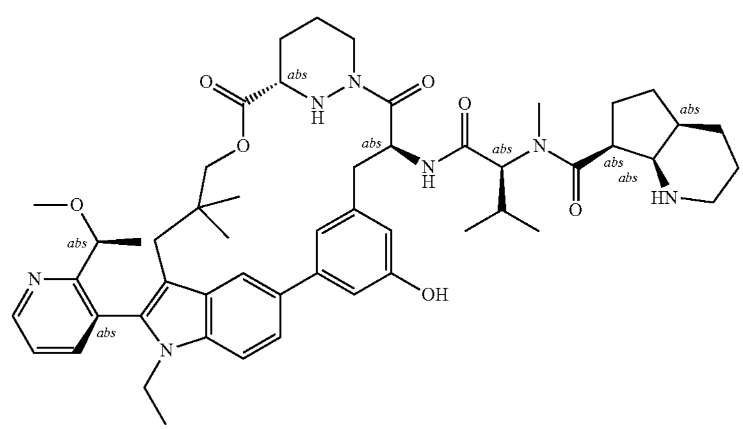 |

TABLE 2-continued
Certain Compounds of the Present Invention
| Ex# | Structure |
|---|---|
| B184 | 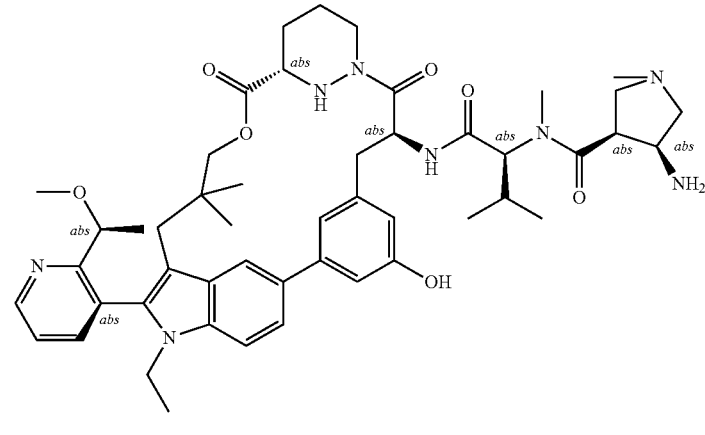 |
| B185 | 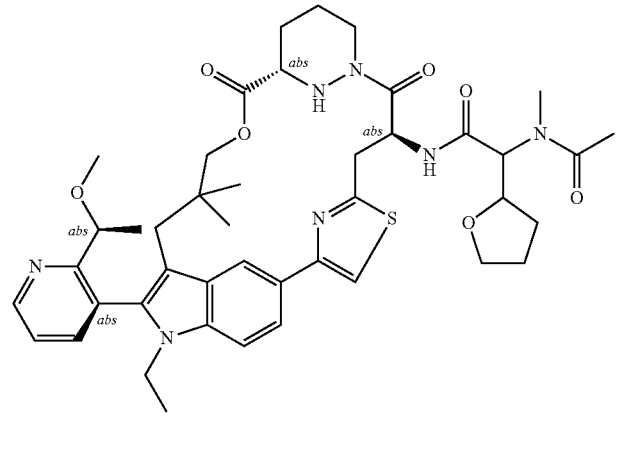 |
| B186 | 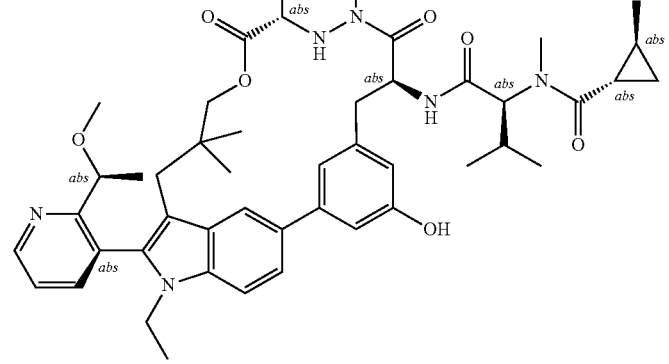 |

TABLE 2-continued

Certain Compounds of the Present Invention

| Ex# | Structure |
|---|---|
| B187 | 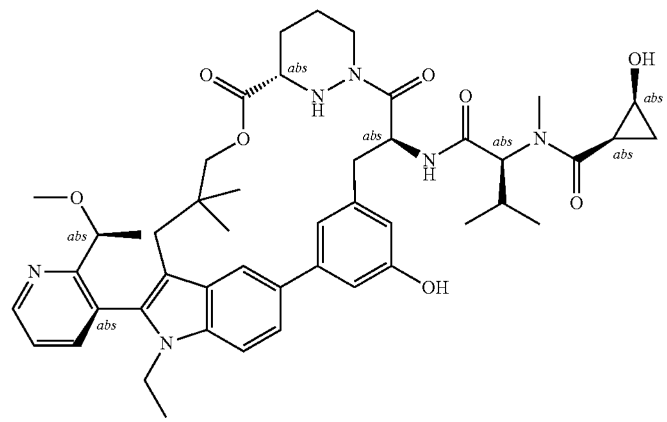 |
| B188 | 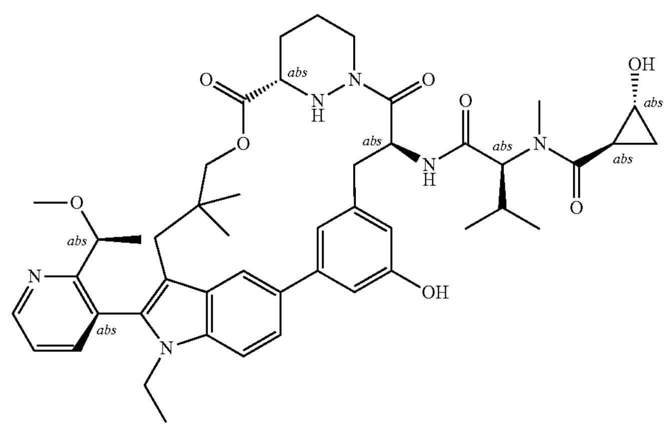 |
| B189 | 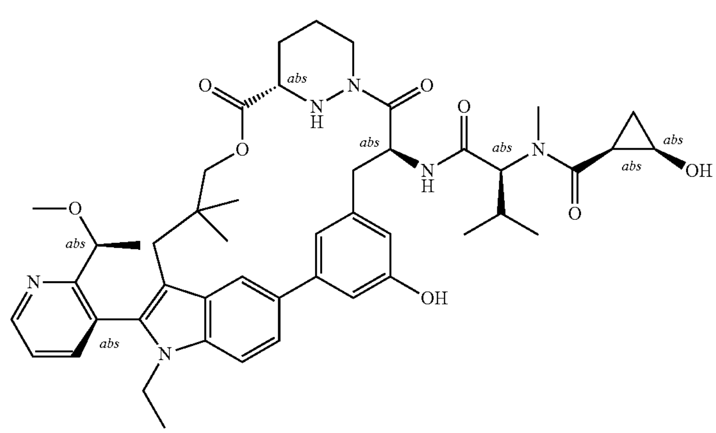 |

TABLE 2-continued
Certain Compounds of the Present Invention
| Ex# | Structure |
|---|---|
| B190 | 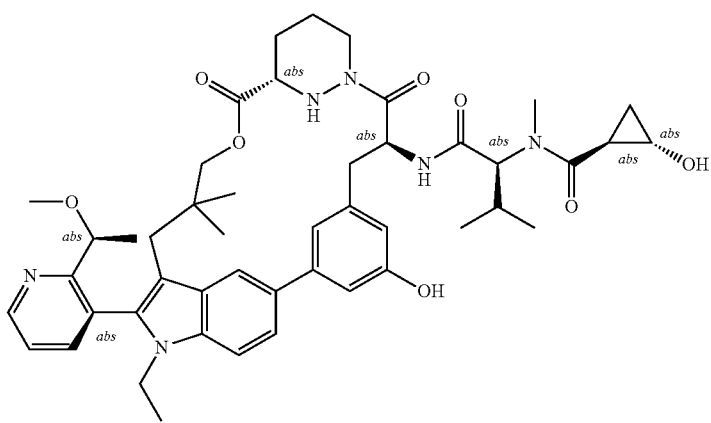 |
| B191 | 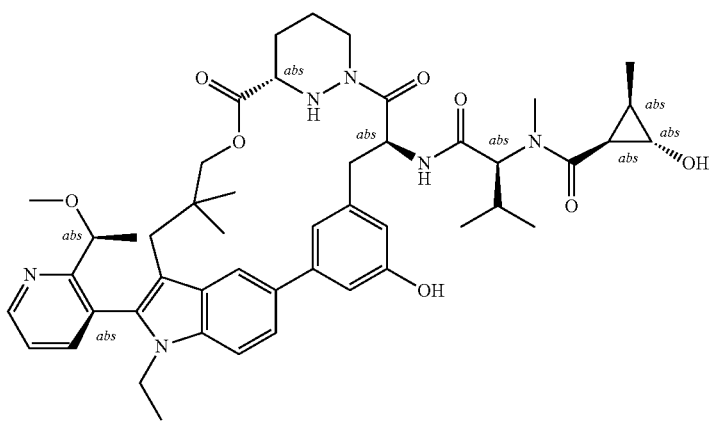 |
| B192 | 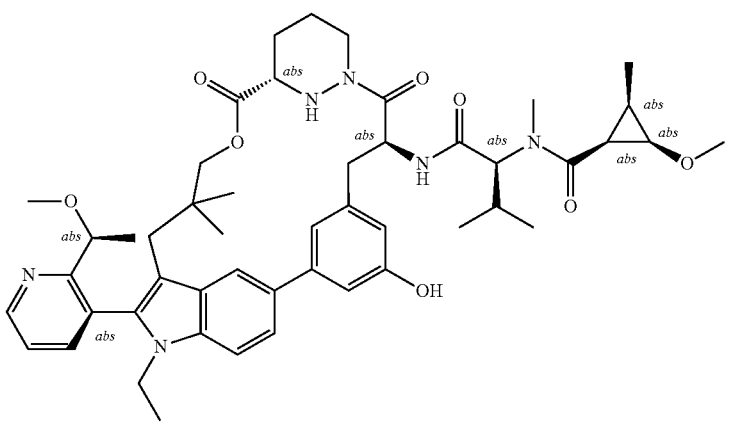 |

TABLE 2-continued
Certain Compounds of the Present Invention
| Ex# | Structure |
|---|---|
| B193 | 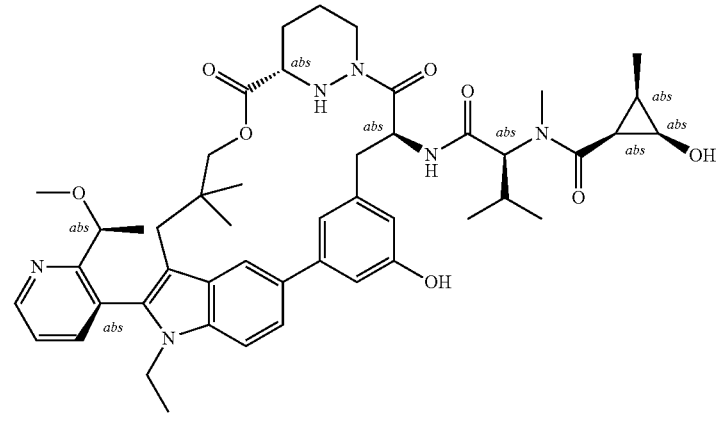 |
| B194 | 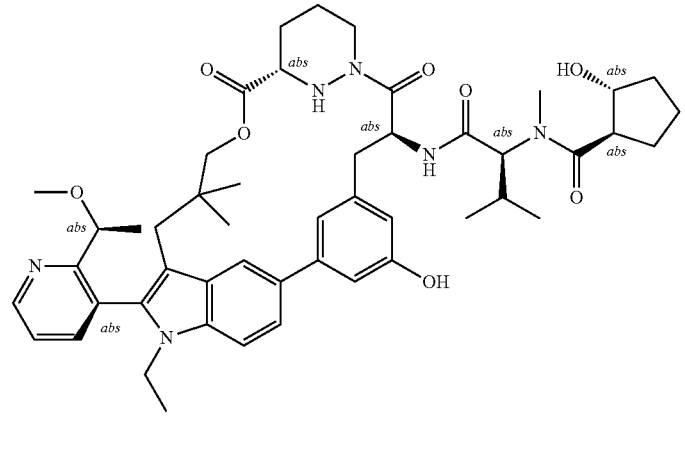 |
| B195 | 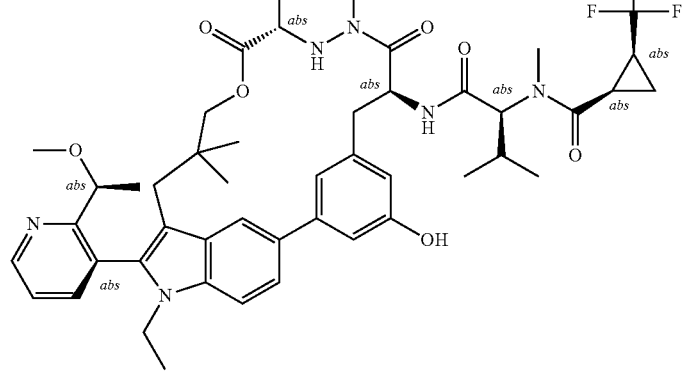 |

TABLE 2-continued
Certain Compounds of the Present Invention
| Ex# | Structure |
|---|---|
| B196 | 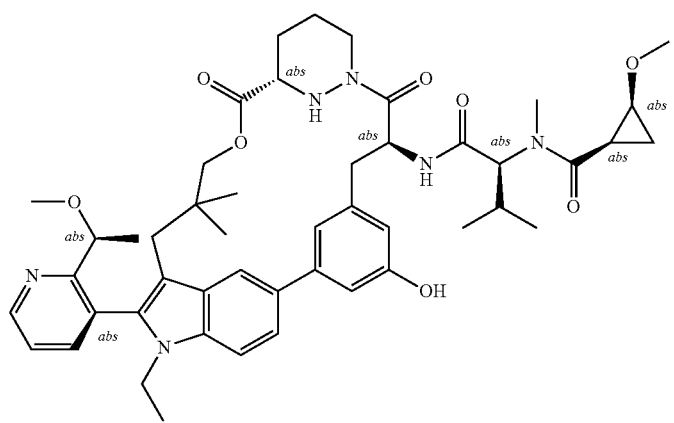 |
| B197 | 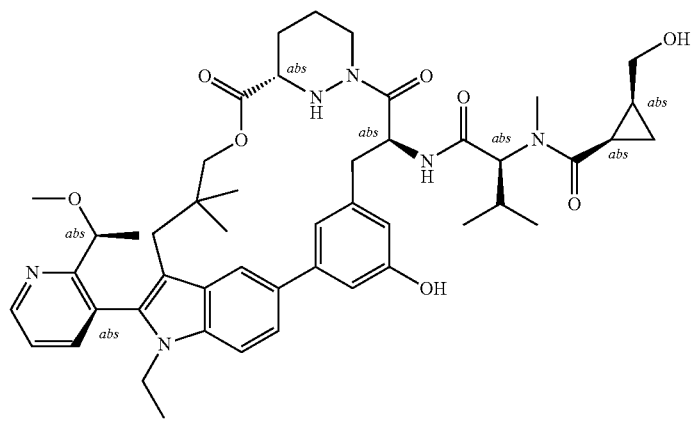 |
| B198 | 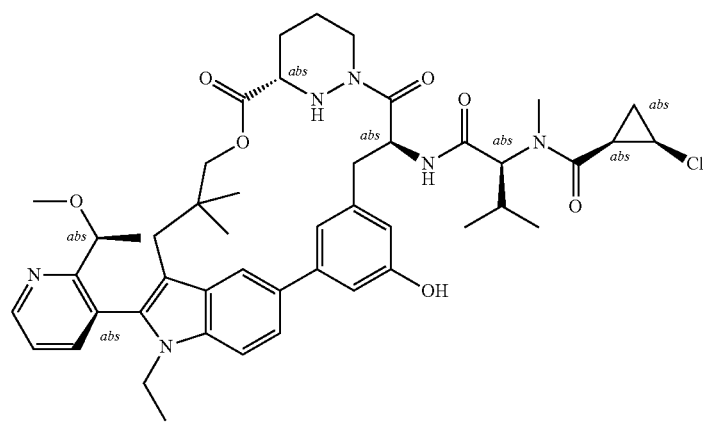 |

TABLE 2-continued

Certain Compounds of the Present Invention

| Ex# | Structure |
|---|---|
| B199 | 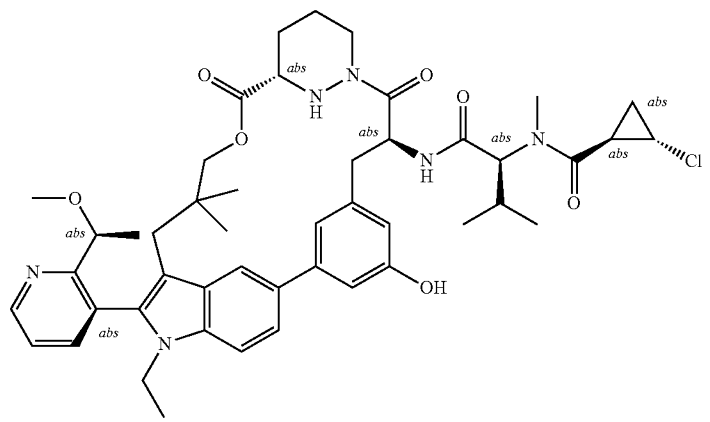 |
| B200 | 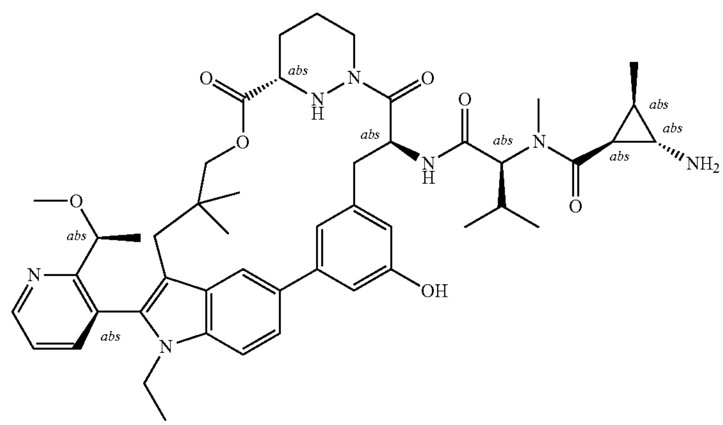 |
| B201 | 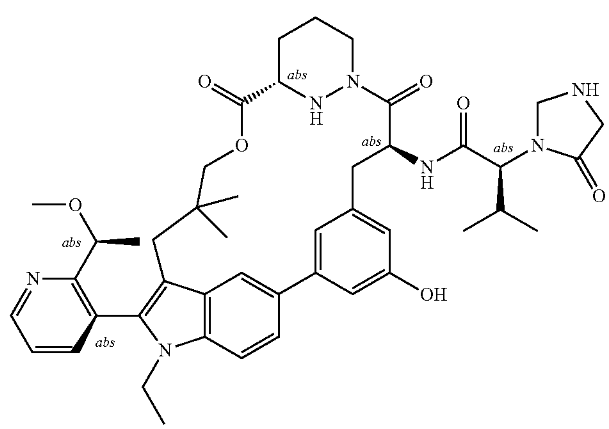 |

TABLE 2-continued
Certain Compounds of the Present Invention
| Ex# | Structure |
|---|---|
| B202 | 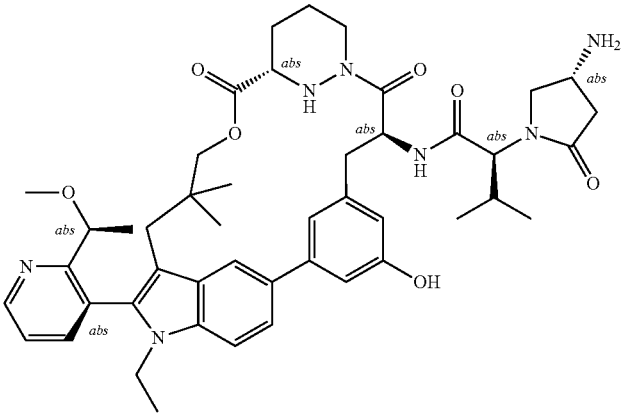 |
| B203 | 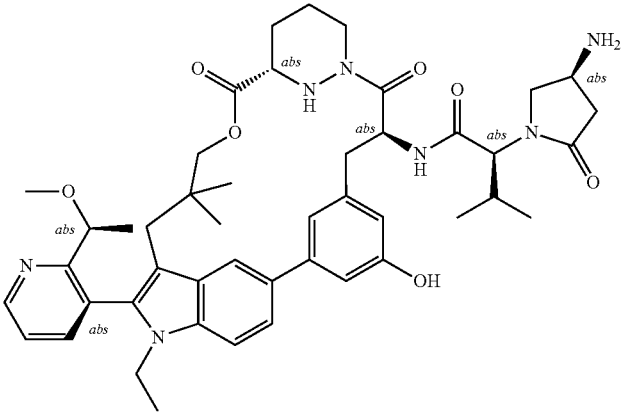 |
| B204 | 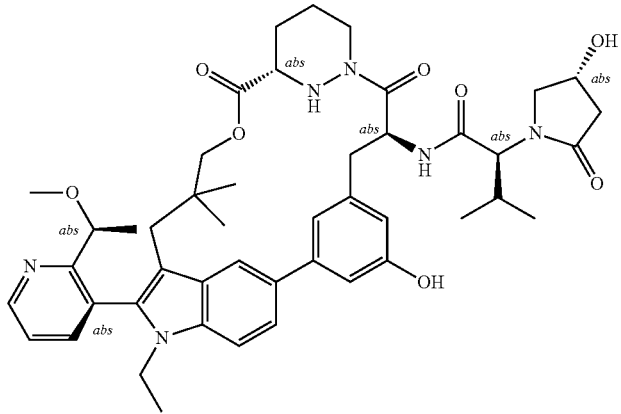 |

TABLE 2-continued
Certain Compounds of the Present Invention
| Ex# | Structure |
|---|---|
| B205 | 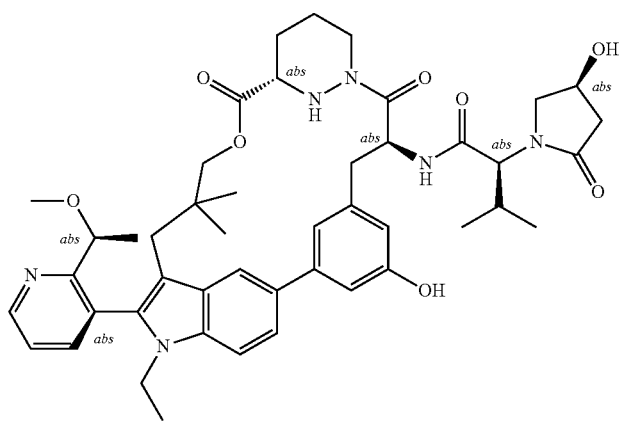 |
| B206 | 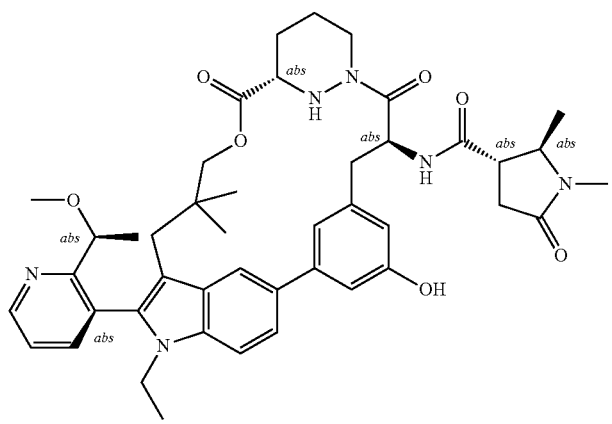 |
| B207 | 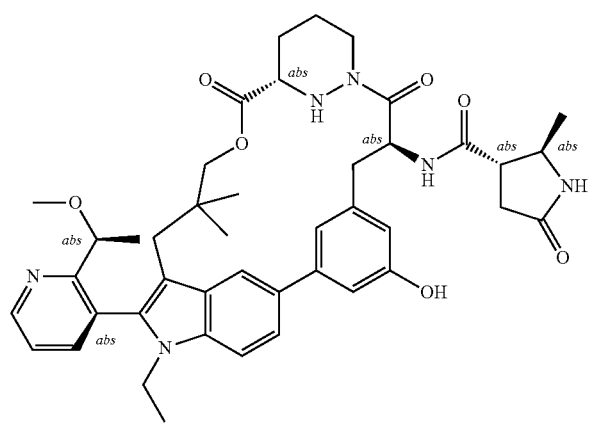 |

TABLE 2-continued
Certain Compounds of the Present Invention
| Ex# | Structure |
|---|---|
| B208 | 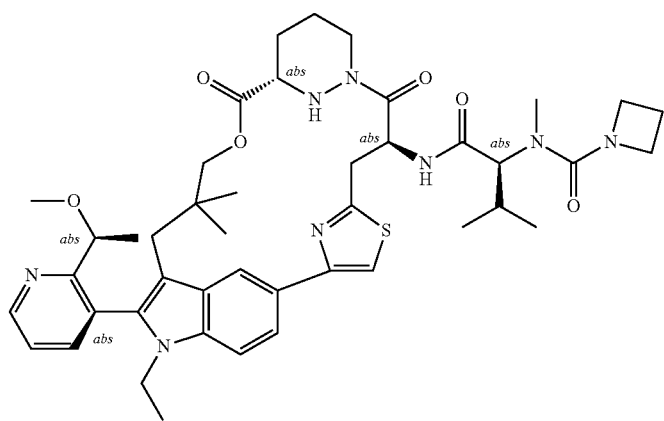 |
| B209 | 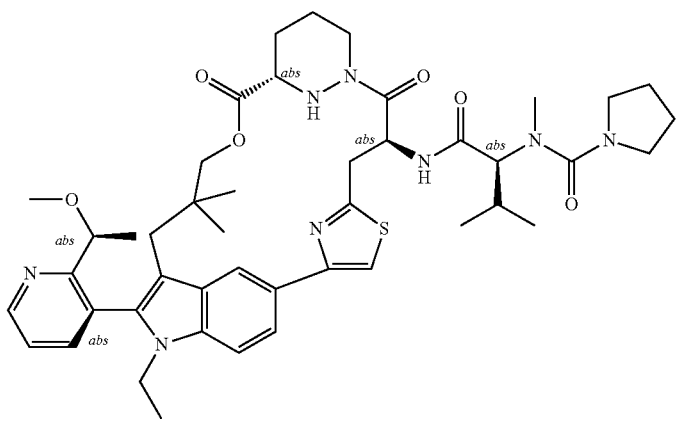 |
| B210 | 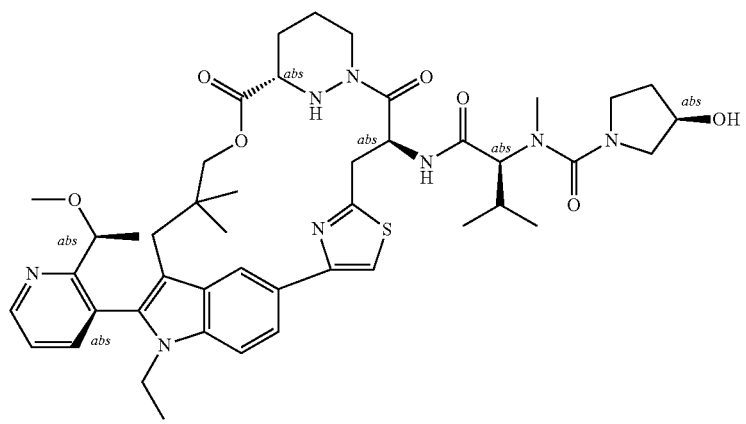 |

TABLE 2-continued
Certain Compounds of the Present Invention
| Ex# | Structure |
|---|---|
| B211 | 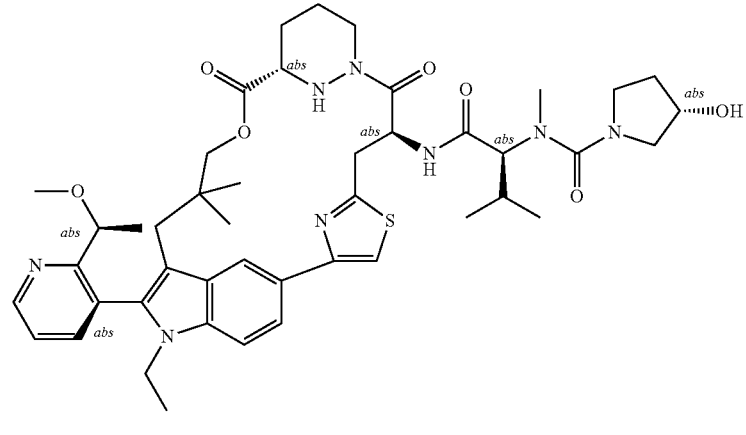 |
| B212 | 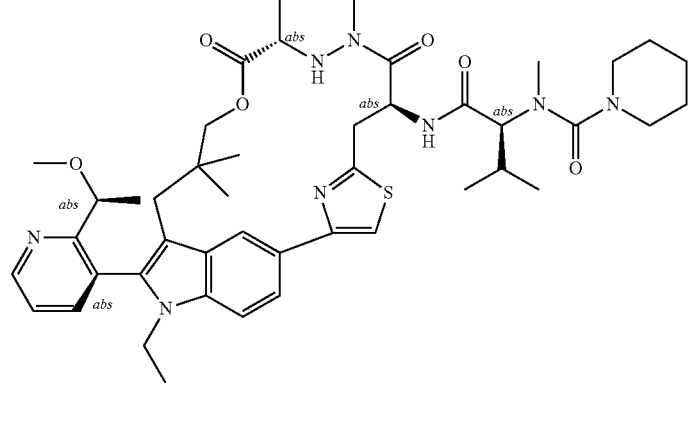 |
| B213 | 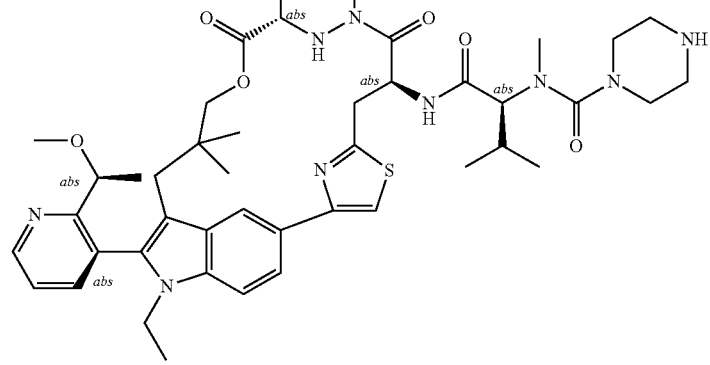 |

TABLE 2-continued
Certain Compounds of the Present Invention
| Ex# | Structure |
|---|---|
| B214 | 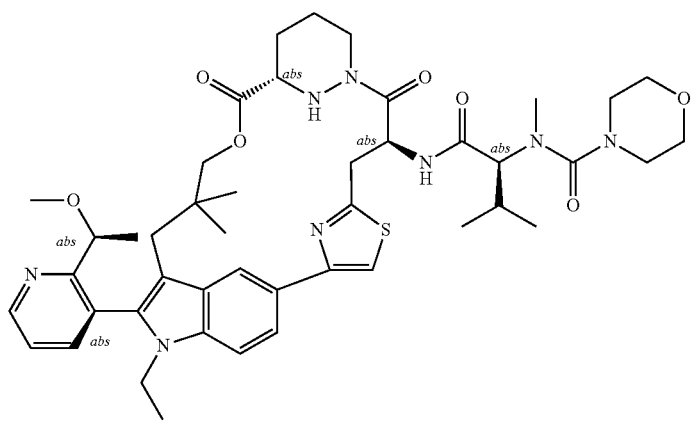 |
| B215 | 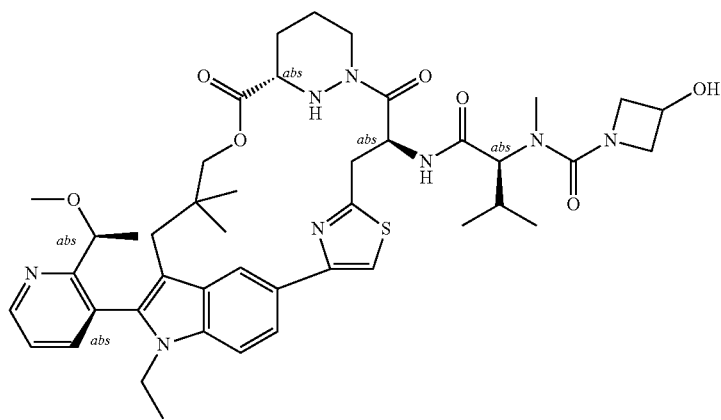 |
| B216 | 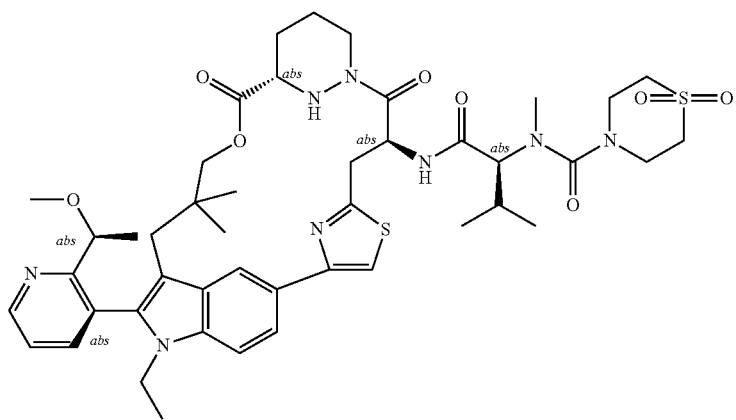 |

TABLE 2-continued
Certain Compounds of the Present Invention
| Ex# | Structure |
|---|---|
| B217 | 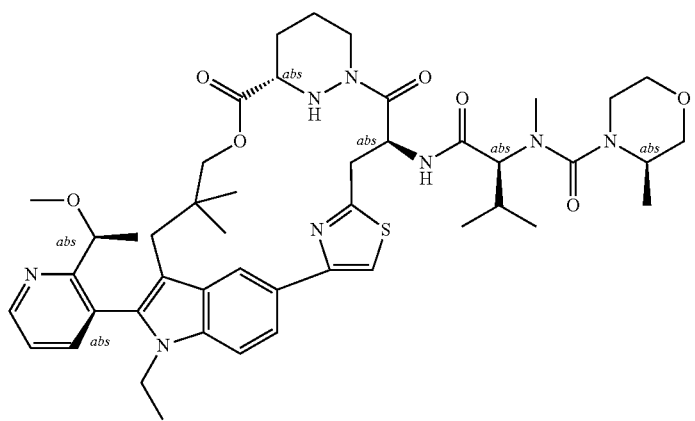 |
| B218 | 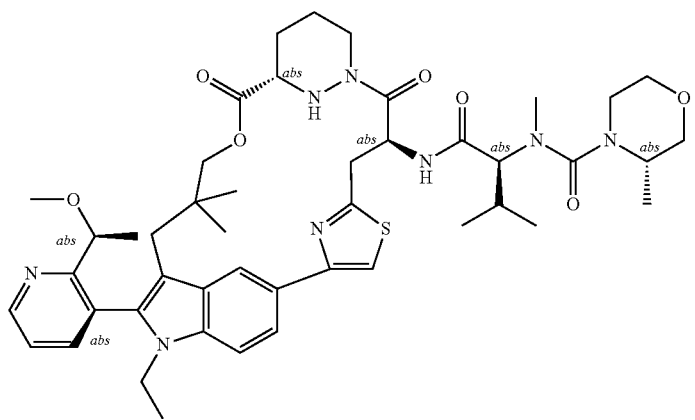 |
| B219 | 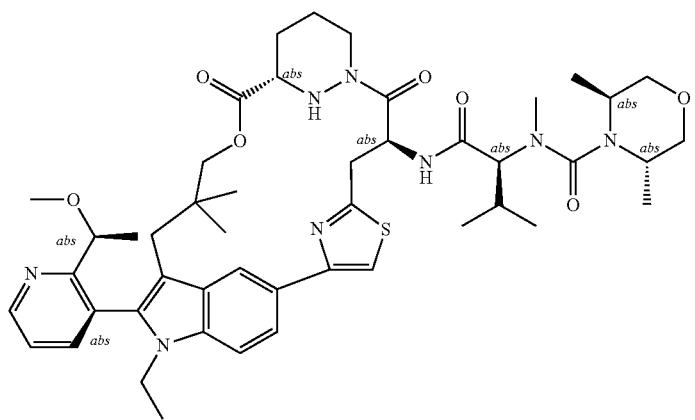 |

TABLE 2-continued

Certain Compounds of the Present Invention

| Ex# | Structure |
|---|---|
| B220 | 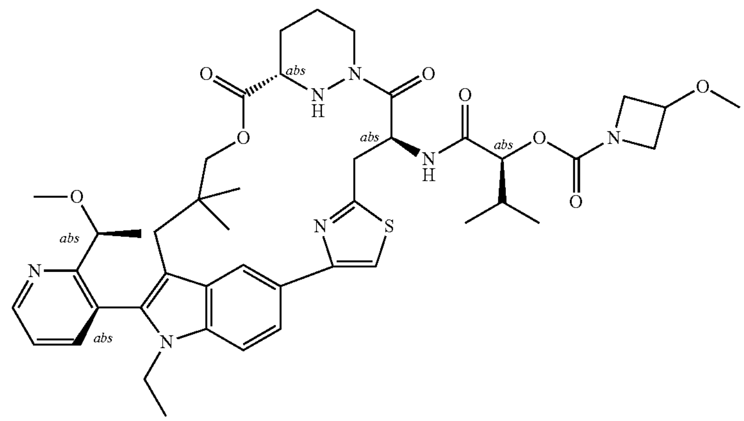 |
| B221 | 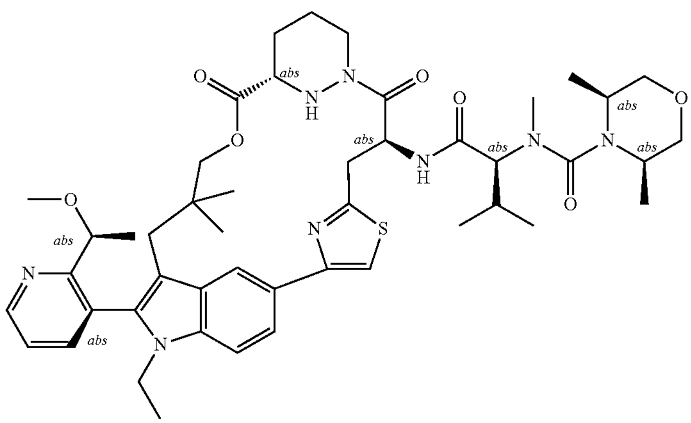 |
| B222 | 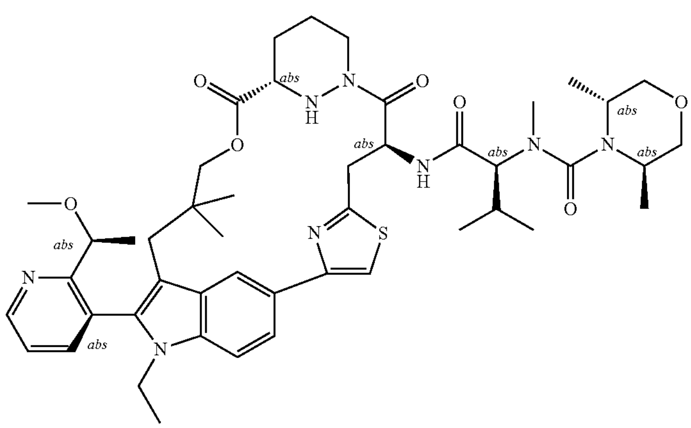 |

TABLE 2-continued
Certain Compounds of the Present Invention
| Ex# | Structure |
|---|---|
| B223 | 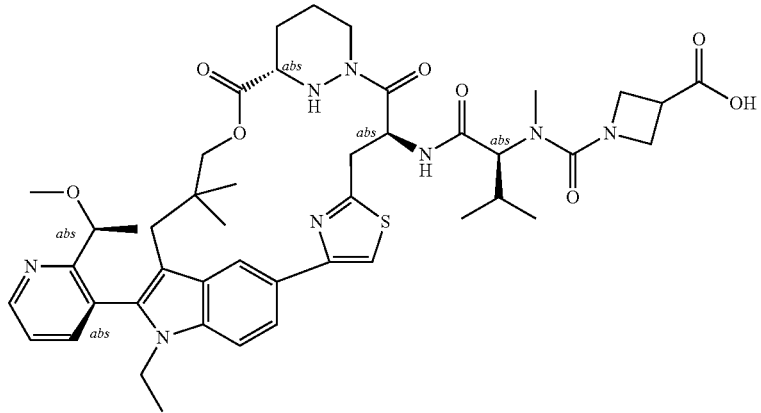 |
| B224 | 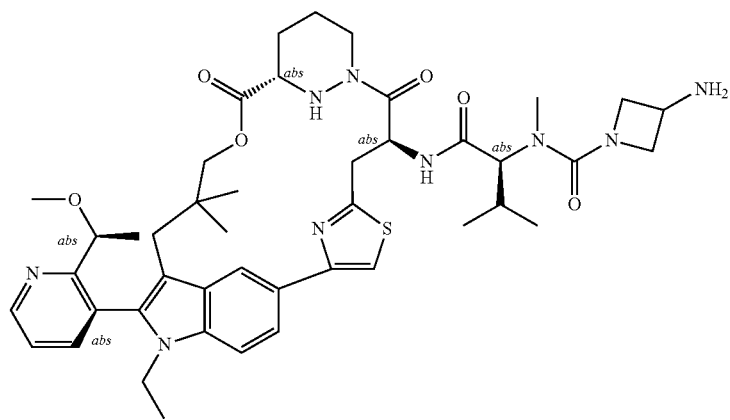 |
| B225 | 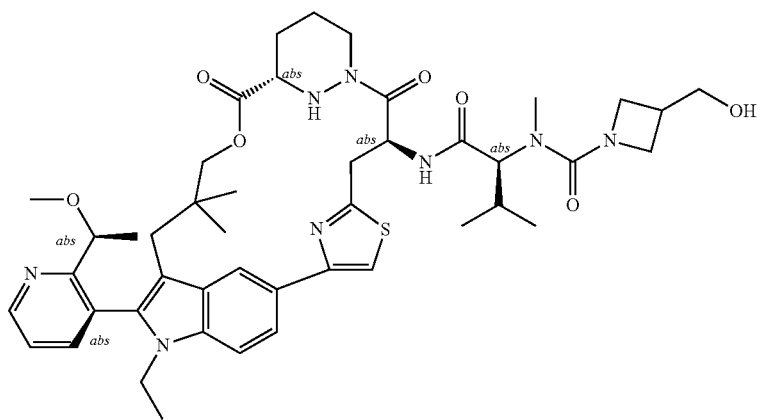 |

TABLE 2-continued

Certain Compounds of the Present Invention

| Ex# | Structure |
|---|---|
| B226 | 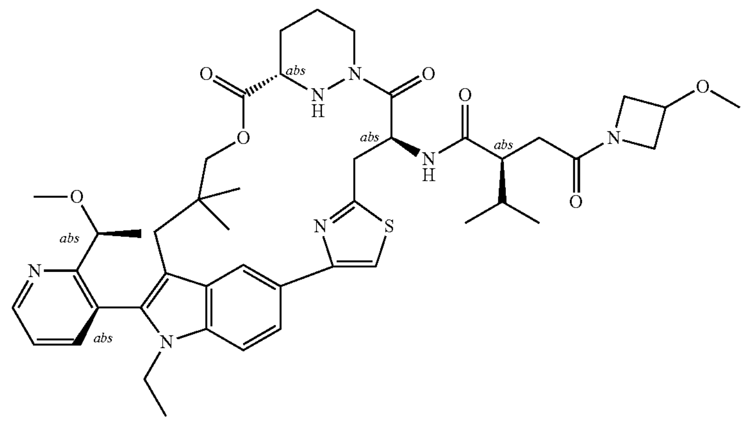 |
| B227 | 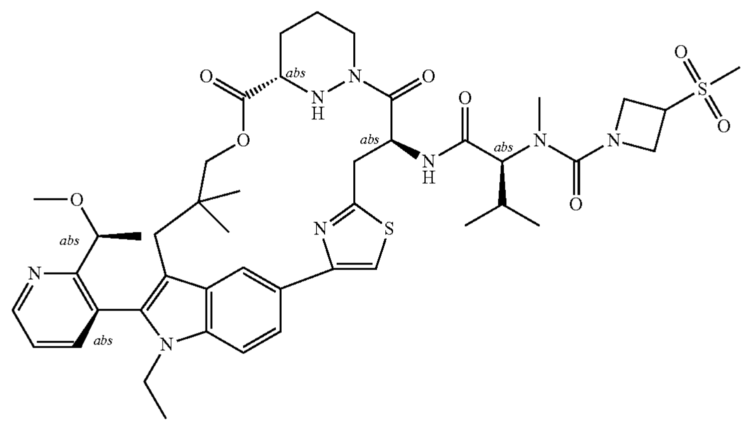 |
| B228 | 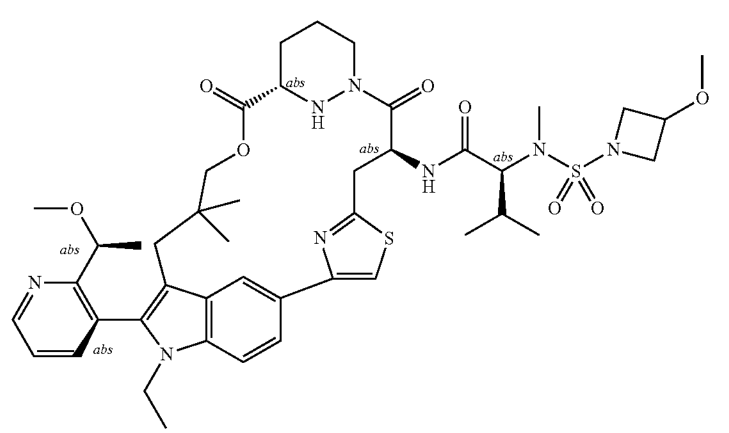 |

TABLE 2-continued

Certain Compounds of the Present Invention

| Ex# | Structure |
|---|---|
| B229 | 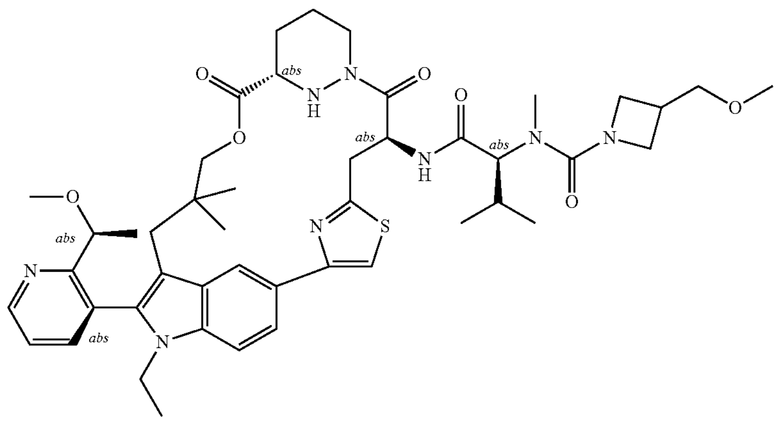 |
| B230 | 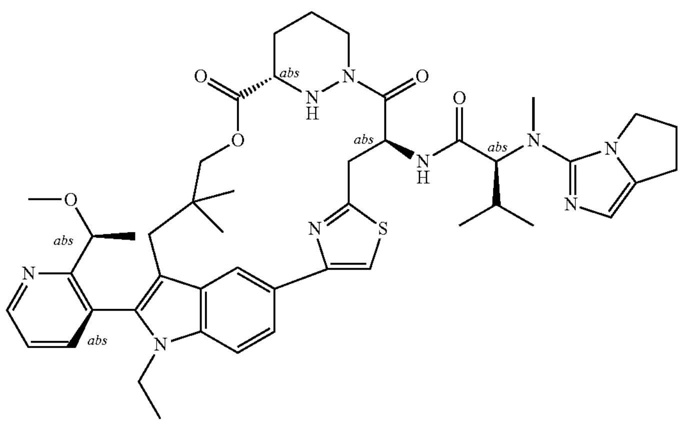 |
| B231 | 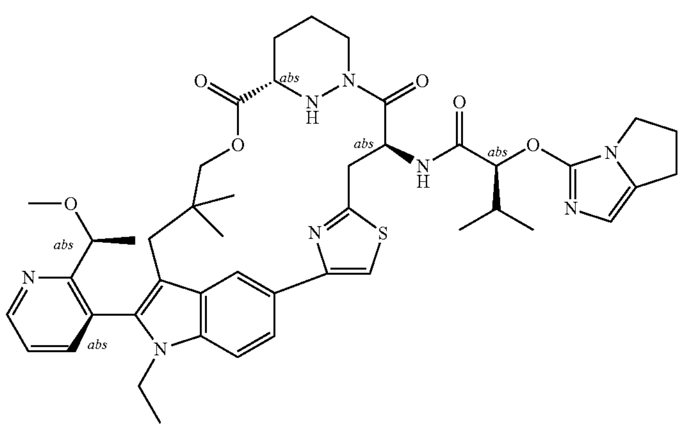 |

TABLE 2-continued
Certain Compounds of the Present Invention
| Ex# | Structure |
|---|---|
| B232 | 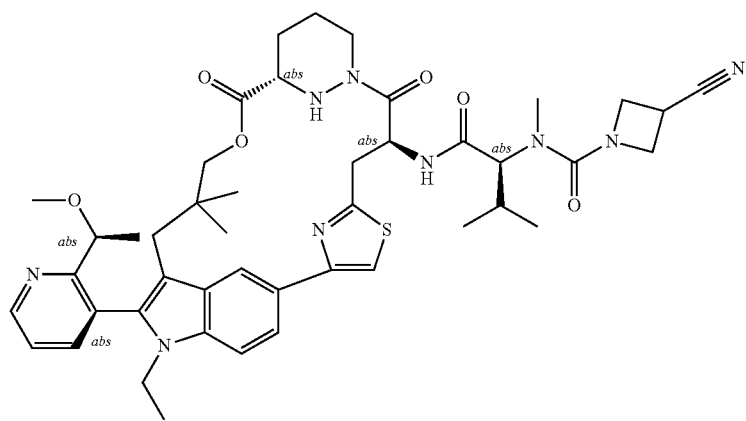 |
| B233 | 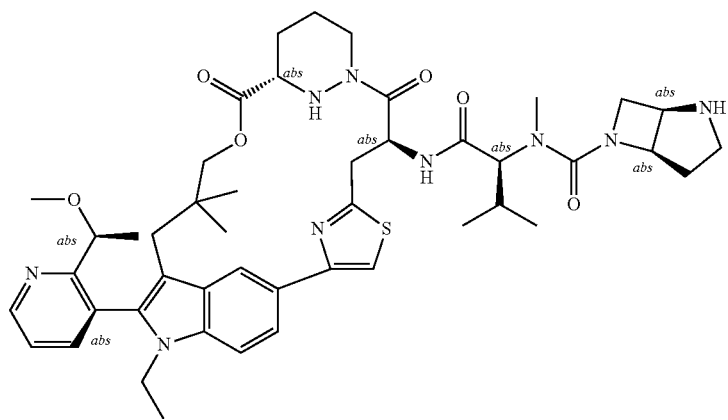 |
| B234 | 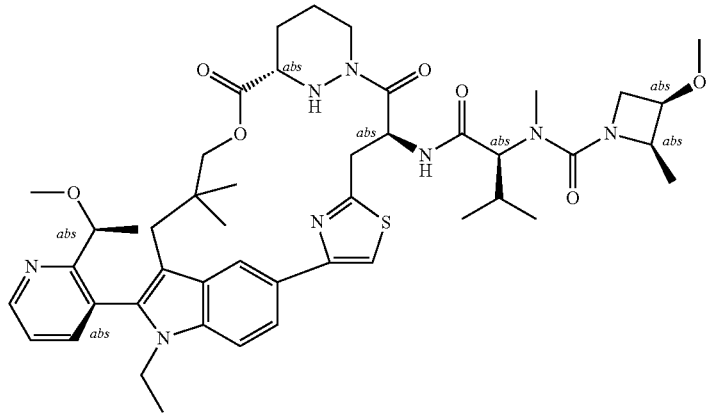 |

TABLE 2-continued
Certain Compounds of the Present Invention
| Ex# | Structure |
| --- | --- |
| B235 | 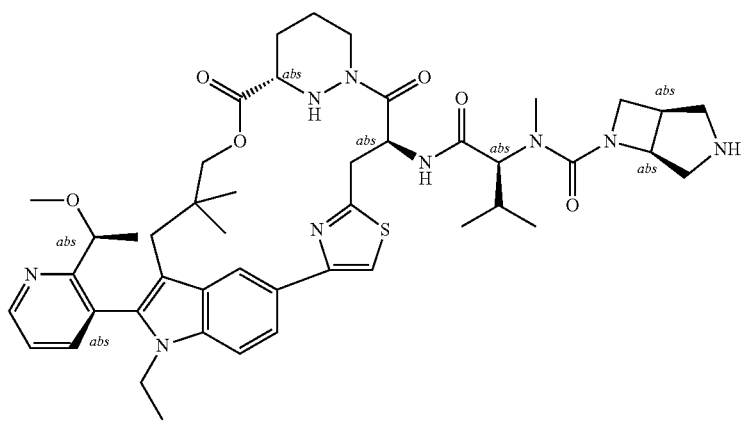 |
| B236 | 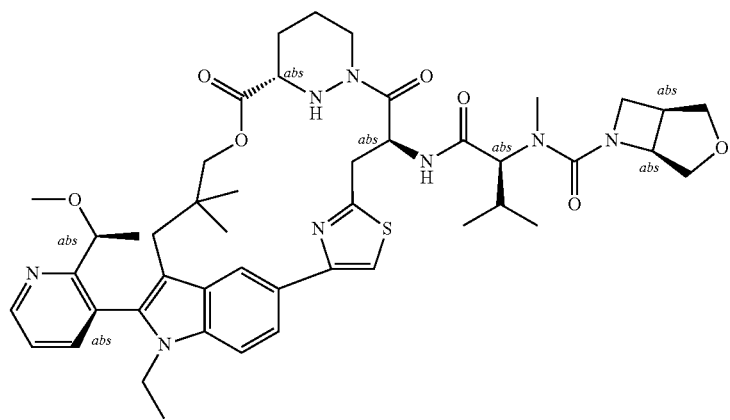 |
| B237 | 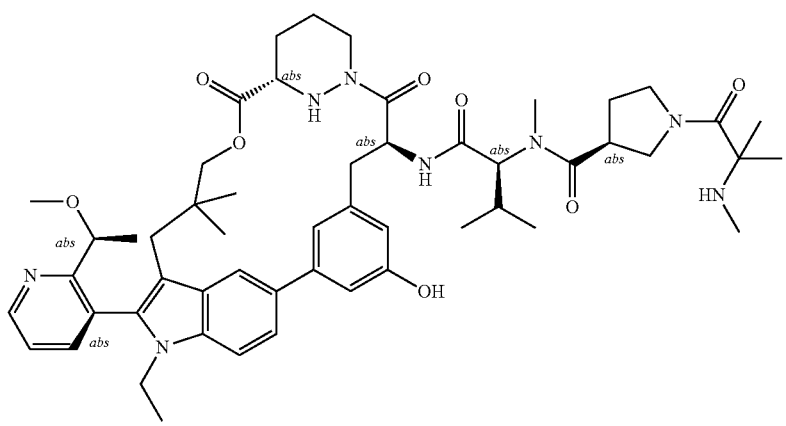 |

TABLE 2-continued
Certain Compounds of the Present Invention
| Ex# | Structure |
|---|---|
| B238 | 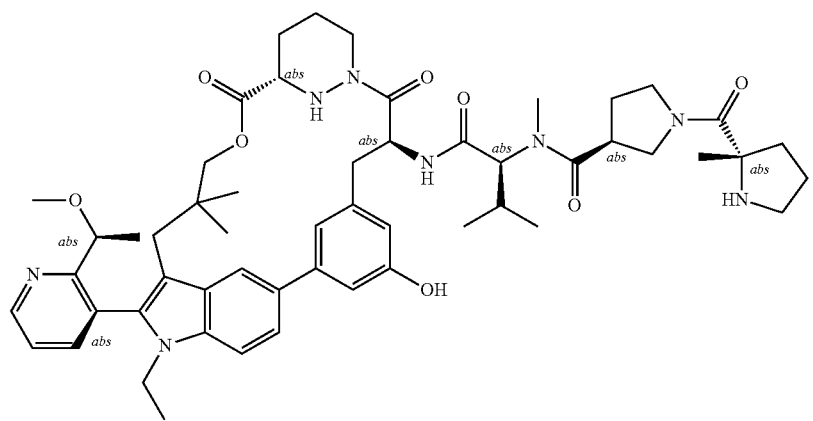 |
| B239 | 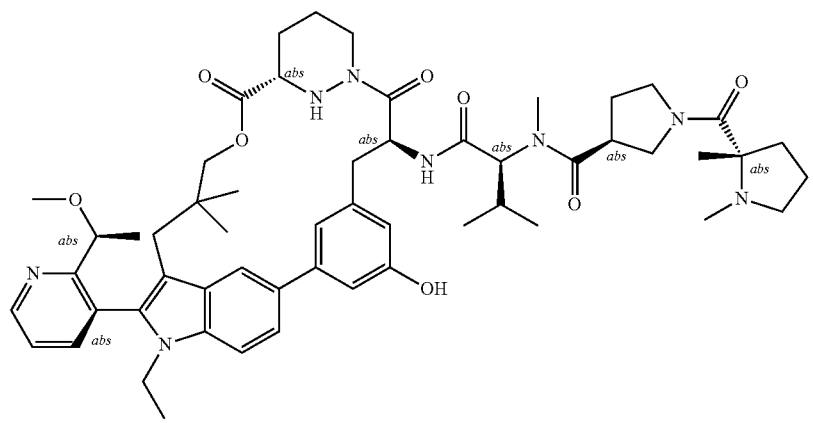 |
| B240 | 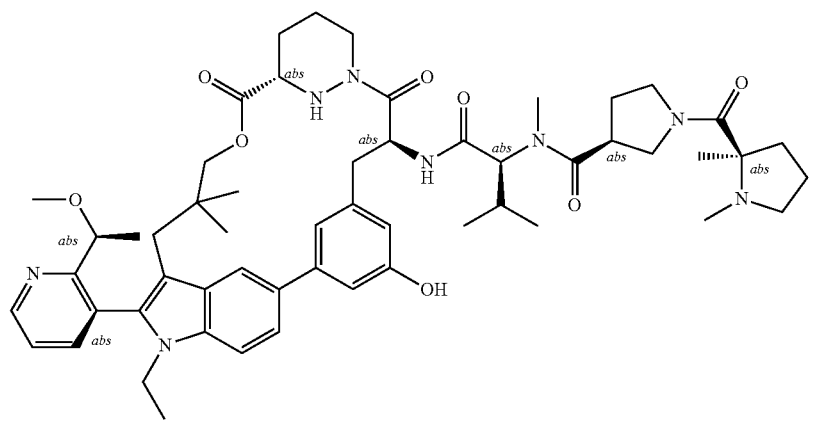 |

TABLE 2-continued
Certain Compounds of the Present Invention
| Ex# | Structure |
|---|---|
| B241 | 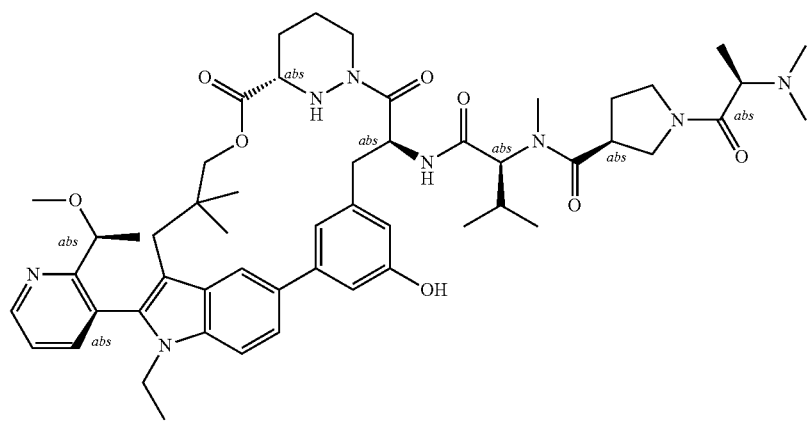 |
| B242 | 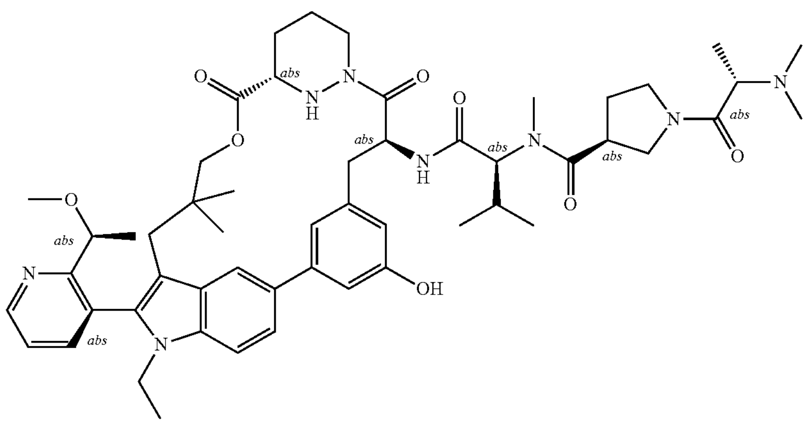 |
| B243 | 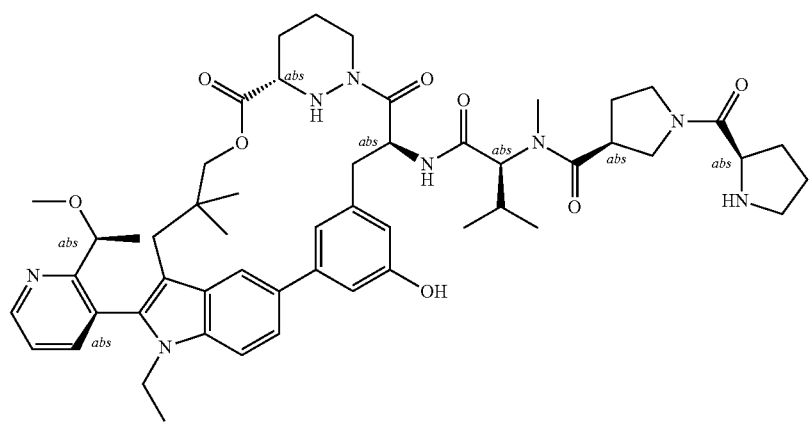 |

TABLE 2-continued
Certain Compounds of the Present Invention
| Ex# | Structure |
|---|---|
| B244 | 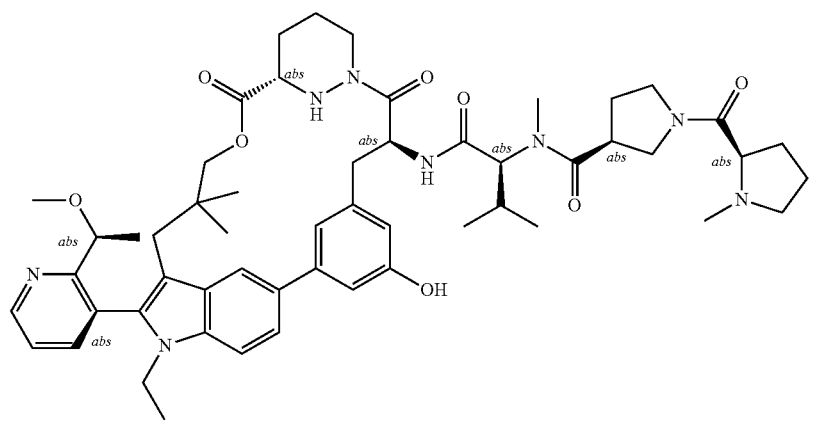 |
| B245 | 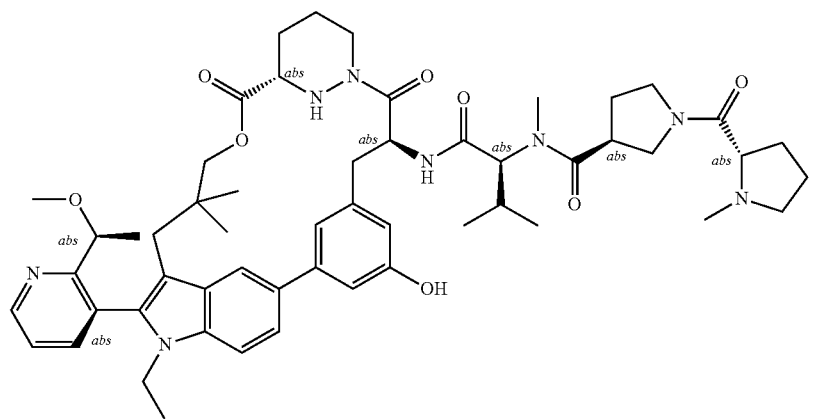 |
| B246 | 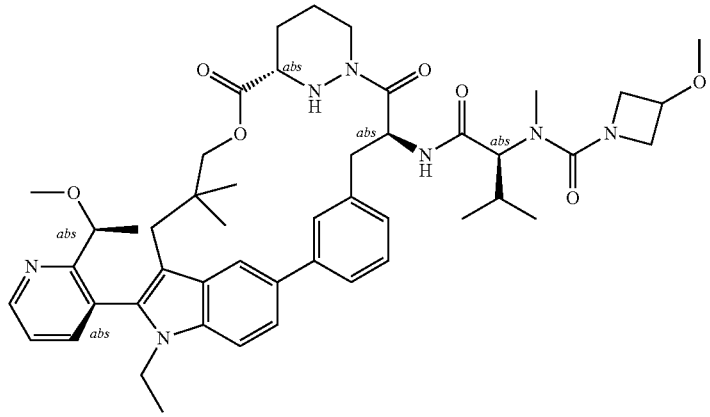 |

TABLE 2-continued

Certain Compounds of the Present Invention

| Ex# | Structure |
|---|---|
| B247 | 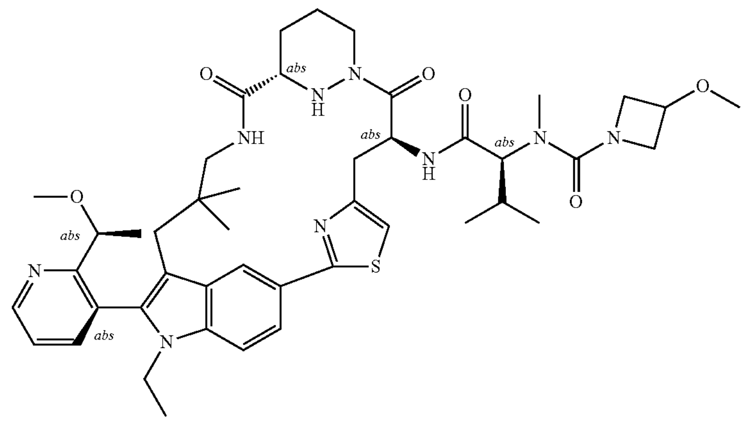 |
| B248 | 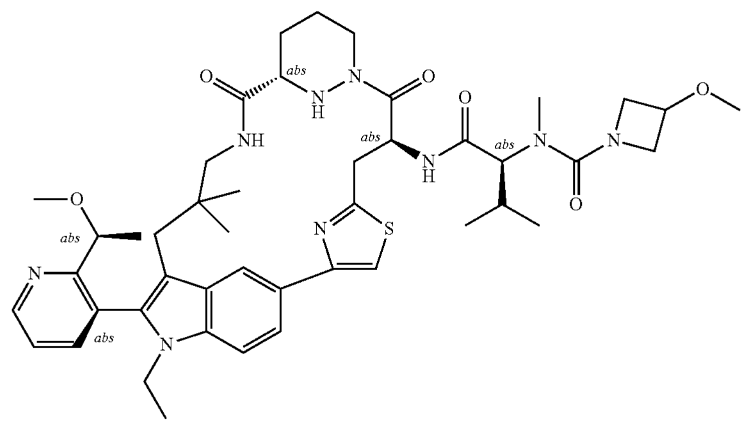 |
| B249 | 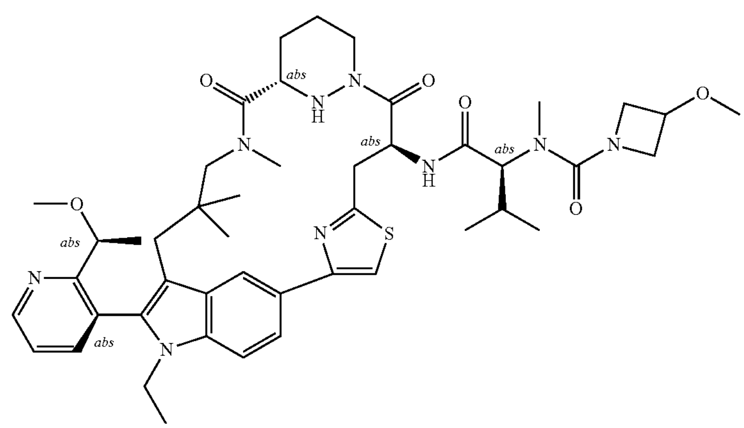 |

TABLE 2-continued
Certain Compounds of the Present Invention
| Ex# | Structure |
|---|---|
| B250 | 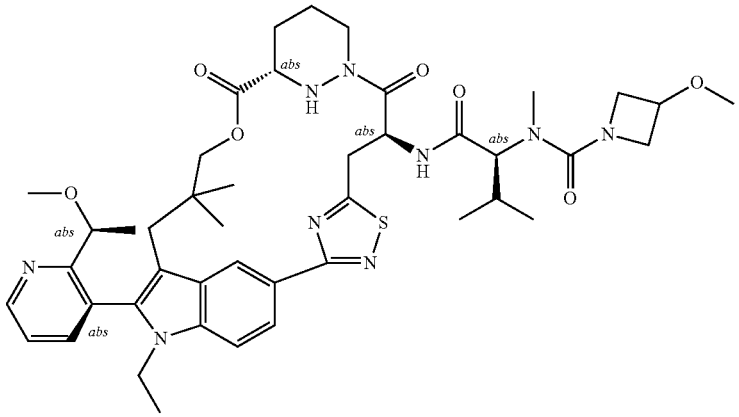 |
| B251 | 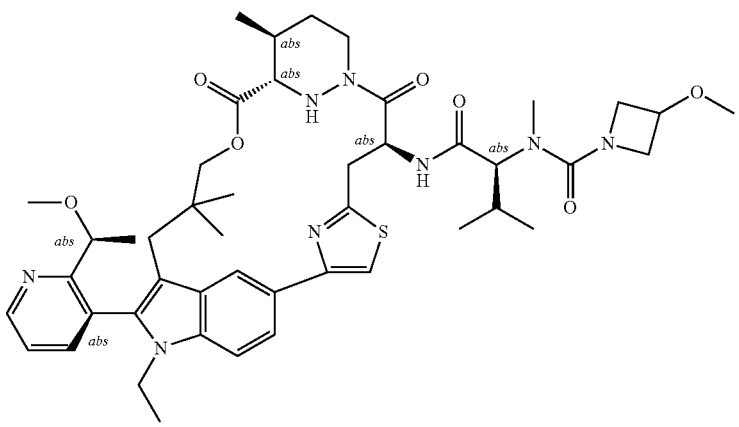 |
| B252 | 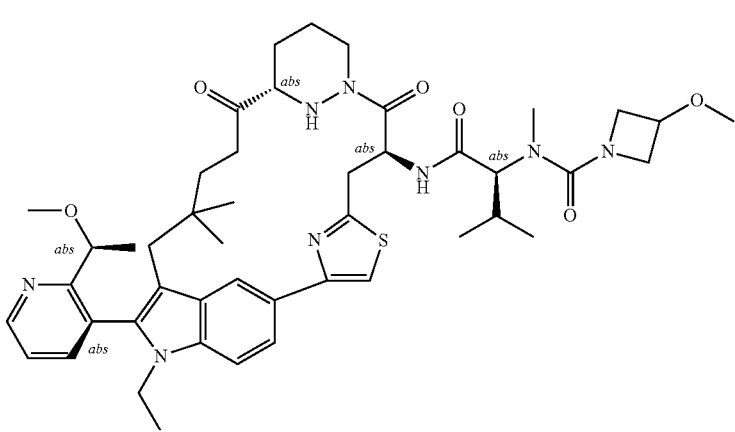 |

| Ex# | Structure |
|---|---|
| B253 | 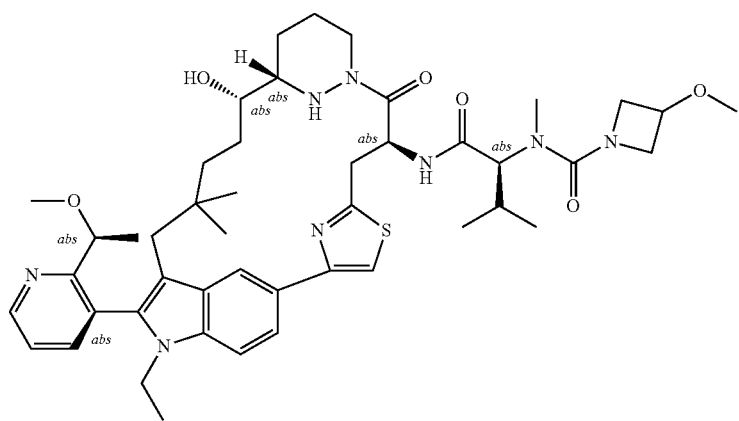 |
| B254 | 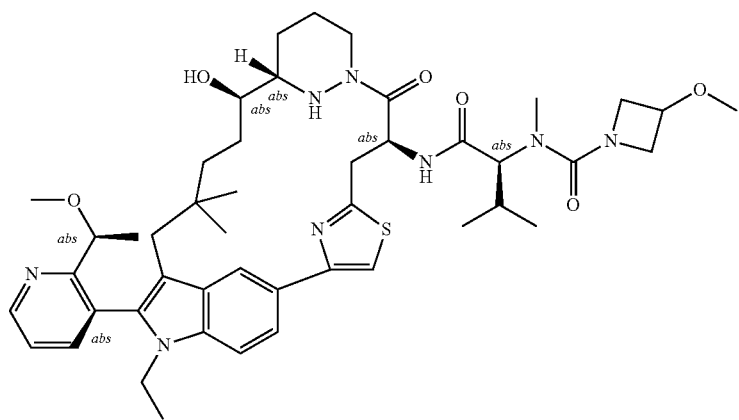 |
| B255 | 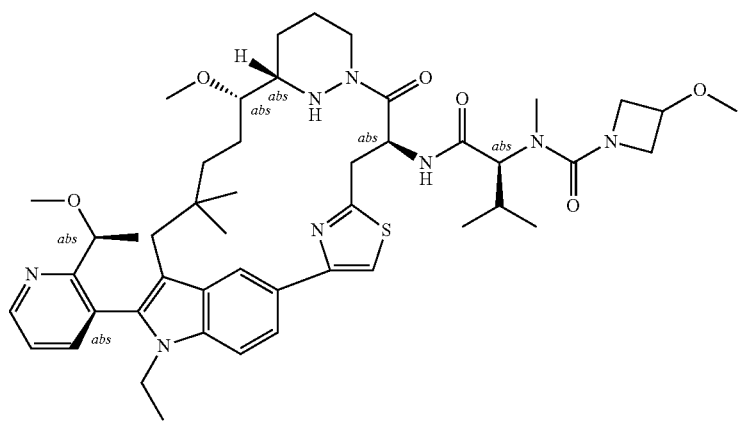 |

TABLE 2-continued
Certain Compounds of the Present Invention
| Ex# | Structure |
|---|---|
| B256 | 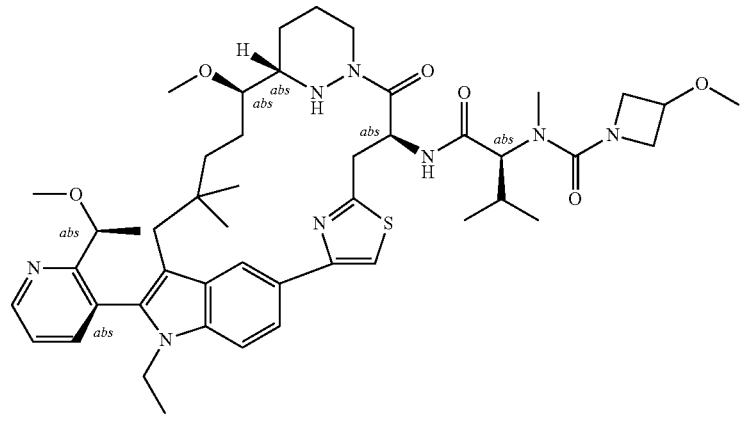 |
| B257 | 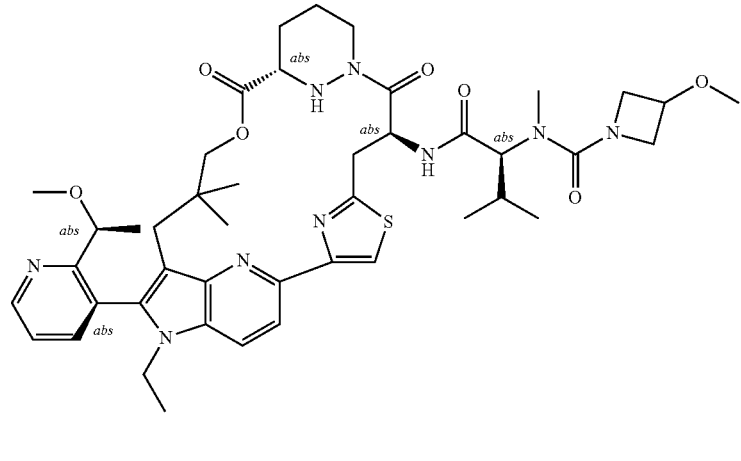 |
| B258 | 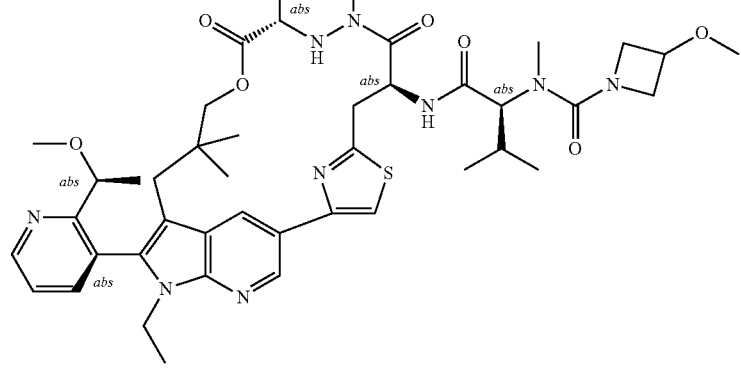 |

TABLE 2-continued
Certain Compounds of the Present Invention
| Ex# | Structure |
|---|---|
| B259 | 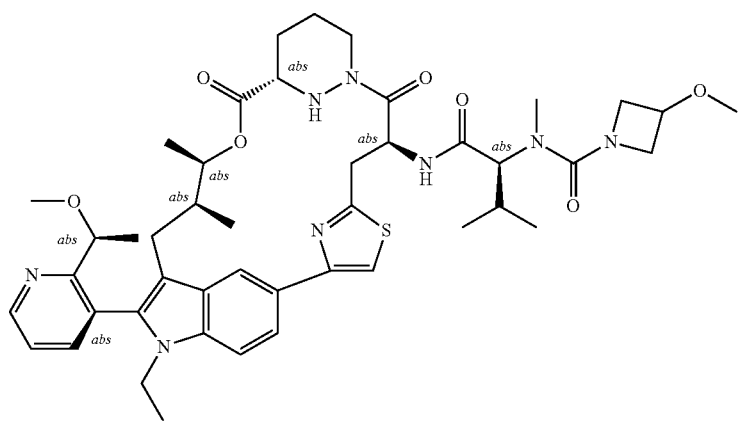 |
| B260 | 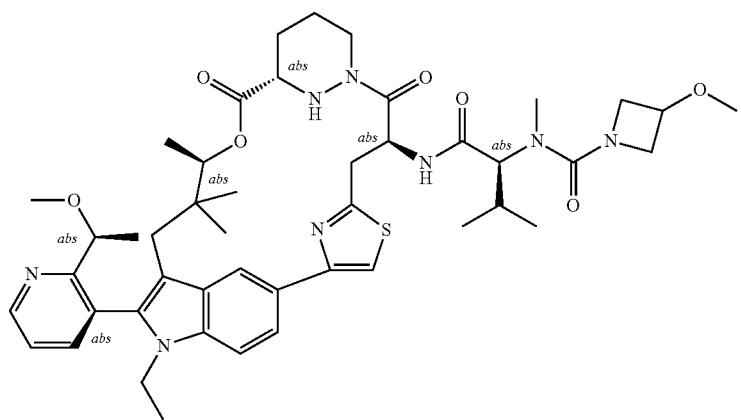 |
| B261 | 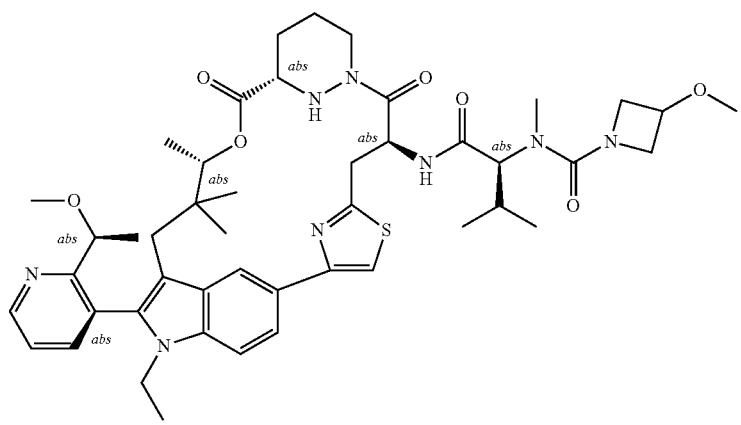 |

TABLE 2-continued

Certain Compounds of the Present Invention

| Ex# | Structure |
|---|---|
| B262 | 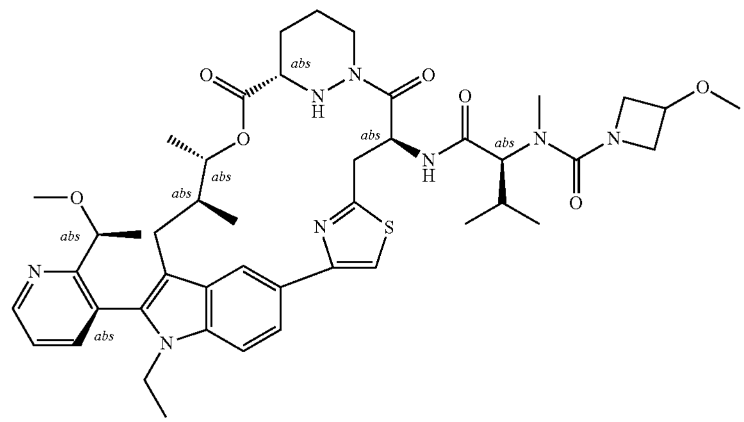 |
| B263 | 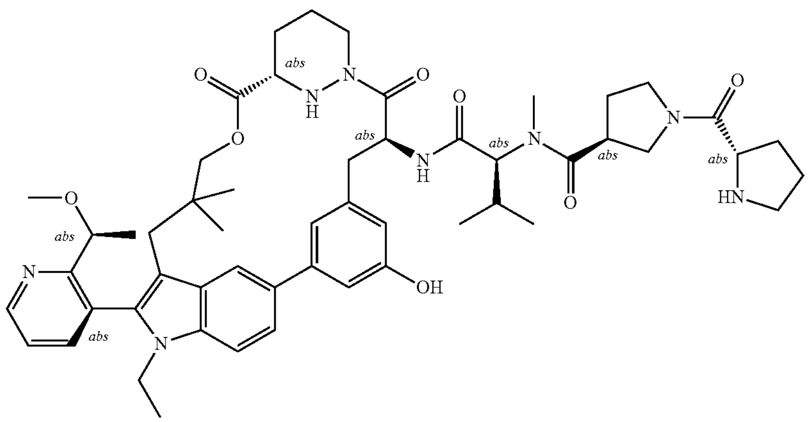 |

Note that some compounds are shown with bonds as flat or wedged. In some instances, the relative stereochemistry of stereoisomers has been determined; in some instances, the absolute stereochemistry has been determined. All stereoisomers of the compounds of the foregoing table are contemplated by the present invention. In particular embodiments, an atropisomer of a compound of the foregoing table is contemplated.

In some embodiments, a compound of the present invention is or acts as a prodrug, such as with respect to administration to a cell or to a subject in need thereof.

Also provided are pharmaceutical compositions comprising a compound of the present invention, or a pharmaceutically acceptable salt thereof, and a pharmaceutically acceptable excipient.

Further provided is a method of treating cancer in a subject in need thereof, the method comprising administering to the subject a therapeutically effective amount of a compound of the present invention, or a pharmaceutically acceptable salt thereof. The cancer may, for example, be pancreatic cancer, colorectal cancer, non-small cell lung cancer, acute myeloid leukemia, multiple myeloma, thyroid gland adenocarcinoma, a myelodysplastic syndrome, or squamous cell lung carcinoma. In some embodiments, the cancer comprises a Ras mutation, such as K-Ras G12C, K-Ras G12D, K-Ras G12V, K-Ras G12S, K-Ras G13C, K-Ras G13D, or K-Ras Q61L. Other Ras mutations are described herein.

Further provided is a method of treating a Ras protein-related disorder in a subject in need thereof, the method comprising administering to the subject a therapeutically effective amount of a compound of the present invention, or a pharmaceutically acceptable salt thereof.

Further provided is a method of inhibiting a Ras protein in a cell, the method comprising contacting the cell with an effective amount of a compound of the present invention, or a pharmaceutically acceptable salt thereof. For example, the Ras protein is K-Ras G12C, K-Ras G12D, K-Ras G12V, K-Ras G12S, K-Ras G13C, K-Ras G13D, or K-Ras Q61L. Other Ras proteins are described herein. The cell may be a cancer cell, such as a pancreatic cancer cell, a colorectal cancer cell, a non-small cell lung cancer cell, an acute myeloid leukemia cell, a multiple myeloma cell, a thyroid gland adenocarcinoma cell, a myelodysplastic syndrome cell, or a squamous cell lung carcinoma cell. Other cancer types are described herein. The cell may be in vivo or in vitro.

With respect to compounds of the present invention, one stereoisomer may exhibit better inhibition than another stereoisomer. For example, one atropisomer may exhibit inhibition, whereas the other atropisomer may exhibit little or no inhibition.

In some embodiments, a method or use described herein further comprises administering an additional anti-cancer therapy. In some embodiments, the additional anti-cancer therapy is a HER2 inhibitor, an EGFR inhibitor, a second Ras inhibitor, a SHP2 inhibitor, a SOS1 inhibitor, a Raf inhibitor, a MEK inhibitor, an ERK inhibitor, a PI3K inhibitor, a PTEN inhibitor, an AKT inhibitor, an mTORC1 inhibitor, a BRAF inhibitor, a PD-L1 inhibitor, a PD-1 inhibitor, a CDK4/6 inhibitor, or a combination thereof. In some embodiments, the additional anticancer therapy is a SHP2 inhibitor. Other additional anti-cancer therapies are described herein.

Methods of Synthesis

The compounds described herein may be made from commercially available starting materials or synthesized using known organic, inorganic, or enzymatic processes.

The compounds of the present invention can be prepared in a number of ways well known to those skilled in the art of organic synthesis. By way of example, compounds of the present invention can be synthesized using the methods described in the Schemes below, together with synthetic methods known in the art of synthetic organic chemistry, or variations thereon as appreciated by those skilled in the art. These methods include but are not limited to those methods described in the Schemes below.

Compounds of Table 1 herein were prepared using methods disclosed herein or were prepared using methods disclosed herein combined with the knowledge of one of skill in the art. Compounds of Table 2 may be prepared using methods disclosed herein or may be prepared using methods disclosed herein combined with the knowledge of one of skill in the art.

Scheme 1. General synthesis of macrocyclic esters

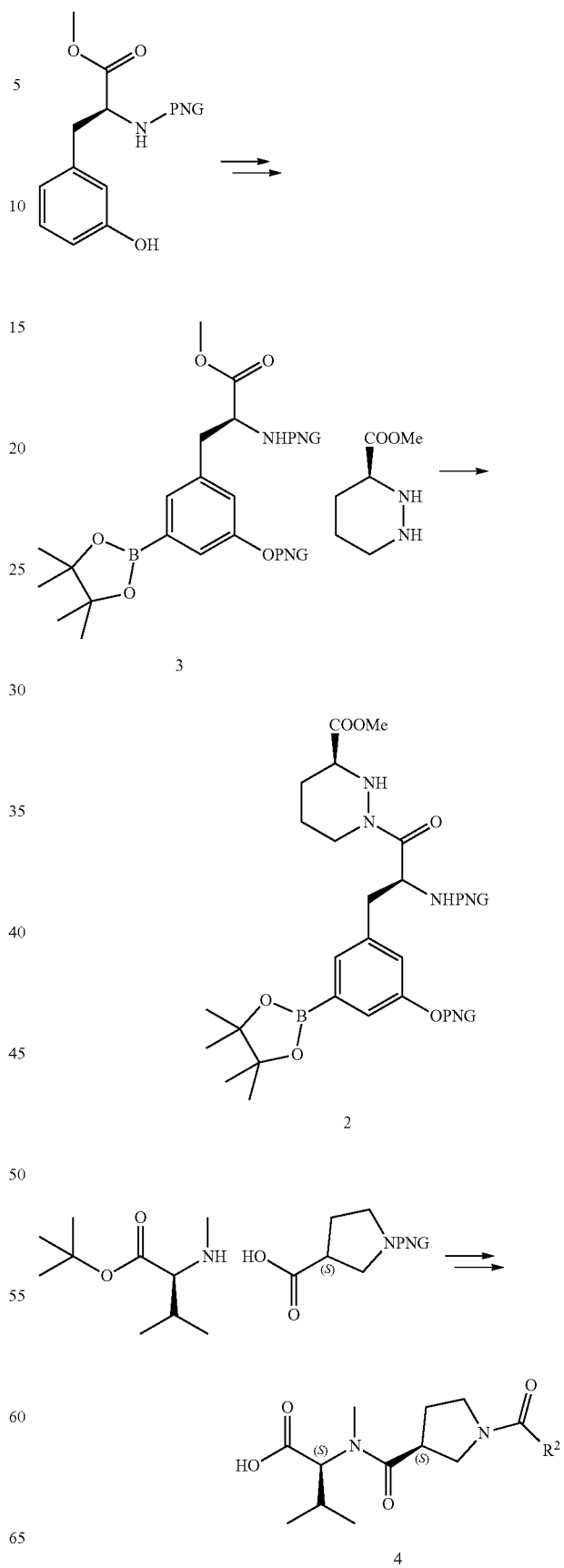

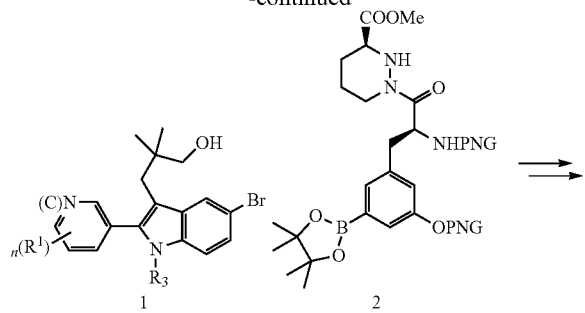

1

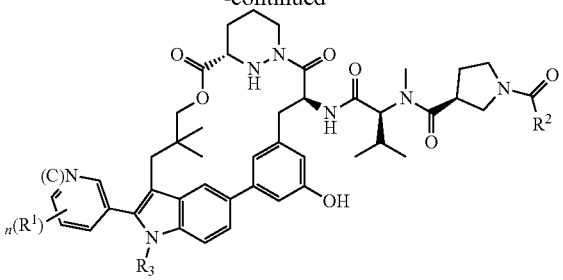

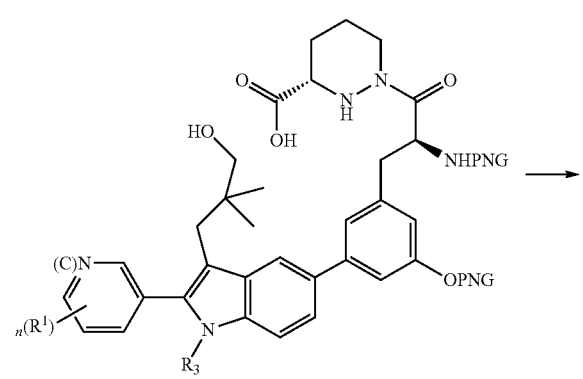

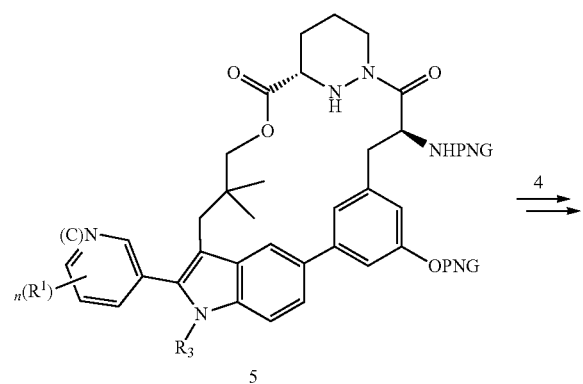

5

A general synthesis of macrocyclic esters is outlined in Scheme 1. An appropriately substituted Aryl Indole intermediate (1) can be prepared in three steps starting from protected 3-(5-bromo-2-iodo-1H-indol-3-yl)-2,2-dimethyl-propan-1-ol and appropriately substituted boronic acid, including Palladium mediated coupling, alkylation, and de-protection reactions. Methyl-amino-hexahydropyridazine-3-carboxylate-boronic ester (2) can be prepared in three steps, including protection, Iridium catalyst mediated borylation, and coupling with methyl (S)-hexahydropyridazine-3-carboxylate.

An appropriately substituted acetylpyrrolidine-3-carbonyl-N-methyl-L-valine (4) can be made by coupling of methyl-L-valinate and protected (S)-pyrrolidine-3-carboxylic acid, followed by deprotection, coupling with an appropriately substituted carboxylic acid, and a hydrolysis step.

The final macrocyclic esters can be made by coupling of methyl-amino-hexahydropyridazine-3-carboxylate-boronic ester (2) and intermediate (1) in the presence of Pd catalyst followed by hydrolysis and macrolactonization steps to result in an appropriately protected macrocyclic intermediate (5). Deprotection and coupling with an appropriately substituted acetylpyrrolidine-3-carbonyl-N-methyl-L-valine (4) results in a macrocyclic product. Additional deprotection or functionalization steps are be required to produce a final compound. For example, a person of skill in the art would be able to install into a macrocyclic ester a desired —B-L-W group of a compound of Formula (I), where B, L and W are defined herein, including by using methods exemplified in the Example section herein.

Scheme 2. Alternative general synthesis of macrocyclic esters

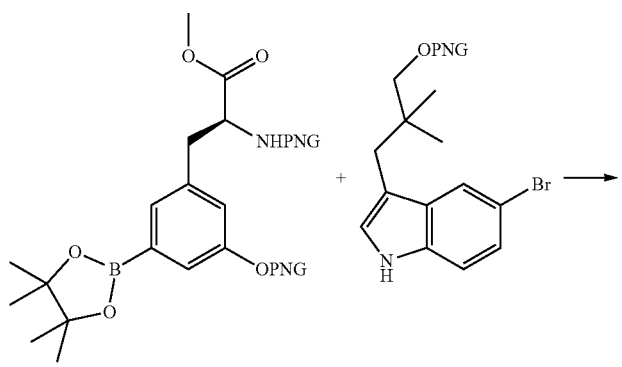

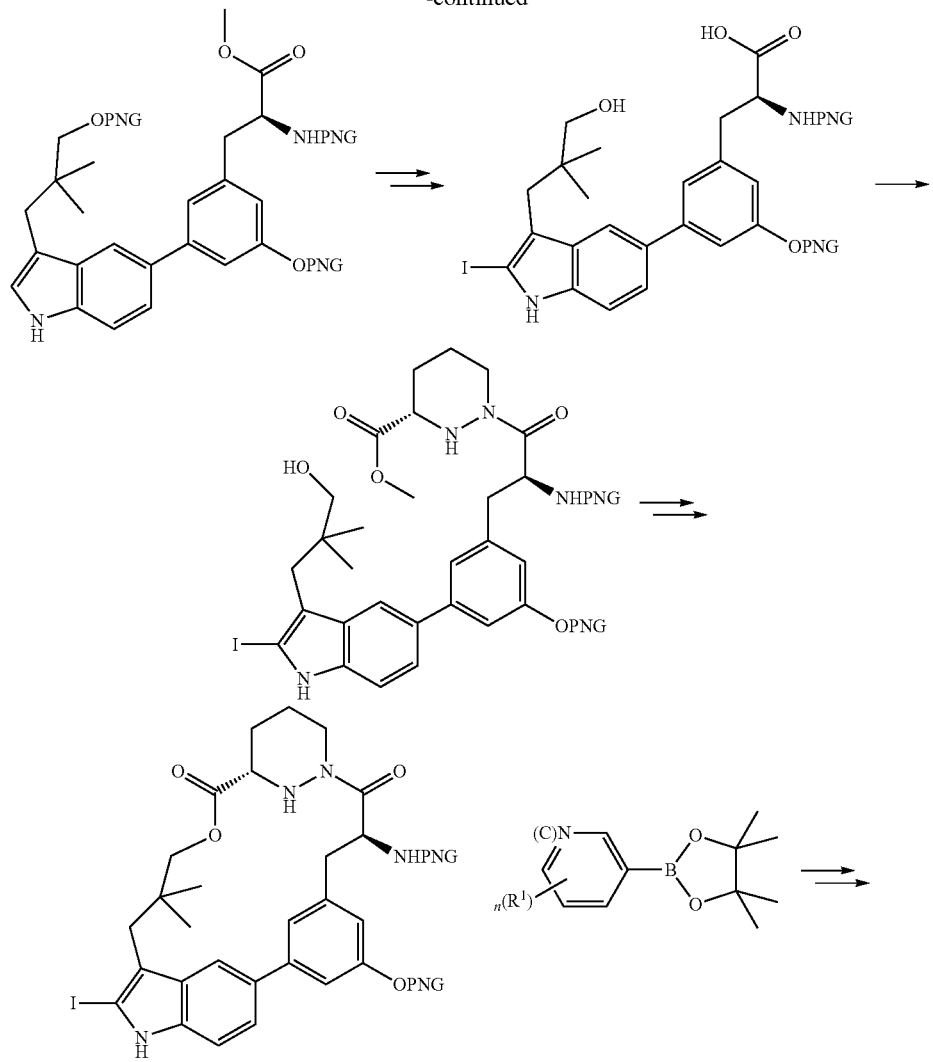

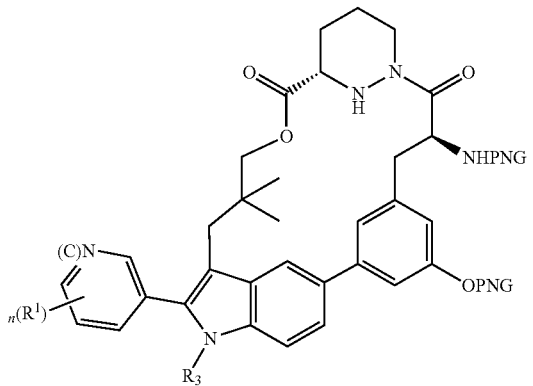

Alternatively, macrocyclic esters can be prepared as described in Scheme 2. An appropriately protected bromoindolyl (6) can be coupled in the presence of Pd catalyst with boronic ester (3), followed by iodination, deprotection, and ester hydrolysis. Subsequent coupling with methyl (S)-hexahydropyridazine-3-carboxylate, followed by hydrolysis and macrolactonization can result in iodo intermediate (7). Coupling in the presence of Pd catalyst with an appropriately substituted boronic ester and alkylation can yield fully a protected macrocycle (5). Additional deprotection or functionalization steps are required to produce a final compound. For example, a person of skill in the art would be able to install into a macrocyclic ester a desired —B-L-W group of a compound of Formula (I), where B, L and W are defined herein, including by using methods exemplified in the Example section herein.

Scheme 3. General synthesis of macrocyclic esters

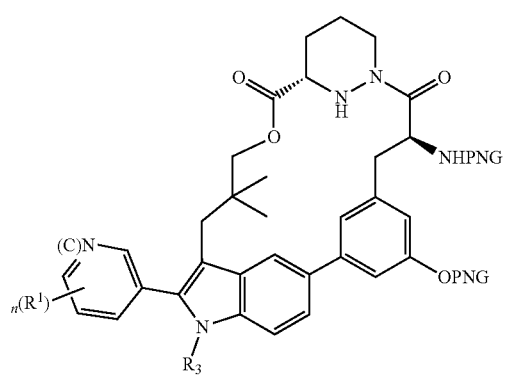

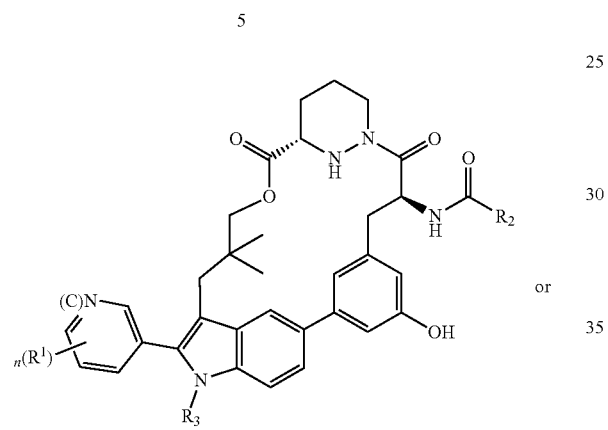

or

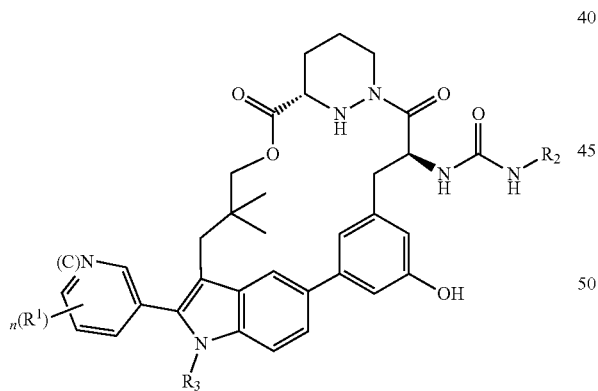

Alternatively, fully a protected macrocycle (5) can be deprotected and coupled with an appropriately substituted coupling partners, and deprotected to results in a macrocyclic product. Additional deprotection or functionalization steps are be required to produce a final compound. For example, a person of skill in the art would be able to install into a macrocyclic ester a desired —B-L-W group of a compound of Formula (I), where B, L and W are defined herein, including by using methods exemplified in the Example section herein.

Scheme 4. General synthesis of macrocyclic esters

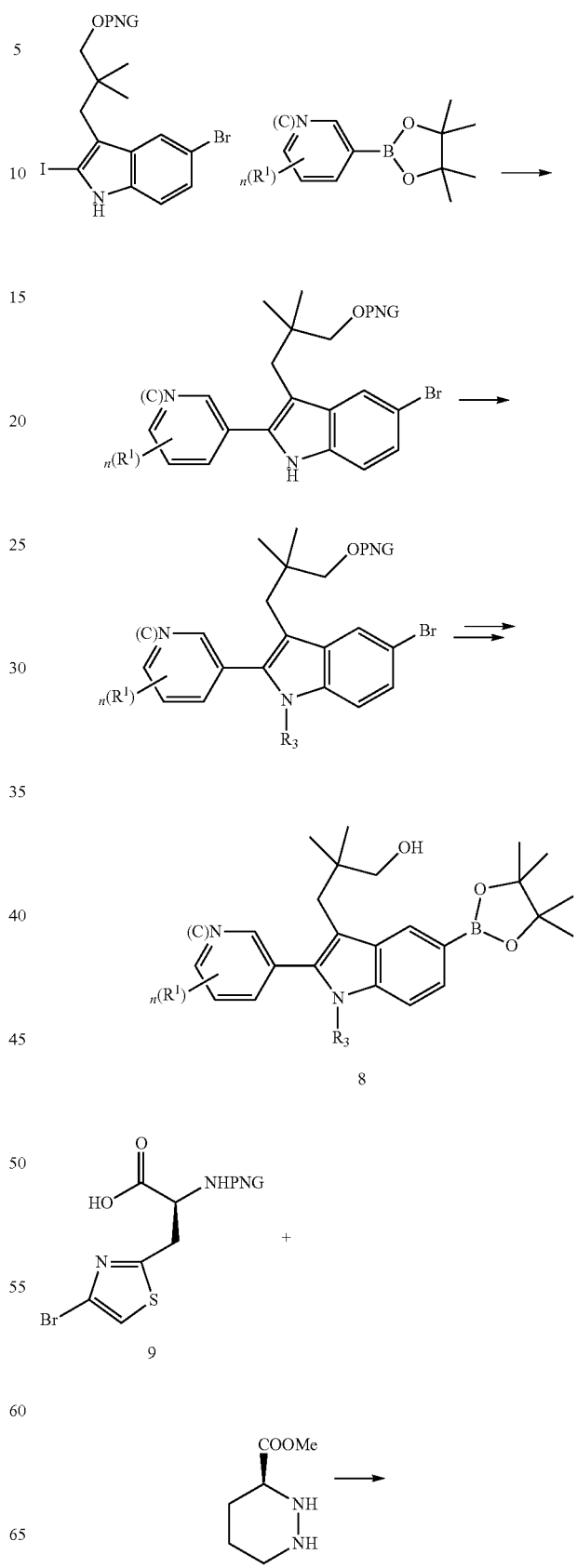

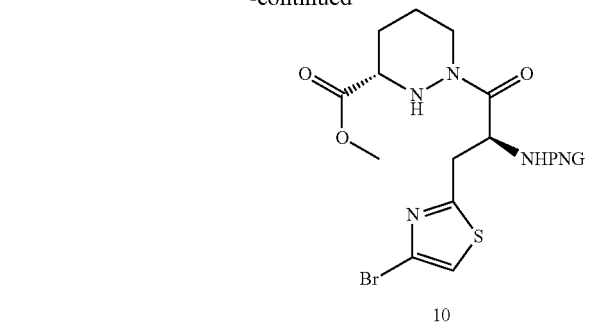

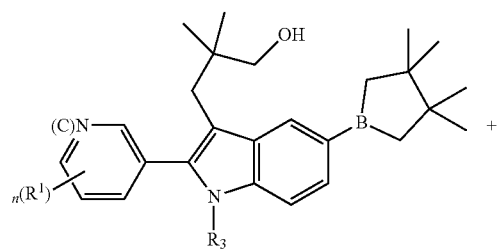

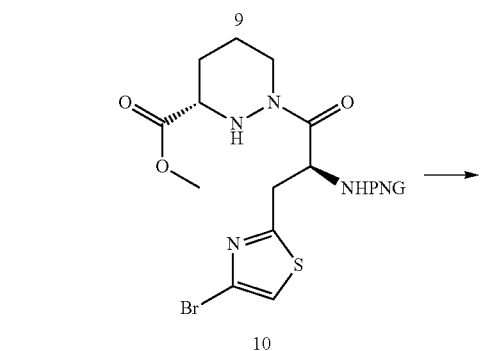

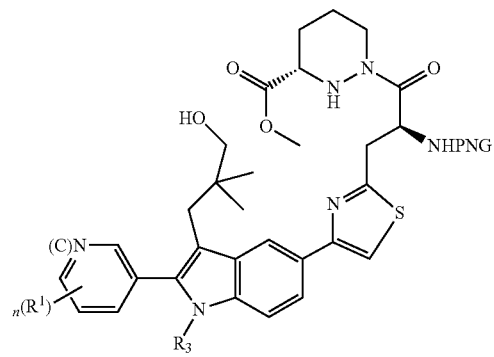

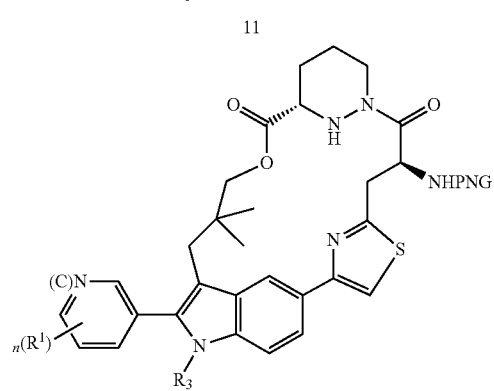

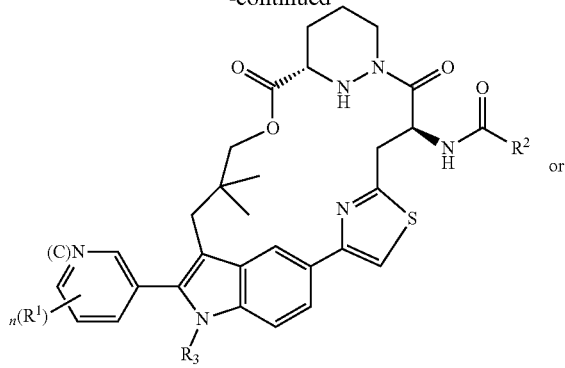

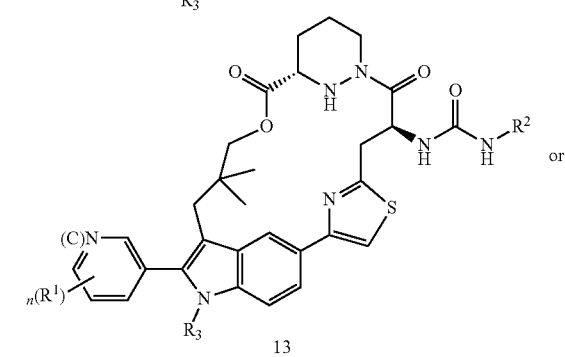

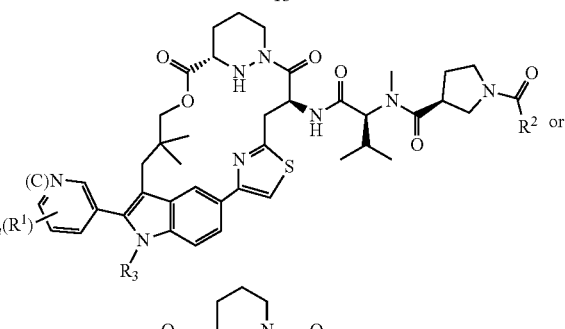

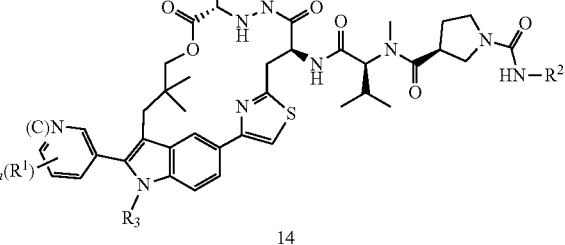

An alternative general synthesis of macrocyclic esters is outlined in Scheme 4. An appropriately substituted indolyl boronic ester (8) can be prepared in four steps starting from protected 3-(5-bromo-2-iodo-1H-indol-3-yl)-2,2-dimethyl-propan-1-ol and appropriately substituted boronic acid, including Palladium mediated coupling, alkylation, de-protection, and Palladium mediated borylation reactions.

Methyl-amino-3-(4-bromothiazol-2-yl)propanoyl)hexahydropyridazine-3-carboxylate (10) can be prepared via coupling of (S)-2-amino-3-(4-bromothiazol-2-yl)propanoic acid (9) with methyl (S)-hexahydropyridazine-3-carboxylate.

The final macrocyclic esters can be made by coupling of Methyl-amino-3-(4-bromothiazol-2-yl)propanoyl)hexahydropyridazine-3-carboxylate (10) and an appropriately substituted indolyl boronic ester (8) in the presence of Pd catalyst followed by hydrolysis and macrolactonization steps to result in an appropriately protected macrocyclic intermediate (11). Deprotection and coupling with an appropriately substituted carboxylic acid (or other coupling partner) or intermediate 4 can result in a macrocyclic product. Additional deprotection or functionalization steps could be required to produce a final compound 13 or 14.

In addition, compounds of the disclosure can be synthesized using the methods described in the Examples below, together with synthetic methods known in the art of synthetic organic chemistry, or variations thereon as appreciated by those skilled in the art. These methods include but are not limited to those methods described in the Examples below. For example, a person of skill in the art would be able to install into a macrocyclic ester a desired —B-L-W group of a compound of Formula (I), where B, L and W are defined herein, including by using methods exemplified in the Example section herein.

Pharmaceutical Compositions and Methods of Use

Pharmaceutical Compositions and Methods of Administration

The compounds with which the invention is concerned are Ras inhibitors, and are useful in the treatment of cancer. Accordingly, one embodiment of the present invention provides pharmaceutical compositions containing a compound of the invention or a pharmaceutically acceptable salt thereof, and a pharmaceutically acceptable excipient, as well as methods of using the compounds of the invention to prepare such compositions.

As used herein, the term "pharmaceutical composition" refers to a compound, such as a compound of the present invention, or a pharmaceutically acceptable salt thereof, formulated together with a pharmaceutically acceptable excipient.

In some embodiments, a compound is present in a pharmaceutical composition in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

A "pharmaceutically acceptable excipient," as used herein, refers any inactive ingredient (for example, a vehicle capable of suspending or dissolving the active compound) having the properties of being nontoxic and non-inflammatory in a subject. Typical excipients include, for example: antiadherents, antioxidants, binders, coatings, compression aids, d is integrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Excipients include, but are not limited to: butylated optionally substituted hydroxyltoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, optionally substituted hydroxylpropyl cellulose, optionally substituted hydroxylpropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol. Those of ordinary skill in the art are familiar with a variety of agents and materials useful as excipients. See, e.g., e.g., Ansel, et al., Ansel's Pharmaceutical Dosage Forms and Drug Delivery Systems. Philadelphia: Lippincott, Williams & Wilkins, 2004; Gennaro, et al., Remington: The Science and Practice of Pharmacy. Philadelphia: Lippincott, Williams & Wilkins, 2000; and Rowe, Handbook of Pharmaceutical Excipients. Chicago, Pharmaceutical Press, 2005. In some embodiments, a composition includes at least two different pharmaceutically acceptable excipients.

Compounds described herein, whether expressly stated or not, may be provided or utilized in salt form, e.g., a pharmaceutically acceptable salt form, unless expressly stated to the contrary. The term "pharmaceutically acceptable salt," as use herein, refers to those salts of the compounds described herein that are, within the scope of sound medical judgment, suitable for use in contact with the tissues of humans and other animals without undue toxicity, irritation, allergic response and the like, and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention, be prepared from inorganic or organic bases. In some embodiments, the compounds are prepared or used as pharmaceutically acceptable salts prepared as addition products of pharmaceutically acceptable acids or bases. Suitable pharmaceutically acceptable acids and bases are well-known in the art, such as hydrochloric, sulfuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-optionally substituted hydroxyl-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

As used herein, the term "subject" refers to any member of the animal kingdom. In some embodiments, "subject" refers to humans, at any stage of development. In some embodiments, "subject" refers to a human patient. In some embodiments, "subject" refers to non-human animals. In some embodiments, the non-human animal is a mammal (e.g., a rodent, a mouse, a rat, a rabbit, a monkey, a dog, a cat, a sheep, cattle, a primate, or a pig). In some embodiments, subjects include, but are not limited to, mammals, birds, reptiles, amphibians, fish, or worms. In some embodiments, a subject may be a transgenic animal, genetically-engineered animal, or a clone.

As used herein, the term "dosage form" refers to a physically discrete unit of a compound (e.g., a compound of the present invention) for administration to a subject. Each unit contains a predetermined quantity of compound. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or compound administered to a particular subject is determined by one or more attending physicians and may involve administration of multiple dosage forms.

As used herein, the term "dosing regimen" refers to a set of unit doses (typically more than one) that are administered individually to a subject, typically separated by periods of time. In some embodiments, a given therapeutic compound (e.g., a compound of the present invention) has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

A "therapeutic regimen" refers to a dosing regimen whose administration across a relevant population is correlated with a desired or beneficial therapeutic outcome.

The term "treatment" (also "treat" or "treating"), in its broadest sense, refers to any administration of a substance (e.g., a compound of the present invention) that partially or completely alleviates, ameliorates, relieves, inhibits, delays onset of, reduces severity of, or reduces incidence of one or more symptoms, features, or causes of a particular disease, disorder, or condition. In some embodiments, such treatment may be administered to a subject who does not exhibit signs of the relevant disease, disorder or condition or of a subject who exhibits only early signs of the disease, disorder, or condition. Alternatively, or additionally, in some embodiments, treatment may be administered to a subject who exhibits one or more established signs of the relevant disease, disorder or condition. In some embodiments, treatment may be of a subject who has been diagnosed as suffering from the relevant disease, disorder, or condition. In some embodiments, treatment may be of a subject known to have one or more susceptibility factors that are statistically correlated with increased risk of development of the relevant disease, disorder, or condition.

The term "therapeutically effective amount" means an amount that is sufficient, when administered to a population suffering from or susceptible to a disease, disorder, or condition in accordance with a therapeutic dosing regimen, to treat the disease, disorder, or condition. In some embodiments, a therapeutically effective amount is one that reduces the incidence or severity of, or delays onset of, one or more symptoms of the disease, disorder, or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. It is specifically understood that particular subjects may, in fact, be "refractory" to a "therapeutically effective amount." In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine). Those of ordinary skill in the art will appreciate that, in some embodiments, a therapeutically effective amount may be formulated or administered in a single dose. In some embodiments, a therapeutically effective amount may be formulated or administered in a plurality of doses, for example, as part of a dosing regimen.

For use as treatment of subjects, the compounds of the invention, or a pharmaceutically acceptable salt thereof, can be formulated as pharmaceutical or veterinary compositions. Depending on the subject to be treated, the mode of administration, and the type of treatment desired, e.g., prevention, prophylaxis, or therapy, the compounds, or a pharmaceutically acceptable salt thereof, are formulated in ways consonant with these parameters. A summary of such techniques may be found in *Remington: The Science and Practice of Pharmacy*, 21$^{st}$ *Edition*, Lippincott Williams & Wilkins, (2005); and *Encyclopedia of Pharmaceutical Technology*, eds. J. Swarbrick and J. C. Boylan, 1988-1999, Marcel Dekker, New York, each of which is incorporated herein by reference.

Compositions can be prepared according to conventional mixing, granulating or coating methods, respectively, and the present pharmaceutical compositions can contain from about 0.1% to about 99%, from about 5% to about 90%, or from about 1% to about 20% of a compound of the present invention, or pharmaceutically acceptable salt thereof, by weight or volume. In some embodiments, compounds, or a pharmaceutically acceptable salt thereof, described herein may be present in amounts totaling 1-95% by weight of the total weight of a composition, such as a pharmaceutical composition.

The composition may be provided in a dosage form that is suitable for intraarticular, oral, parenteral (e.g., intravenous, intramuscular), rectal, cutaneous, subcutaneous, topical, transdermal, sublingual, nasal, vaginal, intravesicular, intraurethral, intrathecal, epidural, aural, or ocular administration, or by injection, inhalation, or direct contact with the nasal, genitourinary, reproductive or oral mucosa. Thus, the pharmaceutical composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, preparations suitable for iontophoretic delivery, or aerosols. The compositions may be formulated according to conventional pharmaceutical practice.

As used herein, the term "administration" refers to the administration of a composition (e.g., a compound, or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal or vitreal.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. A formulation will generally include a diluent as well as, in some cases, adjuvants, buffers, preservatives and the like. Compounds, or a pharmaceutically acceptable salt thereof, can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised. See, for example, U.S. Pat. No. 5,624,677.

Systemic administration may also include relatively non-invasive methods such as the use of suppositories, transdermal patches, transmucosal delivery and intranasal administration. Oral administration is also suitable for compounds of the invention, or a pharmaceutically acceptable salt thereof. Suitable forms include syrups, capsules, and tablets, as is understood in the art.

Each compound, or a pharmaceutically acceptable salt thereof, as described herein, may be formulated in a variety of ways that are known in the art. For example, the first and second agents of the combination therapy may be formulated together or separately. Other modalities of combination therapy are described herein.

The individually or separately formulated agents can be packaged together as a kit. Non-limiting examples include, but are not limited to, kits that contain, e.g., two pills, a pill and a powder, a suppository and a liquid in a vial, two topical creams, etc. The kit can include optional components that aid in the administration of the unit dose to subjects, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one subject, multiple uses for a particular subject (at a constant dose or in which the individual compounds, or a pharmaceutically acceptable salt thereof, may vary in potency as therapy progresses); or the kit may contain multiple doses suitable for administration to multiple subjects ("bulk packaging"). The kit components may be assembled in cartons, blister packs, bottles, tubes, and the like.

Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, oralginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, optionally substituted hydroxylpropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Two or more compounds may be mixed together in a tablet, capsule, or other vehicle, or may be partitioned. In one example, the first compound is contained on the inside of the tablet, and the second compound is on the outside, such that a substantial portion of the second compound is released prior to the release of the first compound.

Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Dissolution or diffusion-controlled release can be achieved by appropriate coating of a tablet, capsule, pellet, or granulate formulation of compounds, or by incorporating the compound, or a pharmaceutically acceptable salt thereof, into an appropriate matrix. A controlled release coating may include one or more of the coating substances mentioned above or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-optionally substituted hydroxylmethacrylate, methacrylate hydrogels, 1,3 butylene glycol, ethylene glycol methacrylate, or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, or halogenated fluorocarbon.

The liquid forms in which the compounds, or a pharmaceutically acceptable salt thereof, and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Generally, when administered to a human, the oral dosage of any of the compounds of the invention, or a pharmaceutically acceptable salt thereof, will depend on the nature of the compound, and can readily be determined by one skilled in the art. A dosage may be, for example, about 0.001 mg to about 2000 mg per day, about 1 mg to about 1000 mg per day, about 5 mg to about 500 mg per day, about 100 mg to about 1500 mg per day, about 500 mg to about 1500 mg per day, about 500 mg to about 2000 mg per day, or any range derivable therein.

In some embodiments, the pharmaceutical composition may further comprise an additional compound having antiproliferative activity. Depending on the mode of administration, compounds, or a pharmaceutically acceptable salt thereof, will be formulated into suitable compositions to permit facile delivery. Each compound, or a pharmaceutically acceptable salt thereof, of a combination therapy may be formulated in a variety of ways that are known in the art. For example, the first and second agents of the combination therapy may be formulated together or separately. Desirably, the first and second agents are formulated together for the simultaneous or near simultaneous administration of the agents.

It will be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics or procedures and the desired therapeutic effect to be achieved. It will also be appreciated that the therapies employed may achieve a desired effect for the same disorder, or they may achieve different effects (e.g., control of any adverse effects).

Administration of each drug in a combination therapy, as described herein, can, independently, be one to four times daily for one day to one year, and may even be for the life of the subject. Chronic, long-term administration may be indicated.

Methods of Use

In some embodiments, the invention discloses a method of treating a disease or disorder that is characterized by aberrant Ras activity due to a Ras mutant. In some embodiments, the disease or disorder is a cancer.

Accordingly, also provided is a method of treating cancer in a subject in need thereof, the method comprising administering to the subject a therapeutically effective amount of a compound of the present invention, or a pharmaceutically acceptable salt thereof, or a pharmaceutical composition comprising such a compound or salt. In some embodiments, the cancer is colorectal cancer, non-small cell lung cancer, small-cell lung cancer, pancreatic cancer, appendiceal cancer, melanoma, acute myeloid leukemia, small bowel cancer, ampullary cancer, germ cell cancer, cervical cancer, cancer of unknown primary origin, endometrial cancer, esophagogastric cancer, GI neuroendocrine cancer, ovarian cancer, sex cord stromal tumor cancer, hepatobiliary cancer, or bladder cancer. In some embodiments, the cancer is appendiceal, endometrial or melanoma. Also provided is a method of treating a Ras protein-related disorder in a subject in need thereof, the method comprising administering to the subject a therapeutically effective amount of a compound of the present invention, or a pharmaceutically acceptable salt thereof, or a pharmaceutical composition comprising such a compound or salt.

In some embodiments, the compounds of the present invention or pharmaceutically acceptable salts thereof, pharmaceutical compositions comprising such compounds or salts, and methods provided herein may be used for the treatment of a wide variety of cancers including tumors such as lung, prostate, breast, brain, skin, cervical carcinomas, testicular carcinomas, etc. More particularly, cancers that may be treated by the compounds or salts thereof, pharmaceutical compositions comprising such compounds or salts, and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. Other cancers include, for example:

Cardiac, for example: sarcoma (angiosarcoma, fibrosarcoma, rhabdomyosarcoma, liposarcoma), myxoma, rhabdomyoma, fibroma, lipoma and teratoma; Lung, for example: bronchogenic carcinoma (squamous ceil, undifferentiated small cell, undifferentiated large cell, adenocarcinoma), alveolar (bronchiolar) carcinoma, bronchial adenoma, sarcoma, lymphoma, chondromatous hamartoma, mesothelioma;

Gastrointestinal, for example: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma);

Genitourinary tract, for example: kidney (adenocarcinoma, Wilm's tumor (nephroblastoma), lymphoma, leukemia), bladder and urethra (squamous ceil carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

Liver, for example: hepatoma (hepatocellular carcinoma), cholangiocarcinoma, hepatoblastoma, angiosarcoma, hepatocellular adenoma, hemangioma;

Biliary tract, for example: gall bladder carcinoma, ampullary carcinoma, cholangiocarcinoma;

Bone, for example: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

Nervous system, for example: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, neurofibromatosis type 1, meningioma, glioma, sarcoma);

Gynecological, for example: uterus (endometrial carcinoma, uterine carcinoma, uterine corpus endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig ceil tumors, dysgerminoma, malignant teratoma), vulva (squamous ceil carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma);

Hematologic, for example: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma);

Skin, for example: malignant melanoma, basal cell carcinoma, squamous cell carcinoma, Kaposi's sarcoma, moles dysplastic nevi, lipoma, angioma, dermatofibroma, keloids, psoriasis; and Adrenal glands, for example: neuroblastoma.

In some embodiments, the Ras protein is wild-type (Ras™). Accordingly, in some embodiments, a compound of the present invention is employed in a method of treating a patient having a cancer comprising a Ras$^{WT}$ (e.g., K-Ras$^{WT}$, H-Ras$^{WT}$ or N-Ras$^{WT}$). In some embodiments, the Ras protein is Ras amplification (e.g., K-Ras$^{amp}$). Accordingly, in some embodiments, a compound of the present invention is employed in a method of treating a patient having a cancer comprising a Ras$^{amp}$ (K-Ras$^{amp}$, H-Ras$^{amp}$ or N-Ras$^{amp}$). In some embodiments, the cancer comprises a Ras mutation, such as a Ras mutation described herein. In some embodiments, a mutation is selected from:

(a) the following K-Ras mutants: G12D, G12V, G12C, G13D, G12R, G12A, Q61H, G12S, A146T, G13C, Q61L, Q61R, K117N, A146V, G12F, Q61K, L19F, Q22K, V14I, A59T, A146P, G13R, G12L, or G13V, and combinations thereof;

(b) the following H-Ras mutants: Q61R, G13R, Q61K, G12S, Q61L, G12D, G13V, G13D, G12C, K117N, A59T, G12V, G13C, Q61H, G13S, A18V, D119N, G13N, A146T, A66T, G12A, A146V, G12N, or G12R, and combinations thereof; and (c) the following N-Ras mutants: Q61R, Q61K, G12D, Q61L, Q61H, G13R, G13D, G12S, G12C, G12V, G12A, G13V, G12R, P185S, G13C, A146T, G60E, Q61P, A59D, E132K, E49K, T50I, A146V, or A59T, and combinations thereof;

or a combination of any of the foregoing. In some embodiments, the cancer comprises a K-Ras mutation selected from the group consisting of G12C, G12D, G13C, G12V, G13D, G12R, G12S, Q61H, Q61K and Q61L. In some embodiments, the cancer comprises an N-Ras mutation selected from the group consisting of G12C, Q61H, Q61K, Q61L, Q61P and Q61R. In some embodiments, the cancer comprises an H-Ras mutation selected from the group consisting of Q61H and Q61L. In some embodiments, the cancer comprises a Ras mutation selected from the group consisting of G12C, G13C, G12A, G12D, G13D, G12S, G13S, G12V and G13V. In some embodiments, the cancer comprises at least two Ras mutations selected from the group consisting of G12C, G13C, G12A, G12D, G13D, G12S, G13S, G12V and G13V. In some embodiments, a compound of the present invention inhibits more than one Ras mutant. For example, a compound may inhibit both K-Ras G12C and K-Ras G13C. A compound may inhibit both N-Ras G12C and K-Ras G12C. In some embodiments, a compound may inhibit both K-Ras G12C and K-Ras G12D. In some embodiments, a compound may inhibit both K-Ras G12V and K-Ras G12C. In some embodiments, a compound may inhibit both K-Ras G12V and K-Ras G12S. In some embodiments, a compound of the present invention inhibits Ras$^{WT}$ in addition to one or more additional Ras mutations (e.g., K-, H- or N-Ras$^{WT}$ and K-Ras G12D, G12V, G12C, G13D, G12R, G12A, Q61H, G12S, A146T, G13C, Q61L, Q61R, K117N, A146V, G12F, Q61K, L19F, Q22K, V14I, A59T, A146P, G13R, G12L, or G13V; K-, H- or N-Ras$^{WT}$ and H-Ras Q61R, G13R, Q61K, G12S, Q61L, G12D, G13V, G13D, G12C, K117N, A59T, G12V, G13C, Q61H, G13S, A18V, D119N, G13N, A146T, A66T, G12A, A146V, G12N, or G12R; or K-, H- or N-Ras$^{WT}$ and N-Ras Q61R, Q61K, G12D, Q61L, Q61H, G13R, G13D, G12S, G12C, G12V, G12A, G13V, G12R, P185S, G13C, A146T, G60E, Q61P, A59D, E132K, E49K, T50I, A146V, or A59T). In some embodiments, a compound of the present invention inhibits Ras$^{amp}$ in addition to one or more additional Ras mutations (e.g., K-, H- or N-Ras$^{amp}$ and K-Ras G12D, G12V, G12C, G13D, G12R, G12A, Q61H, G12S, A146T, G13C, Q61L, Q61R, K117N, A146V, G12F, Q61K, L19F, Q22K, V14I, A59T, A146P, G13R, G12L, or G13V; K-, H- or N-Ras$^{amp}$ and H-Ras Q61R, G13R, Q61K, G12S, Q61L, G12D, G13V, G13D, G12C, K117N, A59T, G12V, G13C, Q61H, G13S, A18V, D119N, G13N, A146T, A66T, G12A, A146V, G12N, or G12R; or K-, H- or N-Ras$^{amp}$ and N-Ras Q61R, Q61K, G12D, Q61L, Q61H, G13R, G13D, G12S, G12C, G12V, G12A, G13V, G12R, P185S, G13C, A146T, G60E, Q61P, A59D, E132K, E49K, T50I, A146V, or A59T).

Methods of detecting Ras mutations are known in the art. Such means include, but are not limited to direct sequencing, and utilization of a high-sensitivity diagnostic assay (with CE-IVD mark), e.g., as described in Domagala, et al., Pol J Pathol 3: 145-164 (2012), incorporated herein by reference in its entirety, including TheraScreen PCR; AmoyDx; PNA-CIamp; RealQuality; EntroGen; LightMix; StripAssay; Hybcell plexA; Devyser; Surveyor; Cobas; and TheraScreen Pyro. See, also, e.g., WO 2020/106640.

In some embodiments, the cancer is non-small cell lung cancer and the Ras mutation comprises a K-Ras mutation, such as K-Ras G12C, K-Ras G12V or K-Ras G12D. In some embodiments, the cancer is colorectal cancer and the Ras mutation comprises a K-Ras mutation, such as K-Ras G12C, K-Ras G12V or K-Ras G12D. In some embodiments, the cancer is pancreatic cancer and the Ras mutation comprises an K-Ras mutation, such as K-Ras G12D or K-Ras G12V. In some embodiments, the cancer is pancreatic cancer and the Ras mutation comprises an N-Ras mutation, such as N-Ras G12D. In some embodiments, the cancer is melanoma and the Ras mutation comprises an N-Ras mutation, such as N-Ras Q61R or N-Ras Q61K. In some embodiments, the cancer is non-small cell lung cancer and the Ras protein is K-Ras$^{amp}$P. In any of the foregoing if not already specified, a compound may inhibit Ras$^{WT}$ (e.g., K-, H- or N-Ras$^{WT}$) or Ras$^{amp}$ (e.g., K-, H- or N-Ras$^{amp}$P) as well.

In some embodiments, a cancer comprises a Ras mutation and an STK11$^{LOF}$, a KEAP1, an EPHA5 or an NF1 mutation. In some embodiments, the cancer is non-small cell lung cancer and comprises a K-Ras G12C mutation. In some embodiments, the cancer is non-small cell lung cancer and comprises a K-Ras G12C mutation and an STK11$^{LOF}$ mutation. In some embodiments, the cancer is non-small cell lung cancer and comprises a K-Ras G12C mutation and an STK11$^{LOF}$ mutation. In some embodiments, a cancer comprises a K-Ras G13C Ras mutation and an STK11$^{LOF}$, a KEAP1, an EPHA5 or an NF1 mutation. In some embodiments, the cancer is non-small cell lung cancer and comprises a K-Ras G12D mutation. In some embodiments, the cancer is non-small cell lung cancer and comprises a K-Ras G12V mutation. In some embodiments, the cancer is colorectal cancer and comprises a K-Ras G12C mutation. In some embodiments, the cancer is pancreatic cancer and comprises a K-Ras G12D mutation. In some embodiments, the cancer is pancreatic cancer and comprises a K-Ras G12V mutation. In some embodiments, the cancer is endometrial cancer and comprises a K-Ras G12C mutation. In some embodiments, the cancer is gastric cancer and comprises a K-Ras G12C mutation. In any of the foregoing, a compound may inhibit Ras$^{WT}$ (e.g., K-, H- or N-Ras$^{WT}$) or Ras$^{amp}$ (e.g., K-, H- or N-Ras$^{amp}$) as well.

Also provided is a method of inhibiting a Ras protein in a cell, the method comprising contacting the cell with an effective amount of a compound of the present invention, or a pharmaceutically acceptable salt thereof. A method of inhibiting RAF-Ras binding, the method comprising contacting the cell with an effective amount of a compound of the present invention, or a pharmaceutically acceptable salt thereof, is also provided. The cell may be a cancer cell. The cancer cell may be of any type of cancer described herein. The cell may be in vivo or in vitro.

Combination Therapy

The methods of the invention may include a compound of the invention used alone or in combination with one or more additional therapies (e.g., non-drug treatments or therapeutic agents). The dosages of one or more of the additional therapies (e.g., non-drug treatments or therapeutic agents) may be reduced from standard dosages when administered alone. For example, doses may be determined empirically from drug combinations and permutations or may be deduced by isobolographic analysis (e.g., Black et al., *Neurology* 65:S3-S6 (2005)).

A compound of the present invention may be administered before, after, or concurrently with one or more of such additional therapies. When combined, dosages of a compound of the invention and dosages of the one or more additional therapies (e.g., non-drug treatment or therapeutic agent) provide a therapeutic effect (e.g., synergistic or additive therapeutic effect). A compound of the present invention and an additional therapy, such as an anti-cancer agent, may be administered together, such as in a unitary pharmaceutical composition, or separately and, when administered separately, this may occur simultaneously or sequentially. Such sequential administration may be close or remote in time.

In some embodiments, the additional therapy is the administration of side-effect limiting agents (e.g., agents intended to lessen the occurrence or severity of side effects of treatment. For example, in some embodiments, the compounds of the present invention can also be used in combination with a therapeutic agent that treats nausea. Examples of agents that can be used to treat nausea include: dronabinol, granisetron, metoclopramide, ondansetron, and prochlorperazine, or pharmaceutically acceptable salts thereof.

In some embodiments, the one or more additional therapies includes a non-drug treatment (e.g., surgery or radiation therapy). In some embodiments, the one or more additional therapies includes a therapeutic agent (e.g., a compound or biologic that is an anti-angiogenic agent, signal transduction inhibitor, antiproliferative agent, glycolysis inhibitor, or autophagy inhibitor). In some embodiments, the one or more additional therapies includes a non-drug treatment (e.g., surgery or radiation therapy) and a therapeutic agent (e.g., a compound or biologic that is an anti-angiogenic agent, signal transduction inhibitor, antiproliferative agent, glycolysis inhibitor, or autophagy inhibitor). In other embodiments, the one or more additional therapies includes two therapeutic agents. In still other embodiments, the one or more additional therapies includes three therapeutic agents. In some embodiments, the one or more additional therapies includes four or more therapeutic agents.

In this Combination Therapy section, all references are incorporated by reference for the agents described, whether explicitly stated as such or not.

Non-Drug Therapies

Examples of non-drug treatments include, but are not limited to, radiation therapy, cryotherapy, hyperthermia, surgery (e.g., surgical excision of tumor tissue), and T cell adoptive transfer (ACT) therapy.

In some embodiments, the compounds of the invention may be used as an adjuvant therapy after surgery. In some embodiments, the compounds of the invention may be used as a neo-adjuvant therapy prior to surgery.

Radiation therapy may be used for inhibiting abnormal cell growth or treating a hyperproliferative disorder, such as cancer, in a subject (e.g., mammal (e.g., human)). Techniques for administering radiation therapy are known in the art. Radiation therapy can be administered through one of several methods, or a combination of methods, including, without limitation, external-beam therapy, internal radiation therapy, implant radiation, stereotactic radiosurgery, systemic radiation therapy, radiotherapy and permanent or temporary interstitial brachy therapy. The term "brachy therapy," as used herein, refers to radiation therapy delivered by a spatially confined radioactive material inserted into the body at or near a tumor or other proliferative tissue disease site. The term is intended, without limitation, to include exposure to radioactive isotopes (e.g., At-211, I-131, I-125, Y-90, Re-186, Re-188, Sm-153, Bi-212, P-32, and radioactive isotopes of Lu). Suitable radiation sources for use as a ceil conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, or Y-90. Moreover, the radionuciide(s) can be embodied in a gel or radioactive micro spheres.

In some embodiments, the compounds of the present invention can render abnormal cells more sensitive to treatment with radiation for purposes of killing or inhibiting the growth of such cells. Accordingly, this invention further relates to a method for sensitizing abnormal cells in a mammal to treatment with radiation which comprises administering to the mammal an amount of a compound of the present invention, which amount is effective to sensitize abnormal cells to treatment with radiation. The amount of the compound in this method can be determined according to the means for ascertaining effective amounts of such compounds described herein. In some embodiments, the compounds of the present invention may be used as an adjuvant therapy after radiation therapy or as a neo-adjuvant therapy prior to radiation therapy.

In some embodiments, the non-drug treatment is a T cell adoptive transfer (ACT) therapy. In some embodiments, the T cell is an activated T cell. The T cell may be modified to express a chimeric antigen receptor (CAR). CAR modified T (CAR-T) cells can be generated by any method known in the art. For example, the CAR-T cells can be generated by introducing a suitable expression vector encoding the CAR to a T cell. Prior to expansion and genetic modification of the T cells, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art may be used. In some embodiments, the T cell is an autologous T cell. Whether prior to or after genetic modification of the T cells to express a desirable protein (e.g., a CAR), the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 7,572,631; 5,883,223; 6,905,874; 6,797,514; and 6,867,041.

Therapeutic Agents

A therapeutic agent may be a compound used in the treatment of cancer or symptoms associated therewith.

For example, a therapeutic agent may be a steroid. Accordingly, in some embodiments, the one or more additional therapies includes a steroid. Suitable steroids may include, but are not limited to, 21-acetoxypregnenolone, alclometasone, algestone, amcinonide, beclometasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, fiucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts or derivatives thereof.

Further examples of therapeutic agents that may be used in combination therapy with a compound of the present invention include compounds described in the following patents: U.S. Pat. Nos. 6,258,812, 6,630,500, 6,515,004, 6,713,485, 5,521,184, 5,770,599, 5,747,498, 5,990,141, 6,235,764, and 8,623,885, and International Patent Applications WO01/37820, WO01/32651, WO02/68406, WO02/66470, WO02/55501, WO04/05279, WO04/07481, WO04/07458, WO04/09784, WO02/59110, WO99/45009, WO00/59509, WO99/61422, WO00/12089, and WO00/02871.

A therapeutic agent may be a biologic (e.g., cytokine (e.g., interferon or an interleukin such as IL-2)) used in treatment of cancer or symptoms associated therewith. In some embodiments, the biologic is an immunoglobulin-based biologic, e.g., a monoclonal antibody (e.g., a humanized antibody, a fully human antibody, an Fc fusion protein, or a functional fragment thereof) that agonizes a target to stimulate an anti-cancer response or antagonizes an antigen important for cancer. Also included are antibody-drug conjugates.

A therapeutic agent may be a T-cell checkpoint inhibitor. In one embodiment, the checkpoint inhibitor is an inhibitory antibody (e.g., a monospecific antibody such as a monoclonal antibody). The antibody may be, e.g., humanized or fully human. In some embodiments, the checkpoint inhibitor is a fusion protein, e.g., an Fc-receptor fusion protein. In some embodiments, the checkpoint inhibitor is an agent, such as an antibody, that interacts with a checkpoint protein. In some embodiments, the checkpoint inhibitor is an agent, such as an antibody, that interacts with the ligand of a checkpoint protein. In some embodiments, the checkpoint inhibitor is an inhibitor (e.g., an inhibitory antibody or small molecule inhibitor) of CTLA-4 (e.g., an anti-CTLA-4 antibody or fusion a protein). In some embodiments, the checkpoint inhibitor is an inhibitor or antagonist (e.g., an inhibitory antibody or small molecule inhibitor) of PD-1. In some embodiments, the checkpoint inhibitor is an inhibitor or antagonist (e.g., an inhibitory antibody or small molecule inhibitor) of PDL-1. In some embodiments, the checkpoint inhibitor is an inhibitor or antagonist (e.g., an inhibitory antibody or Fc fusion or small molecule inhibitor) of PDL-2 (e.g., a PDL-2/Ig fusion protein). In some embodiments, the checkpoint inhibitor is an inhibitor or antagonist (e.g., an inhibitory antibody or small molecule inhibitor) of B7-H3, B7-H4, BTLA, HVEM, TIM3, GAL9, LAG3, VISTA, KIR, 2B4, CD160, CGEN-15049, CHK 1, CHK2, A2aR, B-7 family ligands, or a combination thereof. In some embodiments, the checkpoint inhibitor is pembrolizumab, nivolumab, PDR001 (NVS), REGN2810 (Sanofi/Regeneron), a PD-L1 antibody such as, e.g., avelumab, durvalumab, atezolizumab, pidilizumab, JNJ-63723283 (JNJ), BGB-A317 (BeiGene & Celgene) or a checkpoint inhibitor disclosed in Preusser, M. et al. (2015) Nat. Rev. Neurol., including, without limitation, ipilimumab, tremelimumab, nivolumab, pembrolizumab, AMP224, AMP514/MEDI0680, BMS936559, MEDI4736, MPDL3280A, MSB0010718C, BMS986016, IMP321, lirilumab, IPH2101, 1-7F9, and KW-6002. A therapeutic agent may be an anti-TIGIT antibody, such as MBSA43, BMS-986207, MK-7684, COM902, AB154, MTIG7192A or OMP-313M32 (etigilimab).

A therapeutic agent may be an agent that treats cancer or symptoms associated therewith (e.g., a cytotoxic agent, non-peptide small molecules, or other compound useful in the treatment of cancer or symptoms associated therewith, collectively, an "anti-cancer agent"). Anti-cancer agents can be, e.g., chemotherapeutics or targeted therapy agents.

Anti-cancer agents include mitotic inhibitors, intercalating antibiotics, growth factor inhibitors, cell cycle inhibitors, enzymes, topoisomerase inhibitors, biological response modifiers, alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Further anti-cancer agents include leucovorin (LV), irenotecan, oxaliplatin, capecitabine, paclitaxel, and doxetaxel. In some embodiments, the one or more additional therapies includes two or more anti-cancer agents. The two or more anti-cancer agents can be used in a cocktail to be administered in combination or administered separately. Suitable dosing regimens of combination anti-cancer agents are known in the art and described in, for example, Saltz et al., *Proc. Am. Soc. Clin. Oncol.* 18:233a (1999), and Douillard et al., *Lancet* 355(9209):1041-1047 (2000).

Other non-limiting examples of anti-cancer agents include Gleevec® (imatinib Mesylate); Kyprolis® (carfilzomib); Velcade® (bortezomib); Casodex (bicalutamide); Iressa® (gefitinib); alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; sarcodictyin A; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, such as calicheamicin gammaII and calicheamicin omegaII (see, e.g., *Agnew, Chem. Inti. Ed Engl.* 33:183-186 (1994)); dynemicin such as dynemicin A; bisphosphonates such as clodronate; an esperamicin; neocarzinostatin chromophore and related chromoprotein enediyne antiobiotic chromophores, aclacinomysins, actinomycin, authramycin, azaserine, bleomycins, cactinomycin, calicheamicin, carabicin, caminomycin, carminomycin, carzinophilin, chromomycins, dactinomycin, daunorubicin, detorubicin, 6-diazo-5-oxo-L-norleucine, adriamycin (doxorubicin), morpholino-doxorubicin, cyanomorpholino-doxorubicin, 2-pyrrolino-doxorubicin, deoxydoxorubicin, epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenishers such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone such as epothilone B; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes such as T-2 toxin, verracurin A, roridin A and anguidine; urethane; vindesine; dacarbazine; mannomustine; mitobronitol; mitolactol; pipobroman; gacytosine; arabinoside ("Ara-C"); cyclophosphamide; thiotepa; taxoids, e.g., Taxol® (paclitaxel), Abraxane® (cremophor-free, albumin-engineered nanoparticle formulation of paclitaxel), and Taxotere® (doxetaxel); chloranbucil; tamoxifen (Nolvadex™); raloxifene; aromatase inhibiting 4(5)-imidazoies; 4-hydroxytamoxifen; trioxifene; keoxifene; LY 117018; onapristone; toremifene (Fareston®); flutamide, nilutamide, bicalutamide, leuprolide, goserelin; chlorambucil; Gemzar® gemcitabine; 6-thioguanine; mercaptopurine; platinum coordination complexes such as cisplatin, oxaliplatin and carboplatin; vinblastine; platinum; etoposide (VP-16); ifosfamide; mitoxantrone; vincristine; Navelbine® (vinorelbine); novantrone; teniposide; edatrexate; daunomycin; aminopterin; ibandronate; irinotecan (e.g., CPT-11); topoisomerase inhibitor RFS 2000; difluoromethylornithine (DMFO); retinoids such as retinoic acid; esperamicins; capecitabine (e.g., Xeloda®); and pharmaceutically acceptable salts of any of the above.

Additional non-limiting examples of anti-cancer agents include trastuzumab (Herceptin®), bevacizumab (Avastin®), cetuximab (Erbitux®), rituximab (Rituxan®), Taxol®, Arimidex®, ABVD, avicine, abagovomab, acridine carboxamide, adecatumumab, 17-N-allylamino-17-demethoxygeldanamycin, alpharadin, alvocidib, 3-aminopyridine-2-carboxaldehyde thiosemicarbazone, amonafide, anthracenedione, anti-CD22 immunotoxins, antineoplastics (e.g., cell-cycle nonspecific antineoplastic agents, and other antineoplastics described herein), antitumorigenic herbs, apaziquone, atiprimod, azathioprine, belotecan, bendamustine, BIBW2992, biricodar, brostallicin, bryostatin, buthionine sulfoximine, CBV (chemotherapy), calyculin, dichloroacetic acid, discodermolide, elsamitrucin, enocitabine, eribulin, exatecan, exisulind, ferruginol, forodesine, fosfestrol, ICE chemotherapy regimen, IT-101, imexon, imiquimod, indolocarbazole, irofulven, laniquidar, larotaxel, lenalidomide, lucanthone, lurtotecan, mafosfamide, mitozolomide, nafoxidine, nedaplatin, olaparib, ortataxel, PAC-1, pawpaw, pixantrone, proteasome inhibitors, rebeccamycin, resiquimod, rubitecan, SN-38, salinosporamide A, sapacitabine, Stanford V, swainsonine, talaporfin, tariquidar, tegafur-uracil, temodar, tesetaxel, triplatin tetranitrate, tris(2-chloroethyl)amine, troxacitabine, uramustine, vadimezan, vinflunine, ZD6126, and zosuquidar.

Further non-limiting examples of anti-cancer agents include natural products such as vinca alkaloids (e.g., vinblastine, vincristine, and vinorelbine), epidipodophyllotoxins (e.g., etoposide and teniposide), antibiotics (e.g., dactinomycin (actinomycin D), daunorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., a CDK4/6 inhibitor such as abemaciclib, ribociclib, palbociclib; seliciclib, UCN-01, P1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs, pyrimidine analogs (e.g., fluorouracil, floxuridine, and cytarabine), purine analogs and related inhibitors (e.g., mercaptopurine, thioguanine, pentostatin, and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTOR inhibitors (e.g., vistusertib, temsirolimus, everolimus, ridaforolimus, and sirolimus), KSP(Eg5) inhibitors (e.g., Array 520), DNA binding agents (e.g., Zalypsis®), PI3K inhibitors such as PI3K delta inhibitor (e.g., GS-1101 and TGR-1202), PI3K delta and gamma inhibitor (e.g., CAL-130), copanlisib, alpelisib and idelalisib; multi-kinase inhibitor (e.g., TG02 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., LY2127399), IKK inhibitors, p38MAPK inhibitors, anti-IL-6 (e.g., CNT0328), telomerase inhibitors (e.g., GRN 163L), aurora kinase inhibitors (e.g., MLN8237), cell surface monoclonal antibodies (e.g., anti-CD38 (HU-MAX-CD38), anti-CSI (e.g., elotuzumab), HSP90 inhibitors (e.g., 17 AAG and KOS 953), P13K/Akt inhibitors (e.g., perifosine), Akt inhibitors (e.g., GSK-2141795), PKC inhibitors (e.g., enzastaurin), FTIs (e.g., Zarnestra™), anti-CD138 (e.g., BT062), Torcl/2 specific kinase inhibitors (e.g., INK128), ER/UPR targeting agents (e.g., MKC-3946), cFMS inhibitors (e.g., ARRY-382), JAK1/2 inhibitors (e.g., CYT387), PARP inhibitors (e.g., olaparib and veliparib (ABT-888)), and BCL-2 antagonists.

In some embodiments, an anti-cancer agent is selected from mechlorethamine, camptothecin, ifosfamide, tamoxifen, raloxifene, gemcitabine, Navelbine®, sorafenib, or any analog or derivative variant of the foregoing.

In some embodiments, the anti-cancer agent is a HER2 inhibitor. Non-limiting examples of HER2 inhibitors include monoclonal antibodies such as trastuzumab (Herceptin®) and pertuzumab (Perjeta®); small molecule tyrosine kinase inhibitors such as gefitinib (Iressa®), erlotinib (Tarceva®), pilitinib, CP-654577, CP-724714, canertinib (CI 1033), HKI-272, lapatinib (GW-572016; Tykerb®), PKI-166, AEE788, BMS-599626, HKI-357, BIBW2992, ARRY-334543, and JNJ-26483327.

In some embodiments, an anti-cancer agent is an ALK inhibitor. Non-limiting examples of ALK inhibitors include ceritinib, TAE-684 (NVP-TAE694), PF02341066 (crizotinib or 1066), alectinib; brigatinib; entrectinib; ensartinib (X-396); lorlatinib; ASP3026; CEP-37440; 4SC-203; TL-398; PLB1003; TSR-011; CT-707; TPX-0005, and AP26113. Additional examples of ALK kinase inhibitors are described in examples 3-39 of WO05016894.

In some embodiments, an anti-cancer agent is an inhibitor of a member downstream of a Receptor Tyrosine Kinase (RTK)/Growth Factor Receptor (e.g., a SHP2 inhibitor (e.g., SHP099, TN0155, RMC-4550, RMC-4630, JAB-3068, RLY-1971), a SOS1 inhibitor (e.g., BI-1701963, BI-3406), a Raf inhibitor, a MEK inhibitor, an ERK inhibitor, a PI3K inhibitor, a PTEN inhibitor, an AKT inhibitor, or an mTOR inhibitor (e.g., mTORC1 inhibitor or mTORC2 inhibitor). In some embodiments, the anti-cancer agent is JAB-3312. In some embodiments, an anti-cancer agent is an additional Ras inhibitor (e.g., AMG 510, MRTX1257, MRTX849, JNJ-74699157 (ARS-3248), LY3499446, ARS-853 or ARS-1620), or a Ras vaccine, or another therapeutic modality designed to directly or indirectly decrease the oncogenic activity of Ras. Other examples of Ras inhibitors that may be combined with a Ras inhibitor of the present invention are provided in the following, incorporated herein by reference in their entireties: WO 2020050890, WO 2020047192, WO 2020035031, WO 2020028706, WO 2019241157, WO 2019232419, WO 2019217691, WO 2019217307, WO 2019215203, WO 2019213526, WO 2019213516, WO 2019155399, WO 2019150305, WO 2019110751, WO 2019099524, WO 2019051291, WO 2018218070, WO 2018217651, WO 2018218071, WO 2018218069, WO 2018206539, WO 2018143315, WO 2018140600, WO 2018140599, WO 2018140598, WO 2018140514, WO 2018140513, WO 2018140512, WO 2018119183, WO 2018112420, WO 2018068017, WO 2018064510, WO 2017201161, WO 2017172979, WO 2017100546, WO 2017087528, WO 2017058807, WO 2017058805, WO 2017058728, WO 2017058902, WO 2017058792, WO 2017058768, WO 2017058915, WO 2017015562, WO 2016168540, WO 2016164675, WO 2016049568, WO 2016049524, WO 2015054572, WO 2014152588, WO 2014143659, and WO 2013155223.

In some embodiments, a therapeutic agent that may be combined with a compound of the present invention is an inhibitor of the MAP kinase (MAPK) pathway (or "MAPK inhibitor"). MAPK inhibitors include, but are not limited to, one or more MAPK inhibitor described in Cancers (Basel) 2015 September; 7(3): 1758-1784. For example, the MAPK inhibitor may be selected from one or more of trametinib, binimetinib, selumetinib, cobimetinib, LErafAON (NeoPharm), ISIS 5132; vemurafenib, pimasertib, TAK733, RO4987655 (CH4987655); CI-1040; PD-0325901; CH5126766; MAP855; AZD6244; refametinib (RDEA 119/BAY 86-9766); GDC-0973/XL581; AZD8330 (ARRY-424704/ARRY-704); RO5126766 (Roche, described in PLoS One. 2014 Nov. 25; 9(11)); and GSK1120212 (or JTP-74057, described in Clin Cancer Res. 2011 Mar. 1; 17(5):989-1000). The MAPK inhibitor may be PLX8394, LXH254, GDC-5573, or LY3009120.

In some embodiments, an anti-cancer agent is a disrupter or inhibitor of the RAS-RAF-ERK or PI3K-AKT-TOR or PI3K-AKT signaling pathways. The PI3K/AKT inhibitor may include, but is not limited to, one or more PI3K/AKT inhibitor described in Cancers (Basel) 2015 September; 7(3): 1758-1784. For example, the PI3K/AKT inhibitor may be selected from one or more of NVP-BEZ235; BGT226; XL765/SAR245409; SF1126; GDC-0980; PI-103; PF-04691502; PKI-587; GSK2126458.

In some embodiments, an anti-cancer agent is a PD-1 or PD-L1 antagonist.

In some embodiments, additional therapeutic agents include ALK inhibitors, HER2 inhibitors, EGFR inhibitors, IGF-1R inhibitors, MEK inhibitors, PI3K inhibitors, AKT inhibitors, TOR inhibitors, MCL-1 inhibitors, BCL-2 inhibitors, SHP2 inhibitors, proteasome inhibitors, and immune therapies. In some embodiments, a therapeutic agent may be a pan-RTK inhibitor, such as afatinib.

IGF-1R inhibitors include linsitinib, or a pharmaceutically acceptable salt thereof.

EGFR inhibitors include, but are not limited to, small molecule antagonists, antibody inhibitors, or specific antisense nucleotide or siRNA. Useful antibody inhibitors of EGFR include cetuximab (Erbitux®), panitumumab (Vectibix®), zalutumumab, nimotuzumab, and matuzumab. Further antibody-based EGFR inhibitors include any anti-EGFR antibody or antibody fragment that can partially or completely block EGFR activation by its natural ligand. Non-limiting examples of antibody-based EGFR inhibitors include those described in Modjtahedi et al., Br. J. Cancer 1993, 67:247-253; Teramoto et al., Cancer 1996, 77:639-645; Goldstein et al., Clin. Cancer Res. 1995, 1:1311-1318; Huang et al., 1999, Cancer Res. 15:59(8):1935-40; and Yang et al., Cancer Res. 1999, 59:1236-1243. The EGFR inhibitor can be monoclonal antibody Mab E7.6.3 (Yang, 1999 supra), or Mab C225 (ATCC Accession No. HB-8508), or an antibody or antibody fragment having the binding specificity thereof.

Small molecule antagonists of EGFR include gefitinib (Iressa®), erlotinib (Tarceva®), and lapatinib (TykerB®). See, e.g., Yan et al., Pharmacogenetics and Pharmacogenomics In Oncology Therapeutic Antibody Development, BioTechniques 2005, 39(4):565-8; and Paez et al., EGFR Mutations In Lung Cancer Correlation With Clinical Response To Gefitinib Therapy, Science 2004, 304(5676): 1497-500. In some embodiments, the EGFR inhibitor is osimertinib (Tagrisso®). Further non-limiting examples of small molecule EGFR inhibitors include any of the EGFR inhibitors described in the following patent publications, and all pharmaceutically acceptable salts of such EGFR inhibitors: EP 0520722; EP 0566226; WO96/33980; U.S. Pat. No. 5,747,498; WO96/30347; EP 0787772; WO97/30034; WO97/30044; WO97/38994; WO97/49688; EP 837063; WO98/02434; WO97/38983; WO95/19774; WO95/19970; WO97/13771; WO98/02437; WO98/02438; WO97/32881; DE 19629652; WO98/33798; WO97/32880; WO97/32880; EP 682027; WO97/02266; WO97/27199; WO98/07726; WO97/34895; WO96/31510; WO98/14449; WO98/14450; WO98/14451; WO95/09847; WO97/19065; WO98/17662; U.S. Pat. Nos. 5,789,427; 5,650,415; 5,656,643; WO99/35146; WO99/35132; WO99/07701; and WO92/20642. Additional non-limiting examples of small molecule EGFR inhibitors include any of the EGFR inhibitors described in Traxler et al., Exp. Opin. Ther. Patents 1998, 8(12):1599-1625. In some embodiments, an EGFR inhibitor is an ERBB inhibitor. In humans, the ERBB family contains HER1 (EGFR, ERBB1), HER2 (NEU, ERBB2), HER3 (ERBB3), and HER (ERBB4). MEK inhibitors include, but are not limited to, pimasertib, selumetinib, cobimetinib (Cotellic®), trametinib (Mekinist®), and binimetinib (Mektovi®). In some embodiments, a MEK inhibitor targets a MEK mutation that is a Class I MEK1 mutation selected from D67N; P124L; P124S; and L177V. In some embodiments, the MEK mutation is a Class II MEK1 mutation selected from ΔE51-Q58; ΔF53-Q58; E203K; L177M; C121S; F53L; K57E; Q56P; and K57N.

PI3K inhibitors include, but are not limited to, wortmannin; 17-hydroxywortmannin analogs described in WO06/044453; 4-[2-(1H-Indazol-4-yl)-6-[[4-(methylsulfonyl)piperazin-1-yl]methyl]thieno[3,2-d]pyrimidin-4-yl]morpholine (also known as pictilisib or GDC-0941 and described in WO09/036082 and WO09/055730); 2-methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in WO06/122806); (S)—I-(4-((2-(2-aminopyrimidin-5-yl)-7-methyl-4-morpholinothieno[3,2-d]pyrimidin-6-yl)methyl)piperazin-1-yl)-2-hydroxypropan-1-one (described in WO08/070740); LY294002 (2-(4-morpholinyl)-8-phenyl-4H-I-benzopyran-4-one (available from Axon Medchem); PI 103 hydrochloride (3-[4-(4-morpholinylpyrido-[3',2':4,5]furo[3,2-d]pyrimidin-2-yl]phenol hydrochloride (available from Axon Medchem); PIK 75 (2-methyl-5-nitro-2-[(6-bromoimidazo[1,2-a]pyridin-3-yl)methylene]-1-methylhydrazide-benzenesulfonic acid, monohydrochloride) (available from Axon Medchem); PIK 90 (N-(7,8-dimethoxy-2,3-dihydro-imidazo[1,2-c]quinazolin-5-yl)-nicotinamide (available from Axon Medchem); AS-252424 (5-[l-[5-(4-fluoro-2-hydroxy-phenyl)-furan-2-yl]-meth-(Z)-ylidene]-thiazolidine-2,4-dione (available from Axon Medchem); TGX-221 (7-methyl-2-(4-morpholinyl)-9-[1-(phenylamino)ethyl]-4H-pyrido-[1,2-a] pyrirnidin-4-one (available from Axon Medchem); XL-765; and XL-147. Other PI3K inhibitors include demethoxyviridin, perifosine, CAL101, PX-866, BEZ235, SF1126, INK1117, IPI-145, BKM120, XL147, XL765, Palomid 529, GSK1059615, ZSTK474, PWT33597, IC87114, TGI 00-115, CAL263, PI-103, GNE-477, CUDC-907, and AEZS-136.

AKT inhibitors include, but are not limited to, Akt-1-1 (inhibits Aktl) (Barnett et al., Biochem. J. 2005, 385(Pt. 2): 399-408); Akt-1-1,2 (inhibits Akl and 2) (Barnett et al., Biochem. J. 2005, 385(Pt. 2): 399-408); API-59CJ-Ome (e.g., Jin et al., Br. J. Cancer 2004, 91:1808-12); 1-H-imidazo[4,5-c]pyridinyl compounds (e.g., WO 05/011700); indole-3-carbinol and derivatives thereof (e.g., U.S. Pat. No. 6,656,963; Sarkar and Li J Nutr. 2004, 134(12 Suppl): 3493S-3498S); perifosine (e.g., interferes with Akt membrane localization; Dasmahapatra et al. Clin. Cancer Res. 2004, 10(15):5242-52); phosphatidylinositol ether lipid analogues (e.g., Gills and Dennis Expert. Opin. Investig. Drugs 2004, 13:787-97); and triciribine (TCN or API-2 or NCI identifier: NSC 154020; Yang et al., Cancer Res. 2004, 64:4394-9).

mTOR inhibitors include, but are not limited to, ATP-competitive mTORC1/mTORC2 inhibitors, e.g., PI-103, PP242, PP30; Torin 1; FKBP12 enhancers; 4H-1-benzopyran-4-one derivatives; and rapamycin (also known as sirolimus) and derivatives thereof, including: temsirolimus (Torisel®); everolimus (Afinitor®; WO94/09010); ridaforolimus (also known as deforolimus or AP23573); rapalogs, e.g., as disclosed in WO98/02441 and WO01/14387, e.g. AP23464 and AP23841; 40-(2-hydroxyethyl) rapamycin; 40-[3-hydroxy(hydroxymethyl)methylpropanoate]-rapamycin (also known as CC1779); 40-epi-(tetrazolyt)-rapamycin (also called ABT578); 32-deoxorapamycin; 16-pentynyloxy-32(S)-dihydrorapanycin; derivatives disclosed in WO05/005434; derivatives disclosed in U.S. Pat. Nos. 5,258,389, 5,118,677, 5,118,678, 5,100,883, 5,151,413, 5,120,842, and 5,256,790, and in WO94/090101, WO92/05179, WO93/111130, WO94/02136, WO94/02485, WO95/14023, WO94/02136, WO95/16691, WO96/41807, WO96/41807, and WO2018204416; and phosphorus-containing rapamycin derivatives (e.g., WO05/016252). In some embodiments, the mTOR inhibitor is a bisteric inhibitor (see, e.g., WO2018204416, WO2019212990 and WO2019212991), such as RMC-5552.

BRAF inhibitors that may be used in combination with compounds of the invention include, for example, vemurafenib, dabrafenib, and encorafenib. A BRAF may comprise a Class 3 BRAF mutation. In some embodiments, the Class 3 BRAF mutation is selected from one or more of the following amino acid substitutions in human BRAF:

D287H; P367R; V459L; G466V; G466E; G466A; S467L; G469E; N581S; N581I; D594N; D594G; D594A; D594H; F595L; G596D; G596R and A762E.

MCL-1 inhibitors include, but are not limited to, AMG-176, MIK665, and S63845. The myeloid cell leukemia-1 (MCL-1) protein is one of the key anti-apoptotic members of the B-cell lymphoma-2 (BCL-2) protein family. Over-expression of MCL-1 has been closely related to tumor progression as well as to resistance, not only to traditional chemotherapies but also to targeted therapeutics including BCL-2 inhibitors such as ABT-263.

In some embodiments, the additional therapeutic agent is a SHP2 inhibitor. SHP2 is a non-receptor protein tyrosine phosphatase encoded by the PTPN11 gene that contributes to multiple cellular functions including proliferation, differentiation, cell cycle maintenance and migration. SHP2 has two N-terminal Src homology 2 domains (N—SH2 and C—SH2), a catalytic domain (PTP), and a C-terminal tail. The two SH2 domains control the subcellular localization and functional regulation of SHP2. The molecule exists in an inactive, self-inhibited conformation stabilized by a binding network involving residues from both the N—SH2 and PTP domains. Stimulation by, for example, cytokines or growth factors acting through receptor tyrosine kinases (RTKs) leads to exposure of the catalytic site resulting in enzymatic activation of SHP2.

SHP2 is involved in signaling through the RAS-mitogen-activated protein kinase (MAPK), the JAK-STAT or the phosphoinositol 3-kinase-AKT pathways. Mutations in the PTPN11 gene and subsequently in SHP2 have been identified in several human developmental diseases, such as Noonan Syndrome and Leopard Syndrome, as well as human cancers, such as juvenile myelomonocytic leukemia, neuroblastoma, melanoma, acute myeloid leukemia and cancers of the breast, lung and colon. Some of these mutations destabilize the auto-inhibited conformation of SHP2 and promote autoactivation or enhanced growth factor driven activation of SHP2. SHP2, therefore, represents a highly attractive target for the development of novel therapies for the treatment of various diseases including cancer. A SHP2 inhibitor (e.g., RMC-4550 or SHP099) in combination with a RAS pathway inhibitor (e.g., a MEK inhibitor) have been shown to inhibit the proliferation of multiple cancer cell lines in vitro (e.g., pancreas, lung, ovarian and breast cancer). Thus, combination therapy involving a SHP2 inhibitor with a RAS pathway inhibitor could be a general strategy for preventing tumor resistance in a wide range of malignancies.

Non-limiting examples of such SHP2 inhibitors that are known in the art, include: Chen et al. Mol Pharmacol. 2006, 70, 562; Sarver et al., J. Med. Chem. 2017, 62, 1793; Xie et al., J. Med. Chem. 2017, 60, 113734; and Igbe etai, Oncotarget, 2017, 8, 113734; and PCT applications: WO2015107493; WO2015107494; WO201507495; WO2016203404; WO2016203405; WO2016203406; WO2011022440; WO2017156397; WO2017079723; WO2017211303; WO2012041524; WO2017211303; WO2019051084; WO2017211303; US20160030594; US20110281942; WO2010011666; WO2014113584; WO2014176488; WO2017100279; WO2019051469; U.S. Pat. No. 8,637,684; WO2007117699; WO2015003094; WO2005094314; WO2008124815; WO2009049098; WO2009135000; WO2016191328; WO2016196591; WO2017078499; WO2017210134; WO2018013597; WO2018129402; WO2018130928; WO20181309928; WO2018136264; WO2018136265; WO2018160731; WO2018172984; and WO2010121212, each of which is incorporated herein by reference.

In some embodiments, a SHP2 inhibitor binds in the active site. In some embodiments, a SHP2 inhibitor is a mixed-type irreversible inhibitor. In some embodiments, a SHP2 inhibitor binds an allosteric site e.g., a non-covalent allosteric inhibitor. In some embodiments, a SHP2 inhibitor is a covalent SHP2 inhibitor, such as an inhibitor that targets the cysteine residue (C333) that lies outside the phosphatase's active site. In some embodiments a SHP2 inhibitor is a reversible inhibitor. In some embodiments, a SHP2 inhibitor is an irreversible inhibitor. In some embodiments, the SHP2 inhibitor is SHP099. In some embodiments, the SHP2 inhibitor is TN0155. In some embodiments, the SHP2 inhibitor is RMC-4550. In some embodiments, the SHP2 inhibitor is RMC-4630. In some embodiments, the SHP2 inhibitor is JAB-3068. In some embodiments, the SHP2 inhibitor is RLY-1971.

In some embodiments, the additional therapeutic agent is selected from the group consisting of a MEK inhibitor, a HER2 inhibitor, a SHP2 inhibitor, CDK4/6 inhibitor, an mTOR inhibitor, a SOS1 inhibitor, and a PD-L1 inhibitor. In some embodiments, the additional therapeutic agent is selected from the group consisting of a MEK inhibitor, a SHP2 inhibitor, and a PD-L1 inhibitor. See, e.g., Hallin et al., Cancer Discovery, DOI: 10.1158/2159-8290 (Oct. 28, 2019) and Canon et al., Nature, 575:217 (2019). In some embodiments, a Ras inhibitor of the present invention is used in combination with a MEK inhibitor and a SOS1 inhibitor. In some embodiments, a Ras inhibitor of the present invention is used in combination with a PDL-1 inhibitor and a SOS1 inhibitor. In some embodiments, a Ras inhibitor of the present invention is used in combination with a PDL-1 inhibitor and a SHP2 inhibitor. In some embodiments, a Ras inhibitor of the present invention is used in combination with a MEK inhibitor and a SHP2 inhibitor. In some embodiments, the cancer is colorectal cancer and the treatment comprises administration of a Ras inhibitor of the present invention in combination with a second or third therapeutic agent.

Proteasome inhibitors include, but are not limited to, carfilzomib (Kyprolis®), bortezomib (Velcade®), and oprozomib.

Immune therapies include, but are not limited to, monoclonal antibodies, immunomodulatory imides (IMiDs), GITR agonists, genetically engineered T-cells (e.g., CAR-T cells), bispecific antibodies (e.g., BiTEs), and anti-PD-1, anti-PDL-1, anti-CTLA4, anti-LAGI, and anti-OX40 agents).

Immunomodulatory agents (IMiDs) are a class of immunomodulatory drugs (drugs that adjust immune responses) containing an imide group. The IMiD class includes thalidomide and its analogues (lenalidomide, pomalidomide, and apremilast).

Exemplary anti-PD-1 antibodies and methods for their use are described by Goldberg et al., Blood 2007, 110(1):186-192; Thompson et al., Clin. Cancer Res. 2007, 13(6):1757-1761; and WO06/121168 A1), as well as described elsewhere herein.

GITR agonists include, but are not limited to, GITR fusion proteins and anti-GITR antibodies (e.g., bivalent anti-GITR antibodies), such as, a GITR fusion protein described in U.S. Pat. Nos. 6,111,090, 8,586,023, WO2010/003118 and WO2011/090754; or an anti-GITR antibody described, e.g., in U.S. Pat. No. 7,025,962, EP 1947183, U.S. Pat. Nos. 7,812,135, 8,388,967, 8,591,886, 7,618,632, EP 1866339, and WO2011/028683, WO2013/039954, WO05/007190, WO07/133822, WO05/055808, WO99/40196, WO01/03720, WO99/20758, WO06/083289, WO05/115451, and WO2011/051726.

Another example of a therapeutic agent that may be used in combination with the compounds of the invention is an anti-angiogenic agent. Anti-angiogenic agents are inclusive of, but not limited to, in vitro synthetically prepared chemical compositions, antibodies, antigen binding regions, radionuclides, and combinations and conjugates thereof. An anti-angiogenic agent can be an agonist, antagonist, allosteric modulator, toxin or, more generally, may act to inhibit or stimulate its target (e.g., receptor or enzyme activation or inhibition), and thereby promote cell death or arrest cell growth. In some embodiments, the one or more additional therapies include an anti-angiogenic agent.

Anti-angiogenic agents can be MMP-2 (matrix-metalloproteinase 2) inhibitors, MMP-9 (matrix-metalloprotienase 9) inhibitors, and COX-II (cyclooxygenase 11) inhibitors. Non-limiting examples of anti-angiogenic agents include rapamycin, temsirolimus (CCI-779), everolimus (RAD001), sorafenib, sunitinib, and bevacizumab. Examples of useful COX-II inhibitors include alecoxib, valdecoxib, and rofecoxib. Examples of useful matrix metalloproteinase inhibitors are described in WO96/33172, WO96/27583, WO98/07697, WO98/03516, WO98/34918, WO98/34915, WO98/33768, WO98/30566, WO90/05719, WO99/52910, WO99/52889, WO99/29667, WO99007675, EP0606046, EP0780386, EP1786785, EP1181017, EP0818442, EP1004578, and US20090012085, and U.S. Pat. Nos. 5,863,949 and 5,861,510. Preferred MMP-2 and MMP-9 inhibitors are those that have little or no activity inhibiting MMP-1. More preferred, are those that selectively inhibit MMP-2 or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors are AG-3340, RO 32-3555, and RS 13-0830.

Further exemplary anti-angiogenic agents include KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF (e.g., bevacizumab), or soluble VEGF receptors or a ligand binding region thereof) such as VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as Vectibix® (panitumumab), erlotinib (Tarceva®), anti-Angl and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). Other anti-angiogenic agents include Campath, IL-8, B-FGF, Tek antagonists (US2003/0162712; U.S. Pat. No. 6,413,932), anti-TWEAK agents (e.g., specifically binding antibodies or antigen binding regions, or soluble TWEAK receptor antagonists; see U.S. Pat. No. 6,727,225), ADAM distintegrin domain to antagonize the binding of integrin to its ligands (US 2002/0042368), specifically binding anti-eph receptor or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto). Additional anti-angiogenic agents include: SD-7784 (Pfizer, USA); cilengitide (Merck KGaA, Germany, EPO 0770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol (EntreMed, USA); TLC ELL-12 (Elan, Ireland); anecortave acetate (Alcon, USA); alpha-D148 Mab (Amgen, USA); CEP-7055 (Cephalon, USA); anti-Vn Mab (Crucell, Netherlands), DACantiangiogenic (ConjuChem, Canada); Angiocidin (InKine Pharmaceutical, USA); KM-2550 (Kyowa Hakko, Japan); SU-0879 (Pfizer, USA); CGP-79787 (Novartis, Switzerland, EP 0970070); ARGENT technology (Ariad, USA); YIGSR-Stealth (Johnson & Johnson, USA); fibrinogen-E fragment (BioActa, UK); angiogenic inhibitor (Trigen, UK); TBC-1635 (Encysive Pharmaceuticals, USA); SC-236 (Pfizer, USA); ABT-567 (Abbott, USA); Metastatin (EntreMed, USA); maspin (Sosei, Japan); 2-methoxyestradiol (Oncology Sciences Corporation, USA); ER-68203-00 (IV AX, USA); BeneFin (Lane Labs, USA); Tz-93 (Tsumura, Japan); TAN-1120 (Takeda, Japan); FR-111142 (Fujisawa, Japan, JP 02233610); platelet factor 4 (RepliGen, USA, EP 407122); vascular endothelial growth factor antagonist (Borean, Denmark); bevacizumab (pINN) (Genentech, USA); angiogenic inhibitors (SUGEN, USA); XL 784 (Exelixis, USA); XL 647 (Exelixis, USA); MAb, alpha5beta3 integrin, second generation (Applied Molecular Evolution, USA and MedImmune, USA); enzastaurin hydrochloride (Lilly, USA); CEP 7055 (Cephalon, USA and Sanofi-Synthelabo, France); BC 1 (Genoa Institute of Cancer Research, Italy); rBPI 21 and BPI-derived antiangiogenic (XOMA, USA); PI 88 (Progen, Australia); cilengitide (Merck KGaA, German; Munich Technical University, Germany, Scripps Clinic and Research Foundation, USA); AVE 8062 (Ajinomoto, Japan); AS 1404 (Cancer Research Laboratory, New Zealand); SG 292, (Telios, USA); Endostatin (Boston Childrens Hospital, USA); ATN 161 (Attenuon, USA); 2-methoxyestradiol (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX478, (ProIX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenic, (EntreMed, USA); urokinase plasminogen activator inhibitor, (Dendreon, USA); oglufanide (pINN), (Melmotte, USA); HIF-lalfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol; anginex (Maastricht University, Netherlands, and Minnesota University, USA); ABT 510 (Abbott, USA); AAL 993 (Novartis, Switzerland); VEGI (ProteomTech, USA); tumor necrosis factor-alpha inhibitors; SU 11248 (Pfizer, USA and SUGEN USA); ABT 518, (Abbott, USA); YH16 (Yantai Rongchang, China); S-3APG (Boston Childrens Hospital, USA and EntreMed, USA); MAb, KDR (ImClone Systems, USA); MAb, alpha5 beta (Protein Design, USA); KDR kinase inhibitor (Celltech Group, UK, and Johnson & Johnson, USA); GFB 116 (South Florida University, USA and Yale University, USA); CS 706 (Sankyo, Japan); combretastatin A4 prodrug (Arizona State University, USA); chondroitinase AC (IBEX, Canada); BAY RES 2690 (Bayer, Germany); AGM 1470 (Harvard University, USA, Takeda, Japan, and TAP, USA); AG 13925 (Agouron, USA); Tetrathiomolybdate (University of Michigan, USA); GCS 100 (Wayne State University, USA) CV 247 (Ivy Medical, UK); CKD 732 (Chong Kun Dang, South Korea); irsogladine, (Nippon Shinyaku, Japan); RG 13577 (Aventis, France); WX 360 (Wilex, Germany); squalamine, (Genaera, USA); RPI 4610 (Sirna, USA); heparanase inhibitors (InSight, Israel); KL 3106 (Kolon, South Korea); Honokiol (Emory University, USA); ZK CDK (Schering AG, Germany); ZK Angio (Schering AG, Germany); ZK 229561 (Novartis, Switzerland, and Schering AG, Germany); XMP 300 (XOMA, USA); VGA 1102 (Taisho, Japan); VE-cadherin-2 antagonists (ImClone Systems, USA); Vasostatin (National Institutes of Health, USA); Flk-1 (ImClone Systems, USA); TZ 93 (Tsumura, Japan); TumStatin (Beth Israel Hospital, USA); truncated soluble FLT 1 (vascular endothelial growth factor receptor 1) (Merck & Co, USA); Tie-2 ligands (Regeneron, USA); and thrombospondin 1 inhibitor (Allegheny Health, Education and Research Foundation, USA).

Further examples of therapeutic agents that may be used in combination with compounds of the invention include agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor, c-Met.

Another example of a therapeutic agent that may be used in combination with compounds of the invention is an autophagy inhibitor. Autophagy inhibitors include, but are not limited to chloroquine, 3-methyladenine, hydroxychloroquine (Plaquenil™), bafilomycin A1,5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used. In some embodiments, the one or more additional therapies include an autophagy inhibitor.

Another example of a therapeutic agent that may be used in combination with compounds of the invention is an anti-neoplastic agent. In some embodiments, the one or more additional therapies include an anti-neoplastic agent. Non-limiting examples of anti-neoplastic agents include acemannan, aclarubicin, aldesleukin, alemtuzumab, alitretinoin, altretamine, amifostine, aminolevulinic acid, amrubicin, amsacrine, anagrelide, anastrozole, ancer, ancestim, arglabin, arsenic trioxide, BAM-002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-NI, interferon alfa-n3, interferon alfacon-1, interferon alpha, natural, interferon beta, interferon beta-la, interferon beta-lb, interferon gamma, natural interferon gamma-la, interferon gamma-lb, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburiembodiment, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, virulizin, zinostatin stimalamer, orzoledronic acid; abarelix; AE 941 (Aeterna), ambamustine, antisense oligonucleotide, bcl-2 (Genta), APC 8015 (Dendreon), decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techni clone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Additional examples of therapeutic agents that may be used in combination with compounds of the invention include ipilimumab (Yervoy®); tremelimumab; galiximab; nivolumab, also known as BMS-936558 (Opdivo®); pembrolizumab (Keytruda®); avelumab (Bavencio®); AMP224; BMS-936559; MPDL3280A, also known as RG7446; MEDI-570; AMG557; MGA271; IMP321; BMS-663513; PF-05082566; CDX-1127; anti-OX40 (Providence Health Services); huMAbOX40L; atacicept; CP-870893; lucatumumab; dacetuzumab; muromonab-CD3; ipilumumab; MEDI4736 (Imfinzi®); MSB0010718C; AMP 224; adalimumab (Humira®); ado-trastuzumab emtansine (Kadcyla®); aflibercept (Eylea®); alemtuzumab (Campath®); basiliximab (Simulect®); belimumab (Benlysta®); basiliximab (Simulect®); belimumab (Benlysta®); brentuximab vedotin (Adcetris®); canakinumab (Maris®); certolizumab pegol (Cimzia®); daclizumab (Zenapax®); daratumumab (Darzalex®); denosumab (Prolia®); eculizumab (Soliris®); efalizumab (Raptiva®); gemtuzumab ozogamicin (Mylotarg®); golimumab (Simponi®); ibritumomab tiuxetan (Zevalin®); infliximab (Remicade®); motavizumab (Numax®); natalizumab (Tysabri®); obinutuzumab (Gazyva®); ofatumumab (Arzerra®); omalizumab (Xolair®); palivizumab (Synagis®); pertuzumab (Perjeta®); pertuzumab (Perjeta®); ranibizumab (Lucentis®); raxibacumab (Abthrax®); tocilizumab (Actemra®); tositumomab; tositumomab-i-131; tositumomab and tositumomab-i-131 (Bexxar®); ustekinumab (Stelara®); AMG 102; AMG 386; AMG 479; AMG 655; AMG 706; AMG 745; and AMG 951.

The compounds described herein can be used in combination with the agents disclosed herein or other suitable agents, depending on the condition being treated. Hence, in some embodiments the one or more compounds of the disclosure will be co-administered with other therapies as described herein. When used in combination therapy, the compounds described herein may be administered with the second agent simultaneously or separately. This administration in combination can include simultaneous administration of the two agents in the same dosage form, simultaneous administration in separate dosage forms, and separate administration. That is, a compound described herein and any of the agents described herein can be formulated together in the same dosage form and administered simultaneously. Alternatively, a compound of the invention and any of the therapies described herein can be simultaneously administered, wherein both the agents are present in separate formulations. In another alternative, a compound of the present disclosure can be administered and followed by any of the therapies described herein, or vice versa. In some embodiments of the separate administration protocol, a compound of the invention and any of the therapies described herein are administered a few minutes apart, or a few hours apart, or a few days apart.

In some embodiments of any of the methods described herein, the first therapy (e.g., a compound of the invention) and one or more additional therapies are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up to 18 hours, up to 19 hours up to 20 hours, up to 21 hours, up to 22 hours, up to 23 hours, up to 24 hours, or up to 1-7, 1-14, 1-21 or 1-30 days before or after the one or more additional therapies.

The invention also features kits including (a) a pharmaceutical composition including an agent (e.g., a compound of the invention) described herein, and (b) a package insert with instructions to perform any of the methods described herein. In some embodiments, the kit includes (a) a pharmaceutical composition including an agent (e.g., a compound of the invention) described herein, (b) one or more additional therapies (e.g., non-drug treatment or therapeutic agent), and (c) a package insert with instructions to perform any of the methods described herein.

As one aspect of the present invention contemplates the treatment of the disease or symptoms associated therewith with a combination of pharmaceutically active compounds that may be administered separately, the invention further relates to combining separate pharmaceutical compositions in kit form. The kit may comprise two separate pharmaceutical compositions: a compound of the present invention, and one or more additional therapies. The kit may comprise a container for containing the separate compositions such as a divided bottle or a divided foil packet. Additional examples of containers include syringes, boxes, and bags. In some embodiments, the kit may comprise directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

Numbered Embodiments

[1] A compound, or pharmaceutically acceptable salt thereof, having the structure of Formula I:

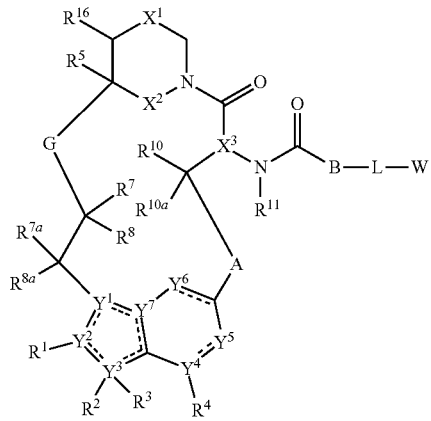

Formula I wherein the dotted lines represent zero, one, two, three, or four non-adjacent double bonds;

A is —N(H or $CH_3$)C(O)—($CH_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— or >C=C$R^9R^{9'}$ where the carbon is bound to the carbonyl carbon of —N($R^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

G is optionally substituted $C_1$-$C_4$ alkylene, optionally substituted $C_1$-$C_4$ alkenylene, optionally substituted $C_1$-$C_4$ heteroalkylene, —C(O)O—CH($R^6$)— where C is bound to —C($R^7R^8$)—, —C(O)NH—CH($R^6$)— where C is bound to —C($R^7R^8$)—, optionally substituted $C_1$-$C_4$ heteroalkylene, or 3 to 8-membered heteroarylene;

L is absent or a linker;

W is hydrogen, cyano, optionally substituted amino, optionally substituted $C_1$-$C_4$ alkoxy, optionally substituted $C_1$-$C_4$ hydroxyalkyl, optionally substituted $C_1$-$C_4$ aminoalkyl, optionally substituted $C_1$-$C_4$ haloalkyl, optionally substituted $C_1$-$C_4$ alkyl, optionally substituted $C_1$-$C_4$ guanidinoalkyl, $C_0$-$C_4$ alkyl optionally substituted 3 to 11-membered heterocycloalkyl, optionally substituted 3 to 8-membered cycloalkyl, optionally substituted 6 to 10-membered aryl, or optionally substituted 3 to 8-membered heteroaryl;

$X^1$ is optionally substituted $C_1$-$C_2$ alkylene, NR, O, or S(O)$_n$;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ is CH, CH$_2$, or N;

$Y^6$ is C(O), CH, CH$_2$, or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl, or $R^1$ and $R^2$ combine with the atoms to which they are attached to form an optionally substituted 3 to 14-membered heterocycloalkyl;

$R^2$ is absent, hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=CR$^{7'}$R$^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7a}$ and $R^{8a}$ are, independently, hydrogen, halo, optionally substituted $C_1$-$C_3$ alkyl, or combine with the carbon to which they are attached to form a carbonyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is hydrogen, F, optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl;

$R^9$ and L combine with the atoms to which they are attached to form an optionally substituted 3 to 14-membered heterocycloalkyl;

$R^{9'}$ is hydrogen or optionally substituted $C_1$-$C_6$ alkyl;

$R^{10}$ is hydrogen, halo, hydroxy, $C_1$-$C_3$ alkoxy, or $C_1$-$C_3$ alkyl;

$R^{10a}$ is hydrogen or halo;

$R^{11}$ is hydrogen or $C_1$-$C_3$ alkyl; and $R^{16}$ is hydrogen or $C_1$-$C_3$ alkyl.

[2] The compound, or pharmaceutically acceptable salt thereof, of paragraph [1], wherein G is optionally substituted $C_1$-$C_4$ heteroalkylene.

[3] The compound, or pharmaceutically acceptable salt thereof, of paragraph [1] or [2], wherein the compound has the structure of Formula Ic:

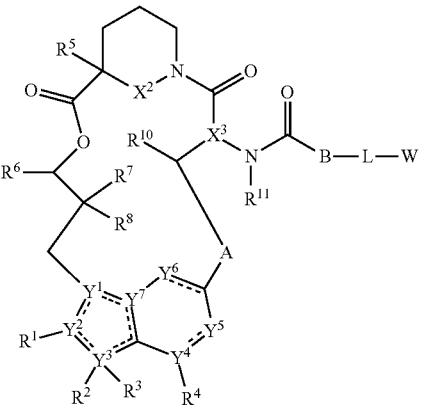

Formula Ic wherein the dotted lines represent zero, one, two, three, or four non-adjacent double bonds;

A is —N(H or CH₃)C(O)—(CH₂)— where the amino nitrogen is bound to the carbon atom of —CH(R¹⁰)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH(R⁹)— where the carbon is bound to the carbonyl carbon of —N(R¹¹)C(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is hydrogen, optionally substituted amino, optionally substituted C₁-C₄ alkoxy, optionally substituted C₁-C₄ hydroxyalkyl, optionally substituted C₁-C₄ aminoalkyl, optionally substituted C₁-C₄ haloalkyl, optionally substituted C₁-C₄ alkyl, optionally substituted C₁-C₄ guanidinoalkyl, C₀-C₄ alkyl optionally substituted 3 to 11-membered heterocycloalkyl, optionally substituted 3 to 8-membered cycloalkyl, or optionally substituted 3 to 8-membered heteroaryl;

X² is O or NH;
X³ is N or CH;
n is 0, 1, or 2;

R is hydrogen, cyano, optionally substituted C₁-C₄ alkyl, optionally substituted C₂-C₄ alkenyl, optionally substituted C₂-C₄ alkynyl, C(O)R', C(O)OR', C(O)N(R')₂, S(O)R', S(O)₂R', or S(O)₂N(R')₂;

each R' is, independently, H or optionally substituted C₁-C₄ alkyl;

Y¹ is C, CH, or N;
Y², Y³, Y⁴, and Y⁷ are, independently, C or N;
Y⁵ and Y⁶ are, independently, CH or N;

R¹ is cyano, optionally substituted C₁-C₆ alkyl, optionally substituted C₁-C₆ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

R² is hydrogen, optionally substituted C₁-C₆ alkyl, optionally substituted C₂-C₆ alkenyl, optionally substituted 3 to 6-membered cycloalkyl, optionally substituted 3 to 7-membered heterocycloalkyl, optionally substituted 6-membered aryl, optionally substituted 5 or 6-membered heteroaryl; R³ is absent or R² and R³ combine with the atom to which they are attached to form an optionally substituted 3 to 8-membered cycloalkyl or optionally substituted 3 to 14-membered heterocycloalkyl;

R⁴ is absent, hydrogen, halogen, cyano, or methyl optionally substituted with 1 to 3 halogens;

R⁵ is hydrogen, C₁-C₄ alkyl optionally substituted with halogen, cyano, hydroxy, or C₁-C₄ alkoxy, cyclopropyl, or cyclobutyl;

R⁶ is hydrogen or methyl; R⁷ is hydrogen, halogen, or optionally substituted C₁-C₃ alkyl, or R⁶ and R⁷ combine with the carbon atoms to which they are attached to form an optionally substituted 3 to 6-membered cycloalkyl or optionally substituted 3 to 7-membered heterocycloalkyl;

R⁸ is hydrogen, halogen, hydroxy, cyano, optionally substituted C₁-C₃ alkoxy, optionally substituted C₁-C₃ alkyl, optionally substituted C₂-C₆ alkenyl, optionally substituted C₂-C₆ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or R⁷ and R⁸ combine with the carbon atom to which they are attached to form C=CR⁷'R⁸'; C=N(OH), C=N(O—C₁-C₃ alkyl), C=O, C=S, C=NH, optionally substituted 3 to 6-membered cycloalkyl, or optionally substituted 3 to 7-membered heterocycloalkyl;

R⁷' is hydrogen, halogen, or optionally substituted C₁-C₃ alkyl; R⁸' is hydrogen, halogen, hydroxy, cyano, optionally substituted C₁-C₃ alkoxy, optionally substituted C₁-C₃ alkyl, optionally substituted C₂-C₆ alkenyl, optionally substituted C₂-C₆ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or R⁷' and R⁸' combine with the carbon atom to which they are attached to form optionally substituted 3 to 6-membered cycloalkyl or optionally substituted 3 to 7-membered heterocycloalkyl;

R⁹ is optionally substituted C₁-C₆ alkyl, optionally substituted C₁-C₆ heteroalkyl, optionally substituted 3 to 6-membered cycloalkyl, or optionally substituted 3 to 7-membered heterocycloalkyl;

R¹⁰ is hydrogen, hydroxy, C₁-C₃ alkoxy, or C₁-C₃ alkyl; and

R¹¹ is hydrogen or C₁-C₃ alkyl.

[4] The compound, or pharmaceutically acceptable salt thereof, of any one of paragraphs [1] to [3], wherein X² is NH.

[5] The compound, or pharmaceutically acceptable salt thereof, of any one of paragraphs [1] to [4], wherein X³ is CH.

[6] The compound, or pharmaceutically acceptable salt thereof, of any one of paragraphs [1] to [5], wherein R¹¹ is hydrogen.

[7] The compound, or pharmaceutically acceptable salt thereof, of any one of paragraphs [1] to [5], wherein R¹¹ is C₁-C₃ alkyl.

[8] The compound, or pharmaceutically acceptable salt thereof, of paragraph [7], wherein R¹¹ is methyl.

[9] The compound, or pharmaceutically acceptable salt thereof, of any one of paragraphs [1] to [6], wherein the compound has the structure of Formula Id:

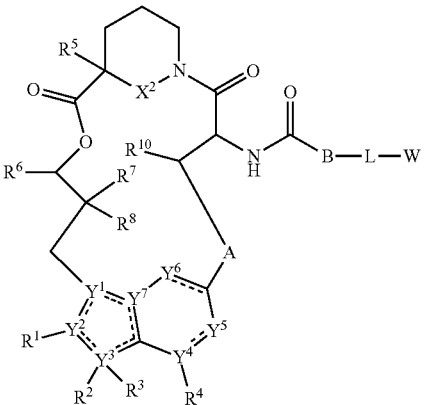

Formula Id wherein the dotted lines represent zero, one, two, three, or four non-adjacent double bonds;

A is —N(H or CH₃)C(O)—(CH₂)— where the amino nitrogen is bound to the carbon atom of —CH(R¹⁰)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is hydrogen, optionally substituted amino, optionally substituted $C_1$-$C_4$ alkoxy, optionally substituted $C_1$-$C_4$ hydroxyalkyl, optionally substituted $C_1$-$C_4$ aminoalkyl, optionally substituted $C_1$-$C_4$ haloalkyl, optionally substituted $C_1$-$C_4$ alkyl, optionally substituted $C_1$-$C_4$ guanidinoalkyl, $C_0$-$C_4$ alkyl optionally substituted 3 to 11-membered heterocycloalkyl, optionally substituted 3 to 8-membered cycloalkyl, or optionally susbtituted 3 to 8-membered heteroaryl;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$R', or S(O)$_2$N(R')$_2$; each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ and $Y^6$ are, independently, CH or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

$R^2$ is hydrogen, optionally substituted $C_1$-$C_6$ alkyl, optionally substituted $C_2$-$C_6$ alkenyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=C$R^{7'}R^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl; and $R^{10}$ is hydrogen, hydroxy, $C_1$-$C_3$ alkoxy, or $C_1$-$C_3$ alkyl.

[10] The compound, or pharmaceutically acceptable salt thereof, of any one of paragraphs [1] to [9] wherein $X^1$ is optionally substituted $C_1$-$C_2$ alkylene.

[11] The compound, or pharmaceutically acceptable salt thereof, of paragraph [10], wherein $X^1$ is methylene.

[12] The compound, or pharmaceutically acceptable salt thereof, of any one of paragraphs [1] to [11], wherein $R^5$ is hydrogen.

[13] The compound, or pharmaceutically acceptable salt thereof, of any one of paragraphs [1] to [11], wherein $R^5$ is $C_1$-$C_4$ alkyl optionally substituted with halogen.

[14] The compound, or pharmaceutically acceptable salt thereof, of paragraph [13], wherein $R^5$ is methyl.

[15] The compound, or pharmaceutically acceptable salt thereof, of any one of paragraphs [1] to [14], wherein $Y^4$ is C.

[16] The compound, or pharmaceutically acceptable salt thereof, of any one of paragraphs [1] to [15], wherein $R^4$ is hydrogen.

[17] The compound, or pharmaceutically acceptable salt thereof, of any one of paragraphs [1] to [16], wherein $Y^5$ is CH.

[18] The compound, or pharmaceutically acceptable salt thereof, of any one of paragraphs [1] to [17], wherein $Y^6$ is CH.

[19] The compound, or pharmaceutically acceptable salt thereof, of any one of paragraphs [1] to [18], wherein $Y^1$ is C.

[20] The compound, or pharmaceutically acceptable salt thereof, of any one of paragraphs [1] to [19], wherein $Y^2$ is C.

[21] The compound, or pharmaceutically acceptable salt thereof, of any one of paragraphs [1] to [20], wherein $Y^3$ is N.

[22] The compound, or pharmaceutically acceptable salt thereof, of any one of paragraphs [1] to [21], wherein $R^3$ is absent.

[23] The compound, or pharmaceutically acceptable salt thereof, of any one of paragraphs [1] to [22], wherein $Y^7$ is C.

[24] The compound, or pharmaceutically acceptable salt thereof, of any one of paragraphs [1] to [6] or [9] to [23], wherein the compound has the structure of Formula Ie:

Formula Ie

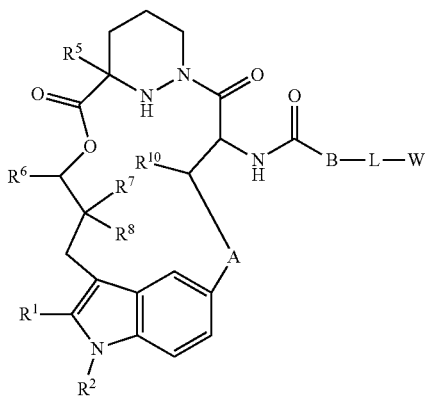

wherein A is —N(H or CH₃)C(O)—(CH₂)— where the amino nitrogen is bound to the carbon atom of —CH(R¹⁰)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH(R⁹)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is hydrogen, optionally substituted amino, optionally substituted C₁-C₄ alkoxy, optionally substituted C₁-C₄ hydroxyalkyl, optionally substituted C₁-C₄ aminoalkyl, optionally substituted C₁-C₄ haloalkyl, optionally substituted C₁-C₄ alkyl, optionally substituted C₁-C₄ guanidinoalkyl, C₀-C₄ alkyl optionally substituted 3 to 11-membered heterocycloalkyl, optionally substituted 3 to 8-membered cycloalkyl, or optionally susbtituted 3 to 8-membered heteroaryl;

R¹ is cyano, optionally substituted C₁-C₆ alkyl, optionally substituted C₁-C₆ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

R² is hydrogen, optionally substituted C₁-C₆ alkyl, optionally substituted C₂-C₆ alkenyl, optionally substituted 3 to 6-membered cycloalkyl, optionally substituted 3 to 7-membered heterocycloalkyl, optionally substituted 6-membered aryl, optionally substituted 5 or 6-membered heteroaryl; R³ is absent or R² and R³ combine with the atom to which they are attached to form an optionally substituted 3 to 8-membered cycloalkyl or optionally substituted 3 to 14-membered heterocycloalkyl;

R⁵ is hydrogen, C₁-C₄ alkyl optionally substituted with halogen, cyano, hydroxy, or C₁-C₄ alkoxy, cyclopropyl, or cyclobutyl;

R⁶ is hydrogen or methyl; R⁷ is hydrogen, halogen, or optionally substituted C₁-C₃ alkyl, or R⁶ and R⁷ combine with the carbon atoms to which they are attached to form an optionally substituted 3 to 6-membered cycloalkyl or optionally substituted 3 to 7-membered heterocycloalkyl;

R⁸ is hydrogen, halogen, hydroxy, cyano, optionally substituted C₁-C₃ alkoxy, optionally substituted C₁-C₃ alkyl, optionally substituted C₂-C₆ alkenyl, optionally substituted C₂-C₆ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or R⁷ and R⁸ combine with the carbon atom to which they are attached to form C=CR⁷'R⁸'; C=N(OH), C=N(O—C₁-C₃ alkyl), C=O, C=S, C=NH, optionally substituted 3 to 6-membered cycloalkyl, or optionally substituted 3 to 7-membered heterocycloalkyl;

R⁷' is hydrogen, halogen, or optionally substituted C₁-C₃ alkyl; R⁸' is hydrogen, halogen, hydroxy, cyano, optionally substituted C₁-C₃ alkoxy, optionally substituted C₁-C₃ alkyl, optionally substituted C₂-C₆ alkenyl, optionally substituted C₂-C₆ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or R⁷' and R⁸' combine with the carbon atom to which they are attached to form optionally substituted 3 to 6-membered cycloalkyl or optionally substituted 3 to 7-membered heterocycloalkyl;

R⁹ is optionally substituted C₁-C₆ alkyl, optionally substituted C₁-C₆ heteroalkyl, optionally substituted 3 to 6-membered cycloalkyl, or optionally substituted 3 to 7-membered heterocycloalkyl; and R¹⁰ is hydrogen, hydroxy, C₁-C₃ alkoxy, or C₁-C₃ alkyl.

[25] The compound, or pharmaceutically acceptable salt thereof, of any one of paragraphs [3] to [24], wherein R⁶ is hydrogen.

[26] The compound, or pharmaceutically acceptable salt thereof, of any one of paragraphs [1] to [25], wherein R² is hydrogen, cyano, optionally substituted C₁-C₆ alkyl, optionally substituted 3 to 6-membered cycloalkyl, or optionally substituted 3 to 6-membered heterocycloalkyl.

[27] The compound, or pharmaceutically acceptable salt thereof, of paragraph [26], wherein R² is optionally substituted C₁-C₆ alkyl.

[28] The compound, or pharmaceutically acceptable salt thereof, of paragraph [27], wherein R² is ethyl.

[29] The compound, or pharmaceutically acceptable salt thereof, of any one of paragraphs [1] to [28], wherein R⁷ is optionally substituted C₁-C₃ alkyl.

[30] The compound, or pharmaceutically acceptable salt thereof, of paragraph [29], wherein R⁷ is C₁-C₃ alkyl.

[31] The compound, or pharmaceutically acceptable salt thereof, of any one of paragraphs [1] to [30], wherein R⁸ is optionally substituted C₁-C₃ alkyl.

[32] The compound, or pharmaceutically acceptable salt thereof, of paragraph [31], wherein R⁸ is C₁-C₃ alkyl.

[33] The compound, or pharmaceutically acceptable salt thereof, of any one of paragraphs [1] to [32], wherein the compound has the structure of Formula If:

Formula If

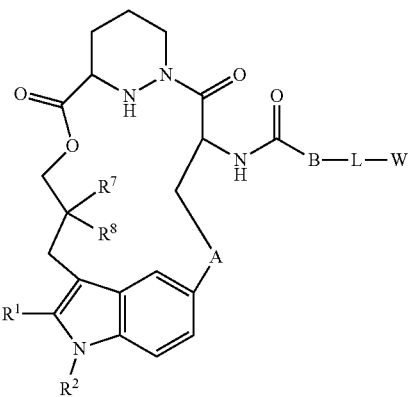

Formula Ig

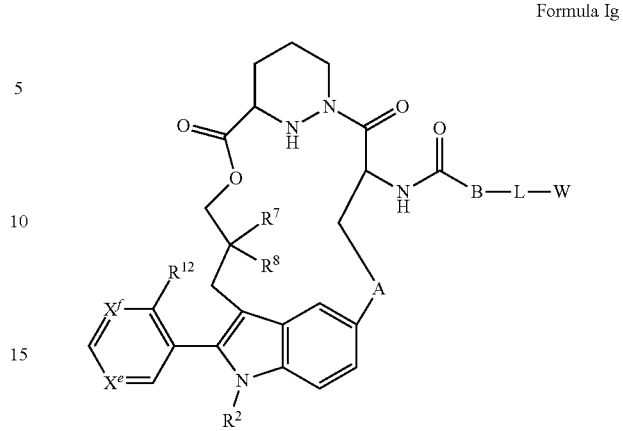

wherein A is —N(H or CH₃)C(O)—(CH₂)— where the amino nitrogen is bound to the carbon atom of —CH(R¹⁰)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH(R⁹)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is hydrogen, optionally substituted amino, optionally substituted $C_1$-$C_4$ alkoxy, optionally substituted $C_1$-$C_4$ hydroxyalkyl, optionally substituted $C_1$-$C_4$ aminoalkyl, optionally substituted $C_1$-$C_4$ haloalkyl, optionally substituted $C_1$-$C_4$ alkyl, optionally substituted $C_1$-$C_4$ guanidinoalkyl, $C_0$-$C_4$ alkyl optionally substituted 3 to 11-membered heterocycloalkyl, optionally substituted 3 to 8-membered cycloalkyl, or optionally susbtituted 3 to 8-membered heteroaryl;

R¹ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

R² is $C_1$-$C_6$ alkyl or 3 to 6-membered cycloalkyl;

R⁷ is $C_1$-$C_3$ alkyl;

R⁸ is $C_1$-$C_3$ alkyl; and

R⁹ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl.

[34] The compound, or pharmaceutically acceptable salt thereof, of any one of paragraphs [1] to [33], wherein R¹ is 5 to 10-membered heteroaryl.

[35] The compound, or pharmaceutically acceptable salt thereof, of paragraph [34], wherein R¹ is optionally substituted 6-membered aryl or optionally substituted 6-membered heteroaryl.

[36] The compound, or pharmaceutically acceptable salt thereof, of any one of paragraphs [1] to [35], wherein the compound has the structure of Formula Ig:

wherein A is, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH(R⁹)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is hydrogen, optionally substituted amino, optionally substituted $C_1$-$C_4$ alkoxy, optionally substituted $C_1$-$C_4$ hydroxyalkyl, optionally substituted $C_1$-$C_4$ aminoalkyl, optionally substituted $C_1$-$C_4$ haloalkyl, optionally substituted $C_1$-$C_4$ alkyl, optionally substituted $C_1$-$C_4$ guanidinoalkyl, $C_0$-$C_4$ alkyl optionally substituted 3 to 11-membered heterocycloalkyl, optionally substituted 3 to 8-membered cycloalkyl, or optionally susbtituted 3 to 8-membered heteroaryl;

R² is $C_1$-$C_6$ alkyl or 3 to 6-membered cycloalkyl;

R⁷ is $C_1$-$C_3$ alkyl;

R⁸ is $C_1$-$C_3$ alkyl;

R⁹ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl;

$X^e$ is N, CH, or CR¹⁷;

$X^f$ is N or CH;

R¹² is optionally substituted $C_1$-$C_6$ alkyl or optionally substituted $C_1$-$C_6$ heteroalkyl; and R¹⁷ is optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl.

[37] The compound, or pharmaceutically acceptable salt thereof, of paragraph [36], wherein $X^e$ is N and $X^f$ is CH.

[38] The compound, or pharmaceutically acceptable salt thereof, of paragraph [36], wherein $X^e$ is CH and $X^f$ is N.

[39] The compound, or pharmaceutically acceptable salt thereof, of paragraph [36], wherein $X^e$ is CR¹⁷ and $X^f$ is N.

[40] The compound, or pharmaceutically acceptable salt thereof, of any one of paragraphs [36] to [39], wherein R¹² is optionally substituted $C_1$-$C_6$ heteroalkyl.

[41] The compound, or pharmaceutically acceptable salt thereof, of any one of paragraphs [36] to [40], wherein $R^{12}$ is

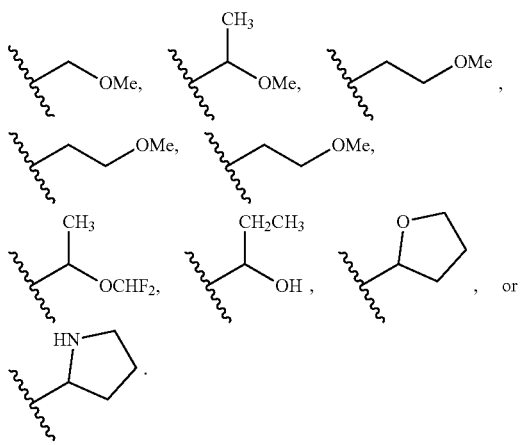

[42] The compound, or pharmaceutically acceptable salt thereof, of any one of paragraphs [1] to [41], wherein the compound has the structure of Formula Ih:

Formula Ih

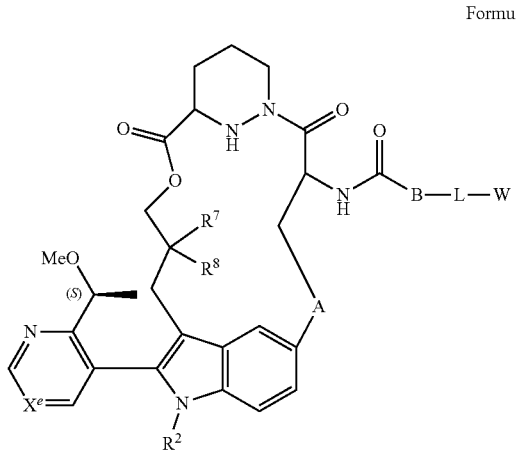

wherein A is optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is hydrogen, optionally substituted amino, optionally substituted $C_1$-$C_4$ alkoxy, optionally substituted $C_1$-$C_4$ hydroxyalkyl, optionally substituted $C_1$-$C_4$ aminoalkyl, optionally substituted $C_1$-$C_4$ haloalkyl, optionally substituted $C_1$-$C_4$ alkyl, optionally substituted $C_1$-$C_4$ guanidinoalkyl, $C_0$-$C_4$ alkyl optionally substituted 3 to 11-membered heterocycloalkyl, optionally substituted 3 to 8-membered cycloalkyl, or optionally substituted 3 to 8-membered heteroaryl;

$R^2$ is $C_1$-$C_6$ alkyl or 3 to 6-membered cycloalkyl;

$R^7$ is $C_1$-$C_3$ alkyl;

$R^8$ is $C_1$-$C_3$ alkyl;

$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl;

$X^e$ is CH, or $CR^{17}$; and $R^{17}$ is optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl.

[43] The compound, or pharmaceutically acceptable salt thereof, of any one of paragraphs [1] to [42], wherein the compound has the structure of Formula Ii:

Formula Ii

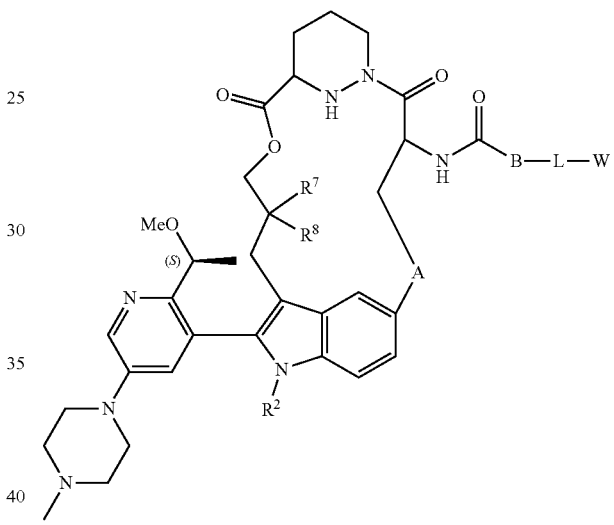

wherein A is optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is hydrogen, optionally substituted amino, optionally substituted $C_1$-$C_4$ alkoxy, optionally substituted $C_1$-$C_4$ hydroxyalkyl, optionally substituted $C_1$-$C_4$ aminoalkyl, optionally substituted $C_1$-$C_4$ haloalkyl, optionally substituted $C_1$-$C_4$ alkyl, optionally substituted $C_1$-$C_4$ guanidinoalkyl, $C_0$-$C_4$ alkyl optionally substituted 3 to 11-membered heterocycloalkyl, optionally substituted 3 to 8-membered cycloalkyl, or optionally substituted 3 to 8-membered heteroaryl;

$R^2$ is $C_1$-$C_6$ alkyl or 3 to 6-membered cycloalkyl;

$R^7$ is $C_1$-$C_3$ alkyl;

$R^8$ is $C_1$-$C_3$ alkyl; and $R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl.

[44] The compound, or pharmaceutically acceptable salt thereof, of any one of paragraphs [1] to [43], wherein A is optionally substituted 6-membered arylene.

[45] The compound, or pharmaceutically acceptable salt thereof, of paragraph [44], wherein A has the structure:

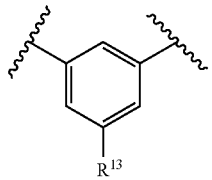

wherein $R^{13}$ is hydrogen, hydroxy, amino, cyano, optionally substituted $C_1$-$C_6$ alkyl, or optionally substituted $C_1$-$C_6$ heteroalkyl. [46] The compound, or pharmaceutically acceptable salt thereof, of paragraph [45], wherein $R^{13}$ is hydrogen.

[47] The compound, or pharmaceutically acceptable salt thereof, of paragraph [45], wherein $R^{13}$ is hydroxy.

[48] The compound, or pharmaceutically acceptable salt thereof, of any one of paragraphs [1] to [43], wherein A is optionally substituted 5 to 6-membered heteroarylene.

[49] The compound, or pharmaceutically acceptable salt thereof, of paragraph [48], wherein A is:

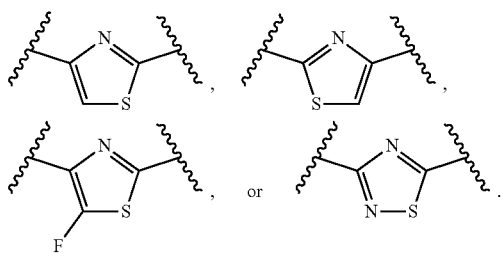

[50] The compound, or pharmaceutically acceptable salt thereof, of paragraph [49], wherein A is

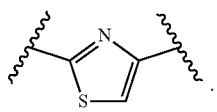 [SMILES: *c1csc(*)n1]

[51] The compound, or pharmaceutically acceptable salt thereof, of any one of paragraphs [1] to [50], wherein B is —CHR$^9$—.

[52] The compound, or pharmaceutically acceptable salt thereof, of paragraph [51], wherein $R^9$ is optionally substituted $C_1$-$C_6$ alkyl or optionally substituted 3 to 6-membered cycloalkyl.

[53] The compound, or pharmaceutically acceptable salt thereof, of paragraph [52], wherein $R^9$ is:

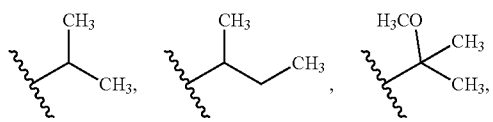

-continued

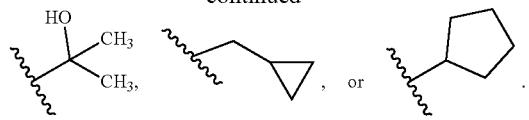

[54] The compound, or pharmaceutically acceptable salt thereof, of paragraph [53], wherein $R^9$ is:

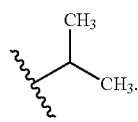

[55] The compound, or pharmaceutically acceptable salt thereof, of any one of paragraphs [1] to [50], wherein B is optionally substituted 6-membered arylene.

[56] The compound, or pharmaceutically acceptable salt thereof, of paragraph [55], wherein B is 6-membered arylene.

[57] The compound, or pharmaceutically acceptable salt thereof, of paragraph [56], wherein B is:

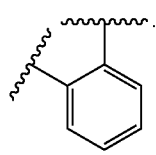

[58] The compound, or pharmaceutically acceptable salt thereof, of any one of paragraphs [1] to [50], wherein B is absent.

[59] The compound, or pharmaceutically acceptable salt thereof, of any one of paragraphs [1] to [58], wherein $R^7$ is methyl.

[60] The compound, or pharmaceutically acceptable salt thereof, of any one of paragraphs [1] to [59], wherein $R^8$ is methyl.

[61] The compound, or pharmaceutically acceptable salt thereof, of any one of paragraphs [1] to [60], wherein the linker is the structure of Formula II:

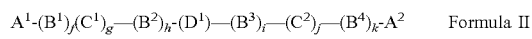

$$A^1\text{-}(B^1)_f(C^1)_g\text{—}(B^2)_h\text{-}(D^1)\text{—}(B^3)_i\text{—}(C^2)_j\text{—}(B^4)_k\text{-}A^2 \quad \text{Formula II}$$

where $A^1$ is a bond between the linker and B; $A^2$ is a bond between W and the linker; $B^1$, $B^2$, $B^3$, and $B^4$ each, independently, is selected from optionally substituted $C_1$-$C_2$ alkylene, optionally substituted $C_1$-$C_3$ heteroalkylene, O, S, and NR$^N$; R$^N$ is hydrogen, optionally substituted $C_1$-$C_4$ alkyl, optionally substituted $C_1$-$C_3$ cycloalkyl, optionally substituted $C_2$-$C_4$ alkenyl, optionally substituted $C_2$-$C_4$ alkynyl, optionally substituted 3 to 14-membered heterocycloalkyl, optionally substituted 6 to 10-membered aryl, or optionally substituted $C_1$-$C_7$ heteroalkyl; $C^1$ and $C^2$ are each, independently, selected from carbonyl, thiocarbonyl, sulphonyl, or phosphoryl; f, g, h, i, j, and k are each, independently, 0 or 1; and $D^1$ is optionally substituted $C_1$-$C_{10}$ alkylene, optionally substituted $C_2$-$C_{10}$ alkenylene, optionally substituted $C_2$-$C_{10}$ alkynylene, optionally substituted 3 to 14-membered heterocycloalkylene, optionally substituted 5 to 10-membered heteroarylene, optionally substituted 3 to 8-membered cycloalkylene, optionally substituted 6 to 10-membered arylene, optionally substituted $C_2$-$C_{10}$ polyethylene glycolene, or optionally substituted $C_1$-$C_{10}$ heteroalkylene, or a chemical bond linking $A^1$-$(B^1)_f$—$(C^1)_g$—$(B^2)_h$— to —$(B^3)_i$—$(C^2)_j$—$(B^4)_k$-$A^2$.

[62] The compound, or a pharmaceutically acceptable salt thereof, of any one of paragraphs [1] to [61], wherein the linker is acyclic.

[63] The compound, or a pharmaceutically acceptable salt thereof, of paragraph [62], wherein the linker has the structure of Formula IIa:

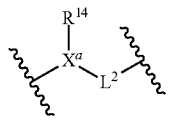

Formula IIa wherein $X^a$ is absent or N;

$R^{14}$ is absent, hydrogen, optionally substituted $C_1$-$C_6$ alkyl, or optionally substituted $C_1$-$C_3$ cycloalkyl; and $L^2$ is absent, —C(O)—, —SO$_2$—, optionally substituted $C_1$-$C_4$ alkylene or optionally substituted $C_1$-$C_4$ heteroalkylene, wherein at least one of $X^a$, $R^{14}$, or $L^2$ is present.

[64] The compound, or a pharmaceutically acceptable salt thereof, of paragraph [63], wherein the linker has the structure:

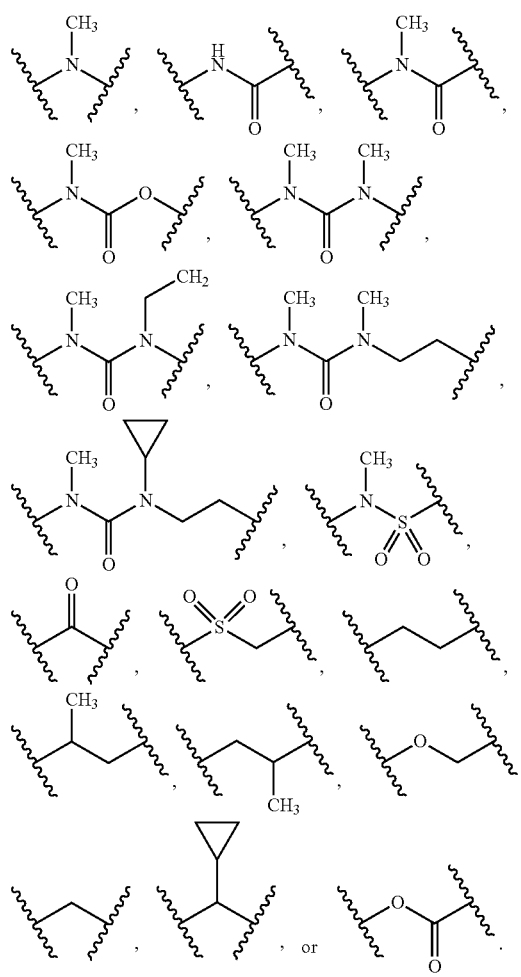

[65] The compound, or a pharmaceutically acceptable salt thereof, of paragraph [64], wherein the linker has the structure

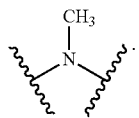

[66] The compound, or a pharmaceutically acceptable salt thereof, of any one of paragraphs [1] to [61], wherein the linker is or comprises a cyclic group.

[67] The compound, or a pharmaceutically acceptable salt thereof, of any one of paragraphs [1] to [61] or [66], wherein the linker has the structure of Formula Mb:

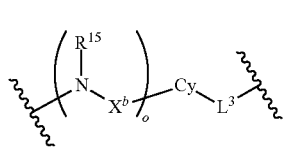

Formula IIb wherein o is 0 or 1;

$X^b$ is C(O) or SO$_2$;

$R^{15}$ is hydrogen or optionally substituted $C_1$-$C_6$ alkyl;

Cy is optionally substituted 3 to 8-membered cycloalkylene, optionally substituted 3 to 8-membered heterocycloalkylene, optionally substituted 6-10 membered arylene, or optionally substituted 5 to 10-membered heteroarylene; and $L^3$ is absent, —C(O)—, —SO$_2$—, optionally substituted $C_1$-$C_4$ alkylene or optionally substituted $C_1$-$C_4$ heteroalkylene.

[68] The compound, or a pharmaceutically acceptable salt thereof, of paragraph [67], wherein the linker has the structure:

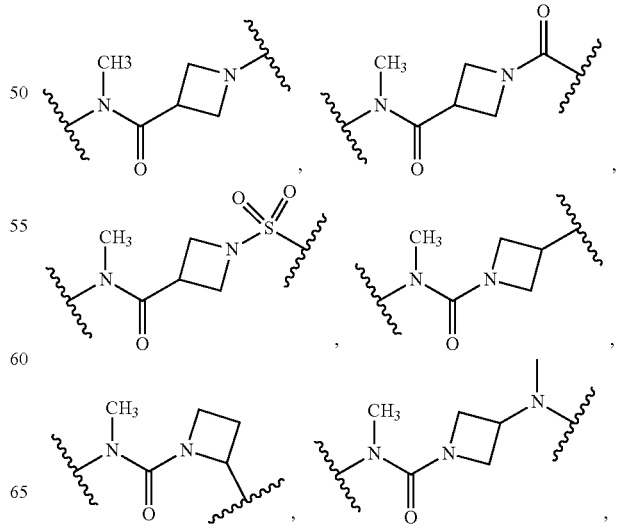

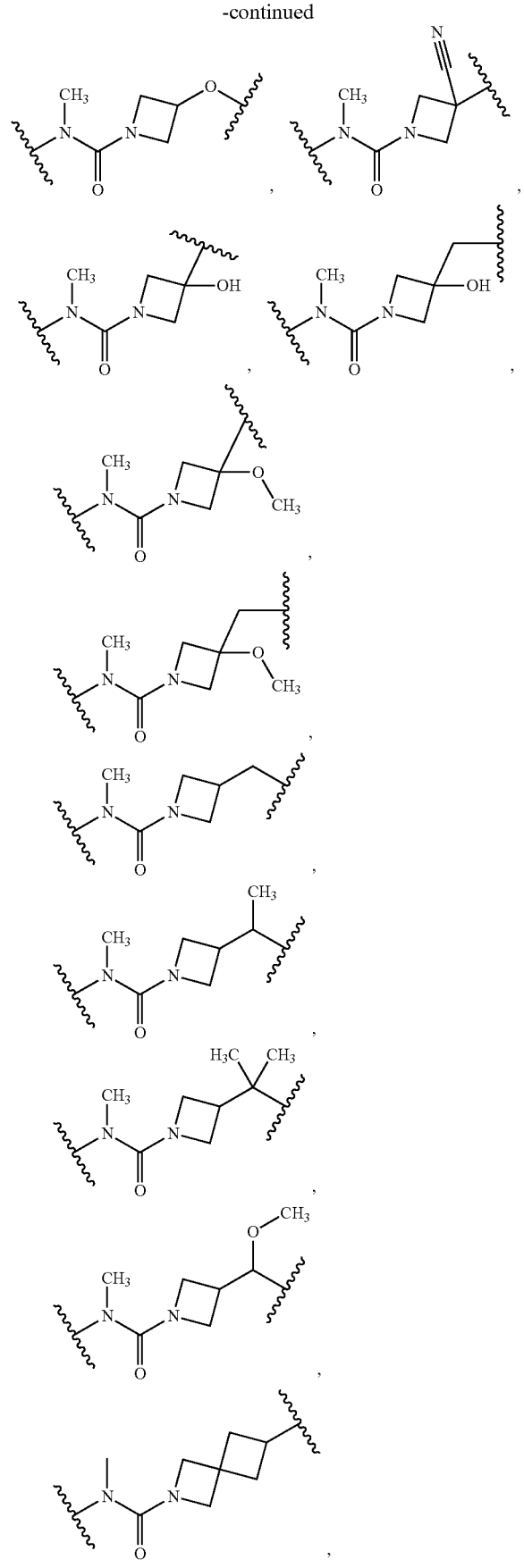
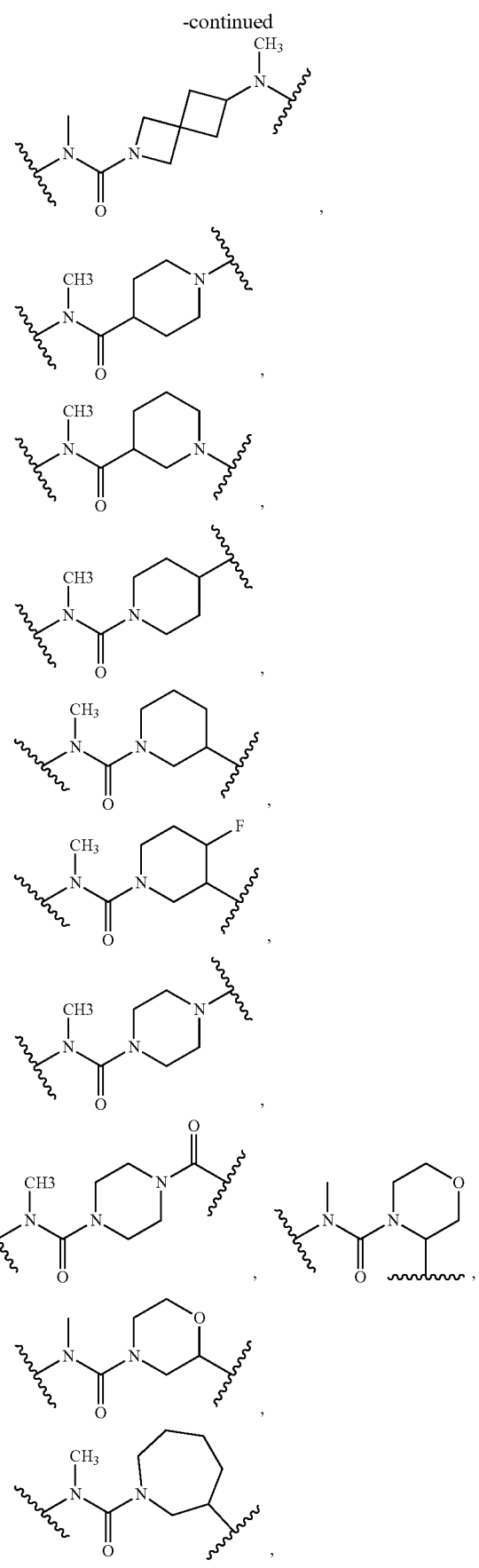

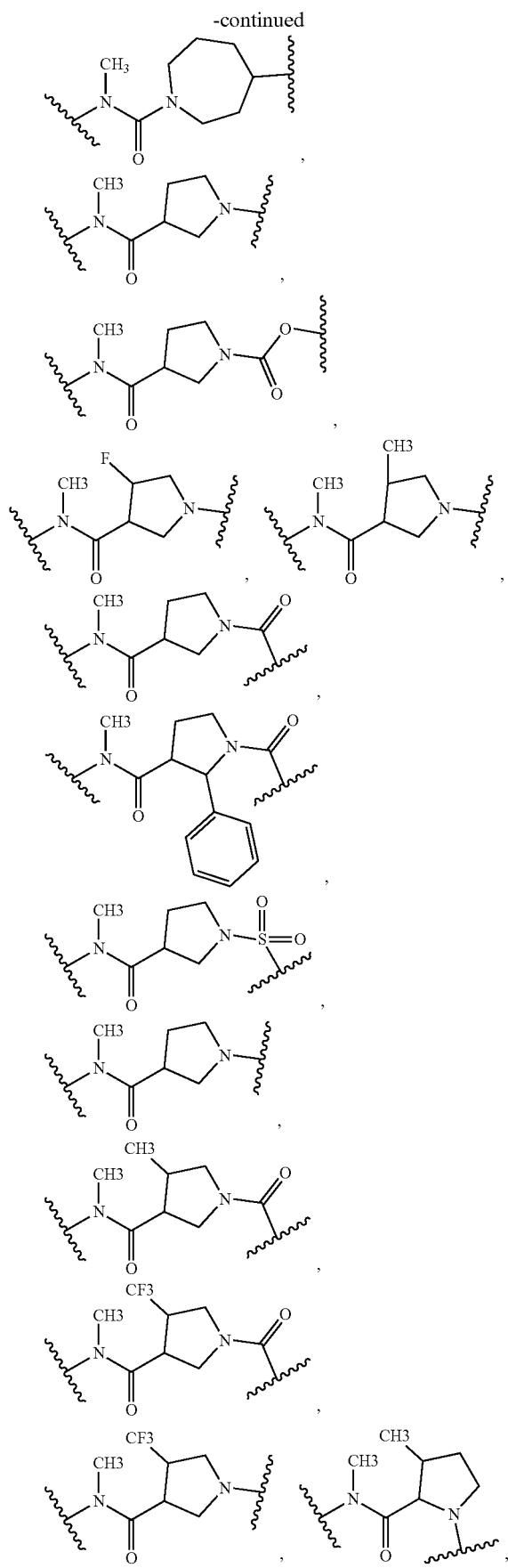

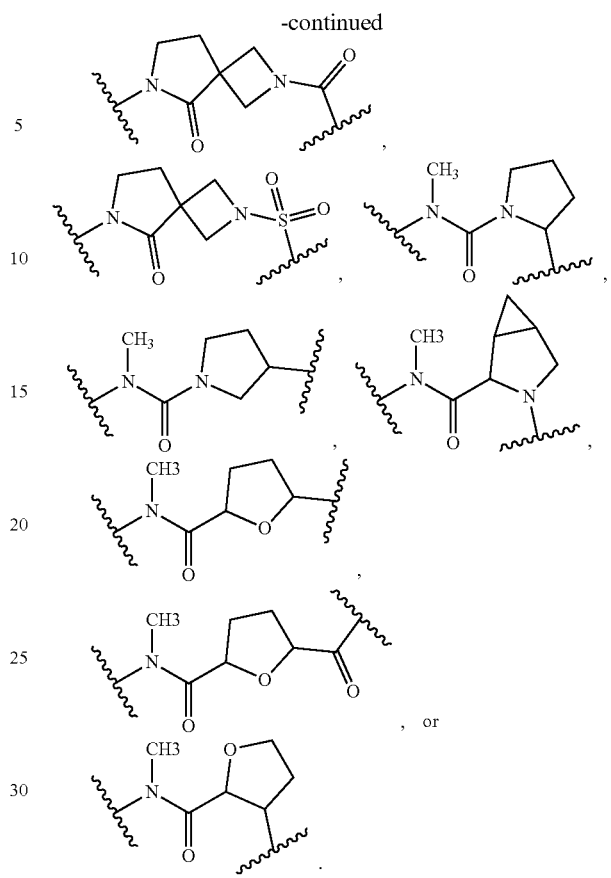

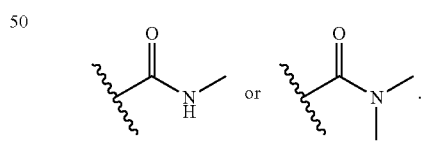

, or

[69] The compound, or a pharmaceutically acceptable salt thereof, of any one of paragraphs [1] to [68], wherein W is hydrogen.

[70] The compound, or a pharmaceutically acceptable salt thereof, of any one of paragraphs [1] to [68], wherein W is optionally substituted amino.

[71] The compound, or a pharmaceutically acceptable salt thereof, of paragraph [70], wherein W is —NHCH$_3$ or —N(CH$_3$)$_2$.

[72] The compound, or a pharmaceutically acceptable salt thereof, of any one of paragraphs [1] to [68], wherein W is optionally substituted amido.

[73] The compound, or a pharmaceutically acceptable salt thereof, of paragraph [72], wherein W

[74] The compound, or a pharmaceutically acceptable salt thereof, of any one of paragraphs [1] to [68], wherein W is optionally substituted C$_1$-C$_4$ alkoxy.

[75] The compound, or a pharmaceutically acceptable salt thereof, of paragraph [74], wherein W is methoxy or iso-propoxy.

[76] The compound, or a pharmaceutically acceptable salt thereof, of any one of paragraphs [1] to [68], wherein W is optionally substituted C$_1$-C$_4$ alkyl.

[77] The compound, or a pharmaceutically acceptable salt thereof, of paragraph [76], wherein W is methyl, ethyl, iso-propyl, tert-butyl, or benzyl.

[78] The compound, or a pharmaceutically acceptable salt thereof, of any one of paragraphs [1] to [68], wherein W is optionally substituted $C_1$-$C_4$ hydroxyalkyl.

[79] The compound, or a pharmaceutically acceptable salt thereof, of paragraph [78], wherein W is

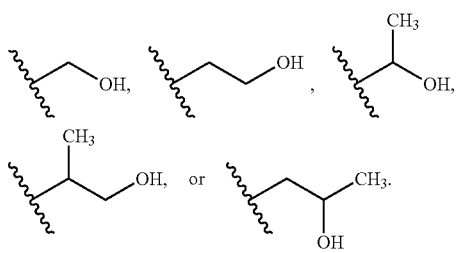

[80] The compound, or a pharmaceutically acceptable salt thereof, of any one of paragraphs [1] to [68], wherein W is optionally substituted $C_1$-$C_4$ aminoalkyl.

[81] The compound, or a pharmaceutically acceptable salt thereof, of paragraph [80], wherein W is

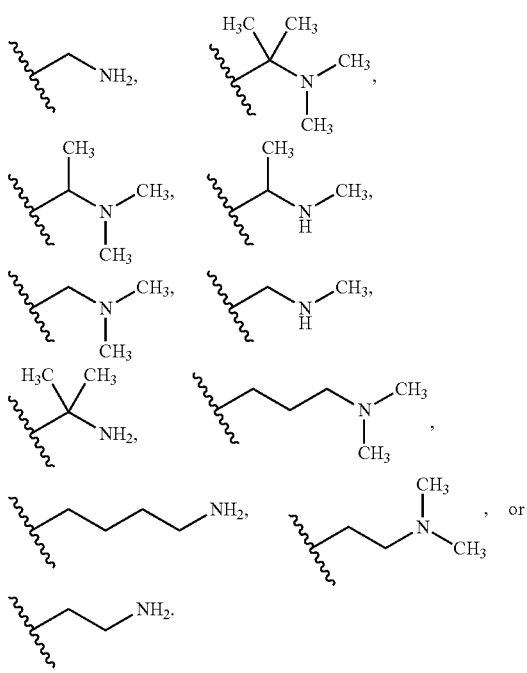

[82] The compound, or a pharmaceutically acceptable salt thereof, of any one of paragraphs [1] to [68], wherein W is optionally substituted $C_1$-$C_4$ haloalkyl.

[83] The compound, or a pharmaceutically acceptable salt thereof, of paragraph [82], wherein W is

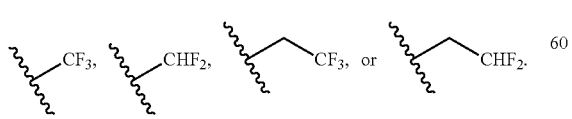

[84] The compound, or a pharmaceutically acceptable salt thereof, of any one of paragraphs [1] to [68], wherein W is optionally substituted $C_1$-$C_4$ guanidinoalkyl.

[85] The compound, or a pharmaceutically acceptable salt thereof, of paragraph [84], wherein W is

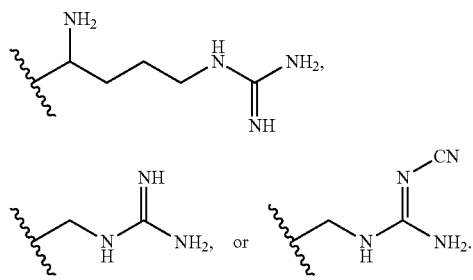

[86] The compound, or a pharmaceutically acceptable salt thereof, of any one of paragraphs [1] to [68], wherein W is $C_0$-$C_4$ alkyl optionally substituted 3 to 11-membered heterocycloalkyl.

[87] The compound, or a pharmaceutically acceptable salt thereof, of paragraph [86], wherein W is

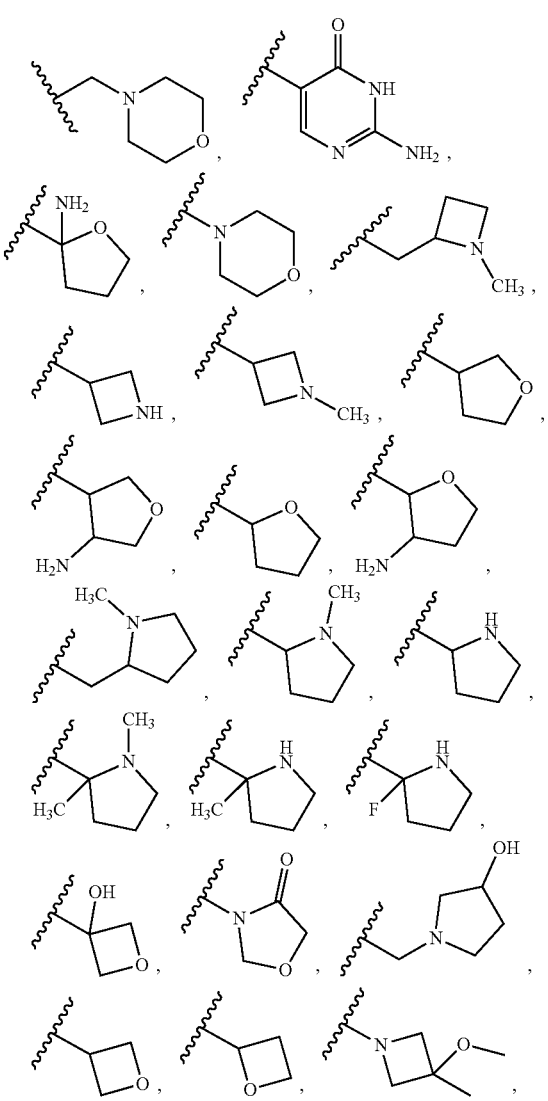

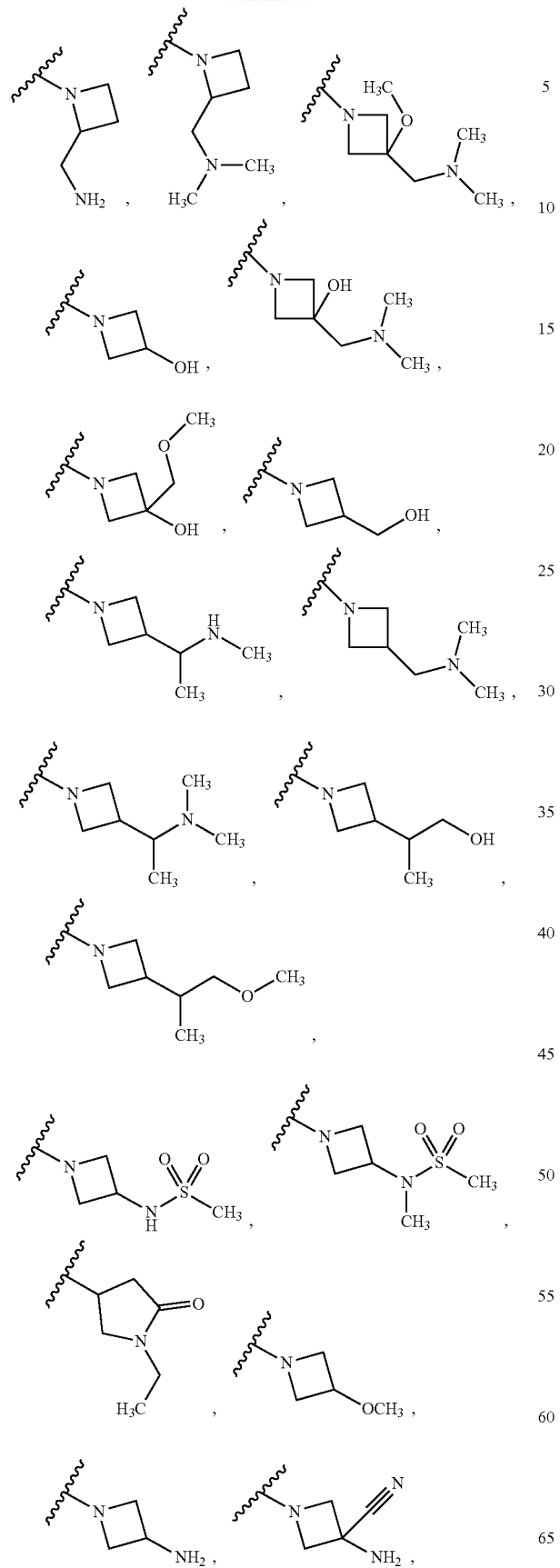
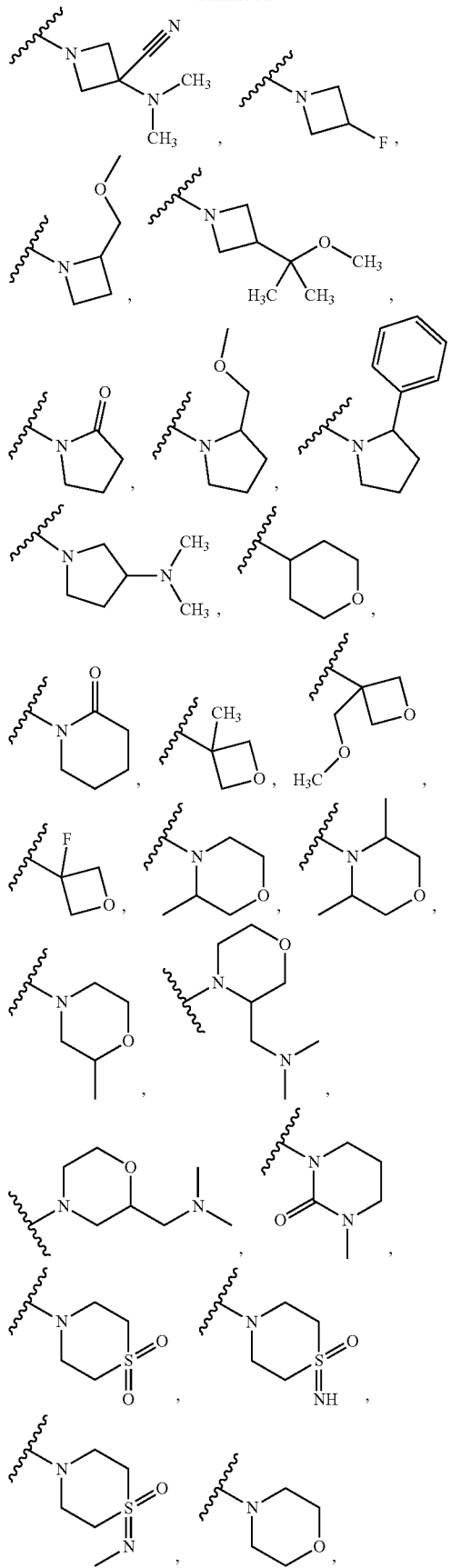

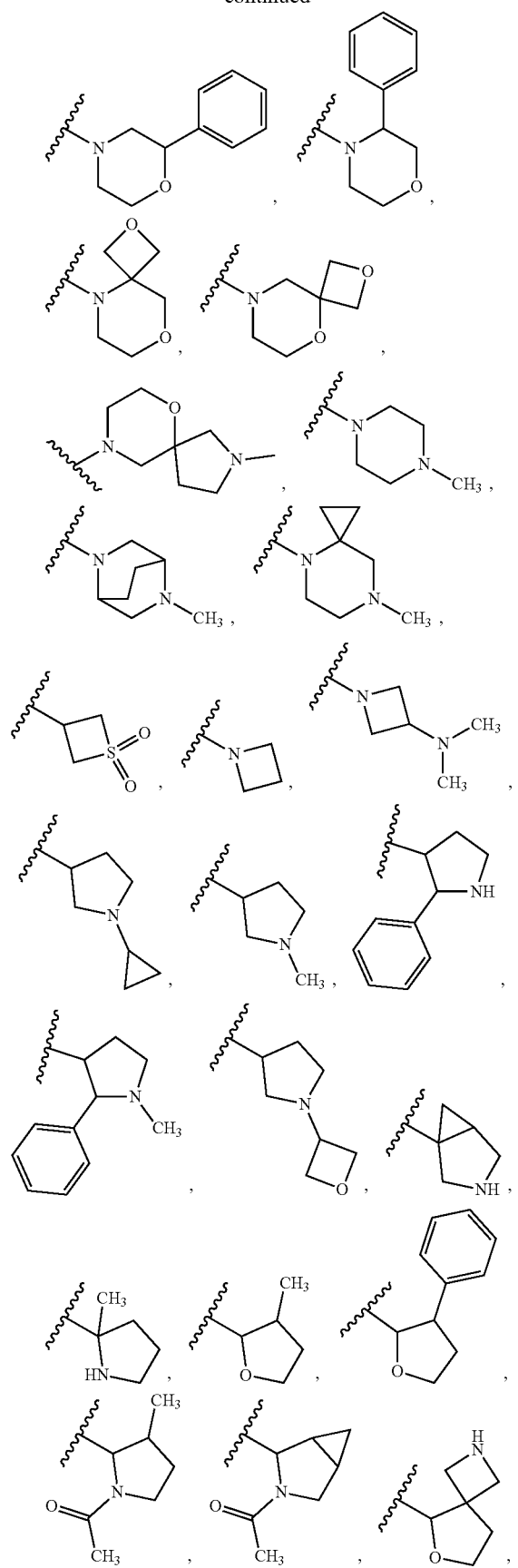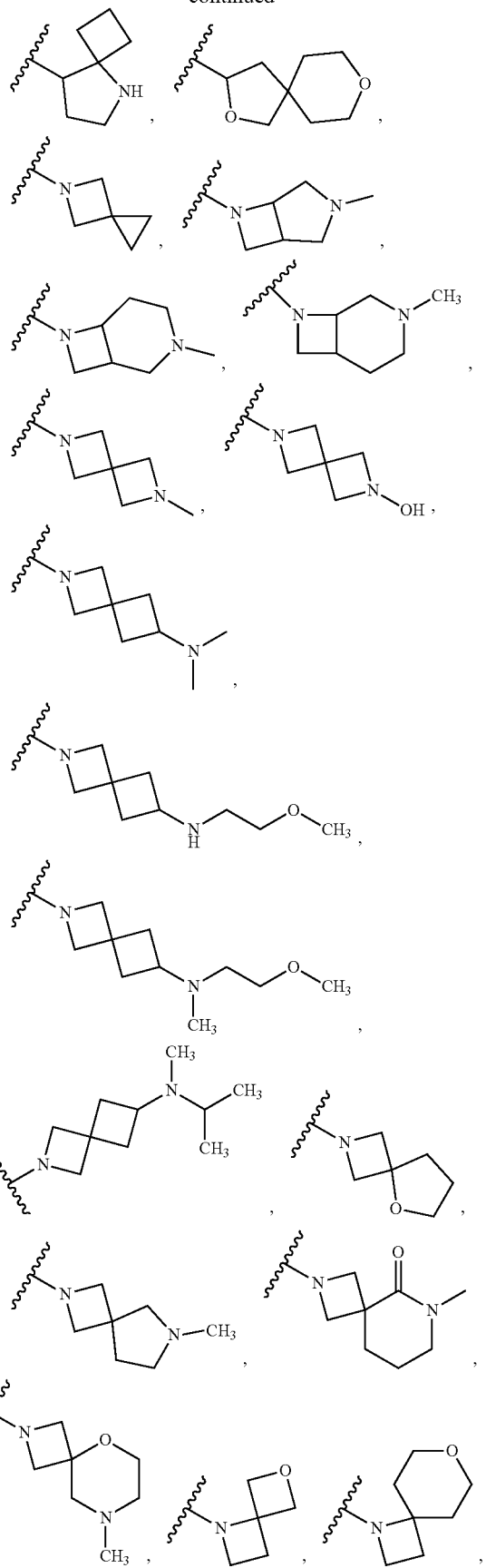

-continued
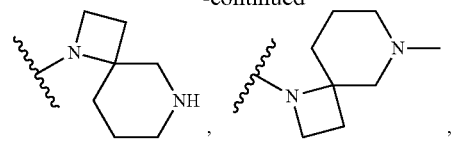
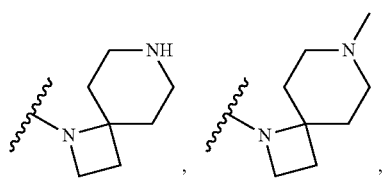
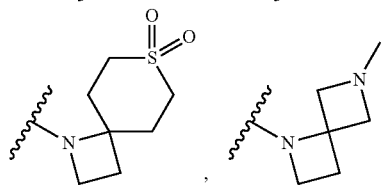
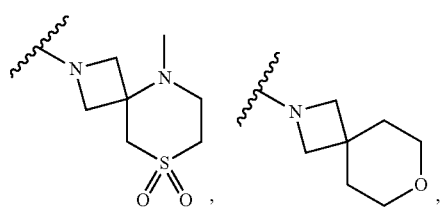
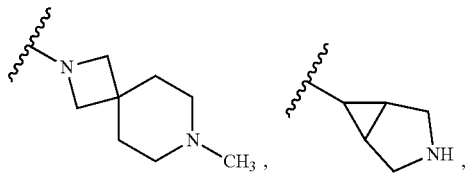
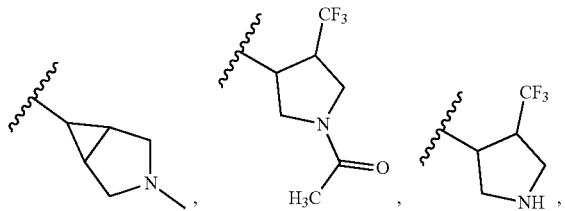
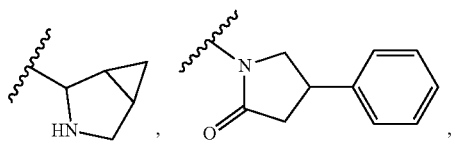
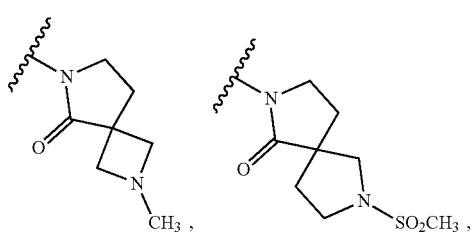
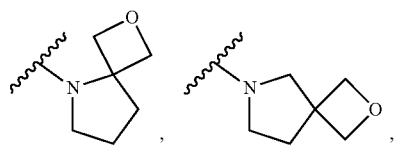
-continued
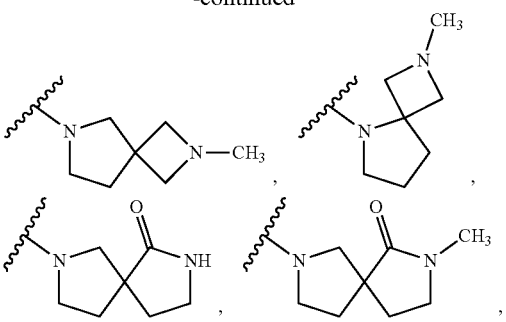
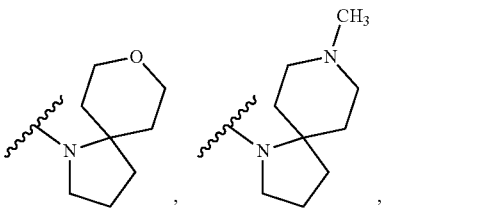
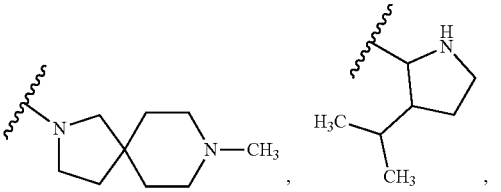
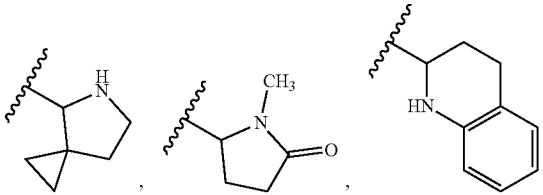
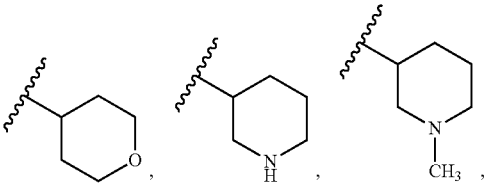
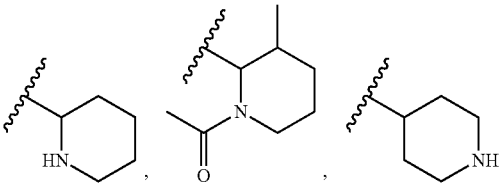
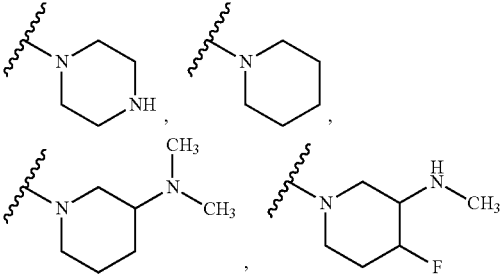
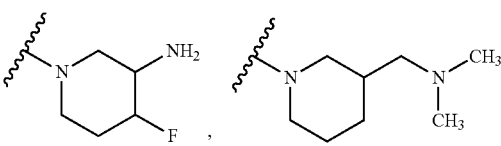

647
-continued
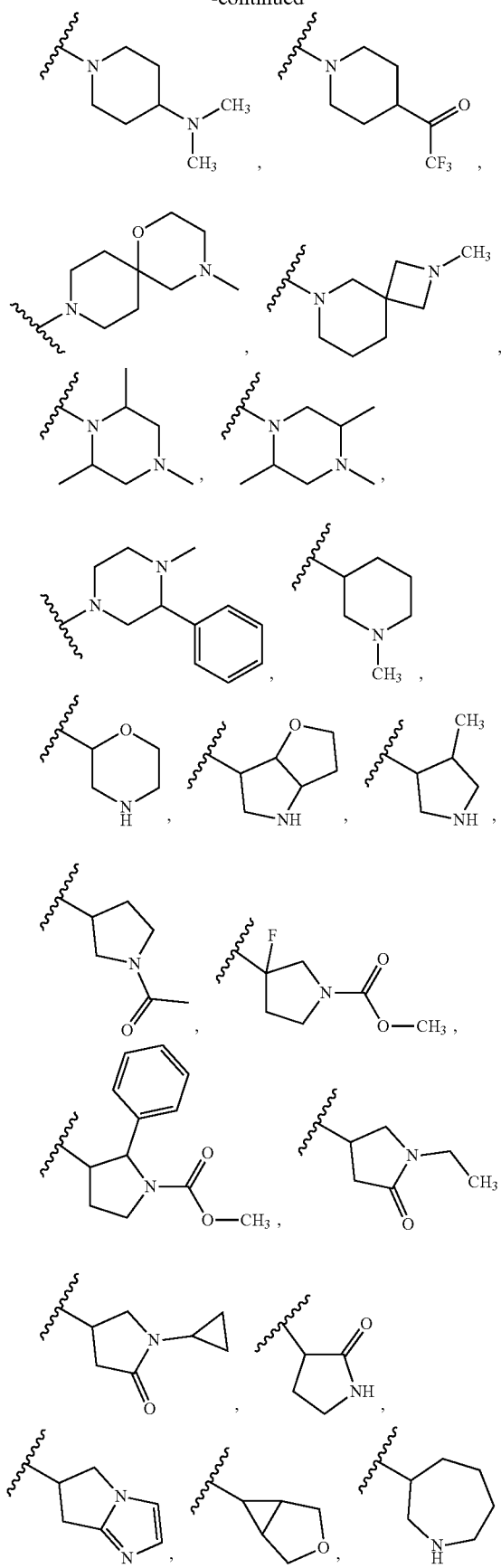
648
-continued
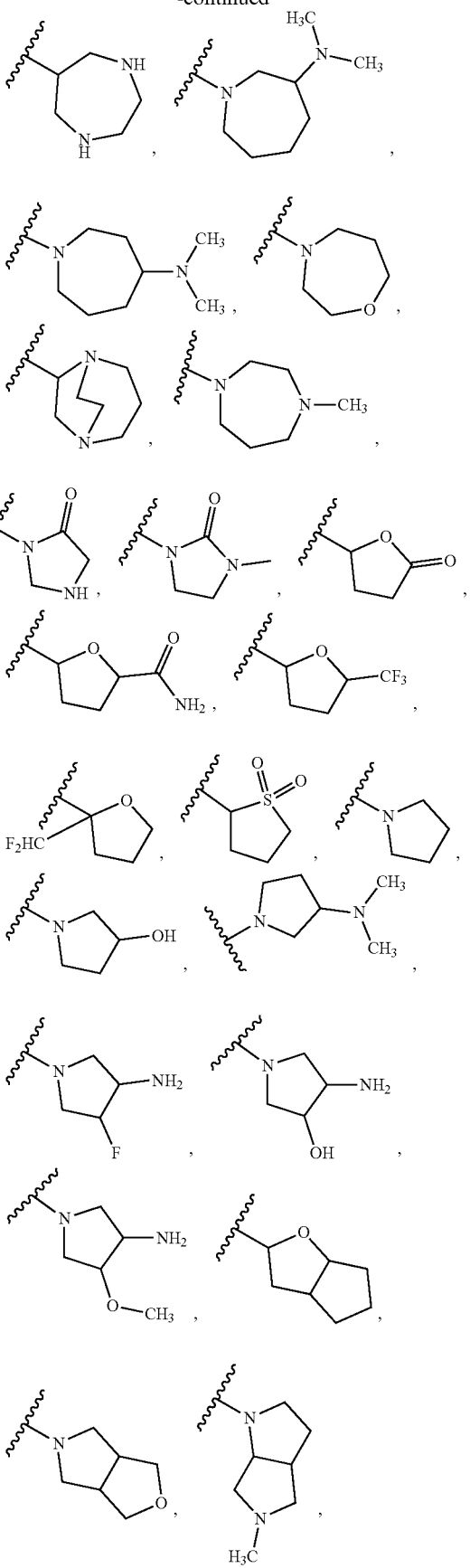

-continued

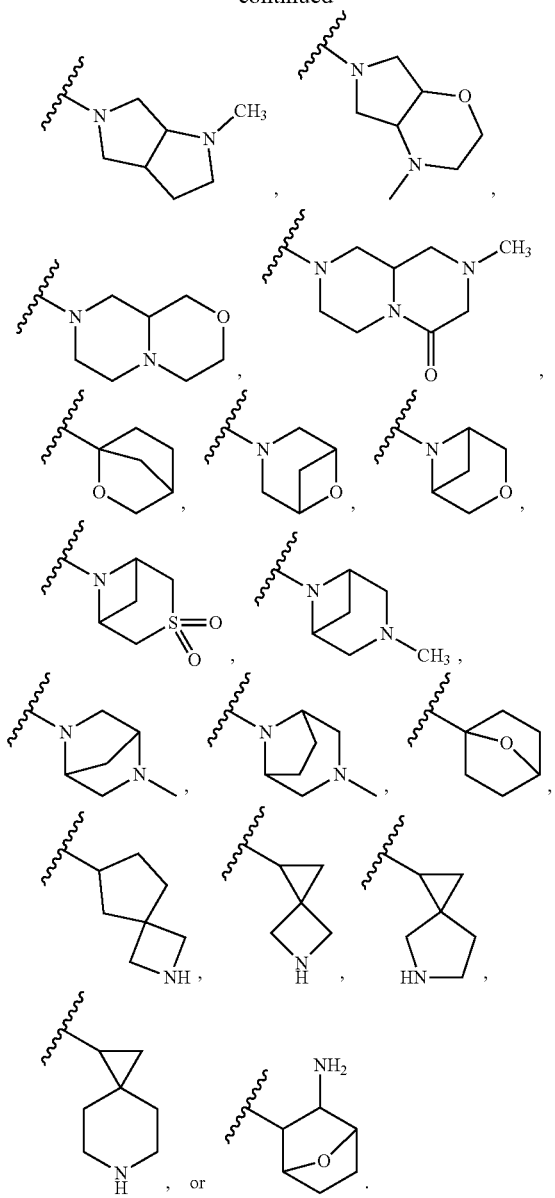

[88] The compound, or a pharmaceutically acceptable salt thereof, of any one of paragraphs [1] to [68], wherein W is optionally substituted 3 to 8-membered cycloalkyl.

[89] The compound, or a pharmaceutically acceptable salt thereof, of paragraph [88], wherein W is

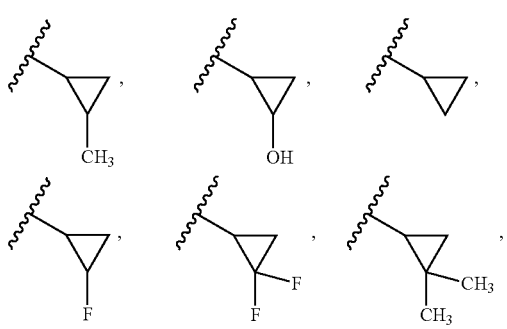

-continued

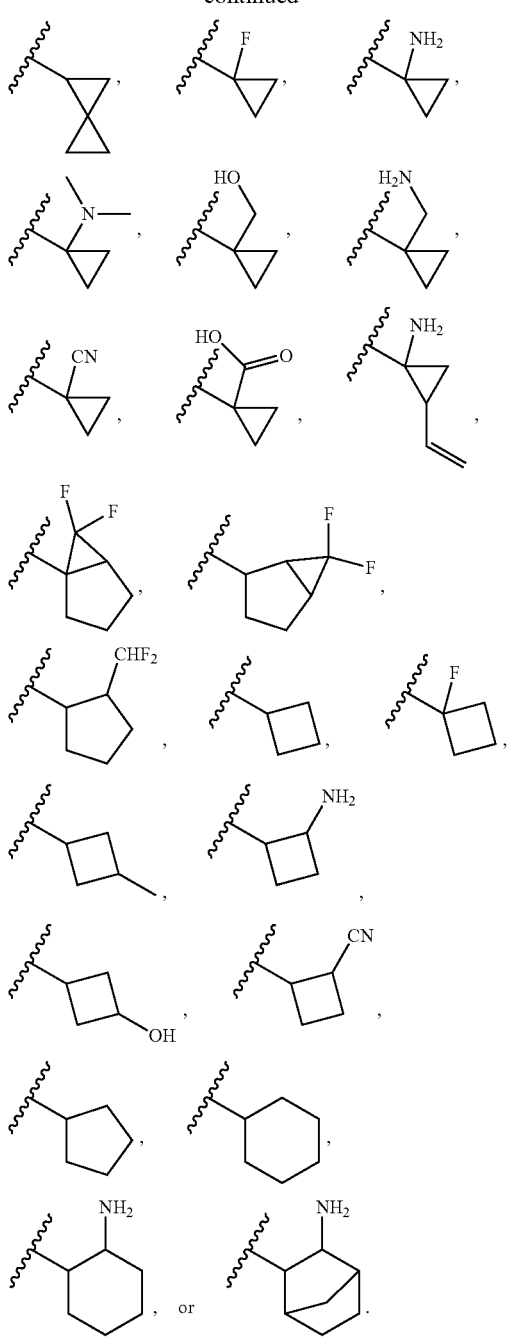

[90] The compound, or a pharmaceutically acceptable salt thereof, of any one of paragraphs [1] to [68], wherein W is optionally substituted 3 to 8-membered heteroaryl.

[91] The compound, or a pharmaceutically acceptable salt thereof, of paragraph [90], wherein W is

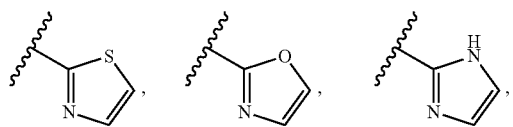

-continued

[92] The compound, or a pharmaceutically acceptable salt thereof, of any one of paragraphs [1] to [68], wherein W is optionally substituted 6- to 10-membered aryl.

[93] The compound, or a pharmaceutically acceptable salt thereof, or paragraph [92], wherein W is phenyl, 4-hydroxyphenyl, or 2,4-methoxy-phenyl.

[94] A compound, or a pharmaceutically acceptable salt thereof, of Table 1 or 2.

[95] A pharmaceutical composition comprising a compound, or a pharmaceutically acceptable salt thereof, of any one of paragraphs [1] to [94] and a pharmaceutically acceptable excipient.

[96] A method of treating cancer in a subject in need thereof, the method comprising administering to the subject a therapeutically effective amount of a compound, or a pharmaceutically acceptable salt thereof, of any one of paragraphs [1] to [94] or a pharmaceutical composition of paragraph [95],

[97] The method of paragraph [96], wherein the cancer is pancreatic cancer, colorectal cancer, non-small cell lung cancer, gastric cancer, esophageal cancer, ovarian cancer or uterine cancer.

[98] The method of paragraph [97], wherein the cancer comprises a Ras mutation.

[99] The method of paragraph [98] wherein the Ras mutation is at position 12, 13 or 61.

The method of paragraph [98] wherein the Ras mutation is K-Ras G12C, K-Ras G12D, K-Ras G12V, K-Ras G12S, K-Ras G13C, K-Ras G13D, or K-Ras Q61L.

A method of treating a Ras protein-related disorder in a subject in need thereof, the method comprising administering to the subject a therapeutically effective amount of a compound, or a pharmaceutically acceptable salt thereof, of any one of paragraphs [1] to [94] or a pharmaceutical composition of paragraph [95].

[102] A method of inhibiting a Ras protein in a cell, the method comprising contacting the cell with an effective amount of a compound, or a pharmaceutically acceptable salt thereof, of any one of paragraphs [1] to [94] or a pharmaceutical composition of paragraph [95].

[103] The method of paragraph [101] or [102], wherein the Ras protein is K-Ras G12C, K-Ras G12D, K-Ras G12V, K-Ras G12S, K-Ras G13C, K-Ras G13D, or K-Ras Q61L.

[104] The method of paragraph [102] or [103], wherein the cell is a cancer cell.

[105] The method of paragraph [104], wherein the cancer cell is a pancreatic cancer cell, a colorectal cancer cell, a non-small cell lung cancer cell, a gastric cancer cell, an esophageal cancer cell, an ovarian cancer cell, or a uterine cancer cell.

[106] The method or use of any one of paragraphs [96] to [105], wherein the method further comprises administering an additional anticancer therapy.

[107] The method of paragraph [106], wherein the additional anticancer therapy is an EGFR inhibitor, a second Ras inhibitor, a SHP2 inhibitor, a SOS1 inhibitor, a Raf inhibitor, a MEK inhibitor, an ERK inhibitor, a PI3K inhibitor, a PTEN inhibitor, an AKT inhibitor, an mTORC1 inhibitor, a BRAF inhibitor, a PD-L1 inhibitor, a PD-1 inhibitor, a CDK4/6 inhibitor, a HER2 inhibitor, or a combination thereof.

[108] The method of paragraph [106] or [107], wherein the additional anticancer therapy is a SHP2 inhibitor.

Examples

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure or scope of the appended claims.

Chemical Syntheses

Definitions used in the following examples and elsewhere herein are:
CH$_2$Cl$_2$, DCM Methylene chloride, Dichloromethane
CH$_3$CN, MeCN Acetonitrile
CuI Copper (I) iodide
DIPEA Diisopropylethyl amine
DMF N,N-Dimethylformamide
EtOAc Ethyl acetate
h hour
H$_2$O Water
HCl Hydrochloric acid
K$_3$PO$_4$ Potassium phosphate (tribasic)
MeOH Methanol
Na$_2$SO$_4$ Sodium sulfate
NMP N-methyl pyrrolidone
Pd(dppf)Cl$_2$ [1,1'-Bis(diphenylphosphino)ferrocene]dichloropalladium(II)

Instrumentation

Mass spectrometry data collection took place with a Shimadzu LCMS-2020, an Agilent 1260LC-6120/6125MSD, a Shimadzu LCMS-2010EV, or a Waters Acquity UPLC, with either a QDa detector or SQ Detector 2. Samples were injected in their liquid phase onto a C-18 reverse phase. The compounds were eluted from the column using an acetonitrile gradient and fed into the mass analyzer.

Initial data analysis took place with either Agilent ChemStation, Shimadzu LabSolutions, or Waters MassLynx. NMR data was collected with either a Bruker AVANCE III HD 400 MHz, a Bruker Ascend 500 MHz instrument, or a Varian 400 MHz, and the raw data was analyzed with either TopSpin or Mestrelab Mnova.

Synthesis of Intermediates

Intermediate 1. Synthesis of 3-(5-bromo-1-ethyl-2-[2-[(1S)-1-methoxyethyl]pyridin-3-yl]indol-3-yl)-2,2-dimethylpropan-1-ol

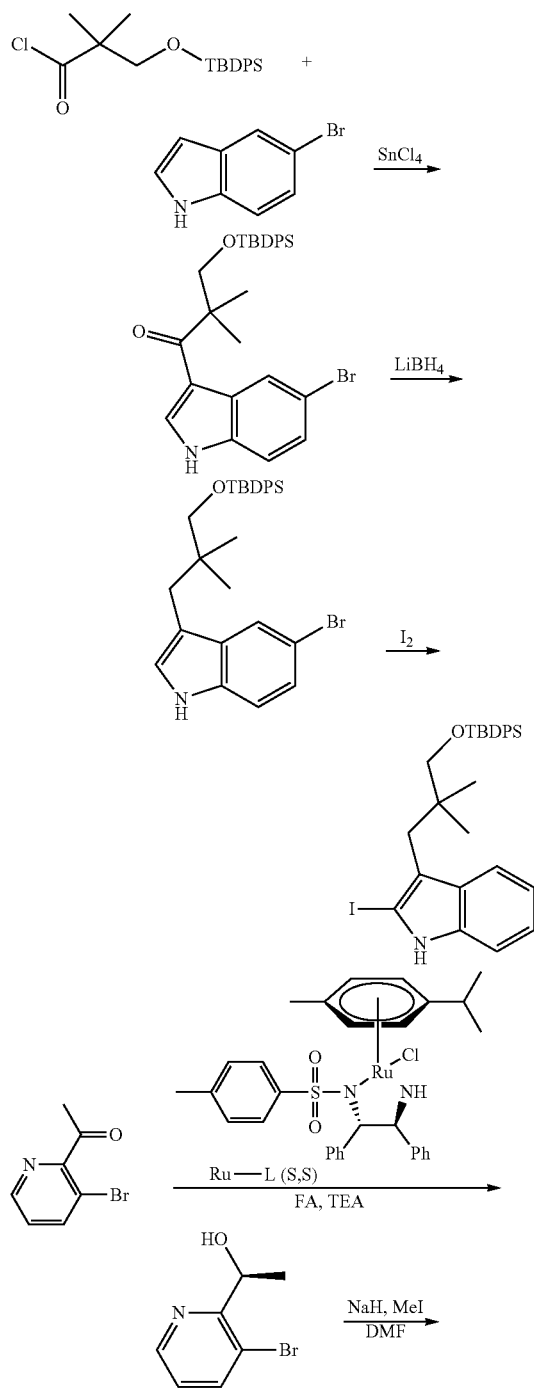

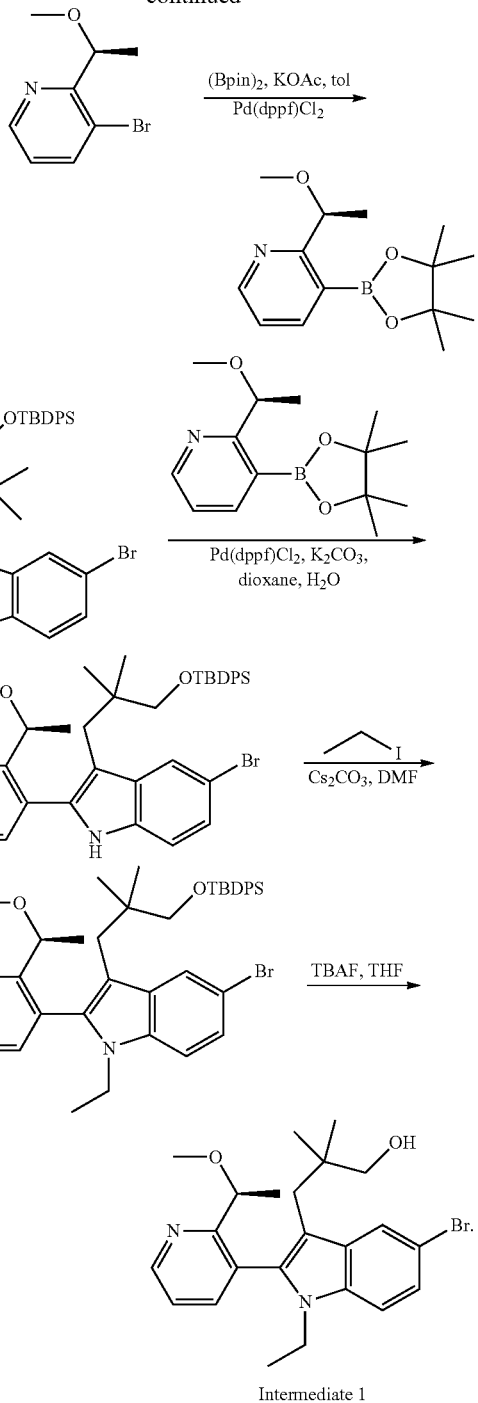

Intermediate 1

Step 1. To a mixture of 3-((tert-butyldiphenylsilyl)oxy)-2,2-dimethylpropanoyl chloride (65 g, 137 mmol, crude) in DCM (120 mL) at 0° C. under an atmosphere of $N_2$ was added 1M $SnCl_4$ in DCM (137 mL, 137 mmol) slowly. The mixture was stirred at 0° C. for 30 min, then a solution of 5-bromo-1H-indole (26.8 g, 137 mmol) in DCM (40 mL) was added dropwise. The mixture was stirred at 0° C. for 45 min, then diluted with EtOAc (300 mL), washed with brine (100 mL×4), dried over $Na_2SO_4$ and filtered. The filtrate was concentrated under reduced pressure and the residue was purified by silica gel column chromatography to give 1-(5-bromo-1H-indol-3-yl)-3-((tert-butyldiphenylsilyl)oxy)-2,2- dimethylpropan-1-one (55 g, 75% yield). LCMS (ESI): m/z [M+Na] calc'd for $C_{29}H_{32}BrNO_2SiNa$ 556.1; found 556.3.

Step 2. To a mixture of 1-(5-bromo-1H-indol-3-yl)-3-((tert-butyldiphenylsilyl)oxy)-2,2-dimethylpropan-1-one (50 g, 93.6 mmol) in THF (100 mL) at 0° C. under an atmosphere of $N_2$ was added $LiBH_4$ (6.1 g, 281 mmol). The mixture was heated to 60° C. and stirred for 20 h, then MeOH (10 mL) and EtOAc (100 mL) were added and the mixture washed with brine (50 mL), dried over $Na_2SO_4$, filtered and the filtrate concentrated under reduced pressure. The residue was diluted with DCM (50 mL), cooled to 10° C. and diludine (9.5 g, 37.4 mmol) and $TsOH.H_2O$ (890 mg, 4.7 mmol) added. The mixture was stirred at 10° C. for 2 h, filtered, the filtrate concentrated under reduced pressure and the residue was purified by silica gel column chromatography to give 1-(5-bromo-1H-indol-3-yl)-3-((tert-butyldiphenylsilyl)oxy)-2,2-dimethylpropan-1-one (41 g, 84% yield). LCMS (ESI): m/z [M+H] calc'd for $C_{29}H_{34}BrNOSi$ 519.2; found 520.1; $^1H$ NMR (400 MHz, $CDCl_3$) δ 7.96 (s, 1H), 7.75-7.68 (m, 5H), 7.46-7.35 (m, 6H), 7.23-7.19 (m, 2H), 6.87 (d, J=2.1 Hz, 1H), 3.40 (s, 2H), 2.72 (s, 2H), 1.14 (s, 9H), 0.89 (s, 6H).

Step 3. To a mixture of 1-(5-bromo-1H-indol-3-yl)-3-((tert-butyldiphenylsilyl)oxy)-2,2-dimethylpropan-1-one (1.5 g, 2.9 mmol) and $I_2$ (731 mg, 2.9 mmol) in THF (15 mL) at rt was added AgOTf (888 mg, 3.5 mmol). The mixture was stirred at rt for 2 h, then diluted with EtOAc (200 mL) and washed with saturated $Na_2S_2O_3$ (100 mL), dried over anhydrous $Na_2SO_4$ and filtered. The filtrate was concentrated under reduced pressure and the residue was purified by silica gel column chromatography to give 5-bromo-3-(3-((tert-butyldiphenylsilyl)oxy)-2,2-dimethylpropyl)-2-iodo-1H-indole (900 mg, 72% yield) as a solid. $^1H$ NMR (400 MHz, DMSO-$d_6$) δ 11.70 (s, 1H), 7.68 (d, J=1.3 Hz, 1H), 7.64-7.62 (m, 4H), 7.46-7.43 (m, 6H), 7.24-7.22 (d, 1H), 7.14-7.12 (dd, J=8.6, 1.6 Hz, 1H), 3.48 (s, 2H), 2.63 (s, 2H), 1.08 (s, 9H), 0.88 (s, 6H).

Step 4. To a stirred mixture of HCOOH (66.3 g, 1.44 mol) in TEA (728 g, 7.2 mol) at 0° C. under an atmosphere of Ar was added (4S,5S)-2-chloro-2-methyl-1-(4-methylbenzenesulfonyl)-4,5-diphenyl-1,3-diaza-2-ruthenacyclopentane cymene (3.9 g, 6.0 mmol) portion-wise. The mixture was heated to 40° C. and stirred for 15 min, then cooled to rt and 1-(3-bromopyridin-2-yl)ethanone (120 g, 600 mmol) added in portions. The mixture was heated to 40° C. and stirred for an additional 2 h, then the solvent was concentrated under reduced pressure. Brine (2 L) was added to the residue, the mixture was extracted with EtOAc (4×700 mL), dried over anhydrous $Na_2SO_4$ and filtered. The filtrate was concentrated under reduced pressure and the residue was purified by silica gel column chromatography to give (1S)-1-(3-bromopyridin-2-yl)ethanol (100 g, 74% yield) a an oil. LCMS (ESI): m/z [M+H] calc'd for $C_7H_8BrNO$ 201.1; found 201.9.

Step 5. To a stirred mixture of (1S)-1-(3-bromopyridin-2-yl)ethanol (100 g, 495 mmol) in DMF (1 L) at 0° C. was added NaH, 60% dispersion in oil (14.25 g, 594 mmol) in portions. The mixture was stirred at 0° C. for 1 h. MeI (140.5 g, 990 mmol) was added dropwise at 0° C. and the mixture was allowed to warm to rt and stirred for 2 h. The mixture was cooled to 0° C. and saturated $NH_4Cl$ (5 L) was added. The mixture was extracted with EtOAc (3×1.5 L), dried over anhydrous $Na_2SO_4$ and filtered. The filtrate was concentrated under reduced pressure and the residue was purified by silica gel column chromatography to give 3-bromo-2-[(1S)-1-methoxyethyl]pyridine (90 g, 75% yield) as an oil. LCMS (ESI): m/z [M+H] calc'd for $C_8H_{10}BrNO$ 215.0; found 215.9.

Step 6. To a stirred mixture of 3-bromo-2-[(1S)-1-methoxyethyl]pyridine (90 g, 417 mmol) and $Pd(dppf)Cl_2$ (30.5 g, 41.7 mmol) in toluene (900 mL) at rt under an atmosphere of Ar was added bis(pinacolato)diboron (127 g, 500 mmol) and KOAc (81.8 g, 833 mmol) in portions. The mixture was heated to 100° C. and stirred for 3 h. The filtrate was concentrated under reduced pressure and the residue was purified by $Al_2O_3$ column chromatography to give 2-[(1S)-1-methoxyethyl]-3-(4,4,5,5-tetramethyl-1,3,2-dioxaborolan-2-yl)pyridine (100 g, 63% yield) as a semi-solid. LCMS (ESI): m/z [M+H] calc'd for $C_{14}H_{22}BNO_3$ 263.2; found 264.1.

Step 7. To a stirred mixture of 5-bromo-3-[3-[(tert-butyldiphenylsilyl)oxy]-2,2-dimethylpropyl]-2-iodo-1H-indole (140 g, 217 mmol) and 2-[(1S)-1-methoxyethyl]-3-(4,4,5,5-tetramethyl-1,3,2-dioxaborolan-2-yl)pyridine (100 g, 380 mmol) in 1,4-dioxane (1.4 L) at rt under an atmosphere of Ar was added $K_2CO_3$ (74.8 g, 541 mmol), $Pd(dppf)Cl_2$ (15.9 g, 21.7 mmol) and $H_2O$ (280 mL) in portions. The mixture was heated to 85° C. and stirred for 4 h, then cooled, $H_2O$ (5 L) added and the mixture extracted with EtOAc (3×2 L). The combined organic layers were washed with brine (2×1 L), dried over anhydrous $Na_2SO_4$ and filtered. The filtrate was concentrated under reduced pressure and the residue was purified by silica gel column chromatography to give 5-bromo-3-[3-[(tert-butyldiphenylsilyl)oxy]-2,2-dimethylpropyl]-2-[2-[(1S)-1-methoxyethyl]pyridin-3-yl]-1H-indole (71 g, 45% yield) as a solid. LCMS (ESI): m/z [M+H] calc'd for $C_{37}H_{43}BrN_2O_2Si$ 654.2; found 655.1.

Step 8. To a stirred mixture of 5-bromo-3-[3-[(tert-butyldiphenylsilyl)oxy]-2,2-dimethylpropyl]-2-[2-[(1S)-1-methoxyethyl]pyridin-3-yl]-1H-indole (71 g, 108 mmol) in DMF (0.8 L) at 0° C. under an atmosphere of $N_2$ was added $Cs_2CO_3$ (70.6 g, 217 mmol) and EtI (33.8 g, 217 mmol) in portions. The mixture was warmed to rt and stirred for 16 h then $H_2O$ (4 L) added and the mixture extracted with EtOAc (3×1.5 L). The combined organic layers were washed with brine (2×1 L), dried over anhydrous $Na_2SO_4$ and filtered. The filtrate was concentrated under reduced pressure and the residue was purified by silica gel column chromatography to give 5-bromo-3-[3-[(tert-butyldiphenylsilyl)oxy]-2,2-dimethylpropyl]-1-ethyl-2-[2-[(1S)-1-methoxyethyl]pyridin-3-yl]indole (66 g, 80% yield) as an oil. LCMS (ESI): m/z [M+H] calc'd for $C_{39}H_{47}BrN_2O_2Si$ 682.3; found 683.3.

Step 9. To a stirred mixture of TBAF (172.6 g, 660 mmol) in THF (660 mL) at rt under an atmosphere of N2 was added 5-bromo-3-[3-[(tert-butyldiphenylsilyl)oxy]-2,2-dimethylpropyl]-1-ethyl-2-[2-[(1S)-1-methoxyethyl]pyridin-3-yl]indole (66 g, 97 mmol) in portions. The mixture was heated to 50° C. and stirred for 16 h, cooled, diluted with $H_2O$ (5 L) and extracted with EtOAc (3×1.5 L). The combined organic layers were washed with brine (2×1 L), dried over anhydrous $Na_2SO_4$ and filtered. After filtration, the filtrate was concentrated under reduced pressure. The filtrate was concentrated under reduced pressure and the residue was purified by silica gel column chromatography to give 3-(5-bromo-1-ethyl-2-[2-[(1S)-1-methoxyethyl]pyridin-3-yl]indol-3-yl)-2,2-dimethylpropan-1-ol (30 g, 62% yield) as a solid. LCMS (ESI): m/z [M+H] calc'd for $C_{23}H_{29}BrN_2O_2$ 444.1; found 445.1.

Intermediate 1. Alternative Synthesis Through Fisher Indole Route

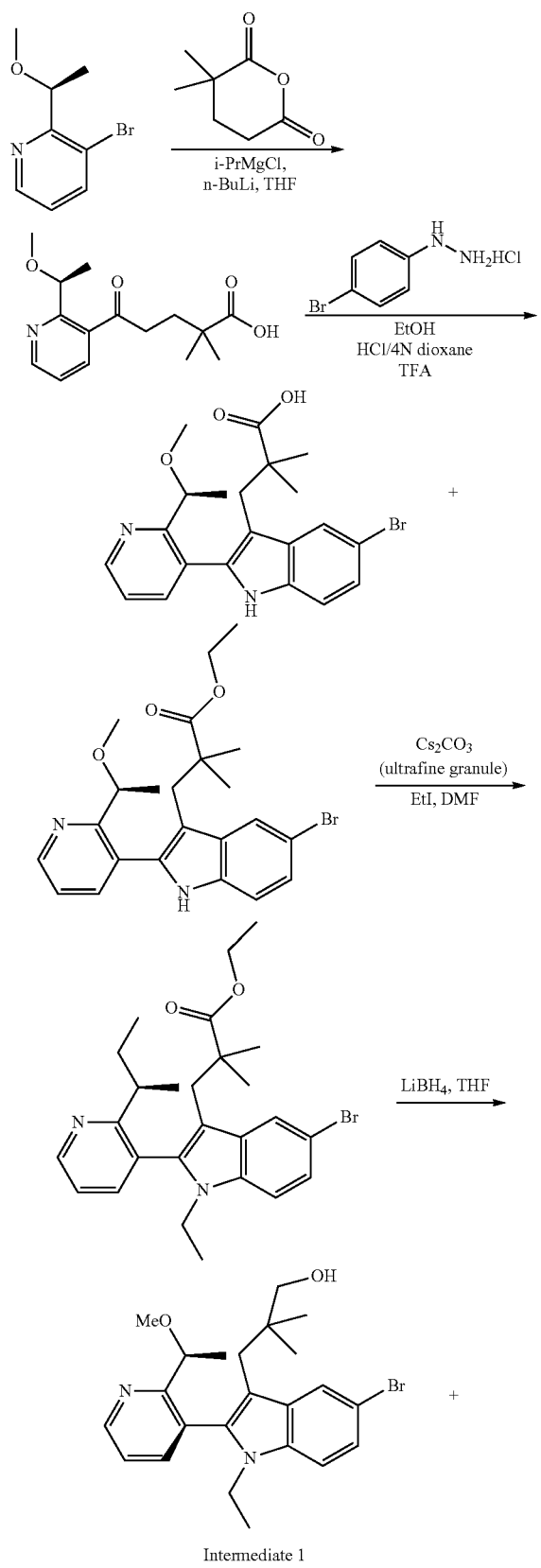

Intermediate 1

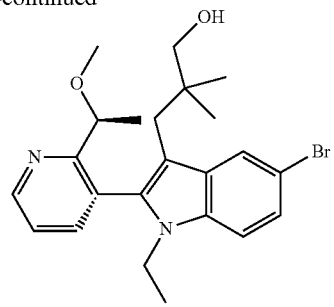

Step 1. To a mixture of i-PrMgCl (2M in in THF, 0.5 L) at −10° C. under an atmosphere of N2 was added n-BuLi, 2.5 M in hexane (333 mL, 833 mmol) dropwise over 15 min. The mixture was stirred for 30 min at −10° C. then 3-bromo-2-[(1S)-1-methoxyethyl]pyridine (180 g, 833 mmol) in THF (0.5 L) added dropwise over 30 min at −10° C. The resulting mixture was warmed to −5° C. and stirred for 1 h, then 3,3-dimethyloxane-2,6-dione (118 g, 833 mmol) in THF (1.2 L) was added dropwise over 30 min at −5° C. The mixture was warmed to 0° C. and stirred for 1.5 h, then quenched with the addition of pre-cooled 4M HCl in 1,4-dioxane (0.6 L) at 0° C. to adjust pH 5. The mixture was diluted with ice-water (3 L) and extracted with EtOAc (3×2.5 L). The combined organic layers were dried over anhydrous $Na_2SO_4$, filtered, the filtrate was concentrated under reduced pressure and the residue was purified by silica gel column chromatography to give 5-[2-[(1S)-1-methoxyethyl]pyridin-3-yl]-2,2-dimethyl-5-oxopentanoic acid (87 g, 34% yield) as a solid. LCMS (ESI): m/z [M+H] calc'd for $C_{15}H_{21}NO_4$ 279.2; found 280.1.

Step 2. To a mixture of 5-[2-[(1S)-1-methoxyethyl]pyridin-3-yl]-2,2-dimethyl-5-oxopentanoic acid (78 g, 279 mmol) in EtOH (0.78 L) at rt under an atmosphere of N2 was added (4-bromophenyl)hydrazine HCl salt (68.7 g, 307 mmol) in portions. The mixture was heated to 85° C. and stirred for 2 h, cooled to rt, then 4M HCl in 1,4-dioxane (69.8 mL, 279 mmol) added dropwise. The mixture was heated to 85° C. and stirred for an additional 3 h, then concentrated under reduced pressure and the residue was dissolved in TFA (0.78 L). The mixture was heated to 60° C. and stirred for 1.5, concentrated under reduced pressure and the residue adjusted to pH 5 with saturated $NaHCO_3$, then extracted with EtOAc (3×1.5 L). The combined organic layers were dried over anhydrous $Na_2SO_4$, filtered, the filtrate concentrated under reduced pressure and the residue was purified by silica gel column chromatography to give 3-(5-bromo-2-[2-[(1S)-1-methoxyethyl]pyridin-3-yl]-1H-indol-3-yl)-2,2-dimethylpropanoic acid and ethyl (S)-3-(5-bromo-2-(2-(1-methoxyethyl)pyridin-3-yl)-1H-indol-3-yl)-2,2-dimethylpropanoate (78 g, crude). LCMS (ESI): m/z [M+H] calc'd for $C_{21}H_{23}BrN_2O_3$ 430.1 and $C_{23}H_{27}BrN_2O_3$ 458.1; found 431.1 and 459.1.

Step 3. To a mixture of 3-(5-bromo-2-[2-[(1S)-1-methoxyethyl]pyridin-3-yl]-1H-indol-3-yl)-2,2-dimethylpropanoic acid and ethyl (S)-3-(5-bromo-2-(2-(1-methoxyethyl)pyridin-3-yl)-1H-indol-3-yl)-2,2-dimethylpropanoate (198 g, 459 mmol) in DMF (1.8 L) at 0° C. under an atmosphere of $N_2$ was added $Cs_2CO_3$ (449 g, 1.38 mol) in portions. EtI (215 g, 1.38 mmol) in DMF (200 mL) was then added dropwise at 0° C. The mixture was warmed to rt and stirred for 4 h then diluted with brine (5 L) and extracted with EtOAc (3×2.5 L). The combined organic layers were washed with brine (2×1.5 L), dried over anhydrous $Na_2SO_4$ and filtered. The filtrate was concentrated under reduced pressure and the residue was purified by silica gel column chromatography to give ethyl 3-(5-bromo-1-ethyl-2-[2-[(1S)-1-methoxyethyl]pyridin-3-yl]indol-3-yl)-2,2-dimethylpropanoate (160 g, 57% yield) as a solid. LCMS (ESI): m/z [M+H] calc'd for $C_{25}H_{31}BrN_2O_3$ 486.2; found 487.2.

Step 4. To a mixture of ethyl 3-(5-bromo-1-ethyl-2-[2-[(1S)-1-methoxyethyl]pyridin-3-yl]indol-3-yl)-2,2-dimethylpropanoate (160 g, 328 mmol) in THF (1.6 L) at 0° C. under an atmosphere of $N_2$ was added $LiBH_4$ (28.6 g, 1.3 mol). The mixture was heated to 60° C. for 16 h, cooled, and quenched with pre-cooled (0° C.) aqueous $NH_4Cl$ (5 L). The mixture was extracted with EtOAc (3×2 L) and the combined organic layers were washed with brine (2×1 L), dried over anhydrous $Na_2SO_4$ and filtered. The filtrate was concentrated under reduced pressure and the residue was purified by silica gel column chromatography to give to two atropisomers of 3-(5-bromo-1-ethyl-2-(2-((S)-1-methoxyethyl)pyridin-3-yl)-1H-indol-3-yl)-2,2-dimethylpropan-1-ol (as single atropisomers) (60 g, 38% yield) and (40 g, 26% yield) both as solids. LCMS (ESI): m/z [M+H] calc'd for $C_{23}H_{29}BrN_2O_2$ 444.1; found 445.2.

Intermediate 2 and Intermediate 4. Synthesis of (S)-1-((S)-2-((tert-butoxycarbonyl)amino)-3-(3-(4,4,5,5-tetramethyl-1,3,2-dioxaborolan-2-yl)-5-((triisopropylsilyl)oxy)phenyl)propanoyl)hexahydropyridazine-3-carboxylate

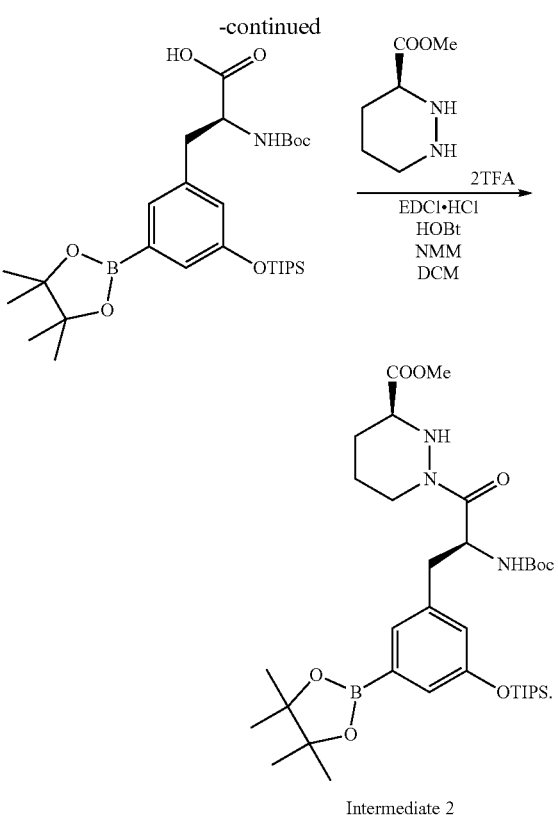

Intermediate 2

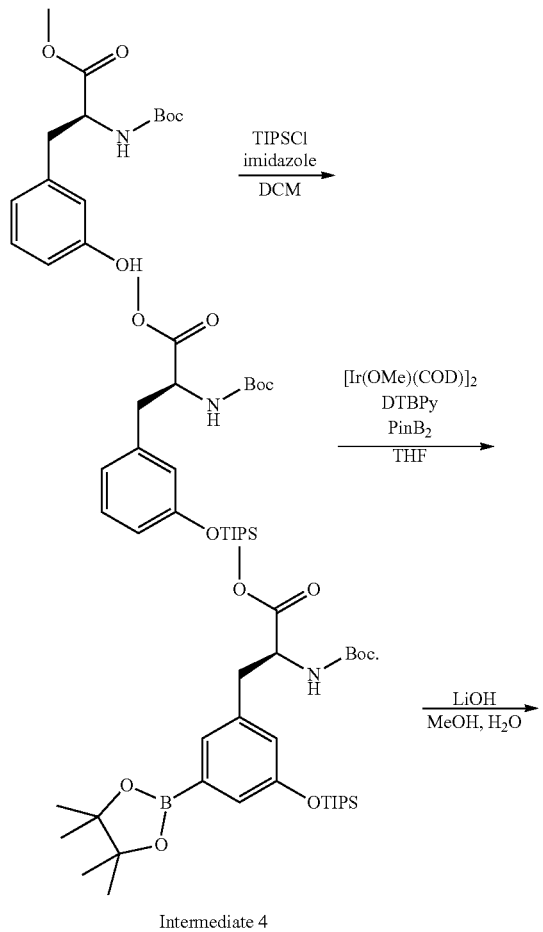

Intermediate 4

Step 1. To a mixture of (S)-methyl 2-(tert-butoxycarbonylamino)-3-(3-hydroxyphenyl)propanoate (10.0 g, 33.9 mmol) in DCM (100 mL) was added imidazole (4.6 g, 67.8 mmol) and TIPSCl (7.8 g, 40.7 mmol). The mixture was stirred at rt overnight then diluted with DCM (200 mL) and washed with $H_2O$ (150 mL×3). The organic layer was dried over anhydrous $Na_2SO_4$, filtered, concentrated under reduced pressure and the residue was purified by silica gel column chromatography to give (S)-methyl 2-(tert-butoxycarbonylamino)-3-(3-(triisopropylsilyloxy)phenyl)-propanoate (15.0 g, 98% yield) as an oil. LCMS (ESI): m/z [M+Na] calc'd for $C_{24}H_{41}NO_5SiNa$ 474.3; found 474.2.

Step 2. A mixture of (S)-methyl 2-(tert-butoxycarbonylamino)-3-(3-(triisopropylsilyloxy)phenyl)-propanoate (7.5 g, 16.6 mmol), $PinB_2$ (6.3 g, 24.9 mmol), [Ir(OMe)(COD)]2 (1.1 g, 1.7 mmol) and 4-tert-butyl-2-(4-tert-butyl-2-pyridyl)pyridine (1.3 g, 5.0 mmol) was purged with Ar (×3), then THF (75 mL) was added and the mixture placed under an atmosphere of Ar and sealed. The mixture was heated to 80° C. and stirred for 16 h, concentrated under reduced pressure and the residue was purified by silica gel column chromatography to give (S)-methyl 2-(tert-butoxycarbonylamino)-3-(3-(4,4,5,5-tetramethyl-1,3,2-dioxaborolan-2-yl)-5-(triisopropylsilyloxy)phenyl)-propanoate (7.5 g, 78% yield) as a solid. LCMS (ESI): m/z [M+Na] calc'd for $C_{30}H_{52}BNO_7SiNa$ 600.4; found 600.4; $^1H$ NMR (300 MHz, $CD_3OD$) δ 7.18 (s, 1H), 7.11 (s, 1H), 6.85 (s, 1H), 4.34 (m, 1H), 3.68 (s, 3H), 3.08 (m, 1H), 2.86 (m, 1H), 1.41-1.20 (m, 26H), 1.20-1.01 (m, 22H), 0.98-0.79 (m, 4H).

Step 3. To a mixture of triisopropylsilyl (S)-2-((tert-butoxycarbonyl)amino)-3-(3-(4,4,5,5-tetramethyl-1,3,2-dioxaborolan-2-yl)-5-(((triisopropylsilyl)oxy)phenyl)propanoate (4.95 g, 6.9 mmol) in MeOH (53 mL) at 0° C. was added LiOH (840 mg, 34.4 mmol) in $H_2O$ (35 mL). The mixture was stirred at 0° C. for 2 h, then acidified to pH 5 with 1M HCl and extracted with EtOAc (250 mL×2). The combined organic layers were washed with brine (100 mL×3), dried over anhydrous $Na_2SO_4$, filtered and the filtrate concentrated under reduced pressure to give (S)-2-((tert-butoxycarbonyl)amino)-3-(3-(4,4,5,5-tetramethyl-1,3,2-dioxaborolan-2-yl)-5-((triisopropylsilyl)oxy)phenyl)propanoic acid (3.7 g, 95% yield), which was used directly in the next step without further purification. LCMS (ESI): m/z $[M+NH_4]$ calc'd for $C_{29}H_{50}BNO_7SiNH_4$ 581.4; found 581.4.

Step 4. To a mixture of methyl (S)-hexahydropyridazine-3-carboxylate (6.48 g, 45.0 mmol) in DCM (200 mL) at 0° C. was added NMM (41.0 g, 405 mmol), (S)-2-((tert-butoxycarbonyl)amino)-3-(3-(4,4,5,5-tetramethyl-1,3,2-dioxaborolan-2-yl)-5-((triisopropylsilyl)oxy)phenyl)propanoic acid (24 g, 42.6 mmol) in DCM (50 mL) then HOBt (1.21 g, 9.0 mmol) and EDCl HCl salt (12.9 g, 67.6 mmol). The mixture was warmed to rt and stirred for 16 h, then diluted with DCM (200 mL) and washed with $H_2O$ (3×150 mL). The organic layer was dried over anhydrous $Na_2SO$, filtered, the filtrate concentrated under reduced pressure and the residue was purified by silica gel column chromatography to give methyl (S)-1-((S)-2-((tert-butoxycarbonyl)amino)-3-(3-(4,4,5,5-tetramethyl-1,3,2-dioxaborolan-2-yl)-5-((triisopropylsilyl)oxy)phenyl)propanoyl)hexahydropyridazine-3-carboxylate (22 g, 71% yield) as an oil. LCMS (ESI): m/z [M+H] calc'd for $C_{35}H_{60}BN_3O_8Si$ 689.4; found 690.5.

Intermediate 3. Synthesis of (S)-tert-butyl 3-methyl-2-((S)—N-methylpyrrolidine-3-carboxamido)butanoate

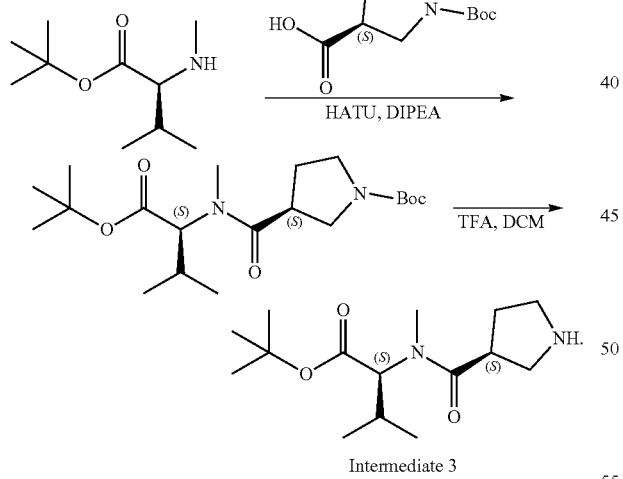

Intermediate 3

Step 1. To a mixture of (S)-1-(tert-butoxycarbonyl)pyrrolidine-3-carboxylic acid (2.2 g, 10.2 mmol) in DMF (10 mL) at rt was added HATU (7.8 g, 20.4 mmol) and DIPEA (5 mL). After stirring at rt for 10 min, tert-butyl methyl-L-valinate (3.8 g, 20.4 mmol) in DMF (10 mL) was added. The mixture was stirred at rt for 3 h, then diluted with DCM (40 mL) and $H_2O$ (30 mL). The aqueous and organic layers were separated, and the organic layer was washed with $H_2O$ (3×30 mL), brine (30 mL), dried over anhydrous $Na_2SO_4$ and filtered. The filtrate was concentrated under reduced pressure and the residue was purified by silica gel column chromatography to give (S)-tert-butyl 3-(((S)-1-(tert-butoxy)-3-methyl-1-oxobutan-2-yl)(methyl)carbamoyl)pyrrolidine-1-carboxylate (3.2 g, 82% yield) as an oil. LCMS (ESI): m/z [M+Na] calc'd for $C_{20}H_{36}N_2O_5Na$ 407.3; found 407.2.

Step 2. A mixture of (S)-tert-butyl 3-(((S)-1-(tert-butoxy)-3-methyl-1-oxobutan-2-yl)(methyl)carbamoyl)pyrrolidine-1-carboxylate (3.2 g, 8.4 mmol) in DCM (13 mL) and TFA (1.05 g, 9.2 mmol) was stirred at rt for 5 h. The mixture was concentrated under reduced pressure to give (S)-tert-butyl 3-methyl-2-((S)—N-methylpyrrolidine-3-carboxamido)butanoate (2.0 g, 84% yield) as an oil. LCMS (ESI): m/z [M+H] calc'd for $C_{15}H_{28}N_2O_3$ 284.2; found 285.2.

Intermediate 5. Synthesis of tert-butyl ((6$^3$S,4S)-11-ethyl-12-(2-((S)-1-methoxyethyl)pyridin-3-yl)-10,10-dimethyl-5,7-dioxo-25-((triisopropylsilyl)oxy)-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)carbamate

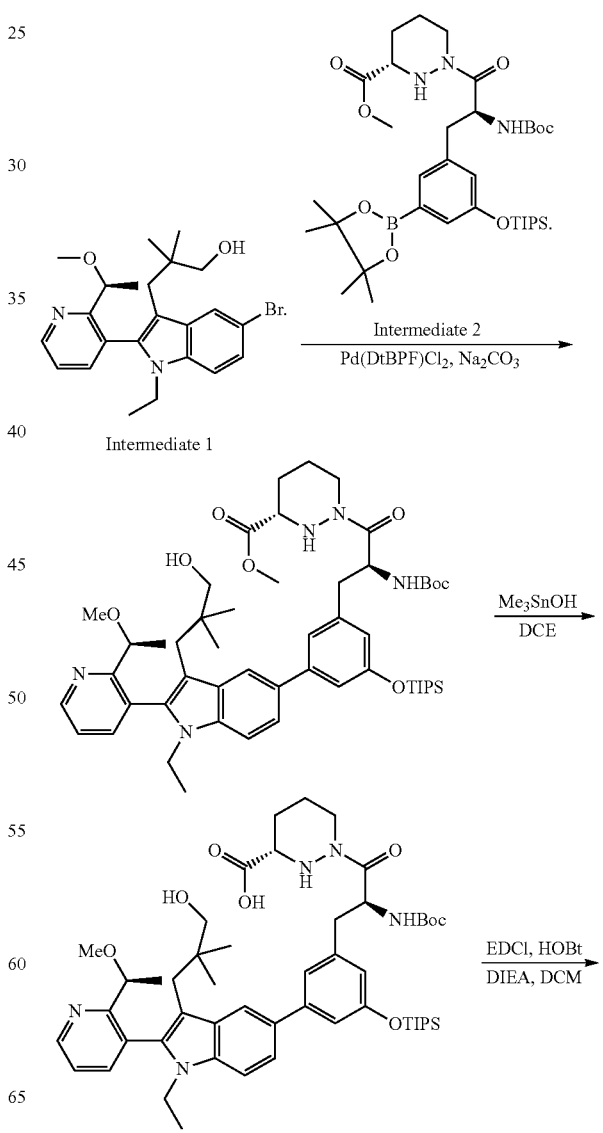

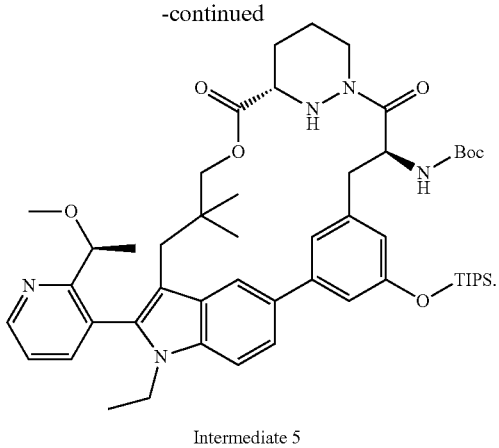

Intermediate 5

Step 1. To a stirred mixture of 3-(5-bromo-1-ethyl-2-[2-[(1S)-1-methoxyethyl]pyridin-3-yl]indol-3-yl)-2,2-dimethylpropan-1-ol (30 g, 67 mmol) and methyl (3S)-1-[(2S)-2-[(tert-butoxycarbonyl)amino]-3-[3-(4,4,5,5-tetramethyl-1,3,2-dioxaborolan-2-yl)-5-[(triisopropylsilyl)oxy]phenyl]propanoyl]-1,2-diazinane-3-carboxylate (55.8 g, 80.8 mmol) in 1,4-dioxane (750 mL) at rt under an atmosphere of Ar was added Na$_2$CO$_3$ (17.9 g, 168.4 mmol), Pd(DtBPF)Cl$_2$ (4.39 g, 6.7 mmol) and H$_2$O (150.00 mL) in portions. The mixture was heated to 85° C. and stirred for 3 h, cooled, diluted with H$_2$O (2 L) and extracted with EtOAc (3×1 L). The combined organic layers were washed with brine (2×500 mL), dried over anhydrous Na$_2$SO$_4$ and filtered. The filtrate was concentrated under reduced pressure and the residue was purified by silica gel column chromatography to give methyl (3S)-1-[(2S)-2-[(tert-butoxycarbonyl)amino]-3-[3-[1-ethyl-3-(3-hydroxy-2,2-dimethylpropyl)-2-[2-[(1S)-1-methoxyethyl]pyridin-3-yl]indol-5-yl]-5-[(triisopropylsilyl)oxy]phenyl]propanoyl]-1,2-diazinane-3-carboxylate (50 g, 72% yield) as a solid. LCMS (ESI): m/z [M+H] calc'd for C$_{52}$H$_{77}$N$_5$O$_8$Si 927.6; found 928.8.

Step 2. To a stirred mixture of methyl (3S)-1-[(2S)-2-[(tert-butoxycarbonyl)amino]-3-[3-[1-ethyl-3-(3-hydroxy-2,2-dimethylpropyl)-2-[2-[(1S)-1-methoxyethyl]pyridin-3-yl]indol-5-yl]-5-[(triisopropylsilyl)oxy]phenyl]propanoyl]-1,2-diazinane-3-carboxylate (50 g, 54 mmol) in DCE (500 mL) at rt was added trimethyltin hydroxide (48.7 g, 269 mmol) in portion. The mixture was heated to 65° C. and stirred for 16 h, then filtered and the filter cake washed with DCM (3×150 mL). The filtrate was concentrated under reduced pressure to give (3S)-1-[(2S)-2-[(tert-butoxycarbonyl)amino]-3-[3-[1-ethyl-3-(3-hydroxy-2,2-dimethylpropyl)-2-[2-[(1S)-1-methoxyethyl]pyridin-3-yl]indol-5-yl]-5-[(triisopropylsilyl)oxy]phenyl]propanoyl]-1,2-diazinane-3-carboxylic acid (70 g, crude), which was used directly in the next step without further purification. LCMS (ESI): m/z [M+H] calc'd for C$_{51}$H$_{75}$N$_5$O$_8$Si 913.5; found 914.6.

Step 3. To a stirred mixture of (3S)-1-[(2S)-2-[(tert-butoxycarbonyl)amino]-3-[3-[1-ethyl-3-(3-hydroxy-2,2-dimethylpropyl)-2-[2-[(1S)-1-methoxyethyl]pyridin-3-yl]indol-5-yl]-5-[(triisopropylsilyl)oxy]phenyl]propanoyl]-1,2-diazinane-3-carboxylic acid (70 g) in DCM (5 L) at 0° C. under an atmosphere of N$_2$ was added DIPEA (297 g, 2.3 mol), HOBT (51.7 g, 383 mmol) and EDCl (411 g, 2.1 mol) in portions. The mixture was warmed to rt and stirred for 16 h, then diluted with DCM (1 L), washed with brine (3×1 L), dried over anhydrous Na$_2$SO$_4$ and filtered. The filtrate was concentrated under reduced pressure and the residue was purified by silica gel column chromatography to give tert-butyl ((6$^3$S,4S)-1$^1$-ethyl-1$^2$-(2-((S)-1-methoxyethyl)pyridin-3-yl)-10,10-dimethyl-5,7-dioxo-2$^5$-((triisopropylsilyl)oxy)-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl) carbamate (36 g, 42% yield) as a solid. LCMS (ESI): m/z [M+H] calc'd for C$_{51}$H$_{73}$N$_5$O$_7$Si 895.5; found 896.5.

Intermediate 6. Synthesis of tert-butyl N-[(8S,14S)-21-iodo-18,18-dimethyl-9,15-dioxo-4-[(triisopropylsilyl)oxy]-16-oxa-10,22,28-triazapentacyclo[18.5.2.1˜[2,6]0.1˜10,14]0.0˜[23,27]]nonacosa-1 (26),2,4,6 (29),20,23(27),24-heptaen-8-yl]carbamate

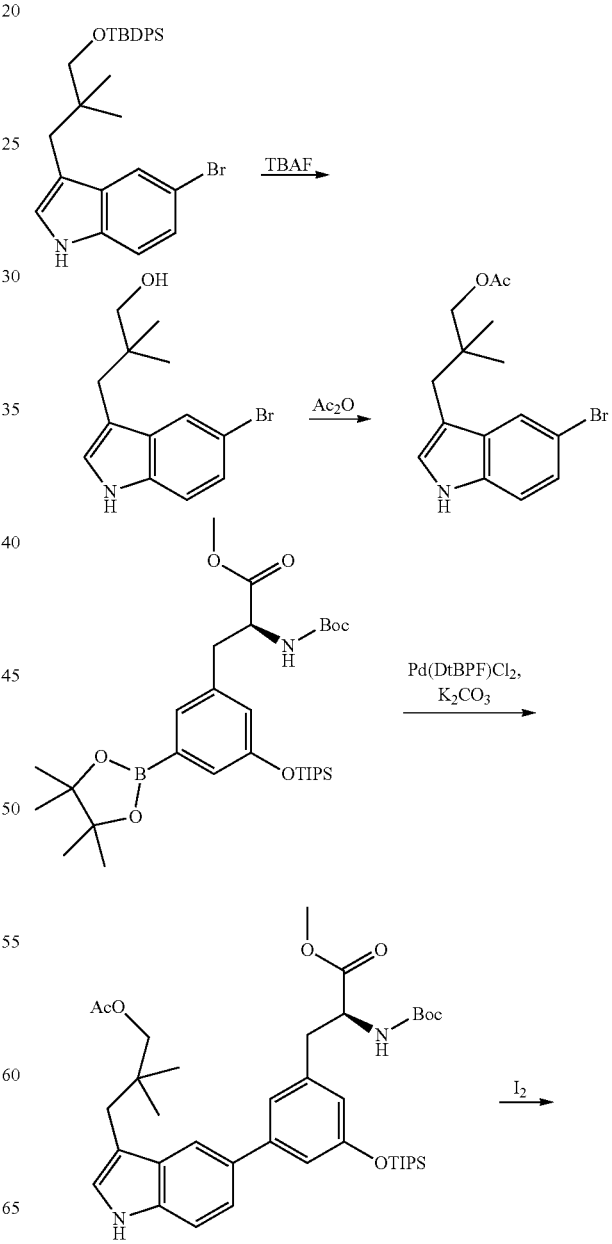

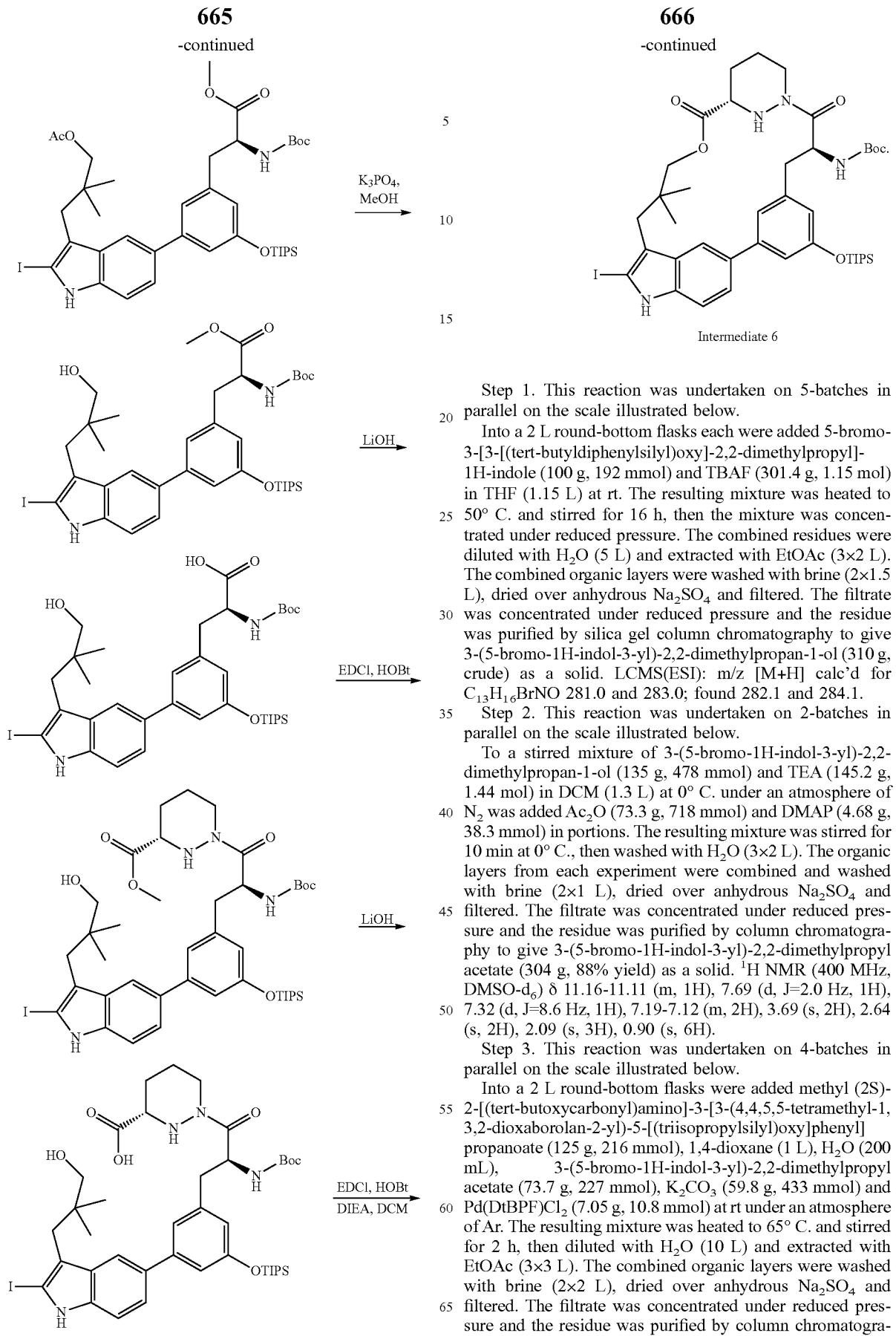

Intermediate 6

Step 1. This reaction was undertaken on 5-batches in parallel on the scale illustrated below.

Into a 2 L round-bottom flasks each were added 5-bromo-3-[3-[(tert-butyldiphenylsilyl)oxy]-2,2-dimethylpropyl]-1H-indole (100 g, 192 mmol) and TBAF (301.4 g, 1.15 mol) in THF (1.15 L) at rt. The resulting mixture was heated to 50° C. and stirred for 16 h, then the mixture was concentrated under reduced pressure. The combined residues were diluted with $H_2O$ (5 L) and extracted with EtOAc (3×2 L). The combined organic layers were washed with brine (2×1.5 L), dried over anhydrous $Na_2SO_4$ and filtered. The filtrate was concentrated under reduced pressure and the residue was purified by silica gel column chromatography to give 3-(5-bromo-1H-indol-3-yl)-2,2-dimethylpropan-1-ol (310 g, crude) as a solid. LCMS(ESI): m/z [M+H] calc'd for $C_{13}H_{16}BrNO$ 281.0 and 283.0; found 282.1 and 284.1.

Step 2. This reaction was undertaken on 2-batches in parallel on the scale illustrated below.

To a stirred mixture of 3-(5-bromo-1H-indol-3-yl)-2,2-dimethylpropan-1-ol (135 g, 478 mmol) and TEA (145.2 g, 1.44 mol) in DCM (1.3 L) at 0° C. under an atmosphere of $N_2$ was added $Ac_2O$ (73.3 g, 718 mmol) and DMAP (4.68 g, 38.3 mmol) in portions. The resulting mixture was stirred for 10 min at 0° C., then washed with $H_2O$ (3×2 L). The organic layers from each experiment were combined and washed with brine (2×1 L), dried over anhydrous $Na_2SO_4$ and filtered. The filtrate was concentrated under reduced pressure and the residue was purified by column chromatography to give 3-(5-bromo-1H-indol-3-yl)-2,2-dimethylpropyl acetate (304 g, 88% yield) as a solid. $^1$H NMR (400 MHz, DMSO-$d_6$) δ 11.16-11.11 (m, 1H), 7.69 (d, J=2.0 Hz, 1H), 7.32 (d, J=8.6 Hz, 1H), 7.19-7.12 (m, 2H), 3.69 (s, 2H), 2.64 (s, 2H), 2.09 (s, 3H), 0.90 (s, 6H).

Step 3. This reaction was undertaken on 4-batches in parallel on the scale illustrated below.

Into a 2 L round-bottom flasks were added methyl (2S)-2-[(tert-butoxycarbonyl)amino]-3-[3-(4,4,5,5-tetramethyl-1,3,2-dioxaborolan-2-yl)-5-[(triisopropylsilyl)oxy]phenyl]propanoate (125 g, 216 mmol), 1,4-dioxane (1 L), $H_2O$ (200 mL), 3-(5-bromo-1H-indol-3-yl)-2,2-dimethylpropyl acetate (73.7 g, 227 mmol), $K_2CO_3$ (59.8 g, 433 mmol) and Pd(DtBPF)$Cl_2$ (7.05 g, 10.8 mmol) at rt under an atmosphere of Ar. The resulting mixture was heated to 65° C. and stirred for 2 h, then diluted with $H_2O$ (10 L) and extracted with EtOAc (3×3 L). The combined organic layers were washed with brine (2×2 L), dried over anhydrous $Na_2SO_4$ and filtered. The filtrate was concentrated under reduced pressure and the residue was purified by column chromatography to give methyl (2S)-3-(3-[3-[3-(acetyloxy)-2,2-dimethylpropyl]-1H-indol-5-yl]-5-[(triisopropylsilyl)oxy]phenyl)-2-[(tert-butoxycarbonyl)amino]propanoate (500 g, 74% yield) as an oil. LCMS (ESI): m/z [M+Na] calc'd for $C_{39}H_{28}N_2O_7SiNa$ 717.4; found 717.3.

Step 4. This reaction was undertaken on 3-batchs' in parallel on the scale illustrated below.

To a stirred mixture of methyl (2S)-3-(3-[3-[3-(acetyloxy)-2,2-dimethylpropyl]-1H-indol-5-yl]-5-[(triisopropylsilyl)oxy]phenyl)-2-[(tert-butoxycarbonyl)amino]propanoate (150 g, 216 mmol) and NaHCO$_3$ (21.76 g, 259 mmol) in THF (1.5 L) was added AgOTf (66.5 g, 259 mmol) in THF dropwise at 0° C. under an atmosphere of nitrogen. I$_2$ (49.3 g, 194 mmol) in THF was added dropwise over 1 h at 0° C. and the resulting mixture was stirred for an additional 10 min at 0° C. The combined experiments were diluted with aqueous Na$_2$S$_2$O$_3$ (5 L) and extracted with EtOAc (3×3 L). The combined organic layers were washed with brine (2×1.5 L), dried over anhydrous Na$_2$SO$_4$ and filtered. The filtrate was concentrated under reduced pressure and the residue was purified by column chromatography to give methyl (2S)-3-(3-[3-[3-(acetyloxy)-2,2-dimethylpropyl]-2-iodo-1H-indol-5-yl]-5-[(triisopropylsilyl)oxy]phenyl)-2-[(tert-butoxycarbonyl)amino]propanoate (420 g, 71% yield) as an oil. LCMS (ESI): m/z [M+Na] calc'd for $C_{39}H_{57}IN_2O_7SiNa$, 843.3; found 842.9.

Step 5. This reaction was undertaken on 3-batches in parallel on the scale illustrated below.

To a 2 L round-bottom flask were added methyl (2S)-3-(3-[3-[3-(acetyloxy)-2,2-dimethylpropyl]-2-iodo-1H-indol-5-yl]-5-[(triisopropylsilyl)oxy]phenyl)-2-[(tert-butoxycarbonyl)amino]propanoate (140 g, 171 mmol), MeOH (1.4 L) and K$_3$PO$_4$ (108.6 g, 512 mmol) at 0° C. The mixture was warmed to rt and stirred for 1 h, then the combined experiments were diluted with H$_2$O (9 L) and extracted with EtOAc (3×3 L). The combined organic layers were washed with brine (2×2 L), dried over anhydrous Na$_2$SO$_4$, filtered and the filtrate was concentrated under reduced pressure to give methyl (2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoate (438 g, crude) as a solid. LCMS (ESI): m/z [M+Na] calc'd for $C_{37}H_{55}IN_2O_6SiNa$ 801.3; found 801.6.

Step 6. This reaction was undertaken on 3-batches in parallel on the scale illustrated below.

To a stirred mixture of methyl (2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoate (146 g, 188 mmol) in THF (1.46 L) was added LiOH (22.45 g, 937 mmol) in H$_2$O (937 mL) dropwise at 0° C. The resulting mixture was warmed to rt and stirred for 1.5 h [note: LCMS showed 15% de-TIPS product]. The mixture was acidified to pH 5 with 1M HCl (1M) and the combined experiments were extracted with EtOAc (3×3 L). The combined organic layers were washed with brine (2×2 L), dried over anhydrous Na$_2$SO$_4$, filtered and the filtrate was concentrated under reduced pressure to give (2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoic acid (402 g, crude) as a solid. LCMS (ESI): m/z [M+Na] calc'd for $C_{36}H_{53}IN_2O_6SiNa$ 787.3; found 787.6.

Step 7. To a stirred mixture of (2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoic acid (340 g, 445 mmol) and methyl (3S)-1,2-diazinane-3-carboxylate (96.1 g, 667 mmol) in DCM (3.5 L) was added NMM (225 g, 2.2 mol), EDCl (170 g, 889 mmol), HOBT (12.0 g, 88.9 mmol) portionwise at 0° C. The mixture was warmed to rt and stirred for 16 h, then washed with H$_2$O (3×2.5 L), brine (2×1 L), dried over anhydrous Na$_2$SO$_4$ and filtered. The filtrate was concentrated under reduced pressure and the residue was purified by column chromatography to give methyl (3S)-1-[(2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoyl]-1,2-diazinane-3-carboxylate (310 g, 62% yield) as an oil. LCMS (ESI): m/z [M+H] calc'd for $C_{42}H_{63}IN_4O_7Si$ 890.4; found 890.8.

Step 8. This reaction was undertaken on 3-batches in parallel on the scale illustrated below.

To a stirred mixture of methyl (3S)-1-[(2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoyl]-1,2-diazinane-3-carboxylate (85.0 g, 95.4 mmol) in THF (850 mL) each added LiOH (6.85 g, 286 mmol) in H$_2$O (410 mL) dropwise at 0° C. under an atmosphere of N2. The mixture was stirred at 0° C. for 1.5 h [note: LCMS showed 15% de-TIPS product], then acidified to pH 5 with 1M HCl and the combined experiments extracted with EtOAc (3×2 L). The combined organic layers were washed with brine (2×1.5 L), dried over anhydrous Na$_2$SO$_4$, filtered and the filtrate was concentrated under reduced pressure to give (3S)-1-[(2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoyl]-1,2-diazinane-3-carboxylic acid (240 g, crude) as a solid. LCMS (ESI): m/z [M+H] calc'd for $C_{41}H_{61}IN_4O_7Si$ 876.3; found 877.6.

Step 9. This reaction was undertaken on 2-batches in parallel on the scale illustrated below.

To a stirred mixture of (3S)-1-[(2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoyl]-1,2-diazinane-3-carboxylic acid (120 g, 137 mmol) in DCM (6 L) was added DIPEA (265 g, 2.05 mol), EDCl (394 g, 2.05 mol), HOBT (37 g, 274 mmol) in portions at 0° C. under an atmosphere of N2. The mixture was warmed to rt and stirred overnight, then the combined experiments were washed with H$_2$O (3×6 L), brine (2×6 L), dried over anhydrous Na$_2$SO$_4$ and filtered. After filtration, the filtrate was concentrated under reduced pressure. The filtrate was concentrated under reduced pressure and the residue was purified by column chromatography to give tert-butyl N-[(8S,14S)-21-iodo-18,18-dimethyl-9,15-dioxo-4-[(triisopropylsilyl)oxy]-16-oxa-10,22,28-triazapentacyclo [18.5.2.1^[2,6]0.1^[10,14]0.0^[23,27]]nonacosa-1(26),2,4,6 (29),20,23(27),24-heptaen-8-yl]carbamate (140 g, 50% yield) as a solid. LCMS (ESI): m/z [M+H] calc'd for $C_{41}H_{59}IN_4O_6Si$ 858.9; found 858.3.

Intermediate 7. Synthesis of (6$^3$S,4$^5$)-4-amino-1$^1$-ethyl-2$^5$-hydroxy-1$^2$-(4-(methoxymethyl)pyridin-3-yl)-10,10-dimethyl-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-5,7-dione

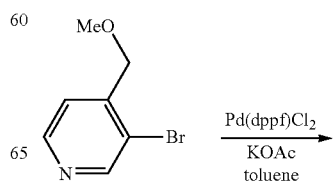

-continued

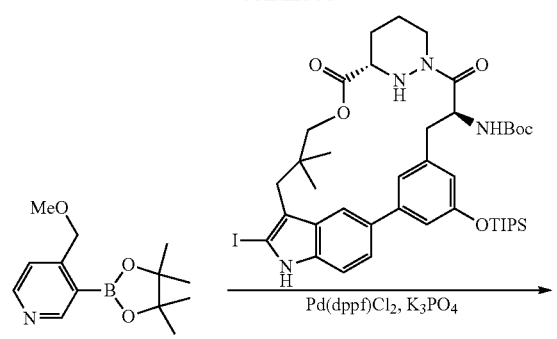

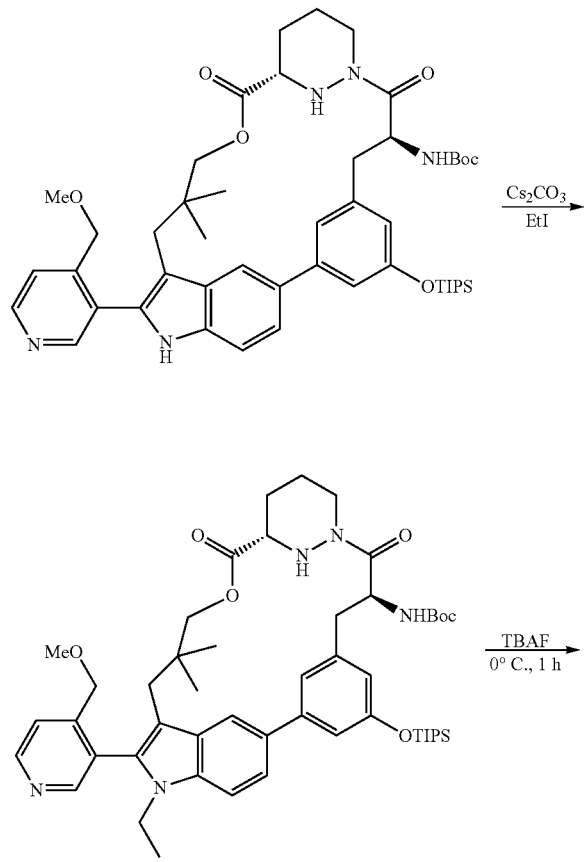

-continued

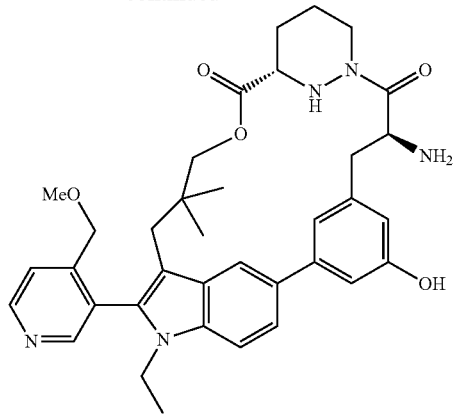 [SMILES: CCn1c(-c2cnccc2COC)c2c3cc(ccc31)-c1cc(O)cc(c1)C[C@H](N)C(=O)N1CCC[C@H](N1)C(=O)OCC(C)(C)C2]

Step 1. To a mixture of 3-bromo-4-(methoxymethyl) pyridine (1.00 g, 5.0 mmol), 4,4,5,5-tetramethyl-2-(tetramethyl-1,3,2-dioxaborolan-2-yl)-1,3,2-dioxaborolane (1.51 g, 5.9 mmol) and KOAc (1.21 g, 12.3 mmol) in toluene (10 mL) at rt under an atmosphere of Ar was added Pd(dppf)Cl$_2$ (362 mg, 0.5 mmol). The mixture was heated to 110° C. and stirred overnight, then concentrated under reduced pressure to give 4-(methoxymethyl)-3-(4,4,5,5-tetramethyl-1,3,2-dioxaborolan-2-yl)pyridine, which was used directly in the next step directly without further purification. LCMS (ESI): m/z [M+H] calc'd for $C_{13}H_{20}BNO_3$ 249.2; found 250.3.

Step 2. To a mixture of 4-(methoxymethyl)-3-(4,4,5,5-tetramethyl-1,3,2-dioxaborolan-2-yl)pyridine (290 mg, 1.16 mmol), K$_3$PO$_4$ (371 mg, 1.75 mmol) and tert-butyl N-[(8S,14S)-21-iodo-18,18-dimethyl-9,15-dioxo-4-[(triisopropylsilyl)oxy]-16-oxa-10,22,28-triazapentacyclo[18.5.2.1ˆ[2,6]0.1ˆ[10,14]0.0ˆ[23,27]]nonacosa-1(26),2,4,6(29),20,23(27),24-heptaen-8-yl]carbamate (500 mg, 0.58 mmol) in 1,4-dioxane (5 mL) and H$_2$O (1 mL) at rt under an atmosphere of Ar was added Pd(dppf)Cl$_2$ (43 mg, 0.06 mmol). The mixture was heated to 70° C. and stirred for 2 h, then H$_2$O added and the mixture extracted with EtOAc (2×10 mL). The combined organic layers were washed with brine (10 mL), dried over anhydrous Na$_2$SO$_4$ and filtered. The filtrate was concentrated under reduced pressure and the residue was purified by silica gel column chromatography to give tert-butyl N-[(8S,14S)-21-[4-(methoxymethyl)pyridin-3-yl]-18,18-dimethyl-9,15-dioxo-4-[(triisopropylsilyl)oxy]-16-oxa-10,22,28-triazapentacyclo[18.5.2.1ˆ[2,6]0.1ˆ[10,14]0.0ˆ[23,27]]nonacosa-1(26),2,4,6(29),20,23(27),24-heptaen-8-yl]carbamate (370 mg, 74% yield) as a foam. LCMS (ESI): m/z [M+H] calc'd for $C_{48}H_{67}N_5O_7Si$ 853.6; found 854.6.

Step 3. A mixture of tert-butyl N-[(8S,14S)-21-[4-(methoxymethyl)pyridin-3-yl]-18,18-dimethyl-9,15-dioxo-4-[(triisopropylsilyl)oxy]-16-oxa-10,22,28-triazapentacyclo[18.5.2.1ˆ[2,6]0.1ˆ[10,14]0.0ˆ[23,27]]nonacosa-1(26),2,4,6(29),20,23(27),24-heptaen-8-yl]carbamate (350 mg, 0.41 mmol), Cs$_2$CO$_3$ (267 mg, 0.82 mmol) and EtI (128 mg, 0.82 mmol) in DMF (4 mL) was stirred at 35° C. overnight. H$_2$O was added and the mixture was extracted with EtOAc (2×15 mL). The combined organic layers were washed with brine (15 mL), dried over anhydrous Na$_2$SO$_4$ and filtered. The filtrate was concentrated under reduced pressure and the residue was purified by silica gel column chromatography to give tert-butyl N-[(8S,14S)-22-ethyl-21-[4-(methoxymethyl)pyridin-3-yl]-18,18-dimethyl-9,15-dioxo-4-[(triisopropylsilyl)oxy]-16-oxa-10,22,28-triazapentacyclo

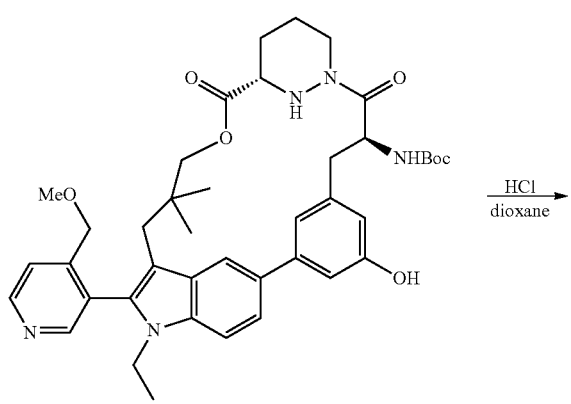

[18.5.2.1^[2,6]0.1^[10,14]0.0^[23,27]]nonacosa-1(26),2,4,6 (29),20,23(27),24-heptaen-8-yl]carbamate (350 mg, 97% yield) as an oil. LCMS (ESI): m/z [M+H] calc'd for $C_{50}H_{71}N_5O_7Si$ 881.5; found 882.6.

Step 4. A mixture of tert-butyl N-[(8S,14S)-22-ethyl-21-[4-(methoxymethyl)pyridin-3-yl]-18,18-dimethyl-9,15-dioxo-4-[(triisopropylsilyl)oxy]-16-oxa-10,22,28-triazapentacyclo[18.5.2.1^[2,6]0.1^[10,14]0.0^[23,27]]nonacosa-1(26),2,4,6(29),20,23(27),24-heptaen-8-yl]carbamate (350 mg, 0.4 mmol) and 1M TBAF in THF (0.48 mL, 0.480 mmol) in THF (3 mL) at 0° C. under an atmosphere of Ar was stirred for 1 h. The mixture was concentrated under reduced pressure and the residue was purified by silica gel column chromatography to give tert-butyl N-[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1^[2,6]0.1^[10,14]0.0^[23,27]]nonacosa-1(26),2,4,6(29),20,23(27),24-heptaen-8-yl]carbamate (230 mg, 80% yield) as an oil. LCMS (ESI): m/z [M+H] calc'd for $C_{41}H_{51}N_5O_7$ 725.4; found 726.6.

Step 5. To a mixture of tert-butyl N-[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1^[2,6]0.1^[10,14]0.0^[23,27]]nonacosa-1(26),2,4,6(29),20,23(27),24-heptaen-8-yl]carbamate (200 mg, 0.28 mmol) in 1,4-dioxane (2 mL) at 0° C. under an atmosphere of Ar was added 4M HCl in 1,4-dioxane (2 mL, 8 mmol). The mixture was allowed to warm to rt and was stirred overnight, then concentrated under reduced pressure to give $(6^3S,4^S)$-4-amino-$1^1$-ethyl-$2^5$-hydroxy-$1^2$-(4-(methoxymethyl)pyridin-3-yl)-10,10-dimethyl-$6^1,6^2,6^3,6^4,6^5,6^6$-hexahydro-$1^1$H-8-oxa-1(5,3)-indola-6(1,3)-pyridazina-2(1,3)-benzenacycloundecaphane-5,7-dione (200 mg). LCMS (ESI): m/z [M+H] calc'd for $C_{36}H_{43}N_5O_5$ 625.3; found 626.5.

Intermediate 8. Synthesis of tert-butyl (($6^3$S,4S,Z)-$1^1$-ethyl-$1^2$-(2-((S)-1-methoxyethyl)pyridin-3-yl)-10,10-dimethyl-5,7-dioxo-$6^1,6^2,6^3,6^4,6^5,6^6$-hexahydro-$1^1$H-8-oxa-2(4,2)-thiazola-1(5,3)-indola-6(1,3)-pyridazinacycloundecaphane-4-yl)carbamate

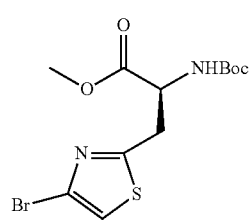

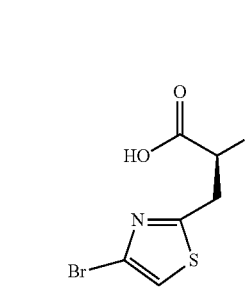

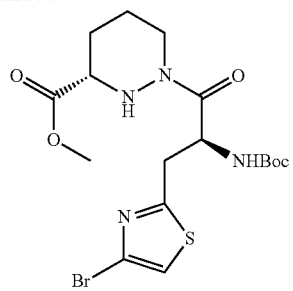

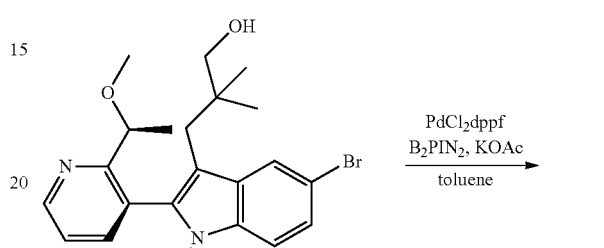

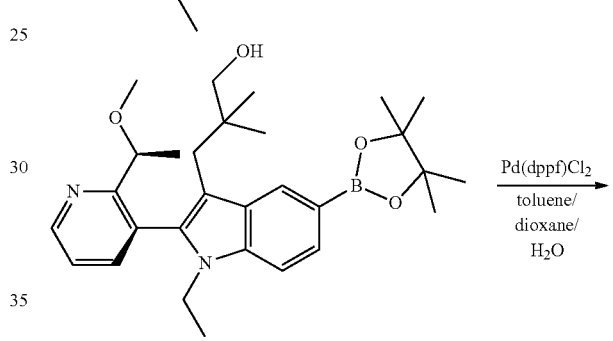

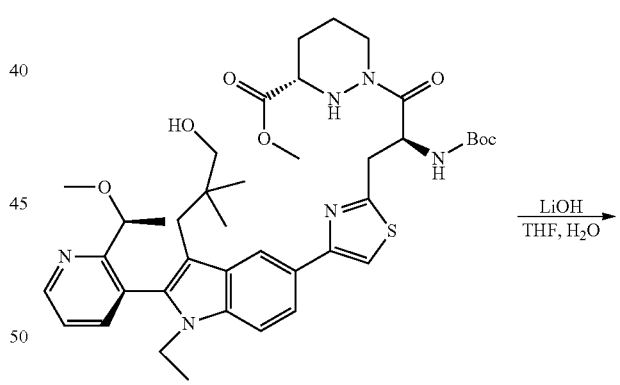

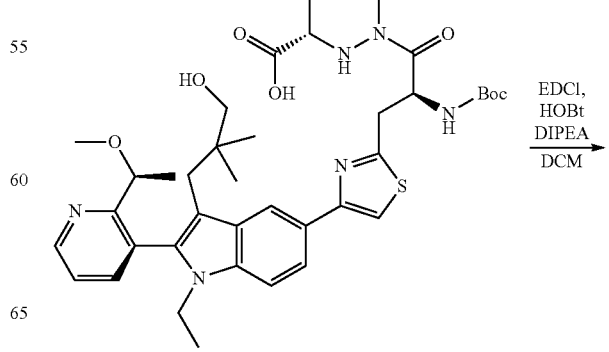

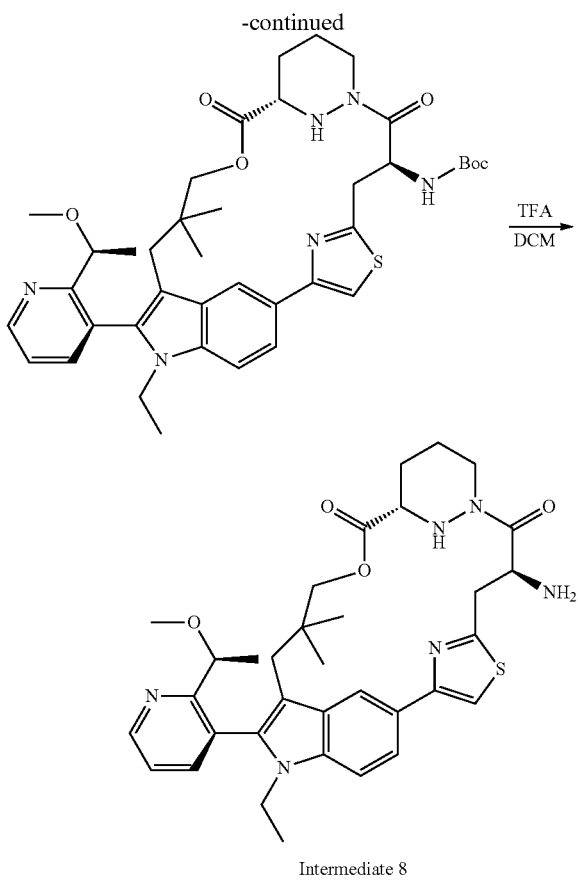

Intermediate 8

Step 1. To a solution of methyl (2S)-3-(4-bromo-1,3-thiazol-2-yl)-2-[(tert-butoxycarbonyl)amino]propanoate (110 g, 301.2 mmol) in THF (500 mL) and H$_2$O (200 mL) at room temperature was added LiOH (21.64 g, 903.6 mmol). The solution was stirred for 1 h and was then concentrated under reduced pressure. The residue was adjusted to pH 6 with 1 M HCl and then extracted with DCM (3×500 mL). The combined organic layers were, dried over Na$_2$SO$_4$, filtered, and concentrated under reduced pressure to give (S)-3-(4-bromothiazol-2-yl)-2-((tert-butoxycarbonyl)amino)propanoic acid (108 g, crude). LCMS (ESI): m/z [M+H] calc'd for C$_{11}$H$_{16}$BrN$_2$O$_4$S 351.0; found 351.0.

Step 2. To a solution of (S)-3-(4-bromothiazol-2-yl)-2-((tert-butoxycarbonyl)amino)propanoic acid (70 g, 199.3 mmol) in DCM (500 mL) at 0° C. was added methyl (3S)-1,2-diazinane-3-carboxylate bis(trifluoroacetic acid) salt (111.28 g, 298.96 mmol), NMM (219.12 mL. 1993.0 mmol), EDCl (76.41 g, 398.6 mmol) and HOBt (5.39 g, 39.89 mmol). The reaction was warmed to room temperature and stirred for 1 h. The reaction was then quenched with H$_2$O (500 mL) and was extracted with EtOAc (3×500 mL). The combined organic layers were dried over Na$_2$SO$_4$, filtered, and concentrated under reduced pressured. The residue was purified by silica gel column chromatography to give methyl (S)-1-((S)-3-(4-bromothiazol-2-yl)-2-((tert-butoxycarbonyl)amino)propanoyl)hexahydropyridazine-3-carboxylate (88.1 g, 93% yield). LCMS (ESI): m/z [M+H] calc'd for C$_{17}$H$_{26}$BrN$_4$O$_5$S 477.1; found 477.1.

Step 3. To a solution of 3-(5-bromo-1-ethyl-2-(2-((S)-1-methoxyethyl)pyridin-3-yl)-1H-indol-3-yl)-2,2-dimethylpropan-1-ol (60 g, 134.7 mmol) in toluene (500 mL) at room temperature was added bis(pinacolato)diboron (51.31 g, 202.1 mmol), Pd(dppf)Cl$_2$ (9.86 g, 13.4 mmol), and KOAc (26.44 g, 269 mmol). The reaction mixture was then heated to 90° C. and stirred for 2 h. The reaction solution was then cooled to room temperature and concentrated under reduced pressure. The residue was purified by silica gel column chromatography to give (S)-3-(1-ethyl-2-(2-(1-methoxyethyl)pyridin-3-yl)-5-(4,4,5,5-tetramethyl-1,3,2-dioxaborolan-2-yl)-1H-indol-3-yl)-2,2-dimethylpropan-1-ol (60.6 g, 94% yield). LCMS (ESI): m/z [M+H] calc'd for C$_{29}$H$_{42}$BN$_2$O$_4$ 493.32; found 493.3.

Step 4. To a solution of (S)-3-(1-ethyl-2-(2-(1-methoxyethyl)pyridin-3-yl)-5-(4,4,5,5-tetramethyl-1,3,2-dioxaborolan-2-yl)-1H-indol-3-yl)-2,2-dimethylpropan-1-ol (30 g, 60.9 mmol) in toluene (600 mL), dioxane (200 mL), and H$_2$O (200 mL) at room temperature was added methyl (S)-1-((S)-3-(4-bromothiazol-2-yl)-2-((tert-butoxycarbonyl)amino)propanoyl)hexahydropyridazine-3-carboxylate (43.62 g, 91.4 mmol), K$_3$PO$_4$ (32.23 g, 152.3 mmol) and Pd(dppf)Cl$_2$ (8.91 g, 12.18 mmol). The resulting solution was heated to 70° C. and stirred overnight. The reaction mixture was then cooled to room temperature and was quenched with H$_2$O (200 mL). The mixture was extracted with EtOAc and the combined organic layers were dried over Na$_2$SO$_4$, filtered, and concentrated under reduced pressure. The residue was purified by silica gel column chromatography to give methyl (S)-1-((S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-indol-5-yl)thiazol-2-yl)propanoyl) hexahydropyridazine-3-carboxylate (39.7 g, 85% yield). LCMS (ESI): m/z [M+H] calc'd for C$_{40}$H$_{55}$N6O$_7$S 763.4; found 763.3.

Step 5. To a solution of methyl (S)-1-((S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-indol-5-yl)thiazol-2-yl)propanoyl)hexahydropyridazine-3-carboxylate (39.7 g, 52.0 mmol) in THF (400 mL) and H$_2$O (100 mL) at room temperature was added LiOH.H$_2$O (3.74 g, 156.2 mmol). The mixture was stirred for 1.5 h and was then concentrated under reduced pressure. The residue was acidified to pH 6 with 1 M HCl and extracted with DCM (3×1000 mL). The combined organic layers were dried over Na$_2$SO$_4$, filtered, and concentrated under reduced pressure to give (S)-1-((S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-indol-5-yl)thiazol-2-yl)propanoyl)hexahydropyridazine-3-carboxylic acid (37.9 g, crude). LCMS (ESI): m/z [M+H] calc'd for C$_{39}$H$_{53}$N$_6$O$_7$S 749.4; found 749.4.

Step 6. To a solution of (S)-1-((S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-indol-5-yl)thiazol-2-yl)propanoyl)hexahydropyridazine-3-carboxylic acid (37.9 g, 50.6 mmol), HOBt (34.19 g, 253.0 mmol) and DIPEA (264.4 mL, 1518 mmol) in DCM (4 L) at 0° C. was added EDCl (271.63 g, 1416.9 mmol). The resulting mixture was warmed to room temperature and stirred overnight. The reaction mixture was then quenched with H$_2$O and washed with 1 M HCl (4×1 L). The organic layer was separated and concentrated under reduced pressure. The residue was purified by silica gel column chromatography to give tert-butyl ((6$^3$S,4S,Z)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl) carbamate (30 g, 81% yield). LCMS (ESI): m/z [M+H] calc'd for C$_{39}$H$_{51}$N$_6$O$_6$S 731.4; found 731.3.

Step 7. To a solution of tert-butyl ((6³S,4S,Z)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-2(4,2)-thiazola-1(5,3)-indola-6(1,3)- pyridazinacycloundecaphane-4-yl)carbamate (6 g, 8.21 mmol) in DCM (60 mL) at 0° C. was added TFA (30 mL). The mixture was stirred for 1 h and was then concentrated under reduced pressure to give (6³S,4S,Z)-4-amino-1¹-ethyl-1²-(2-((S)-1-methoxyethyl)pyridin-3-yl)-10,10-dimethyl-6¹,6²,6³,6⁴,6⁵,6⁶-hexahydro-1¹H-8-oxa-2(4,2)-thiazola-1(5,3)-indola-6(1,3)-pyridazinacycloundecaphane-5,7-dione (7.0 g, crude). LCMS (ESI): m/z [M+H] calc'd for $C_{34}H_{42}N_6O_4S$ 631.3; found: 630.3.

Intermediate 9. Synthesis of (S)-3-bromo-5-iodo-2-(1-methoxyethyl) pyridine

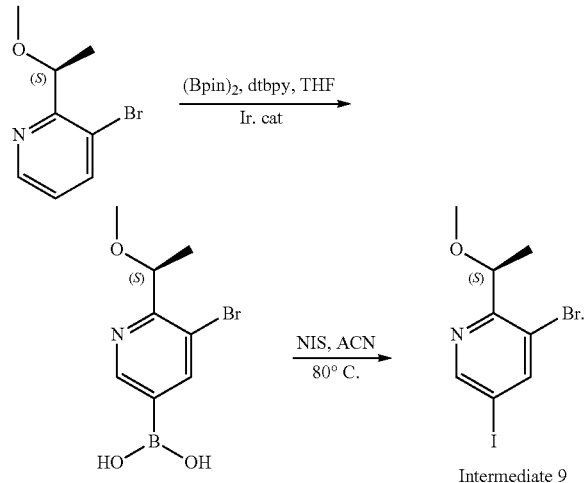

Intermediate 9

Step 1. To a stirred solution of 3-bromo-2-[(1S)-1-methoxyethyl]pyridine (80.00 g, 370.24 mmol, 1.00 equiv) and bis(pinacolato)diboron (141.03 g, 555.3 mmol, 1.50 equiv) in THF (320 mL) was added dtbpy (14.91 g, 55.5 mmol) and chloro(1,5-cyclooctadiene)iridium(I) dimer (7.46 g, 11.1 mmol) under argon atmosphere. The resulting mixture was stirred for 16 h at 75° C. under argon atmosphere. The mixture was concentrated under reduced pressure. The resulting mixture was dissolved in EtOAc (200 mL) and the mixture was adjusted to pH 10 with $Na_2CO_3$ (40 g) and NaOH (10 g) (mass 4:1) in water (600 mL). The aqueous layer was extracted with EtOAc (800 mL). The aqueous phase was acidified to pH=6 with HCl (6 N) to precipitate the desired solid to afford 5-bromo-6-[(1S)-1-methoxyethyl]pyridin-3-ylboronic acid (50 g, 52.0% yield) as a light-yellow solid. LCMS (ESI): m/z [M+H] calc'd for $C_8H_{11}BBrNO_3$ 259.0; found 260.0.

Step 2. To a stirred solution of 5-bromo-6-[(1S)-1-methoxyethyl]pyridin-3-ylboronic acid (23.00 g, 88.5 mmol) in ACN (230 mL) were added NIS (49.78 g, 221.2 mmol) at room temperature under argon atmosphere. The resulting mixture was stirred for overnight at 80° C. under argon atmosphere. The resulting mixture was concentrated under reduced pressure. The resulting mixture was dissolved in DCM (2.1 L) and washed with $Na_2S_2O_3$ (3×500 mL). The organic layer was dried over anhydrous $Na_2SO_4$. After filtration, the filtrate was concentrated under reduced pressure. The residue was purified by silica gel column chromatography to afford (S)-3-bromo-5-iodo-2-(1-methoxyethyl)pyridine (20 g, 66.0% yield). LCMS (ESI): m/z [M+H] calc'd for $C_8H_9BrINO$ 340.9; found 341.7.

Intermediate 10. Synthesis of tert-butyl ((6³S,4S,Z)-11-ethyl-1²-(2-((S)-1-methoxyethyl)-5-(4-methylpiperazin-1-yl)pyridin-3-yl)-10,10-dimethyl-5,7-dioxo-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)carbamate

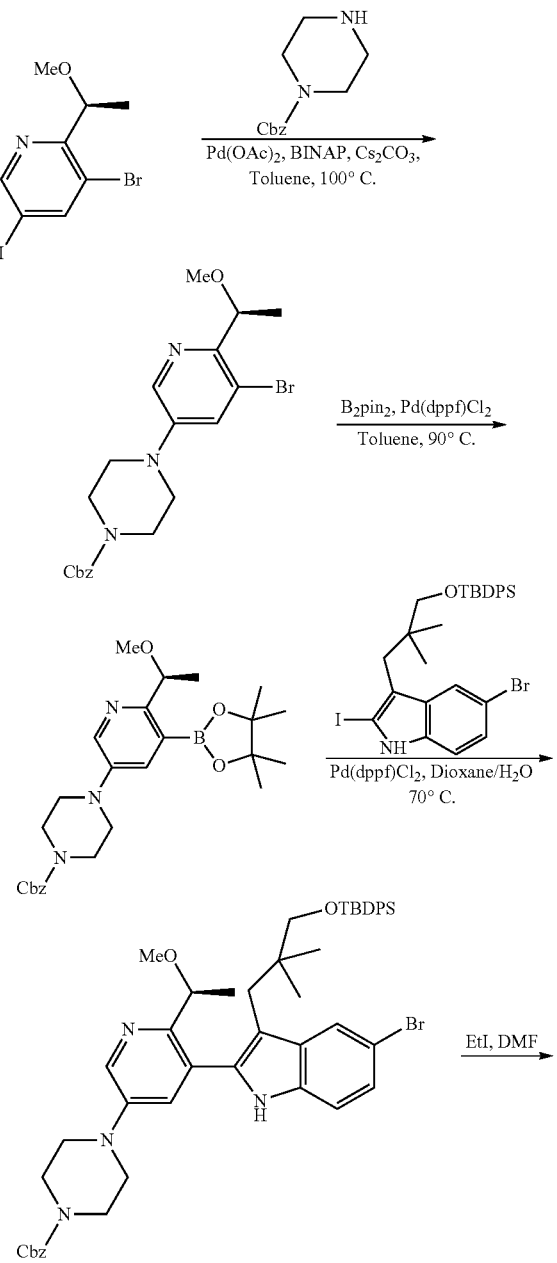

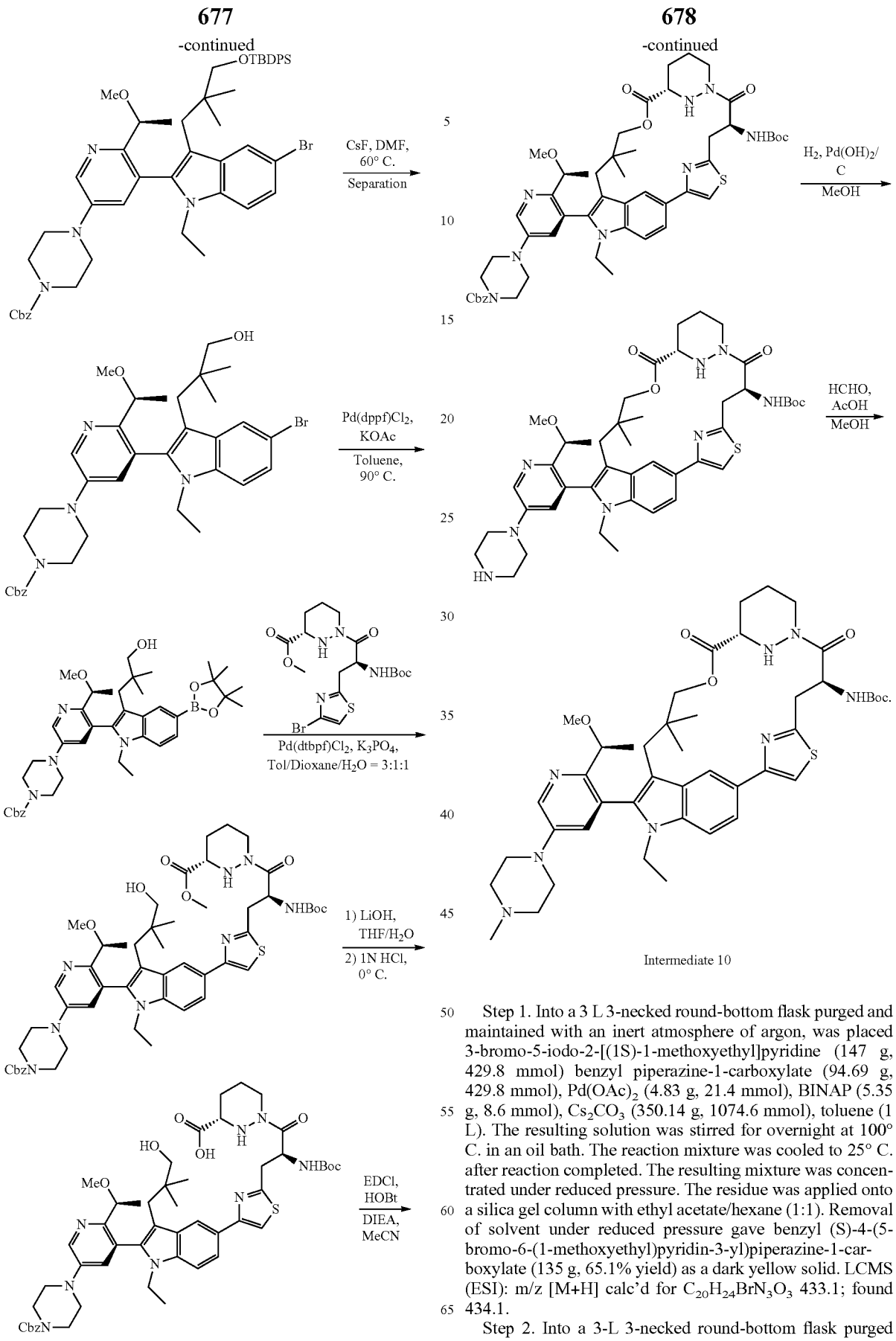

Intermediate 10

Step 1. Into a 3 L 3-necked round-bottom flask purged and maintained with an inert atmosphere of argon, was placed 3-bromo-5-iodo-2-[(1S)-1-methoxyethyl]pyridine (147 g, 429.8 mmol) benzyl piperazine-1-carboxylate (94.69 g, 429.8 mmol), Pd(OAc)$_2$ (4.83 g, 21.4 mmol), BINAP (5.35 g, 8.6 mmol), Cs$_2$CO$_3$ (350.14 g, 1074.6 mmol), toluene (1 L). The resulting solution was stirred for overnight at 100° C. in an oil bath. The reaction mixture was cooled to 25° C. after reaction completed. The resulting mixture was concentrated under reduced pressure. The residue was applied onto a silica gel column with ethyl acetate/hexane (1:1). Removal of solvent under reduced pressure gave benzyl (S)-4-(5-bromo-6-(1-methoxyethyl)pyridin-3-yl)piperazine-1-carboxylate (135 g, 65.1% yield) as a dark yellow solid. LCMS (ESI): m/z [M+H] calc'd for C$_{20}$H$_{24}$BrN$_3$O$_3$ 433.1; found 434.1.

Step 2. Into a 3-L 3-necked round-bottom flask purged and maintained with an inert atmosphere of argon, was placed benzyl 4-[5-bromo-6-[(1S)-1-methoxyethyl]pyridin-3-yl]piperazine-1-carboxylate (135 g, 310.8 mmol), bis(pinacolato)diboron (86.82 g, 341.9 mmol), Pd(dppf)Cl$_2$ (22.74 g, 31.0 mmol), KOAc (76.26 g, 777.5 mmol), Toluene (1 L). The resulting solution was stirred for 2 days at 90° C. in an oil bath. The reaction mixture was cooled to 25° C. The resulting mixture was concentrated under vacuum. The residue was applied onto a neutral alumina column with ethyl acetate/hexane (1:3). Removal of solvent under reduced pressure gave benzyl (S)-4-(6-(1-methoxyethyl)-5-(4,4,5,5-tetramethyl-1,3,2-dioxaborolan-2-yl)pyridin-3-yl)piperazine-1-carboxylate (167 g, crude) as a dark yellow solid. LCMS (ESI): m/z [M+H] calc'd for C$_{26}$H$_{36}$BN$_3$O$_5$ 481.3; found 482.1.

Step 3. Into a 3-L 3-necked round-bottom flask purged and maintained with an inert atmosphere of argon, was placed (S)-4-(6-(1-methoxyethyl)-5-(4,4,5,5-tetramethyl-1,3,2-dioxaborolan-2-yl)pyridin-3-yl)piperazine-1-carboxylate (167 g, 346.9 mmol), 5-bromo-3-[3-[(tert-butyldiphenylsilyl)oxy]-2,2-dimethylpropyl]-2-iodo-1H-indole (224.27 g, 346.9 mmol), Pd(dppf)Cl$_2$ (25.38 g, 34.6 mmol), dioxane (600 mL), H$_2$O (200 mL), K$_3$PO$_4$ (184.09 g, 867.2 mmol), Toluene (200 mL). The resulting solution was stirred for overnight at 70° C. in an oil bath. The reaction mixture was cooled to 25° C. after reaction completed. The resulting mixture was concentrated under vacuum. The residue was applied onto a silica gel column with ethyl acetate/hexane (1:1). Removal of solvent under reduced pressure gave benzyl (S)-4-(5-(5-bromo-3-(3-((tert-butyldiphenylsilyl)oxy)-2,2-dimethylpropyl)-1H-indol-2-yl)-6-(1-methoxyethyl)pyridin-3-yl)piperazine-1-carboxylate (146 g, 48.1% yield) as a yellow solid. LCMS (ESI): m/z [M+H] calc'd for C$_{49}$H$_{57}$BrN$_4$O$_4$Si 872.3; found 873.3.

Step 4. To a stirred mixture of benzyl (S)-4-(5-(5-bromo-3-(3-((tert-butyldiphenylsilyl)oxy)-2,2-dimethylpropyl)-1H-indol-2-yl)-6-(1-methoxyethyl)pyridin-3-yl)piperazine-1-carboxylate (146 g, 167.0 mmol) and Cs$_2$CO$_3$ (163.28 g, 501.1 mmol) in DMF (1200 mL) was added C$_2$H$_5$I (52.11 g, 334.0 mmol) in portions at 0° C. under N2 atmosphere. The final reaction mixture was stirred at 25° C. for 12 h. Desired product could be detected by LCMS. The resulting mixture was diluted with EA (1 L) and washed with brine (3×1,5 L). The organic layers were dried over anhydrous Na$_2$SO$_4$. After filtration, the filtrate was concentrated under reduced pressure to give benzyl (S)-4-(5-(5-bromo-3-(3-((tert-butyldiphenylsilyl)oxy)-2,2-dimethylpropyl)-1-ethyl-1H-indol-2-yl)-6-(1-methoxyethyl)pyridin-3-yl)piperazine-1-carboxylate (143 g, crude) as a yellow solid that was used directly for next step without further purification. LCMS (ESI): m/z [M+H] calc'd for C$_{51}$H$_{61}$BrN$_4$O$_4$Si 900.4; found 901.4.

Step 5. To a stirred mixture of benzyl benzyl (S)-4-(5-(5-bromo-3-(3-((tert-butyldiphenylsilyl)oxy)-2,2-dimethylpropyl)-1-ethyl-1H-indol-2-yl)-6-(1-methoxyethyl)pyridin-3-yl)piperazine-1-carboxylate (143 g, 158.5 mmol) in DMF (1250 mL) was added CsF (72.24 g, 475.5 mmol). Then the reaction mixture was stirred at 60° C. for 2 days under N$_2$ atmosphere. Desired product could be detected by LCMS. The resulting mixture was diluted with EA (1 L) and washed with brine (3×1 L). Then the organic phase was concentrated under reduced pressure. The residue was purified by silica gel column chromatography, eluted with PE/EA (1/3) to afford two atropisomers of benzyl (S)-4-(5-(5-bromo-1-ethyl-3-(3-hydroxy-2,2-dimethylpropyl)-1H-indol-2-yl)-6-(1-methoxyethyl)pyridin-3-yl)piperazine-1-carboxylate A (38 g, 36% yield, RT=1.677 min in 3 min LCMS (0.1% FA)) and B (34 g, 34% yield, RT=1.578 min in 3 min LCMS (0.1% FA)) both as yellow solid. LCMS (ESI): m/z [M+H] calc'd for C$_{35}$H$_{43}$BrN$_4$O$_4$ 663.2; found 662.2.

Step 6. Into a 500-mL 3-necked round-bottom flask purged and maintained with an inert atmosphere of nitrogen, was placed benzyl (S)-4-(5-(5-bromo-1-ethyl-3-(3-hydroxy-2,2-dimethylpropyl)-1H-indol-2-yl)-6-(1-methoxyethyl)pyridin-3-yl)piperazine-1-carboxylate A (14 g, 21.1 mmol), bis(pinacolato)diboron (5.89 g, 23.21 mmol), Pd(dppf)Cl$_2$ (1.54 g, 2.1 mmol), KOAc (5.18 g, 52.7 mmol), Toluene (150 mL). The resulting solution was stirred for 5 h at 90° C. in an oil bath. The reaction mixture was cooled to 25° C. The resulting mixture was concentrated under vacuum. The residue was purified by silica gel column chromatography, eluted with PE/EA (1/3) to give benzyl (S)-4-(5-(1-ethyl-3-(3-hydroxy-2,2-dimethylpropyl)-5-(4,4,5,5-tetramethyl-1,3,2-dioxaborolan-2-yl)-1H-indol-2-yl)-6-(1-methoxyethyl)pyridin-3-yl)piperazine-1-carboxylate (12 g, 76.0% yield) as a yellow solid. LCMS (ESI): m/z [M+H] calc'd for C$_{41}$H$_{55}$BN$_4$O$_6$ 710.4; found 711.3.

Step 7. Into a 250-mL round-bottom flask purged and maintained with an inert atmosphere of argon, was placed benzyl (S)-4-(5-(1-ethyl-3-(3-hydroxy-2,2-dimethylpropyl)-5-(4,4,5,5-tetramethyl-1,3,2-dioxaborolan-2-yl)-1H-indol-2-yl)-6-(1-methoxyethyl)pyridin-3-yl)piperazine-1-carboxylate (10.8 g, 15.2 mmol), methyl (3S)-1-[(2S)-3-(4-bromo-1,3-thiazol-2-yl)-2-[(tert-butoxycarbonyl)amino]propanoyl]-1,2-diazinane-3-carboxylate (7.98 g, 16.7 mmol), Pd(dtbpf)Cl$_2$ (0.99 g, 1.52 mmol), K$_3$PO$_4$ (8.06 g, 37.9 mmol), Toluene (60 mL), dioxane (20 mL), H$_2$O (20 mL). The resulting solution was stirred for 3 h at 70° C. in an oil bath. The reaction mixture was cooled to 25° C. The resulting solution was extracted with EtOAc (2×50 mL) and concentrated under reduced pressure. The residue was applied onto a silica gel column with ethyl acetate/hexane (10:1). Removal of solvent to give methyl (S)-1-((S)-3-(4-(2-(5-(4-((benzyloxy)carbonyl)piperazin-1-yl)-2-((S)-1-methoxyethyl)pyridin-3-yl)-1-ethyl-3-(3-hydroxy-2,2-dimethylpropyl)-1H-indol-5-yl)thiazol-2-yl)-2-((tert-butoxycarbonyl)amino)propanoyl)hexahydropyridazine-3-carboxylate (8 g, 50.9% yield) as a yellow solid. LCMS (ESI): m/z [M+H] calc'd for C$_{52}$H$_{68}$N$_8$O$_9$S 980.5; found 980.9.

Step 8. To a stirred mixture of methyl (S)-1-((S)-3-(4-(2-(5-(4-((benzyloxy)carbonyl)piperazin-1-yl)-2-((S)-1-methoxyethyl)pyridin-3-yl)-1-ethyl-3-(3-hydroxy-2,2-dimethylpropyl)-1H-indol-5-yl)thiazol-2-yl)-2-((tert-butoxycarbonyl)amino)propanoyl)hexahydropyridazine-3-carboxylate (12 g, 12.23 mmol) in THF (100 mL)/H$_2$O (100 mL) was added LiOH (2.45 g, 61.1 mmol) under N2 atmosphere and the resulting mixture was stirred for 2 h at 25° C. Desired product could be detected by LCMS. THF was concentrated under reduced pressure. The pH of aqueous phase was acidified to 5 with HCL (1N) at 0° C. The aqueous layer was extracted with DCM (3×100 ml). The organic phase was concentrated under reduced pressure to give (S)-1-((S)-3-(4-(2-(5-(4-((benzyloxy)carbonyl)piperazin-1-yl)-2-((S)-1-methoxyethyl)pyridin-3-yl)-1-ethyl-3-(3-hydroxy-2,2-dimethylpropyl)-1H-indol-5-yl)thiazol-2-yl)-2-((tert-butoxycarbonyl)amino)propanoyl)hexahydropyridazine-3-carboxylic acid (10 g, 84.5% yield)

as a light yellow solid. LCMS (ESI): m/z [M+H] calc'd for $C_{51}H_{66}N_8O_9S$ 966.5; found 967.0.

Step 9. Into a 3-L round-bottom flask purged and maintained with an inert atmosphere of nitrogen, was placed (S)-1-((S)-3-(4-(2-(5-(4-((benzyloxy)carbonyl)piperazin-1-yl)-2-((S)-1-methoxyethyl)pyridin-3-yl)-1-ethyl-3-(3-hydroxy-2,2-dimethylpropyl)-1H-indol-5-yl)thiazol-2-yl)-2-((tert-butoxycarbonyl)amino)propanoyl) hexahydropyridazine-3-carboxylic acid (18 g, 18.61 mmol), ACN (1.8 L), DIEA (96.21 g, 744.4 mmol), EDCl (107.03 g, 558.3 mmol), HOBT (25.15 g, 186.1 mmol). The resulting solution was stirred for overnight at 25° C. The resulting mixture was concentrated under reduced pressure after reaction completed. The resulting solution was diluted with DCM (1 L). The resulting mixture was washed with HCl (3×1 L, 1N aqueous). The resulting mixture was washed with water (3×1 L). Then the organic layer was concentrated, the residue was applied onto a silica gel column with ethyl acetate/hexane (1:1). Removal of solvent under reduced pressure gave benzyl 4-(5-(($6^3$S,4S,Z)-4-((tert-butoxycarbonyl)amino)-1$^1$-ethyl-10,10-dimethyl-5,7-dioxo-$6^1,6^2,6^3,6^4,6^5,6^6$-hexahydro-1$^1$H-8-oxa-2(4,2)-thiazola-1(5,3)-indola-6(1,3)-pyridazinacycloundecaphane-1$^2$-yl)-6-((S)-1-methoxyethyl)pyridin-3-yl)piperazine-1-carboxylate (10.4 g, 54.8% yield) as a light yellow solid. LCMS (ESI): m/z [M+H] calc'd for $C_{51}H_{64}N_8O_8S$ 948.5; found 949.3.

Step 10. Into a 250-mL round-bottom flask purged and maintained with an inert atmosphere of nitrogen, was placed benzyl 4-(5-(($6^3$S,4S,Z)-4-((tert-butoxycarbonyl)amino)-1$^1$-ethyl-10,10-dimethyl-5,7-dioxo-$6^1,6^2,6^3,6^4,6^5,6^6$-hexahydro-1$^1$H-8-oxa-2(4,2)-thiazola-1(5,3)-indola-6(1,3)-pyridazinacycloundecaphane-1$^2$-yl)-6-((S)-1-methoxyethyl)pyridin-3-yl)piperazine-1-carboxylate (10.40 g, 10.9 mmol), Pd(OH)$_2$/C (5 g, 46.9 mmol), MeOH (100 mL). The resulting solution was stirred for 3 h at 25° C. under 2 atm H$_2$ atmosphere. The solids were filtered out and the filter cake was washed with MeOH (3×100 mL). Then combined organic phase was concentrated under reduced pressure to give tert-butyl (($6^3$S,4S,Z)-1 f-ethyl-1$^2$-(2-((S)-1-methoxyethyl)-5-(piperazin-1-yl)pyridin-3-yl)-10,10-dimethyl-5,7-dioxo-$6^1,6^2,6^3,6^4,6^5,6^6$-hexahydro-1$^1$H-8-oxa-2(4,2)-thiazola-1(5,3)-indola-6(1,3)-pyridazinacycloundecaphane-4-yl)carbamate (8.5 g, 90.4% yield) as a light yellow solid. LCMS (ESI): m/z [M+H] calc'd for $C_{43}H_{58}N_8O_6S$ 814.4; found 815.3.

Step 11. Into a 1000-mL round-bottom flask purged and maintained with an inert atmosphere of nitrogen, was placed tert-butyl (($6^3$S,4S,Z)-1 f-ethyl-1$^2$-(2-((S)-1-methoxyethyl)-5-(piperazin-1-yl)pyridin-3-yl)-10,10-dimethyl-5,7-dioxo-$6^1,6^2,6^3,6^4,6^5,6^6$-hexahydro-1$^1$H-8-oxa-2(4,2)-thiazola-1(5,3)-indola-6(1,3)-pyridazinacycloundecaphane-4-yl) carbamate (8.5 g, 10.4 mmol), MeOH (100 mL), AcOH (1.88 g, 31.2 mmol) and stirred for 15 mins. Then HCHO (1.88 g, 23.15 mmol, 37% aqueous solution) and NaBH$_3$CN (788 mg, 12.5 mmol) was added at 25° C. The resulting solution was stirred for 3 h at 25° C. The resulting mixture was quenched with 100 mL water and concentrated under reduced pressure to remove MeOH. The resulting solution was diluted with 300 mL of DCM. The resulting mixture was washed with water (3×100 mL). Removal of solvent gave tert-butyl (($6^3$S,4S,Z)-1$^1$-ethyl-1$^2$-(2-((S)-1-methoxyethyl)-5-(4-methylpiperazin-1-yl)pyridin-3-yl)-10,10-dimethyl-5,7-dioxo-$6^1,6^2,6^3,6^4,6^5,6^6$-hexahydro-1$^1$H-8-oxa-2 (4,2)-thiazola-1(5,3)-indola-6(1,3)-pyridazinacycloundecaphane-4-yl)carbamate (8.2 g, 90.1% yield) as a yellow solid. LCMS (ESI): m/z [M+H] calc'd for $C_{44}H_{60}N_8O_6S$ 828.4; found 829.3.

Example A11. Synthesis of methyl (3S)-3-{[(1S)-1-{[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1$^{2,6}$0.1$^{10,14}$0.0$^{23,27}$]nonacosa-1(26),2,4,6(29),20,23(27),24-heptaen-8-yl]carbamoyl}-2-methylpropyl] (methyl)carbamoyl}pyrrolidine-1-carbyoxylate

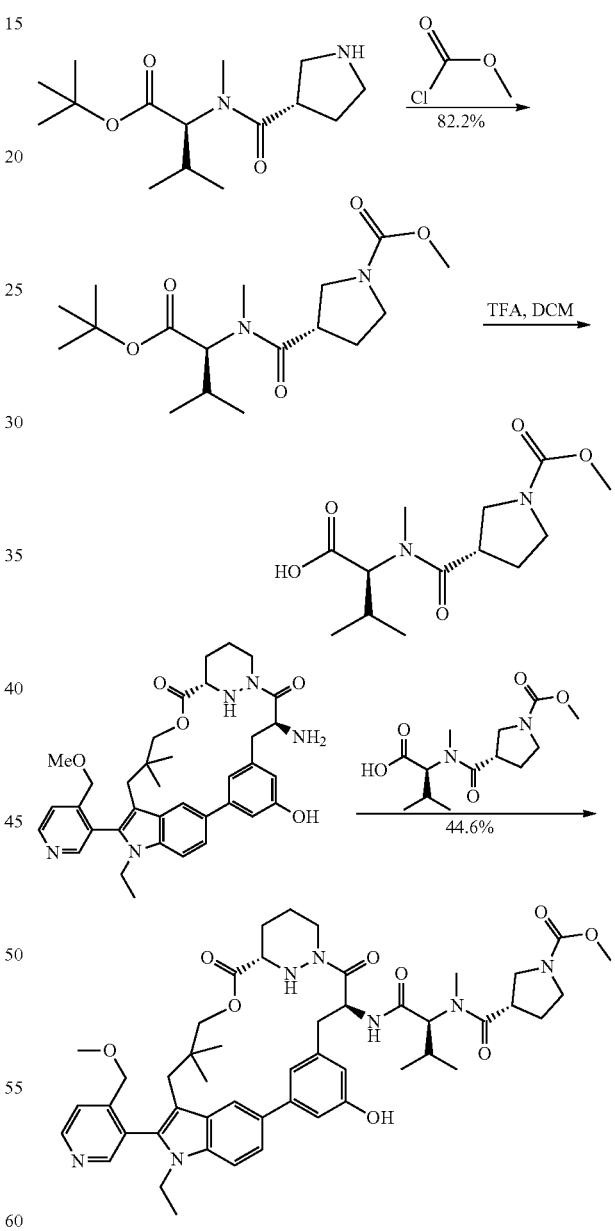

Step 1. To a mixture of tert-butyl N-methyl-N—((S)-pyrrolidine-3-carbonyl)-L-valinate (500 mg, 1.8 mmol) and TEA (356 mg, 3.5 mmol) in DCM (10 mL) at 0° C. was added methyl carbonochloridate (199 mg, 2.1 mmol) dropwise. The mixture was allowed to warm to rt and was stirred for 12 then concentrated under reduced pressure and the residue was purified by silica gel column chromatography to give methyl (S)-3-(((S)-1-(tert-butoxy)-3-methyl-1-oxobutan-2-yl)(methyl)carbamoyl)pyrrolidine-1-carboxylate (550 mg, 82%) as an oil. LCMS (ESI): m/z [M+H] calc'd for $C_{17}H_{30}N_2O_5$ 342.2; found 343.2.

Step 2. A mixture of methyl (S)-3-(((S)-1-(tert-butoxy)-3-methyl-1-oxobutan-2-yl)(methyl)carbamoyl)pyrrolidine-1-carboxylate (500 mg, 1.46 mmol), DCM (8 mL) and TFA (2 mL) was stirred at rt for 3 h. The mixture was concentrated under reduced pressure with azeotropic removal of $H_2O$ using toluene (5 mL) to give N—((S)-1-(methoxycarbonyl)pyrrolidine-3-carbonyl)-N-methyl-L-valine (400 mg) as an oil. LCMS (ESI): m/z [M+H] calc'd for $C_{13}H_{22}N_2O_5$ 286.2; found 287.2.

Step 3. To a mixture of $(6^3S,4S)$-4-amino-$1^1$-ethyl-$2^5$-hydroxy-$1^2$-(4-(methoxymethyl)pyridin-3-yl)-10,10-dimethyl-$6^1,6^2,6^3,6^4,6^5,6^6$-hexahydro-$1^1H$-8-oxa-1(5,3)-indola-6(1,3)-pyridazina-2(1,3)-benzenacycloundecaphane-5,7-dione (80 mg, 0.13 mmol), N—((S)-1-(methoxycarbonyl)pyrrolidine-3-carbonyl)-N-methyl-L-valine (55 mg, 0.19 mmol) and DIPEA (165 mg, 1.3 mmol) in DMF (2 mL) at 0° C. was added COMU (77 mg, 0.18 mmol). The mixture was stirred at 0° C. for 2 h, then concentrated under reduced pressure and the residue was purified by prep-HPLC to give methyl (3S)-3-{[(1S)-1-{[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1$^{2,6}$.0$^{10,14}$0$^{23,27}$]nonacosa-1(26),2,4,6(29),20,23(27),24-heptaen-8-yl]carbamoyl}-2-methylpropyl](methyl)carbamoyl}pyrrolidine-1-carboxylate (51 mg, 45% yield) as a solid. LCMS (ESI): m/z [M+H] calc'd for $C_{49}H_{63}N_7O_9$ 893.5; found 894.7; $^1$H NMR (400 MHz, DMSO-$d_6$) δ 9.33 (s, 1H), 8.88-8.66 (m, 2H), 8.62 (s, 1H), 8.17-8.06 (m, 1H), 7.92 (d, J=8.7 Hz, 1H), 7.79-7.68 (m, 1H), 7.65-7.49 (m, 2H), 7.21-7.11 (m, 1H), 7.01 (d, J=11.8 Hz, 1H), 6.71-6.40 (m, 1H), 5.54-5.30 (m, 1H), 5.28-4.99 (m, 1H), 4.87-4.56 (m, 1H), 4.46-4.21 (m, 3H), 4.11-3.89 (m, 3H), 3.70 (s, 1H), 3.65-3.59 (m, 4H), 3.35 (s, 2H), 3.24 (s, 2H), 3.18-3.07 (s, 1H), 3.00-2.58 (m, 8H), 2.22-2.01 (m, 4H), 1.81 (d, J=11.4 Hz, 2H), 1.72-1.42 (m, 2H), 1.15-0.64 (m, 13H), 0.43 (d, J=16.4 Hz, 3H).

Example A17. Synthesis of (2S)—N-[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1$^{2,6}$0.1$^{10,14}$0.0$^{23,27}$]nonacosa-1(26),2,4,6(29),20,23(27),24-heptaen-8-yl]-2-{1-[(3S)-1-formylpyrrolidin-3-yl]-N-methylformamido}-3-methylbutanamide

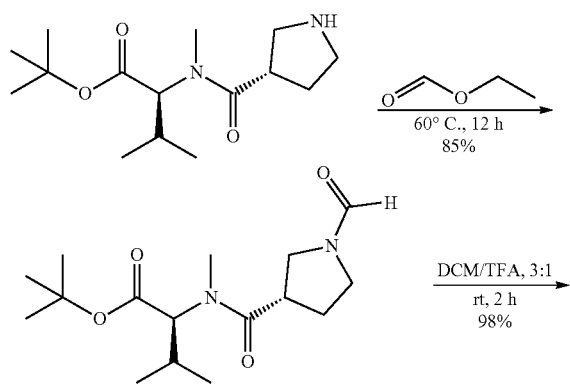

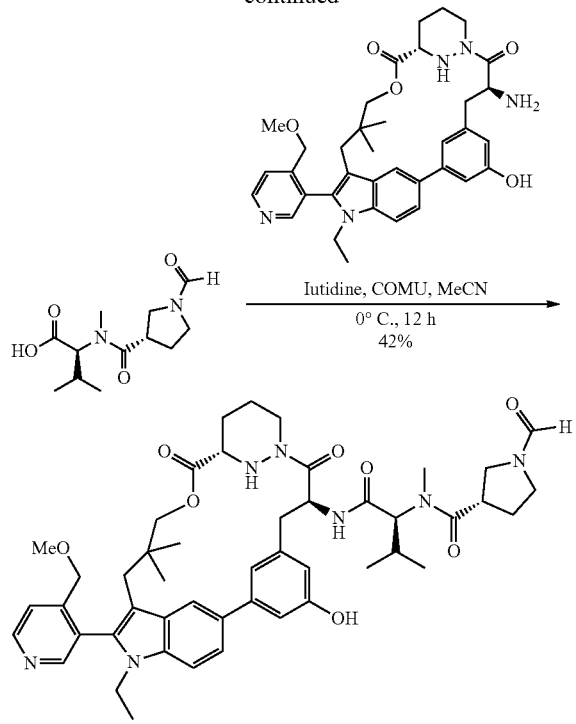

Step 1. A mixture of tert-butyl (2S)-3-methyl-2-[N-methyl-1-(3S)-pyrrolidin-3-ylformamido]butanoate (290 mg, 1.0 mmol) and ethyl formate (755 mg, 10.2 mmol) was heated to 60° C. and stirred for 12 h. The mixture was concentrated under reduced pressure to give tert-butyl (2S)-2-[1-[(3S)-1-formylpyrrolidin-3-yl]-N-methylformamido]-3-methylbutanoate (300 mg, 85% yield) as a solid. LCMS (ESI): m/z [M+H-tBu] calc'd for $C_{12}H_{20}N_2O_4$ 256.1; found 257.2.

Step 2. To a mixture of tert-butyl (2S)-2-[1-[(3S)-1-formylpyrrolidin-3-yl]-N-methylformamido]-3-methylbutanoate (290 mg, 0.93 mmol) in DCM (3 mL) at rt was added TFA (1 mL). The mixture was stirred at rt for 2 h, then concentrated under reduced pressure to give (2S)-2-[1-[(3S)-1-formylpyrrolidin-3-yl]-N-methylformamido]-3-methylbutanoic acid (260 mg, 98%) as an oil. LCMS (ESI): m/z [M+H] calc'd for $C_{12}H_{20}N_2O_4$ 256.1; found 257.2.

Step 3. To a mixture of $(6^3S,4S)$-4-amino-$1^1$-ethyl-$2^5$-hydroxy-$1^2$-(4-(methoxymethyl)pyridin-3-yl)-10,10-dimethyl-$6^1,6^2,6^3,6^4,6^5,6^6$-hexahydro-$1^1H$-8-oxa-1(5,3)-indola-6(1,3)-pyridazina-2(1,3)-benzenacycloundecaphane-5,7-dione (60 mg, 0.1 mmol), 2,6-dimethylpyridine (15.4 mg, 0.14 mmol) and (2S)-2-[1-[(3S)-1-formylpyrrolidin-3-yl]-N-methylformamido]-3-methylbutanoic acid (37 mg, 0.14 mmol) in MeCN (2 mL) at 0° C. under an atmosphere of N2 was added COMU (62 mg, 0.14 mmol). The mixture was stirred at 0° C. for 12 h, then concentrated under reduced pressure and the residue was purified by prep-HPLC to give (2S)—N-[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1$^{2,6}$0.1$^{10,14}$0.0$^{23,27}$]nonacosa-1(26),2,4,6(29),20,23(27),24-heptaen-8-yl]-2-{1-[(3S)-1-formylpyrrolidin-3-yl]-N-methylformamido}-3-methylbutanamide (35 mg, 42%) as a solid. LCMS (ESI): m/z [M+H] calc'd for $C_{48}H_{61}N_7O_8$ 863.5; found 864.5; $^1$H NMR (400 MHz, DMSO-06) δ 8.79-8.61 (m, 2H), 8.51 (d, J=7.8 Hz, 3H), 8.31-8.09 (m, 1H), 7.93 (s, 1H), 7.68-7.48 (m, 3H), 7.25-6.97 (m, 2H), 6.71-6.43 (m, 1H), 5.40 (d, J=24.8 Hz, 1H), 5.22 (s, 1H), 4.86-4.34 (m, 1H), 4.23 (t, J=13.8 Hz, 3H), 4.12-3.84 (m, 3H), 3.83-3.54 (m, 4H), 3.22 (d, J=1.7 Hz, 2H), 3.09 (d, J=14.3 Hz, 1H), 3.01-2.92 (m, 1H), 2.99-2.93 (m, 2H), 2.92-2.65 (m, 5H), 2.07 (d, J=12.2 Hz, 4H), 1.80 (s, 1H), 1.74-1.48 (m, 2H), 1.08 (t, J=7.1 Hz, 2H), 1.03-0.54 (m, 12H), 0.43 (d, J=16.2 Hz, 3H).
Example A6. Synthesis of (2S)—N-[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1$^{2,6}$0.1$^{10,14}$0.0$^{23,27}$]nonacosa-1(26),2,4,6(29),20,23(27),24-heptaen-8-yl]-2-{1-[(3S)-1-{2-[(3R)-3-hydroxypyrrolidin-1-yl]acetyl}pyrrolidin-3-yl]-N-methylformamido}-3-methylbutanamide
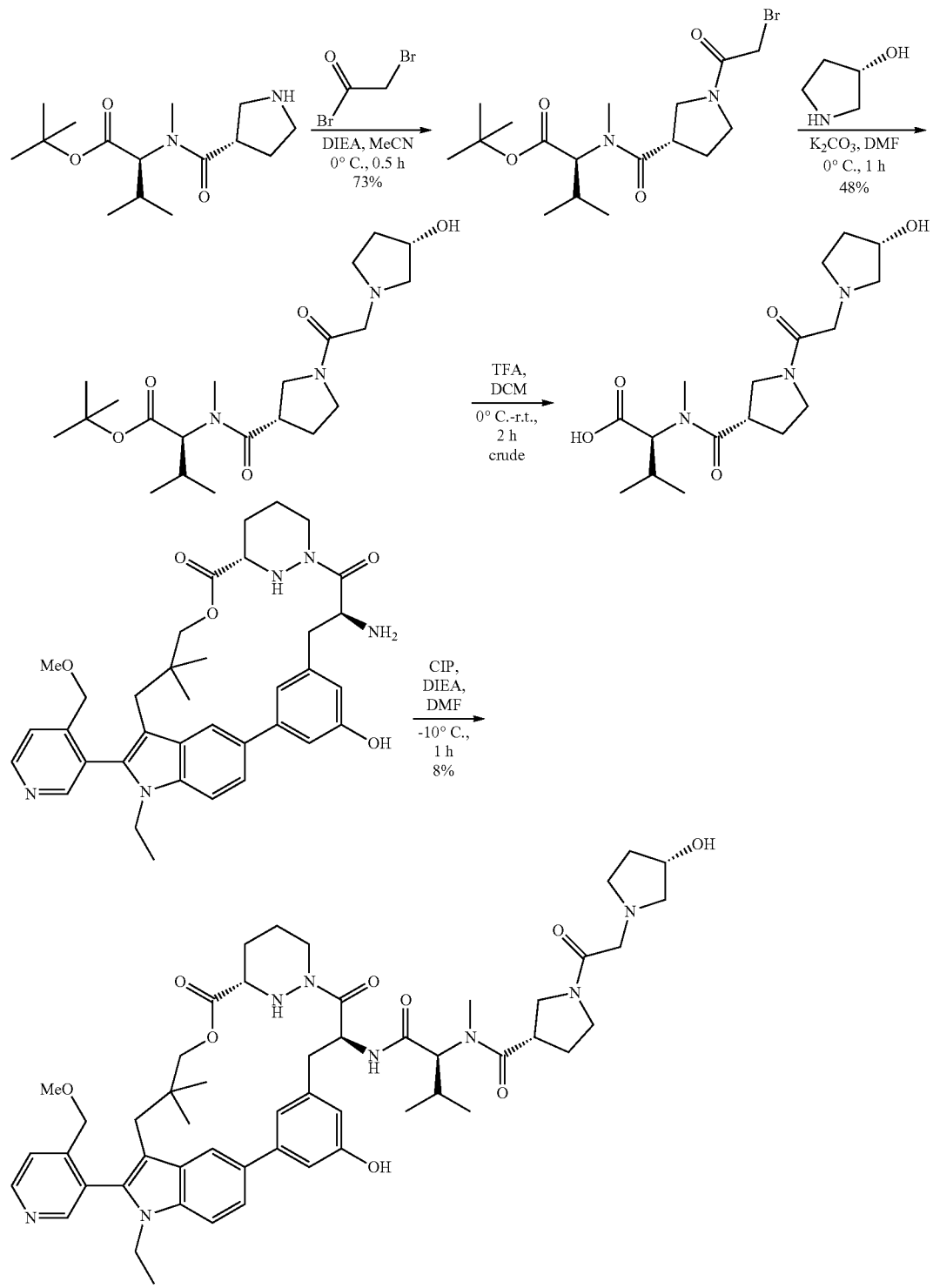

Step 1. A mixture of tert-butyl (2S)-3-methyl-2-[N-methyl-1-(3S)-pyrrolidin-3-ylformamido]butanoate (300 mg, 1.1 mmol) and DIPEA (409 mg, 3.2 mmol) in MeCN (4 mL) at 0° C. was added bromoacetyl bromide (256 mg, 1.3 mmol) dropwise. The mixture was stirred at 0° C. for 30 min, then concentrated under reduced pressure and the residue was purified by $C_{18}$-silica gel column chromatography to give tert-butyl (2S)-2-[1-[(3S)-1-(2-bromoacetyl)pyrrolidin-3-yl]-N-methylformamido]-3-methylbutanoate (350 mg, 73% yield) as an oil. LCMS (ESI): m/z [M+H] calc'd for $C_{17}H_{29}BrN_2O_4$ 404.1; found 405.2 and 407.2.

Step 2. To a mixture of tert-butyl (2S)-2-[1-[(3S)-1-(2-bromoacetyl)pyrrolidin-3-yl]-N-methylformamido]-3-methylbutanoate (110 mg, 0.27 mmol) and $K_2CO_3$ (75 mg, 0.54 mmol) in DMF (2 mL) at 0° C. was added (3S)-pyrrolidin-3-ol (36 mg, 0.41 mmol) dropwise. The mixture was stirred at 0° C. for 1 h, then concentrated under reduced pressure and the residue was purified by prep-HPLC to give tert-butyl (2S)-2-[1-[(3S)-1-[2-[(3S)-3-hydroxypyrrolidin-1-yl]acetyl]pyrrolidin-3-yl]-N-methylformamido]-3-methylbutanoate (60 mg, 48% yield) as an oil. LCMS (ESI): m/z [M+H] calc'd for $C_{21}H_{37}N_3O_5$ 411.3; found 412.5.

Step 3. To a mixture of tert-butyl (2S)-2-[1-[(3S)-1-[2-[(3S)-3-hydroxypyrrolidin-1-yl]acetyl]pyrrolidin-3-yl]-N-methylformamido]-3-methylbutanoate (60 mg, 0.15 mmol) in DCM (0.50 mL) at 0° C. was added TFA (0.50 mL, 6.7 mmol) dropwise. The mixture was warmed to rt and stirred for 2 h, then concentrated under reduced pressure with toluene (×3) to give (2S)-2-[1-[(3S)-1-[2-[(3S)-3-hydroxypyrrolidin-1-yl]acetyl]pyrrolidin-3-yl]-N-methylformamido]-3-methylbutanoic acid (70 mg, crude) as an oil. LCMS (ESI): m/z [M+H] calc'd for $C_{17}H_{29}N_3O_5$ 355.2; found 356.4.

Step 4. To a mixture of $(6^3S,4S)$-4-amino-$1^1$-ethyl-$2^5$-hydroxy-$1^2$-(4-(methoxymethyl)pyridin-3-yl)-10,10-dimethyl-$6^1,6^2,6^3,6^4,6^5,6^6$-hexahydro-$1^1$H-8-oxa-1(5,3)-indola-6(1,3)-pyridazina-2(1,3)-benzenacycloundecaphane-5,7-dione (60 mg, 0.1 mmol) and DIPEA (124 mg, 1.0 mmol) in DMF (1 mL) at −10° C. was added (2S)-2-[1-[(3S)-1-[2-[(3S)-3-hydroxypyrrolidin-1-yl]acetyl]pyrrolidin-3-yl]-N-methylformamido]-3-methylbutanoic acid (51 mg, 0.14 mmol) and CIP (40 mg, 0.14 mmol) in portions. The mixture was stirred at −10° C. for 1 h, then diluted with $H_2O$ (30 mL) and extracted with EtOAc (3×10 mL). The combined organic layers were washed with brine (1×10 mL), dried over anhydrous $Na_2SO_4$ and filtered. The filtrate was concentrated under reduced pressure and the residue was purified by prep-HPLC to give (2S)—N-[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1$^{2,6}$0.1$^{10,14}$0.0$^{23,27}$]nonacosa-1(26),2,4,6(29),20,23(27),24-heptaen-8-yl]-2-{1-[(3S)-1-{2-[(3R)-3-hydroxypyrrolidin-1-yl]acetyl}pyrrolidin-3-yl]-N-methylformamido}-3-methylbutanamide (8.6 mg, 8% yield) as a solid. LCMS (ESI): m/z [M+H] calc'd for $C_{53}H_{79}N_8O_9$ 962.5; found 963.5; $^1$H NMR (400 MHz, $CD_3OD$) δ 8.70 (td, J=5.1, 1.6 Hz, 1H), 8.66-8.48 (m, 1H), 8.07-7.90 (m, 1H), 7.76 (dd, J=9.9, 5.2 Hz, 1H), 7.61 (tt, J=9.9, 2.0 Hz, 1H), 7.52 (dt, J=8.7, 3.5 Hz, 1H), 7.11-6.97 (m, 1H), 6.62-6.47 (m, 1H), 5.68-5.48 (m, 1H), 4.79 (dt, J=11.2, 9.1 Hz, 1H), 4.53-4.18 (m, 4H), 4.16-3.86 (m, 3H), 3.85-3.56 (m, 7H), 3.55-3.46 (m, 1H), 3.42 (d, J=4.6 Hz, 4H), 3.26-3.01 (m, 3H), 3.01-2.60 (m, 9H), 2.42-2.01 (m, 6H), 1.92 (s, 1H), 1.75 (s, 2H), 1.62 (q, J=12.7 Hz, 1H), 1.26-0.80 (m, 13H), 0.61-0.40 (m, 3H).

Example A24. Synthesis of (2S)—N-[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1$^{2,6}$0.1$^{10,14}$0.0$^{23,27}$]nonacosa-1(26),2,4,6(29),20,23(27),24-heptaen-8-yl]-2-{1-[(3S)-1-methanesulfonylpyrrolidin-3-yl]-N-methylformamido}-3-methylbutanamide

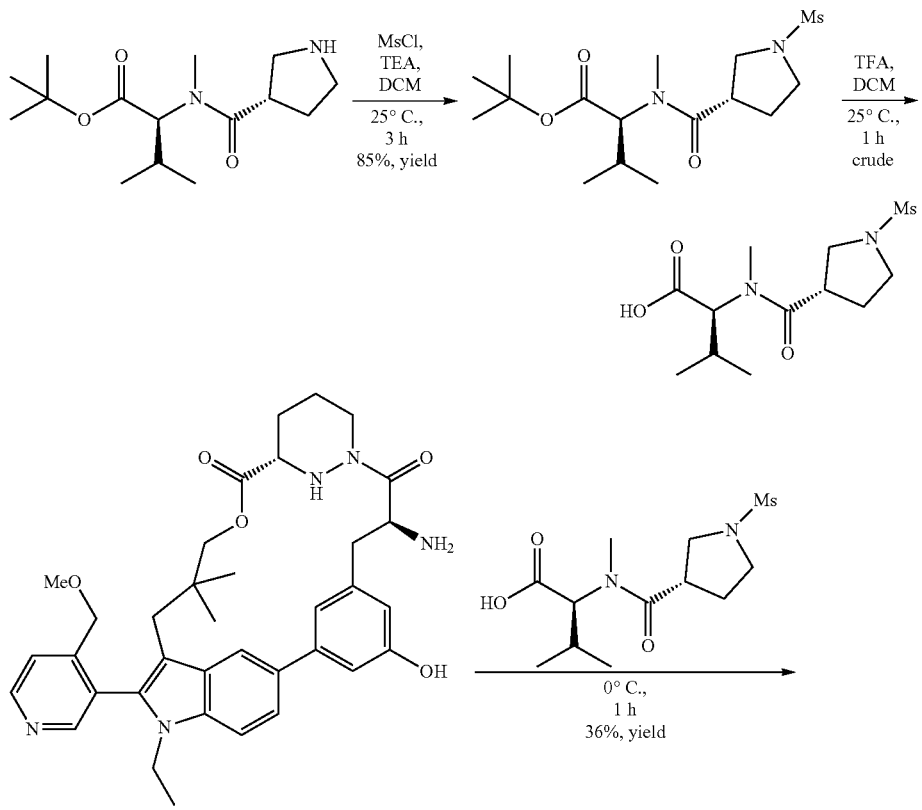

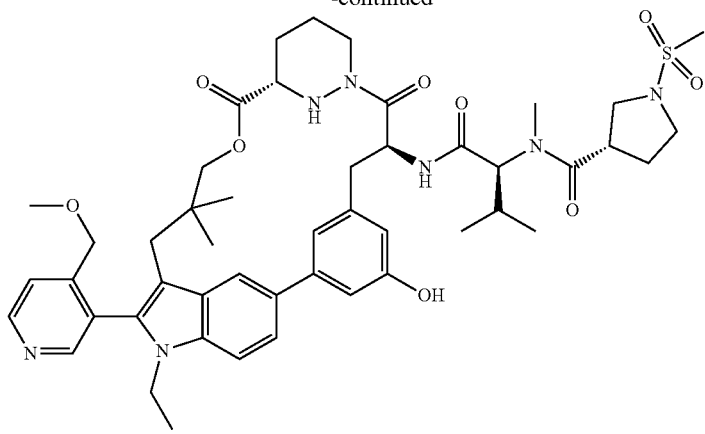

Step 1. To a mixture of tert-butyl N-methyl-N—((S)-pyrrolidine-3-carbonyl)-L-valinate (500 mg, 1.8 mmol) in DCM (8 mL) at 0° C. under an atmosphere of $N_2$ was added TEA (356 mg, 3.5 mmol), followed by MsCl (242 mg, 2.1 mmol). The mixture was warmed to rt and was stirred for 3 h, then washed with brine (2×10 mL). The combined organic layers were dried over anhydrous $Na_2SO_4$, filtered, and the filtrate concentrated under reduced pressure and the residue was by purified by silica gel column chromatography to give tert-butyl N-methyl-N—((S)-1-(methylsulfonyl)pyrrolidine-3-carbonyl)-L-valinate (540 mg, 85%) as an oil. LCMS (ESI): m/z [M+H] calc'd for $C_{16}H_{30}N_2O_5S$ 362.2; found 363.1.

Step 2. A mixture of tert-butyl N-methyl-N—((S)-1-(methylsulfonyl)pyrrolidine-3-carbonyl)-L-valinate (570 mg, 1.6 mmol), DCM (8 mL) and TFA (2 mL) at rt under an atmosphere of $N_2$ was stirred for 1 h. The mixture was concentrated under reduced pressure with toluene (5 mL) to give N-methyl-N—((S)-1-(methylsulfonyl)pyrrolidine-3-carbonyl)-L-valine (500 mg) as an oil. LCMS (ESI): m/z [M+H] calc'd for $C_{12}H_{22}N_2O_5S$ 305.1; found 306.2.

Step 3. To a mixture of $(6^3S,4S)$-4-amino-$1^1$-ethyl-$2^5$-hydroxy-$1^2$-(4-(methoxymethyl)pyridin-3-yl)-10,10-dimethyl-$6^1,6^2,6^3,6^4,6^5,6^6$-hexahydro-$1^1$H-8-oxa-1(5,3)-indola-6(1,3)-pyridazina-2(1,3)-benzenacycloundecaphane-5,7-dione (80 mg, 0.13 mmol) in DMF (2 mL) at 0° C. under an atmosphere of $N_2$ was added DIPEA (165 mg, 1.3 mmol), N-methyl-N—((S)-1-(methylsulfonyl)pyrrolidine-3-carbonyl)-L-valine (59 mg, 0.19 mmol) and COMU (71 mg, 0.17 mmol). The mixture was stirred at 0° C. for 1 h, then concentrated under reduced pressure and the residue was purified by prep-HPLC to give (2S)—N-[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1$^{2,6}$.0$^{10,14}$.0$^{23,27}$]nonacosa-1(26),2,4,6(29),20,23(27),24-heptaen-8-yl]-2-{1-[(3S)-1-methanesulfonylpyrrolidin-3-yl]-N-methylformamido}-3-methylbutanamide (42 mg, 36% yield) as a solid. LCMS (ESI): m/z [M+H] calc'd for $C_{48}H_{63}N7O_9S$ 913.4; found 914.6; $^1$H NMR (400 MHz, DMSO-$d_6$) δ 9.35-9.33 (m, 1H), 8.74-8.62 (m, 2H), 8.52 (s, 1H), 8.19-8.11 (m, 1H), 7.92 (s, 1H), 7.64-7.60 (m, 2H), 7.53 (t, J=9.0 Hz, 1H), 7.22-7.10 (m, 1H), 7.02 (s, 1H), 6.58-6.48 (m, 1H), 5.37-5.24 (m, 1H), 5.19-5.04 (m, 1H), 4.30-4.18 (m, 3H), 4.07-3.91 (m, 3H), 3.75-3.49 (m, 6H), 3.22 (d, J=1.5 Hz, 2H), 2.97-2.91 (m, 4H), 2.92-2.65 (m, 7H), 2.27 (s, 1H), 2.06 (d, J=14.4 Hz, 3H), 1.85 (d, J=35.3 Hz, 2H), 1.70-1.50 (m, 2H), 1.09-0.88 (m, 8H), 0.85-0.72 (m, 5H), 0.43 (d, J=17.8 Hz, 3H).

Example A37. Synthesis of (2S)—N-[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1$^{2,6}$.0$^{10,14}$.0$^{23,27}$] nonacosa-1(26),2,4,6(29),20,23(27),24-heptaen-8-yl]-2-{1-[(3S)-1-[(3-hydroxyazetidin-1-yl)sulfonyl]pyrrolidin-3-yl]-N-methylformamido}-3-methylbutanamide

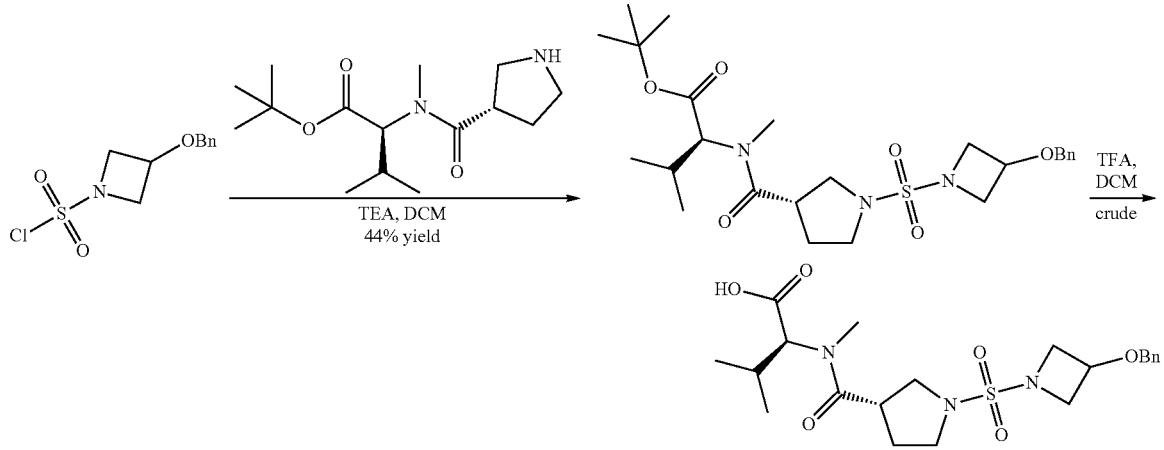

-continued

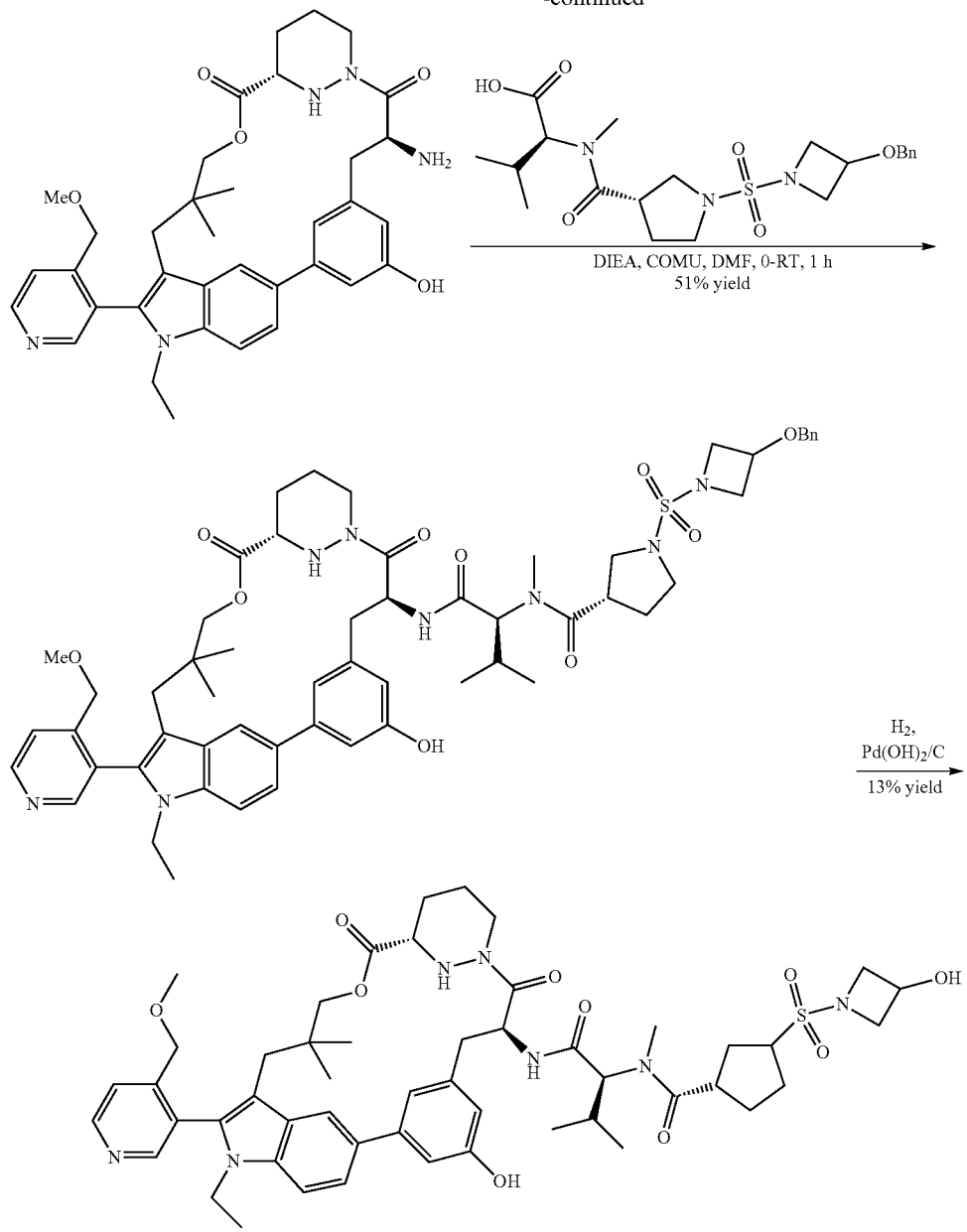

Step 1. To a mixture of tert-butyl N-methyl-N—((S)-pyrrolidine-3-carbonyl)-L-valinate (500 mg, 1.8 mmol) in DCM (20 mL) ar rt was added TEA (356 mg, 3.5 mmol) and 3-(benzyloxy)azetidine-1-sulfonyl chloride (460 mg, 1.8 mmol). The mixture was stirred at rt overnight, then concentrated under reduced pressure and the residue was purified by prep-HPLC to give tert-butyl N—((S)-1-((3-(benzyloxy)azetidin-1-yl)sulfonyl)pyrrolidine-3-carbonyl)-N-methyl-L-valinate (390 mg, 44% yield) of as an oil. LCMS (ESI): m/z [M+H] calc'd for $C_{25}H_{39}N3O_6S$ 509.3; found 510.5.

Step 2. A mixture of tert-butyl N—((S)-1-((3-(benzyloxy)azetidin-1-yl)sulfonyl)pyrrolidine-3-carbonyl)-N-methyl-L-valinate (390 mg, 0.77 mmol), DCM (4 mL) and TFA (1 mL) at rt under an atmosphere of N2 was stirred at rt for 2 h. The mixture was concentrated under reduced pressure with toluene (10 mL×2) to give N—((S)-1-((3-(benzyloxy)azetidin-1-yl)sulfonyl)pyrrolidine-3-carbonyl)-N-methyl-L-valine (370 mg, crude) as a solid. LCMS (ESI): m/z [M+H] calc'd for $C_{21}H_{31}N_3O_6S$ 453.2; found 454.5.

Step 3. To a mixture of $(6^3S,4S)$-4-amino-$1^1$-ethyl-$2^5$-hydroxy-$1^2$-(4-(methoxymethyl)pyridin-3-yl)-10,10-dimethyl-$6^1,6^2,6^3,6^4,6^5,6^6$-hexahydro-$1^1H$-8-oxa-1(5,3)-indola-6(1,3)-pyridazina-2(1,3)-benzenacycloundecaphane-5,7-dione (60 mg, 0.1 mmol) in DMF (8 mL) at 0° C. under an atmosphere of N2 was added DIPEA (124 mg, 0.96 mmol), N—((S)-1-((3-(benzyloxy)azetidin-1-yl)sulfonyl)pyrrolidine-3-carbonyl)-N-methyl-L-valine (65 mg, 0.14 mmol) and COMU (58 mg, 0.13 mmol). The mixture was stirred at 0° C. for 1 h, then concentrated under reduced pressure and the residue was purified by prep-HPLC to give (3S)-1-((3-(benzyloxy)azetidin-1-yl)sulfonyl)-N-((2S)-1-((($6^3S,4S$)-$1^1$-ethyl-$2^5$-hydroxy-$1^2$-(4-(methoxymethyl)pyridin-3-yl)-10,10-dimethyl-5,7-dioxo-$6^1,6^2,6^3,6^4,6^5,6^6$-hexahydro-$1^1H$-8-oxa-1(5,3)-indola-6(1,3)-pyridazina-2(1,3)-benzenacycloundecaphane-4-yl)amino)-3-methyl-1-oxobutan-2-yl)-N-methylpyrrolidine-3-carboxamide (52 mg, 51% yield) as an oil. LCMS (ESI): m/z [M+H] calc'd for $C_{57}H_{72}N8O_{10}S$ 1060.5; found 1061.3.

Step 4. A mixture of (3S)-1-((3-(benzyloxy)azetidin-1-yl)sulfonyl)-N-((2S)-1-(((6³S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)-N-methylpyrrolidine-3-carboxamide (55 mg, 0.05 mmol), MeOH (3 mL) and Pd(OH)$_2$/C (11 mg, 20% by weight) was stirred under a H$_2$ atmosphere for 12 h. The mixture was filtered, the filtrate was concentrated under reduced pressure and the residue was purified by prep-HPLC to give (2S)—N-[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1²,⁶0.1¹⁰,¹⁴0.0²³,²⁷]nonacosa-1(26),2,4,6(29),20,23(27),24-heptaen-8-yl]-2-{1-[(3S)-1-[(3-hydroxyazetidin-1-yl)sulfonyl]pyrrolidin-3-yl]-N-methylformamido}-3-methylbutanamide (6.5 mg, 13% yield) as a solid. LCMS (ESI): m/z [M+H] calc'd for C$_{50}$H$_{66}$N$_8$O$_{10}$S 970.5; found 971.2; $^1$H NMR (400 MHz, DMSO-d$_6$) δ 9.33-9.29 (m, 1H), 8.75-8.65 (m, 2H), 8.52 (s, 0.5H), 8.15-8.06 (m, 0.5H), 7.92 (s, 1H), 7.65-7.50 (m, 3H), 7.22-7.14 (m, 1H), 7.02 (s, 1H), 6.58-6.46 (m, 1H), 5.84-5.80 (m, 1H), 5.28-5.22 (m, 0.6H), 4.75-4.69 (m, 0.4H), 4.45-4.12 (m, 4H), 4.05-3.88 (m, 5H), 3.72-3.50 (m, 7H), 3.22 (s, 2H), 3.12-3.04 (m, 1H), 2.94-2.70 (m, 7H), 2.29-2.03 (m, 5H), 1.90-1.77 (m, 2H), 1.76-1.45 (m, 2H), 1.24 (s, 1H), 1.08-1.02 (m, 2H), 1.01-0.72 (m, 12H), 0.5-0.43 (m, 3H).

Example A42. Synthesis of (3S)-N3-[(1S)-1-{[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1²,⁶0.1¹⁰,¹⁴0.0²³,²⁷]nonacosa-1(26),2,4,6(29),20,23(27),24-heptaen-8-yl]carbamoyl}-2-methylpropyl]-N1,N1,N3-trimethylpyrrolidine-1,3-dicarboxamide

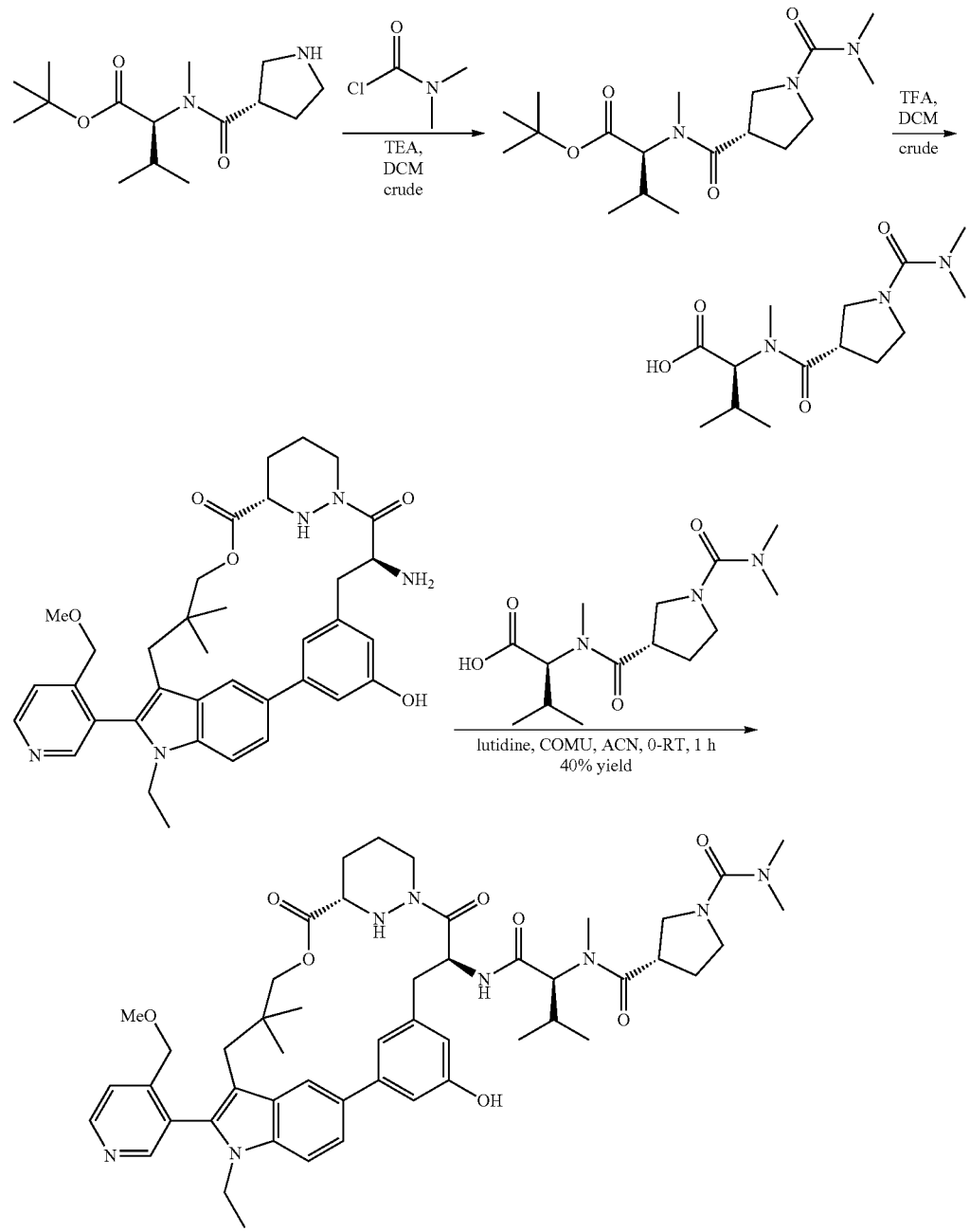

Step 1. To a mixture of tert-butyl (2S)-3-methyl-2-[N-methyl-1-(3S)-pyrrolidin-3-ylformamido]butanoate (200 mg, 0.7 mmol) and TEA (142 mg, 1.4 mmol) in DCM (10 mL) at 0° C. under an atmosphere of $N_2$ was added dimethylcarbamyl chloride (91 mg, 0.84 mmol) in portions. The mixture was warmed to rt and stirred for 1 h, then $H_2O$ added and the mixture extracted with DCM (3×50 mL). The combined organic layers were washed with brine (1×5 mL), dried over anhydrous $Na_2SO_4$, filtered and the filtrate concentrated under reduced pressure to give tert-butyl (2S)-2-[1-[(3S)-1-(dimethylcarbamoyl)pyrrolidin-3-yl]-N-methylformamido]-3-methylbutanoate, which was used in the next step without further purification.

Step 2. A mixture of tert-butyl (2S)-2-[1-[(3S)-1-(dimethylcarbamoyl)pyrrolidin-3-yl]-N-methylformamido]-3-methylbutanoate (335 mg, 0.94 mmol) in DCM (10 mL) and TFA (2 mL, 26.9 mmol) was stirred at rt for 2 h. The mixture was concentrated under reduced pressure to give (2S)-2-[1-[(3S)-1-(dimethylcarbamoyl)pyrrolidin-3-yl]-N-methylformamido]-3-methylbutanoic acid, which was used directly in the next step without further purification. LCMS (ESI): m/z [M+H] calc'd for $C_{14}H_{25}N_3O_4$ 299.2; found 300.2.

Step 3. To a mixture of $(6^3S,4S)$-4-amino-$1^1$-ethyl-$2^5$-hydroxy-$1^2$-(4-(methoxymethyl)pyridin-3-yl)-10,10-dimethyl-$6^1,6^2,6^3,6^4,6^5,6^6$-hexahydro-$1^1H$-8-oxa-1(5,3)-indola-6(1,3)-pyridazina-2(1,3)-benzenacycloundecaphane-5,7-dione (80 mg, 0.13 mmol) and (2S)-2-[1-[(3S)-1-(dimethylcarbamoyl)pyrrolidin-3-yl]-N-methylformamido]-3-methylbutanoic acid (57 mg, 0.19 mmol) in MeCN (3 mL) at 0° C. under an atmosphere of N2 was added lutidine (137 mg, 1.3 mmol) and COMU (77 mg, 0.18 mmol) in portions. The mixture was stirred at 0° C. for 1 h, then concentrated under reduced pressure and the residue was purified by prep-HPLC to give (3S)-N3-[(1S)-1-{[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1$^{2,6}$.0$^{10,14}$.0$^{23,27}$]nonacosa-1(26),2,4,6(29),20,23(27),24-heptaen-8-yl]carbamoyl}-2-methylpropyl]N1,N1,N3-trimethylpyrrolidine-1,3-dicarboxamide (45.6 mg, 39% yield) as a solid. LCMS (ESI): m/z [M+H] calc'd for $C_{50}H_{66}N_8O_8$ 906.5; found 907.4; $^1$H NMR (400 MHz, DMSO-$d_6$) δ 9.31-9.30 (m, 1H), 8.72-8.71 (m, 1H), 8.59 (d, J=50.4 Hz, 1H), 7.92-7.90 (m, 1H), 7.74-7.42 (m, 3H), 7.23-7.08 (m, 1H), 7.00 (d, J=13.4 Hz, 1H), 6.56-6.49 (m, 1H), 5.45-5.32 (m, 1H), 5.26-5.04 (m, 1H), 4.87-4.64 (m, 1H), 4.53-4.35 (m, 1H), 4.32-4.09 (m, 3H), 4.12-3.81 (m, 3H), 3.81-3.37 (m, 6H), 3.23 (t, J=1.6 Hz, 2H), 3.12-3.10 (m, 1H), 3.01-2.52 (m, 13H), 2.23-1.95 (m, 4H), 1.81 (s, 1H), 1.67 (s, 1H), 1.60-1.47 (m, 1H), 1.28-1.22 (m, 1H), 1.21-1.14 (m, 1H), 1.11-1.02 (m, 2H), 1.02-0.66 (m, 12H), 0.43 (d, 0=16.8 Hz, 3H).

Example A27. Synthesis of (2S)—N-[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1$^{2,6}$.0$^{10,14}$.0$^{23,27}$]nonacosa-1(26),2,4,6(29),20,23(27),24-heptaen-8-yl]-3-methyl-2-{N-methyl-1-[(3S)-1-methylpyrrolidin-3-yl]formamido}butanamide

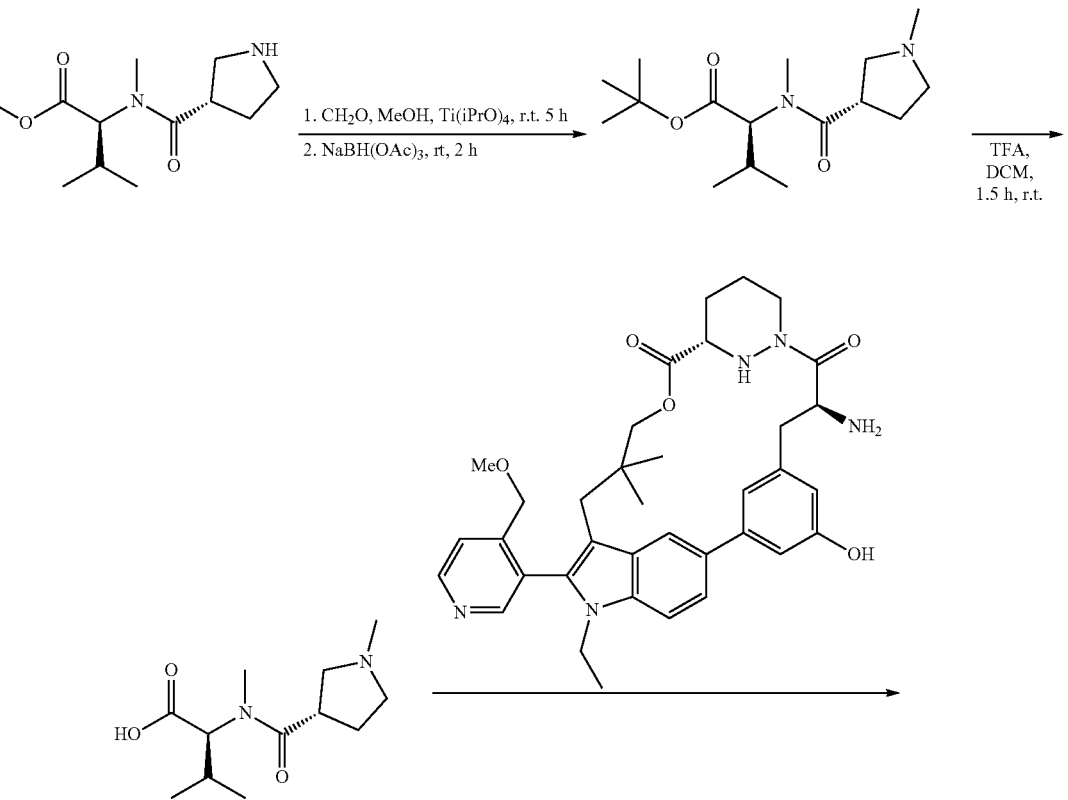

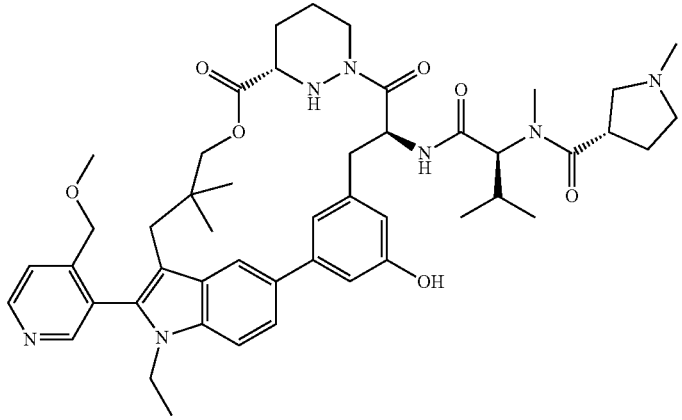

Step 1. A mixture of tert-butyl (2S)-3-methyl-2-[N-methyl-1-(3S)-pyrrolidin-3-ylformamido]butanoate (80 mg 0.28 mmol), Ti(Oi-Pr)$_4$ (88 mg, 0.31 mmol) and paraformaldehyde (26 mg 0.29 mmol) in MeOH (2 mL) was stirred at rt under an atmosphere of air overnight. The mixture was cooled to 0° C. and NaBH(OAc)$_3$ (107 mg, 0.51 mmol) was added. The mixture was warmed to rt and stirred for 2 h, then cooled to 0° C. and H$_2$O (0.2 mL) added. The mixture was concentrated under reduced pressure and the residue was purified by C18-silica gel column chromatography to give tert-butyl (2S)-3-methyl-2-[N-methyl-1-[(3S)-1-methylpyrrolidin-3-yl]formamido]butanoate (97 mg, crude) as an oil. LCMS (ESI): m/z [M+H] calc'd for C$_{16}$H$_{30}$N$_2$O$_3$ 298.2; found 299.3.

Step 2. A mixture of tert-butyl (2S)-3-methyl-2-[N-methyl-1-[(3S)-1-methylpyrrolidin-3-yl]formamido]butanoate (97 mg, 0.32 mmol) in DCM (2 mL) and TFA (1 mL, 13.5 mmol) was stirred at rt for 1 h, then the mixture was concentrated under reduced pressure to give (2S)-3-methyl-2-[N-methyl-1-[(3S)-1-methylpyrrolidin-3-yl]formamido] butanoic acid (100 mg, crude) as an oil. LCMS (ESI): m/z [M+H] calc'd for C$_{12}$H$_{22}$N$_2$O$_3$ 242.2; found 243.2.

Step 3. To a mixture of (6$^3$S,4S)-4-amino-1$^1$-ethyl-2$^5$-hydroxy-1$^2$-(4-(methoxymethyl)pyridin-3-yl)-10,10-dimethyl-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-5,7-dione (80 mg, 0.13 mmol) and (2S)-3-methyl-2-[N-methyl-1-[(3S)-1-methylpyrrolidin-3-yl]formamido]butanoic acid (47 mg, 0.19 mmol) in MeCN (2 mL) at 0° C. was added 2,6-dimethylpyridine (137 mg, 1.3 mmol) and COMU (77 mg, 0.18 mmol). The mixture was warmed to rt and stirred for 1 h, then concentrated under reduced pressure and the residue was purified by prep-HPLC to give (2S)—N-[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1$^{2,6}$0.1$^{10,14}$0.0$^{23,27}$]nonacosa-1 (26),2,4,6 (29),20,23(27),24-heptaen-8-yl]-3-methyl-2-{N-methyl-1-[(3S)-1-methylpyrrolidin-3-yl]formamido}butanamide (28 mg, 26% yield) as a solid. LCMS (ESI): m/z [M+H] calc'd for C$_{48}$H$_{63}$N$_7$O$_7$ 849.5; found 850.5; $^1$H NMR (400 MHz, DMSO-d$_6$) δ 9.31 (s, 1H), 8.72 (t, J=5.1 Hz, 1H), 8.67-8.50 (m, 1H), 7.98-7.87 (m, 1H), 7.67-7.47 (m, 3H), 7.22-7.07 (m, 1H), 7.01 (s, 1H), 6.53 (d, J=40.1 Hz, 1H), 5.44-5.00 (m, 2H), 4.46-4.12 (m, 3H), 4.08-3.79 (m, 3H), 3.79-3.45 (m, 3H), 3.22 (d, J=1.2 Hz, 2H), 3.14-2.94 (m, 2H), 2.92-2.55 (m, 10H), 2.43-2.20 (m, 4H), 2.19-1.92 (m, 4H), 1.81 (d, J=11.9 Hz, 2H), 1.67 (s, 1H), 1.53 (s, 1H), 1.09 (t, J=7.1 Hz, 1H), 1.02-0.91 (m, 3H), 0.91-0.80 (m, 5H), 0.80-0.67 (m, 3H), 0.42 (d, J=21.7 Hz, 3H).

Example A23. Synthesis of (2S)—N-[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1$^{2,6}$0.1$^{10,14}$0.0$^{23,27}$] nonacosa-1(26),2,4,6(29),20,23(27),24-heptaen-8-yl]-2-{1-[(3S)-1-(2-hydroxyethyl)pyrrolidin-3-yl]-N-methylformamido}-3-methylbutanamide

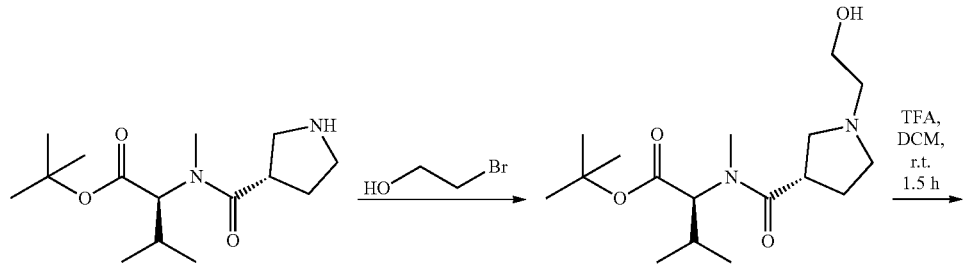

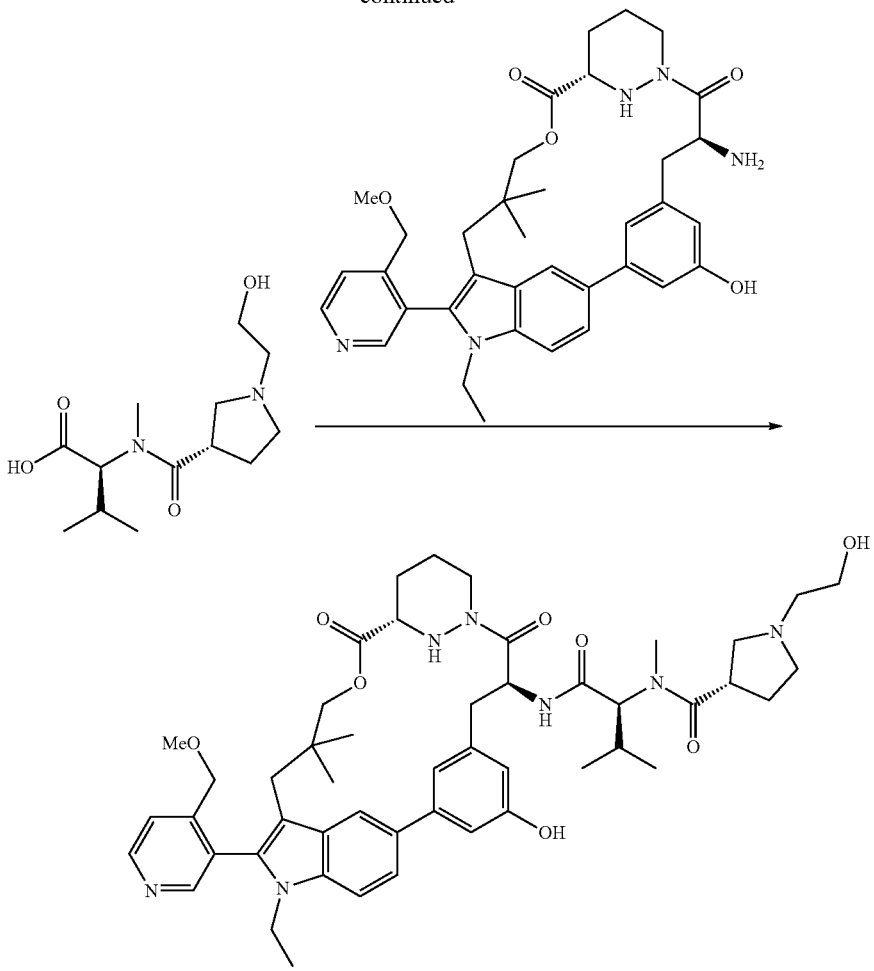

Step 1. To a mixture of tert-butyl (2S)-3-methyl-2-[N-methyl-1-(3S)-pyrrolidin-3-ylformamido]butanoate vanadium (200 mg, 0.6 mmol) and 2-bromoethanol (224 mg, 1.8 mmol) in DMF (5 mL) at rt was added $Cs_2CO_3$ (777 mg, 2.4 mmol) and $K_I$ (50 mg, 0.3 mmol). The mixture was stirred at rt for 16 h then diluted with $H_2O$ and extracted with EtOAc (3×100 mL). The combined organic layers were washed with brine (2×100 mL), dried over anhydrous $Na_2SO_4$ and filtered. The filtrate was concentrated under reduced pressure and the residue was purified by $C_{18}$-silica gel column chromatography to give tert-butyl (2S)-2-[1-[(3S)-1-(2-hydroxyethyl)pyrrolidin-3-yl]-N-methylformamido]-3-methylbutanoate (201 mg, crude) as a solid. LCMS (ESI): m/z [M+H] calc'd for $C_{17}H_{32}N_2O_4$ 328.2; found 329.4.

Step 2. A mixture of tert-butyl (2S)-2-[1-[(3S)-1-(2-hydroxyethyl)pyrrolidin-3-yl]-N-methylformamido]-3-methylbutanoate (100 mg, 0.3 mmol) in DCM (1 mL) and TFA (0.50 mL) at rt was stirred for 1 h, then concentrated under reduced pressure to give (2S)-2-[1-[(3S)-1-(2-hydroxyethyl)pyrrolidin-3-yl]-N-methylformamido]-3-methylbutanoic acid (110 mg, crude) as an oil. LCMS (ESI): m/z [M+H] calc'd for $C_{13}H_{24}N_2O_4$ 272.2; found 273.2.

Step 3. To a mixture of ($6^3$S,4S)-4-amino-$1^1$-ethyl-$2^5$-hydroxy-$1^2$-(4-(methoxymethyl)pyridin-3-yl)-10,10-dimethyl-$6^1,6^2,6^3,6^4,6^5,6^6$-hexahydro-$1^1$H-8-oxa-1(5,3)-indola-6(1,3)-pyridazina-2(1,3)-benzenacycloundecaphane-5,7-dione (60 mg, 0.1 mmol) and (2S)-2-[1-[(3S)-1-(2-hydroxyethyl)pyrrolidin-3-yl]-N-methylformamido]-3-methylbutanoic acid (31 mg, 0.11 mmol) in MeCN (2 mL) at 0° C. under an atmosphere of N2 was added 2,6-dimethylpyridine (103 mg, 1.0 mmol) and COMU (58 mg, 0.13 mmol). The mixture was warmed to rt and stirred for 1 h, then concentrated under reduced pressure and the residue was purified by prep-HPLC to give (2S)—N-[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.$1^{2,6}$.$0^{10,14}$.$0^{23,27}$]nonacosa-1(26),2,4,6(29),20,23(27),24-heptaen-8-yl]-2-{1-[(3S)-1-(2-hydroxyethyl)pyrrolidin-3-yl]-N-methylformamido}-3-methylbutanamide (13 mg, 16% yield) as a solid. LCMS (ESI): m/z [M+H] calc'd for $C_{49}H_{65}N_7O_8$ 879.5; found 880.3; $^1$H NMR (400 MHz, DMSO-$d_6$) δ 8.72 (t, J=5.3 Hz, 1H), 8.68-8.58 (m, 1H), 8.52 (s, 1H), 7.93 (d, J=10.6 Hz, 1H), 7.68-7.58 (m, 2H), 7.53 (d, J=7.1 Hz, 1H), 7.21-7.07 (m, 1H), 7.01 (s, 1H), 6.52 (d, J=42.8 Hz, 1H), 5.35 (d, J=25.5 Hz, 1H), 5.22-4.97 (m, 1H), 4.59-4.35 (m, 1H), 4.23 (t, J=13.8 Hz, 3H), 4.11-3.81 (m, 3H), 3.81-3.56 (m, 2H), 3.56-3.47 (m, 3H), 3.22 (d, J=1.2 Hz, 2H), 3.09 (d, J=12.6 Hz, 1H), 2.99-2.65 (m, 10H), 2.57-2.53 (m, 1H), 2.47-2.19 (m, 2H), 2.14-2.08 (m, 1H), 2.08 (s, 1H), 2.06-1.98 (m, 2H), 1.81 (s, 2H), 1.59 (d, J=55.9 Hz, 2H), 1.14-0.67 (m, 13H), 0.42 (d, J=22.1 Hz, 3H).

Example A57. Synthesis of (2S)—N-[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1$^{2,6}$.0.1$^{10,14}$0.0$^{23,27}$]nonacosa-1(26),2,4,6(29),20,23(27),24-heptaen-8-yl]-3-methyl-2-(N-methylmethanesulfonamido)butanamide

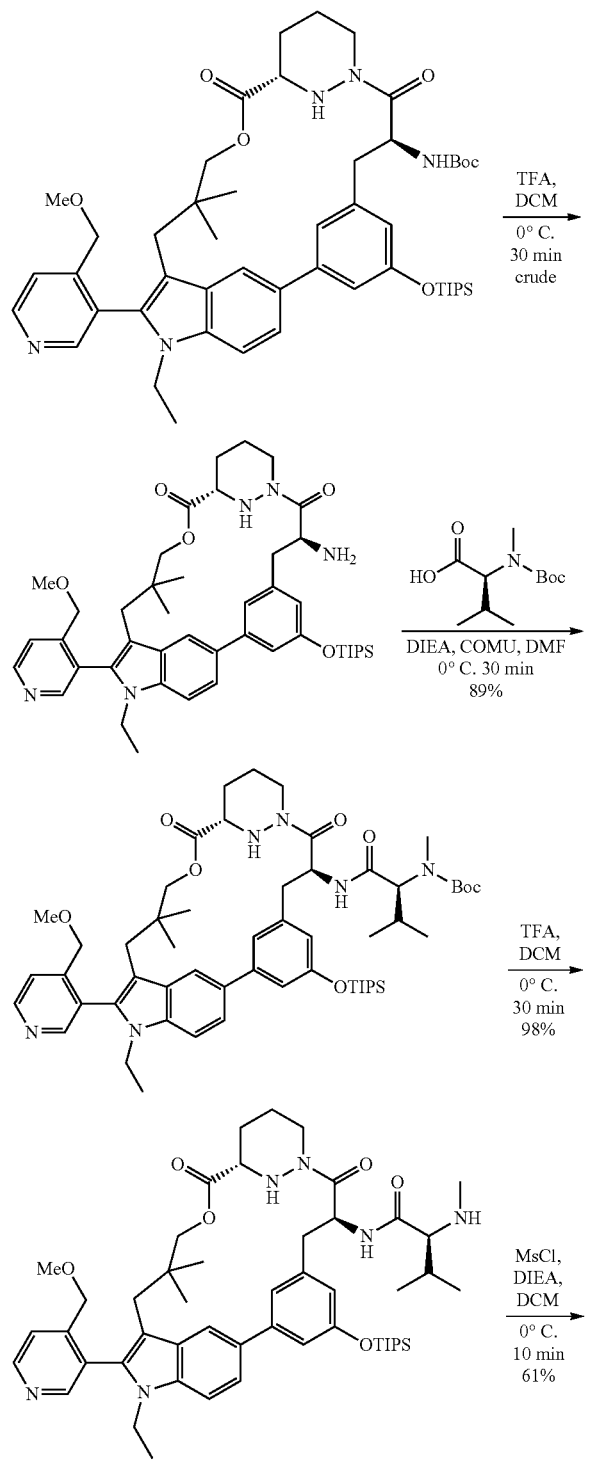

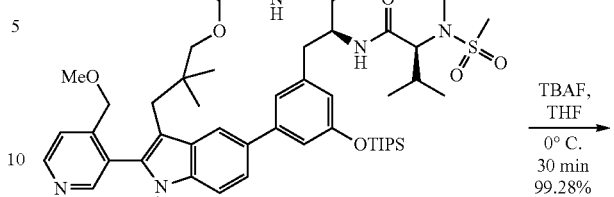

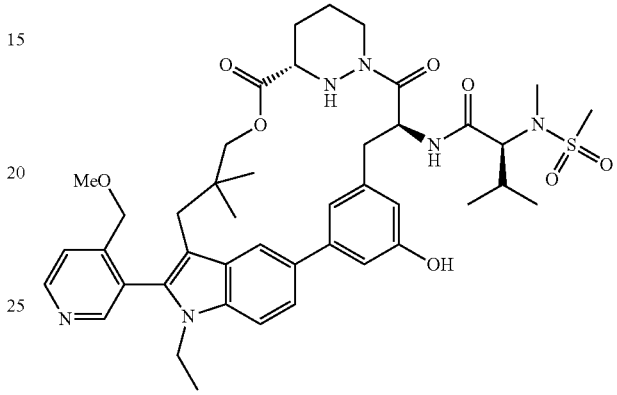

Step 1. A mixture of tert-butyl N-[(8S,14S)-22-ethyl-21-[2-(2-methoxyethyl)phenyl]-18,18-dimethyl-9,15-dioxo-16-oxa-10,22,28-triazapentacyclo[18.5.2.1 ^[2,6]0.1^[10,14]0.0^[23,27]]nonacosa-1(26),2,4,6(29),20,23(27),24-heptaen-8-yl]carbamate (880 mg, 1.2 mmol), DCM (10 mL) and TFA (5 mL) was stirred at 0° C. for 30 min. The mixture was concentrated under reduced pressure to give (8S,14S)-8-amino-22-ethyl-21-[4-(methoxymethyl)pyridin-3-yl]-18,18-dimethyl-4-[(triisopropylsilyl)oxy]-16-oxa-10,22,28-triazapentacyclo[18.5.2.1^[2,6]0.1^[10,14]0.0^[23,27]]nonacosa-1(26),2,4,6(29),20,23(27),24-heptaene-9,15-dione, that was used directly in the next step without further purification. LCMS (ESI): m/z [M+H] calc'd for $C_{45}H_{63}N_5O_5Si$ 781.5; found 782.7.

Step 2. To a mixture of (8S,14S)-8-amino-22-ethyl-21-[4-(methoxymethyl)pyridin-3-yl]-18,18-dimethyl-4-[(triisopropylsilyl)oxy]-16-oxa-10,22,28-triazapentacyclo [18.5.2.1^[2,6]0.1^[10,14]0.0^[23,27]]nonacosa-1(26),2,4,6 (29),20,23(27),24-heptaene-9,15-dione (880 mg, 1.13 mmol) and (2S)-2-[(tert-butoxycarbonyl)(methyl)amino]-3-methylbutanoic acid (521 mg, 2.3 mmol) in DMF (8.8 mL) at 0° C. was added DIPEA (1.45 g, 11.3 mmol) and COMU (88 mg, 0.21 mmol). The mixture was stirred at 0° C. for 30 min, then diluted with H$_2$O (100 mL) and extracted with EtOAc (3×100 mL). The combined organic layers were washed with brine (3×100 mL), dried over anhydrous Na$_2$SO$_4$ and filtered. The filtrate was concentrated under reduced pressure and the residue was purified by prep-TLC to give tert-butyl N-[(1S)-1-[[(8S,14S)-22-ethyl-21-[4-(methoxymethyl)pyridin-3-yl]-18,18-dimethyl-9,15-dioxo-4-[(triisopropylsilyl)oxy]-16-oxa-10,22,28-triazapentacyclo

[18.5.2.1^[2,6]0.1^[10,14]0.0^[23,27]]nonacosa-1(26),2,4,6(29),20,23(27),24-heptaen-8-yl]carbamoyl]-2-methylpropyl]-N-methylcarbamate (1 g, 89% yield) as a solid. LCMS (ESI): m/z [M+H] calc'd for $C_{56}H_{82}N_6O_8Si$ 994.6; found 995.5.

Step 3. A mixture of tert-butyl N-[(1S)-1-[[(8S,14S)-22-ethyl-21-[4-(methoxymethyl)pyridin-3-yl]-18,18-dimethyl-9,15-dioxo-4-[(triisopropylsilyl)oxy]-16-oxa-10,22,28-triazapentacyclo[18.5.2.1^[2,6]0.1^[10,14]0.0^[23,27]]nonacosa-1(26),2,4,6(29),20,23(27),24-heptaen-8-yl]carbamoyl]-2-methylpropyl]-N-methylcarbamate (1.0 g, 1.0 mmol), DCM (10 mL) and TFA (5 mL) was stirred for 30 min. The mixture was concentrated under reduced pressure and the residue was basified to pH 8 with saturated NaHCO$_3$, then extracted with EtOAc (3×10 mL). The combined organic layers were washed with brine (3×10 mL), dried over anhydrous Na$_2$SO$_4$, filtered and the filtrate concentrated under reduced pressure to give (2S)—N-[(8S,14S)-22-ethyl-21-[4-(methoxymethyl)pyridin-3-yl]-18,18-dimethyl-9,15-dioxo-4-[(triisopropylsilyl)oxy]-16-oxa-10,22,28-triazapentacyclo[18.5.2.1^[2,6]0.1^[10,14]0.0^[23,27]]nonacosa-1(26),2,4,6(29),20,23(27),24-heptaen-8-yl]-3-methyl-2-(methylamino)butanamide (880 mg, 98% yield) as a solid. LCMS (ESI): m/z [M+H] calc'd for $C_{51}H_{74}N_6O_6Si$ 894.5; found 895.5.

Step 4. To a mixture of (2S)—N-[(8S,14S)-22-ethyl-21-[4-(methoxymethyl)pyridin-3-yl]-18,18-dimethyl-9,15-dioxo-4-[(triisopropylsilyl)oxy]-16-oxa-10,22,28-triazapentacyclo[18.5.2.1^[2,6]0.1^[10,14]0.0^[23,27]]nonacosa-1(26),2,4,6(29),20,23(27),24-heptaen-8-yl]-3-methyl-2-(methylamino)butanamide (90 mg, 0.1 mmol) in DCM (2 mL) at 0° C. was added DIPEA (65 mg, 0.5 mmol) and MsCl (14 mg, 0.12 mmol). The mixture was stirred at 0° C. for 30 min, then concentrated under reduced pressure and the residue diluted with H$_2$O (5 mL) and extracted with EtOAc (3×5 mL). The combined organic layers were washed with brine (3×5 mL), dried over anhydrous Na$_2$SO$_4$ and filtered. The filtrate was concentrated under reduced pressure and the residue was purified by prep-TLC to give (2S)—N-[(8S,14S)-22-ethyl-21-[4-(methoxymethyl)pyridin-3-yl]-18,18-dimethyl-9,15-dioxo-4-[(triisopropylsilyl)oxy]-16-oxa-10,22,28-triazapentacyclo[18.5.2.1^[2,6]0.1^[10,14]0.0^[23,27]]nonacosa-1(26),2,4,6(29),20,23(27),24-heptaen-8-yl]-3-methyl-2-(N-methylmethanesulfonamido)butanamide (60 mg, 61% yield) as a solid. LCMS (ESI): m/z [M+H] calc'd for $C_{52}H_{76}N_6O_8SSi$ 972.5; found 973.7.

Step 5. To a mixture of (2S)—N-[(8S,14S)-22-ethyl-21-[4-(methoxymethyl)pyridin-3-yl]-18,18-dimethyl-9,15-dioxo-4-[(triisopropylsilyl)oxy]-16-oxa-10,22,28-triazapentacyclo[18.5.2.1^[2,6]0.1^[10,14]0.0^[23,27]]nonacosa-1(26),2,4,6(29),20,23(27),24-heptaen-8-yl]-3-methyl-2-(N-methylmethanesulfonamido)butanamide (60 mg, 0.06 mmol) in THF (2 mL) at 0° C. was added 1M TBAF in THF (6 DL, 0.006 mmol). The mixture was stirred at 0° C. for 30 min, then diluted with H$_2$O (5 mL) and extracted with EtOAc (3×5 mL). The combined organic layers were washed with brine (3×5 mL), dried over anhydrous Na$_2$SO$_4$ and filtered. The filtrate was concentrated under reduced pressure and the residue was purified by prep-TLC to give (2S)—N-[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1$^{2,6}$0.1$^{10,14}$0.0$^{23,27}$]nonacosa-1(26),2,4,6(29),20,23(27),24-heptaen-8-yl]-3-methyl-2-(N-methylmethanesulfonamido)butanamide (50 mg, 99% yield) as a solid. LCMS (ESI): m/z [M+H] calc'd for $C_{43}H_{56}N_6O_8S$ 816.4; found 817.5; $^1$H NMR (400 MHz, DMSO-d$_6$) δ 9.34 (d, J=1.8 Hz, 1H), 8.72 (t, J=5.2 Hz, 1H), 8.65 (d, J=5.8 Hz, 1H), 7.99-7.86 (m, 1H), 7.71-7.45 (m, 3H), 7.19 (d, J=41.5 Hz, 1H), 7.03 (t, J=1.9 Hz, 1H), 6.66 (d, J=10.4 Hz, 1H), 5.34 (q, J=8.1 Hz, 1H), 5.14 (dd, J=62.7, 12.2 Hz, 1H), 4.55-4.15 (m, 3H), 4.14-3.80 (m, 4H), 3.80-3.46 (m, 3H), 3.23 (s, 1H), 3.02-2.72 (m, 8H), 2.68 (s, 2H), 2.15-1.89 (m, 3H), 1.82 (d, J=12.4 Hz, 1H), 1.76-1.62 (m, 1H), 1.54 (q, 0=12.7 Hz, 1H), 1.24 (s, 1H), 1.08 (t, J=7.1 Hz, 2H), 1.03-0.86 (m, 9H), 0.81 (s, 2H), 0.46 (s, 3H).

Example A43. Synthesis of (2S)—N-[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1$^{2,6}$0.1$^{10,14}$0.0$^{23,27}$]nonacosa-1(26),2,4,6(29),20,23(27),24-heptaen-8-yl]-2-(2-hydroxy-N-methylacetamido)-3-methylbutanamide

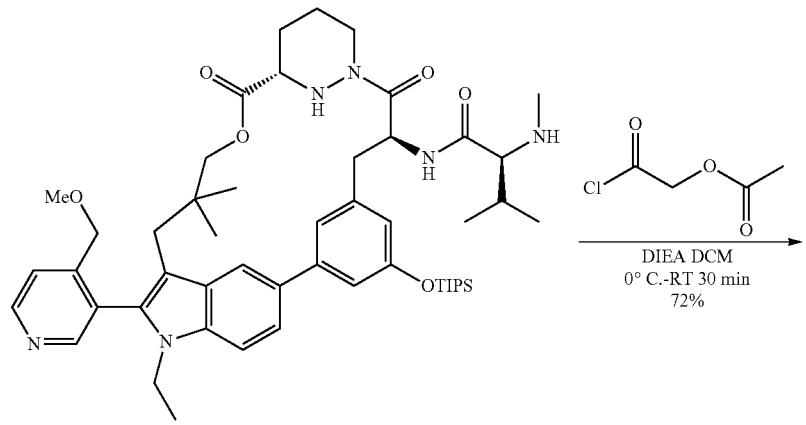

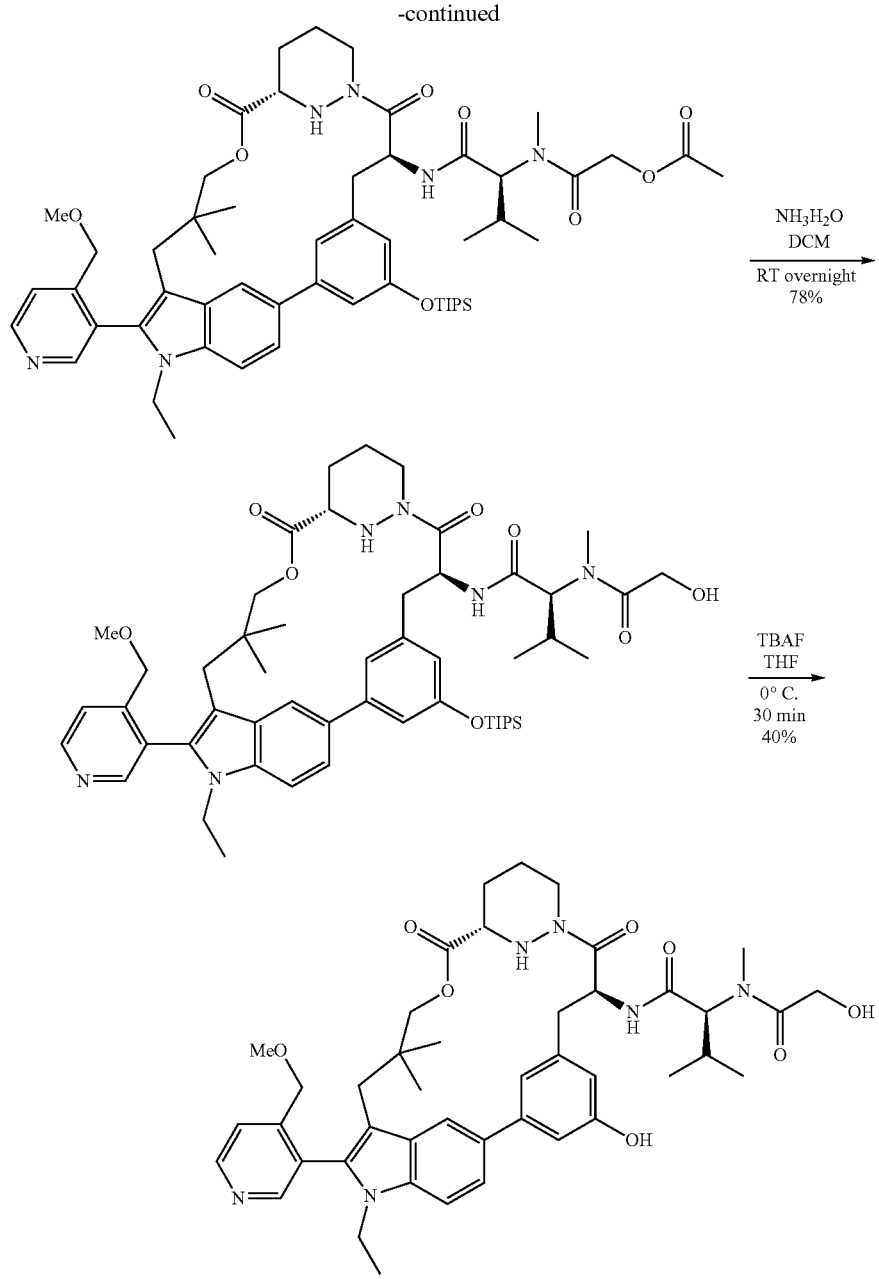

Step 1. To a mixture of (2S)—N-[(8S,14S)-22-ethyl-21-[4-(methoxymethyl)pyridin-3-yl]-18,18-dimethyl-9,15-dioxo-4-[(triisopropylsilyl)oxy]-16-oxa-10,22,28-triazapentacyclo[18.5.2.1^[2,6]0.1^[10,14]0.0^[23,27]]nonacosa-1(26),2,4,6(29),20,23(27),24-heptaen-8-yl]-3-methyl-2-(methylamino)butanamide (100 mg, 0.11 mmol) in DCM (1 mL) at 0° C. was added DIPEA (72 mg, 0.56 mmol) and 2-chloro-2-oxoethyl acetate (11.53 mg, 0.11 mmol). The mixture was warmed to rt and stirred for 30 min, then concentrated under reduced pressure, diluted with water (3 mL) and extracted with EtOAc (3×3 mL). The combined organic layers were washed with brine (3×3 mL), dried over anhydrous Na$_2$SO$_4$ and filtered. The filtrate was concentrated under reduced pressure and the residue was purified by prep-TLC to give [[(1S)-1-[[(8S,14S)-22-ethyl-21-[4-(methoxymethyl)pyridin-3-yl]-18,18-dimethyl-9,15-dioxo-4-[(triisopropylsilyl)oxy]-16-oxa-10,22,28-triazapentacyclo[18.5.2.1^[2,6]0.1^[10,14]0.0^[23,27]]nonacosa-1(26),2,4,6(29),20,23(27),24-heptaen-8-yl]carbamoyl]-2-methylpropyl](methyl)carbamoyl]methyl acetate (80 mg, 72% yield) as a solid. LCMS (ESI): m/z [M+H] calc'd for C$_{55}$H$_{78}$N$_6$O$_9$Si 994.6; found 995.7.

Step 2. A mixture of [[(1S)-1-[[(8S,14S)-22-ethyl-21-[4-(methoxymethyl)pyridin-3-yl]-18,18-dimethyl-9,15-dioxo-4-[(triisopropylsilyl)oxy]-16-oxa-10,22,28-triazapentacyclo[18.5.2.1^[2,6]0.1^[10,14]0.0^[23,27]]nonacosa-1(26),2,4,6(29),20,23(27),24-heptaen-8-yl]carbamoyl]-2-methylpropyl](methyl)carbamoyl]methyl acetate (80 mg, 0.080 mmol), DCM (1 mL) and aqueous NH$_4$OH (0.8 mL) was stirred at rt overnight. H2O (5 mL) was added and the mixture was extracted with EtOAc (3×5 mL). The combined organic layers were washed with brine (3×5 mL), dried over anhydrous Na$_2$SO$_4$ and filtered. The filtrate was concentrated under reduced pressure and the residue was purified by prep-TLC to give (2S)—N-[(8S,14S)-22-ethyl-21-[4-(methoxymethyl)pyridin-3-yl]-18,18-dimethyl-9,15-dioxo- 4-[(triisopropylsilyl)oxy]-16-oxa-10,22,28-triazapentacyclo[18.5.2.1^[2,6]0.1^[10,14]0.0^[23,27]]nonacosa-1(26),2,4,6(29),20,23(27),24-heptaen-8-yl]-2-(2-hydroxy-N-methylacetamido)-3-methylbutanamide (60 mg, 78% yield) as a solid. LCMS (ESI): m/z [M+H] calc'd for $C_{53}H_{76}N_6O_8Si$ 952.6; found 953.7.

Step 3. A mixture of (2S)—N-[(8S,14S)-22-ethyl-21-[4-(methoxymethyl)pyridin-3-yl]-18,18-dimethyl-9,15-dioxo-4-[(triisopropylsilyl)oxy]-16-oxa-10,22,28-triazapentacyclo[18.5.2.1^[2,6]0.1^[10,14]0.0^[23,27]]nonacosa-1(26),2,4,6(29),20,23(27),24-heptaen-8-yl]-2-(2-hydroxy-N-methylacetamido)-3-methylbutanamide (60 mg, 0.06 mmol), THF (2 mL) and 1M TBAF in THF (6 DL, 0.006 mmol) at 0° C. was stirred for 30 min. $H_2O$ (3 mL) was added and the mixture was extracted with EtOAc (3×3 mL). The combined organic layers were washed with brine (3×3 mL), dried over anhydrous $Na_2SO_4$. The filtrate was concentrated under reduced pressure and the residue was purified by prep-TLC to give (2S)—N-[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1^[2,6]0.0^[10,14]0.0^[23,27]]nonacosa-1(26),2,4,6(29),20,23(27),24-heptaen-8-yl]-2-(2-hydroxy-N-methylacetamido)-3-methylbutanamide (20 mg, 40% yield) as a solid. LCMS (ESI): m/z [M+H] calc'd for $C_{44}H_{56}N_6O_8$ 796.4; found 797.6; $^1H$ NMR (400 MHz, $CD_3OD$) δ 8.70 (dd, J=5.7, 4.4 Hz, 1H), 8.66-8.49 (m, 1H), 8.00 (dd, J=4.6, 1.7 Hz, 1H), 7.76 (dd, J=9.9, 5.2 Hz, 1H), 7.60 (dt, J=8.7, 1.6 Hz, 1H), 7.56-7.47 (m, 1H), 7.29-7.18 (m, 1H), 7.10-6.98 (m, 1H), 6.54 (dt, J=3.6, 1.7 Hz, 1H), 5.67-5.55 (m, 1H), 4.77 (dd, J=11.2, 8.4 Hz, 1H), 4.57-4.39 (m, 3H), 4.39-4.20 (m, 3H), 4.19-3.91 (m, 2H), 3.90-3.65 (m, 3H), 3.60 (dd, J=11.0, 1.8 Hz, 1H), 3.42 (s, 1H), 3.32 (s, 1H), 3.29-3.15 (m, 1H), 3.10-2.97 (m, 1H), 2.97-2.82 (m, 5H), 2.82-2.63 (m, 2H), 2.35-2.11 (m, 3H), 1.94 (d, J=13.2 Hz, 1H), 1.82-1.49 (m, 3H), 1.31 (s, 1H), 1.19 (t, J=7.2 Hz, 2H), 1.09-0.95 (m, 7H), 0.95-0.83 (m, 5H), 0.50 (d, J=32.4 Hz, 3H).

Example A50. Synthesis of oxolan-3-yl-N-[(1S)-1-{[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1^{2,6}0.1^{10,14}0.0^{23,27}]nonacosa-1(26),2,4,6(29),20,23(27),24-heptaen-8-yl]carbamoyl}-2-methylpropyl]-N-methylcarbamate

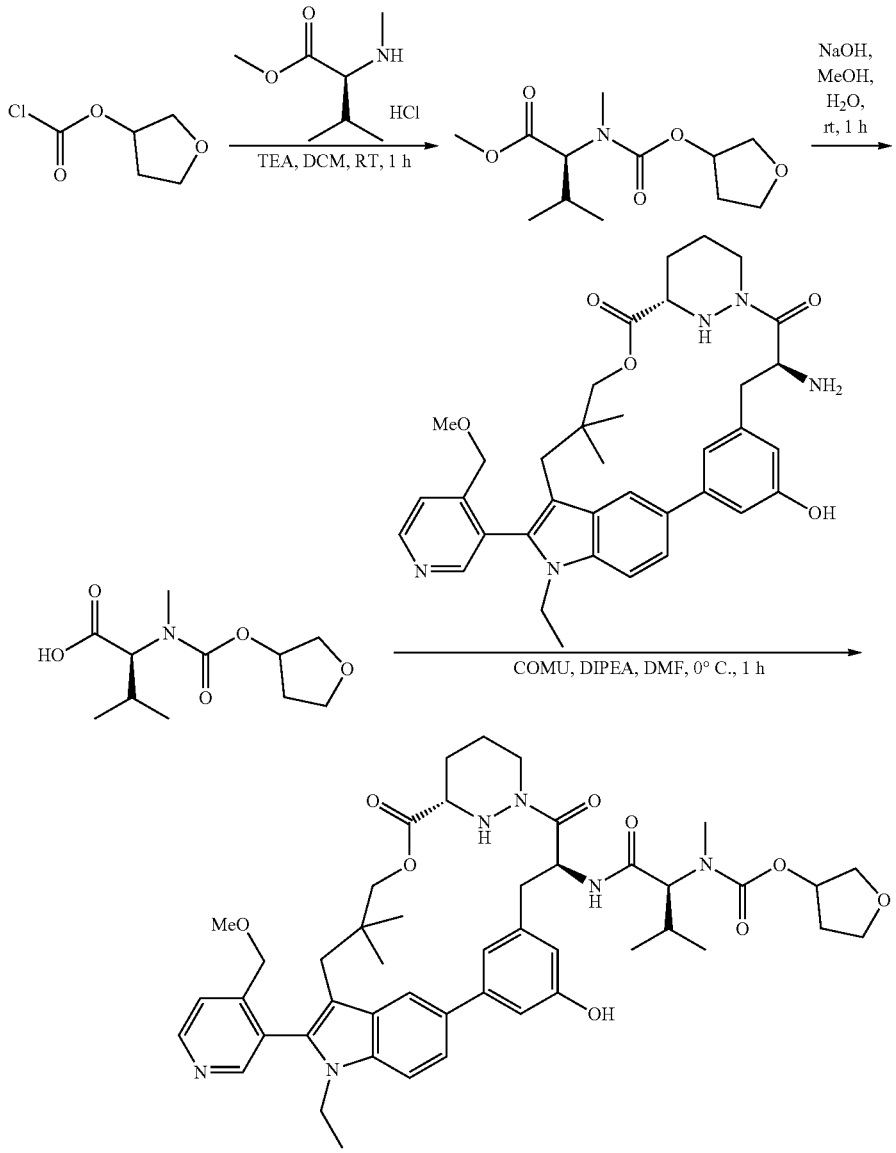

Step 1. To a mixture of methyl (2S)-3-methyl-2-(methylamino)butanoate (500 mg, 3.4 mmol) and TEA (1.44 mL, 14.2 mmol) in DCM (20 mL) at rt was added oxolan-3-yl carbonochloridate (1.04 g, 6.9 mmol). The mixture was stirred at rt for 1 h, then sat. NH$_4$Cl added and the mixture extracted with DCM (3×10 mL). The combined organic layers were washed with brine (1×10 mL), dried over anhydrous Na$_2$SO$_4$ and filtered. The filtrate was concentrated under reduced pressure and the residue was purified by silica gel column chromatography to give methyl (2S)-3-methyl-2 [methyl (oxolan-3-yloxy)carbonyl]amino]butanoate (800 mg, 89% yield) as an oil. $^1$H NMR (300 MHz, CDCl$_3$) δ 4.57-4.05 (m, 1H), 3.99-3.78 (m, 4H), 3.70 (s, 3H), 3.26 (s, 1H), 2.99-2.68 (m, 3H), 2.26-1.83 (m, 3H), 1.06-0.76 (m, 6H).

Step 2. A mixture of methyl (2S)-3-methyl-2 [methyl (oxolan-3-yloxy)carbonyl]amino]butanoate (1 g, 3.9 mmol) and 2M NaOH (19.3 mL, 38.6 mmol) in MeOH (20 mL) was stirred at rt for 1 h. The mixture was concentrated under reduced pressure and the residue was extracted with MTBE (3×10 mL). The aqueous layer was acidified to pH 2 with 2 M HCl then extracted with DCM (3×20 mL). The combined organic layers were washed with brine (2×10 mL), dried over anhydrous Na$_2$SO$_4$, filtered and the filtrate was concentrated under reduced pressure to give (2S)-3-methyl-2-[methyl[(oxolan-3-yloxy)carbonyl]amino]butanoic acid (630 mg, 67% yield) as an oil. $^1$H NMR (300 MHz, CDCl$_3$) δ 5.32 (br. s, 1H), 4.45-4.08 (m, 1H), 4.04-3.81 (m, 4H), 2.93 (d, J=6.9 Hz, 3H), 2.38-1.93 (m, 3H), 1.06 (t, J=5.6 Hz, 3H), 0.94 (d, J=6.7 Hz, 3H).

Step 3. To a mixture of (6$^3$S,4S)-4-amino-1$^1$-ethyl-2$^5$-hydroxyl-1$^2$-(4-(methoxymethyl)pyridin-3-yl)-10,10-dimethyl-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-5,7-dione (80 mg, 0.13 mmol), (2S)-3-methyl-2-[methyl[(oxolan-3-yloxy)carbonyl]amino]butanoic acid (63 mg, 0.26 mmol) and DIPEA (165 mg, 1.3 mmol) in DMF (2 mL) at 0° C. was added COMU (38 mg, 0.19 mmol). The mixture was stirred at 0° C. for 30 min, then the mixture was concentrated under reduced pressure and the residue was purified by prep-HPLC to give oxolan-3-yl-N-[(1S)-1-{[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1$^{2,6}$0.1$^{10,14}$0.0$^{23,27}$]nonacosa-1(26),2,4,6(29),20,23(27),24-heptaen-8-yl]carbamoyl}-2-methylpropyl]-N-methylcarbamate (50 mg, 45% yield) as a solid. LCMS (ESI): m/z [M+H] calc'd for C$_{47}$H$_{60}$N$_6$O$_9$ 852.4; found 853.5; $^1$H NMR (400 MHz, DMSO-d$_6$) δ 9.34-9.18 (m, 1H), 8.72 (t, J=5.1 Hz, 1H), 8.58 (d, J=47.8 Hz, 1H), 8.48-8.15 (m, 1H), 7.91 (s, 1H), 7.70-7.57 (m, 2H), 7.55-7.46 (m, 1H), 7.13 (d, J=24.7 Hz, 1H), 7.01 (s, 1H), 6.56 (d, J=9.2 Hz, 1H), 5.34 (s, 1H), 5.28-5.00 (m, 2H), 4.40 (d, J=13.3 Hz, 1H), 4.33-4.14 (m, 4H), 4.12-3.45 (m, 10H), 3.23 (s, 1H), 3.10 (d, J=14.5 Hz, 1H), 2.99-2.62 (m, 6H), 2.20-1.99 (m, 4H), 1.80 (s, 1H), 1.66 (s, 1H), 1.52 (d, J=12.2 Hz, 1H), 1.09 (t, J=7.1 Hz, 2H), 0.99-0.89 (m, 6H), 0.87-0.76 (m, 5H), 0.42 (d, J=24.2 Hz, 3H).

Example A277. The synthesis of (2S)—N-((6$^3$S,4S,Z)-1$^1$-ethyl-1$^2$-(2-((S)-1-methoxyethyl)-5-(4-methylpiperazin-1-yl)pyridin-3-yl)-10,10-trimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)-3-methyl-2-(1,3,3-trimethylureido)butanamide

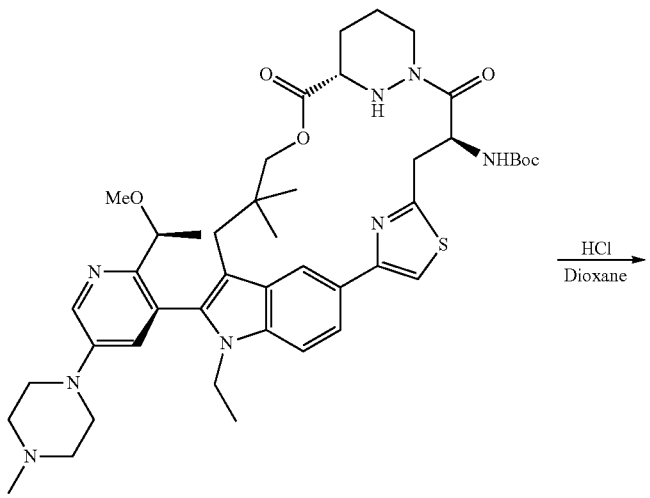

Intermediate 10

-continued

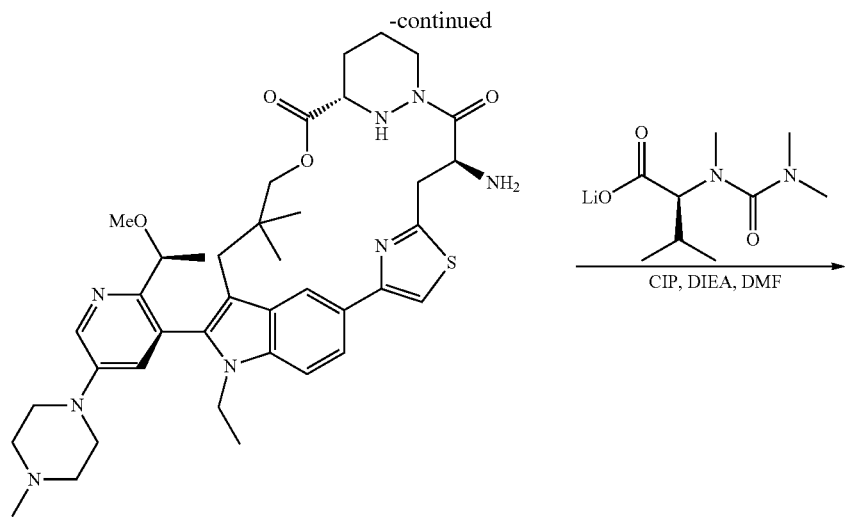

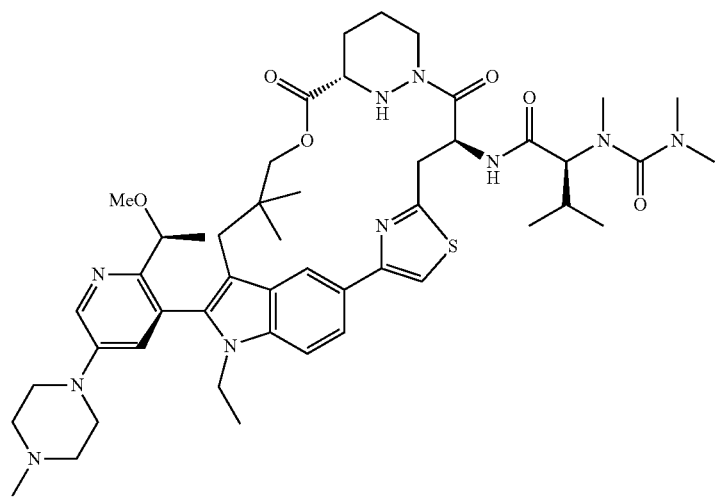

Step 1. A solution of Intermediate 10 (8.2 g, 9.89 mmol) in dioxane (40 mL) at 0° C. under nitrogen atmosphere, was added HCl (40 mL, 4M in dioxane). The reaction solution was stirred at 0° C. for 1 h, then concentrated under reduced pressure. The resulting mixture was diluted with DCM (600 mL) and saturated sodium bicarbonate aqueous solution (400 mL). The organic phase was separated and washed with brine (500 mL×2), then concentrated under reduced pressure to afford (6$^3$S,4S,Z)-4-amino-1'-ethyl-1$^2$-(2-((S)-1-methoxyethyl)-5-(4-methylpiperazin-1-yl)pyridin-3-yl)-10,10-dimethyl-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-5,7-dione (7.2 g, 94.8% yield) as solid. LCMS (ESI): m/z [M+H] calc'd for $C_{39}H_{52}N_8O_4S$ 728.4; found 729.3.

Step 2. A mixture of (6$^3$S,4S,Z)-4-amino-1'-ethyl-1$^2$-(2-((S)-1-methoxyethyl)-5-(4-methylpiperazin-1-yl)pyridin-3-yl)-10,10-dimethyl-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-5,7-dione (6 g, 8.23 mmol) and lithium N-(dimethylcarbamoyl)-N-methyl-L-valinate (4.28 g, 20.58 mmol) in DMF (80 mL), was added DIEA (53.19 g, 411.55 mmol). The reaction mixture was stirred for 5 minutes, then added CIP (3.43 g, 12.35 mmol) in one portion. The resulting solution was stirred at 25° C. for 1 h, then quenched with water (100 mL), extracted with EtOAc (300 mL). The organic layer was separated and washed with saturated ammonium chloride aqueous solution (100 mL×3) and water (100 mL×2). The combined organic layers were concentrated under reduced pressure. The residue was purified by reverse phase chromatography to afford (2S)—N-((6$^3$S,4S,Z)-1'-ethyl-1$^2$-(2-((S)-1-methoxyethyl)-5-(4-methylpiperazin-1-yl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)-3-methyl-2-(1,3,3-trimethylureido)butanamide (2.5 g, 33.2% yield) as a solid. $^1$H NMR (400 MHz, DMSO-d$_6$) δ 8.52-8.34 (m, 3H), 7.82 (s, 1H), 7.79-7.69 (m, 1H), 7.60-7.50 (m, 1H), 7.26-7.16 (m, 1H), 5.64-5.50 (m, 1H), 5.20-5.09 (m, 1H), 4.40-4.08 (m, 5H), 3.92-3.82 (m, 1H), 3.66-3.50 (m, 2H), 3.37-3.35 (m. 1H), 3.30-3.28 (m, 1H), 3.28-3.20 (m, 4H), 3.19-3.15 (m, 3H), 3.12-3.04 (m, 1H), 2.99-2.89 (m, 1H), 2.81 (s, 6H), 2.77 (s, 4H), 2.48-2.38 (m, 5H), 2.22 (s, 3H), 2.16-2.04 (m, 2H), 1.88-1.78 (m, 2H), 1.60-1.45 (m, 2H), 1.39-1.29 (m, 3H), 0.97-0.80 (m, 12H), 0.34 (s, 3H). LCMS (ESI): m/z [M+H] calc'd for $C_{48}H_{68}N_{10}O_6S$ 912.5; found 913.6.

Example A265. The synthesis of N-((6³S,4S,Z)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)-4-methylpiperazine-1-carboxamide

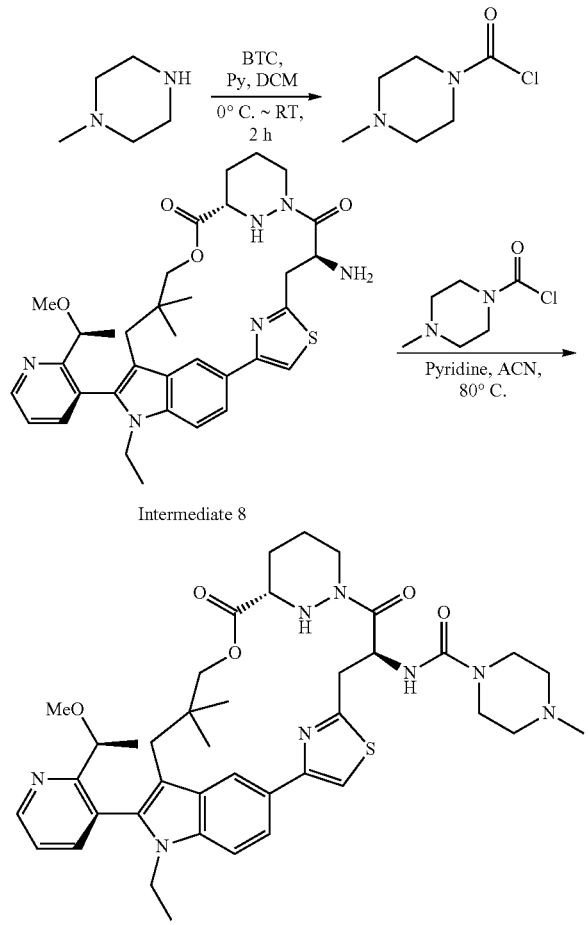

Intermediate 8

Step 1. To a stirred solution of 1-methylpiperazine (100 mg, 1.148 mmol) and Pyridine (275.78 mg, 3.44 mmol) in DCM (3 mL) were added BTC (112.5 mg, 0.38 mmol) in DCM (1 mL) dropwise at 0° C. under nitrogen atmosphere. The reaction was stirred for 2 hh 0° C. under nitrogen atmosphere. The resulting mixture was concentrated under reduced pressure to afford 4-methylpiperazine-1-carbonyl chloride (250 mg, crude) as an oil.

Step 2. To a stirred solution of Intermediate 8 (100 mg, 0.16 mmol) and pyridine (100 mg, 1.272 mmol) in ACN (2 mL) was added 4-methylpiperazine-1-carbonyl chloride (38.67 mg, 0.24 mmol) dropwise at 0° C. under nitrogen atmosphere. The reaction mixture was stirred for 2 hh at 0° C. under nitrogen atmosphere. The resulting mixture was diluted with water (100 mL) and extracted with EtOAc (100 mL×3). The combined organic layers were washed with brine (50 mL×3), dried over anhydrous $Na_2SO_4$, then filtered and concentrated under reduced pressure. The residue was purified by reverse flash chromatography to give N-((6³S,4S,Z)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)-4-methylpiperazine-1-carboxamide (20 mg, 16.7% yield) as a solid. ¹H NMR (400 MHz, DMSO-$d_6$) δ 8.76 (dd, J=4.8, 1.7 Hz, 1H), 8.50 (s, 1H), 8.14 (d, J=2.5 Hz, 1H), 7.79 (d, J=9.1 Hz, 2H), 7.77-7.72 (m, 1H), 7.58 (d, J=8.6 Hz, 1H), 7.52 (dd, J=7.7, 4.7 Hz, 1H), 6.82 (d, 0=9.0 Hz, 1H), 5.32 (t, J=9.0 Hz, 1H), 4.99 (d, J=12.1 Hz, 1H), 4.43-4.02 (m, 5H), 3.57 (d, J=3.1 Hz, 2H), 3.26 (d, J=8.4 Hz, 6H), 2.97 (d, J=14.3 Hz, 1H), 2.80-2.66 (m, 1H), 2.55 (s, 1H), 2.40 (d, J=14.4 Hz, 1H), 2.32 (d, J=5.9 Hz, 4H), 2.21 (s, 3H), 2.09 (d, J=12.1 Hz, 1H), 1.77 (d, J=18.8 Hz, 2H), 1.52 (dd, J=11.8, 5.4 Hz, 1H), 1.37 (d, J=6.0 Hz, 3H), 1.24 (s, 1H), 0.90 (s, 3H), 0.85 (t, J=7.0 Hz, 3H), 0.32 (s, 3H). LCMS (ESI): m/z [M+H] calc'd for $C_{40}H_{52}N_8O_5S$ 756.38; found 757.3.

Example A598. The synthesis of (2S)—N-((6³S,3S,4S,Z)-1¹-ethyl-3-methoxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)-3-methyl-2-(1,3,3-trimethylureido)butanamide

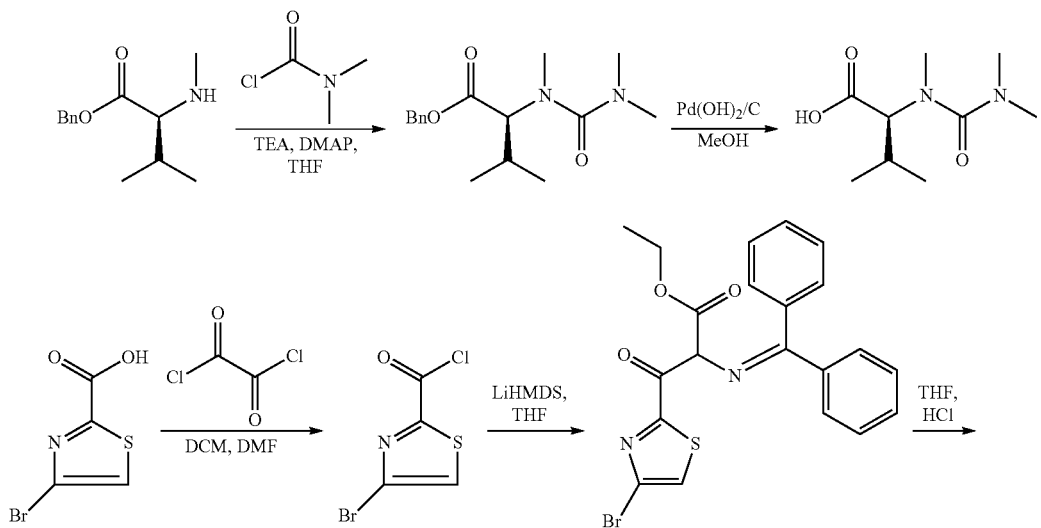

715
716
-continued
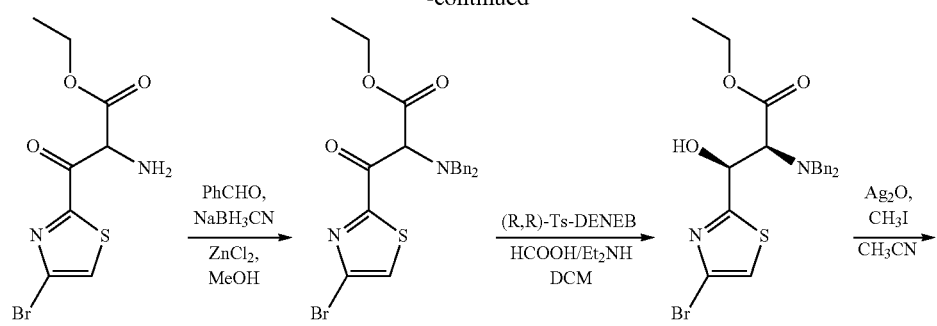
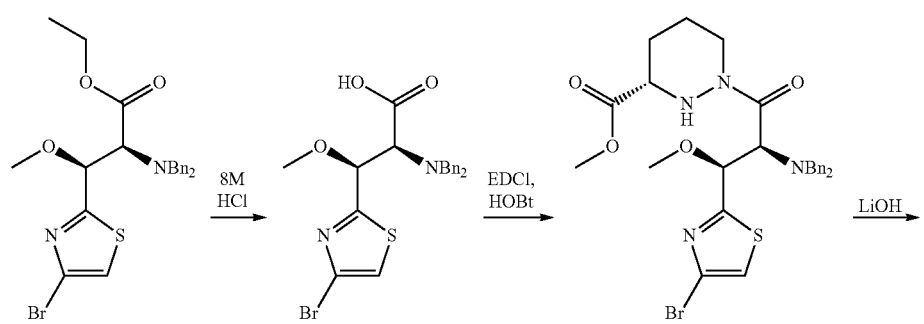
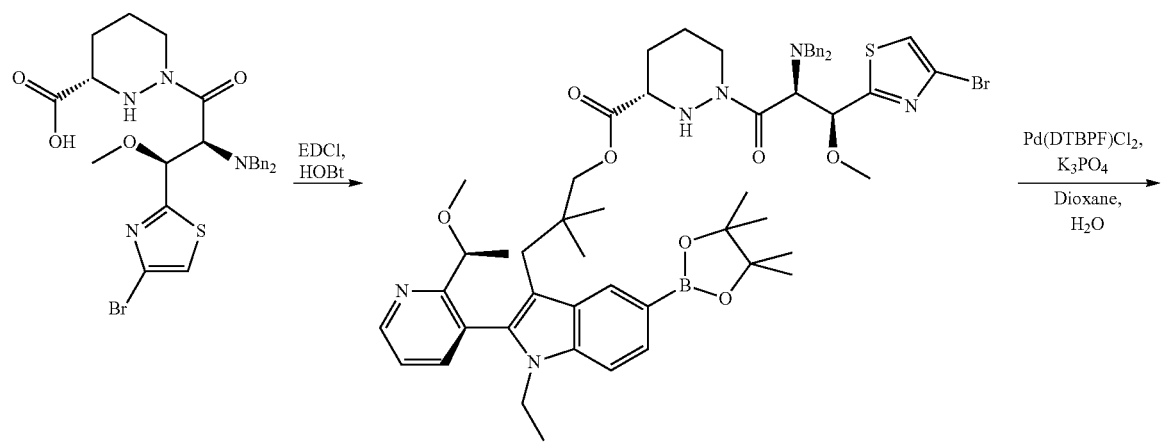
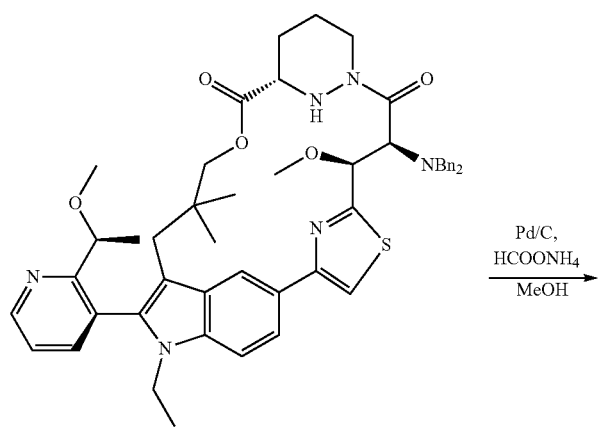

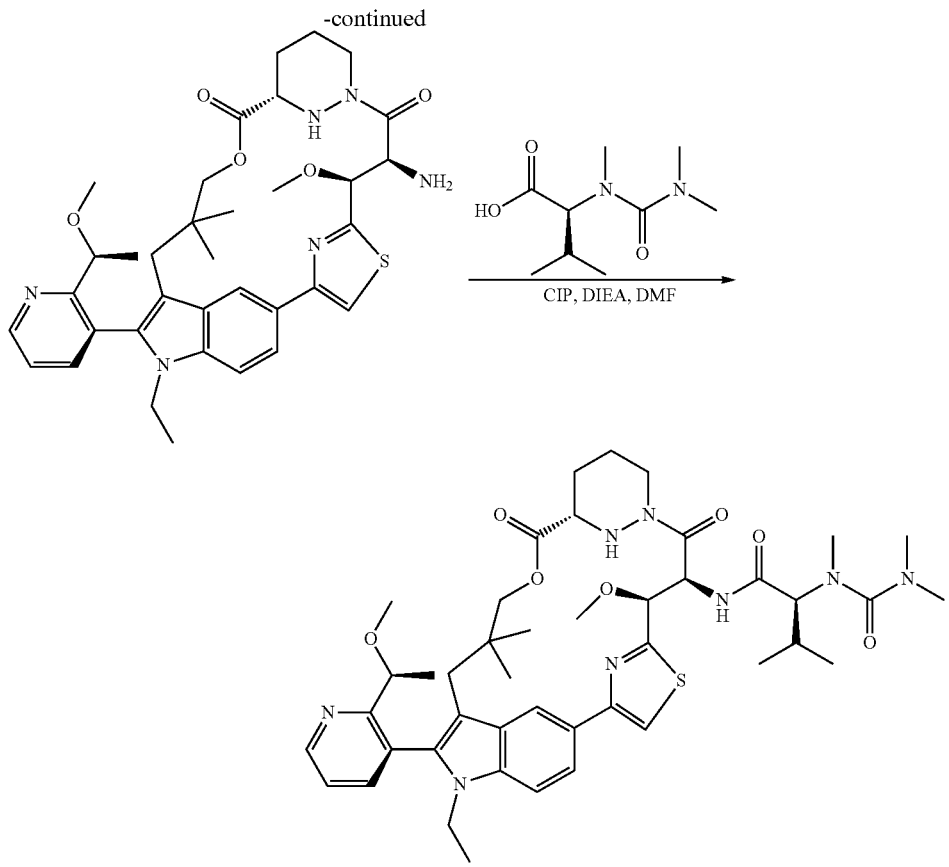

Step 1. A mixture of benzyl (2S)-3-methyl-2-(methylamino)butanoate (500 mg, 2.26 mmol) and dimethylcarbamyl chloride (1.215 g, 11.3 mmol) in THF (5 mL), was added TEA (2.286 g, 22.59 mmol) and DMAP (276.02 mg, 2.26 mmol) in portions under nitrogen atmosphere. The reaction mixture was stirred at 65° C. for 12 hh under nitrogen atmosphere, then quenched with water (100 mL) and was extracted with EtOAc (50 mL×3). The combined organic phase was dried over anhydrous sodium sulfate, filtered and concentrated under reduced pressure. The residue was purified by reverse phase chromatography to afford benzyl N-(dimethylcarbamoyl)-N-methyl-L-valinate (400 mg, 58.3% yield) as an oil. LCMS (ESI): m/z [M+H] calc'd for $C_{16}H_{24}N_2O_3$ 292.2; found 293.1.

Step 2. A mixture of benzyl N-(dimethylcarbamoyl)-N-methyl-L-valinate (400 mg, 1.37 mmol) and palladium hydroxide on carbon (400 mg, 2.85 mmol) in MeOH (10 mL) was stirred for 4 hh under hydrogen atmosphere. The reaction mixture was filtered and the filter cake was washed with MeOH (100 mL×3). The filtrate was concentrated under reduced pressure to afford N-(dimethylcarbamoyl)-N-methyl-L-valine (200 mg, crude) as an oil. LCMS (ESI): m/z [M+H] calc'd for $C_9H_{18}N_2O_3$ 202.1; found 203.1.

Step 3. A solution of 4-bromo-1,3-thiazole-2-carboxylic acid (10 g, 48.07 mmol) in DCM (100 mL), was added oxalyl chloride (16.27 mL, 192.28 mmol) and DMF (0.11 mL, 1.53 mmol) at 0° C. The reaction was stirred for at room temperature for 2 hh, then concentrated under reduced pressure to afford 4-bromo-1,3-thiazole-2-carbonyl chloride (10.8 g, crude).

Step 4. A solution of ethyl 2-[(diphenylmethylidene)amino]acetate (12.75 g, 47.69 mmol) in THF (100 mL) at −78° C., was added LiHMDS (47.69 mL, 47.69 mmol), and stirred at −40° C. for 30 minutes. Then the reaction mixture was added a solution of 4-bromo-1,3-thiazole-2-carbonyl chloride (10.8 g, 47.69 mmol) in THF (100 mL) at −78° C. and stirred at room temperature for 12 hh. The resulting mixture was quenched with water (100 mL), extracted with EtOAc (100 mL×3). The combined organic layers were dried over anhydrous sodium sulfate, filtered and concentrated under reduced pressure to afford ethyl 3-(4-bromothiazol-2-yl)-2-((diphenylmethylene)amino)-3-oxopropanoate (27 g, crude) as a solid. LCMS (ESI): m/z [M+H] calc'd for $C_{21}H_{17}BrN_2O_3S$ 456.0; found 457.0.

Step 5. A solution of ethyl 3-(4-bromothiazol-2-yl)-2-((diphenylmethylene)amino)-3-oxopropanoate (20 g, 43.73 mmol) in THF (150 mL) at 0° C., was added 1 M HCl (100 mL) and stirred at room temperature for 2 hh. The resulting solution was concentrated and washed with ethyl ether (200 mL×2). The water phase was adjusted pH to 8 with sodium bicarbonate solution, then extracted with EtOAc (100 mL×3). The combined organic layers were dried over anhydrous sodium sulfate, filtered and concentrated under reduced pressure to afford ethyl 2-amino-3-(4-bromothiazol-2-yl)-3-oxopropanoate as an oil (9 g, crude). LCMS (ESI): m/z [M+H] calc'd for $C_8H_9BrN_2O_3S$ 292.0; found 292.9.

Step 6. A solution of ethyl 2-amino-3-(4-bromothiazol-2-yl)-3-oxopropanoate (10 g, 34.11 mmol) in MeOH (200 mL) at 0° C., was added benzaldehyde (7.24 g, 68.23 mmol), zinc chloride (9.3 g, 68.23 mmol) and $NaBH_3CN$ (4.29 g, 68.23 mmol). The reaction was stirred at room temperature for 2 hh, then quenched with water (100 mL) and concentrated. The resulting mixture was extracted with EtOAc (100 mL×3). The combined organic layers were dried over anhydrous sodium sulfate, filtered and concentrated under reduced pressure. The residue was purified by silica gel chromatography to afford ethyl 3-(4-bromothiazol-2-yl)-2-(dibenzylamino)-3-oxopropanoate as a solid (8.4 g, 52% yield). LCMS (ESI): m/z [M+H] calc'd for $C_{22}H_{21}BrN_2O_3S$ 472.1; found 473.0.

Step 7. A mixture of ethyl 3-(4-bromothiazol-2-yl)-2-(dibenzylamino)-3-oxopropanoate (5 g, 10.56 mmol) and (R,R)-TS-DENEB (1.375 g, 2.11 mmol) in DCM (100 mL), was added HCOOH (1.99 mL, 43.29 mmol) and diethylamine (2.2 mL, 2.11 mmol) dropwise at room temperature under nitrogen atmosphere. The reaction mixture was stirred at 50° C. for 12 hh under nitrogen atmosphere. The resulting mixture was concentrated under reduced pressure. The residue was purified by silica gel column chromatography to afford ethyl (2S,3S)-3-(4-bromothiazol-2-yl)-2-(dibenzylamino)-3-hydroxypropanoate (3.148 g, 60% yield) as an oil. LCMS (ESI): m/z [M+H] calc'd for $C_{22}H_{23}BrN_2O_3S$ 474.1; found 475.0.

Step 8. A mixture of ethyl (2S,3S)-3-(4-bromothiazol-2-yl)-2-(dibenzylamino)-3-hydroxypropanoate (1 g, 2.1 mmol) and $Ag_2O$ (4.88 g, 21.06 mmol) in acetonitrile (10 mL), was added iodomethane (3.58 g, 25.22 mmol) in portions. The reaction mixture was stirred at 50° C. for 12 hh, then filtered. The filter cake was washed with MeOH (50 mL×2). The filtrate was concentrated under reduced pressure to afford ethyl (2S,3S)-3-(4-bromothiazol-2-yl)-2-(dibenzylamino)-3-methoxypropanoate (1.06 g, crude) as an oil. LCMS (ESI): m/z [M+H] calc'd for $C_{23}H_{25}BrN_2O_3S$ 488.1; found 489.3.

Step 9. A mixture of ethyl (2S,3S)-3-(4-bromothiazol-2-yl)-2-(dibenzylamino)-3-hydroxypropanoate (1.06 g, 2.3 mmol) in HCl (10 ml, 8 M) was stirred at 80° C. for 12 hh and concentrated by reduced pressure. The residue was purified by reverse phase chromatography to afford (2S,3S)-3-(4-bromothiazol-2-yl)-2-(dibenzylamino)-3-methoxypropanoic acid (321 mg, 31.7% yield) as a solid. LCMS (ESI): m/z [M+H] calc'd for $C_{21}H_{21}BrN_2O_3S$ 460.1; found 461.1.

Step 10. A solution of (2S,3S)-3-(4-bromothiazol-2-yl)-2-(dibenzylamino)-3-methoxypropanoic acid (4.61 g, 10 mmol) in DCM (100 mL) at 0° C. was added methyl (3S)-1,2-diazinane-3-carboxylate bis(trifluoroacetic acid) salt (3.72 g, 15 mmol), NMM (10.1 mL. 100 mmol), EDCl (3.8 g, 20 mmol) and HOBt (5.39 g, 39.89 mmol). The solution was warmed to room temperature and stirred for 1 h. The reaction was then quenched with $H_2O$ (100 mL) and was extracted with EtOAc (100 mL×3). The combined organic layers were dried over anhydrous sodium sulfate, filtered, and concentrated under reduced pressured. The residue was purified by silica gel column chromatography to give methyl (S)-1-((2S,3S)-3-(4-bromothiazol-2-yl)-2-(dibenzylamino)-3-methoxypropanoyl)hexahydropyridazine-3-carboxylate (5.11 g, 90% yield) as a solid. LCMS (ESI): m/z [M+H] calc'd for $C_{27}H_{31}BrN_4O_4S$ 587.1; found 586.1.

Step 11. A solution of methyl (S)-1-((2S,3S)-3-(4-bromothiazol-2-yl)-2-(dibenzylamino)-3-methoxypropanoyl) hexahydropyridazine-3-carboxylate (5.11 g, 9 mmol) in THF (100 mL)/$H_2O$ (100 mL) was added LiOH (1.81 g, 45 mmol) under $N_2$ atmosphere and the resulting mixture was stirred for 2 hh at 25° C. The resulting mixture was concentrated under reduced pressure, the residue was acidified to pH 5 with HCL (1N). The aqueous layer was extracted with DCM (50 mL×3). The combined organic phase was concentrated under reduced pressure to give (S)-1-((2S,3S)-3-(4-bromothiazol-2-yl)-2-(dibenzylamino)-3-methoxypropanoyl)hexahydropyridazine-3-carboxylic acid (4.38 g, 85% yield) as a solid. LCMS (ESI): m/z [M+H] calc'd for $C_{26}H_{29}BrN_4O_4S$ 572.1; found 573.1.

Step 12. A mixture of (S)-1-((2S,3S)-3-(4-bromothiazol-2-yl)-2-(dibenzylamino)-3-methoxypropanoyl)hexahydropyridazine-3-carboxylic acid (1.15 g, 2 mmol) and (S)-3-(1-ethyl-2-(2-(1-methoxyethyl)pyridin-3-yl)-5-(4,4,5,5-tetramethyl-1,3,2-dioxaborolan-2-yl)-1H-indol-3-yl)-2,2-dimethylpropan-1-ol (985 mg, 2 mmol) in DCM (50 mL), was added DIEA (1.034 g, 8 mmol), EDCl (1.15 g, 558.3 mmol), HOBT (270.2 mg, 2 mmol). The reaction solution was stirred at 25° C. for 16 hh. The resulting mixture was diluted with DCM (200 mL), washed with water (50 mL×2) and brine (50 mL×3) and dried over anhydrous sodium sulfate, filtered and concentrated under reduced pressure. The residue was purified by silica gel column chromatography to afford 3-(1-ethyl-2-(2-((S)-1-methoxyethyl)pyridin-3-yl)-5-(4,4,5,5-tetramethyl-1,3,2-dioxaborolan-2-yl)-1H-indol-3-yl)-2,2-dimethylpropyl (S)-1-((2S,3S)-3-(4-bromothiazol-2-yl)-2-(dibenzylamino)-3-methoxypropanoyl)hexahydropyridazine-3-carboxylate (1.13 g, 54% yield) as a solid. LCMS (ESI): m/z [M+H] calc'd for $C_{55}H_{68}BBrN_6O_7S$ 1046.4; found 1047.4.

Step 13. A mixture of 3-(1-ethyl-2-(2-((S)-1-methoxyethyl)pyridin-3-yl)-5-(4,4,5,5-tetramethyl-1,3,2-dioxaborolan-2-yl)-1H-indol-3-yl)-2,2-dimethylpropyl (S)-1-((2S,3S)-3-(4-bromothiazol-2-yl)-2-(dibenzylamino)-3-methoxypropanoyl)hexahydropyridazine-3-carboxylate (250 mg, 0.24 mmol) and Pd(DtBPF)Cl$_2$ (15.55 mg, 0.024 mmol) in dioxane (5 mL) and water (1 mL), was added $K_3PO_4$ (126.59 mg, 0.6 mmol) in portions under nitrogen atmosphere. The reaction mixture was stirred at 80° C. for 2 hh under nitrogen atmosphere. The resulting mixture was diluted with water (20 mL) and extracted with EtOAc (10 mL×3), dried over anhydrous sodium sulfate, filtered and concentrated under reduced pressure. The residue was purified by silica gel column chromatography to afford ($6^3$S,3S,4S,Z)-4-(dibenzylamino)-$1^1$-ethyl-3-methoxy-$1^2$-(2-((S)-1-methoxyethyl)pyridin-3-yl)-10,10-dimethyl-$6^1,6^2,6^3,6^4,6^5$,$6^6$-hexahydro-$1^1$H-8-oxa-2(4,2)-thiazola-1(5,3)-indola-6(1,3)-pyridazinacycloundecaphane-5,7-dione (137 mg, 44.38%) as a solid. LCMS (ESI): m/z [M+H] calc'd for $C_{49}H_{56}N6O_5S$ 840.4; found 841.5.

Step 14. A mixture of (($6^3$S,3S,4S,Z)-4-(dibenzylamino)-$1^1$-ethyl-3-methoxy-$1^2$-(2-((S)-1-methoxyethyl)pyridin-3-yl)-10,10-dimethyl-$6^1,6^2,6^3,6^4,6^5,6^6$-hexahydro-$1^1$H-8-oxa-2(4,2)-thiazola-1(5,3)-indola-6(1,3)-pyridazinacycloundecaphane-5,7-dione (100 mg, 0.12 mmol) and Pd/C (253.06 mg, 2.38 mmol) in MeOH (10 mL), was added HCOONH$_4$ (149.94 mg, 2.38 mmol) in portions. The reaction mixture was stirred at 60° C. for 6 hh under hydrogen atmosphere. The resulting mixture was filtered, the filter cake was washed with MeOH (100 mL×10). The filtrate was concentrated under reduced pressure to afford ($6^3$S,3S,4S,Z)-4-amino-$1^1$-ethyl-3-methoxy-$1^2$-(2-((S)-1-methoxyethyl)pyridin-3-yl)-10,10-dimethyl-$6^1,6^2,6^3,6^4,6^5$, $6^6$-hexahydro-$1^1$H-8-oxa-2(4,2)-thiazola-1(5,3)-indola-6(1,3)-pyridazinacycloundecaphane-5,7-dione (56 mg, crude) as an oil. LCMS (ESI): m/z [M+H] calc'd for $C_{35}H_{44}N_6O_5S$ 660.3; found 661.2.

Step 15. A mixture of ($6^3$S,3S,4S,Z)-4-amino-$1^1$-ethyl-3-methoxy-$1^2$-(2-((S)-1-methoxyethyl)pyridin-3-yl)-10,10-dimethyl-$6^1,6^2,6^3,6^4,6^5,6^6$-hexahydro-$1^1$H-8-oxa-2(4,2)-thiazola-1(5,3)-indola-6(1,3)-pyridazinacycloundecaphane-5,7-dione (56 mg, 0.085 mmol) and N-(dimethylcarbamoyl)-N-methyl-L-valine (51.42 mg, 0.25 mmol) in DMF (2 mL), was added 2-Chloro-1,3-dimethylimidazolidinium hexafluorophosphate (47.55 mg, 0.17 mmol) and DIEA (547.62 mg, 4.24 mmol) in portions. The reaction mixture was stirred for 12 hh. The resulting mixture was purified by reverse phase chromatography to afford (2S)—N-(($6^3$S,3S, 4S,Z)-$1^1$-ethyl-3-methoxy-$1^2$-(2-((S)-1-methoxyethyl)pyridin-3-yl)-10,10-dimethyl-5,7-dioxo-$6^1,6^2,6^3,6^4,6^5,6^6$-hexahydro-1¹H-8-oxa-2(4,2)-thiazola-1(5,3)-indola-6(1,3)-pyridazinacycloundecaphane-4-yl)-3-methyl-2-(1,3,3-trimethylureido)butanamide (1.5 mg, 2.06% yield) as a solid. ¹H NMR (400 MHz, Methanol-d₄) δ 8.74-8.77 (m, 1H), 8.61 (d, J=1.6 Hz, 1H), 7.99-7.87 (m, 1H), 7.73-7.66 (m, 1H), 7.68 (s, 1H), 7.60-7.55 (m, 1H), 7.49 (d, J=8.7 Hz, 1H), 7.31 (d, J=51.0 Hz, 0H), 5.89 (s, 1H), 4.95 (s, 1H), 4.43 (d, J=13.0 Hz, 1H), 4.36 (q, J=6.2 Hz, 1H), 4.33-4.19 (m, 2H), 4.10-4.03 (m, 1H), 4.03 (d, J=11.2 Hz, 1H), 3.78-3.67 (m, 2H), 3.65 (s, 0H), 3.46 (s, 3H), 3.34 (s, 4H), 3.01 (d, J=10.3 Hz, 1H), 2.93 (s, 6H), 2.88-2.81 (m, 1H), 2.78 (s, 3H), 2.70-2.60 (m, 1H), 2.23-2.01 (m, 2H), 2.03 (s, 0H), 1.99 (d, J=13.3 Hz, 1H), 1.91-1.74 (m, 1H), 1.69-1.54 (m, 1H), 1.45 (d, J=6.2 Hz, 3H), 1.37-1.32 (m, 1H), 1.28 (s, 1H), 0.94 (p, J=6.7 Hz, 12H), 0.51 (s, 3H), 0.10 (s, 1H). LCMS (ESI): m/z [M+H] calc'd for $C_{44}H_{60}N_8O_7$ 844.4; found 845.4.

Example A286. The synthesis of (1S,2S)—N-((6³S,4S,Z)-1¹-ethyl-1²-(2-((S)-1-methoxyethyl)pyridin-3-yl)-6⁴,10,10-trimethyl-5,7-dioxo-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)-2-methylcyclopropane-1-carboxamide

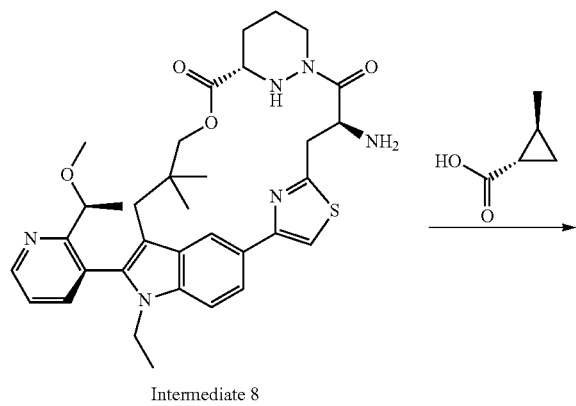

Intermediate 8

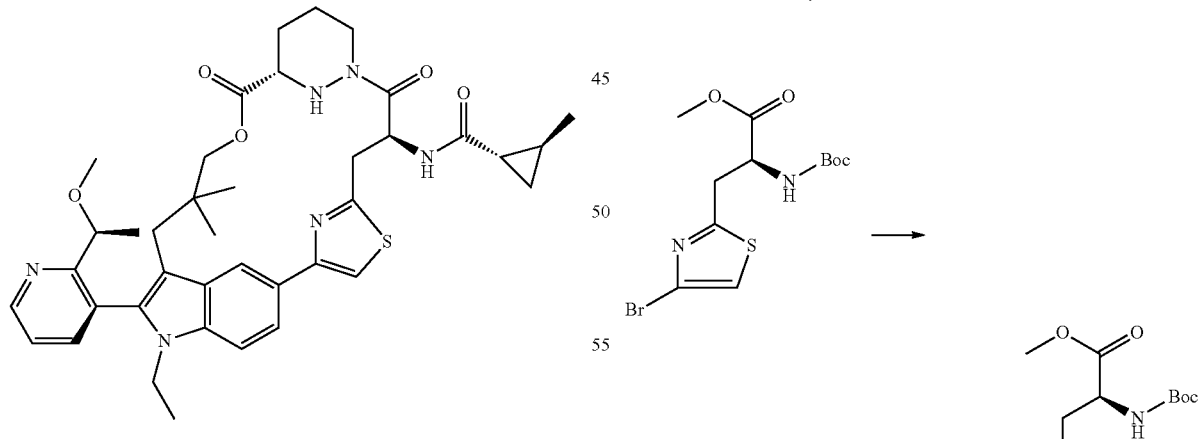

Step 1. A solution of Intermediate 8 (8 g, 10.95 mmol) in HCl (200 mL, 4M in 1,4-dioxane) was stirred at 0° C. for 2 hh, then concentrated under reduced pressure. The resulting mixture was diluted with DCM (60 mL) and saturated NaHCO₃ aqueous solution (40 mL). The organic phase was separated and washed with brine (50 mL×2) and concentrated under reduced pressure to give (6³S,4S,Z)-4-amino-1¹-ethyl-1²-(2-((S)-1-methoxyethyl)pyridin-3-yl)-10,10-di-methyl-6¹,6²,6³,6⁴,6⁵,6⁶-hexahydro-1¹H-8-oxa-2(4,2)-thiazola-1(5,3)-indola-6(1,3)-pyridazinacycloundecaphane-5,7-dione (10.3 g, crude) as solid. LCMS (ESI): m/z [M+H] calc'd for $C_{34}H_{42}N_6O_4S$ 630.3; found 631.2.

Step 2. A stirred solution of (6³S,4S,Z)-4-amino-1¹-ethyl-1²-(2-((S)-1-methoxyethyl)pyridin-3-yl)-10,10-dimethyl-6¹,6²,6³,6⁴,6⁵,6⁶-hexahydro-1¹H-8-oxa-2(4,2)-thiazola-1(5,3)-indola-6(1,3)-pyridazinacycloundecaphane-5,7-dione (8 g, 12.68 mmol) in DMF (50 mL) at 0° C., was added DIEA (9.83 g, 76.09 mmol), (1S,2S)-2-methylcyclopropane-1-carboxylic acid (1.52 g, 15.22 mmol) and HATU (14.47 g, 38.05 mmol). The reaction mixture was stirred at 0° C. for 2 hh and concentrated under reduced pressure. The residue was purified by reverse phase chromatography to afford (1 S,2S)—N-((6³S,4S,Z)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)-2-methylcyclopropane-1-carboxamide (6.84 g, 56.37% yield) as a solid. ¹H NMR (400 MHz, DMSO-d₆) δ 8.79 (dd, J=4.7, 1.9 Hz, 1H), 8.59-8.40 (m, 2H), 7.95-7.86 (m, 1H), 7.82-7.71 (m, 2H), 7.66-7.53 (m, 2H), 5.57 (t, J=9.0 Hz, 1H), 5.07 (s, 1H), 4.41-4.28 (m, 2H), 4.25 (d, J=12.4 Hz, 1H), 4.17 (d, J=10.8 Hz, 1H), 4.09 (d, J=7.2 Hz, 1H), 3.58 (s, 2H), 3.32 (d, J=14.6 Hz, 1H), 3.28 (s, 3H), 3.16 (dd, J=14.7, 9.1 Hz, 1H), 2.95 (d, J=14.4 Hz, 1H), 2.75 (m, J=12.1, 7.1 Hz, 1H), 2.43 (d, J=14.4 Hz, 1H), 2.13-2.00 (m, 1H), 1.76 (d, J=22.0 Hz, 2H), 1.60-1.44 (m, 2H), 1.38 (d, J=6.1 Hz, 3H), 1.07 (d, J=1.9 Hz, 4H), 0.86 (dd, J=14.1, 7.1 Hz, 7H), 0.59-0.49 (m, 1H), 0.34 (s, 3H). LCMS (ESI): m/z [M+H] calc'd for $C_{39}H_{48}N_6O_5S$ 712.3; found 713.2.

Example A613. The synthesis of N-((2S)-1-(((6³S,4S,Z)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-2(4,2)-thiazola-1(5,3)-pyrrolo[3,2-b]pyridina-6(1,3)-pyridazinacycloundecaphane-4-yl)amino)-3-methyl-1-oxobutan-2-yl)-3-methoxy-N-methylazetidine-1-carboxamide

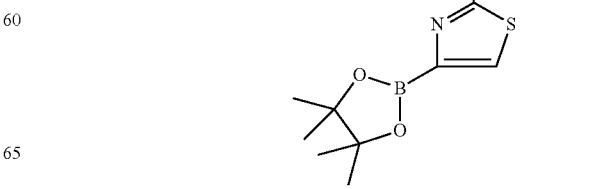

723
-continued
724
-continued
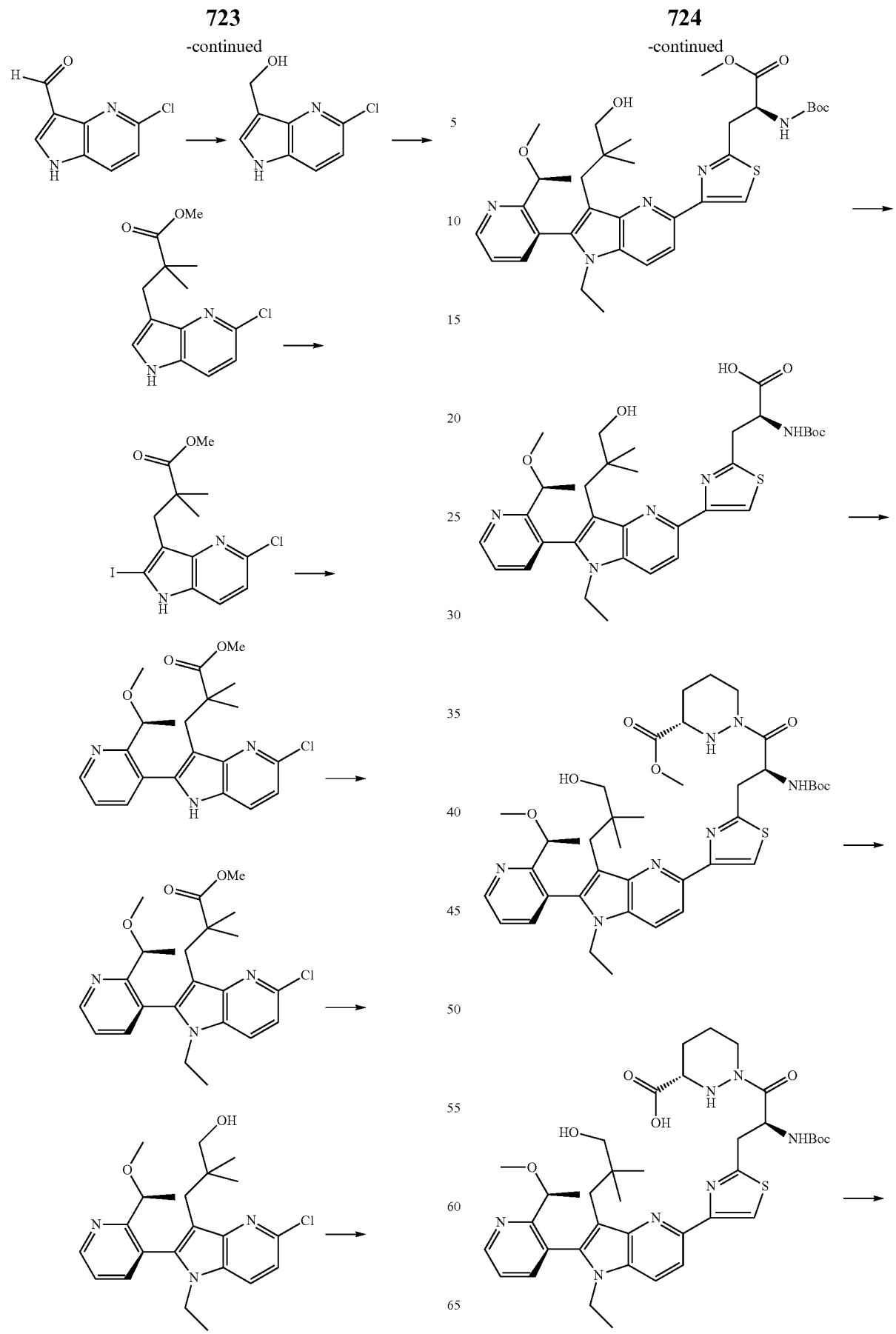

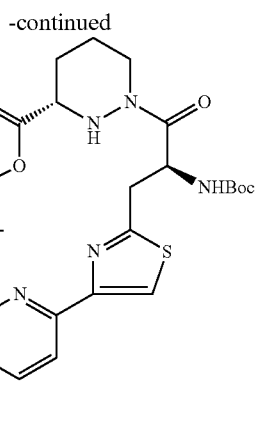

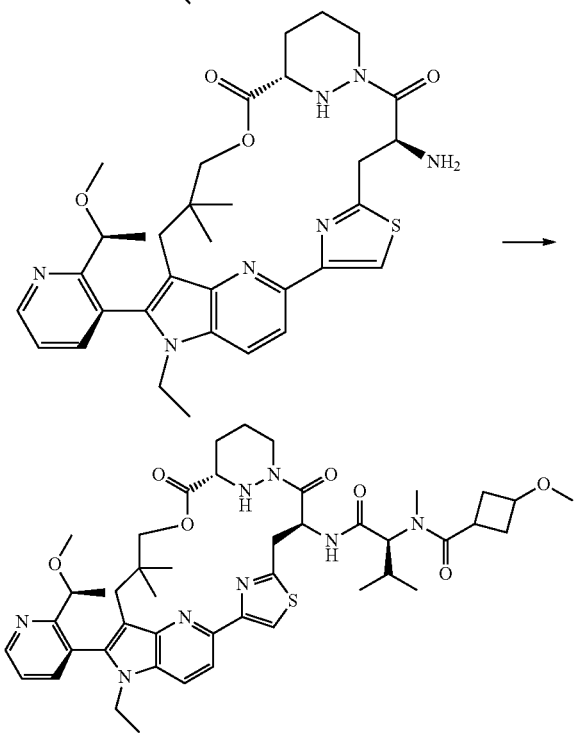

Step 1. A mixture of methyl (S)-3-(4-bromothiazol-2-yl)-2-((tert-butoxycarbonyl)amino)propanoate (920 mg, 2.5 mmol), 4,4,5,5-tetramethyl-2-(4,4,5,5-tetramethyl-1,3,2-dioxaborolan-2-yl)-1,3,2-dioxaborolane (1.6 g, 6.3 mmol), x-Phos (180 mg, 0.5 mmol), Pd$_2$(dba)$_3$-chloroform (130 mg, 0.13 mmol) and potassium acetate (740 mg, 7.5 mmol) in dioxane (25 mL) in a sealed tube under N$_2$ atmosphere, was stirred at 110° C. for 8 hh to afford crude methyl (S)-2-((tert-butoxycarbonyl)amino)-3-(4-(4,4,5,5-tetramethyl-1,3,2-dioxaborolan-2-yl)thiazol-2-yl)propanoate as a solution. LCMS (ESI): m/z [M+H] calc'd for C$_{18}$H$_{29}$BN$_2$O$_6$S 412.2; found 331.1.

Step 2. A mixture of 5-chloro-1H-pyrrolo[3,2-b]pyridine-3-carbaldehyde (7 g, 39 mmol) in MeOH (140 mL) under N$_2$ atmosphere, was added NaBH$_4$ (2.9 g, 78 mmol) at 0° C. The reaction mixture was stirred at 10° C. for 2 hh and concentrated under reduced pressure. The residue was diluted with EtOAc (200 mL), washed with brine (25 mL), dried over anhydrous sodium sulfate and concentrated under reduced pressure. The residue was purified by silica gel column chromatography to afford (5-chloro-1H-pyrrolo[3,2-b]pyridin-3-yl)methanol (3.5 g, 55% yield) as a solid. LCMS (ESI): m/z [M+H] calc'd for C$_8$H$_7$ClN$_2$O 182.0; found 183.0.

Step 3. A mixture of (5-chloro-1H-pyrrolo[3,2-b]pyridin-3-yl)methanol (3.5 g, 19 mmol) and ((1-methoxy-2-methylprop-1-en-1-yl)oxy)trimethylsilane (6.7 g, 38 mmol) in THF (50 mL), was dropwise added TMSOTf (3.8 g, 17.1 mmol) at 0° C. The reaction mixture was stirred at 5° C. for 2 hh, then diluted with EtOAc (100 mL), washed with saturated NaHCO$_3$ aqueous (50 mL), and brine (50 mL×2). The organic layer was dried over anhydrous sodium sulfate and concentrated under reduced pressure. The residue was purified by silica gel column chromatography to afford methyl 3-(5-chloro-1H-pyrrolo[3,2-b]pyridin-3-yl)-2,2-dimethylpropanoate (3 g, 59% yield) as a solid. LCMS (ESI): m/z [M+H] calc'd for C$_{13}$H$_{15}$ClN$_2$O$_2$ 266.1; found 267.1.

Step 4. A mixture of methyl 3-(5-chloro-1H-pyrrolo[3,2-b]pyridin-3-yl)-2,2-dimethylpropanoate (3 g, 11 mmol) in anhydrous THF (50 mL) at 0° C., was added AgOTf (4.3 g, 17 mmol) and I$_2$ (2.9 g, 11 mmol). The reaction mixture was stirred at 0° C. for 2 hh, then quench with conc. Na$_2$SO$_3$ (20 mL), diluted with EtOAc (50 mL) and filtered. The filtrate was washed with brine (50 mL). The organic layer was dried over anhydrous sodium sulfate and concentrated under reduced pressure. The residue was purified with silica gel column chromatography to afford methyl 3-(5-chloro-2-iodo-1H-pyrrolo[3,2-b]pyridin-3-yl)-2,2-dimethylpropanoate (2.3 g, 52% yield) as a solid. LCMS (ESI): m/z [M+H] calc'd for C$_{13}$H$_{14}$ClIN$_2$O$_2$ 393.0; found 392.0.

Step 5. A mixture of methyl 3-(5-chloro-2-iodo-1H-pyrrolo[3,2-b]pyridin-3-yl)-2,2-dimethylpropanoate (2.3 g, 5.9 mmol), 2-(2-(2-methoxyethyl)phenyl)-4,4,5,5-tetramethyl-1,3,2-dioxaborolane (1.6 g, 7.1 mmol) and K$_2$C$_{O3}$ (2.4 g, 18 mol) in dioxane (25 mL) and water (5 mL) under N$_2$ atmosphere, was added Pd(dppf)Cl2.DCM (480 mg, 0.59 mmol). The reaction mixture was stirred at 70° C. for 4 hh, then diluted with EtOAc (200 mL) and washed with brine (25 mL). The separated organic layer was dried over anhydrous sodium sulfate and concentrated under reduced pressure. The residue was purified by silica gel column chromatography to afford methyl (S)-3-(5-chloro-2-(2-(1-methoxyethyl)pyridin-3-yl)-1H-pyrrolo[3,2-b]pyridin-3-yl)-2,2-dimethylpropanoate (2 g, yield 84%) as a solid. LCMS (ESI): m/z [M+H] calc'd for C$_{21}$H$_{24}$ClN$_3$O$_3$ 401.2; found 402.2.

Step 6. A mixture of methyl (S)-3-(5-chloro-2-(2-(1-methoxyethyl)pyridin-3-yl)-1H-pyrrolo[3,2-b]pyridin-3-yl)-2,2-dimethylpropanoate (2 g, 5 mmol), cesium carbonate (3.3 g, 10 mmol) and EtI (1.6 g, 10 mmol) in DMF (30 mL) was stirred at 25° C. for 10 hh. The resulting mixture was diluted with EtOAc (100 mL), washed with brine (20 mL×4). The separated organic layer was dried over anhydrous sodium sulfate, filtered and concentrated under reduced pressure. The residue was purified by silica gel column chromatography to afford methyl (S)-3-(5-chloro-1-ethyl-2-(2-(1-methoxyethyl)pyridin-3-yl)-1H-pyrrolo[3,2-b]pyridin-3-yl)-2,2-dimethylpropanoate as two diastereomers (P1: 0.7 g, 32% yield; P2: 0.6 g, 28% yield) both as a solid. LCMS (ESI): m/z [M+H] calc'd for C$_{23}$H$_{28}$ClN$_3$O$_3$ 429.2; found 430.2.

Step 7. A mixture of methyl (S)-3-(5-chloro-1-ethyl-2-(2-(1-methoxyethyl)pyridin-3-yl)-1H-pyrrolo[3,2-b]pyridin-3-yl)-2,2-dimethylpropanoate (P2, 1.2 g, 2.8 mmol) in anhydrous THF (20 mL) at 5° C., was added LiBH$_4$ (120 mg, 5.6 mmol). The reaction mixture was stirred at 60° C. for 4 hh, then quenched with conc. NH$_4$Cl (20 mL), diluted with EtOAc (50 mL) and washed with brine (30 mL). The organic layer was separated, dried over anhydrous sodium sulfate and concentrated under reduced pressure. The residue was purified with silica gel column chromatography to afford (S)-3-(5-chloro-1-ethyl-2-(2-(1-methoxyethyl)pyridin-3-yl)-1H-pyrrolo[3,2-b]pyridin-3-yl)-2,2-dimethylpropan-1-ol (1 g, 89% yield) as a solid. LCMS (ESI): m/z [M+H] calc'd for $C_{22}H_{28}ClN_3O_2$ 401.2; found 402.2.

Step 8. A mixture of solution from Step 1 (360 mg, crude, 1 mmol) in dioxane (10 mL) and water (2 mL), was added (S)-3-(5-chloro-1-ethyl-2-(2-(1-methoxyethyl)pyridin-3-yl)-1H-pyrrolo[3,2-b]pyridin-3-yl)-2,2-dimethylpropan-1-ol (200 mg, 0.5 mmol), potassium carbonate (200 mg, 1.5 mmol) and Pd-118 (30 mg, 0.05 mmol). This reaction mixture was stirred at 70° C. for 3 hh, then diluted with EtOAc (40 mL), filtered. The filtrate was washed with brine, dried over anhydrous sodium sulfate, filtered and concentrated under reduced pressure. The residue was purified with silica gel column chromatography to afford methyl (S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-pyrrolo[3,2-b]pyridin-5-yl)thiazol-2-yl)propanoate (300 mg, 65% yield) as a solid. LCMS (ESI): m/z [M+H] calc'd for $C_{34}H_{45}N_5O_6S$ 651.3; found 652.3.

Step 9. A solution of methyl (S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-pyrrolo[3,2-b]pyridin-5-yl)thiazol-2-yl)propanoate (280 mg, 0.43 mmol) in MeOH (4 mL), was added a solution of lithium hydroxide (51 mg, 2.15 mmol) in water (2 mL) at 20° C. The reaction was stirred at 20° C. for 5 hh, then adjusted to pH=34 with HCl (1 N). The resulting mixture was diluted with water (30 mL) and extracted with EtOAc (15 mL*3). The combined organic phase was washed with brine (10 mL), dried over anhydrous sodium sulfate, filtered and concentrated under reduced pressure to give (S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-pyrrolo[3,2-b]pyridin-5-yl)thiazol-2-yl)propanoic acid (280 mg, crude) as a solid. LCMS (ESI): m/z [M+H] calc'd for $C_{33}H_{43}N_5O_6S$ 637.3; found 638.3.

Step 10. A solution of (S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-pyrrolo[3,2-b]pyridin-5-yl)thiazol-2-yl)propanoic acid (274 mg, 0.43 mmol) and methyl (S)-hexahydropyridazine-3-carboxylate (280 mg, 0.64 mmol) in DMF (3 mL) at 5° C., was added a solution of HATU (245 mg, 0.64 mmol) and DIEA (555 mg, 4.3 mmol) in DMF (2 mL). The reaction was stirred for 1 h, then diluted with EtOAc (20 mL) and water (20 mL). The organic layer was separated and washed with water (20 mL×3) and brine (20 mL), dried over anhydrous sodium sulfate, filtered concentrated under reduced pressure. The residue was purified by silica gel chromatography to give methyl (S)-1-((S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-pyrrolo[3,2-b]pyridin-5-yl)thiazol-2-yl)propanoyl)hexahydropyridazine-3-carboxylate (230 mg, 70% yield) as solid. LCMS (ESI): m/z [M+H] calc'd for $C_{39}H_{53}N_7O_7S$ 763.4; found 764.3.

Step 11. A solution of methyl (S)-1-((S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-pyrrolo[3,2-b]pyridin-5-yl)thiazol-2-yl)propanoyl)hexahydropyridazine-3-carboxylate (230 mg, 0.3 mmol) in DCE (3 mL), was added trimethyltin hydroxide (300 mg, 1.4 mmol) under N2 atmosphere. The reaction was stirred at 65° C. for 16 hh, then concentrated under reduced pressure. The residue was diluted with EtOAc (20 mL), washed with water (20 mL) and brine (10 mL), dried over anhydrous sodium sulfate, filtered and concentrated under reduced pressure to afford (S)-1-((S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-pyrrolo[3,2-b]pyridin-5-yl)thiazol-2-yl)propanoyl)hexahydropyridazine-3-carboxylic acid (200 mg, crude) as foam. LCMS (ESI): m/z [M+H] calc'd for $C_{38}H_{51}N_7O_7S$ 749.4; found 750.3.

Step 12. A solution of (S)-1-((S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-pyrrolo[3,2-b]pyridin-5-yl)thiazol-2-yl)propanoyl)hexahydropyridazine-3-carboxylic acid (245 mg, 0.32 mmol) in DCM (50 mL) at 5° C., were added HOBt (432 mg, 3.2 mmol), EDCl (1.8 g, 9.6 mmol) and DIEA (1.65 g, 12.8 mmol). The reaction mixture was stirred at 20° C. for 16 hh, then concentrated under reduced pressure. The residue was diluted with EtOAc (20 mL) and water (20 mL). The organic layer was separated and washed with water (30 mL×3) and brine (30 mL), dried over anhydrous sodium sulfate, filtered and concentrated under reduced pressure. The residue was purified by silica gel chromatography to give tert-butyl (($6^3$S,4S,Z)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-pyrrolo[3,2-b]pyridina-6(1,3)-pyridazinacycloundecaphane-4-yl)carbamate (100 mg, 43% yield) as solid. LCMS (ESI): m/z [M+H] calc'd for $C_{38}H_{49}N_7O_6S$ 731.4; found 732.3.

Step 13. A solution of tert-butyl (($6^3$S,4S,Z)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-pyrrolo[3,2-b]pyridina-6(1,3)-pyridazinacycloundecaphane-4-yl)carbamate (80 mg, 0.11 mmol) in TFA (0.2 mL) and DCM (0.6 mL) was stirred at 20° C. for 1 h. The reaction was concentrated to afford ($6^3$S,4S,Z)-4-amino-$1'$-ethyl-$1^2$-(2-((S)-1-methoxyethyl)pyridin-3-yl)-10,10-dimethyl-$6^1$,$6^2$,$6^3$,$6^4$,$6^5$,$6^6$-hexahydro-$1^1$H-8-oxa-2(4,2)-thiazola-1(5,3)-pyrrolo[3,2-b]pyridina-6(1,3)-pyridazinacycloundecaphane-5,7-dione (72 mg, 95% yield) as a solid. LCMS (ESI): m/z [M+H] calc'd for $C_{33}H_{41}N_7O_4S$ 631.3; found 632.3.

Step 14. A solution of ($6^3$S,4S,Z)-4-amino-$1^1$-ethyl-$1^2$-(2-((S)-1-methoxyethyl)pyridin-3-yl)-10,10-dimethyl-$6^1$,$6^2$,$6^3$,$6^4$,$6^5$,$6^6$-hexahydro-$1^1$H-8-oxa-2(4,2)-thiazola-1(5,3)-pyrrolo[3,2-b]pyridina-6(1,3)-pyridazinacycloundecaphane-5,7-dione (100 mg, 0.16 mmol) and (2S)-2-[(3-methoxyazetidin-1-yl)carbonyl(methyl)amino]-3-methylbutanoic acid (78 mg, 0.32 mmol) in DMF (5 mL) at 0° C., was dropwise added a solution of DIEA (620 mg, 4.8 mmol) and HATU (91 mg, 0.24 mmol) in DMF (5 mL). The reaction mixture was stirred at 0° C. for 2 hh, then diluted with EtOAc (50 mL), washed with water (25 mL×3), dried over anhydrous sodium sulfate, filtered and concentrated under reduced pressure. The residue was purified by silica gel column chromatography to afford N-((2S)-1-((($6^3$S,4S,Z)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-pyrrolo[3,2-b]pyridina-6(1,3)-pyridazinacycloundecaphane-4-yl)amino)-3-methyl-1-oxobutan-2-yl)-3-methoxy-N-methylazetidine-1-carboxamide (112.9 mg, 82% yield) as a solid. $^1$H NMR (400 MHz, CD$_3$OD) δ 8.77-8.75 (dd, J=4.8, 1.7 Hz, 1H), 7.96-7.94 (d, J=8.6 Hz, 1H), 7.89-7.87 (dd, J=8.4, 2.3 Hz, 2H), 7.77-7.74 (d, J=8.6 Hz, 1H), 7.58-7.55 (dd, J=7.8, 4.8 Hz, 1H), 5.73-5.70 (dd, J=8.0, 2.7 Hz, 1H), 4.41-4.38 (dt, J=8.5, 4.3 Hz, 2H), 4.33-4.26 (m, 3H), 4.24-4.17 (m, 3H), 4.04-4.01 (dd, J=11.9, 3.0 Hz, 1H), 3.99-3.96 (m, 1H), 3.89-3.83 (m, 2H), 3.53-3.49 (dd, J=9.7, 7.3 Hz, 2H), 3.46-3.45 (d, J=3.0 Hz, 1H), 3.35 (s, 3H), 3.34-3.33 (d, J=4.5 Hz, 3H), 3.28 (s, 1H), 2.89 (s, 3H), 2.78-2.71 (td, J=13.2, 3.4 Hz, 1H), 2.52-2.48 (d, J=14.1 Hz, 1H), 2.23-2.20 (m, 1H), 2.19-2.11 (d, J=10.2 Hz, 1H), 1.91-1.88 (d, J=13.5 Hz, 1H), 1.73-1.70 (dd, J=9.0, 3.9 Hz, 1H), 1.56-1.50 (m, 1H), 1.47-1.46 (d, J=6.1 Hz, 3H), 0.98-0.91 (m, 9H), 0.88 (s, 3H), 0.45 (s, 3H). LCMS (ESI): m/z [M+H] calc'd for $C_{44}H_{59}N_9O_7S$ 857.4; found 858.3.

Example A579. The synthesis of N-((2S)-1-(((6$^3$S, 6$^4$S,4S,Z)-1$^1$-ethyl-1$^2$-(2-((S)-1-methoxyethyl)pyridin-3-yl)-6$^4$,10,10-trimethyl-5,7-dioxo-6$^1$,6$^2$,6$^3$,6$^4$, 6$^5$,6$^6$-hexahydro-1$^1$H-8-oxa-2(4,2)-thiazola-1(5,3)-indola-6(1,3)-pyridazinacycloundecaphane-4-yl) amino)-3-methyl-1-oxobutan-2-yl)-3-methoxy-N-methylazetidine-1-carboxamide

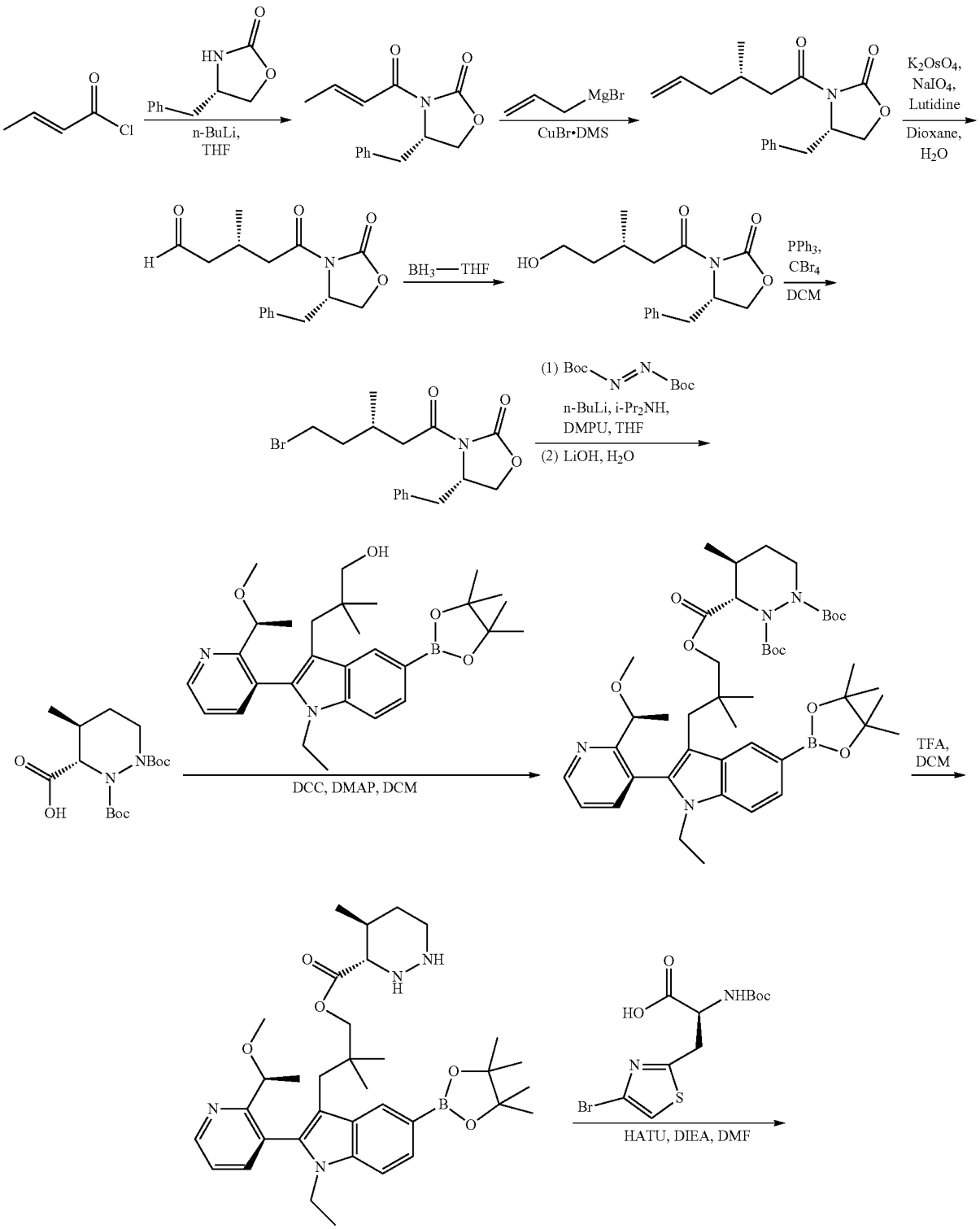

-continued
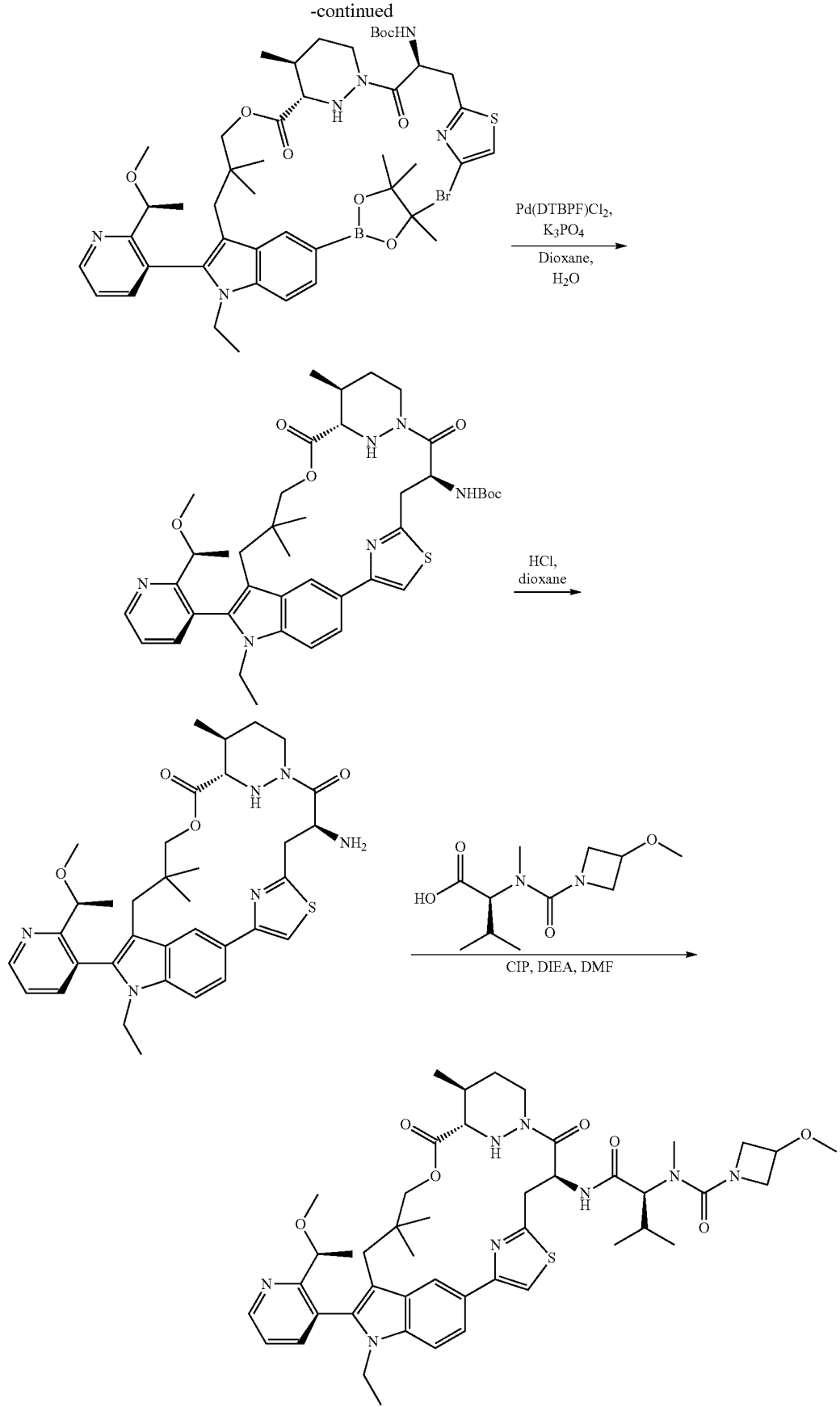

Step 1. A solution of (S)-4-benzyloxazolidin-2-one (10 g, 56.43 mmol) in THF (100 mL) was purged with nitrogen, was added of n-butyllithium (24.83 mL, 62.08 mmol) at −78° C. under nitrogen atmosphere, then stirred for at −78° C. for 15 minutes. The reaction mixture was added 2-butenoyl chloride (6.49 g, 62.08 mmol). The resulting solution was stirred at −78° C. for 30 minutes, then slowly warmed up to 0° C. and stirred for 15 minutes, quenched with saturated ammonium chloride solution (100 mL). The resulting solution was extracted with EtOAc (100 mL×3) and the combined organic phase was dried over anhydrous sodium sulfate and concentrated under reduced pressure. The residue was purified by silica gel column chromatography to afford (4S)-4-benzyl-3-[(2E)-but-2-enoyl]-1,3-oxazolidin-2-one (12.26 g, 88.57% yield) as an oil. LCMS (ESI): m/z [M+H] calc'd for $C_{14}H_{15}NO_3$ 245.1; found 246.1.

Step 2. A solution of CuBr.DMS (12.07 g, 58.71 mmol) in THF (120 mL) was purged and maintained nitrogen atmosphere, added of allylmagnesium bromide (58.71 mL, 58.71 mmol) at −78° C. The reaction was stirred at −60° C. for 30 minutes under nitrogen atmosphere followed by addition of (4S)-4-benzyl-3-[(2E)-but-2-enoyl]-1,3-oxazolidin-2-one (12 g, 48.92 mmol) at −78° C. The resulting solution was stirred at −50° C. for 3 more hh, then quenched with saturated ammonium chloride solution (100 mL) and extracted with EtOAc (60 mL×3). The combined organic phase was dried over anhydrous sodium sulfate and concentrated under reduced pressure. The residue was purified by silica gel column chromatography to afford (S)-4-benzyl-3-((S)-3-methylhex-5-enoyl)oxazolidin-2-one (13.2 g, 93.89% yield) as an oil. LCMS (ESI): m/z [M+H] calc'd for $C_{17}H_{21}NO_3$ 287.2; found 288.2.

Step 3. A solution of (S)-4-benzyl-3-((S)-3-methylhex-5-enoyl)oxazolidin-2-one (13.2 g, 45.94 mmol) in dioxane (200 mL) and water (200 mL), was added 2,4-Lutidine (9.84 g, 91.87 mmol) followed with $K_2OsO_4.2H_2O$ (1.69 g, 4.59 mmol) at 0° C. The reaction solution was stirred at 0° C. for 15 minutes, then was added $NaIO_4$ (39.3 g, 183.74 mmol). The resulting mixture was stirred at 0° C. for 1 h, then extracted with EtOAc (150 mL×3). The combined organic phase was hydrochloric acid (100 mL×3), dried over anhydrous sodium sulfate and concentrated under reduced pressure to afford (S)-5-((S)-4-benzyl-2-oxooxazolidin-3-yl)-3-methyl-5-oxopentanal (12.3 g, crude) as an oil. LCMS (ESI): m/z [M+H] calc'd for $C_{16}H_{19}NO_4$ 289.1; found 290.1.

Step 4. A solution of (S)-5-((S)-4-benzyl-2-oxooxazolidin-3-yl)-3-methyl-5-oxopentanal (12.3 g, 42.51 mmol) in THF (200 mL) was purged and maintained with nitrogen atmosphere, then added borane-tetrahydrofuran complex (55.27 mL, 55.27 mmol) at 0° C. The reaction was stirred at 0° C. for 30 minutes, then quenched with methanol (40 mL). The resulting mixture was concentrated under reduced pressure. The residue was purified by silica gel column chromatography to afford (S)-4-benzyl-3-((S)-5-hydroxy-3-methylpentanoyl)oxazolidin-2-one (9.6 g, 77.51% yield) as an oil. LCMS (ESI): m/z [M+H] calc'd for $C_{16}H_{21}NO_4$ 291.1; found 292.1.

Step 5. A solution of (S)-4-benzyl-3-((S)-5-hydroxy-3-methylpentanoyl)oxazolidin-2-one (9.6 g, 32.95 mmol) and $CBr_4$ (16.39 g, 49.43 mmol) in DCM (120 mL) at 0° C., was added triphenylphosphine (12.96 g, 49.41 mmol). The reaction was stirred at 0° C. for 1 h, then quenched with ice water (100 mL) and extracted with DCM (100 mL×3). The combined organic phase was dried over anhydrous sodium sulfate and concentrated under reduced pressure. The residue was purified by silica gel column chromatography to afford (S)-4-benzyl-3-((R)-5-bromo-3-methylpentanoyl)oxazolidin-2-one (10 g, 85.67% yield) as an oil. LCMS (ESI): m/z [M+H] calc'd for $C_{16}H_{20}BrNO_4$ 353.1; found 354.1.

Step 6. A mixture of n-BuLi (2.26 mL, 5.65 mmol) and diisopropylamine (571.3 mg, 5.65 mmol) in THF (10 mL) under nitrogen at −78° C., was added a cooled (−78° C.) solution of (S)-4-benzyl-3-((R)-5-bromo-3-methylpentanoyl)oxazolidin-2-one (2 g, 5.65 mmol) in THF (9 mL). The reaction mixture was stirred at −78° C. for 30 minutes, then was added a solution of (E)-N-[(tert-butoxycarbonyl)imino](tert-butoxy)formamide (1.3 g, 5.65 mmol) in THF (10 mL), stirred for another 30 minutes at −78° C. The resulting mixture was added DMPU (16 mL, 132.82 mmol) and warmed up to 0° C. and stirred for 90 minutes, followed by addition of a solution of $LiOH H_2O$ (1.18 g, 28.12 mmol) in water (20 mL). Then THF was removed under reduced pressure. The residue was washed with DCM (80 mL×3). The aqueous phase was acidified to pH 56 with HCl (aq.), extracted with mixture of DCM/methanol (80 mL×3, 10:1). The combined organic layers were dried over anhydrous sodium sulfate, filtered, concentrated under reduced pressure. The residue was purified by reverse phase chromatography to afford (3S,4S)-1,2-bis(tert-butoxycarbonyl)-4-methylhexahydropyridazine-3-carboxylic acid (296 mg, 15.22% yield) as a solid. LCMS (ESI): m/z [M−H] calc'd for $C_{16}H_{28}N_2O_6$ 344.2; found 343.1.

Step 7. A mixture of (3S,4S)-1,2-bis(tert-butoxycarbonyl)-4-methylhexahydropyridazine-3-carboxylic acid (289 mg, 0.84 mmol) and (S)-3-(1-ethyl-2-(2-(1-methoxyethyl)pyridin-3-yl)-5-(4,4,5,5-tetramethyl-1,3,2-dioxaborolan-2-yl)-1H-indol-3-yl)-2,2-dimethylpropan-1-ol (413.24 mg, 0.84 mmol) in DMF (10 mL) at 0° C., was added DMAP (51.26 mg, 0.42 mmol) and DCC (692.53 mg, 3.36 mmol). The reaction solution was stirred at room temperature for 1 h, then quenched with water/ice (10 mL), extracted with EtOAc (15 mL×3). The combined organic layers were washed with brine (50 mL×3), dried over anhydrous sodium sulfate and concentrated under reduced pressure. The residue was purified by silica gel column chromatography to afford 1,2-di-tert-butyl 3-(3-(1-ethyl-2-(2-((S)-1-methoxyethyl)pyridin-3-yl)-5-(4,4,5,5-tetramethyl-1,3,2-dioxaborolan-2-yl)-1H-indol-3-yl)-2,2-dimethylpropyl) (3S,4S)-4-methyltetrahydropyridazine-1,2,3-tricarboxylate (538 mg, 78.3% yield) as a solid. LCMS (ESI): m/z [M−H]calc'd for $C_{45}H_{67}BN_4O_9$ 818.5; found 819.4.

Step 8. A solution of 1,2-di-tert-butyl 3-(3-(1-ethyl-2-(2-((S)-1-methoxyethyl)pyridin-3-yl)-5-(4,4,5,5-tetramethyl-1,3,2-dioxaborolan-2-yl)-1H-indol-3-yl)-2,2-dimethylpropyl) (3S,4S)-4-methyltetrahydropyridazine-1,2,3-tricarboxylate (508 mg, 0.62 mmol) in DCM (25 mL), was added TFA (25 mL) at 0° C. The reaction solution was stirred at room temperature for 1 h. The resulting mixture was concentrated to afford 3-(1-ethyl-2-(2-((S)-1-methoxyethyl)pyridin-3-yl)-5-(4,4,5,5-tetramethyl-1,3,2-dioxaborolan-2-yl)-1H-indol-3-yl)-2,2-dimethylpropyl (3S,4S)-4-methylhexahydropyridazine-3-carboxylate (508 mg, crude) as an oil. LCMS (ESI): m/z [M−H] calc'd for $C_{35}H_{51}BN_4O_5$ 618.4; found 619.3.

Step 9. A solution of 3-(1-ethyl-2-(2-((S)-1-methoxyethyl)pyridin-3-yl)-5-(4,4,5,5-tetramethyl-1,3,2-dioxaborolan-2-yl)-1H-indol-3-yl)-2,2-dimethylpropyl (3S,4S)-4-methylhexahydropyridazine-3-carboxylate (508 mg, 0.82 mmol) and (S)-3-(4-bromothiazol-2-yl)-2-((tert-butoxycarbonyl)amino)propanoic acid (288.41 mg, 0.82 mmol) in DMF (50 mL) at 0° C., was added DIEA (1061.31 mg, 8.21 mmol), HATU (468.35 mg, 1.23 mmol). The reaction solution was stirred at room temperature for 1 h, then quenched with ice water (30 mL) and extracted with EtOAc (30 mL×3). The combined organic phase was washed with brine (50 mL×3), dried over anhydrous sodium sulfate and concentrated under reduced pressure. The residue was purified by silica gel column chromatography to afford 3-(1-ethyl-2-(2-((S)-1-methoxyethyl)pyridin-3-yl)-5-(4,4,5,5-tetramethyl-1,3,2-dioxaborolan-2-yl)-1H-indol-3-yl)-2,2-dimethylpropyl (3S,4S)-1-((S)-3-(4-bromothiazol-2-yl)-2-((tert-butoxycarbonyl)amino)propanoyl)-4-methylhexahydropyridazine-3-carboxylate (431 mg, 55.14% yield) as a solid. LCMS (ESI): m/z [M–H]calc'd for $C_{46}H_{64}BBrN_6O_8S$ 950.4; found 951.3.

Step 10. A mixture of $Pd(DTBpf)Cl_2$ (27.39 mg, 0.042 mmol) and $K_3PO_4$ (89.2 mg, 0.42 mmol) in dioxane (5 mL) and water (1 mL) was purged nitrogen, stirred at 60° C. for 5 minutes under nitrogen atmosphere, then added a solution of 3-(1-ethyl-2-(2-((S)-1-methoxyethyl)pyridin-3-yl)-5-(4,4,5,5-tetramethyl-1,3,2-dioxaborolan-2-yl)-1H-indol-3-yl)-2,2-dimethylpropyl (3S,4S)-1-((S)-3-(4-bromothiazol-2-yl)-2-((tert-butoxycarbonyl)amino)propanoyl)-4-methylhexahydropyridazine-3-carboxylate (200 mg, 0.21 mmol) in dioxane (5 mL) and water (1 mL) at 60° C. The reaction mixture was stirred at 60° C. for 1 h, then quenched with ice water (5 mL), extracted with EtOAc (15 mL×3). The combined organic layers were dried over anhydrous sodium sulfate and concentrated under reduced pressure. The residue was purified by silica gel column chromatography to afford tert-butyl (($6^3S,6^4S,4S,Z$)-$1^1$-ethyl-$1^2$-(2-((S)-1-methoxyethyl)pyridin-3-yl)-$6^4$,10,10-trimethyl-5,7-dioxo-$6^1,6^2,6^3,6^4,6^5,6^6$-hexahydro-$1^1$H-8-oxa-2(4,2)-thiazola-1(5,3)-indola-6(1,3)-pyridazinacycloundecaphane-4-yl)carbamate (70 mg, 44.72% yield) as a solid. LCMS (ESI): m/z [M–H] calc'd for $C_{40}H_{52}N_6O_6S$ 744.4; found 745.4.

Step 11. A solution of tert-butyl (($6^3S,6^4S,4S,Z$)-$1^1$-ethyl-$1^2$-(2-((S)-1-methoxyethyl)pyridin-3-yl)-$6^4$,10,10-trimethyl-5,7-dioxo-$6^1,6^2,6^3,6^4,6^5,6^6$-hexahydro-$1^1$H-8-oxa-2(4,2)-thiazola-1(5,3)-indola-6(1,3)- pyridazinacycloundecaphane-4-yl)carbamate (70 mg, 0.094 mmol) in dioxane (5 mL), was added HCl in dioxane (5 mL, 4M). The reaction was stirred at room temperature for 1 h, then concentrated under reduced pressure to afford ($6^3S,6^4S,4S,Z$)-4-amino-$1^1$-ethyl-$1^2$-(2-((S)-1-methoxyethyl)pyridin-3-yl)-$6^4$,10,10-trimethyl-$6^1,6^2,6^3,6^4,6^5,6^6$-hexahydro-$1^1$H-8-oxa-2(4,2)-thiazola-1(5,3)-indola-6(1,3)-pyridazinacycloundecaphane-5,7-dione (124 mg, crude) as an oil. LCMS (ESI): m/z [M–H] calc'd for $C_{36}H_{45}N_5O_4S$ 644.3; found 645.3.

Step 12. A mixture of ($6^3S,6^4S,4S,Z$)-4-amino-$1^1$-ethyl-$1^2$-(2-((S)-1-methoxyethyl)pyridin-3-yl)-$6^4$,10,10-trimethyl-$6^1,6^2,6^3,6^4,6^5,6^6$-hexahydro-$1^1$H-8-oxa-2(4,2)-thiazola-1(5,3)-indola-6(1,3)-pyridazinacycloundecaphane-5,7-dione (112 mg, 0.17 mmol) and N-(3-methoxyazetidine-1-carbonyl)-N-methyl-L-valine (50.92 mg, 0.21 mmol) in DMF (3 mL) at 0° C., was added DIEA (1.795 g, 13.9 mmol), 2-chloro-1,3-dimethylimidazolidinium hexafluorophosphate (72.57 mg, 0.26 mmol). The reaction was stirred at room temperature for 1 h and then filtered. The filtrate was purified by reverse phase chromatography to afford N-((2S)-1-((($6^3S,6^4S,4S,Z$)-$1^1$-ethyl-$1^2$-(2-((S)-1-methoxyethyl)pyridin-3-yl)-$6^4$,10,10-trimethyl-5,7-dioxo-$6^1,6^2,6^3,6^4,6^5,6^6$-hexahydro-$1^1$H-8-oxa-2(4,2)-thiazola-1(5,3)-indola-6(1,3)-pyridazinacycloundecaphane-4-yl)amino)-3-methyl-1-oxobutan-2-yl)-3-methoxy-N-methylazetidine-1-carboxamide (25.6 mg, 16.92% yield) as a solid. $^1$H NMR (400 MHz, DMSO-$d_6$) δ 8.76 (dd, J=4.7, 1.8 Hz, 1H), 8.60 (s, 1H), 8.30-8.20 (m, 1H), 7.86-7.70 (m, 3H), 7.61-7.50 (m, 2H), 5.57-5.43 (m, 1H), 5.07 (d, J=12.1 Hz, 1H), 4.39-4.21 (m, 3H), 4.20-4.01 (m, 5H), 3.96 (d, J=11.1 Hz, 1H), 3.82 (dd, 0=8.9, 3.6 Hz, 1H), 3.77-3.71 (m, 1H), 3.63-3.55 (m, 2H), 3.35-3.27 (m, 2H), 3.24 (s, 3H), 3.23-3.14 (m, 4H), 2.93-2.79 (m, 2H), 2.70 (s, 3H), 2.15-2.01 (m, 1H), 1.83-1.61 (m, 2H), 1.38 (d, J=6.1 Hz, 4H), 0.98 (d, J=6.4 Hz, 3H), 0.94-0.85 (m, 6H), 0.85-0.72 (m, 6H), 0.43 (s, 3H). LCMS (ESI): m/z [M–H] calc'd for $C_{46}H_{62}N_8O_7S$ 870.4; found 871.4.

The following table of compounds (Table 3) were prepared using the aforementioned methods or variations thereof, as is known to those of skill in the art.

TABLE 3

Exemplary Compounds Prepared by Methods of the Present Invention

| Ex# | LCMS (ESI): m/z [M + H] Found | Ex# | LCMS (ESI): m/z [M + H] Found |
|---|---|---|---|
| A1 | 907.5 | A38 | 835.0 |
| A2 | 963.5 | A39 | 839.7 |
| A3 | 908.3 | A40 | 793.7 |
| A4 | 850.4 | A41 | 878.4 |
| A5 | 892.6 | A42 | 907.4 |
| A6 | 963.5 | A43 | 797.6 |
| A7 | 895.8 | A44 | 807.7 |
| A8 | 949.6 | A45 | 920.5 |
| A9 | 920.5 | A46 | 865.5 |
| A10 | 836.6 | A47 | 894.4 |
| A11 | 894.7 | A48 | 895.8 |
| A12 | 893.5 | A49 | 837.4 |
| A13 | 842.5 | A50 | 853.5 |
| A14 | 949.7 | A51 | 892.5 |
| A15 | 921.5 | A52 | 806.3 |
| A16 | 878.7 | A53 | 798.0 |
| A17 | 864.5 | A54 | 786.5 |
| A18 | 837.6 | A55 | 781.6 |
| A19 | 821.6 | A56 | 821.0 |
| A20 | 894.5 | A57 | 817.5 |
| A21 | 795.4 | A58 | 767.4 |
| A22 | 878.5 | A59 | 823.5 |
| A23 | 880.3 | A60 | 876.6 |
| A24 | 914.6 | A61 | 779.6 |
| A25 | 795.4 | A62 | 863.7 |
| A26 | 837.5 | A63 | 848.6 |
| A27 | 850.5 | A64 | 833.7 |
| A28 | 823.6 | A65 | 866.7 |
| A29 | 906.5 | A66 | 838.4 |
| A30 | 852.6 | A67 | 810.5 |
| A31 | 894.8 | A68 | 838.7 |
| A32 | 836.5 | A69 | 851.7 |
| A33 |  | A70 | 823.5 |
| A34 | 906.0 | A71 | 786.5 |
| A35 | 970.7 | A72 | 842.5 |
| A36 | 964.5 | A73 | 864.5 |
| A37 | 971.2 | A74 | 852.5 |
| A75 | 797.6 | A170 | 870.5 |
| A76 | 796.4 | A171 | 879.5 |
| A77 | 822 | A172 | 811.5 |
| A78 | 848.5 | A173 | 871.2 |
| A79 | 904.8 | A174 | 837.4 |
| A80 | 946.5 | A175 | 874.5 |
| A81 | 838.5 | A176 | 807.5 |
| A82 | 853.5 | A177 | 773 |
| A83 | 850.45 | A178 | 787 |
| A84 | 864.5 | A179 | 787 |
| A85 | 864.5 | A180 | 784 |
| A86 | 822.6 | A181 | 784 |
| A87 | 822.3 | A182 | 722.9 |
| A88 | 836.3 | A183 | 722 |
| A89 | 839.6 | A184 | 762 |
| A90 | 837.6 | A185 | 872.18 |
| A91 | 837.5 | A186 | 745.7 |
| A92 | 811.5 | A187 | 829.9 |

TABLE 3-continued

Exemplary Compounds Prepared by Methods of the Present Invention

| Ex# | LCMS (ESI): m/z [M + H] Found | Ex# | LCMS (ESI): m/z [M + H] Found |
|---|---|---|---|
| A93 | 811.5 | A188 | 829.9 |
| A94 | 837.5 | A189 | 759.6 |
| A95 | 935.6 | A190 | 775.9 |
| A96 | 919.6 | A191 | 808.7 |
| A97 | 926.5 | A192 | 770.8 |
| A98 | 905.5 | A193 | 802.7 |
| A99 | 912.3 | A194 | 789.8 |
| A100 | 864.5 | A195 | 796.7 |
| A101 | 852.5 | A196 | 744.7 |
| A102 | 795.4 | A197 | 798.9 |
| A103 | 772.3 | A198 | 840.9 |
| A104 | 781.4 | A199 | 753.9 |
| A105 | 891.5 | A200 | 758.9 |
| A106 | 898.5 | A201 | 984.4 |
| A107 | 848.5 | A202 | 934.4 |
| A108 | 855.5 | A203 | 941.5 |
| A109 | 878.8 | A204 | 950.4 |
| A110 | 885.6 | A205 | 857.3 |
| A111 | 894.6 | A206 | 890.4 |
| A112 | 947.7 | A207 | 791.7 |
| A113 | 954.7 | A208 | 793.6 |
| A114 | 963.6 | A209 | 867.5 |
| A115 | 892.4 | A210 | 858.5 |
| A116 | 889.5 | A211 | 922.6 |
| A117 | 936.5 | A212 | 798.4 |
| A118 | 841.4 | A213 | 867.7 |
| A119 | 834.8 | A214 | 797.5 |
| A120 | 921.5 | A215 | 946.5 |
| A121 | 852.8 | A216 | 904.8 |
| A122 | 865.8 | A217 | 862.6 |
| A123 | 907.8 | A218 | 835.5 |
| A124 | 851.8 | A219 | 849.6 |
| A125 | 838 | A220 | 931.4 |
| A126 | 862.5 | A221 | 911.3 |
| A127 | 864.8 | A222 | 853.2 |
| A128 | 864.8 | A223 | 835.5 |
| A129 | 850.8 | A224 | 821.6 |
| A130 | 906 | A225 | 748.8 |
| A131 | 865.8 | A226 | 913.8 |
| A132 | 838.9 | A227 | 894.0 |
| A133 | 877.9 | A228 | 877.9 |
| A134 | 879.8 | A229 | 897.8 |
| A135 | 961.6 | A230 | 879.9 |
| A136 | 815.5 | A231 | 893.9 |
| A137 | 801.5 | A232 | 852.9 |
| A138 | 802.4 | A233 | 950.6 |
| A139 | 850.5 | A234 | 917.3 |
| A140 | 862.6 | A235 | 897.3 |
| A141 | 811.4 | A236 | 780.8 |
| A142 | 793.3 | A237 | 919.4 |
| A143 | 856.2 | A238 | 842.4 |
| A144 | 793.5 | A239 | 826.4 |
| A145 | 836.2 | A240 | 851.8 |
| A146 | 835.4 | A241 | 851.7 |
| A147 | 835.3 | A242 | 878.9 |
| A148 | 876.6 | A243 | 864.8 |
| A149 | 862.6 | A244 | 883.5 |
| A150 | 865.5 | A245 | 828.4 |
| A151 | 890.3 | A246 | 821.4 |
| A152 | 786.2 | A247 | 912.8 |
| A153 | 819.5 | A248 | 893.6 |
| A154 | 857.2 | A249 | 888.8 |
| A155 | 862.6 | A250 | 899.8 |
| A156 | 847.5 | A251 | 864.7 |
| A157 | 849.5 | A252 | 905.8 |
| A158 | 849.5 | A253 | 750.7 |
| A159 | 846.6 | A254 | 787.8 |
| A160 | 839.6 | A255 | 851.6 |
| A161 | 839.5 | A256 | 795.4 |
| A162 | 839.5 | A257 | 852.6 |
| A163 | 862.6 | A258 | 766.8 |
| A164 | 862.7 | A259 | 864.5 |
| A165 | 839.5 | A260 | 853.4 |
| A166 | 857.5 | A261 | 773.8 |
| A167 | 857.5 | A262 | 878.7 |
| A168 | 836.5 | A263 | 780.8 |
| A169 | 880.3 | | |
| A264 | 758.4 | A293 | 898.7 |
| A265 | 757.3 | A294 | 912.7 |
| A266 | 772.4 | A295 | 882.3 |
| A267 | 728.4 | A296 | 912.3 |
| A268 | 882.4 | A297 | 921.3 |
| A270 | 744.3 | A298 | 883.2 |
| A271 | 871.2 | A299 | 871.3 |
| A272 | 898.6 | A300 | 898.5 |
| A273 | 910.5 | A301 | 869.3 |
| A274 | 882.3 | A302 | 893.5 |
| A275 | 885.5 | A303 | 924.4 |
| A276 | 885.5 | A304 | 841.2 |
| A277 | 913.6 | A305 | 841.5 |
| A278 | 885.6 | A306 | 914.5 |
| A279 | 885.4 | A307 | 896.5 |
| A280 | 910.6 | A308 | 896.4 |
| A281 | 884.3 | A309 | 871.3 |
| A282 | 882.2 | A310 | 871.4 |
| A283 | 898.5 | A311 | 896.5 |
| A284 | 882.5 | A312 | 883.5 |
| A285 | 896.2 | A313 | 896.6 |
| A286 | 713.1 | A314 | 882.6 |
| A287 | 835.3 | A315 | 729.3 |
| A288 | 925.4 | A316 | 906.5 |
| A289 | 885.0 | A317 | 827.4 |
| A290 | 941.3 | A318 | 898.5 |
| A291 | 898.3 | A319 | 898.3 |
| A292 | 898.7 | A320 | 733.2 |
| A321 | 771.4 | A354 | 844.6 |
| A322 | 893.2 | A355 | 850.5 |
| A323 | 837.5 | A356 | 855.5 |
| A324 | 807.3 | A357 | 905.4 |
| A325 | 922.5 | A358 | 843.5 |
| A326 | 882.5 | A359 | 715.2 |
| A327 | 882.5 | A360 | 715.2 |
| A328 | 924.4 | A361 | 731.3 |
| A329 | 896.3 | A362 | 717.3 |
| A330 | 911.1 | A363 | 855.5 |
| A331 | 729.4 | A364 | 866.5 |
| A332 | 857.4 | A365 | 908.6 |
| A333 | 857.5 | A366 | 736.1 |
| A334 | 857.2 | A367 | 699.1 |
| A335 | 871.5 | A368 | 714.1 |
| A336 | 829.5 | A369 | 713.3 |
| A337 | 856.5 | A370 | 947.6 |
| A338 | 912.2 | A371 | 961.4 |
| A339 | 857.5 | A372 | 857.5 |
| A340 | 771.4 | A373 | 857.5 |
| A341 | 870.5 | A374 | 857.5 |
| A342 | 975.3 | A375 | 856.5 |
| A343 | 842.5 | A376 | 857.5 |
| A344 | 871.7 | A377 | 865.6 |
| A345 | 808.5 | A378 | 947.3 |
| A346 | 837.5 | A379 | 975.6 |
| A347 | 837.5 | A380 | 961.3 |
| A348 | 963.5 | A381 | 850.6 |
| A349 | 855.5 | A382 | 852.2 |
| A350 | 843.5 | A383 | 905.1 |
| A351 | 843.5 | A384 | 849.5 |
| A352 | 855.5 | A385 | 961.6 |
| A353 | 841.5 | A386 | 949.3 |
| A387 | 871.5 | A421 | 892.9 |
| A388 | 819.3 | A422 | 951.3 |
| A389 | 813.2 | A423 | 1051.6 |
| A391 | 851.7 | A424 | 939.4 |
| A392 | 851.7 | A425 | 927.4 |
| A393 | 891.8 | A426 | 953.40 |
| A394 | 879.8 | A427 | 978.3 |
| A395 | 879.8 | A428 | 918.2 |

TABLE 3-continued

Exemplary Compounds Prepared by Methods of the Present Invention

| Ex# | LCMS (ESI): m/z [M + H] Found | Ex# | LCMS (ESI): m/z [M + H] Found |
|---|---|---|---|
| A396 | 921.8 | A429 | 911.3 |
| A397 | 909.8 | A430 | 804.5 |
| A398 | 736.4 | A431 | 891.5 |
| A399 | 827.5 | A432 | 879.5 |
| A400 | 841.5 | A433 | 940.7 |
| A401 | 857.5 | A434 | 896.5 |
| A402 | 871.4 | A435 | 896.3 |
| A403 | 871.5 | A436 | 926.2 |
| A404 | 906.9 | A437 | 946.6 |
| A405 | 865.9 | A438 | 896.1 |
| A406 | 863.8 | A439 | 988.1 |
| A407 | 891.9 | A440 | 988.1 |
| A408 | 919.9 | A441 | 926.2 |
| A409 | 908 | A442 | 910.9 |
| A410 | 878.0 | A443 | 967.1 |
| A411 | 878.0 | A444 | 912.1 |
| A412 | 878.0 | A445 | 912.1 |
| A413 | 922.0 | A446 | 882.2 |
| A414 | 894.9 | A447 | 867.1 |
| A415 | 928.0 | A448 | 953.2 |
| A416 | 901.9 | A449 | 953.5 |
| A417 | 890.9 | A450 | 1017.6 |
| A418 | 867.9 | A451 | 912.2 |
| A419 | 879.9 | A452 | 895.2 |
| A420 | 866.9 | A453 | 924.2 |
| A454 | 844.2 | A482 | 960.1 |
| A455 | 901.9 | A483 | 1008.1 |
| A456 | 867.2 | A484 | 912.2 |
| A457 | 940.6 | A485 | 938.6 |
| A458 | 898.5 | A486 | 952.3 |
| A459 | 954.8 | A487 | 885.3 |
| A460 | 896.2 | A488 | 884.3 |
| A461 | 924.2 | A489 | 886.2 |
| A462 | 896.2 | A490 | 1017.9 |
| A463 | 856.2 | A491 | 912.6 |
| A464 | 931.2 | A492 | 912.6 |
| A465 | 981.7 | A493 | 912.6 |
| A466 | 955.3 | A494 | 912.6 |
| A467 | 940.6 | A495 | 924.2 |
| A468 | 910.6 | A496 | 917.0 |
| A469 | 884.5 | A497 | 882.1 |
| A470 | 896.2 | A498 | 924.6 |
| A471 | 896.1 | A499 | 912.1 |
| A472 | 912.1 | A500 | 921.2 |
| A473 | 898.6 | A501 | 984.1 |
| A474 | 899.2 | A502 | 884.6 |
| A475 | 899.1 | A503 | 896.1 |
| A476 | 996.3 | A504 | 898.1 |
| A477 | 968.6 | A505 | 954.7 |
| A478 | 885.5 | A506 | 902.1 |
| A479 | 910.9 | A507 | 1011.2 |
| A480 | 910.1 | A508 | 884.6 |
| A481 | 896.9 | A509 | 943.2 |
| A510 | 883.5 | A538 | 898.2 |
| A511 | 952.3 | A539 | 896.5 |
| A512 | 940.6 | A540 | 870.0 |
| A513 | 910.3 | A541 | 882.1 |
| A514 | 901.2 | A542 | 884.2 |
| A515 | 901.2 | A543 | 940.9 |
| A516 | 896.3 | A544 | 874.2 |
| A517 | 896.2 | A545 | 897.9 |
| A518 | 898.6 | A546 | 928.2 |
| A519 | 898.6 | A547 | 912.5 |
| A520 | 911.2 | A548 | 912.5 |
| A521 | 897.2 | A549 | 920.5 |
| A522 | 883.2 | A550 | 934.5 |
| A523 | 853.2 | A551 | 934.4 |
| A524 | 946.2 | A552 | 920.5 |
| A525 | 896.2 | A553 | 887.1 |
| A526 | 940.3 | A554 | 837.4 |
| A527 | 871.2 | A555 | 955.2 |
| A528 | 883.2 | A556 | 932.2 |
| A529 | 951.8 | A557 | 906.1 |
| A530 | 945.1 | A558 | 856.2 |
| A531 | 898.3 | A559 | 888.2 |
| A532 | 954.5 | A560 | 869.1 |
| A533 | 899.5 | A561 | 883.2 |
| A534 | 899.5 | A562 | 1009.3 |
| A535 | 884.2 | A563 | 884.6 |
| A536 | 939.5 | A564 | 884.6 |
| A537 | 939.5 | A565 | 924.2 |
| A566 | 884.9 | A592 | 961.2 |
| A567 | 874.2 | A593 | 1043.0 |
| A568 | 896.2 | A594 | 1025.8 |
| A569 | 898.2 | A595 | 967.5 |
| A570 | 870.2 | A596 | 967.5 |
| A571 | 899.0 | A597 | 900.1 |
| A572 | 914.2 | A598 | 845.4 |
| A573 | 912.2 | A599 | 917.2 |
| A574 | 913.9 | A600 | 933.1 |
| A575 | 914.2 | A601 | 898.0 |
| A576 | 885.0 | A602 | 897.0 |
| A577 | 1024.7 | A603 | 884.9 |
| A578 | 869.5 | A604 | 933.1 |
| A579 | 871.4 | A605 | 926.1 |
| A580 | 886.9 | A606 | 940.5 |
| A581 | 872.1 | A607 | 924.3 |
| A582 | 933.2 | A608 | 896.3 |
| A583 | 1016.2 | A609 | 898.4 |
| A584 | 927.2 | A610 | 898.5 |
| A585 | 918.2 | A611 | 870.5 |
| A586 | 911.3 | A612 | 858.4 |
| A587 | 899.4 | A613 | 858.3 |
| A588 | 898.6 | A614 | 899.4 |
| A589 | 910.2 | A615 | 926.4 |
| A590 | 914.6 | A616 | 926.4 |
| A591 | 915.4 | | |

Blank = not determined

Biological Assays

Potency Assay: pERK

The purpose of this assay is to measure the ability of test compounds to inhibit K-Ras in cells. Activated K-Ras induces increased phosphorylation of ERK at Threonine 202 and Tyrosine 204 (pERK). This procedure measures a decrease in cellular pERK in response to test compounds. The procedure described below in NCI-H$_{358}$ cells is applicable to K-Ras G12C.

Note: this protocol may be executed substituting other cell lines to characterize inhibitors of other RAS variants, including, for example, AsPC-1 (K-Ras G12D), Capan-1 (K-Ras G12V), or NCI-H1355 (K-Ras G13C).

NCI-H358 cells were grown and maintained using media and procedures recommended by the ATCC. On the day prior to compound addition, cells were plated in 384-well cell culture plates (40 µl/well) and grown overnight in a 37° C., 5% CO2 incubator. Test compounds were prepared in 10, 3-fold dilutions in DMSO, with a high concentration of 10 mM. On day of assay, 40 nl of test compound was added to each well of cell culture plate using an Echo550 liquid handler (LabCyte®). Concentrations of test compound were tested in duplicate. After compound addition, cells were incubated 4 hours at 37° C., 15% CO2. Following incubation, culture medium was removed and cells were washed once with phosphate buffered saline.

In some experiments, cellular pERK level was determined using the AlphaLISA SureFire Ultra p-ERK1/2 Assay Kit (PerkinElmer). Cells were lysed in 25 µl lysis buffer, with shaking at 600 RPM at room temperature. Lysate (10 µl) was transferred to a 384-well Opti-plate (PerkinElmer) and 5 µl acceptor mix was added. After a 2-hour incubation in the dark, 5 µl donor mix was added, plate was sealed and incubated 2 hours at room temperature. Signal was read on an Envision plate reader (PerkinElmer) using standard AlphaLISA settings. Analysis of raw data was carried out in Excel (Microsoft) and Prism (GraphPad). Signal was plotted vs. the decadal logarithm of compound concentration, and IC50 was determined by fitting a 4-parameter sigmoidal concentration response model.

In other experiments, cellular pERK was determined by In-Cell Western. Following compound treatment, cells were washed twice with 200 µl tris buffered saline (TBS) and fixed for 15 minutes with 150 µl 4% paraformaldehyde in TBS. Fixed cells were washed 4 times for 5 minutes with TBS containing 0.1% Triton X-100 (TBST) and then blocked with 100 µl Odyssey blocking buffer (LI-COR) for 60 minutes at room temperature. Primary antibody (pERK, CST-4370, Cell Signaling Technology) was diluted 1:200 in blocking buffer, and 50 µl was added to each well and incubated overnight at 4° C. Cells were washed 4 times for 5 minutes with TBST. Secondary antibody (IR-800CW rabbit, LI-COR, diluted 1:800) and DNA stain DRAQ5 (LI-COR, diluted 1:2000) were added and incubated 1-2 hours at room temperature. Cells were washed 4 times for 5 minutes with TBST. Plates were scanned on a Li-COR Odyssey CLx Imager. Analysis of raw data was carried out in Excel (Microsoft) and Prism (GraphPad). Signal was plotted vs. the decadal logarithm of compound concentration, and $IC_{50}$ was determined by fitting a 4-parameter sigmoidal concentration response model.

Determination of Cell Viability in RAS Mutant Cancer Cell Lines

Protocol: CellTiter-Glo® Cell Viability Assay

Note—The following protocol describes a procedure for monitoring cell viability of K-Ras mutant cancer cell lines in response to a compound of the invention. Other RAS isoforms may be employed, though the number of cells to be seeded will vary based on cell line used.

The purpose of this cellular assay was to determine the effects of test compounds on the proliferation of three human cancer cell lines (NCI-H358 (K-Ras G12C), AsPC-1 (K-Ras G12D), Capan-1 (K-Ras G12V)) over a 5-day treatment period by quantifying the amount of ATP present at endpoint using the CellTiter-Glo® 2.0 Reagent (Promega).

Cells were seeded at 250 cells/well in 40 µl of growth medium in 384-well assay plates and incubated overnight in a humidified atmosphere of 5% $CO_2$ at 37° C. On the day of the assay, 10 mM stock solutions of test compounds were first diluted into 3 mM solutions with 100% DMSO. Well-mixed compound solutions (15 µl) were transferred to the next wells containing 30 µl of 100% DMSO, and repeated until a 9-concentration 3-fold serial dilution was made (starting assay concentration of 10 µM). Test compounds (132.5 nl) were directly dispensed into the assay plates containing cells. The plates were shaken for 15 seconds at 300 rpm, centrifuged, and incubated in a humidified atmosphere of 5% $CO_2$ at 37° C. for 5 days. On day 5, assay plates and their contents were equilibrated to room temperature for approximately 30 minutes. CellTiter-Glo® 2.0 Reagent (25 µl) was added, and plate contents were mixed for 2 minutes on an orbital shaker before incubation at room temperature for 10 minutes. Luminescence was measured using the PerkinElmer Enspire. Data were normalized by the following: (Sample signal/Avg. DMSO)*100. The data were fit using a four-parameter logistic fit.

Disruption of B-Raf Ras-Binding Domain ($BRAF^{RBD}$) Interaction with K-Ras by Compounds of the Invention (Also Called a FRET Assay or an MOA Assay)

Note—The following protocol describes a procedure for monitoring disruption of K-Ras G12C (GMP-PNP) binding to $BRAF^{RBD}$ by a compound of the invention. This protocol may also be executed substituting other Ras proteins or nucleotides.

The purpose of this biochemical assay was to measure the ability of test compounds to facilitate ternary complex formation between a nucleotide-loaded K-Ras isoform and Cyclophilin A; the resulting ternary complex disrupts binding to a $BRAF^{RBD}$ construct, inhibiting K-Ras signaling through a RAF effector. Data is reported as $IC_{50}$ values.

In assay buffer containing 25 mM HEPES pH 7.3, 0.002% Tween20, 0.1% BSA, 100 mM NaCl and 5 mM $MgCl_2$, tagless Cyclophilin A, His6-K-Ras-GMPPNP, and GST-$BRAF^{RBD}$ were combined in a 384-well assay plate at final concentrations of 25 µM, 12.5 nM and 50 nM, respectively. Compound was present in plate wells as a 10-point 3-fold dilution series starting at a final concentration of 30 µM. After incubation at 25° C. for 3 hours, a mixture of Anti-His Eu-W1024 and anti-GST allophycocyanin was then added to assay sample wells at final concentrations of 10 nM and 50 nM, respectively, and the reaction incubated for an additional 1.5 hours. TR-FRET signal was read on a microplate reader (Ex 320 nm, Em 665/615 nm). Compounds that facilitate disruption of a K-Ras:RAF complex were identified as those eliciting a decrease in the TR-FRET ratio relative to DMSO control wells.

TABLE 4

Biological Assay Data for Representative Compounds of the Present Invention

| Ex# | FRET G12C IC50, uM | FRET G12V IC50, uM | FRET G12D IC50, uM | FRET G13C IC50, uM | FRET G13D IC50, uM | H358 pERK EC50, uM | Capan-1 pERK EC50, uM | ASPC-1 pERK EC50, uM | H358 Cell Viability IC50, uM |
|---|---|---|---|---|---|---|---|---|---|
| A74 | 0.45 | 3.67 | 0.228 | 0.091 | 0.212 | 0.334 | 0.413 | 0.468 | |
| A73 | 0.082 | 0.905 | 0.061 | 0.013 | 0.033 | 0.036 | 0.197 | 0.079 | |
| A3 | 0.029 | 0.043 | 0.545 | 0.099 | 0.16 | 0.018 | 0.008 | 0.144 | 0.057 |
| A25 | 0.128 | 0.197 | 1.29 | 0.097 | 0.235 | 0.064 | 0.052 | 0.706 | 0.226 |
| A12 | 0.068 | 0.329 | 0.154 | 0.148 | 0.219 | | | | 4.29 |

Blank = not determined

Additional H358 Cell Viability assay data
*Key:
+++++: IC50≥10 uM
++++: 10 uM>IC50≥1 uM
+++: 1 uM>IC50≥0.1 uM
++: 0.1 uM>IC50≥0.01 uM
+: IC50<0.01 uM

TABLE 5

H358 Cell Viability assay data (K-Ras G12C, IC50, uM):

| IC50* | Examples |
|---|---|
| + | A136, A159, A205, A277, A278, A289, A291, A296, A298, A302, A303, A304, A306, A309, A310, A325, A335, A338, A356, A358, A365, A372, A373, A374, A382, A399, A439, A443, A450, A457, A465, A466, A476, A477, A478, A483, A484, A487, A490, A500, A501, A505, A514, A515, A526, A529, A536, A543, A546, A551, A555, A561, A562, A573, A577, A583, A590, A593, A594, A606, A607 |
| ++ | A114, A117, A13, A131, A138, A141, A147, A156, A160, A162, A164, A165, A170, A202, A204, A211, A217, A218, A223, A224, A233, A240, A242, A247, A248, A249, A250, A252, A273, A279, A280, A285, A286, A288, A290, A293, A294, A295, A297, A299, A3, A301, A305, A307, A311, A312, A313, A316, A318, A319, A326, A329, A330, A333, A334, A336, A337, A342, A348, A349, A350, A351, A352, A353, A357, A363, A364, A375, A376, A377, A379, A383, A387, A389, A391, A392, A400, A401, A402, A403, A406, A415, A422, A433, A436, A440, A441, A444, A445, A451, A452, A454, A458, A459, A467, A481, A485, A486, A488, A489, A491, A492, A493, A494, A495, A498, A499, A502, A503, A506, A507, A509, A510, A511, A512, A513, A518, A520, A521, A522, A523, A525, A527, A528, A531, A532, A533, A534, A537, A538, A540, A541, A542, A547, A548, A549, A550, A552, A553, A557, A559, A560, A563, A564, A565, A566, A567, A568, A569, A570, A571, A574, A576, A578, A582, A584, A585, A587, A588, A589, A591, A595, A596, A597, A601, A603, A605, A614, A615 |
| +++ | A100, A11, A116, A121, A123, A124, A126, A130, A132, A137, A139, A143, A146, A152, A155, A157, A161, A166, A167, A168, A169, A171, A173, A174, A18, A184, A19, A201, A203, A209, A21, A210, A219, A221, A226, A228, A231, A232, A238, A239, A241, A243, A245, A25, A252, A26, A260, A264, A266, A267, A268, A270, A274, A276, A28, A281, A282, A283, A284, A287, A29, A292, A30, A308, A314, A315, A317, A321, A322, A323, A332, A339, A343, A346, A35, A354, A355, A360, A361, A362, A367, A368, A369, A378, A381, A384, A385, A386, A39, A393, A395, A396, A397, A407, A408, A409, A410, A411, A412, A413, A414, A416, A417, A418, A420, A421, A423, A437, A438, A442, A447, A449, A455, A461, A462, A471, A480, A482, A496, A497, A5, A504, A508, A524, A535, A539, A54, A544, A545, A554, A556, A572, A575, A579, A580, A581, A586, A592, A598, A600, A602, A604, A608, A610, A611, A612, A613, A616, A64, A7, A78, A8, A90, A91, A94, A95 |
| ++++ | A1, A10, A101, A102, A104, A111, A117, A12, A120, A125, A127, A128, A129, A134, A148, A15, A16, A163, A17, A2, A20, A216, A22, A227, A23, A24, A244, A254, A254, A256, A258, A259, A261, A262, A27, A3, A320, A359, A36, A36, A37, A38, A4, A40, A405, A41, A42, A43, A44, A45, A453, A46, A464, A50, A51, A517, A519, A52, A53, A54, A55, A57, A58, A59, A599, A6, A60, A609, A61, A65, A66, A67, A70, A82, A83, A85, A9, A92, A97 |
| +++++ | A12, A133, A14, A31, A32, A4, A47, A48, A56, A62, A63, A68, A69, A84, A99 |

*Key:
+++++: IC50 ≥ 10 uM
++++: 10 uM > IC50 ≥ 1 uM
+++: 1 uM > IC50 ≥ 0.1 uM
++: 0.1 uM > IC50 ≥ 0.01 uM
+: IC50 < 0.01 uM

TABLE 6

Capan-1 Cell Viability assay data (K-Ras G12V, IC50, uM):

| IC50* | Examples |
|---|---|
| + | A277, A450, A465, A466, A476, A477, A484, A500, A505, A526, A529, A555, A562, A577, A583, A593, A594 |
| ++ | A114, A117, A132, A136, A138, A141, A156, A159, A162, A165, A170, A202, A204, A205, A210, A211, A218, A224, A233, A240, A247, A250, A278, A279, A280, A285, A288, A289, A290, A291, A293, A295, A296, A298, A3, A302, A303, A304, A306, A309, A310, A312, A313, A316, A318, A319, A325, A329, A330, A334, A335, A336, A338, A353, A356, A357, A358, A363, A364, A365, A372, A373, A374, A376, A377, A382, A383, A387, A389, A399, A400, A401, A402, A403, A415, A433, A436, A439, A440, A443, A444, A445, A451, A452, A454, A458, A467, A472, A474, A475, A478, A481, A483, A485, A486, A487, A490, A491, A494, A499, A503, A506, A509, A510, A511, A512, A513, A514, A515, A518, A520, A521, A523, A525, A527, A528, A531, A532, A533, A534, A536, A537, A538, A540, A543, A546, A547, A548, A549, A550, A551, A561, A563, A565, A566, A569, A570, A571, A573, A574, A576, A587, A590, A591, A601, A603, A606, A607, A608, A614, A615 |
| +++ | A102, A11, A116, A121, A123, A126, A13, A131, A137, A139, A143, A146, A147, A152, A157, A160, A161, A164, A166, A167, A168, A169, A171, A173, A174, A18, A19, A201, A203, A209, A21, A217, A219, A221, A223, A226, A228, A232, A238, A239, A241, A242, A244, A245, A248, A249, A25, A252, A252, A254, A26, A264, A266, A267, A268, A273, A274, A275, A276, A281, A282, A283, A284, A286, A287, A292, A294, A297, A299, A30, A301, A305, A307, A308, A311, A314, A315, A320, A321, A322, A323, A326, A332, A333, A337, A342, A343, A346, A347, A348, A349, A350, A351, A352, A354, A355, A360, A361, A362, A367, A368, A369, A375, A379, A384, A385, A386, A39, A395, A396, A397, A406, A407, A409, A410, A411, A412, A413, A416, A419, A420, A422, A423, A437, A441, A447, A449, A455, A459, A461, A462, A468, A469, A470, A471, A473, A480, A482, A488, A489, A492, A493, A495, A496, A497, A498, A5, A501, A502, A504, A507, A508, A516, A517, A522, A524, A530, A535, A539, A54, A541, A542, A544, A545, A552, A553, A556, A557, A558, A559, A560, A564, A567, A568, A575, A578, A579, A580, A582, A584, A585, A586, A588, A589, A595, A596, A597, A598, A600, A602, A605, A609, A610, A611, A612, A613, A616, A90, A91, A94, A95 |

TABLE 6-continued

Capan-1 Cell Viability assay data (K-Ras G12V, IC50, uM):

| IC50* | Examples |
|---|---|
| ++++ | A1, A100, A101, A106, A107, A111, A112, A113, A115, A124, A125, A129, A130, A135, A144, A148, A149, A155, A158, A16, A17, A175, A176, A179, A180, A182, A183, A184, A185, A200, A216, A220, A225, A225, A229, A230, A231, A235, A236, A237, A24, A246, A253, A254, A259, A260, A261, A262, A265, A270, A272, A28, A29, A300, A317, A324, A327, A331, A339, A345, A359, A366, A370, A371, A378, A380, A381, A388, A391, A392, A393, A394, A398, A40, A405, A408, A414, A417, A418, A421, A43, A434, A435, A438, A442, A453, A456, A460, A463, A464, A479, A519, A54, A554, A572, A581, A592, A599, A604, A61, A7, A76, A78, A8, A80, A82, A83, A85, A89, A93, A96, A97 |
| +++++ | A104, A104, A105, A108, A109, A110, A116, A117, A118, A119, A120, A122, A127, A128, A133, A134, A140, A142, A145, A150, A151, A153, A154, A163, A172, A177, A178, A179, A181, A186, A187, A188, A189, A190, A191, A192, A193, A194, A195, A196, A197, A198, A199, A206, A207, A208, A212, A213, A214, A215, A222, A227, A227, A234, A236, A243, A251, A253, A255, A258, A271, A328, A340, A341, A344, A4, A404, A446, A448, A75, A79, A84, A86, A87, A87, A88, A92, A98, A99 |

Additional Ras-Raf Disruption/FRET/MOA Assay Data (IC$_{50}$, uM):
*Key:
+++++: IC50>10 uM
++++: 10 uM>IC50≥1 uM
+++: 1 uM>IC50≥0.1 uM
++: 0.1 uM>IC50≥0.01 uM
+: IC50<0.01 uM

TABLE 7

KRAS G12D FRET data

| IC50* | Examples |
|---|---|
| + | None |
| ++ | A1, A100, A111, A120, A124, A125, A127, A128, A129, A131, A133, A134, A135, A139, A140, A148, A159, A164, A223, A227, A228, A231, A242, A243, A247, A249, A325, A342, A348, A365, A370, A371, A378, A379, A380, A381, A385, A386, A391, A392, A393, A395, A397, A4, A415, A419, A427, A483, A494, A501, A507, A546, A573, A577, A584, A594, A605, A95 |
| +++ | A10, A101, A102, A106, A114, A12, A121, A122, A123, A126, A130, A132, A136, A14, A146, A147, A149, A15, A151, A155, A156, A157, A158, A160, A161, A162, A163, A165, A166, A167, A168, A169, A171, A174, A2, A201, A202, A204, A205, A209, A211, A216, A217, A218, A219, A224, A227, A229, A23, A230, A232, A233, A240, A241, A248, A248, A250, A251, A252, A252, A255, A259, A264, A265, A266, A267, A268, A27, A270, A273, A274, A275, A277, A278, A279, A280, A285, A286, A287, A288, A289, A290, A291, A294, A298, A3, A302, A303, A304, A306, A309, A31, A310, A311, A312, A313, A314, A32, A321, A323, A332, A333, A334, A335, A336, A343, A346, A347, A349, A350, A351, A353, A356, A358, A363, A364, A372, A373, A374, A376, A377, A382, A383, A384, A394, A396, A399, A400, A401, A402, A404, A405, A406, A407, A408, A409, A41, A410, A411, A412, A413, A414, A416, A417, A418, A420, A421, A422, A423, A424, A426, A432, A434, A435, A436, A438, A441, A443, A444, A447, A45, A450, A454, A457, A458, A459, A463, A465, A466, A467, A468, A469, A471, A475, A476, A477, A478, A48, A484, A485, A487, A488, A491, A492, A493, A498, A5, A500, A502, A503, A505, A506, A509, A514, A515, A518, A520, A523, A526, A528, A529, A531, A533, A534, A536, A537, A538, A542, A543, A545, A549, A551, A552, A554, A555, A557, A558, A559, A560, A561, A562, A563, A564, A565, A566, A567, A568, A569, A571, A574, A576, A578, A580, A581, A582, A583, A586, A587, A588, A589, A590, A591, A593, A595, A596, A6, A600, A601, A603, A606, A607, A608, A610, A611, A614, A615, A616, A62, A66, A67, A68, A7, A78, A79, A8, A80, A81, A83, A85, A87, A87, A88, A89, A99 |
| ++++ | A105, A107, A108, A109, A11, A110, A112, A113, A117, A118, A119, A12, A13, A137, A138, A144, A152, A16, A17, A170, A173, A175, A176, A177, A178, A179, A179, A18, A184, A19, A20, A208, A21, A210, A213, A215, A22, A222, A225, A226, A236, A239, A24, A25, A253, A254, A254, A257, A26, A260, A262, A272, A276, A28, A282, A283, A284, A292, A293, A295, A296, A297, A299, A30, A300, A301, A305, A307, A308, A315, A316, A318, A319, A320, A322, A324, A326, A329, A33, A330, A331, A337, A338, A339, A344, A345, A35, A352, A354, A355, A357, A359, A36, A36, A360, A361, A362, A366, A367, A368, A369, A375, A38, A387, A389, A39, A4, A40, A403, A425, A428, A43, A431, A433, A437, A439, A44, A440, A442, A445, A448, A449, A451, A452, A455, A456, A46, A460, A461, A462, A464, A47, A470, A472, A473, A474, A479, A480, A481, A486, A489, A49, A490, A495, A496, A497, A499, A50, A504, A508, A51, A510, A511, A512, A513, A516, A517, A519, A521, A522, A524, A525, A527, A530, A532, A535, A539, A540, A541, A544, A547, A548, A550, A553, A556, A570, A572, A575, A579, A585, A592, A597, A598, A599, A602, A604, A609, A612, A64, A65, A69, A70, A76, A82, A84, A9, A90, A91, A92, A93, A94, A96, A97, A98, A613 |
| +++++ | A103, A103, A104, A104, A115, A116, A116, A117, A141, A142, A143, A145, A150, A153, A154, A172, A178, A180, A181, A182, A183, A185, A186, A187, A188, A189, A190, A191, A192, A193, A194, A195, A196, A197, A198, A199, A200, A203, A206, A207, A212, A214, A220, A221, A225, A234, A235, A236, A237, A238, A244, A245, A246, A253, A256, A258, A261, A271, A281, A29, A3, A317, A327, A328, A340, A341, A37, A388, A398, A42, A429, A430, A446, A453, A482, A52, A53, A54, A54, A55, A56, A57, A58, A59, A60, A61, A63, A75, A77, A86 |

TABLE 8

KRAS G12C FRET data

| IC50* | Examples |
|---|---|
| + | A323, A325, A347, A501, A546, A577, A594 |
| ++ | A1, A10, A100, A11, A111, A114, A117, A12, A120, A121, A125, A126, A127, A128, A129, A13, A131, A132, A135, A136, A139, A14, A140, A146, A147, A148, A149, A15, A151, A155, A156, A157, A159, A16, A160, A162, A164, A165, A166, A168, A17, A18, A19, A2, A20, A201, A202, A204, A205, A211, A216, A217, A218, A219, A223, A224, A226, A227, A228, A229, A230, A231, A233, A240, A241, A242, A243, A247, A248, A248, A249, A250, A252, A252, A255, A262, A264, A265, A266, A273, A274, A275, A277, A278, A279, A280, A285, A288, A289, A290, A291, A298, A3, A302, A303, A304, A306, A309, A310, A312, A316, A321, A330, A333, A334, A335, A336, A338, A342, A343, A346, A348, A349, A350, A351, A353, A356, A358, A363, A364, A365, A370, A371, A372, A373, A374, A376, A377, A378, A379, A380, A381, A382, A383, A384, A385, A386, A387, A391, A392, A393, A395, A396, A397, A399, A4, A400, A401, A402, A405, A406, A407, A408, A409, A410, A411, A412, A413, A414, A415, A418, A419, A420, A422, A424, A426, A427, A432, A438, A443, A444, A450, A452, A454, A457, A458, A459, A465, A466, A467, A471, A475, A477, A478, A483, A484, A487, A488, A489, A491, A493, A494, A498, A5, A500, A503, A505, A507, A509, A510, A514, A515, A523, A526, A528, A529, A533, A534, A536, A537, A538, A540, A543, A549, A550, A551, A552, A554, A555, A557, A558, A560, A561, A562, A565, A567, A569, A571, A573, A574, A576, A578, A581, A582, A583, A584, A586, A590, A591, A593, A595, A596, A598, A6, A600, A601, A605, A606, A607, A608, A614, A615, A616, A62, A67, A68, A7, A8, A87, A9, A95 |
| +++ | A101, A102, A105, A106, A12, A122, A123, A124, A130, A133, A134, A137, A138, A144, A158, A161, A163, A167, A169, A170, A171, A173, A174, A176, A178, A179, A179, A182, A183, A184, A207, A208, A209, A21, A210, A215, A22, A225, A227, A23, A232, A236, A24, A25, A251, A253, A254, A257, A259, A26, A260, A267, A268, A27, A270, A276, A28, A282, A283, A284, A286, A287, A29, A292, A293, A294, A295, A296, A297, A299, A30, A301, A305, A308, A31, A311, A313, A314, A315, A318, A319, A32, A320, A322, A324, A326, A329, A33, A331, A332, A337, A339, A34, A344, A345, A35, A352, A354, A355, A357, A359, A36, A36, A360, A361, A362, A366, A367, A368, A37, A375, A38, A389, A39, A394, A4, A40, A403, A404, A41, A416, A417, A42, A421, A423, A425, A43, A431, A433, A434, A435, A436, A437, A439, A44, A440, A441, A445, A447, A449, A45, A451, A453, A455, A456, A46, A460, A461, A462, A463, A468, A469, A47, A472, A473, A474, A476, A479, A48, A480, A481, A485, A486, A49, A490, A492, A495, A496, A497, A499, A50, A502, A504, A506, A508, A51, A511, A512, A513, A518, A519, A52, A520, A521, A522, A524, A525, A527, A53, A530, A531, A532, A535, A541, A542, A544, A545, A547, A548, A553, A556, A559, A563, A564, A566, A568, A570, A579, A580, A585, A587, A588, A589, A592, A597, A602, A603, A610, A611, A612, A64, A65, A66, A69, A76, A78, A79, A80, A81, A82, A83, A84, A85, A86, A87, A88, A89, A90, A91, A93, A94, A96, A97, A98, A99 |
| ++++ | A104, A107, A108, A109, A110, A112, A113, A115, A116, A117, A118, A119, A141, A142, A143, A150, A152, A175, A177, A178, A180, A181, A185, A199, A203, A206, A212, A213, A214, A220, A221, A222, A225, A236, A237, A238, A239, A244, A245, A246, A253, A256, A258, A261, A271, A272, A281, A3, A300, A307, A317, A388, A398, A428, A429, A442, A446, A448, A464, A470, A482, A516, A517, A539, A54, A54, A55, A56, A57, A572, A575, A58, A59, A599, A60, A604, A609, A61, A63, A70, A75, A77, A92, A613 |
| +++++ | A103, A103, A104, A116, A145, A153, A154, A172, A186, A187, A188, A189, A190, A191, A192, A193, A194, A195, A196, A197, A198, A200, A234, A235, A327, A328, A340, A341, A430 |

TABLE 9

KRAS G12S FRET data

| IC50* | Examples |
|---|---|
| + | A501, A577, A594 |
| ++ | A1, A10, A100, A111, A114, A120, A121, A124, A125, A127, A128, A129, A131, A135, A139, A140, A147, A148, A156, A159, A162, A164, A165, A2, A202, A204, A211, A217, A218, A219, A223, A224, A227, A228, A230, A242, A243, A247, A248, A248, A249, A250, A252, A252, A273, A275, A277, A291, A3, A312, A323, A325, A335, A342, A347, A348, A349, A351, A363, A365, A370, A371, A377, A378, A379, A380, A381, A385, A386, A391, A392, A393, A395, A396, A397, A4, A400, A405, A406, A407, A408, A409, A411, A414, A415, A418, A419, A422, A424, A427, A459, A465, A483, A491, A494, A498, A5, A500, A503, A507, A526, A529, A537, A546, A554, A555, A558, A561, A565, A573, A578, A584, A590, A6, A605, A606, A607, A615, A68, A7, A87, A95 |
| +++ | A101, A102, A11, A117, A119, A12, A122, A123, A126, A13, A130, A132, A133, A134, A136, A14, A146, A149, A15, A151, A155, A157, A158, A16, A160, A161, A163, A166, A167, A168, A169, A17, A170, A171, A173, A174, A184, A19, A20, A201, A205, A209, A21, A215, A216, A22, A226, A229, A23, A231, A232, A233, A236, A24, A240, A241, A25, A251, A254, A254, A255, A257, A259, A26, A260, A262, A264, A265, A266, A267, A268, A27, A270, A274, A276, A278, A279, A28, A280, A284, A285, A286, A287, A288, A289, A29, A290, A293, A294, A295, A296, A297, A298, A30, A301, A302, A303, A304, A306, A309, A31, A310, A311, A313, A314, A315, A316, A318, A319, A32, A320, A321, A324, A326, A329, A33, A330, A331, A332, A333, A334, A336, A337, A338, A343, A344, A346, A35, A350, A352, A353, A354, A356, A357, A358, A36, A360, A361, A362, A364, A367, A368, A369, A37, A372, A373, A374, A375, A376, A38, A382, A383, A384, A387, A39, A394, A399, A40, A401, A402, A403, A404, A41, A410, A412, A413, A416, A417, A420, A421, A423, A426, A43, A431, A432, A433, A434, A435, A436, A437, A438, A441, A443, A444, A445, A447, A45, A450, A451, A452, A454, A455, A456, A457, A458, A46, A463, A466, A467, A468, A469, A47, A471, A472, A473, A474, A475, A476, A477, A478, A48, A480, A484, A485, A486, A487, A488, A489, A490, A492, A493, A495, A502, A505, A506, A508, A509, A51, A510, A511, A512, A513, A514, A515, A518, A520, A521, A522, A523, A525, A527, A528, A530, A531, A532, A533, A534, A535, A536, A538, A540, A541, A542, A543, A545, A547, |

TABLE 9-continued

KRAS G12S FRET data

| IC50* | Examples |
|---|---|
| | A549, A550, A551, A552, A556, A557, A559, A560, A562, A563, A564, A566, A567, A568, A569, A570, A571, A574, A576, A580, A581, A582, A583, A585, A586, A587, A588, A589, A591, A593, A595, A596, A597, A598, A600, A601, A602, A603, A608, A610, A611, A614, A616, A62, A64, A65, A66, A67, A69, A76, A78, A79, A8, A80, A81, A83, A84, A85, A87, A88, A89, A9, A90, A91, A93, A94 |
| ++++ | A105, A106, A107, A108, A109, A110, A112, A113, A115, A116, A118, A12, A137, A138, A141, A142, A143, A144, A152, A175, A176, A177, A178, A178, A179, A179, A180, A181, A182, A183, A185, A203, A207, A208, A210, A213, A214, A220, A221, A222, A225, A225, A236, A237, A238, A239, A244, A245, A246, A253, A256, A258, A261, A271, A272, A281, A282, A283, A292, A299, A3, A300, A305, A307, A308, A317, A322, A339, A34, A345, A355, A359, A36, A366, A388, A389, A398, A4, A42, A425, A428, A439, A44, A440, A442, A446, A448, A449, A453, A460, A461, A462, A464, A470, A479, A481, A482, A49, A496, A497, A499, A50, A504, A516, A517, A519, A52, A524, A53, A539, A54, A54, A544, A548, A55, A553, A56, A57, A572, A575, A579, A58, A59, A592, A599, A60, A604, A609, A61, A612, A63, A70, A75, A82, A86, A92, A96, A97, A98, A99, A613 |
| +++++ | A103, A103, A104, A104, A116, A117, A145, A150, A153, A154, A172, A186, A187, A188, A189, A190, A191, A192, A193, A194, A195, A196, A197, A198, A199, A200, A206, A212, A234, A235, A253, A327, A328, A340, A341, A429, A430, A77 |

TABLE 10

KRAS G13C FRET data

| IC50* | Examples |
|---|---|
| + | A381, A325, A501, A594 |
| ++ | A1, A10, A100, A101, A102, A111, A114, A121, A123, A124, A125, A126, A127, A128, A129, A130, A131, A132, A133, A134, A135, A139, A140, A146, A147, A148, A149, A151, A155, A156, A159, A160, A162, A164, A165, A166, A168, A169, A171, A184, A201, A202, A204, A21, A211, A215, A216, A217, A218, A219, A223, A224, A226, A227, A227, A228, A229, A23, A230, A231, A233, A240, A241, A242, A243, A247, A248, A248, A249, A25, A250, A251, A252, A252, A255, A266, A27, A275, A277, A3, A31, A323, A324, A342, A346, A347, A348, A349, A351, A364, A365, A370, A371, A377, A378, A379, A380, A384, A385, A386, A391, A392, A393, A394, A395, A396, A397, A4, A405, A406, A407, A408, A409, A41, A410, A413, A414, A415, A418, A419, A420, A421, A422, A424, A426, A427, A432, A459, A465, A500, A507, A509, A526, A529, A546, A554, A555, A562, A573, A577, A578, A584, A605, A607, A615, A616, A67, A68, A78, A87, A88, A89, A95 |
| +++ | A105, A106, A107, A109, A11, A117, A118, A119, A12, A120, A122, A13, A136, A138, A14, A142, A144, A15, A157, A158, A16, A161, A163, A167, A17, A170, A174, A175, A176, A177, A178, A178, A179, A179, A18, A180, A181, A182, A183, A185, A19, A2, A20, A205, A207, A208, A209, A214, A22, A225, A225, A232, A236, A236, A24, A253, A254, A254, A256, A257, A258, A259, A26, A262, A264, A265, A267, A268, A270, A273, A274, A276, A278, A279, A28, A280, A284, A285, A286, A287, A288, A289, A290, A291, A293, A294, A295, A296, A297, A298, A30, A302, A303, A304, A306, A309, A310, A311, A312, A313, A314, A315, A316, A318, A319, A32, A320, A321, A322, A329, A33, A330, A331, A332, A333, A334, A335, A336, A337, A338, A343, A344, A345, A35, A350, A352, A353, A354, A355, A356, A357, A358, A359, A360, A361, A362, A363, A366, A367, A368, A369, A37, A372, A373, A374, A375, A376, A382, A383, A387, A388, A39, A398, A399, A4, A40, A400, A401, A402, A403, A404, A411, A412, A416, A417, A423, A425, A43, A431, A433, A434, A435, A436, A437, A438, A439, A441, A443, A444, A445, A447, A449, A45, A450, A451, A452, A454, A456, A457, A458, A46, A462, A463, A466, A467, A468, A469, A47, A470, A471, A472, A473, A474, A475, A476, A477, A478, A48, A480, A483, A484, A485, A486, A487, A488, A489, A490, A491, A492, A493, A494, A495, A497, A498, A5, A502, A503, A504, A505, A506, A508, A51, A510, A511, A512, A513, A514, A515, A518, A520, A521, A522, A523, A524, A525, A528, A530, A531, A532, A533, A534, A535, A536, A537, A538, A540, A541, A542, A543, A544, A545, A547, A548, A549, A55, A550, A551, A552, A553, A556, A557, A558, A559, A560, A561, A563, A564, A565, A566, A567, A568, A569, A570, A571, A574, A576, A579, A580, A581, A582, A583, A585, A586, A587, A588, A589, A590, A591, A592, A593, A595, A596, A597, A598, A6, A600, A601, A602, A603, A606, A608, A610, A611, A614, A62, A65, A66, A69, A7, A75, A76, A79, A8, A80, A81, A82, A83, A84, A85, A86, A87, A9, A90, A91, A92, A93, A94, A96, A98, A99 |
| ++++ | A104, A104, A108, A110, A112, A113, A115, A116, A12, A137, A141, A143, A150, A152, A172, A173, A188, A199, A203, A206, A210, A212, A213, A220, A221, A222, A234, A235, A237, A238, A239, A244, A245, A246, A253, A260, A261, A271, A272, A281, A282, A283, A29, A292, A299, A3, A300, A301, A305, A307, A308, A317, A326, A339, A34, A36, A36, A38, A389, A42, A428, A44, A440, A442, A446, A448, A453, A455, A460, A461, A464, A479, A481, A482, A49, A496, A499, A50, A516, A517, A519, A52, A527, A53, A539, A54, A54, A56, A57, A572, A575, A58, A599, A604, A609, A61, A612, A63, A64, A70, A77, A97, A613 |
| +++++ | A103, A103, A116, A117, A145, A153, A154, A186, A187, A189, A190, A191, A192, A193, A194, A195, A196, A197, A198, A200, A327, A328, A340, A341, A429, A430, A59, A60 |

TABLE 11

KRAS G12V FRET data

| IC50* | Examples |
|---|---|
| + | A325 |
| ++ | A1, A11, A114, A117, A121, A135, A139, A140, A146, A147, A156, A159, A160, A162, A164, A165, A2, A201, A202, A204, A211, A218, A219, A223, A224, A230, A233, A247, A248, A249, A250, A252, A264, A265, A266, A275, A277, A278, A279, A3, A323, A342, A347, A348, A349, A365, A370, A371, A377, A378, A379, A380, A385, A391, A396, A399, A405, A407, A415, A422, A423, A424, A427, A454, A465, A477, A487, A5, A500, A501, A507, A526, A529, A546, A554, A555, A562, A577, A578, A584, A594, A605, A607, A615, A95 |
| +++ | A10, A100, A102, A12, A120, A123, A124, A125, A126, A127, A128, A129, A13, A131, A132, A136, A137, A138, A14, A148, A149, A15, A151, A155, A157, A158, A16, A161, A166, A167, A168, A17, A170, A171, A174, A176, A18, A184, A19, A20, A205, A209, A21, A215, A217, A22, A226, A227, A228, A229, A231, A232, A236, A24, A240, A241, A242, A243, A248, A25, A251, A252, A254, A254, A255, A257, A26, A262, A267, A268, A270, A273, A274, A28, A280, A285, A286, A287, A288, A289, A29, A290, A291, A293, A294, A295, A296, A297, A298, A30, A301, A302, A303, A304, A306, A309, A310, A311, A312, A313, A314, A315, A316, A318, A319, A320, A321, A322, A324, A326, A329, A33, A330, A331, A332, A333, A334, A335, A336, A337, A338, A343, A344, A345, A346, A35, A350, A351, A352, A353, A354, A355, A356, A357, A358, A359, A36, A36, A360, A361, A362, A363, A364, A366, A367, A368, A369, A37, A372, A373, A374, A375, A376, A38, A381, A382, A383, A384, A386, A387, A39, A392, A393, A394, A395, A397, A4, A40, A400, A401, A402, A403, A406, A408, A409, A410, A411, A412, A413, A414, A416, A418, A419, A420, A425, A426, A43, A431, A433, A436, A437, A438, A44, A441, A443, A444, A445, A450, A451, A452, A456, A457, A458, A459, A463, A466, A467, A471, A472, A474, A475, A476, A478, A480, A483, A484, A485, A486, A488, A489, A49, A490, A491, A492, A493, A494, A495, A496, A498, A503, A505, A506, A509, A510, A511, A512, A513, A514, A515, A520, A521, A522, A523, A525, A528, A530, A531, A532, A533, A534, A535, A536, A537, A538, A540, A541, A543, A545, A547, A548, A549, A550, A551, A552, A553, A557, A558, A559, A560, A561, A564, A565, A566, A567, A568, A569, A570, A571, A573, A574, A575, A576, A579, A580, A581, A582, A583, A585, A586, A589, A590, A591, A593, A595, A596, A597, A598, A6, A600, A601, A602, A603, A606, A608, A610, A614, A616, A62, A64, A67, A68, A7, A76, A78, A8, A83, A87, A89, A9, A90, A91, A93, A94 |
| ++++ | A101, A105, A106, A111, A112, A113, A115, A116, A117, A12, A122, A130, A133, A134, A141, A142, A143, A144, A152, A163, A169, A173, A177, A178, A178, A179, A179, A180, A181, A182, A183, A185, A199, A203, A207, A208, A210, A212, A214, A216, A220, A221, A225, A227, A23, A236, A237, A238, A239, A244, A245, A246, A253, A253, A256, A258, A259, A260, A261, A27, A271, A276, A281, A282, A283, A284, A292, A299, A3, A300, A305, A307, A308, A31, A317, A32, A339, A34, A388, A389, A398, A404, A41, A417, A42, A421, A428, A432, A434, A435, A439, A440, A442, A447, A449, A453, A455, A46, A460, A461, A462, A464, A468, A469, A470, A473, A479, A48, A481, A482, A497, A499, A50, A502, A504, A508, A51, A516, A517, A518, A519, A52, A524, A527, A53, A539, A54, A54, A542, A544, A55, A556, A56, A563, A57, A572, A575, A58, A587, A588, A59, A592, A599, A60, A604, A609, A61, A611, A612, A63, A65, A66, A69, A75, A79, A80, A81, A82, A84, A85, A86, A87, A88, A92, A96, A97, A98, A99, A613 |
| +++++ | A103, A103, A104, A104, A107, A108, A109, A110, A116, A118, A119, A145, A150, A153, A154, A172, A175, A186, A187, A188, A189, A190, A191, A192, A193, A194, A195, A196, A197, A198, A200, A206, A213, A222, A234, A235, A272, A327, A328, A340, A341, A4, A429, A430, A446, A448, A45, A47, A70, A77 |

TABLE 12

KRAS WT FRET data

| IC50* | Examples |
|---|---|
| + | A594 |
| ++ | A1, A10, A100, A111, A114, A121, A124, A125, A126, A127, A128, A129, A130, A131, A135, A139, A140, A146, A147, A148, A149, A151, A155, A156, A157, A159, A160, A162, A164, A165, A166, A168, A2, A202, A204, A211, A216, A217, A218, A219, A223, A224, A227, A228, A23, A230, A231, A241, A242, A243, A247, A248, A249, A252, A252, A274, A275, A277, A278, A287, A290, A291, A298, A3, A306, A312, A323, A325, A333, A335, A336, A342, A346, A347, A348, A349, A351, A363, A365, A370, A371, A372, A373, A374, A377, A378, A379, A380, A381, A385, A386, A391, A392, A393, A395, A396, A397, A4, A400, A402, A405, A406, A407, A409, A410, A411, A412, A413, A415, A418, A419, A422, A424, A426, A427, A443, A454, A459, A465, A475, A483, A487, A491, A493, A494, A498, A500, A501, A503, A505, A507, A526, A528, A529, A536, A537, A545, A546, A554, A555, A558, A560, A561, A562, A565, A571, A573, A574, A577, A578, A584, A590, A596, A600, A605, A606, A607, A615, A616, A87, A95 |
| +++ | A101, A102, A106, A11, A117, A12, A120, A122, A123, A13, A132, A133, A134, A136, A137, A138, A14, A144, A15, A158, A16, A161, A163, A167, A169, A17, A170, A171, A173, A174, A176, A178, A179, A179, A18, A184, A19, A20, A201, A205, A208, A209, A21, A210, A215, A22, A226, A227, A229, A232, A233, A236, A24, A240, A248, A25, A250, A251, A254, A254, A255, A257, A259, A26, A260, A262, A264, A265, A266, A267, A268, A27, A270, A273, A276, A279, A28, A280, A283, A284, A285, A286, A288, A289, A292, A293, A294, A295, A296, A297, A299, A30, A301, A302, A303, A304, A308, A309, A31, A310, A311, A313, A314, A315, A316, A318, A319, A32, A320, A321, A322, A324, A326, A329, A330, A331, A332, A334, A337, A338, A339, A343, A344, A345, A35, A350, A352, A353, A354, A355, A356, A357, A358, A360, A361, A362, A364, A367, A368, A369, A37, A375, A376, A38, A382, A383, A384, A387, A39, A394, A399, A40, A401, A403, A404, A408, A41, A414, A416, A417, A420, A421, A423, A43, A432, A433, A434, A435, A436, A437, A438, A439, A44, A440, A441, A444, A445, A447, A449, A45, A450, A451, A452, A455, A456, A457, A458, A46, A461, A463, A466, A467, A468, A469, A47, A471, A472, A473, A474, A476, A477, A478, A48, A480, A484, A485, A486, A488, A489, A49, |

TABLE 12-continued

KRAS WT FRET data

| IC50* | Examples |
|---|---|
| | A490, A492, A495, A496, A5, A50, A502, A504, A506, A508, A509, A51, A510, A511, A512, A513, A514, A515, A518, A519, A520, A521, A522, A523, A524, A525, A527, A530, A531, A532, A533, A534, A535, A538, A540, A541, A542, A543, A547, A548, A549, A550, A551, A552, A553, A556, A557, A559, A563, A564, A566, A567, A568, A569, A570, A576, A579, A580, A581, A582, A583, A585, A586, A587, A588, A589, A591, A593, A595, A597, A598, A6, A601, A602, A603, A608, A610, A611, A614, A62, A64, A65, A66, A67, A68, A7, A76, A78, A79, A8, A80, A81, A82, A83, A84, A85, A87, A88, A89, A9, A90, A91, A93, A94, A99 |
| ++++ | A105, A107, A108, A109, A110, A112, A113, A115, A116, A118, A119, A12, A141, A142, A143, A150, A152, A175, A177, A178, A180, A181, A182, A183, A185, A199, A203, A206, A207, A213, A214, A220, A221, A222, A225, A225, A234, A235, A236, A237, A238, A239, A244, A245, A246, A253, A253, A256, A258, A261, A271, A272, A281, A282, A29, A3, A300, A305, A307, A317, A33, A34, A359, A36, A36, A366, A388, A389, A398, A4, A42, A425, A428, A429, A431, A442, A446, A448, A453, A460, A462, A464, A470, A479, A481, A482, A497, A499, A516, A517, A52, A53, A539, A54, A54, A544, A55, A56, A57, A572, A575, A58, A59, A592, A599, A60, A604, A609, A61, A612, A63, A69, A70, A75, A86, A92, A96, A97, A98, A613 |
| +++++ | A103, A103, A104, A104, A116, A117, A145, A153, A154, A172, A186, A187, A188, A189, A190, A191, A192, A193, A194, A195, A196, A197, A198, A200, A212, A327, A328, A340, A341, A430, A77 |

TABLE 13

KRAS G13D FRET data

| IC50* | Examples (Example A55 not tested) |
|---|---|
| + | None |
| ++ | A1, A10, A100, A111, A114, A121, A124, A125, A127, A128, A129, A130, A131, A133, A134, A135, A139, A140, A148, A151, A155, A159, A162, A163, A164, A165, A169, A2, A202, A204, A211, A216, A217, A223, A224, A227, A227, A228, A229, A23, A231, A242, A243, A247, A248, A249, A251, A252, A255, A27, A275, A277, A3, A323, A325, A342, A347, A348, A349, A365, A370, A371, A378, A379, A380, A381, A385, A386, A391, A392, A393, A395, A396, A397, A4, A405, A407, A409, A41, A415, A419, A424, A426, A427, A432, A45, A459, A501, A507, A529, A546, A558, A573, A577, A578, A584, A594, A605, A607, A615, A67, A87, A88, A95 |
| +++ | A101, A102, A11, A117, A119, A12, A120, A122, A123, A126, A13, A132, A136, A14, A146, A147, A149, A15, A156, A157, A158, A16, A160, A161, A166, A167, A168, A17, A170, A171, A174, A176, A179, A18, A184, A19, A20, A201, A205, A209, A21, A215, A218, A219, A226, A230, A232, A233, A236, A24, A240, A241, A248, A25, A250, A252, A254, A254, A257, A259, A26, A262, A264, A265, A266, A267, A268, A270, A273, A274, A278, A279, A28, A280, A284, A285, A286, A287, A288, A289, A290, A291, A293, A294, A295, A298, A302, A303, A304, A306, A309, A31, A310, A311, A312, A313, A314, A315, A316, A318, A319, A32, A321, A324, A329, A330, A332, A333, A334, A335, A336, A337, A338, A343, A345, A346, A35, A350, A351, A352, A353, A356, A357, A358, A361, A363, A364, A369, A372, A373, A374, A375, A376, A377, A38, A382, A383, A384, A387, A39, A394, A399, A4, A40, A400, A401, A402, A403, A404, A406, A408, A410, A411, A412, A413, A414, A416, A417, A418, A420, A421, A422, A423, A43, A433, A434, A435, A436, A437, A438, A441, A442, A443, A444, A445, A447, A450, A452, A454, A457, A458, A46, A463, A465, A466, A467, A468, A469, A47, A471, A473, A475, A476, A477, A478, A48, A480, A483, A484, A485, A486, A487, A488, A489, A491, A492, A493, A494, A498, A5, A500, A502, A503, A504, A505, A506, A509, A51, A510, A512, A513, A514, A515, A518, A520, A523, A525, A526, A528, A531, A532, A533, A534, A535, A536, A537, A538, A540, A542, A543, A545, A549, A550, A551, A552, A554, A555, A557, A559, A560, A561, A562, A563, A564, A565, A566, A567, A568, A569, A570, A571, A574, A576, A580, A581, A582, A583, A586, A587, A588, A589, A590, A591, A593, A595, A596, A597, A598, A6, A600, A601, A602, A603, A606, A608, A610, A611, A614, A616, A62, A64, A65, A66, A68, A7, A76, A78, A79, A8, A80, A81, A83, A84, A85, A87, A89, A9, A90, A93, A94 |
| ++++ | A105, A106, A107, A108, A109, A110, A112, A113, A115, A116, A118, A12, A137, A138, A141, A142, A143, A144, A152, A173, A175, A177, A178, A179, A180, A181, A182, A183, A185, A199, A203, A206, A207, A208, A210, A213, A214, A22, A222, A225, A225, A236, A238, A239, A246, A253, A256, A258, A260, A261, A272, A276, A281, A282, A283, A29, A292, A296, A297, A299, A30, A300, A301, A305, A307, A308, A317, A320, A322, A326, A33, A331, A339, A34, A344, A354, A355, A359, A36, A36, A360, A362, A366, A367, A368, A37, A388, A389, A398, A42, A425, A431, A439, A44, A440, A446, A448, A449, A451, A455, A456, A460, A461, A462, A464, A470, A472, A474, A479, A481, A482, A49, A490, A495, A496, A497, A499, A50, A508, A511, A516, A517, A519, A52, A521, A522, A524, A527, A53, A530, A539, A54, A541, A544, A547, A548, A553, A556, A56, A57, A572, A575, A579, A58, A585, A59, A592, A599, A604, A609, A61, A612, A63, A69, A70, A75, A77, A82, A86, A91, A92, A96, A97, A98, A99, A613 |
| +++++ | A103, A103, A104, A104, A116, A117, A145, A150, A153, A154, A172, A186, A187, A188, A189, A190, A191, A192, A193, A194, A195, A196, A197, A198, A200, A212, A220, A221, A234, A235, A237, A244, A245, A253, A271, A3, A327, A328, A340, A341, A428, A429, A430, A453, A60 |

TABLE 14

KRAS Q61H FRET data

| IC50* | Examples |
|---|---|
| + | A159, A275, A415, A501, A546, A577, A594, A605 |
| ++ | A102, A124, A136, A174, A204, A205, A226, A230, A236, A24, A25, A250, A266, A268, A273, A274, A277, A278, A279, A280, A285, A287, A289, A290, A291, A3, A302, A304, A306, A309, A310, A312, A316, A324, A334, A335, A346, A349, A356, A358, A37, A372, A373, A374, A376, A38, A382, A383, A387, A396, A399, A400, A401, A405, A406, A409, A422, A424, A426, A434, A438, A443, A444, A450, A454, A457, A459, A465, A466, A467, A468, A471, A474, A475, A477, A478, A480, A483, A484, A485, A487, A488, A491, A492, A493, A494, A498, A500, A502, A503, A505, A507, A509, A510, A514, A515, A520, A523, A526, A528, A529, A530, A531, A533, A534, A536, A537, A538, A540, A543, A545, A549, A550, A551, A552, A554, A555, A557, A558, A559, A560, A561, A562, A563, A564, A565, A566, A567, A569, A571, A573, A574, A578, A581, A582, A583, A584, A589, A590, A591, A593, A595, A596, A600, A601, A606, A607, A608, A610, A614, A615, A616, A89 |
| +++ | A138, A144, A152, A163, A170, A176, A177, A178, A178, A179, A179, A180, A181, A207, A208, A210, A225, A225, A253, A264, A265, A267, A270, A271, A272, A276, A281, A282, A283, A284, A286, A293, A297, A299, A305, A315, A320, A321, A331, A337, A344, A354, A357, A359, A360, A361, A362, A366, A367, A368, A369, A375, A388, A389, A423, A433, A435, A436, A437, A439, A440, A441, A442, A445, A447, A449, A451, A452, A453, A455, A456, A458, A460, A461, A462, A463, A464, A469, A470, A472, A473, A476, A479, A481, A482, A486, A489, A490, A495, A496, A497, A499, A504, A506, A508, A511, A512, A513, A518, A519, A521, A522, A524, A525, A527, A532, A535, A54, A541, A542, A544, A547, A548, A553, A556, A568, A57, A570, A572, A576, A579, A580, A585, A586, A587, A588, A592, A597, A598, A599, A602, A603, A604, A609, A61, A611, A612, A99 |
| ++++ | A104, A145, A150, A220, A234, A237, A446, A448, A516, A517, A539, A575, A613 |
| +++++ | A154, A186, A189, A191, A328, A340 |

TABLE 15

NRAS G12C FRET data

| IC50* | Examples |
|---|---|
| + | A323, A325, A501, A577, A578, A594 |
| ++ | A1, A10, A100, A11, A114, A120, A121, A125, A127, A128, A129, A131, A135, A136, A139, A140, A146, A147, A148, A151, A156, A157, A159, A160, A162, A164, A165, A166, A168, A2, A201, A202, A204, A205, A211, A217, A218, A219, A223, A224, A228, A229, A230, A231, A233, A240, A242, A243, A247, A248, A248, A249, A250, A252, A252, A264, A265, A266, A267, A268, A273, A274, A275, A277, A278, A279, A280, A285, A288, A289, A290, A291, A298, A3, A302, A303, A304, A306, A309, A310, A312, A313, A316, A319, A321, A330, A333, A334, A335, A336, A338, A342, A343, A346, A347, A348, A349, A350, A351, A353, A356, A357, A358, A363, A364, A365, A370, A371, A372, A373, A374, A376, A377, A378, A379, A380, A381, A382, A383, A384, A385, A386, A387, A391, A392, A393, A395, A396, A397, A399, A4, A400, A401, A402, A405, A406, A407, A408, A409, A411, A413, A414, A415, A418, A419, A422, A424, A426, A427, A432, A436, A438, A443, A444, A450, A452, A454, A457, A458, A459, A465, A466, A467, A471, A475, A476, A477, A478, A483, A484, A487, A488, A489, A491, A493, A494, A498, A5, A500, A503, A505, A507, A509, A510, A514, A515, A523, A526, A528, A529, A531, A533, A534, A536, A537, A538, A540, A543, A545, A546, A549, A550, A551, A552, A554, A555, A557, A558, A559, A560, A561, A562, A565, A567, A569, A571, A573, A574, A576, A581, A582, A583, A584, A590, A591, A593, A595, A596, A598, A6, A600, A601, A605, A606, A607, A608, A614, A615, A616, A8, A87, A95 |
| +++ | A101, A102, A106, A111, A117, A122, A123, A124, A126, A13, A130, A132, A133, A134, A137, A138, A14, A149, A15, A155, A158, A16, A161, A163, A167, A169, A17, A170, A171, A173, A174, A176, A18, A184, A19, A20, A209, A21, A210, A215, A216, A226, A227, A227, A23, A232, A236, A24, A241, A25, A251, A254, A255, A257, A259, A26, A260, A262, A27, A270, A276, A28, A282, A283, A284, A286, A287, A29, A292, A293, A294, A295, A296, A297, A299, A30, A301, A305, A308, A31, A311, A314, A315, A318, A32, A320, A322, A324, A326, A329, A331, A332, A337, A339, A344, A345, A35, A352, A354, A355, A359, A36, A36, A360, A361, A362, A366, A367, A368, A369, A37, A375, A38, A389, A39, A394, A40, A403, A404, A41, A410, A412, A416, A417, A420, A421, A423, A43, A431, A433, A434, A435, A437, A439, A44, A440, A441, A445, A447, A449, A451, A453, A455, A456, A46, A460, A461, A462, A463, A468, A469, A47, A472, A473, A474, A479, A480, A481, A482, A485, A486, A490, A492, A495, A496, A497, A499, A502, A504, A506, A508, A511, A512, A513, A518, A519, A520, A521, A522, A524, A525, A527, A530, A532, A535, A539, A541, A542, A544, A547, A548, A553, A556, A563, A564, A566, A568, A570, A579, A580, A585, A586, A587, A588, A589, A592, A597, A602, A603, A609, A610, A611, A612, A62, A64, A65, A66, A67, A68, A76, A78, A79, A80, A81, A83, A85, A87, A88, A89, A9, A90, A91, A93, A94, A96, A97, A98, A99 |
| ++++ | A105, A107, A108, A109, A110, A112, A113, A115, A116, A117, A118, A119, A12, A141, A142, A143, A144, A150, A152, A175, A177, A178, A178, A179, A179, A180, A181, A182, A183, A185, A199, A203, A206, A207, A208, A212, A213, A214, A220, A221, A225, A225, A235, A236, A237, A238, A239, A244, A245, A246, A253, A253, A256, A258, A261, A271, A272, A281, A3, A300, A307, A317, A388, A398, A4, A42, A425, A428, A429, A442, A446, A448, A45, A464, A470, A49, A50, A51, A516, A517, A52, A53, A54, A56, A57, A572, A575, A58, A59, A599, A60, A604, A61, A63, A75, A82, A84, A86, A92, A613 |
| +++++ | A103, A103, A104, A104, A116, A145, A153, A154, A172, A186, A187, A188, A189, A190, A191, A192, A193, A194, A195, A196, A197, A198, A200, A222, A234, A327, A328, A340, A341, A430, A77 |

TABLE 16

NRAS WT FRET data

| IC50* | Examples |
|---|---|
| + | A501, A577, A594 |
| ++ | A124, A136, A159, A204, A230, A25, A250, A273, A274, A275, A277, A278, A279, A287, A290, A291, A3, A304, A306, A309, A310, A312, A335, A346, A349, A356, A372, A373, A374, A387, A396, A399, A400, A405, A406, A409, A415, A422, A424, A426, A434, A438, A443, A450, A454, A457, A459, A465, A466, A471, A475, A477, A478, A483, A484, A487, A491, A493, A494, A498, A500, A503, A505, A507, A526, A528, A529, A531, A533, A536, A537, A545, A546, A554, A555, A558, A560, A561, A562, A565, A569, A571, A573, A574, A578, A584, A590, A591, A596, A600, A605, A606, A607, A615 |
| +++ | A102, A138, A144, A163, A170, A174, A176, A178, A179, A179, A205, A208, A210, A225, A226, A236, A24, A253, A264, A265, A266, A267, A268, A270, A276, A280, A283, A284, A285, A286, A289, A293, A297, A299, A302, A305, A315, A316, A320, A321, A324, A331, A334, A337, A344, A354, A357, A358, A359, A360, A361, A362, A366, A367, A368, A369, A37, A375, A376, A38, A382, A383, A401, A423, A433, A435, A436, A437, A439, A440, A441, A444, A445, A447, A449, A451, A452, A455, A456, A458, A463, A467, A468, A469, A472, A473, A474, A476, A479, A480, A481, A485, A486, A488, A489, A490, A492, A495, A496, A497, A502, A504, A506, A508, A509, A510, A511, A512, A513, A514, A515, A518, A519, A520, A521, A522, A523, A524, A525, A527, A530, A532, A534, A535, A538, A540, A541, A542, A543, A547, A548, A549, A550, A551, A552, A553, A556, A557, A559, A563, A564, A566, A567, A568, A570, A576, A579, A580, A581, A582, A583, A585, A586, A587, A588, A589, A593, A595, A597, A598, A601, A602, A603, A608, A610, A611, A612, A614, A616, A89, A99 |
| ++++ | A104, A150, A152, A177, A178, A180, A181, A207, A220, A225, A234, A237, A271, A272, A281, A282, A388, A389, A442, A446, A448, A453, A460, A461, A462, A464, A470, A482, A499, A516, A517, A539, A54, A544, A57, A572, A575, A592, A599, A604, A609, A61, A613 |
| +++++ | A145, A154, A186, A189, A191, A328, A340 |

TABLE 17

NRAS Q61K FRET data

| IC50* | Examples |
|---|---|
| + | A275 |
| ++ | A136, A159, A170, A205, A266, A268, A277, A278, A279, A280, A285, A289, A290, A291, A302, A304, A306, A309, A310, A312, A316, A334, A335, A337, A344, A349, A356, A358, A372, A373, A374, A376, A382, A383, A387, A396, A399, A400, A401, A405, A409, A415, A422, A443, A444, A445, A450, A451, A452, A454, A457, A458, A459, A465, A466, A467, A471, A475, A477, A478, A483, A484, A485, A486, A487, A488, A489, A491, A493, A494, A500, A501, A503, A505, A510, A511, A512, A514, A515, A520, A522, A523, A526, A528, A529, A530, A531, A532, A533, A534, A536, A537, A538, A540, A543, A546, A549, A550, A551, A552, A555, A557, A560, A561, A565, A566, A567, A569, A571, A573, A574, A576, A577, A578, A580, A581, A582, A584, A590, A591, A594, A595, A596, A598, A600, A601, A606, A607, A608, A614 |
| +++ | A102, A124, A138, A144, A152, A174, A176, A204, A208, A210, A226, A230, A236, A24, A25, A250, A264, A265, A267, A270, A271, A273, A274, A276, A281, A283, A284, A286, A287, A293, A297, A299, A3, A305, A315, A320, A321, A324, A331, A346, A354, A357, A359, A360, A361, A362, A366, A367, A368, A369, A375, A38, A389, A406, A424, A426, A433, A434, A436, A437, A438, A439, A440, A441, A447, A449, A453, A455, A456, A460, A461, A462, A468, A469, A472, A474, A476, A479, A480, A481, A482, A490, A492, A495, A496, A497, A498, A499, A502, A506, A507, A509, A513, A521, A524, A525, A527, A535, A541, A542, A544, A545, A547, A548, A553, A554, A556, A558, A559, A562, A563, A564, A568, A570, A579, A583, A585, A586, A587, A588, A589, A592, A593, A597, A602, A603, A604, A605, A609, A610, A611, A612, A613, A615, A616, A89 |
| ++++ | A104, A150, A163, A177, A178, A178, A179, A179, A180, A181, A207, A220, A225, A225, A234, A237, A253, A272, A282, A37, A388, A423, A435, A442, A446, A448, A463, A464, A470, A473, A504, A508, A516, A517, A518, A519, A539, A54, A57, A572, A575, A599, A61, A99 |
| +++++ | A145, A154, A186, A189, A191, A328, A340 |

TABLE 18

NRAS Q61R FRET data

| IC50* | Examples |
|---|---|
| + | A577, A594 |
| ++ | A136, A159, A275, A277, A278, A279, A291, A304, A306, A309, A310, A312, A335, A349, A356, A372, A373, A374, A396, A399, A400, A415, A422, A450, A454, A459, A465, A466, A475, A477, A483, A487, A494, A500, A501, A503, A505, A520, A526, A528, A529, A536, A546, A555, A560, A561, A562, A565, A578, A583, A584, A593, A601, A606, A607 |
| +++ | A102, A138, A170, A174, A204, A205, A210, A226, A230, A24, A25, A250, A264, A265, A266, A267, A268, A270, A273, A274, A276, A280, A283, A285, A286, A287, A289, A290, A293, A297, A299, A3, A302, A305, A316, A321, A334, A337, A344, A346, A354, A357, A358, A361, A369, A375, A376, A38, A382, A383, A387, A401, A405, A406, A409, A423, A424, A426, A433, A434, A436, A437, A438, A439, A440, A441, A443, A444, A445, A449, A451, A452, A453, A455, A456, A457, A458, A461, A467, A468, A471, A472, A474, A476, A478, A480, A484, A485, A486, A488, A489, A490, A491, A492, A493, A495, A498, A499, A502, A506, A507, A509, A510, A511, A512, A513, A514, A515, A521, A522, |

TABLE 18-continued

NRAS Q61R FRET data

| IC50* | Examples |
|---|---|
|  | A523, A525, A527, A530, A531, A532, A533, A534, A535, A537, A538, A540, A541, A542, A543, A545, A547, A548, A549, A550, A551, A552, A553, A554, A556, A557, A558, A559, A563, A564, A566, A567, A568, A569, A570, A571, A573, A574, A576, A579, A580, A581, A582, A585, A586, A587, A589, A590, A591, A595, A596, A597, A598, A600, A602, A603, A605, A608, A609, A610, A611, A614, A615, A616, A89 |
| ++++ | A124, A144, A152, A163, A176, A177, A178, A179, A180, A207, A208, A220, A225, A225, A236, A237, A253, A271, A272, A281, A282, A284, A315, A320, A324, A331, A359, A360, A362, A366, A367, A368, A37, A388, A389, A435, A442, A447, A448, A460, A462, A463, A464, A469, A470, A473, A479, A481, A482, A496, A497, A504, A508, A516, A517, A518, A519, A524, A539, A54, A544, A57, A572, A575, A588, A592, A599, A604, A61, A612, A99, A613 |
| +++++ | A104, A145, A150, A154, A178, A181, A186, A189, A191, A234, A328, A340, A446 |

In Vitro Cell Proliferation Panels

Potency for inhibition of cell growth was assessed at CrownBio using standard methods. Briefly, cell lines were cultured in appropriate medium, and then plated in 3D methylcellulose. Inhibition of cell growth was determined by CellTiter-Glo® after 5 days of culture with increasing concentrations of compounds. Compound potency was reported as the 50% inhibition concentration (absolute IC50). The assay took place over 7 days. On day 1, cells in 2D culture were harvested during logarithmic growth and suspended in culture medium at 1×105 cells/ml. Higher or lower cell densities were used for some cell lines based on prior optimization. 3.5 ml of cell suspension was mixed with 6.5% growth medium with 1% methylcellulose, resulting in a cell suspension in 0.65% methylcellulose. 90 µl of this suspension was distributed in the wells of 2 96-well plates. One plate was used for day 0 reading and 1 plate was used for the end-point experiment. Plates were incubated overnight at 37° C. with 5% CO2. On day 2, one plate (for t0 reading) was removed and 10 µl growth medium plus 100 µl CellTiter-Glo® Reagent was added to each well. After mixing and a 10 minute incubation, luminescence was recorded on an EnVision Multi-Label Reader (Perkin Elmer). Compounds in DMSO were diluted in growth medium such that the final, maximum concentration of compound was 10 µM, and serial 4-fold dilutions were performed to generate a 9-point concentration series. 10 µl of compound solution at 10 times final concentration was added to wells of the second plate. Plate was then incubated for 120 hours at 37 C and 5% CO2. On day 7 the plates were removed, 100 µl CellTiter-Glo® Reagent was added to each well, and after mixing and a 10 minute incubation, luminescence was recorded on an EnVision Multi-Label Reader (Perkin Elmer). Data was exported to GeneData Screener and modeled with a sigmoidal concentration response model in order to determine the $IC_{50}$ for compound response.

Not all cell lines with a given RAS mutation may be equally sensitive to a RAS inhibitor targeting that mutation, due to differential expression of efflux transporters, varying dependencies on RAS pathway activation for growth, or other reasons. This has been exemplified by the cell line KYSE-410 which, despite having a KRAS G12C mutation, is insensitive to the KRAS G12C (OFF) inhibitor MRTX-849 (Hallin et al., Cancer Discovery 10:54-71 (2020)), and the cell line SW1573, which is insensitive to the KRAS G12C (OFF) inhibitor AMG510 (Canon et al., Nature 575: 217-223 (2019)).

TABLE 19

IC50 values for various cancer cell lines with Compound B, Compound C, and Compound D

| Cell Line | Histotype | Mutant | Cmpd B IC50* | Cmpd C IC50* | Cmpd D IC50* |
|---|---|---|---|---|---|
| A-375 | Skin | BRAF V600E | low sensitivity | low sensitivity | low sensitivity |
| KYSE-410 | HN/Esophagus | KRAS G12C | moderately sensitive |  | very sensitive |
| MIA PaCa-2 | Pancreas | KRAS G12C | moderately sensitive | very sensitive | very sensitive |
| NCI-H358 | Lung | KRAS G12C | moderately sensitive | very sensitive | very sensitive |
| SW1573 | Lung | KRAS G12C | low sensitivity | low sensitivity | low sensitivity |
| SW837 | Intestine/Large/Colorectum | KRAS G12C | moderately sensitive |  | moderately sensitive |
| LS513 | Intestine/Large/Colorectum | KRAS G12D | moderately sensitive |  | moderately sensitive |
| HuCCT1 | Liver/Bile duct | KRAS G12D | moderately sensitive |  | very sensitive |
| HCC1588 | Lung | KRAS G12D | low sensitivity | low sensitivity | moderately sensitive |
| HPAC | Pancreas | KRAS G12D | moderately sensitive |  | very sensitive |
| AsPC-1 | Pancreas | KRAS G12D | moderately sensitive | moderately sensitive | moderately sensitive |
| AGS | Stomach | KRAS G12D | moderately sensitive | very sensitive | moderately sensitive |

TABLE 19-continued

IC50 values for various cancer cell lines with Compound B, Compound C, and Compound D

| Cell Line | Histotype | Mutant | Cmpd B IC50* | Cmpd C IC50* | Cmpd D IC50* |
|---|---|---|---|---|---|
| HEC-1-A | Uterus | KRAS G12D | moderately sensitive | | moderately sensitive |
| SW403 | Intestine/Large/Colorectum | KRAS G12V | moderately sensitive | | very sensitive |
| NOZ | Liver/Bile duct | KRAS G12V | moderately sensitive | | moderately sensitive |
| NCI-H441 | Lung | KRAS G12V | moderately sensitive | moderately sensitive | moderately sensitive |
| NCI-H727 | Lung | KRAS G12V | moderately sensitive | very sensitive | very sensitive |
| OVCAR-5 | Ovary | KRAS G12V | moderately sensitive | | very sensitive |
| Capan-2 | Pancreas | KRAS G12V | moderately sensitive | | very sensitive |
| SW48 | Intestine/Large/Colorectum | not MAPK (PIK3CA G914R, EGFR G719S) | low sensitivity | low sensitivity | low sensitivity |
| NCI-H2009 | Lung | other KRAS (G12A) | moderately sensitive | | moderately sensitive |
| CAL-62 | HN/Thyroid | other KRAS (G12R) | moderately sensitive | | |
| A549 | Lung | other KRAS (G12S) | moderately sensitive | moderately sensitive | moderately sensitive |
| TOV-21G | Ovary | other KRAS (G13C) | low sensitivity | | moderately sensitive |
| DV-90 | Lung | other KRAS (G13D) | low sensitivity | | moderately sensitive |
| HCT116 | Intestine/Large/Colorectum | other KRAS (G13D) | moderately sensitive | | very sensitive |
| NCI-H747 | Intestine/Large/Colorectum | other KRAS (G13D) | moderately sensitive | | very sensitive |
| NCI-H460 | Lung | other KRAS (Q61H) | moderately sensitive | moderately sensitive | moderately sensitive |
| Calu-6 | Lung | other KRAS (Q61K) | moderately sensitive | very sensitive | moderately sensitive |
| SNU-668 | Stomach | other KRAS (Q61K) | moderately sensitive | | very sensitive |
| OZ | Liver/Bile duct | other KRAS (Q61L) | moderately sensitive | | moderately sensitive |
| SW948 | Intestine/Large/Colorectum | other KRAS (Q61L) | low sensitivity | moderately sensitive | moderately sensitive |
| BxPC-3 | Pancreas | other MAPK (BRAF V487_P492delinsA) | low sensitivity | low sensitivity | low sensitivity |
| NCI-H1975 | Lung | other MAPK (EGFR T790M, L858R) | moderately sensitive | moderately sensitive | very sensitive |
| NCI-H3122 | Lung | other MAPK (EML4-ALK(E13, A20)) | moderately sensitive | | moderately sensitive |
| YCC-1 | Stomach | other MAPK (KRAS Amp) | | | moderately sensitive |
| MeWo | Skin | other MAPK (NF1 mut) | low sensitivity | moderately sensitive | moderately sensitive |
| NCI-H1838 | Lung | other MAPK (NF1 mut) | moderately sensitive | moderately sensitive | moderately sensitive |
| RL95-2 | Uterus | other RAS (HRAS Q61H) | | | very sensitive |
| NCI-H1915 | Lung | other RAS (HRAS Q61L) | | moderately sensitive | moderately sensitive |
| L-363 | Blood/Leukemia | other RAS (NRAS Q61H) | | | low sensitivity |
| CHP-212 | Brain&Nerves | other RAS (NRAS Q61K) | | | moderately sensitive |
| HT-1080 | Soft tissue | other RAS (NRAS Q61K) | | | moderately sensitive |
| NCI-H2087 | Lung | other RAS (NRAS Q61K) | | | very sensitive |
| OCI-LY-19 | Blood/Lymphoma | other RAS (NRAS Q61K) | | | moderately sensitive |
| SNU-387 | Liver/bile duct | other RAS (NRAS Q61K) | | | moderately sensitive |
| Hep G2 | Liver/bile duct | other RAS (NRAS Q61L) | | moderately sensitive | very sensitive |
| HL-60 | Blood/Leukemia | other RAS (NRAS Q61L) | | | very sensitive |

TABLE 19-continued

IC50 values for various cancer cell lines with Compound B, Compound C, and Compound D

| Cell Line | Histotype | Mutant | Cmpd B IC50* | Cmpd C IC50* | Cmpd D IC50* |
|---|---|---|---|---|---|
| MOLP8 | Blood/Myeloma | other RAS (NRAS Q61L) | | | moderately sensitive |
| SNU-719 | Stomach | other RAS (NRAS Q61L) | | | moderately sensitive |
| TF-1 | Blood/Leukemia | other RAS (NRAS Q61P) | | | moderately sensitive |
| ASH-3 | HN/Thyroid | other RAS (NRAS Q61R) | | | moderately sensitive |
| SK-MEL-2 | Skin | other RAS (NRAS Q61R) | | | moderately sensitive |
| SW1271 | Lung | other RAS (NRAS Q61R) | | | moderately sensitive |

*Key:
low sensitivity: IC50 ≥ 1 uM
moderately sensitive: 1 uM > IC50 ≥ 0.1 uM
very sensitive: IC50 < 0.1 uM In Vivo PD and Efficacy Data with Compound A, a Compound of the Present Invention

FIG. 1A:

Methods: The human pancreatic adenocarcinoma Capan-2 KRASG12V/wt xenograft model was used for a single-day treatment PK/PD study (FIG. 1A). Compound A (Capan-2 pERK K-Ras G12D EC50: 0.0037 uM) was administered at 100 mg/kg as a single dose or bid (second dose administered 8 hours after first dose) orally administered (po). The treatment groups with sample collections at various time points were summarized in Table 20 below. Tumor samples were collected to assess RAS/ERK signaling pathway modulation by measuring the mRNA level of human DUSP6 in qPCR assay, while accompanying blood plasma samples were collected to measure circulating Compound A levels.

TABLE 20

Summary of treatment groups, doses, and time points for single-dose PK/PD study using Capan-2 tumors.

| Compound/group | Dose/Regimen | PK, n = 3/time point | PD, n = 3/time point |
|---|---|---|---|
| Vehicle control | 10 ml/kg ip | 1 h, 24 h | 1 h, 24 h |
| Compound A | 100 mg/kg po | 1 h, 2 h, 8 h, 12 h, 24 h | 1 h, 2 h, 8 h, 10 h, 24 h |
| Compound A | 100 mg/kg po bid | 1 h, 2 h, 8 h, 12 h, 24 h | 1 h, 2 h, 8 h, 10 h, 24 h |

Results: In FIG. 1A, Compound A delivered at 100 mg/kg as a single dose inhibited DUSP6 mRNA levels in tumors>95% through 10 hours. A second dose of Compound A 8 hours following first administration maintained pathway modulation of 93% through 24 hours. These data indicate Compound A provides strong MAPK pathway modulation with continued target coverage.

FIG. 1B:

Methods: Effects of Compound A on tumor cell growth in vivo were evaluated in the human pancreatic adenocarcinoma Capan-2 KRASG12V/wt xenograft model using female BALB/c nude mice (6-8 weeks old). Mice were implanted with Capan-2 tumor cells in 50% Matrigel (4×106 cells/mouse) subcutaneously in the flank. Once tumors reached an average size of 180 mm3, mice were randomized to treatment groups to start the administration of test articles or vehicle. Compound A was orally administered (po) twice daily at 100 mg/kg. A SHP2 inhibitor, RMC-4550 (commercially available), was administered orally every other day at 20 mg/kg. Body weight and tumor volume (using calipers) was measured twice weekly until study endpoints. Tumor regressions calculated as >10% decrease in starting tumor volume. All dosing arms were well tolerated.

Figure 1B:
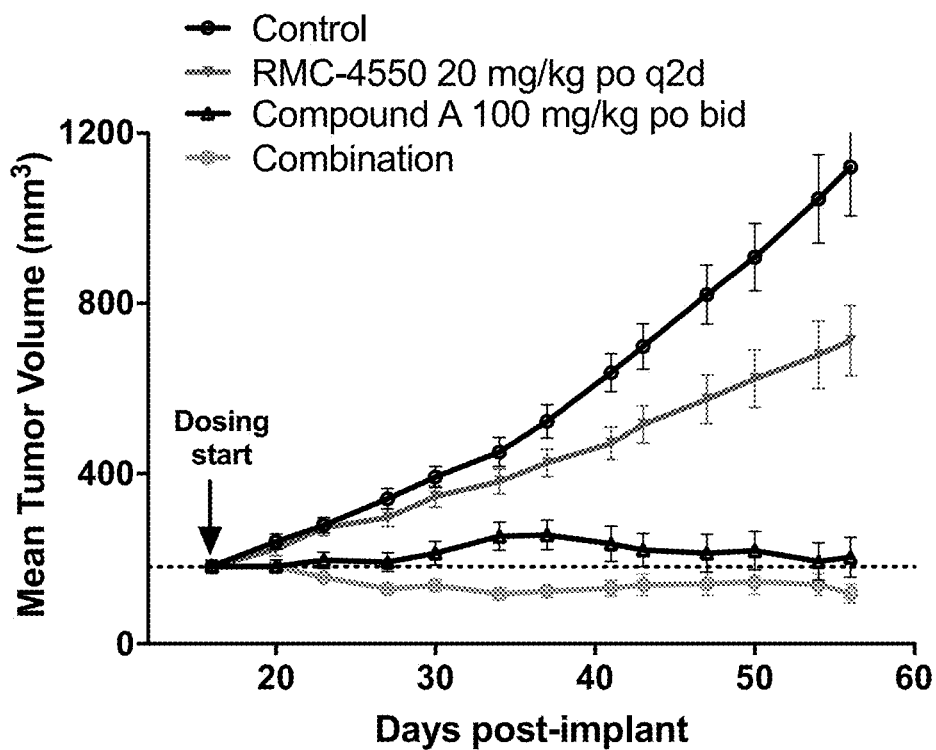
FIG. 1B: Combinatorial anti-tumor activity with a compound of the present invention, Compound A, and upstream SHP2 inhibition in a Capan-2 CDX model (PDAC, KRAS G12V/WT). Capan-2 cells were implanted in 50% Matrigel. Animals were randomized and treatment was initiated at average tumor volume of ~180 mm3. Animals were dosed with SHP2 inhibitor RMC-4550 20 mg/kg po q2d, Compound A 100 mg/kg po bid, combination RMC-4550 and Compound A, or Control for 40 days. All dose levels were tolerated. n=10/group (n=9 in Combination arm). Ns=no significance; ***p<0.001 by one-way ANOVA.

Results: In FIG. 1B, single agent SHP2i RMC-4550 dosed every other day at 20 mg/kg po resulted in 39% TGI. Single-agent Compound A administered at 100 mg/kg po bid daily led to a TGI of 98%, with 4/10 (40%) individual animals achieving tumor regressions. Combination of Compound A and RMC-4550 resulted in total tumor regression of 35%, with individual tumor regressions observed in 7/9 (77.8%) individual animals at the end of treatment (Day 40 after treatment started) in Capan-2 CDX model with heterozygous KRASG12V. The anti-tumor activity of Compound A, and Combination arms was statistically significant compared with control group (***p<0.001, ordinary One-way ANOVA with multiple comparisons via a post-hoc Tukey's test), while RMC-4550 was not significant at these doses.

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features set forth herein.

All publications, patents and patent applications are herein incorporated by reference in their entirety to the same extent as if each individual publication, patent or patent application was specifically and individually indicated to be incorporated by reference in its entirety.

The invention claimed is:

1. A compound, or a pharmaceutically acceptable salt thereof, selected from (Compound A18)

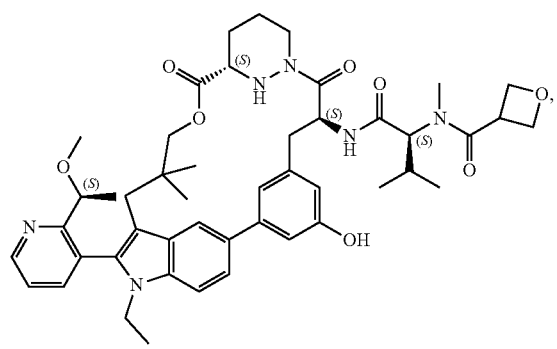

(Compound A25)

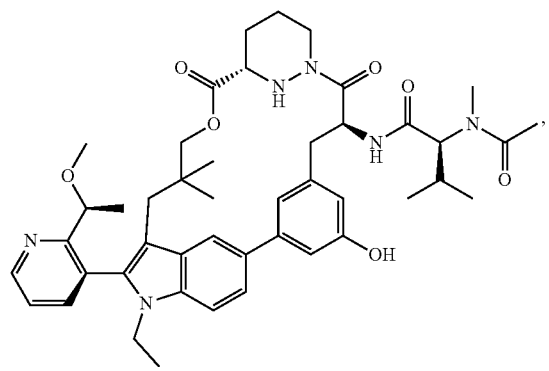

(Compound A268)

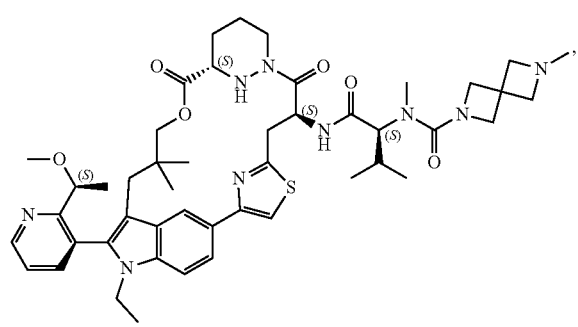

(Compound A280)

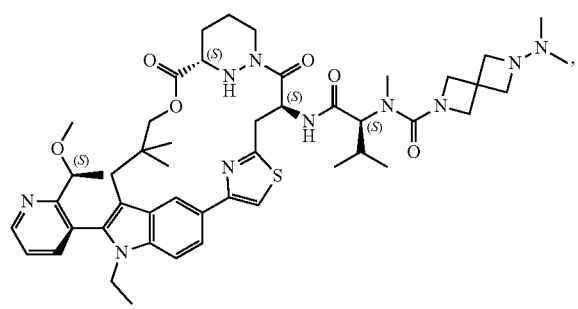

-continued (Compound A384)

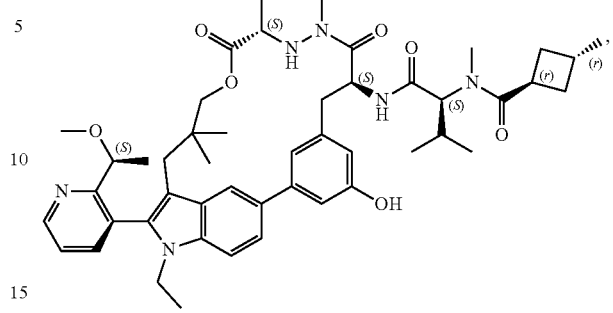

(Compound A385)

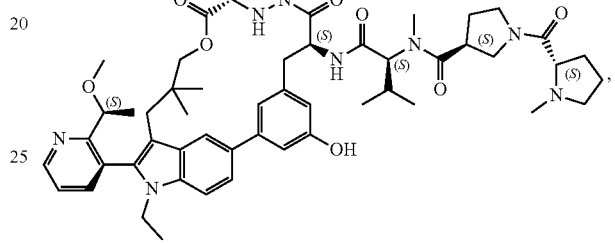

(Compound A549)

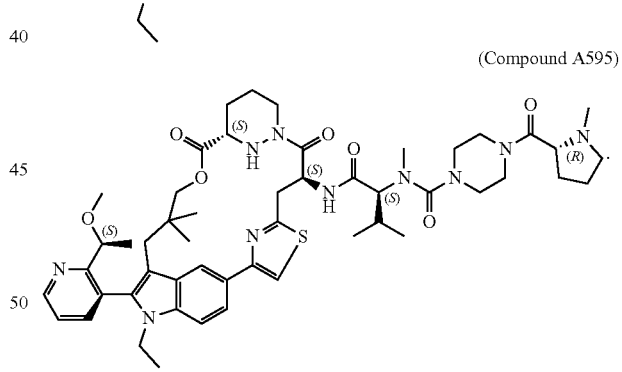

and (Compound A595)

2. A pharmaceutical composition comprising a compound, or a pharmaceutically acceptable salt thereof, of claim 1 and a pharmaceutically acceptable excipient.

3. A method of treating cancer comprising a Ras mutation in a subject in need thereof, the method comprising administering to the subject a therapeutically effective amount of a compound, or a pharmaceutically acceptable salt thereof, of claim 1.

4. A method of treating a Ras protein-related disorder in a subject in need thereof, the method comprising administering to the subject a therapeutically effective amount of a compound, or a pharmaceutically acceptable salt thereof, of claim 1.

5. The method of claim 3, wherein the cancer is pancreatic cancer, colorectal cancer, non-small cell lung cancer, gastric cancer, esophageal cancer, ovarian cancer or uterine cancer.

6. The method of claim 3, wherein the Ras mutation is at position 12, 13, or 61.

7. The method of claim 3, wherein the Ras mutation is K-Ras G12C, K-Ras G12D, K-ras G12V, K-Ras G12S, K-Ras G13C, K-Ras G13D, or K-Ras Q61L.

* * * * *